US011013726B2

(12) United States Patent
Bailey et al.

(10) Patent No.: US 11,013,726 B2
(45) Date of Patent: May 25, 2021

(54) SUBSTITUTED PYRIDINONE-CONTAINING TRYCYCLIC COMPOUNDS, AND METHODS USING SAME

(71) Applicant: Arbutus Biopharma Corporation, Burnaby (CA)

(72) Inventors: Laurèn Danielle Bailey, Hatboro, PA (US); Yingzhi Bi, Plainsboro, NJ (US); Shuai Chen, Warrington, PA (US); Bruce D. Dorsey, Ambler, PA (US); Dimitar B. Gotchev, Hatboro, PA (US); Richard James Holland, Vancouver (CA); Ramesh Kakarla, Doylestown, PA (US); Duyan Nguyen, Ambler, PA (US); Mark Christopher Wood, Port Moody (CA)

(73) Assignee: Arbutus Biopharma Corporation, Burnaby (CA)

( * ) Notice: Subject to any disclaimer, the term of this patent is extended or adjusted under 35 U.S.C. 154(b) by 0 days.

(21) Appl. No.: 16/834,577

(22) Filed: Mar. 30, 2020

(65) Prior Publication Data
US 2020/0261432 A1    Aug. 20, 2020

Related U.S. Application Data

(62) Division of application No. 16/347,766, filed as application No. PCT/US2017/059854 on Nov. 3, 2017.

(60) Provisional application No. 62/512,990, filed on May 31, 2017, provisional application No. 62/506,325, filed on May 15, 2017, provisional application No. 62/418,478, filed on Nov. 7, 2016.

(51) Int. Cl.
| | |
|---|---|
| *A61K 31/4375* | (2006.01) |
| *A61P 31/20* | (2006.01) |
| *A61K 9/51* | (2006.01) |
| *A61K 31/683* | (2006.01) |
| *A61K 31/7105* | (2006.01) |
| *C07D 471/14* | (2006.01) |
| *C07D 491/147* | (2006.01) |
| *C07D 491/22* | (2006.01) |
| *C07D 495/14* | (2006.01) |
| *C07D 513/14* | (2006.01) |
| *C07F 9/6561* | (2006.01) |

(52) U.S. Cl.
CPC ........ *A61K 31/4375* (2013.01); *A61K 9/5123* (2013.01); *A61K 31/683* (2013.01); *A61K 31/7105* (2013.01); *A61P 31/20* (2018.01); *C07D 471/14* (2013.01); *C07D 491/147* (2013.01); *C07D 491/22* (2013.01); *C07D 495/14* (2013.01); *C07D 513/14* (2013.01); *C07F 9/6561* (2013.01)

(58) Field of Classification Search
None
See application file for complete search history.

(56) References Cited

U.S. PATENT DOCUMENTS

| | | |
|---|---|---|
| 6,514,912 B1 | 2/2003 | Guarna et al. |
| 7,307,073 B2 | 12/2007 | Grove et al. |
| 8,063,037 B2 | 11/2011 | Rewinkel et al. |
| 9,458,153 B2 | 10/2016 | Han et al. |
| 10,501,456 B2 † | 12/2019 | Chen |
| 2015/0210682 A1 | 7/2015 | Wang et al. |
| 2016/0122344 A1 | 5/2016 | Han et al. |
| 2016/0296515 A1 | 10/2016 | Han et al. |
| 2017/0057952 A1 | 3/2017 | Yang et al. |

FOREIGN PATENT DOCUMENTS

| | | |
|---|---|---|
| EP | 0093498 A1 | 11/1983 |
| JP | 60-197684 A | 10/1985 |
| JP | H04-77 B2 | 1/1992 |
| WO | 2015113990 A1 | 8/2015 |
| WO | 2015173164 A1 | 11/2015 |
| WO | 2016071215 A1 | 5/2016 |
| WO | 2017013046 A1 | 1/2017 |
| WO | 2017016960 A1 | 2/2017 |
| WO | 2017140821 A1 | 8/2017 |
| WO | 2017216685 A1 | 12/2017 |
| WO | 2017216686 A1 | 12/2017 |
| WO | 2018019297 A1 | 2/2018 |
| WO | 2018022282 A1 | 2/2018 |
| WO | 2018047109 A1 | 3/2018 |
| WO | 2018130152 A1 | 7/2018 |

OTHER PUBLICATIONS

Amii, et al., "Difluorinated Danishefsky's Diene: A Versatile C4 Building Block for the Fluorinated Six-Membered Rings", Organic Letters, vol. 3, No. 20, 2001, pp. 3103-3105.
El-Essawy, F.A., et al., "Anti-Hepatitis B Virus Activity of New 1,2,4-Triazol-2-yl- and 1,3,4-Oxadiazol-2-yl-2-pyridinone Derivatives", Zeitschrift fur Naturforschung C, vol. 63, Nos. 9-10, 2008, pp. 667-674.
Fecik, et al., "Chiral DNA Gyrase Inhibitors. 3. Probing the Chiral Preference of the Active Site of DNA Gyrase. Synthesis of 10-fluoro-6-methyl-6,7-dihydro-9-piperazinyl-2H-benzo[a]quinolizin-20-one-3-carboxylic Acid Analogues", J Med Chem, vol. 48, No. 4, Jan. 1, 2005, pp. 1229-1236.
Georgopapadakou, et al., "Monocyclic and Tricyclic Analos of Quinolones: Mechanism of Action", Antimicrobial Agents and Chemotherapy, vol. 31, No. 4, Apr. 1987, pp. 614-616.

(Continued)

*Primary Examiner* — Zinna Northington Davis
(74) *Attorney, Agent, or Firm* — Saul Ewing Arnstein & Lehr LLP; Domingos J. Silva; Kevin T. O'Brien

(57) ABSTRACT

The present invention includes substituted pyridinone-containing tricyclic compounds, and compositions comprising the same, that can be used to treat or prevent hepatitis B virus (HBV) infection in a patient. In certain embodiments, the compounds and compositions of the invention inhibit and/or reduce HBsAg secretion.

27 Claims, No Drawings
Specification includes a Sequence Listing.

(56) References Cited

OTHER PUBLICATIONS

Kaneko, M., et al., "A Novel Tricyclic Polyketide, Vanitaracin A, Specifically Inhibits the Entry of Hepatitis B and D Viruses by Targeting Sodium Taurocholate Cotransporting Polypeptide", J of Virol, vol. 89, No. 23, 2015, pp. 11945-11953.
Xu, B., et al., "A Facile Synthesis of Novel Tricyclic 4-Pyridones", Tetrahedron Letters, vol. 55, Issue 52, 2014, pp. 7194-7197.

† cited by third party

SEQUENCE LISTING

```
<160> NUMBER OF SEQ ID NOS: 12

<210> SEQ ID NO 1
<211> LENGTH: 21
<212> TYPE: RNA
<213> ORGANISM: Artificial Sequence
<220> FEATURE:
<223> OTHER INFORMATION: Chemically synthesized
<220> FEATURE:
<221> NAME/KEY: modified_base
<222> LOCATION: (1)..(1)
<223> OTHER INFORMATION: unlocked nucleobase analogue (UNA) moiety
<220> FEATURE:
<221> NAME/KEY: modified_base
<222> LOCATION: (5)..(5)
<223> OTHER INFORMATION: 2'-O-methyl modification
<220> FEATURE:
<221> NAME/KEY: modified_base
<222> LOCATION: (6)..(6)
<223> OTHER INFORMATION: 2'-O-methyl modification
<220> FEATURE:
<221> NAME/KEY: modified_base
<222> LOCATION: (12)..(12)
<223> OTHER INFORMATION: 2'-O-methyl modification
<220> FEATURE:
<221> NAME/KEY: modified_base
<222> LOCATION: (16)..(16)
<223> OTHER INFORMATION: 2'-O-methyl modification
<220> FEATURE:
<221> NAME/KEY: modified_base
```

```
<222> LOCATION: (17)..(17)
<223> OTHER INFORMATION: 2'-O-methyl modification
<220> FEATURE:
<221> NAME/KEY: modified_base
<222> LOCATION: (20)..(20)
<223> OTHER INFORMATION: unlocked nucleobase analogue (UNA) moiety
<220> FEATURE:
<221> NAME/KEY: modified_base
<222> LOCATION: (21)..(21)
<223> OTHER INFORMATION: unlocked nucleobase analogue (UNA) moiety

<400> SEQUENCE: 1
ccgugugcac uucgcuucau u                                          21

<210> SEQ ID NO 2
<211> LENGTH: 21
<212> TYPE: RNA
<213> ORGANISM: Artificial Sequence
<220> FEATURE:
<223> OTHER INFORMATION: Chemically synthesized
<220> FEATURE:
<221> NAME/KEY: modified_base
<222> LOCATION: (12)..(12)
<223> OTHER INFORMATION: 2'-O-methyl modification
<220> FEATURE:
<221> NAME/KEY: modified_base
<222> LOCATION: (18)..(18)
<223> OTHER INFORMATION: 2'-O-methyl modification
<220> FEATURE:
<221> NAME/KEY: modified_base
<222> LOCATION: (20)..(20)
<223> OTHER INFORMATION: unlocked nucleobase analogue (UNA) moiety
<220> FEATURE:
<221> NAME/KEY: modified_base
<222> LOCATION: (21)..(21)
<223> OTHER INFORMATION: unlocked nucleobase analogue (UNA) moiety

<400> SEQUENCE: 2
ugaagcgaag ugcacacggu u                                          21

<210> SEQ ID NO 3
<211> LENGTH: 21
<212> TYPE: RNA
<213> ORGANISM: Artificial Sequence
<220> FEATURE:
<223> OTHER INFORMATION: Chemically synthesized
<220> FEATURE:
<221> NAME/KEY: modified_base
<222> LOCATION: (1)..(1)
<223> OTHER INFORMATION: unlocked nucleobase analogue (UNA) moeity
<220> FEATURE:
<221> NAME/KEY: modified_base
<222> LOCATION: (2)..(2)
<223> OTHER INFORMATION: 2'-O-methyl modification
<220> FEATURE:
<221> NAME/KEY: modified_base
<222> LOCATION: (3)..(3)
<223> OTHER INFORMATION: 2'-O-methyl modification
<220> FEATURE:
<221> NAME/KEY: modified_base
<222> LOCATION: (4)..(4)
<223> OTHER INFORMATION: 2'-O-methyl modification
<220> FEATURE:
<221> NAME/KEY: modified_base
<222> LOCATION: (15)..(15)
<223> OTHER INFORMATION: 2'-O-methyl modification
<220> FEATURE:
<221> NAME/KEY: modified_base
<222> LOCATION: (17)..(17)
<223> OTHER INFORMATION: 2'-O-methyl modification
<220> FEATURE:
<221> NAME/KEY: modified_base
<222> LOCATION: (21)..(21)
<223> OTHER INFORMATION: unlocked nucleobase analogue (UNA) moeity
```

```
<400> SEQUENCE: 3
cuggcucagu uuacuagugu u                                              21

<210> SEQ ID NO 4
<211> LENGTH: 21
<212> TYPE: RNA
<213> ORGANISM: Artificial Sequence
<220> FEATURE:
<223> OTHER INFORMATION: Chemically synthesized
<220> FEATURE:
<221> NAME/KEY: modified_base
<222> LOCATION: (6)..(6)
<223> OTHER INFORMATION: 2'-O-methyl modification
<220> FEATURE:
<221> NAME/KEY: modified_base
<222> LOCATION: (13)..(13)
<223> OTHER INFORMATION: 2'-O-methyl modification
<220> FEATURE:
<221> NAME/KEY: modified_base
<222> LOCATION: (15)..(15)
<223> OTHER INFORMATION: 2'-O-methyl modification

<400> SEQUENCE: 4
cacuaguaaa cugagccagu u                                              21

<210> SEQ ID NO 5
<211> LENGTH: 21
<212> TYPE: RNA
<213> ORGANISM: Artificial Sequence
<220> FEATURE:
<223> OTHER INFORMATION: Chemically synthesized
<220> FEATURE:
<221> NAME/KEY: modified_base
<222> LOCATION: (1)..(1)
<223> OTHER INFORMATION: unlocked nucleobase analogue (UNA) moiety
<220> FEATURE:
<221> NAME/KEY: modified_base
<222> LOCATION: (4)..(4)
<223> OTHER INFORMATION: 2'-O-methyl modification
<220> FEATURE:
<221> NAME/KEY: modified_base
<222> LOCATION: (6)..(6)
<223> OTHER INFORMATION: 2'-O-methyl modification
<220> FEATURE:
<221> NAME/KEY: modified_base
<222> LOCATION: (13)..(13)
<223> OTHER INFORMATION: 2'-O-methyl modification
<220> FEATURE:
<221> NAME/KEY: modified_base
<222> LOCATION: (14)..(14)
<223> OTHER INFORMATION: 2'-O-methyl modification
<220> FEATURE:
<221> NAME/KEY: modified_base
<222> LOCATION: (17)..(17)
<223> OTHER INFORMATION: 2'-O-methyl modification
<220> FEATURE:
<221> NAME/KEY: modified_base
<222> LOCATION: (21)..(21)
<223> OTHER INFORMATION: unlocked nucleobase analogue (UNA) moiety

<400> SEQUENCE: 5
gccgauccau acugcggaau u                                              21

<210> SEQ ID NO 6
<211> LENGTH: 21
<212> TYPE: RNA
<213> ORGANISM: Artificial Sequence
<220> FEATURE:
<223> OTHER INFORMATION: Chemically synthesized
<220> FEATURE:
<221> NAME/KEY: modified_base
<222> LOCATION: (8)..(8)
<223> OTHER INFORMATION: 2'-O-methyl modification
```

```
<220> FEATURE:
<221> NAME/KEY: modified_base
<222> LOCATION: (13)..(13)
<223> OTHER INFORMATION: 2'-O-methyl modification
<220> FEATURE:
<221> NAME/KEY: modified_base
<222> LOCATION: (18)..(18)
<223> OTHER INFORMATION: 2'-O-methyl modification

<400> SEQUENCE: 6
uuccgcagua uggaucggcu u                                              21

<210> SEQ ID NO 7
<211> LENGTH: 21
<212> TYPE: RNA
<213> ORGANISM: Artificial Sequence
<220> FEATURE:
<223> OTHER INFORMATION: Chemically synthesized
<220> FEATURE:
<221> NAME/KEY: modified_base
<222> LOCATION: (3)..(3)
<223> OTHER INFORMATION: 2'-O-methyl modification
<220> FEATURE:
<221> NAME/KEY: modified_base
<222> LOCATION: (5)..(5)
<223> OTHER INFORMATION: 2'-O-methyl modification
<220> FEATURE:
<221> NAME/KEY: modified_base
<222> LOCATION: (6)..(6)
<223> OTHER INFORMATION: 2'-O-methyl modification
<220> FEATURE:
<221> NAME/KEY: modified_base
<222> LOCATION: (12)..(12)
<223> OTHER INFORMATION: 2'-O-methyl modification
<220> FEATURE:
<221> NAME/KEY: modified_base
<222> LOCATION: (14)..(14)
<223> OTHER INFORMATION: 2'-O-methyl modification
<220> FEATURE:
<221> NAME/KEY: modified_base
<222> LOCATION: (16)..(16)
<223> OTHER INFORMATION: 2'-O-methyl modification
<220> FEATURE:
<221> NAME/KEY: modified_base
<222> LOCATION: (17)..(17)
<223> OTHER INFORMATION: 2'-O-methyl modification

<400> SEQUENCE: 7
ccgugugcac uucgcuucau u                                              21

<210> SEQ ID NO 8
<211> LENGTH: 21
<212> TYPE: RNA
<213> ORGANISM: Artificial Sequence
<220> FEATURE:
<223> OTHER INFORMATION: Chemically synthesized
<220> FEATURE:
<221> NAME/KEY: modified_base
<222> LOCATION: (5)..(5)
<223> OTHER INFORMATION: 2'-O-methyl modification
<220> FEATURE:
<221> NAME/KEY: modified_base
<222> LOCATION: (7)..(7)
<223> OTHER INFORMATION: 2'-O-methyl modification
<220> FEATURE:
<221> NAME/KEY: modified_base
<222> LOCATION: (11)..(11)
<223> OTHER INFORMATION: 2'-O-methyl modification
<220> FEATURE:
<221> NAME/KEY: modified_base
<222> LOCATION: (12)..(12)
<223> OTHER INFORMATION: 2'-O-methyl modification
<220> FEATURE:
<221> NAME/KEY: modified_base
<222> LOCATION: (15)..(15)
```

```
<223> OTHER INFORMATION: 2'-O-methyl modification
<220> FEATURE:
<221> NAME/KEY: modified_base
<222> LOCATION: (17)..(17)
<223> OTHER INFORMATION: 2'-O-methyl modification
<220> FEATURE:
<221> NAME/KEY: modified_base
<222> LOCATION: (18)..(18)
<223> OTHER INFORMATION: 2'-O-methyl modification

<400> SEQUENCE: 8
ugaagcgaag ugcacacggu u                                              21

<210> SEQ ID NO 9
<211> LENGTH: 21
<212> TYPE: RNA
<213> ORGANISM: Artificial Sequence
<220> FEATURE:
<223> OTHER INFORMATION: Chemically synthesized
<220> FEATURE:
<221> NAME/KEY: modified_base
<222> LOCATION: (2)..(2)
<223> OTHER INFORMATION: 2'-O-methyl modification
<220> FEATURE:
<221> NAME/KEY: modified_base
<222> LOCATION: (3)..(3)
<223> OTHER INFORMATION: 2'-O-methyl modification
<220> FEATURE:
<221> NAME/KEY: modified_base
<222> LOCATION: (4)..(4)
<223> OTHER INFORMATION: 2'-O-methyl modification
<220> FEATURE:
<221> NAME/KEY: modified_base
<222> LOCATION: (6)..(6)
<223> OTHER INFORMATION: 2'-O-methyl modification
<220> FEATURE:
<221> NAME/KEY: modified_base
<222> LOCATION: (10)..(10)
<223> OTHER INFORMATION: 2'-O-methyl modification
<220> FEATURE:
<221> NAME/KEY: modified_base
<222> LOCATION: (12)..(12)
<223> OTHER INFORMATION: 2'-O-methyl modification
<220> FEATURE:
<221> NAME/KEY: modified_base
<222> LOCATION: (14)..(14)
<223> OTHER INFORMATION: 2'-O-methyl modification
<220> FEATURE:
<221> NAME/KEY: modified_base
<222> LOCATION: (15)..(15)
<223> OTHER INFORMATION: 2'-O-methyl modification
<220> FEATURE:
<221> NAME/KEY: modified_base
<222> LOCATION: (17)..(17)
<223> OTHER INFORMATION: 2'-O-methyl modification
<220> FEATURE:
<221> NAME/KEY: modified_base
<222> LOCATION: (18)..(18)
<223> OTHER INFORMATION: 2'-O-methyl modification
<220> FEATURE:
<221> NAME/KEY: modified_base
<222> LOCATION: (19)..(19)
<223> OTHER INFORMATION: 2'-O-methyl modification

<400> SEQUENCE: 9
cuggcucagu uuacuagugu u                                              21

<210> SEQ ID NO 10
<211> LENGTH: 21
<212> TYPE: RNA
<213> ORGANISM: Artificial Sequence
<220> FEATURE:
<223> OTHER INFORMATION: Chemically synthesized
<220> FEATURE:
<221> NAME/KEY: modified_base
```

```
<222> LOCATION: (6)..(6)
<223> OTHER INFORMATION: 2'-O-methoxy modification
<220> FEATURE:
<221> NAME/KEY: modified_base
<222> LOCATION: (7)..(7)
<223> OTHER INFORMATION: 2'-O-methoxy modification
<220> FEATURE:
<221> NAME/KEY: modified_base
<222> LOCATION: (11)..(11)
<223> OTHER INFORMATION: 2'-O-methoxy modification
<220> FEATURE:
<221> NAME/KEY: modified_base
<222> LOCATION: (13)..(13)
<223> OTHER INFORMATION: 2'-O-methoxy modification
<220> FEATURE:
<221> NAME/KEY: modified_base
<222> LOCATION: (15)..(15)
<223> OTHER INFORMATION: 2'-O-methoxy modification
<220> FEATURE:
<221> NAME/KEY: modified_base
<222> LOCATION: (17)..(17)
<223> OTHER INFORMATION: 2'-O-methoxy modification

<400> SEQUENCE: 10
cacuaguaaa cugagccagu u                                              21

<210> SEQ ID NO 11
<211> LENGTH: 21
<212> TYPE: RNA
<213> ORGANISM: Artificial Sequence
<220> FEATURE:
<223> OTHER INFORMATION: Chemically synthesized
<220> FEATURE:
<221> NAME/KEY: modified_base
<222> LOCATION: (2)..(2)
<223> OTHER INFORMATION: 2'-O-methoxy modification
<220> FEATURE:
<221> NAME/KEY: modified_base
<222> LOCATION: (4)..(4)
<223> OTHER INFORMATION: 2'-O-methoxy modification
<220> FEATURE:
<221> NAME/KEY: modified_base
<222> LOCATION: (6)..(6)
<223> OTHER INFORMATION: 2'-O-methoxy modification
<220> FEATURE:
<221> NAME/KEY: modified_base
<222> LOCATION: (8)..(8)
<223> OTHER INFORMATION: 2'-O-methoxy modification
<220> FEATURE:
<221> NAME/KEY: modified_base
<222> LOCATION: (10)..(10)
<223> OTHER INFORMATION: 2'-O-methoxy modification
<220> FEATURE:
<221> NAME/KEY: modified_base
<222> LOCATION: (12)..(12)
<223> OTHER INFORMATION: 2'-O-methoxy modification
<220> FEATURE:
<221> NAME/KEY: modified_base
<222> LOCATION: (14)..(14)
<223> OTHER INFORMATION: 2'-O-methoxy modification

<400> SEQUENCE: 11
accucugccu aaucaucucu u                                              21

<210> SEQ ID NO 12
<211> LENGTH: 21
<212> TYPE: RNA
<213> ORGANISM: Artificial Sequence
<220> FEATURE:
<223> OTHER INFORMATION: Chemically synthesized
<220> FEATURE:
<221> NAME/KEY: modified_base
<222> LOCATION: (7)..(7)
<223> OTHER INFORMATION: 2'-O-methoxy modification
<220> FEATURE:
```

```
<221> NAME/KEY: modified_base
<222> LOCATION: (9)..(9)
<223> OTHER INFORMATION: 2'-O-methoxy modification
<220> FEATURE:
<221> NAME/KEY: modified_base
<222> LOCATION: (13)..(13)
<223> OTHER INFORMATION: 2'-O-methoxy modification
<220> FEATURE:
<221> NAME/KEY: modified_base
<222> LOCATION: (15)..(15)
<223> OTHER INFORMATION: 2'-O-methoxy modification
<220> FEATURE:
<221> NAME/KEY: modified_base
<222> LOCATION: (17)..(17)
<223> OTHER INFORMATION: 2'-O-methoxy modification

<400> SEQUENCE: 12
gagaugauua ggcagagguu u                                               21
```

SUBSTITUTED PYRIDINONE-CONTAINING TRYCYCLIC COMPOUNDS, AND METHODS USING SAME

CROSS-REFERENCE TO RELATED APPLICATIONS

The present application is a division of U.S. application Ser. No. 16/347,766, filed May 6, 2019, now U.S. Pat. No. 10,821,103, which is a 35 U.S.C. § 371 national phase application of PCT International Application No. PCT/US2017/059854, filed Nov. 3, 2017, which claims priority to U.S. Provisional Applications No. 62/512,990, filed May 31, 2017; No. 62/506,325, filed May 15, 2017; and No. 62/418,478, filed Nov. 7, 2016, all of which applications are incorporated herein by reference in their entireties.

BACKGROUND OF THE INVENTION

Hepatitis B is one of the world's most prevalent diseases. Although most individuals resolve the infection following acute symptoms, approximately 30% of cases become chronic. 350-400 million people worldwide are estimated to have chronic hepatitis B, leading to 0.5-1 million deaths per year, due largely to the development of hepatocellular carcinoma, cirrhosis and/or other complications. Hepatitis B is caused by hepatitis B virus (HBV), a noncytopathic, liver tropic DNA virus belonging to Hepadnaviridae family.

A limited number of drugs are currently approved for the management of chronic hepatitis B, including two formulations of alpha-interferon (standard and pegylated) and five nucleoside/nucleotide analogues (lamivudine, adefovir, entecavir, telbivudine, and tenofovir) that inhibit HBV DNA polymerase. At present, the first-line treatment choices are entecavir, tenofovir or peg-interferon alfa-2a. However, peg-interferon alfa-2a achieves desirable serological milestones in only one third of treated patients, and is frequently associated with severe side effects. Entecavir and tenofovir require long-term or possibly lifetime administration to continuously suppress HBV replication, and may eventually fail due to emergence of drug-resistant viruses.

HBV is an enveloped virus with an unusual mode of replication, centering on the establishment of a covalently closed circular DNA (cccDNA) copy of its genome in the host cell nucleus. Pregenomic (pg) RNA is the template for reverse transcriptional replication of HBV DNA. The encapsidation of pg RNA, together with viral DNA polymerase, into a nucleocapsid is essential for the subsequent viral DNA synthesis.

Aside from being a critical structural component of the virion, the HBV envelope is a major factor in the disease process. In chronically infected individuals, serum levels of HBV surface antigen (HBsAg) can be as high as 400 µg/ml, driven by the propensity for infected cells to secrete non-infectious subviral particles at levels far in excess of infectious (Dane) particles.

HBsAg comprises the principal antigenic determinant in HBV infection and is composed of the small, middle and large surface antigens (S, M and L, respectively). These proteins are produced from a single open reading frame as three separate N-glycosylated polypeptides through utilization of alternative transcriptional start sites (for L and M/S mRNAs) and initiation codons (for L, M and S).

Although the viral polymerase and HBsAg perform distinct functions, both are essential proteins for the virus to complete its life cycle and be infectious. HBV lacking HBsAg is completely defective and cannot infect or cause infection. HBsAg protects the virus nucleocapsid, begins the infectious cycle, and mediates morphogenesis and secretion of newly forming virus from the infected cell.

People chronically infected with HBV are usually characterized by readily detectable levels of circulating antibody specific to the viral capsid (HBc), with little, if any detectable levels of antibody to HBsAg. There is evidence that chronic carriers produce antibodies to HBsAg, but these antibodies are complexed with the circulating HBsAg, which can be present in mg/mL amounts in a chronic carrier's circulation. Reducing the amount of circulating levels of HBsAg might allow any present anti-HBsA to manage the infection. Further, even if nucleocapsids free of HBsAg were to be expressed or secreted into circulation (perhaps as a result of cell death), the high levels of anti-HBc would quickly complex with them and result in their clearance.

Studies have shown that the presence of subviral particles in a culture of infected hepatocytes may have a transactivating function on viral genomic replication, and the circulating surface antigen suppresses virus-specific immune response. Furthermore, the scarcity of virus-specific cytotoxic T lymphocytes (CTLs), that is a hallmark of chronic HBV infection, may be due to repression of MHC I presentation by intracellular expression of L and M in infected hepatocytes. Existing FDA-approved therapies do not significantly affect HBsAg serum levels.

There is thus a need in the art for novel compounds and/or compositions that can be used to treat and/or prevent HBV infection in a subject. In certain embodiments, the compounds reduce or minimizing levels of HBsAg, hepatitis B e-antigen (HBeAg), hepatitis B core protein, and/or pg RNA, in a HBV-infected subject. In other embodiments, the compounds can be used in patients that are HBV infected, patients who are at risk of becoming HBV, and/or patients that are infected with drug-resistant HBV. The present invention addresses this need.

BRIEF SUMMARY OF THE INVENTION

The invention provides certain compounds, as well as pharmaceutical compositions comprising at least one compound of the invention and a pharmaceutically acceptable carrier.

The invention further provides a method of treating or preventing hepatitis virus infection in a subject. The invention further provides a method of reducing or minimizing HBsAg levels in a HBV-infected subject. The invention further provides a method of reducing or minimizing HBeAg levels in a HBV-infected subject. The invention further provides a method of reducing or minimizing hepatitis core protein levels in a HBV-infected subject. The invention further provides a method of reducing or minimizing pg RNA levels in a HBV-infected subject.

The invention further provides a compound of formula (IIIa), or a salt, solvate, stereoisomer, geometric isomer, tautomer, or any mixtures thereof:

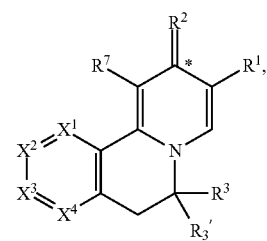

wherein:

R[1] is selected from the group consisting of H; halo; —OR[8]; —C(R[9])(R[9])OR[8]; —C(=O)R[8]; —C(=O)OR[8]; —C(=O)NH—OR[8]; —C(=O)NHNHR[8]; —C(=O)NHNHC(=O)R[8]; —C(=O)NHS(=O)$_2$R[8]; —CH$_2$C(=O)OR[8]; —CN; —NH$_2$; —N(R[8])C(=O)H; —N(R[8])C(=O)R[10]; —N(R[8])C(=O)OR[10]; —N(R[8])C(=O)NHR[8]; —NR[9]S(=O)$_2$R[10]; —P(=O)(OR[8])$_2$; —B(OR[8])$_2$; 2,5-dioxo-pyrrolidin-1-yl; 2H-tetrazol-5-yl; 3-hydroxy-isoxazol-5-yl; 1,4-dihydro-5-oxo-5H-tetrazol-1-yl; pyridin-2-yl optionally substituted with $C_1$-$C_6$ alkyl; pyrimidin-2-yl optionally substituted with $C_1$-$C_6$ alkyl; (pyridin-2-yl)methyl; (pyrimidin-2-yl)methyl; (pyrimidin-2-yl)amino; bis-(pyrimidin-2-yl)-amino; 5-R[8]-1,3,4,-thiadiazol-2-yl; 5-thioxo-4,5-dihydro-1H-1,2,4-triazol-3-yl; 1H-1,2,4-triazol-5-yl; 1,3,4-oxadiazol-2-yl; 1,2,4-oxadiazol-5-yl, and 3-R[10]-1,2,4-oxadiazol-5-yl;

R[2] is selected from the group consisting of =O, =NR[9], =N(OR[9]), and =N(NR[9]R[9]); or R[1] and R[2] combine to form =N—O—C(=O)— or =N—N(R[9])—C(=O)—, wherein the =N group is bound to the ring carbon atom marked "*";

X[1] is selected from the group consisting of CR[6I] and N, X[2] is selected from the group consisting of CR[6II] and N, X[3] is selected from the group consisting of CR[6III] and N, X[4] is selected from the group consisting of CR[6IV] and N, or either X[3] and X[4], or X[1] and X[2], combine to form —S—; wherein 1-2 substituents selected from the group consisting of X[1], X[2], X[3] and X[4] are N; each of which, if present, is optionally alkylated with $C_1$-$C_6$ alkyl if the adjacent carbon atom in the ring is substituted with —OH;

R[6I], R[6II], R[6III] and R[6IV] are independently selected from the group consisting of H, halo, —CN, pyrrolidinyl, optionally substituted $C_1$-$C_6$ alkyl, optionally substituted $C_1$-$C_6$ alkenyl, optionally substituted $C_3$-$C_8$ cycloalkyl, optionally substituted heterocyclyl, —OR, $C_1$-$C_6$ haloalkoxy, —N(R)(R), —NO$_2$, —S(=O)$_2$N(R)(R), acyl, and $C_1$-$C_6$ alkoxycarbonyl, wherein each occurrence of R is independently selected from the group consisting of H, $C_1$-$C_6$ alkyl, R'-substituted $C_1$-$C_6$ alkyl, $C_1$-$C_6$ hydroxyalkyl, optionally substituted ($C_1$-$C_6$ alkoxy)-$C_1$-$C_6$ alkyl, and optionally substituted $C_3$-$C_8$ cycloalkyl, wherein each occurrence of R' is independently selected from the group consisting of —NH$_2$, —NH($C_1$-$C_6$ alkyl), —N($C_1$-$C_6$ alkyl)($C_1$-$C_6$ alkyl), —NHC(=O)O$^t$Bu, —N($C_1$-$C_6$ alkyl)C(=O)O$^t$Bu, or a 5- or 6-membered heterocyclic group, which is optionally N-linked; or X[2] is CR[6II], X[3] is CR[6III], and R[6II] and R[6III] combine to form a divalent group selected from the group consisting of —O(CHF)O—, —O(CF$_2$)O—, —O(CR[9]R[9])O—, —O(CH$_2$)(CH$_2$)O— and —O(CH$_2$)(CR[11]R[11])(CH$_2$)O—;

R[7] is selected from the group consisting of H, OH, halo, $C_1$-$C_6$ alkoxy, and optionally substituted $C_1$-$C_6$ alkyl;

R[8] is selected from the group consisting of H, optionally substituted $C_1$-$C_6$ alkyl, and optionally substituted $C_3$-$C_8$ cycloalkyl;

each occurrence of R[9] is independently selected from the group consisting of H and $C_1$-$C_6$ alkyl;

R[10] is selected from the group consisting of optionally substituted $C_1$-$C_6$ alkyl and optionally substituted phenyl; and, each occurrence of R[11] is independently selected from the group consisting of H, OH, $C_1$-$C_6$ alkyl, $C_1$-$C_6$ alkoxy, alkoxy-$C_1$-$C_6$ alkyl and alkoxy-$C_1$-$C_6$ alkoxy, wherein two R[11] groups bound to the same carbon atom are not simultaneously OH; or two R[11] groups combine with the carbon atom to which they are bound to form a moiety selected from the group consisting of C=O, C=CH$_2$ and oxetane-3,3-diyl.

The invention further provides a compound of formula (Ia), or a salt, solvate, stereoisomer, geometric isomer, tautomer, r or any mixtures thereof:

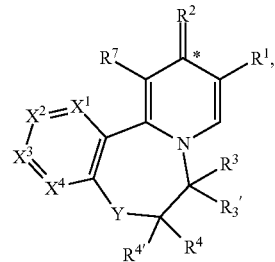

wherein:

Y is selected from the group consisting of CHR[5] and O;

each occurrence of R[5] is independently selected from the group consisting of H, optionally substituted $C_1$-$C_6$ alkyl, and optionally substituted $C_3$-$C_8$ cycloalkyl; R[1] is selected from the group consisting of H; halo; —OR[8]; —C(R[9])(R[9])OR[8]; —C(=O)R[8]; —C(=O)OR[8]; —C(=O)NH—OR[8]; —C(=O)NHNHR[8]; —C(=O)NHNHC(=O)R[8]; —C(=O)NHS(=O)$_2$R[8]; —CH$_2$C(=O)OR[8]; —CN; —NH$_2$; —N(R[8])C(=O)H; —N(R[8])C(=O)R[10]; —N(R[8])C(=O)OR[10]; —N(R[8])C(=O)NHR[8]; —NR[9]S(=O)$_2$R[10]; —P(=O)(OR[8])$_2$; —B(OR[8])$_2$; 2,5-dioxo-pyrrolidin-1-yl; 2H-tetrazol-5-yl; 3-hydroxy-isoxazol-5-yl; 1,4-dihydro-5-oxo-5H-tetrazol-1-yl; pyridin-2-yl optionally substituted with $C_1$-$C_6$ alkyl; pyrimidin-2-yl optionally substituted with $C_1$-$C_6$ alkyl; (pyridin-2-yl)methyl; (pyrimidin-2-yl)methyl; (pyrimidin-2-yl)amino; bis-(pyrimidin-2-yl)-amino; 5-R[8]-1,3,4,-thiadiazol-2-yl; 5-thioxo-4,5-dihydro-1H-1,2,4-triazol-3-yl; 1H-1,2,4-triazol-5-yl; 1,3,4-oxadiazol-2-yl; 1,2,4-oxadiazol-5-yl, and 3-R[10]-1,2,4-oxadiazol-5-yl;

R[2] is selected from the group consisting of =O, =NR[9], =N(OR[9]), and =N(NR[9]R[9]); or R[1] and R[2] combine to form =N—O—C(=O)— or =N—N(R[9])—C(=O)—, wherein the =N group is bound to the ring carbon atom marked "*";

R[3], R[3'], R[4] and R[4'] are each independently selected from the group consisting of H, alkyl-substituted oxetanyl, optionally substituted $C_1$-$C_6$ alkyl and optionally substituted $C_3$-$C_8$ cycloalkyl; or one pair selected from the group consisting of R[3]/R[3'], R[4]/R[4'], and R[3]/R[4] combine to form a divalent group selected from the group consisting of $C_1$-$C_6$ alkanediyl, —(CH$_2$)$_n$O(CH$_2$)$_n$—, —(CH$_2$)$_n$NR[9](CH$_2$)$_n$—, —(CH$_2$)$_n$S(CH$_2$)$_n$—, —(CH$_2$)$_n$S(=O)(CH$_2$)$_n$—, and —(CH$_2$)$_n$S(=O)$_2$(CH$_2$)$_n$—, wherein each occurrence of n is independently selected from the group consisting of 1 and 2 and each divalent group is optionally substituted with at least one $C_1$-$C_6$ alkyl or halo;

X[1] is selected from the group consisting of CR[6I] and N, X[2] is selected from the group consisting of CR[6II] and N, X[3] is selected from the group consisting of CR[6III] and N, X[4] is selected from the group consisting of CR[6IV] and N, or either X[3] and X[4], or X[1] and X[2], combine to form —S—; wherein 0-2 substituents selected from the group consisting of X[1], X[2], X[3] and X[4] are N, each of which, if present, is optionally alkylated with $C_1$-$C_6$ alkyl if the adjacent carbon atom in the ring is substituted with —OH;

R[6I], R[6II], R[6III] and R[6IV] are independently selected from the group consisting of H, halo, —CN, pyrrolidinyl, optionally substituted $C_1$-$C_6$ alkyl, optionally substituted $C_1$-$C_6$ alkenyl, optionally substituted $C_3$-$C_8$ cycloalkyl, optionally substituted heterocyclyl, —OR, $C_1$-$C_6$ haloalkoxy, —N(R)(R), —NO$_2$, —S(=O)$_2$N(R)(R), acyl, and $C_1$-$C_6$ alkoxycarbonyl, wherein each occurrence of R is independently selected from the group consisting of H, $C_1$-$C_6$ alkyl, R'-substituted $C_1$-$C_6$ alkyl, $C_1$-$C_6$ hydroxyalkyl, optionally substituted ($C_1$-$C_6$ alkoxy)-$C_1$-$C_6$ alkyl, and optionally substituted $C_3$-$C_8$ cycloalkyl, wherein each occurrence of R' is independently selected from the group consisting of —NH$_2$, —NH($C_1$-$C_6$ alkyl), —N($C_1$-$C_6$ alkyl)($C_1$-$C_6$ alkyl), —NHC(=O)O$^t$Bu, —N($C_1$-$C_6$ alkyl)C(=O)O$^t$Bu, or a 5- or 6-membered heterocyclic group, which is optionally N-linked; or $X^2$ is $CR^{6II}$, $X^3$ is $CR^{6III}$, and $R^{6II}$ and $R^{6III}$ combine to form a divalent group selected from the group consisting of —O(CHF)O—, —O(CF$_2$)O—, —O(CR$^9$R$^9$)O—, —O(CH$_2$)(CH$_2$)O— and —O(CH$_2$)(CR$^{11}$R$^{11}$)(CH$_2$)O—;

$R^7$ is selected from the group consisting of H, OH, halo, $C_1$-$C_6$ alkoxy, and optionally substituted $C_1$-$C_6$ alkyl;

$R^8$ is selected from the group consisting of H, optionally substituted $C_1$-$C_6$ alkyl, and optionally substituted $C_3$-$C_8$ cycloalkyl;

each occurrence of $R^9$ is independently selected from the group consisting of H and $C_1$-$C_6$ alkyl;

$R^{10}$ is selected from the group consisting of optionally substituted $C_1$-$C_6$ alkyl and optionally substituted phenyl; and, each occurrence of $R^{11}$ is independently selected from the group consisting of H, OH, $C_1$-$C_6$ alkyl, $C_1$-$C_6$ alkoxy, alkoxy-$C_1$-$C_6$ alkyl and alkoxy-$C_1$-$C_6$ alkoxy, wherein two $R^{11}$ groups bound to the same carbon atom are not simultaneously OH; or two $R^{11}$ groups combine with the carbon atom to which they are bound to form a moiety selected from the group consisting of C=O, C=CH$_2$ and oxetane-3,3-diyl.

The invention further provides a compound selected from the group consisting of formula (I), (II), and (III), or a salt, solvate, stereoisomer, geometric isomer, tautomer or any mixtures thereof.

In certain embodiments, for compounds of formulas (I), (II), and/or (III), $R^1$ is selected from the group consisting of H; halo; —OR; —C(R$^9$)(R$^9$)OR$^8$ (such as, for example, —CH$_2$OR$^8$, such as, for example, —CH$_2$OH); —C(=O)R$^8$; —C(=O)OR$^8$ (such as, for example, —C(=O)OH or —C(=O)O—$C_1$-$C_6$ alkyl); —C(=O)NH—OR$^8$ (such as, for example, —C(=O)NH—OH); —C(=O)NHNHR$^8$; —C(=O)NHNHC(=O)R$^8$; —C(=O)NHS(=O)$_2$R$^8$; —CH$_2$C(=O)OR$^8$; —CN; —NH$_2$; —N(R$^8$)C(=O)H; —N(R$^8$)C(=O)R$^{10}$; —N(R$^8$)C(=O)OR$^{10}$; —N(R$^8$)C(=O)NHR$^8$; —NR$^9$S(=O)$_2$R$^{10}$; —P(=O)(OR$^8$)$_2$; —B(OR$^8$)$_2$; 2,5-dioxo-pyrrolidin-1-yl; 2H-tetrazol-5-yl; 3-hydroxy-isoxazol-5-yl; 1,4-dihydro-5-oxo-5H-tetrazol-1-yl; pyridin-2-yl optionally substituted with $C_1$-$C_6$ alkyl; pyrimidin-2-yl optionally substituted with $C_1$-$C_6$ alkyl; (pyridin-2-yl)methyl; (pyrimidin-2-yl)methyl; (pyrimidin-2-yl)amino; bis-(pyrimidin-2-yl)-amino; 5-R$^8$-1,3,4-thiadiazol-2-yl; 5-thioxo-4,5-dihydro-1H-1,2,4-triazol-3-yl; 1H-1,2,4-triazol-5-yl; 1,3,4-oxadiazol-2-yl; 1,2,4-oxadiazol-5-yl; and 3-R$^{10}$-1,2,4-oxadiazol-5-yl.

In certain embodiments, for compounds of formulas (I), (II), and/or (III), $R^2$ is selected from the group consisting of =O, =NR$^9$, =N(OR$^9$), and =N(NR$^9$R$^9$); or $R^1$ and $R^2$ combine to form =N—O—C(=O)— or =N—N(R$^9$)—C(=O)—, wherein the =N group is bound to the ring carbon atom marked "*".

In certain embodiments, for compounds of formulas (I), (II), and/or (III), $X^1$ is selected from the group consisting of $CR^{6I}$ and N, $X^2$ is selected from the group consisting of $CR^{6II}$ and N, $X^3$ is selected from the group consisting of $CR^{6III}$ and N, $X^4$ is selected from the group consisting of $CR^{6IV}$ and N, or either $X^3$ and $X^4$, or $X^1$ and $X^2$, combine to form —S—; wherein 0-2 substituents selected from the group consisting of $X^1$, $X^2$, $X^3$ and $X^4$ are N, each of which, if present, is optionally alkylated with $C_1$-$C_6$ alkyl if the adjacent carbon atom in the ring is substituted with —OH.

In certain embodiments, for compounds of formulas (I), (II), and/or (III), $R^{6I}$, $R^{6II}$, $R^{6III}$ and $R^{6IV}$ are independently selected from the group consisting of H, halo, —CN, pyrrolidinyl, optionally substituted $C_1$-$C_6$ alkyl, optionally substituted $C_1$-$C_6$ alkenyl, optionally substituted $C_3$-$C_8$ cycloalkyl, optionally substituted heterocyclyl, —OR, $C_1$-$C_6$ haloalkoxy, —N(R)(R), —NO$_2$, —S(=O)$_2$N(R)(R), acyl, and $C_1$-$C_6$ alkoxycarbonyl, wherein each occurrence of R is independently selected from the group consisting of H, $C_1$-$C_6$ alkyl, R'-substituted $C_1$-$C_6$ alkyl, $C_1$-$C_6$ hydroxyalkyl, optionally substituted ($C_1$-$C_6$ alkoxy)-$C_1$-$C_6$ alkyl, and optionally substituted $C_3$-$C_8$ cycloalkyl, wherein each occurrence of R' is independently selected from the group consisting of —NH$_2$, —NH($C_1$-$C_6$ alkyl), —N($C_1$-$C_6$ alkyl)($C_1$-$C_6$ alkyl), —NHC(=O)O$^t$Bu, —N($C_1$-$C_6$ alkyl)C(=O)O$^t$Bu, or a 5- or 6-membered heterocyclic group, which is optionally N-linked; or $X^2$ is $CR^{6II}$, $X^3$ is $CR^{6III}$, and $R^{6II}$ and $R^{6III}$ combine to form a divalent group selected from the group consisting of —O(CHF)O—, —O(CF$_2$)O—, —O(CR$^9$R$^9$)O—, —O(CH$_2$)(CH$_2$)O— and —O(CH$_2$)(CR$^{11}$R$^{11}$)(CH$_2$)O—.

In certain embodiments, for compounds of formulas (I), (II), and/or (III), $R^7$ is selected from the group consisting of H, OH, halo, $C_1$-$C_6$ alkoxy, optionally substituted $C_1$-$C_6$ alkyl, and optionally substituted $C_3$-$C_8$ cycloalkyl.

In certain embodiments, for compounds of formulas (I), (II), and/or (III), $R^8$ is selected from the group consisting of H, optionally substituted $C_1$-$C_6$ alkyl, and optionally substituted $C_3$-$C_8$ cycloalkyl.

In certain embodiments, for compounds of formulas (I), (II), and/or (III), each occurrence of $R^9$ is independently selected from the group consisting of H and $C_1$-$C_6$ alkyl.

In certain embodiments, for compounds of formulas (I), (II), and/or (III), $R^{10}$ is selected from the group consisting of optionally substituted $C_1$-$C_6$ alkyl and optionally substituted phenyl.

In certain embodiments, for compounds of formulas (I), (II), and/or (III), each occurrence of $R^{11}$ is independently selected from the group consisting of H, OH, $C_1$-$C_6$ alkyl, $C_1$-$C_6$ alkoxy, alkoxy-$C_1$-$C_6$ alkyl and alkoxy-$C_1$-$C_6$ alkoxy, wherein two $R^{11}$ groups bound to the same carbon atom are not simultaneously OH; or two $R^{11}$ groups combine with the carbon atom to which they are bound to form a moiety selected from the group consisting of C=O, C=CH$_2$ and oxetane-3,3-diyl.

In certain embodiments, the compound of formula (I) is

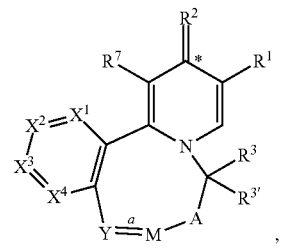

wherein:

bond a is a single or double bond, wherein: (i) if bond a is a single bond, then: Y is C(=O), and M is selected from the group consisting of C($R^4$)($R^{4'}$) and $NR^8$, or Y is selected from the group consisting of $CHR^5$, O, S, S(=O), S(=O)$_2$, and $NR^5$, and M is C($R^4$)($R^{4'}$), wherein, if Y is selected from the group consisting of $CHR^5$, O, and $NR^5$, $R^4$ and $R^{4'}$ optionally combine with each other to form =O; or Y is CH, M is C($R^4$)($R^{4'}$), $R^4$ is $CH_2$, and Y and $R^4$ form a single bond to generate cyclopropyl; (ii) if bond a is a double bond, then Y is selected from the group consisting of $CR^5$ and N, M is C($R^4$)($R^{4'}$), and $R^{4'}$ is absent;

$R^3$, $R^{3'}$, $R^4$ and $R^{4'}$ are each independently selected from the group consisting of H, alkyl-substituted oxetanyl, optionally substituted $C_1$-$C_6$ alkyl (e.g., optionally substituted with 1-3 groups independently selected from the group consisting of F, Cl, Br, I, OH, and OMe) and optionally substituted $C_3$-$C_8$ cycloalkyl (e.g., optionally substituted with 1-3 groups independently selected from the group consisting of F, Cl, Br, I, OH, and OMe); or one pair selected from the group consisting of $R^3$/$R^{3'}$, $R^4$/$R^{4'}$, and $R^3$/$R^4$ combine to form a divalent group selected from the group consisting of $C_1$-$C_6$ alkanediyl, —(CH$_2$)$_n$O(CH$_2$)$_n$—, —(CH$_2$)$_n$NR$^9$(CH$_2$)$_n$—, —(CH$_2$)$_n$S(CH$_2$)$_n$—, —(CH$_2$)$_n$S(=O)(CH$_2$)$_n$—, and —(CH$_2$)$_n$S(=O)$_2$(CH$_2$)$_n$—, wherein each occurrence of n is independently selected from the group consisting of 1 and 2 and each divalent group is optionally substituted with at least one $C_1$-$C_6$ alkyl or halo;

each occurrence of $R^5$ is independently selected from the group consisting of H, optionally substituted $C_1$-$C_6$ alkyl, and optionally substituted $C_3$-$C_8$ cycloalkyl.

In certain embodiments, the compound of formula (I) is a compound of formula (Ia).

In certain embodiments, the compound of formula (II) is

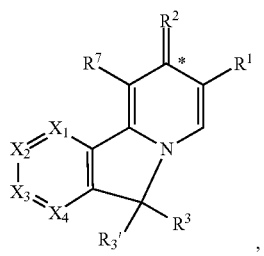

wherein: $R^3$ and $R^{3'}$ are each independently selected from the group consisting of H, alkyl-substituted oxetanyl, optionally substituted $C_1$-$C_6$ alkyl, and optionally substituted $C_3$-$C_8$ cycloalkyl; or $R^3$ and $R^{3'}$ combine to form a divalent group selected from the group consisting of $C_1$-$C_6$ alkanediyl, —(CH$_2$)$_n$O(CH$_2$)$_n$—, —(CH$_2$)$_n$NR$^9$(CH$_2$)$_n$—, —(CH$_2$)$_n$S(CH$_2$)$_n$—, —(CH$_2$)$_n$S(=O)(CH$_2$)$_n$—, and —(CH$_2$)$_n$S(=O)$_2$(CH$_2$)$_n$—, wherein each occurrence of n is independently selected from the group consisting of 1 and 2 and each divalent group is optionally substituted with at least one $C_1$-$C_6$ alkyl or halo.

In certain embodiments, the compound of formula (III) is:

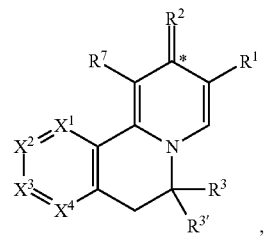

wherein: $R^3$ and $R^{3'}$ are each independently selected from the group consisting of H, alkyl-substituted oxetanyl, optionally substituted $C_1$-$C_6$ alkyl, and optionally substituted $C_3$-$C_8$ cycloalkyl; or $R^3$ and $R^{3'}$ combine to form a divalent group selected from the group consisting of $C_1$-$C_6$ alkanediyl, —(CH$_2$)$_n$O(CH$_2$)$_n$—, —(CH$_2$)$_n$NR$^9$(CH$_2$)$_n$—, —(CH$_2$)$_n$S(CH$_2$)$_n$—, —(CH$_2$)$_n$S(=O)(CH$_2$)$_n$—, and —(CH$_2$)$_n$S(=O)$_2$(CH$_2$)$_n$—, wherein each occurrence of n is independently selected from the group consisting of 1 and 2 and each divalent group is optionally substituted with at least one $C_1$-$C_6$ alkyl or halo.

In certain embodiments, the compound of formula (III) is a compound of formula (IIIa)

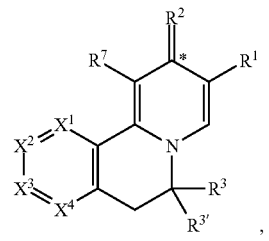

wherein 1-2 substituents selected from the group consisting of $X^1$, $X^2$, $X^3$ and $X^4$ are N. In certain embodiments, the compound of formula (III) is a compound of formula (IIIb)

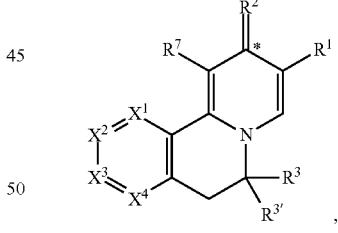

wherein at least one applies: $R^1$ is not —C(=O)OR$^8$, $R^2$ is not =O. In certain embodiments, the compound of formula (III) is a compound of formula (IIIc)

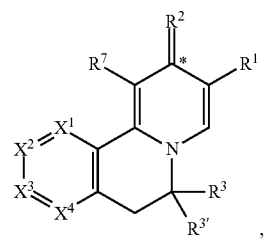

wherein X³ and X⁴, or X¹ and X², combine to form —S—.
In certain embodiments, the compound of formula (III) is a compound of formula (IIId)

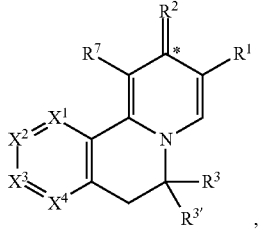

wherein X² is CR⁶ᴵᴵ, X³ is CR⁶ᴵᴵᴵ, and R⁶ᴵᴵ and R⁶ᴵᴵᴵ combine to form a divalent group selected from the group consisting of —O(CHF)O—, —O(CF₂)O—, —O(CR⁹R⁹)O—, —O(CH₂)(CH₂)O— and —O(CH₂)(CR¹¹R¹¹)(CH₂)O—. In certain embodiments, the compound of formula (III) is a compound of formula (IIIe)

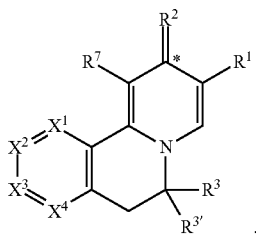

wherein $R^3$ and $R^{3'}$ are each independently selected from the group consisting of H, alkyl-substituted oxetanyl, optionally substituted $C_1$-$C_6$ alkyl, and optionally substituted $C_3$-$C_8$ cycloalkyl, or $R^3$ and $R^{3'}$ combine to form a divalent group selected from the group consisting of $C_1$-$C_6$ alkanediyl, —(CH₂)ₙO(CH₂)ₙ—, —(CH₂)ₙNR⁹(CH₂)ₙ—, —(CH₂)ₙS(CH₂)ₙ—, —(CH₂)ₙS(=O)(CH₂)ₙ—, and —(CH₂)ₙS(=O)₂(CH₂)ₙ—, wherein each occurrence of n is independently selected from the group consisting of 1 and 2, and each divalent group is optionally substituted with at least one $C_1$-$C_6$ alkyl or halo.

In certain embodiments, each occurrence of alkyl or cycloalkyl is independently optionally substituted with at least one substituent selected from the group consisting of $C_1$-$C_6$ alkyl, halo, —OR", phenyl and —N(R")(R"), wherein each occurrence of R" is independently H, $C_1$-$C_6$ alkyl or $C_3$-$C_8$ cycloalkyl.

In certain embodiments, each occurrence of aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR, —N(R")(R"), —NO₂, —S(=O)₂N(R")(R"), acyl, and $C_1$-$C_6$ alkoxycarbonyl, wherein each occurrence of R" is independently H, $C_1$-$C_6$ alkyl or $C_3$-$C_8$ cycloalkyl.

In certain embodiments, the compound of formula (III) or (IIIa) is selected from the group consisting of:

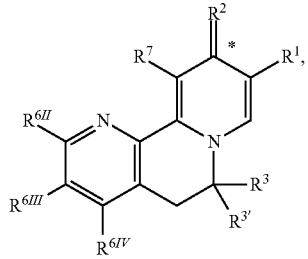
(IIIg)

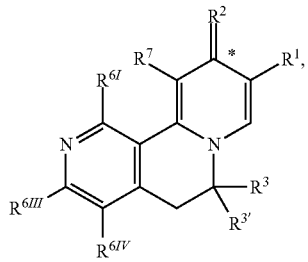
(IIIh)

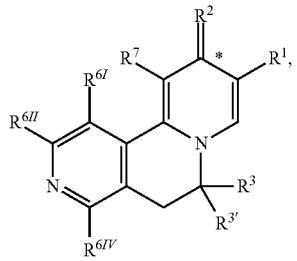
(IIIi)

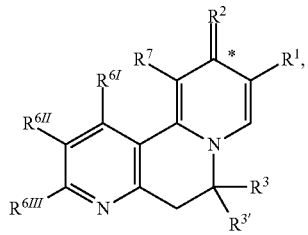
(IIIj)

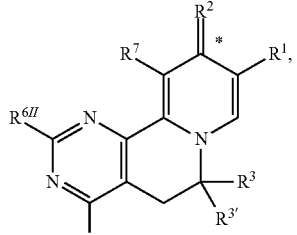
(IIIk)

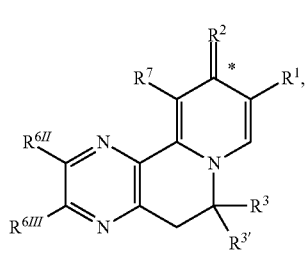
(IIIl)

(IIIm)
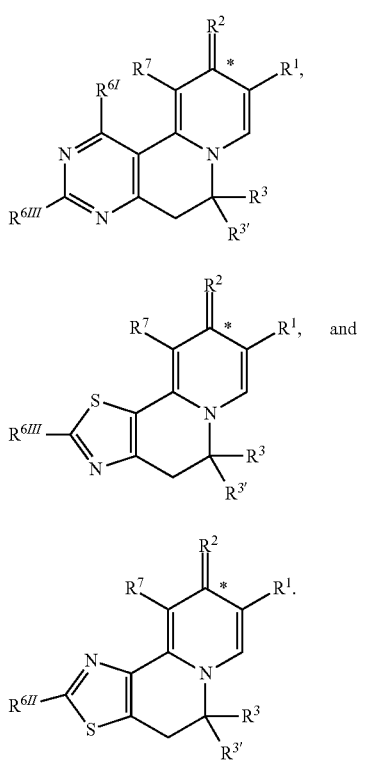
In certain embodiments, the compound of formula (I) or (Ia) is selected from the group consisting of:
(Ij)
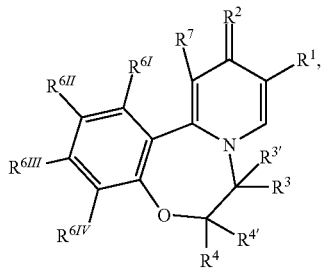
(Ik)
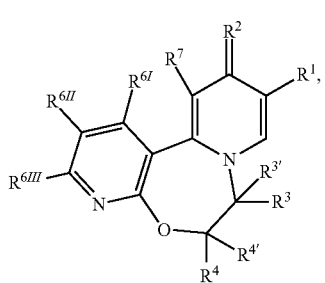
(Il)
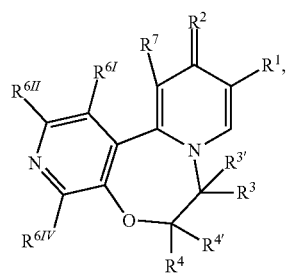
(Im)
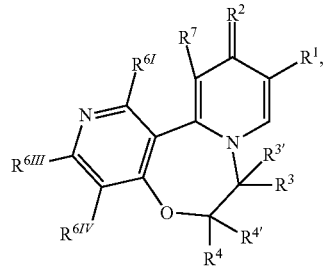
(In)
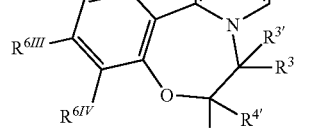
(Io)
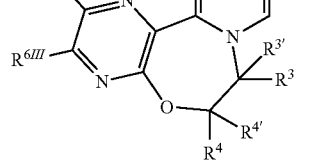
(Ip)
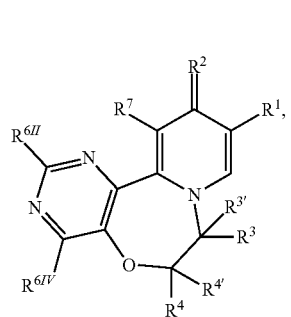

-continued
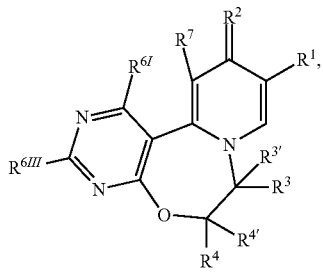
(Iq)
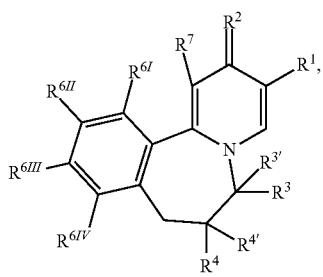
(Ir)
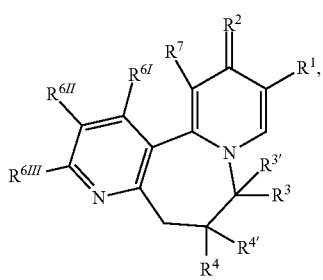
(Is)
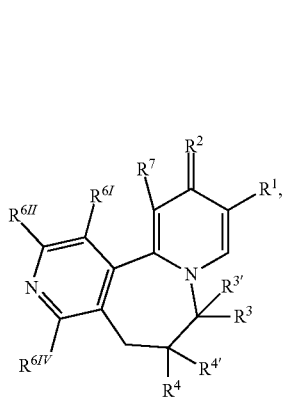
(It)
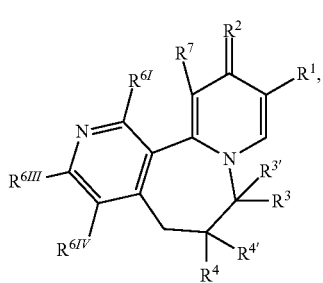
(Iu)
-continued
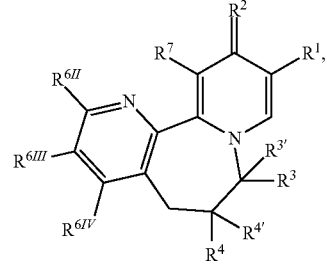
(Iv)
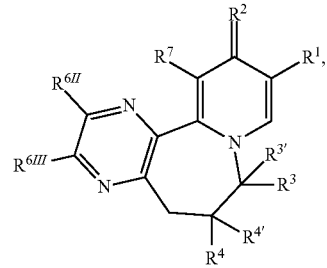
(Iw)
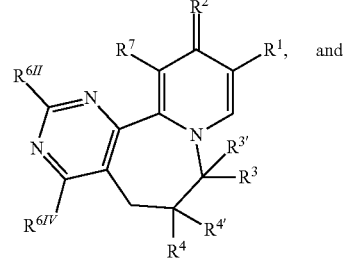
(Ix)
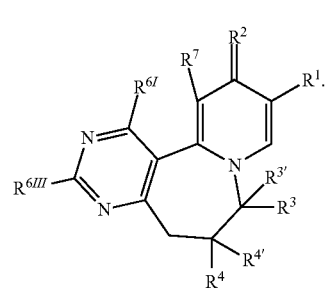
(Iy)
In certain embodiments, the compound of formula (I) is selected from the group consisting of:
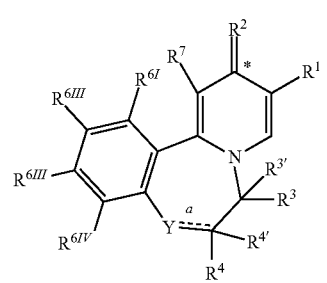
(Ib)

-continued
(Ic)
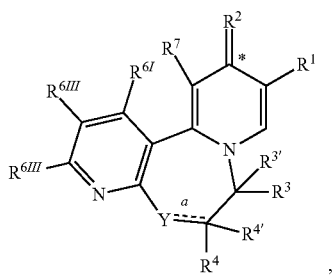
(Id)
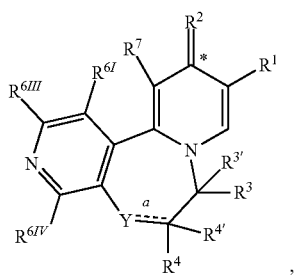
(Ie)
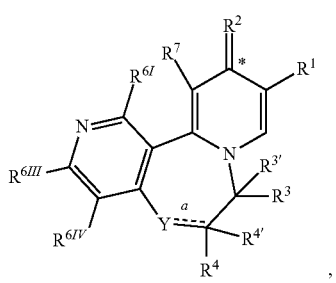
(If)
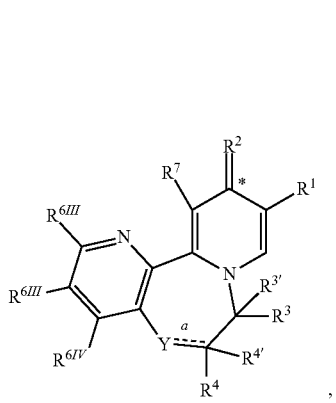
(Ig)
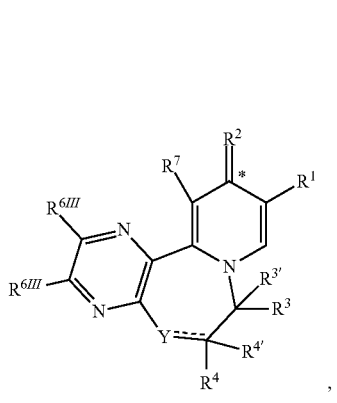
(Ih)
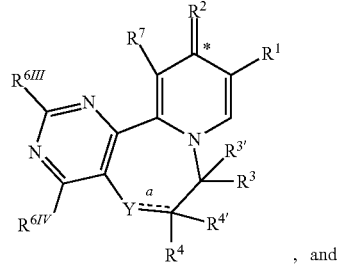
, and
(Ii)
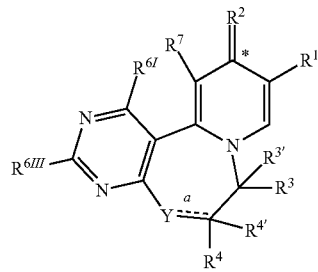
.
In certain embodiments, the compound of formula (II) is selected from the group consisting of:
(IIb)
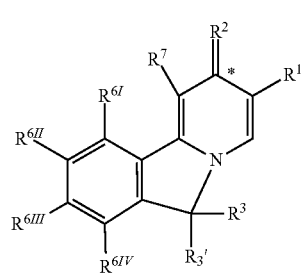
,
(IIc)
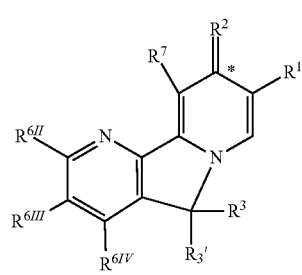
,
(IId)
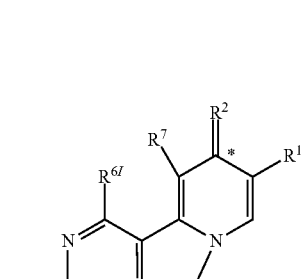
,

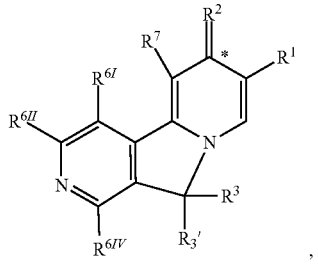 (IIe)
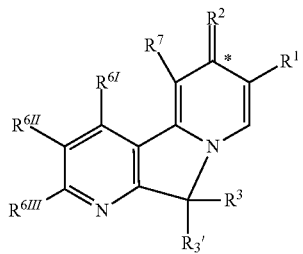 (IIf)
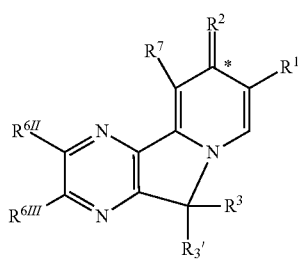 (IIg)
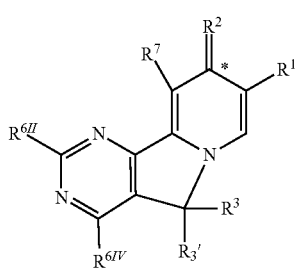 (IIh)
, and
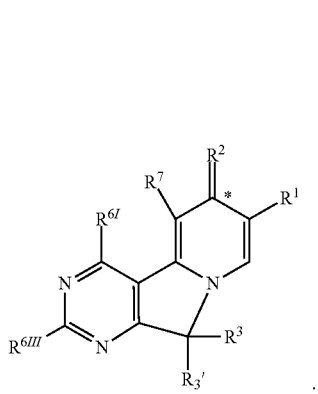 (IIi)
.
In certain embodiments, the compound of formula (III) is selected from the group consisting of:
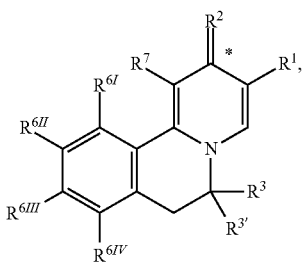 (IIIf)
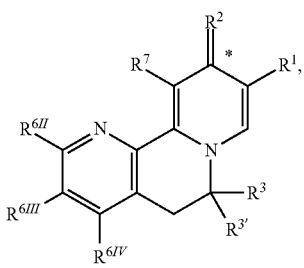 (IIIg)
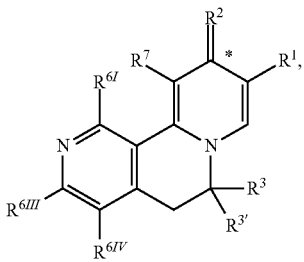 (IIIh)
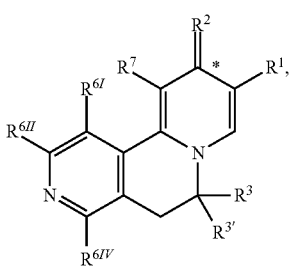 (IIIi)
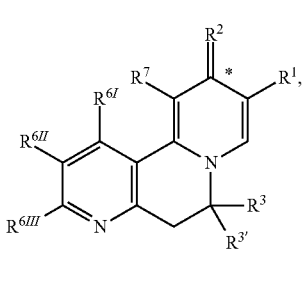 (IIIj)
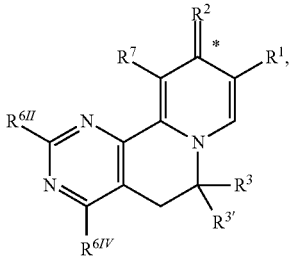 (IIIk)

-continued

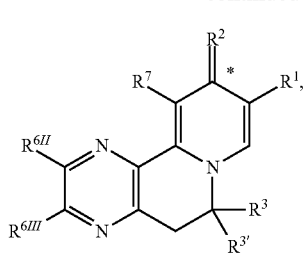
(IIIl)

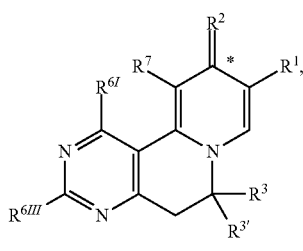
(IIIm)

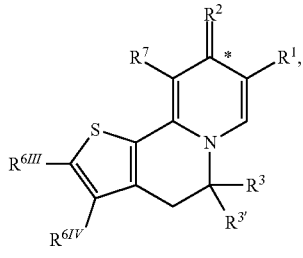
(IIIn)

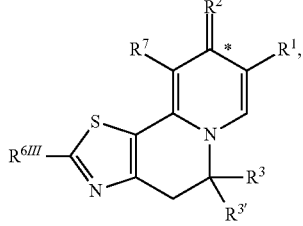
(IIIo)

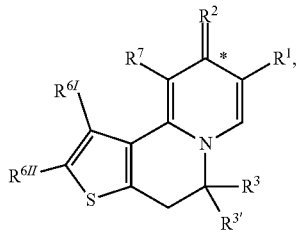
(IIIp)

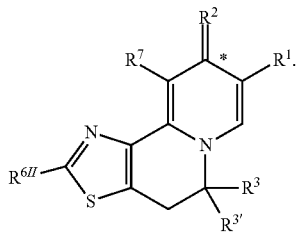
(IIIq)

In certain embodiments, $R^1$ is selected from the group consisting of optionally substituted triazolyl, optionally substituted oxadiazolyl, —C(=O)OH, —C(=O)OMe, —C(=O)OEt, —C(=O)O-nPr, —C(=O)O-iPr, —C(=O)O-cyclopentyl, and —C(=O)O-cyclohexyl.

In certain embodiments, $R^2$ is selected from the group consisting of O, N(OH), N(Me), N(OMe), and N(NH$_2$).

In certain embodiments, $R^3$ and $R^{3'}$ are each independently selected from the group consisting of H, methyl, ethyl, n-propyl, isopropyl, n-butyl, isobutyl, sec-butyl, t-butyl, hydroxymethyl, 2-hydroxy-ethyl, 2-methoxy-ethyl, methoxymethyl, and 2-methyl-1-methoxy-prop-2-yl. In certain embodiments, $R^3$ and $R^{3'}$, and $R^4$ and $R^{4'}$, are each independently selected from the group consisting of H, methyl, ethyl, n-propyl, isopropyl, n-butyl, isobutyl, sec-butyl, t-butyl, hydroxymethyl, 2-hydroxy-ethyl, 2-methoxy-ethyl, methoxymethyl, and 2-methyl-1-methoxy-prop-2-yl. In certain embodiments, at least one applies: $R^3$ is H, $R^{3'}$ is isopropyl; $R^3$ is H, $R^{3'}$ is tert-butyl; $R^3$ is methyl, $R^{3'}$ is isopropyl; $R^3$ is methyl, $R^{3'}$ is tert-butyl; $R^3$ is methyl, $R^{3'}$ is methyl; $R^3$ is methyl, $R^{3'}$ is ethyl; and $R^3$ is ethyl, $R^{3'}$ is ethyl. In certain embodiments, $R^3$ and $R^{3'}$ are not H. In certain embodiments, $R^4$ and $R^{4'}$ are H. In certain embodiments, $R^4$ and $R^{4'}$ are not H. In certain embodiments, $R^3/R^{3'}$ combine to form a divalent group selected from the group consisting of $C_1$-$C_6$ alkanediyl, —(CH$_2$)$_n$O(CH$_2$)$_n$—, —(CH$_2$)$_n$NR$^9$(CH$_2$)$_n$—, —(CH$_2$)$_n$S(CH$_2$)$_n$—, —(CH$_2$)$_n$S(=O)(CH$_2$)$_n$—, and —(CH$_2$)$_n$S(=O)$_2$(CH$_2$)$_n$—, wherein each occurrence of n is independently selected from the group consisting of 1 and 2 and wherein each divalent group is optionally substituted with at least one $C_1$-$C_6$ alkyl or halo.

In certain embodiments, when present, $R^{6I}$, $R^{6II}$, $R^{6III}$ and $R^{6IV}$ are independently selected from the group consisting of H, F, Cl, Br, I, CN, amino, methylamino, dimethylamino, methoxyethylamino, pyrrolidinyl, methoxy, ethoxy, n-propoxy, isopropoxyl, n-butoxy, sec-butoxy, isobutoxy, t-butoxy, 2-methoxy-ethoxy, 2-hydroxy-ethoxy, 3-methoxy-prop-1-yl, 3-hydroxy-prop-1-yl, 3-methoxy-prop-1-oxy, 3-hydroxy-prop-1-oxy, 4-methoxy-but-1-yl, 4-hydroxy-but-1-yl, 4-methoxy-but-1-oxy, 4-hydroxy-but-1-oxy, 2-hydroxy-ethoxy, 3-hydroxy-prop-1-yl, 4-hydroxy-but-1-yl, 3-hydroxy-2,2-dimethyl-prop-1-oxy, cyclopropylmethoxy, 2,2,2-trifluoroethoxy, 2-(2-haloethoxy)-ethoxy, 2-(N-morpholino)-ethyl, 2-(N-morpholino)-ethoxy, 3-(N-morpholino)-prop-1-yl, 3-(N-morpholino)-prop-1-oxy, 4-(N-morpholino)-but-1-yl, 4-(N-morpholino)-butyl-oxy, 2-amino-ethyl, 2-(NHC(=O)O$^t$Bu)-ethyl, 2-amino-ethoxy, 2-(NHC(=O)O$^t$Bu)-ethoxy, 3-amino-prop-1-yl, 3-(NHC(=O)O$^t$Bu)-prop-1-yl, 3-amino-prop-1-oxy, 3-(NHC(=O)O$^t$Bu)-prop-1-oxy, 4-amino-but-1-yl, 4-(NHC(=O)O$^t$Bu)-but-1-yl, 4-amino-but-1-oxy, and 4-(NHC(=O)O$^t$Bu)-but-1-oxy.

In certain embodiments, $X^1$ is CH or N. In certain embodiments, $X^4$ is CH. In certain embodiments, $X^2$ is CR$^{6II}$, $R^{6II}$ is not H, $X^3$ is CR$^{6III}$, and $R^{6III}$ is not H. In certain embodiments, $X^1$ is CH, $X^2$ is CR$^{6II}$, $X^3$ is CR$^{6III}$, and $X^4$ is CH, and one of the following applies: $R^{6II}$ is methoxy, $R^{6III}$ is 3-methoxy-propoxy; $R^{6II}$ is chloro, $R^{6III}$ is 3-methoxy-propoxy; $R^{6II}$ is isopropyl, $R^{6III}$ is 3-methoxy-propoxy; $R^{6II}$ is methoxy, $R^{6III}$ is methoxy; $R^{6II}$ is chloro, $R^{6III}$ is methoxy; and $R^{6II}$ is cyclopropyl, $R^{6III}$ is methoxy. In certain embodiments, $X^1$ is N, $X^2$ is CR$^{6II}$, $X^3$ is CR$^{6III}$, and $X^4$ is CH, and one of the following applies: $R^{6II}$ is methoxy, $R^{6III}$ is 3-methoxy-propoxy; $R^{6II}$ is chloro, $R^{6III}$ is 3-methoxy-propoxy; $R^{6II}$ is cyclopropyl, $R^{6III}$ is 3-methoxy-propoxy; $R^{6II}$ is methoxy, $R^{6III}$ is methoxy; $R^{6II}$ is chloro, $R^{6III}$ is methoxy; and $R^{6II}$ is cyclopropyl, $R^{6III}$ is methoxy. In certain embodiments, $X^2$ is CR$^{6II}$, $X^3$ is CR$^{6III}$, and $R^{6II}$ and $R^{6III}$ combine to form a divalent group selected from the group consisting of —O(CHF)O—, —O(CF$_2$)O—, —O(CR$^9$R$^9$)O—, —O(CH$_2$)(CH$_2$)O—, and —O(CH$_2$)(CR$^{11}$R$^{11}$)(CH$_2$)O—. In certain embodiments, $R^7$ is selected from the group consisting of H, methyl, ethyl, and fluoro.

In certain embodiments, the pharmaceutical compositions further comprise at least one additional agent useful for treating hepatitis virus infection. In other embodiments, the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; and immunostimulator. In yet other embodiments, the oligomeric nucleotide comprises one or more siRNAs. In yet other embodiments, the one or more siRNAs comprise a siRNA comprising a sense sequence of nucleotide sequence of SEQ ID NO: 1 and an antisense sequence of nucleotide sequence of SEQ ID NO:2, a siRNA comprising a sense sequence of nucleotide sequence of SEQ ID NO:3 and an antisense sequence of nucleotide sequence of SEQ ID NO:4, and a siRNA comprising a sense sequence of nucleotide sequence of SEQ ID NO:5 and an antisense sequence of nucleotide sequence of SEQ ID NO:6. In yet other embodiments, the one or more siRNAs comprise a siRNA comprising a sense sequence of nucleotide sequence of SEQ ID NO:7 and an antisense sequence of nucleotide sequence of SEQ ID NO:8, a siRNA comprising a sense sequence of nucleotide sequence of SEQ ID NO:9 and an antisense sequence of nucleotide sequence of SEQ ID NO: 10, and a siRNA comprising a sense sequence of nucleotide sequence of SEQ ID NO: 11 and an antisense sequence of nucleotide sequence of SEQ ID NO: 12. In yet other embodiments, the one or more siRNAs are formulated in a lipid nanoparticle.

In certain embodiments, the method comprises administering to the subject in need thereof a therapeutically effective amount of at least one compound of the invention or at least one pharmaceutical composition of the invention. In other embodiments, the at least one compound is administered to the subject in a pharmaceutically acceptable composition. In yet other embodiments, the subject is further administered at least one additional agent useful for treating the hepatitis virus infection. In yet other embodiments, the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; and immunostimulator. In yet other embodiments, the oligomeric nucleotide comprises one or more siRNAs. In other embodiments, the one or more siRNAs comprise a siRNA comprising a sense sequence of nucleotide sequence of SEQ ID NO: 1 and an antisense sequence of nucleotide sequence of SEQ ID NO:2, a siRNA comprising a sense sequence of nucleotide sequence of SEQ ID NO:3 and an antisense sequence of nucleotide sequence of SEQ ID NO:4, and a siRNA comprising a sense sequence of nucleotide sequence of SEQ ID NO:5 and an antisense sequence of nucleotide sequence of SEQ ID NO:6. In yet other embodiments, the one or more siRNAs comprise a siRNA comprising a sense sequence of nucleotide sequence of SEQ ID NO:7 and an antisense sequence of nucleotide sequence of SEQ ID NO:8, a siRNA comprising a sense sequence of nucleotide sequence of SEQ ID NO:9 and an antisense sequence of nucleotide sequence of SEQ ID NO: 10, and a siRNA comprising a sense sequence of nucleotide sequence of SEQ ID NO: 11 and an antisense sequence of nucleotide sequence of SEQ ID NO: 12. In yet other embodiments, the one or more siRNAs are formulated in a lipid nanoparticle.

In certain embodiments, the subject is co-administered the at least one compound and the at least one additional agent. In other embodiments, the at least one compound and the at least one additional agent are coformulated. In yet other embodiments, the virus comprises hepatitis B virus (HBV).

In certain embodiments, the compound is at least one selected from the group consisting of Examples 20-26, 86-88, 108-118, 142-143, 152-167, and 171, or a salt, solvate, stereoisomer, tautomer, geometric isomer, or any mixtures thereof. In certain embodiments, the compound is at least one selected from the group consisting of Examples 1-14, 15-19, 27-83, 104, 134-141, 150-151, and 168-170, or a salt, solvate, stereoisomer, tautomer, geometric isomer, or any mixtures thereof. In certain embodiments, the compound is at least one selected from the group consisting of Examples 1-88, 90-173, or a salt, solvate, stereoisomer, tautomer, geometric isomer, or any mixtures thereof. In certain embodiments, the compound is Example 172 or 173, or a salt, solvate, stereoisomer, tautomer, geometric isomer, or any mixtures thereof. In certain embodiments, the compound is Example 89, or a salt, solvate, stereoisomer, tautomer, geometric isomer, or any mixtures thereof. In certain embodiments, the compound is any of the Examples in Tables 1-3.

DETAILED DESCRIPTION OF THE INVENTION

The invention relates, in certain aspects, to the discovery of certain substituted tricyclic compounds that are useful to treat and/or prevent HBV infection and related conditions in a subject. In certain embodiments, the compounds inhibit and/or reduce HBsAg secretion in a HBV-infected subject. In other embodiments, the compounds reduce or minimize levels of at least one selected from the group consisting of HBsAg, HBeAg, hepatitis B core protein, and pg RNA, in a HBV-infected subject.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science and organic chemistry are those well-known and commonly employed in the art. It should be understood that the order of steps or order for performing certain actions is immaterial, so long as the present teachings remain operable. Moreover, two or more steps or actions can be conducted simultaneously or not.

The following non-limiting abbreviations are used herein: cccDNA, covalently closed circular DNA; HBc, hepatitis B capsid; HBV, hepatitis B virus; HBeAg, hepatitis B e-antigen; HBsAg, hepatitis B virus surface antigen; pg RNA, pregenomic RNA.

As used herein, the articles "a" and "an" refer to one or to more than one (i.e., to at least one) of the grammatical object of the article. By way of example, "an element" means one element or more than one element.

As used herein, the term "alkenyl," employed alone or in combination with other terms, means, unless otherwise stated, a stable monounsaturated or diunsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkoxy" employed alone or in combination with other terms means, unless otherwise stated, an alkyl group having the designated number of carbon atoms, as defined elsewhere herein, connected to the rest of the molecule via an oxygen atom, such as, for example, methoxy, ethoxy, 1-propoxy, 2-propoxy (or isopropoxy) and the higher homologs and isomers. A specific example is ($C_1$-$C_3$)alkoxy, such as, but not limited to, ethoxy and methoxy.

As used herein, the term "alkyl" by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. A specific embodiment is ($C_1$-$C_6$)alkyl, such as, but not limited to, ethyl, methyl, isopropyl, isobutyl, n-pentyl, n-hexyl and cyclopropylmethyl.

As used herein, the term "alkynyl" employed alone or in combination with other terms means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —CH$_2$—C≡CH. The term "homopropargylic" refers to a group exemplified by —CH$_2$CH$_2$—C≡CH.

As used herein, the term "aromatic" refers to a carbocycle or heterocycle with one or more polyunsaturated rings and having aromatic character, i.e., having (4n+2) delocalized π (pi) electrons, where 'n' is an integer.

As used herein, the term "aryl" employed alone or in combination with other terms means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl and naphthyl. Aryl groups also include, for example, phenyl or naphthyl rings fused with one or more saturated or partially saturated carbon rings (e.g., bicyclo[4.2.0]octa-1,3,5-trienyl, or indanyl), which can be substituted at one or more carbon atoms of the aromatic and/or saturated or partially saturated rings.

As used herein, the term "aryl-($C_1$-$C_6$)alkyl" refers to a functional group wherein a one to six carbon alkanediyl chain is attached to an aryl group, e.g., —CH$_2$CH$_2$-phenyl or —CH$_2$-phenyl (or benzyl). Specific examples are aryl-CH$_2$— and aryl-CH(CH$_3$)—. The term "substituted aryl-($C_1$-$C_6$)alkyl" refers to an aryl-($C_1$-$C_6$)alkyl functional group in which the aryl group is substituted. A specific example is substituted aryl(CH$_2$)—. Similarly, the term "heteroaryl-($C_1$-$C_6$)alkyl" refers to a functional group wherein a one to three carbon alkanediyl chain is attached to a heteroaryl group, e.g., —CH$_2$CH$_2$-pyridyl. A specific example is heteroaryl-(CH$_2$)—. The term "substituted heteroaryl-($C_1$-$C_6$)alkyl" refers to a heteroaryl-($C_1$-$C_6$)alkyl functional group in which the heteroaryl group is substituted. A specific example is substituted heteroaryl-(CH$_2$)—.

In one aspect, the terms "co-administered" and "co-administration" as relating to a subject refer to administering to the subject a compound and/or composition of the invention along with a compound and/or composition that may also treat or prevent a disease or disorder contemplated herein. In certain embodiments, the co-administered compounds and/or compositions are administered separately, or in any kind of combination as part of a single therapeutic approach. The co-administered compound and/or composition may be formulated in any kind of combinations as mixtures of solids and liquids under a variety of solid, gel, and liquid formulations, and as a solution.

As used herein, the term "cycloalkyl" by itself or as part of another substituent refers to, unless otherwise stated, a cyclic chain hydrocarbon having the number of carbon atoms designated (i.e., $C_3$-$C_6$ refers to a cyclic group comprising a ring group consisting of three to six carbon atoms) and includes straight, branched chain or cyclic substituent groups. Examples of ($C_3$-$C_6$)cycloalkyl groups are cyclopropyl, cyclobutyl, cyclopentyl and cyclohexyl. Cycloalkyl rings can be optionally substituted. Non-limiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "halide" refers to a halogen atom bearing a negative charge. The halide anions are fluoride (F$^-$), chloride (Cl$^-$), bromide (Br$^-$), and iodide (I$^-$).

As used herein, the term "halo" or "halogen" alone or as part of another substituent refers to, unless otherwise stated, a fluorine, chlorine, bromine, or iodine atom.

As used herein, the term "heteroalkenyl" by itself or in combination with another term refers to, unless otherwise stated, a stable straight or branched chain monounsaturated or diunsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH═CH—O—CH$_3$, —CH═CH—CH$_2$—OH, —CH$_2$—CH═N—OCH$_3$, —CH═CH—N(CH$_3$)—CH$_3$, and —CH$_2$—CH═CH—CH$_2$—SH.

As used herein, the term "heteroalkyl" by itself or in combination with another term refers to, unless otherwise stated, a stable straight or branched chain alkyl group consisting of the stated number of carbon atoms and one or two heteroatoms selected from the group consisting of 0, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —OCH$_2$CH$_2$CH$_3$, —CH$_2$CH$_2$CH$_2$OH, —CH$_2$CH$_2$NHCH$_3$, —CH$_2$SCH$_2$CH$_3$, and —CH$_2$CH$_2$S(=O)CH$_3$. Up to two heteroatoms may be consecutive, such as, for example, —CH$_2$NH—OCH$_3$, or —CH$_2$CH$_2$SSCH$_3$.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

As used herein, the term "heterocycle" or "heterocyclyl" or "heterocyclic" by itself or as part of another substituent refers to, unless otherwise stated, an unsubstituted or substituted, stable, mono- or multi-cyclic heterocyclic ring system that comprises carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "pharmaceutical composition" or "composition" refers to a mixture of at least one compound useful within the invention with a pharmaceutically acceptable carrier. The pharmaceutical composition facilitates administration of the compound to a subject.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body.

Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and/or bases, including inorganic acids, inorganic bases, organic acids, inorganic bases, solvates (including hydrates) and clathrates thereof.

As used herein, a "pharmaceutically effective amount," "therapeutically effective amount" or "effective amount" of a compound is that amount of compound that is sufficient to provide a beneficial effect to the subject to which the compound is administered.

The term "prevent," "preventing" or "prevention" as used herein means avoiding or delaying the onset of symptoms associated with a disease or condition in a subject that has not developed such symptoms at the time the administering of an agent or compound commences.

Disease, condition and disorder are used interchangeably herein.

By the term "specifically bind" or "specifically binds" as used herein is meant that a first molecule preferentially binds to a second molecule (e.g., a particular receptor or enzyme), but does not necessarily bind only to that second molecule.

As used herein, the terms "subject" and "individual" and "patient" can be used interchangeably and may refer to a human or non-human mammal or a bird. Non-human mammals include, for example, livestock and pets, such as ovine, bovine, porcine, canine, feline and murine mammals. In certain embodiments, the subject is human.

As used herein, the term "substituted" refers to that an atom or group of atoms has replaced hydrogen as the substituent attached to another group.

As used herein, the term "substituted alkyl," "substituted cycloalkyl," "substituted alkenyl" or "substituted alkynyl" refers to alkyl, cycloalkyl, alkenyl or alkynyl, as defined elsewhere herein, substituted by one, two or three substituents independently selected from the group consisting of halogen, —OH, alkoxy, tetrahydro-2-H-pyranyl, —NH$_2$, —NH(C$_1$-C$_6$ alkyl), —N(C$_1$-C$_6$ alkyl)$_2$, 1-methyl-imidazol-2-yl, pyridin-2-yl, pyridin-3-yl, pyridin-4-yl, —C(=O)OH, —C(=O)O(C$_1$-C$_6$)alkyl, trifluoromethyl, —C=N, —C(=O)NH$_2$, —C(=O)NH(C$_1$-C$_6$)alkyl, —C(=O)N((C$_1$-C$_6$)alkyl)$_2$, —SO$_2$NH$_2$, —SO$_2$NH(C$_1$-C$_6$ alkyl), —SO$_2$N(C$_1$-C$_6$ alkyl)$_2$, —C(=NH)NH$_2$, and —NO$_2$, in certain embodiments containing one or two substituents independently selected from halogen, —OH, alkoxy, —NH$_2$, trifluoromethyl, —N(CH$_3$)$_2$, and —C(=O)OH, in certain embodiments independently selected from halogen, alkoxy and —OH. Examples of substituted alkyls include, but are not limited to, 2,2-difluoropropyl, 2-carboxycyclopentyl and 3-chloropropyl.

For aryl, aryl-(C$_1$-C$_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet another embodiments, the substituents vary in number between one and two. In yet other embodiments, the substituents are independently selected from the group consisting of C$_1$-C$_6$ alkyl, —OH, C$_1$-C$_6$ alkoxy, halo, amino, acetamido and nitro. As used herein, where a substituent is an alkyl or alkoxy group, the carbon chain may be branched, straight or cyclic.

Unless otherwise noted, when two substituents are taken together to form a ring having a specified number of ring atoms (e.g., R$^2$ and R$^3$ taken together with the nitrogen to which they are attached to form a ring having from 3 to 7 ring members), the ring can have carbon atoms and optionally one or more (e.g., 1 to 3) additional heteroatoms independently selected from nitrogen, oxygen, or sulfur. The ring can be saturated or partially saturated, and can be optionally substituted.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given elsewhere herein for "alkyl" and "aryl" respectively.

In certain embodiments, substituents of compounds are disclosed in groups or in ranges.

It is specifically intended that the description include each and every individual subcombination of the members of such groups and ranges. For example, the term "C$_{1-6}$ alkyl" is specifically intended to individually disclose C$_1$, C$_2$, C$_3$, C$_4$, C$_5$, C$_6$, C$_1$-C$_6$, C$_1$-C$_5$, C$_1$-C$_4$, C$_1$-C$_3$, C$_1$- C$_2$, C$_2$-C$_6$, C$_2$-C$_5$, C$_2$-C$_4$, C$_2$-C$_3$, C$_3$-C$_6$, C$_3$-C$_8$, C$_3$-C$_4$, C$_4$-C$_6$, C$_4$-C$_5$, and C$_5$- C$_6$ alkyl.

The terms "treat," "treating" and "treatment," as used herein, means reducing the frequency or severity with which symptoms of a disease or condition are experienced by a subject by virtue of administering an agent or compound to the subject.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range.

For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range.

Compounds

The invention includes certain compound recited herein, as well as any salt, solvate, geometric isomer (such as, in a non-limiting example, any geometric isomer and any mixtures thereof, such as, in a non-limiting example, mixtures in any proportion of any geometric isomers thereof), stereoisomer (such as, in a non-limiting example, any enantiomer or diastereoisomer, and any mixtures thereof, such as, in a non-limiting example, mixtures in any proportion of any enantiomers and/or diastereoisomers thereof), tautomer (such as, in a non-limiting example, any tautomer and any mixtures thereof, such as, in a non-limiting example, mixtures in any proportion of any tautomers thereof), and any mixtures thereof.

The invention includes a compound of formula (I), or a salt, solvate, geometric isomer, stereoisomer, tautomer, and any mixtures thereof:

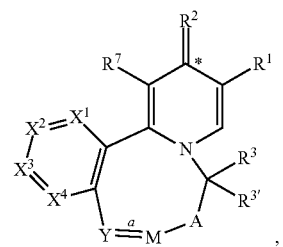

wherein:

A is selected from the group consisting of null (i.e., the two atoms bonded to A are directly bonded through a chemical bond) and CR$^9$R$^9$;

R$^1$ is selected from the group consisting of H; halo; —OR$^8$; —C(R$^9$)(R$^9$)OR$^8$ (such as, for example, —CH$_2$OR$^8$, such as, for example, —CH$_2$OH); —C(=O)R$^8$; —C(=O)OR$^8$ (such as, for example, —C(=O)OH or —C(=O)O—C$_1$-C$_6$ alkyl); —C(=O)NH—OR$^8$ (such as, for example, —C(=O)NH—OH); —C(=O)NHNHR$^8$; —C(=O)

NHNHC(=O)R⁸; —C(=O)NHS(=O)₂R⁸; —CH₂C(=O)OR⁸; —CN; —NH₂; —N(R⁸)C(=O)H; —N(R⁸)C(=O)R¹⁰; —N(R⁸)C(=O)OR¹⁰; —N(R⁸)C(=O)NHR⁸; —NR⁹S(=O)₂R¹⁰; —P(=O)(OR⁸)₂; —B(OR⁸)₂; 2,5-dioxo-pyrrolidin-1-yl; 2H-tetrazol-5-yl; 3-hydroxy-isoxazol-5-yl; 1,4-dihydro-5-oxo-5H-tetrazol-1-yl; pyridin-2-yl optionally substituted with $C_1$-$C_6$ alkyl; pyrimidin-2-yl optionally substituted with $C_1$-$C_6$ alkyl; (pyridin-2-yl)methyl; (pyrimidin-2-yl)methyl; (pyrimidin-2-yl)amino; bis-(pyrimidin-2-yl)-amino; 5-R⁸-1,3,4,-thiadiazol-2-yl; 5-thioxo-4,5-dihydro-1H-1,2,4-triazol-3-yl; 1H-1,2,4-triazol-5-yl; 1,3,4-oxadiazol-2-yl; 1,2,4-oxadiazol-5-yl; and 3-R¹⁰-1,2,4-oxadiazol-5-yl;

R² is selected from the group consisting of =O, =NR⁹, =N(OR⁹), and =N(NR⁹R⁹);

or R¹ and R² combine to form =N—O—C(=O)— or =N—N(R⁹)—C(=O)—, wherein the =N group is bound to the ring carbon atom marked "*";

M is selected from the group consisting of C(R⁴)(R⁴') and NR⁸;

bond a is a single or double bond, wherein:
(i) if bond a is a single bond, then:
Y is C(=O), and M is selected from the group consisting of C(R⁴)(R⁴') and NR⁸, or
Y is selected from the group consisting of CHR⁵, O, S, S(=O), S(=O)₂, and NR⁵, and M is C(R⁴)(R⁴'), wherein, if Y is selected from the group consisting of CHR⁵, O, and NR⁵, R⁴ and R⁴' optionally combine with each other to form =O; or
Y is CH, M is C(R⁴)(R⁴'), R⁴ is CH₂, and Y and R⁴ form a single bond to generate cyclopropyl;
(ii) if bond a is a double bond, then Y is selected from the group consisting of CR⁵ and N, M is C(R⁴)(R⁴'), and R⁴' is absent;

R³, R³', R⁴ and R⁴' are each independently selected from the group consisting of H, alkyl-substituted oxetanyl, optionally substituted $C_1$-$C_6$ alkyl (e.g., optionally substituted with 1-3 groups independently selected from the group consisting of F, Cl, Br, I, OH, and OMe) and optionally substituted $C_3$-$C_8$ cycloalkyl (e.g., optionally substituted with 1-3 groups independently selected from the group consisting of F, Cl, Br, I, OH, and OMe);

or one pair selected from the group consisting of R³/R³', R⁴/R⁴', and R³/R⁴ combine to form a divalent group selected from the group consisting of $C_1$-$C_6$ alkanediyl, —(CH₂)ₙO(CH₂)ₙ—, —(CH₂)ₙNR⁹(CH₂)ₙ—, —(CH₂)ₙS(CH₂)ₙ—, —(CH₂)ₙS(=O)(CH₂)ₙ—, and —(CH₂)ₙS(=O)₂(CH₂)ₙ—, wherein each occurrence of n is independently selected from the group consisting of 1 and 2 and each divalent group is optionally substituted with at least one $C_1$-$C_6$ alkyl or halo;

each occurrence of R⁵ is independently selected from the group consisting of H, optionally substituted $C_1$-$C_6$ alkyl, and optionally substituted $C_3$-$C_8$ cycloalkyl;

X¹ is selected from the group consisting of CR⁶ᴵ and N;
X² is selected from the group consisting of CR⁶ᴵᴵ and N;
X³ is selected from the group consisting of CR⁶ᴵᴵᴵ and N;
X⁴ is selected from the group consisting of CR⁶ᴵⱽ and N;
or either X³ and X⁴, or X¹ and X², combine to form —S—;

wherein 0-2 substituents selected from the group consisting of X¹, X², X³ and X⁴ are N, each of which, if present, is optionally alkylated with $C_1$-$C_6$ alkyl if the adjacent carbon atom in the ring is substituted with —OH;

R⁶ᴵ, R⁶ᴵᴵ, R⁶ᴵᴵᴵ and R⁶ᴵⱽ are independently selected from the group consisting of H, halo, —CN, pyrrolidinyl, optionally substituted $C_1$-$C_6$ alkyl (e.g., $C_1$-$C_6$ hydroxyalkyl, alkoxy-$C_1$-$C_6$ alkyl, and/or $C_1$-$C_6$ haloalkyl), optionally substituted $C_1$-$C_6$ alkenyl, optionally substituted $C_3$-$C_8$ cycloalkyl, optionally substituted heterocyclyl (e.g., morpholinyl), —OR, $C_1$-$C_6$ haloalkoxy, —N(R)(R), —NO₂, —S(=O)₂N(R)(R), acyl, and $C_1$-$C_6$ alkoxycarbonyl, wherein each occurrence of R is independently selected from the group consisting of H, $C_1$-$C_6$ alkyl, R'-substituted $C_1$-$C_6$ alkyl, $C_1$-$C_6$ hydroxyalkyl, optionally substituted ($C_1$-$C_6$ alkoxy)-$C_1$-$C_6$ alkyl, and optionally substituted $C_3$-$C_8$ cycloalkyl, wherein each occurrence of R' is independently selected from the group consisting of —NH₂, —NH($C_1$-$C_6$ alkyl), —N($C_1$-$C_6$ alkyl)($C_1$-$C_6$ alkyl), —NHC(=O)O'Bu, —N($C_1$-$C_6$ alkyl)C(=O)O'Bu, or a 5- or 6-membered heterocyclic group (such as, but not limited to, pyrrolidinyl, morpholinyl, piperidinyl, piperazinyl, and so forth), which is optionally N-linked;

or X² is CR⁶ᴵᴵ, X³ is CR⁶ᴵᴵᴵ, and R⁶ᴵᴵ and R⁶ᴵᴵᴵ combine to form a divalent group selected from the group consisting of —O(CHF)O—, —O(CF₂)O—, —O(CR⁹R⁹)O—, —O(CH₂)(CH₂)O— and —O(CH₂)(CR¹¹R¹¹)(CH₂)O—;

R⁷ is selected from the group consisting of H, OH, halo, $C_1$-$C_6$ alkoxy, optionally substituted $C_1$-$C_6$ alkyl (e.g., optionally substituted with 1-3 independently selected halo groups), and optionally substituted $C_3$-$C_8$ cycloalkyl;

R⁸ is selected from the group consisting of H, optionally substituted $C_1$-$C_6$ alkyl, and optionally substituted $C_3$-$C_8$ cycloalkyl;

each occurrence of R⁹ is independently selected from the group consisting of H and $C_1$-$C_6$ alkyl (e.g., methyl or ethyl);

R¹⁰ is selected from the group consisting of optionally substituted $C_1$-$C_6$ alkyl and optionally substituted phenyl; and, each occurrence of R¹¹ is independently selected from the group consisting of H, OH, $C_1$-$C_6$ alkyl, $C_1$-$C_6$ alkoxy, alkoxy-$C_1$-$C_6$ alkyl and alkoxy-$C_1$-$C_6$ alkoxy, wherein two R¹¹ groups bound to the same carbon atom are not simultaneously OH; or two R¹¹ groups combine with the carbon atom to which they are bound to form a moiety selected from the group consisting of C=O, C=CH₂ and oxetane-3,3-diyl.

In certain embodiments, the compound of formula (I) is a compound of formula (Ia), or a salt, solvate, geometric isomer, stereoisomer, tautomer, and any mixtures thereof:

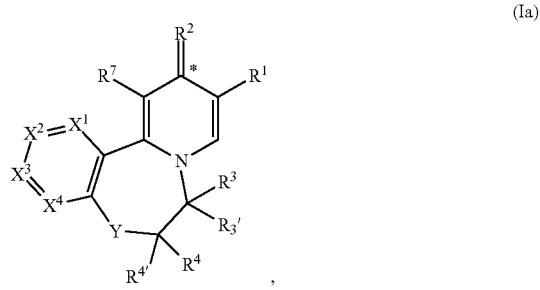

(Ia)

wherein:
Y is selected from the group consisting of CHR⁵ and O; and
R⁷ is selected from the group consisting of H, OH, halo, $C_1$-$C_6$ alkoxy, and optionally substituted $C_1$-$C_6$ alkyl.

In certain embodiments, the compound of formula (I) is a compound of formula

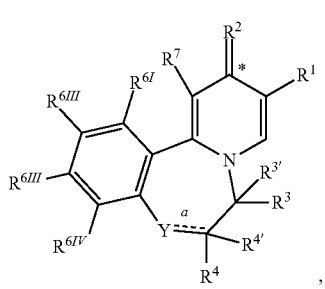
(Ib)

In other embodiments, the compound of formula (I) is a compound of formula

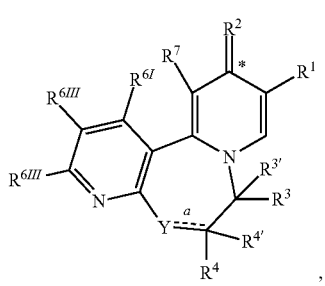
(Ic)

In yet other embodiments, the compound of formula (I) is a compound of formula

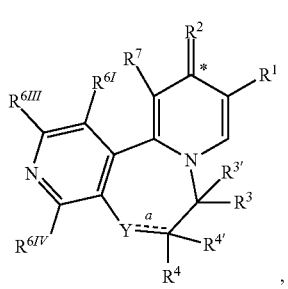
(Id)

In yet other embodiments, the compound of formula (I) is a compound of formula

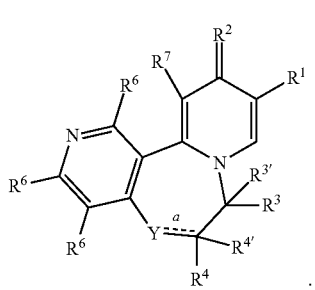
(Ie)

In yet other embodiments, the compound of formula (I) is a compound of formula

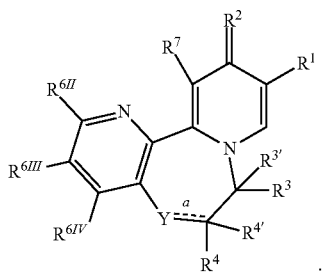
(If)

In yet other embodiments, the compound of formula (I) is a compound of formula

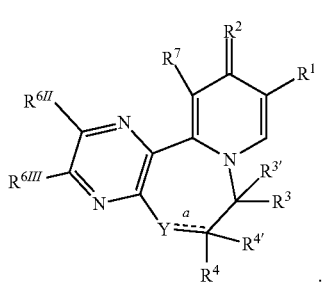
(Ig)

In yet other embodiments, the compound of formula (I) is a compound of formula

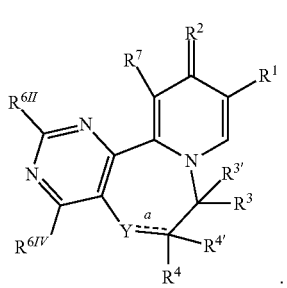
(Ih)

In yet other embodiments, the compound of formula (I) is a compound of formula

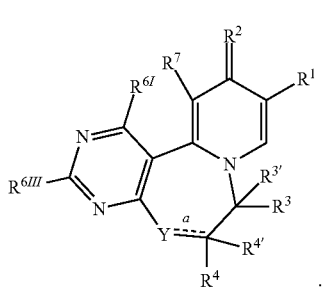
(Ii)

In certain embodiments, the compound of formula (I) is a compound of formula

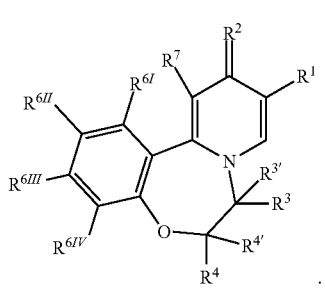
(Ij)

In other embodiments, the compound of formula (I) is a compound of formula

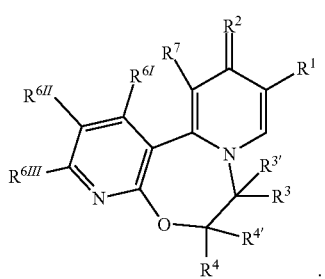
(Ik)

In yet other embodiments, the compound of formula (I) is a compound of formula

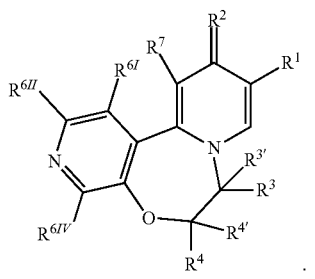
(Il)

In yet other embodiments, the compound of formula (I) is a compound of formula

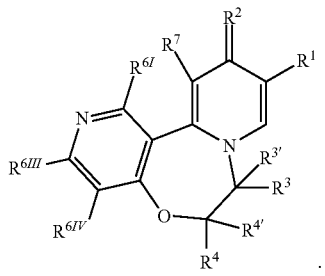
(Im)

In yet other embodiments, the compound of formula (I) is a compound of formula

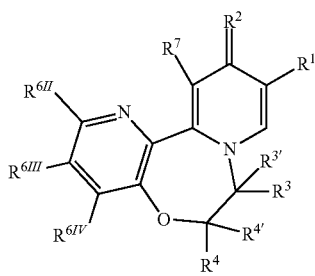
(In)

In yet other embodiments, the compound of formula (I) is a compound of formula

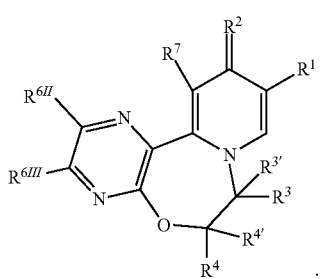
(Io)

In yet other embodiments, the compound of formula (I) is a compound of formula

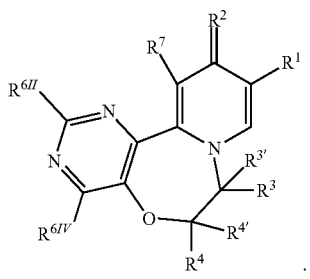
(Ip)

In yet other embodiments, the compound of formula (I) is a compound of formula

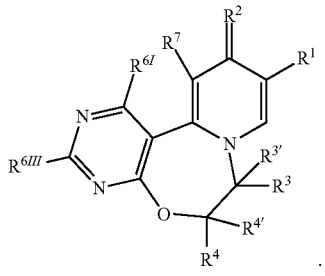
(Iq)

In certain embodiments, the compound of formula (I) is a compound of formula

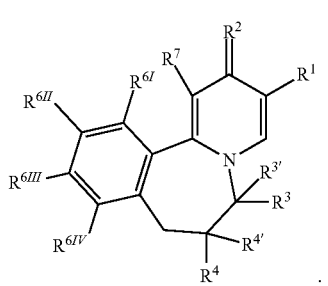

(Ir)

In other embodiments, the compound of formula (I) is a compound of formula

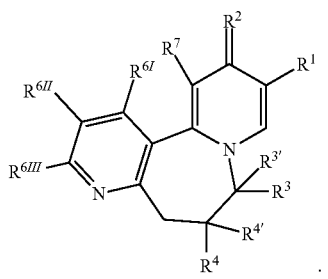

(Is)

In yet other embodiments, the compound of formula (I) is a compound of formula

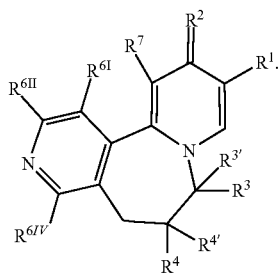

(It)

In yet other embodiments, the compound of formula (I) is a compound of formula

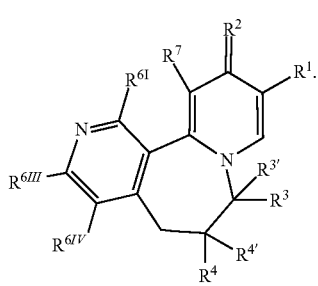

(Iu)

In yet other embodiments, the compound of formula (I) is a compound of formula

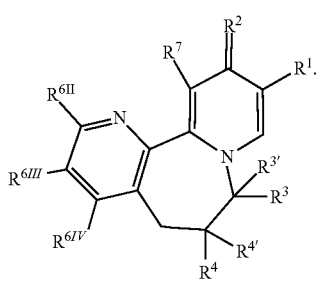

(Iv)

In yet other embodiments, the compound of formula (I) is a compound of formula

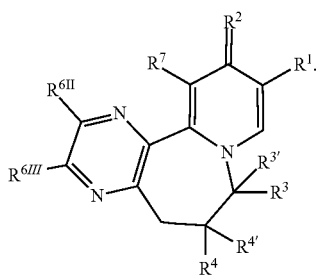

(Iw)

In yet other embodiments, the compound of formula (I) is a compound of formula

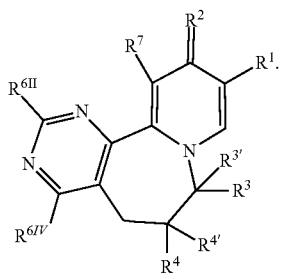

(Ix)

In yet other embodiments, the compound of formula (I) is a compound of formula

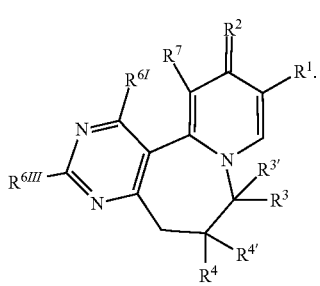

(Iy)

The invention includes a compound of formula (II), or a salt, solvate, geometric isomer, stereoisomer, tautomer and any mixtures thereof:

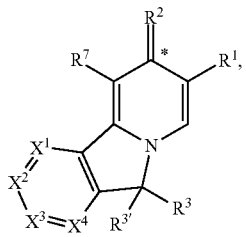

(II)

wherein:

R$^1$ is selected from the group consisting of H; halo; —OR$^8$; —C(R$^9$)(R$^9$)OR$^8$ (such as, for example, —CH$_2$OR$^8$, such as, for example, —CH$_2$OH); —C(=O)R$^8$; —C(=O)OR$^8$ (such as, for example, —C(=O)OH or —C(=O)O—C$_1$-C$_6$ alkyl); —C(=O)NH—OR$^8$ (such as, for example, —C(=O)NH—OH); —C(=O)NHNHR$^8$; —C(=O)NHNHC(=O)R$^8$; —C(=O)NHS(=O)$_2$R$^8$; —CH$_2$C(=O)OR$^8$; —CN; —NH$_2$; —N(R$^8$)C(=O)H; —N(R$^8$)C(=O)R$^{10}$; —N(R$^8$)C(=O)OR$^{10}$; —N(R$^8$)C(=O)NHR$^8$; —NR$^9$S(=O)$_2$R$^{10}$; —P(=O)(OR$^8$)$_2$; —B(OR$^8$)$_2$; 2,5-dioxo-pyrrolidin-1-yl; 2H-tetrazol-5-yl; 3-hydroxy-isoxazol-5-yl; 1,4-dihydro-5-oxo-5H-tetrazol-1-yl; pyridin-2-yl optionally substituted with C$_1$-C$_6$ alkyl; pyrimidin-2-yl optionally substituted with C$_1$-C$_6$ alkyl; (pyridin-2-yl)methyl; (pyrimidin-2-yl)methyl; (pyrimidin-2-yl)amino; bis-(pyrimidin-2-yl)-amino; 5-R$^8$-1,3,4,-thiadiazol-2-yl; 5-thioxo-4,5-dihydro-1H-1,2,4-triazol-3-yl; 1H-1,2,4-triazol-5-yl; 1,3,4-oxadiazol-2-yl; 1,2,4-oxadiazol-5-yl, and 3-R$^{10}$-1,2,4-oxadiazol-5-yl;

R$^2$ is selected from the group consisting of =O, =NR$^9$, =N(OR$^9$), and =N(NR$^9$R$^9$);

or R$^1$ and R$^2$ combine to form =N—O—C(=O)— or =N—N(R$^9$)—C(=O)—, wherein the =N group is bound to the ring carbon atom marked "*";

R$^3$ and R$^{3'}$ are each independently selected from the group consisting of H, alkyl-substituted oxetanyl, optionally substituted C$_1$-C$_6$ alkyl (e.g., optionally substituted with 1-3 groups independently selected from the group consisting of F, Cl, Br, I, OH, and OMe) and optionally substituted C$_3$-C$_8$ cycloalkyl (e.g., optionally substituted with 1-3 groups independently selected from the group consisting of F, Cl, Br, I, OH, and OMe);

or R$^3$ and R$^{3'}$ combine to form a divalent group selected from the group consisting of C$_1$-C$_6$ alkanediyl, —(CH$_2$)$_n$O(CH$_2$)$_n$—, —(CH$_2$)$_n$NR$^9$(CH$_2$)$_n$—, —(CH$_2$)$_n$S(CH$_2$)$_n$—, —(CH$_2$)$_n$S(=O)(CH$_2$)$_n$—, and —(CH$_2$)$_n$S(=O)$_2$(CH$_2$)$_n$—, wherein each occurrence of n is independently selected from the group consisting of 1 and 2 and each divalent group is optionally substituted with at least one C$_1$-C$_6$ alkyl or halo;

X$^1$ is selected from the group consisting of CR$^{6I}$ and N;
X$^2$ is selected from the group consisting of CR$^{6II}$ and N;
X$^3$ is selected from the group consisting of CR$^{6III}$ and N;
X$^4$ is selected from the group consisting of CR$^{6IV}$ and N;
or either X$^3$ and X$^4$, or X$^1$ and X$^2$, combine to form —S—;
wherein 0-2 substituents selected from the group consisting of X$^1$, X$^2$, X$^3$ and X$^4$ are N, each of which, if present, is optionally alkylated with C$_1$-C$_6$ alkyl if the adjacent carbon atom in the ring is substituted with —OH;

R$^{6I}$, R$^{6II}$, R$^{6III}$ and R$^{6IV}$ are independently selected from the group consisting of H, halo, —CN, pyrrolidinyl, optionally substituted C$_1$-C$_6$ alkyl (e.g., C$_1$-C$_6$ hydroxyalkyl, alkoxy-C$_1$-C$_6$ alkyl, and/or C$_1$-C$_6$ haloalkyl), optionally substituted C$_1$-C$_6$ alkenyl, optionally substituted C$_3$-C$_8$ cycloalkyl, optionally substituted heterocyclyl (e.g., morpholinyl), —OR, C$_1$-C$_6$ haloalkoxy, —N(R)(R), —NO$_2$, —S(=O)$_2$N(R)(R), acyl, and C$_1$-C$_6$ alkoxycarbonyl, wherein each occurrence of R is independently selected from the group consisting of H, C$_1$-C$_6$ alkyl, R'-substituted C$_1$-C$_6$ alkyl, C$_1$-C$_6$ hydroxyalkyl, optionally substituted (C$_1$-C$_6$ alkoxy)-C$_1$-C$_6$ alkyl, and optionally substituted C$_3$-C$_8$ cycloalkyl, wherein each occurrence of R' is independently selected from the group consisting of —NH$_2$, —NH(C$_1$-C$_6$ alkyl), —N(C$_1$-C$_6$ alkyl)(C$_1$-C$_6$ alkyl), —NHC(=O)O$^t$Bu, —N(C$_1$-C$_6$ alkyl)C(=O)O$^t$Bu, and a 5- or 6-membered heterocyclic group (such as, but not limited to, pyrrolidinyl, morpholinyl, piperidinyl, piperazinyl, and so forth), which is optionally N-linked;

or X$^2$ is CR$^{6II}$, X$^3$ is CR$^{6III}$ and R$^{6II}$ and R$^{6III}$ combine to form a divalent group selected from the group consisting of —O(CHF)O—, —O(CF$_2$)O—, —O(CR$^9$R$^9$)O—, —O(CH$_2$)(CH$_2$)O— and —O(CH$_2$)(CR$^{11}$R$^{11}$)(CH$_2$)O—;

R$^7$ is selected from the group consisting of H, OH, halo, C$_1$-C$_6$ alkoxy, optionally substituted C$_1$-C$_6$ alkyl (e.g., optionally substituted with 1-3 independently selected halo groups), and optionally substituted C$_3$-C$_8$ cycloalkyl;

R$^8$ is selected from the group consisting of H, optionally substituted C$_1$-C$_6$ alkyl, and optionally substituted C$_3$-C$_8$ cycloalkyl;

each occurrence of R$^9$ is independently selected from the group consisting of H and C$_1$-C$_6$ alkyl (e.g., methyl or ethyl);

R$^{10}$ is selected from the group consisting of optionally substituted C$_1$-C$_6$ alkyl, and optionally substituted phenyl; and, each occurrence of R$^{11}$ is independently selected from the group consisting of H, OH, C$_1$-C$_6$ alkyl, C$_1$-C$_6$ alkoxy, alkoxy-C$_1$-C$_6$ alkyl and alkoxy-C$_1$-C$_6$ alkoxy, wherein two R$^{11}$ groups bound to the same carbon atom are not simultaneously OH; or two R$^{11}$ groups combine with the carbon atom to which they are bound to form a moiety selected from the group consisting of C=O, C=CH$_2$ and oxetane-3,3-diyl.

In certain embodiments, the compound of formula (II) is a compound of formula

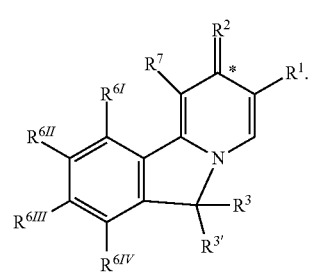

(IIa)

In other embodiments, the compound of formula (II) is a compound of formula

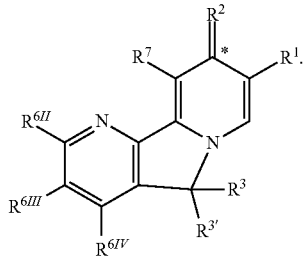

(IIb)

In yet other embodiments, the compound of formula (II) is a compound of formula

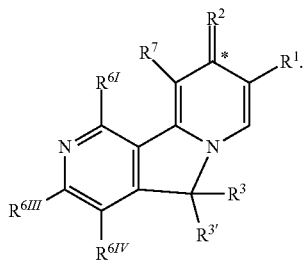

(IIc)

In yet other embodiments, the compound of formula (II) is a compound of formula

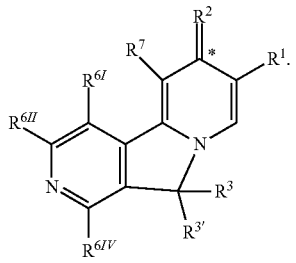

(IId)

In yet other embodiments, the compound of formula (II) is a compound of formula

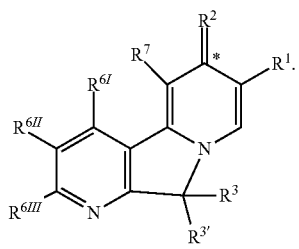

(IIe)

In yet other embodiments, the compound of formula (II) is a compound of formula

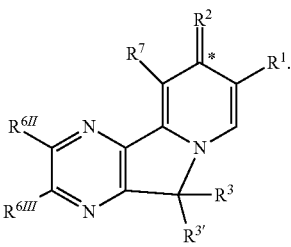

(IIf)

In yet other embodiments, the compound of formula (II) is a compound of formula

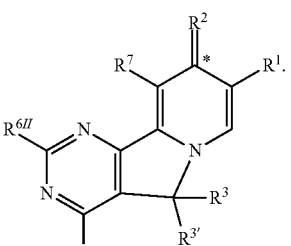

(IIg)

In yet other embodiments, the compound of formula (II) is a compound of formula

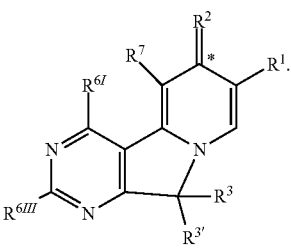

(IIh)

The invention includes a compound of formula (III), or a salt, solvate, geometric isomer, stereoisomer, tautomer and any mixtures thereof:

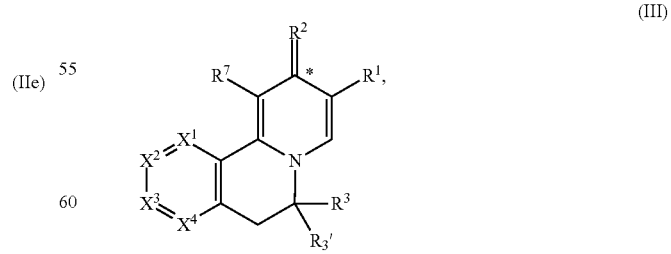

(III)

wherein:
$R^1$ is selected from the group consisting of H; halo; —$OR^8$; —$C(R^9)(R^9)OR^8$ (such as, for example, —$CH_2OR^8$, such as, for example, —$CH_2OH$); —$C(=O)R^8$; —$C(=O)$ OR$^8$ (such as, for example, —C(=O)OH or —C(=O)O—C$_1$-C$_6$ alkyl); —C(=O)NH—OR$^8$ (such as, for example, —C(=O)NH—OH); —C(=O)NHNHR$^8$; —C(=O)NHNHC(=O)R$^8$; —C(=O)NHS(=O)$_2$R$^8$; —CH$_2$C(=O)OR$^8$; —CN; —NH$_2$; —N(R$^8$)C(=O)H; —N(R$^8$)C(=O)R$^{10}$; —N(R$^8$)C(=O)OR$^{10}$; —N(R$^8$)C(=O)NHR$^8$; —NR$^9$S(=O)$_2$R$^{10}$; —P(=O)(OR$^8$)$_2$; —B(OR$^8$)$_2$; 2,5-dioxopyrrolidin-1-yl; 2H-tetrazol-5-yl; 3-hydroxy-isoxazol-5-yl; 1,4-dihydro-5-oxo-5H-tetrazol-1-yl; pyridin-2-yl optionally substituted with C$_1$-C$_6$ alkyl; pyrimidin-2-yl optionally substituted with C$_1$-C$_6$ alkyl; (pyridin-2-yl)methyl; (pyrimidin-2-yl)methyl; (pyrimidin-2-yl)amino; bis-(pyrimidin-2-yl)-amino; 5-R$^8$-1,3,4,-thiadiazol-2-yl; 5-thioxo-4,5-dihydro-1H-1,2,4-triazol-3-yl; 1H-1,2,4-triazol-5-yl; 1,3,4-oxadiazol-2-yl; 1,2,4-oxadiazol-5-yl, and 3-R$^{10}$-1,2,4-oxadiazol-5-yl;

R$^2$ is selected from the group consisting of =O, =NR$^9$, =N(OR$^9$), and =N(NR$^9$R$^9$);

or R$^1$ and R$^2$ combine to form =N—O—C(=O)— or =N—N(R$^9$)—C(=O)—, wherein the =N group is bound to the ring carbon atom marked "*";

R$^3$ and R$^{3'}$ are each independently selected from the group consisting of H, alkyl-substituted oxetanyl, optionally substituted C$_1$-C$_6$ alkyl (e.g., optionally substituted with 1-3 groups independently selected from the group consisting of F, Cl, Br, I, OH and OMe), and optionally substituted C$_3$-C$_8$ cycloalkyl (e.g., optionally substituted with 1-3 groups independently selected from the group consisting of F, Cl, Br, I, OH and OMe);

or R$^3$ and R$^{3'}$ combine to form a divalent group selected from the group consisting of C$_1$-C$_6$ alkanediyl, —(CH$_2$)$_n$O(CH$_2$)$_n$—, —(CH$_2$)$_n$NR$^9$(CH$_2$)$_n$—, —(CH$_2$)$_n$S(CH$_2$)$_n$—, —(CH$_2$)$_n$S(=O)(CH$_2$)$_n$—, and —(CH$_2$)$_n$S(=O)$_2$(CH$_2$)$_n$—, wherein each occurrence of n is independently selected from the group consisting of 1 and 2 and each divalent group is optionally substituted with at least one C$_1$-C$_6$ alkyl or halo;

X$^1$ is selected from the group consisting of CR$^{6I}$ and N;
X$^2$ is selected from the group consisting of CR$^{6II}$ and N;
X$^3$ is selected from the group consisting of CR$^{6III}$ and N;
X$^4$ is selected from the group consisting of CR$^{6IV}$ and N;
or either X$^3$ and X$^4$, or X$^1$ and X$^2$, combine to form —S—;

wherein 0-2 substituents selected from the group consisting of X$^1$, X$^2$, X$^3$ and X$^4$ are N, each of which, if present, is optionally alkylated with C$_1$-C$_6$ alkyl if the adjacent carbon atom in the ring is substituted with —OH;

R$^{6I}$, R$^{6II}$, R$^{6III}$ and R$^{6IV}$ are independently selected from the group consisting of H, halo, —CN, pyrrolidinyl, optionally substituted C$_1$-C$_6$ alkyl (e.g., C$_1$-C$_6$ hydroxyalkyl, alkoxy-C$_1$-C$_6$ alkyl, and/or C$_1$-C$_6$ haloalkyl), optionally substituted C$_1$-C$_6$ alkenyl, optionally substituted C$_3$-C$_8$ cycloalkyl, optionally substituted heterocyclyl (e.g., morpholinyl), —OR, C$_1$-C$_6$ haloalkoxy, —N(R)(R), —NO$_2$, —S(=O)$_2$N(R)(R), acyl, and C$_1$-C$_6$ alkoxycarbonyl, wherein each occurrence of R is independently selected from the group consisting of H, C$_1$-C$_6$ alkyl, R'-substituted C$_1$-C$_6$ alkyl, C$_1$-C$_6$ hydroxyalkyl, optionally substituted (C$_1$-C$_6$ alkoxy)-C$_1$-C$_6$ alkyl, and optionally substituted C$_3$-C$_8$ cycloalkyl, wherein each occurrence of R' is selected from the group consisting of —NH$_2$, —NH(C$_1$-C$_6$ alkyl), —N(C$_1$-C$_6$ alkyl)(C$_1$-C$_6$ alkyl), —NHC(=O)O$^t$Bu, —N(C$_1$-C$_6$ alkyl)C(=O)O$^t$Bu, and a 5- or 6-membered heterocyclic group (such as, but not limited to, pyrrolidinyl, morpholinyl, piperidinyl, piperazinyl, and so forth), which is optionally N-linked;

or X$^2$ is CR$^{6II}$, X$^3$ is CR$^{6III}$ and R$^{6II}$ and R$^{6III}$ combine to form a divalent group selected from the group consisting of —O(CHF)O—, —O(CF$_2$)O—, —O(CR$^9$R$^9$)O—, —O(CH$_2$)(CH$_2$)O— and —O(CH$_2$)(CR$^{11}$R$^{11}$)(CH$_2$)O—;

R$^7$ is selected from the group consisting of H, OH, halo, C$_1$-C$_6$ alkoxy, optionally substituted C$_1$-C$_6$ alkyl (e.g., optionally substituted with 1-3 independently selected halo groups), and optionally substituted C$_3$-C$_8$ cycloalkyl;

R$^8$ is selected from the group consisting of H, optionally substituted C$_1$-C$_6$ alkyl, and optionally substituted C$_3$-C$_8$ cycloalkyl;

each occurrence of R$^9$ is independently selected from the group consisting of H and C$_1$-C$_6$ alkyl (e.g., methyl or ethyl);

R$^{10}$ is selected from the group consisting of optionally substituted C$_1$-C$_6$ alkyl and optionally substituted phenyl; and, each occurrence of R$^{11}$ is independently selected from the group consisting of H, OH, C$_1$-C$_6$ alkyl, C$_1$-C$_6$ alkoxy, alkoxy-C$_1$-C$_6$ alkyl and alkoxy-C$_1$-C$_6$ alkoxy, wherein two R$^{11}$ groups bound to the same carbon atom are not simultaneously OH; or two R$^{11}$ groups combine with the carbon atom to which they are bound to form a moiety selected from the group consisting of C=O, C=CH$_2$ and oxetane-3,3-diyl;

wherein at least one of the following conditions is present:

(a) R$^1$ is not —C(=O)OR$^8$, (b) R$^2$ is selected from the group consisting of =NR$^9$, =N(OR$^9$), and =N(NR$^9$R$^9$), or R$^1$ and R$^2$ combine to form =N—O—C(=O)— or =N—N(R$^9$)—C(=O)—, wherein the =N group is bound to the ring carbon atom marked "*";

(c) either X$^3$ and X$^4$, or X$^1$ and X$^2$, combine to form —S—;

(d) 1-2 substituents selected from the group consisting of X$^1$, X$^2$, X$^3$ and X$^4$ are N;

(e) X$^2$ is CR$^{6II}$, X$^3$ is CR$^{6III}$, and R$^{6II}$ and R$^{6III}$ combine to form a divalent group selected from the group consisting of —O(CHF)O—, —O(CF$_2$)O—, —O(CR$^9$R$^9$)O—, —O(CH$_2$)(CH$_2$)O— and —O(CH$_2$)(CR$^{11}$R$^{11}$)(CH$_2$)O—; and/or (f) R$^3$ and R$^{3'}$ are each independently selected from the group consisting of alkyl-substituted oxetanyl, optionally substituted C$_1$-C$_6$ alkyl (e.g., optionally substituted with 1-3 groups independently selected from the group consisting of F, Cl, Br, I, OH and OMe), and optionally substituted C$_3$-C$_8$ cycloalkyl (e.g., optionally substituted with 1-3 groups independently selected from the group consisting of F, Cl, Br, I, OH and OMe), or R$^3$ and R$^{3'}$ combine to form a divalent group selected from the group consisting of C$_1$-C$_6$ alkanediyl, —(CH$_2$)$_n$O(CH$_2$)$_n$—, —(CH$_2$)$_n$NR$^9$(CH$_2$)$_n$—, —(CH$_2$)$_n$S(CH$_2$)$_n$—, —(CH$_2$)$_n$S(=O)(CH$_2$)$_n$—, and —(CH$_2$)$_n$S(=O)$_2$(CH$_2$)$_n$—, wherein each occurrence of n is independently selected from the group consisting of 1 and 2 and each divalent group is optionally substituted with at least one C$_1$-C$_6$ alkyl or halo.

In certain embodiments, the compound of formula (III) is the compound of formula (IIIa), or a salt, solvate, geometric isomer, stereoisomer, tautomer and any mixtures thereof:

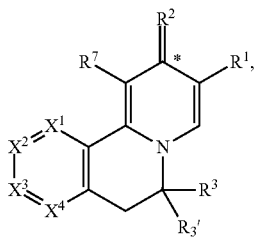

(IIIa)

wherein:

each of $X^1$, $X^2$, $X^3$, and $X^4$ are independently selected from the group consisting of $CR^{6I}$ and N;

wherein 1-2 substituents selected from the group consisting of $X^1$, $X^2$, $X^3$ and $X^4$ are N, each of which is optionally alkylated with $C_1$-$C_6$ alkyl if the adjacent carbon atom in the ring is substituted with —OH;

or either $X^3$ and $X^4$, or $X^1$ and $X^2$, combine to form —S—.

In certain embodiments, the compound of formula (III) is the compound of formula (IIIb), or a salt, solvate, geometric isomer, stereoisomer, tautomer and any mixtures thereof:

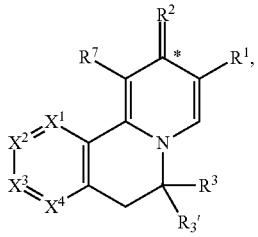

(IIIb)

wherein at least one applies:

$R^1$ is selected from the group consisting of H; halo; —$OR^8$; —$C(R^9)(R^9)OR^8$; —$C(=O)R^8$; —$C(=O)NH$—$OR^8$; —$C(=O)NHNHR^8$; —$C(=O)NHNHC(=O)R^8$; —$C(=O)NHS(=O)_2R^8$; —CN; —$NH_2$; —$N(R^8)C(=O)$H; —$N(R^8)C(=O)R^{10}$; —$N(R^8)C(=O)OR^{10}$; —$N(R^8)C(=O)NHR^8$; —$NR^9S(=O)_2R^{10}$; —$P(=O)(OR^8)_2$; —$B(OR^8)_2$; 2,5-dioxo-pyrrolidin-1-yl; 2H-tetrazol-5-yl; 1,4-dihydro-5-oxo-5H-tetrazol-1-yl; pyridin-2-yl optionally substituted with $C_1$-$C_6$ alkyl; pyrimidin-2-yl optionally substituted with $C_1$-$C_6$ alkyl; (pyrimidin-2-yl)amino; bis-(pyrimidin-2-yl)-amino; 5-$R^8$-1,3,4,-thiadiazol-2-yl; 5-thioxo-4,5-dihydro-1H-1,2,4-triazol-3-yl; 1H-1,2,4-triazol-5-yl; 1,3,4-oxadiazol-2-yl; 1,2,4-oxadiazol-5-yl, and 3-$R^{10}$-1,2,4-oxadiazol-5-yl;

and $R^2$ is selected from the group consisting of $=NR^9$, $=N(OR^9)$, and $=N(NR^9R^9)$, or $R^1$ and $R^2$ combine to form $=N$—O—$C(=O)$— or $=N$—$N(R^9)$—$C(=O)$—, wherein the $=N$ group is bound to the ring carbon atom marked "*".

In certain embodiments, the compound of formula (III) is a compound of formula (IIIc), or a salt, solvate, geometric isomer, stereoisomer, tautomer and any mixtures thereof:

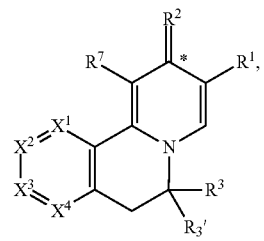

(IIIc)

$X^3$ and $X^4$, or $X^1$ and $X^2$, combine to form —S—;

In certain embodiments, the compound of formula (III) is the compound of formula (IIId), or a salt, solvate, geometric isomer, stereoisomer, tautomer and any mixtures thereof:

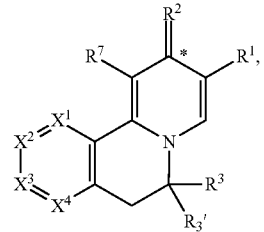

(IIId)

wherein:

$X^2$ is $CR^{6II}$, $X^3$ is $CR^{6III}$, and $R^{6II}$ and $R^{6III}$ combine to form a divalent group selected from the group consisting of —O(CHF)O—, —O(CF$_2$)O—, —O(CR$^9$R$^9$)O—, —O(CH$_2$)(CH$_2$)O— and —O(CH$_2$)(CR$^{11}$R$^{11}$)(CH$_2$)O—.

In certain embodiments, the compound of formula (III) is a compound of formula (IIIe):

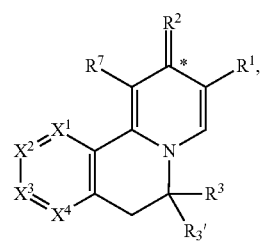

(IIIe)

wherein:

$R^3$ and $R^{3'}$ are each independently selected from the group consisting of H, alkyl-substituted oxetanyl, optionally substituted $C_1$-$C_6$ alkyl (e.g., optionally substituted with 1-3 groups independently selected from the group consisting of F, Cl, Br, I, OH and OMe), and optionally substituted $C_3$-$C_8$ cycloalkyl (e.g., optionally substituted with 1-3 groups independently selected from the group consisting of F, Cl, Br, I, OH and OMe), or $R^3$ and $R^{3'}$ combine to form a divalent group selected from the group consisting of $C_1$-$C_6$ alkanediyl, —(CH$_2$)$_n$O(CH$_2$)$_n$—, —(CH$_2$)$_n$NR$^9$(CH$_2$)$_n$—, —(CH$_2$)$_n$S(CH$_2$)$_n$—, —(CH$_2$)$_n$S(=O)(CH$_2$)$_n$—, and —(CH$_2$)$_n$S(=O)$_2$(CH$_2$)$_n$—, wherein each occurrence of n is independently selected from the group consisting of 1 and 2 and each divalent group is optionally substituted with at least one $C_1$-$C_6$ alkyl or halo.

In certain embodiments, the compound of formula (III) is a compound of formula

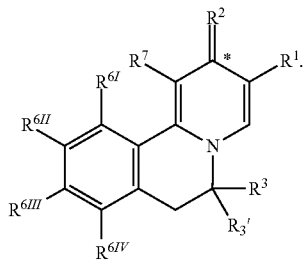
(IIIf)

In other embodiments, the compound of formula (III) is a compound of formula

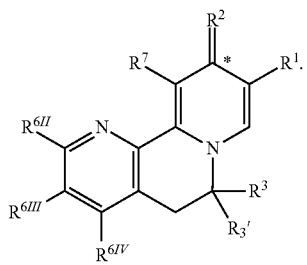
(IIIg)

In yet other embodiments, the compound of formula (III) is a compound of formula

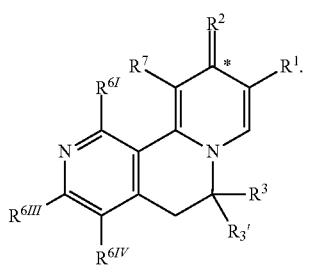
(IIIh)

In yet other embodiments, the compound of formula (III) is a compound of formula

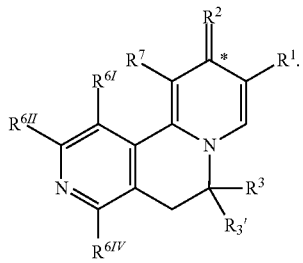
(IIIi)

In yet other embodiments, the compound of formula (III) is a compound of formula

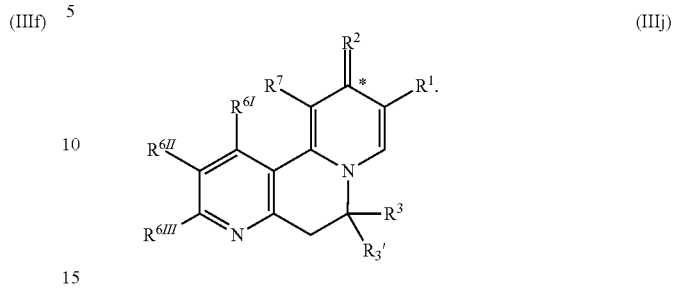
(IIIj)

In yet other embodiments, the compound of formula (III) is a compound of formula

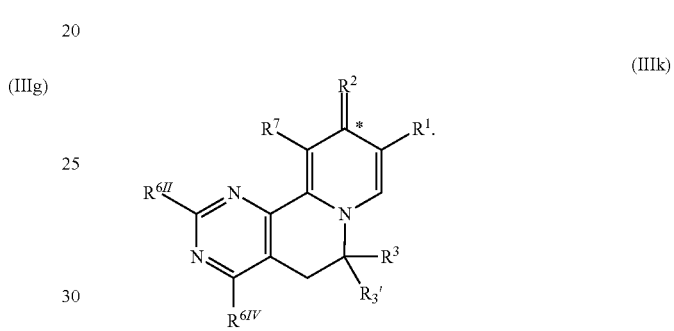
(IIIk)

In yet other embodiments, the compound of formula (III) is a compound of formula

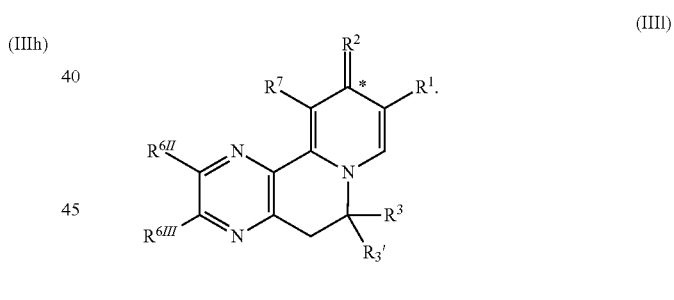
(IIIl)

In yet other embodiments, the compound of formula (III) is a compound of formula

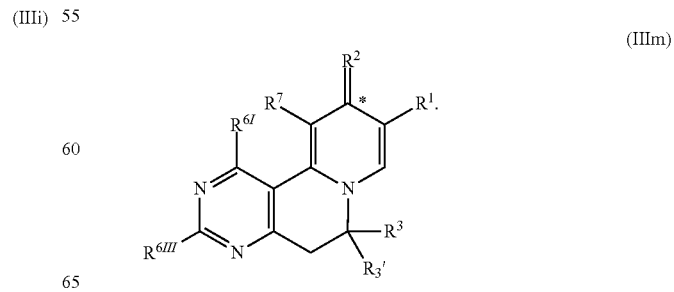
(IIIm)

In yet other embodiments, the compound of formula (III) is a compound of formula

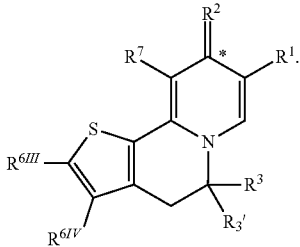
(IIIn)

In yet other embodiments, the compound of formula (III) is a compound of formula

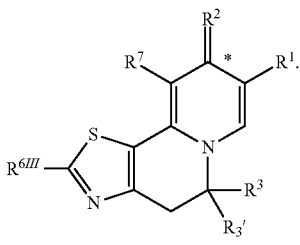
(IIIo)

In yet other embodiments, the compound of formula (III) is a compound of formula

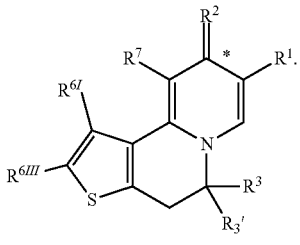
(IIIp)

In yet other embodiments, the compound of formula (III) is a compound of formula

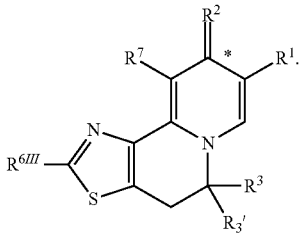
(IIIq)

In certain embodiments, each occurrence of alkyl, alkenyl, or cycloalkyl is independently optionally substituted with at least one substituent selected from the group consisting of $C_1$-$C_6$ alkyl, halo, —OR", phenyl (thus yielding, in non-limiting examples, optionally substituted phenyl-($C_1$-$C_3$ alkyl), such as, but not limited to, benzyl or substituted benzyl) and —N(R")(R"), wherein each occurrence of R" is independently H, $C_1$-$C_6$ alkyl or $C_3$-$C_8$ cycloalkyl.

In certain embodiments, each occurrence of aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR", —N(R")(R"), —NO$_2$, —S(=O)$_2$N(R")(R"), acyl, and $C_1$-$C_6$ alkoxycarbonyl, wherein each occurrence of R" is independently H, $C_1$-$C_6$ alkyl or $C_3$-$C_8$ cycloalkyl.

In certain embodiments, each occurrence of aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR", —N(R")(R"), and $C_1$-$C_6$ alkoxycarbonyl, wherein each occurrence of R" is independently H, $C_1$-$C_6$ alkyl or $C_3$-$C_8$ cycloalkyl.

In certain embodiments, A is null. In certain embodiments, A is $CR^9R^9$.

In certain embodiments, $R^1$ is selected from the group consisting of H; halo; —OR$^8$; —C(R$^9$)(R$^9$)OR$^8$; —C(=O)R$^8$; —C(=O)OR$^8$; —C(=O)NH—OR$^8$; —C(=O)NHNHR$^8$; —C(=O)NHNHC(=O)R$^8$; —C(=O)NHS(=O)$_2$R$^8$; —CH$_2$C(=O)OR$^8$; —CN; —NH$_2$; —N(R$^8$)C(=O)H; —N(R$^8$)C(=O)R$^{10}$; —N(R$^8$)C(=O)OR$^{10}$; —N(R$^8$)C(=O)NHR$^8$; —NR$^9$S(=O)$_2$R$^{10}$; —P(=O)(OR$^8$)$_2$; —B(OR$^8$)$_2$; 2,5-dioxo-pyrrolidin-1-yl; 2H-tetrazol-5-yl; 3-hydroxy-isoxazol-5-yl; 1,4-dihydro-5-oxo-5H-tetrazol-1-yl; pyridin-2-yl optionally substituted with $C_1$-$C_6$ alkyl; pyrimidin-2-yl optionally substituted with $C_1$-$C_6$ alkyl; (pyridin-2-yl)methyl; (pyrimidin-2-yl)methyl; (pyrimidin-2-yl)amino; bis-(pyrimidin-2-yl)-amino; 5-R$^8$-1,3,4,-thiadiazol-2-yl; 5-thioxo-4,5-dihydro-1H-1,2,4-triazol-3-yl; 1H-1,2,4-triazol-5-yl; 1,3,4-oxadiazol-2-yl; 1,2,4-oxadiazol-5-yl, and 3-R$^{10}$-1,2,4-oxadiazol-5-yl.

In certain embodiments, $R^1$ is H. In certain embodiments, $R^1$ is halo. In certain embodiments, $R^1$ is —OR$^8$. In certain embodiments, $R^1$ is —C(R$^9$)(R$^9$)OR$^8$ (such as, for example, —CH$_2$OR$^8$, such as, for example, —CH$_2$OH). In certain embodiments, $R^1$ is —C(=O)R$^8$. In certain embodiments, $R^1$ is —C(=O)OR$^8$ (such as, for example, —C(=O)OH or —C(=O)O—$C_1$-$C_6$ alkyl). In certain embodiments, $R^1$ is —C(=O)NH—OR$^8$ (such as, for example, —C(=O)NH—OH). In certain embodiments, $R^1$ is —C(=O)NHNHR$^8$. In certain embodiments, $R^1$ is —C(=O)NHNHC(=O)R$^8$. In certain embodiments, $R^1$ is —C(=O)NHS(=O)$_2$R$^8$. In certain embodiments, $R^1$ is —CH$_2$C(=O)OR$^8$. In certain embodiments, $R^1$ is —CN. In certain embodiments, $R^1$ is —NH$_2$. In certain embodiments, $R^1$ is —N(R$^8$)C(=O)H. In certain embodiments, $R^1$ is —N(R$^8$)C(=O)R$^{10}$. In certain embodiments, $R^1$ is —N(R$^8$)C(=O)OR$^{10}$. In certain embodiments, $R^1$ is —N(R$^8$)C(=O)NHR$^8$. In certain embodiments, $R^1$ is —NR$^9$S(=O)$_2$R$^{10}$. In certain embodiments, $R^1$ is —P(=O)(OR$^8$)$_2$. In certain embodiments, $R^1$ is —B(OR$^8$)$_2$. In certain embodiments, $R^1$ is 2,5-dioxo-pyrrolidin-1-yl. In certain embodiments, $R^1$ is 2H-tetrazol-5-yl. In certain embodiments, $R^1$ is 3-hydroxy-isoxazol-5-yl. In certain embodiments, $R^1$ is 1,4-dihydro-5-oxo-5H-tetrazol-1-yl. In certain embodiments, $R^1$ is pyridin-2-yl optionally substituted with $C_1$-$C_6$ alkyl. In certain embodiments, $R^1$ is pyrimidin-2-yl optionally substituted with $C_1$-$C_6$ alkyl. In certain embodiments, $R^1$ is (pyridin-2-yl)methyl. In certain embodiments, $R^1$ is (pyrimidin-2-yl)methyl. In certain embodiments, $R^1$ is (pyrimidin-2-yl)amino. In certain embodiments, $R^1$ is bis-(pyrimidin-2-yl)-amino. In certain embodiments, $R^1$ is 5-R$^8$-1,3,4,-thiadiazol-2-yl. In certain embodiments, $R^1$ is 5-thioxo-4,5-dihydro-1H-1,2,4-triazol-3-yl. In certain embodiments, $R^1$ is 1H-1,2,4-triazol-5-yl. In certain embodiments, $R^1$ is 1,3,4-oxadiazol-2-yl. In certain embodiments, $R^1$ is 1,2,4-oxadiazol-5-yl. In certain embodiments, $R^1$ is 3-$R^{10}$-1,2,4-oxadiazol-5-yl. In certain embodiments, $R^1$ is selected from the group consisting of —C(=O)OH, —C(=O)OMe, —C(=O)OEt, —C(=O)O-nPr, —C(=O)O-iPr, —C(=O)O-cyclopentyl, and —C(=O)O-cyclohexyl.

In certain embodiments, $R^2$ is O. In certain embodiments, $R^2$ is N(OH). In certain embodiments, $R^2$ is N(Me). In certain embodiments, $R^2$ is N(OMe). In certain embodiments, $R^2$ is N(NH$_2$). In certain embodiments, $R^2$ is =$NR^9$. In certain embodiments, $R^2$ is =N(O$R^9$). In certain embodiments, $R^2$ is =N(N$R^9R^9$). In certain embodiments, $R^1$ and $R^2$ combine to form =N—O—C(=O)—, wherein the =N group is bound to the ring carbon atom marked "*". In certain embodiments, $R^1$ and $R^2$ combine to form =N—N($R^9$)—C(=O)—, wherein the =N group is bound to the ring carbon atom marked "*".

In certain embodiments, M is C($R^4$)($R^{4'}$). In certain embodiments, M is $NR^8$.

In certain embodiments, bond a is a single bond. In other embodiments, bond a is a double bond.

In certain embodiments, bond a is a single bond, and Y is C(=O), and M is selected from the group consisting of C($R^4$)($R^{4'}$) and $NR^8$. In certain embodiments, bond a is a single bond, and Y is selected from the group consisting of CH$R^5$, O, S, S(=O), S(=O)$_2$, and $NR^5$, and M is C($R^4$)($R^{4'}$). In certain embodiments, if Y is selected from the group consisting of CH$R^5$, 0, and $NR^5$, $R^4$ and $R^{4'}$ optionally combine with each other to form =O. In certain embodiments, Y is CH, M is C($R^4$)($R^4$), $R^4$ is CH$_2$, and Y and $R^4$ form a single bond to generate cyclopropyl. In certain embodiments, bond a is a double bond, and Y is selected from the group consisting of C$R^5$ and N, M is C($R^4$)($R^{4'}$), and $R^{4'}$ is absent.

In certain embodiments, $R^3$ is H. In certain embodiments, $R^3$ is not H. In certain embodiments, $R^3$ is alkyl-substituted oxetanyl. In certain embodiments, $R^3$ is optionally substituted $C_1$-$C_6$ alkyl. In certain embodiments, $R^3$ is optionally substituted $C_3$-$C_8$ cycloalkyl. In certain embodiments, $R^{3'}$ is H. In certain embodiments, $R^{3'}$ is not H. In certain embodiments, $R^{3'}$ is alkyl-substituted oxetanyl. In certain embodiments, $R^{3'}$ is optionally substituted $C_1$-$C_6$ alkyl. In certain embodiments, $R^{3'}$ is optionally substituted $C_3$-$C_8$ cycloalkyl. In certain embodiments, $R^4$ is H. In certain embodiments, $R^4$ is alkyl-substituted oxetanyl. In certain embodiments, $R^4$ is optionally substituted $C_1$-$C_6$ alkyl. In certain embodiments, $R^4$ is optionally substituted $C_3$-$C_8$ cycloalkyl. In certain embodiments, $R^{4'}$ is H. In certain embodiments, $R^{4'}$ is alkyl-substituted oxetanyl. In certain embodiments, $R^{4'}$ is optionally substituted $C_1$-$C_6$ alkyl. In certain embodiments, $R^{4'}$ is optionally substituted $C_3$-$C_8$ cycloalkyl. In certain embodiments, the $C_1$-$C_6$ alkyl is optionally substituted with 1-3 groups independently selected from the group consisting of F, Cl, Br, I, OH, and OMe. In certain embodiments, the $C_3$-$C_8$ cycloalkyl is optionally substituted with 1-3 groups independently selected from the group consisting of F, $C_1$, Br, I, OH, and OMe. In certain embodiments, $R^3$ is H and $R^{3'}$ is isopropyl. In certain embodiments, $R^3$ is H and $R^{3'}$ is tert-butyl. In certain embodiments, $R^3$ is methyl and $R^{3'}$ is isopropyl. In certain embodiments, $R^3$ is methyl and $R^{3'}$ is tert-butyl. In certain embodiments, $R^3$ is methyl and $R^{3'}$ is methyl. In certain embodiments, $R^3$ is methyl and $R^{3'}$ is ethyl. In certain embodiments, $R^3$ is ethyl and $R^{3'}$ is ethyl.

In certain embodiments, one pair selected from the group consisting of $R^3$/$R^{3'}$, $R^4$/$R^{4'}$, and $R^3$/$R^4$ combine to form $C_1$-$C_6$ alkanediyl. In certain embodiments, one pair selected from the group consisting of $R^3$/$R^{3'}$, $R^4$/$R^{4'}$, and $R^3$/$R^4$ combine to form —(CH$_2$)$_n$O(CH$_2$)$_n$—, which is optionally substituted with at least one $C_1$-$C_6$ alkyl or halo, and wherein each occurrence of n is independently selected from the group consisting of 1 and 2. In certain embodiments, one pair selected from the group consisting of $R^3$/$R^{3'}$, $R^4$/$R^{4'}$, and $R^3$/$R^4$ combine to form —(CH$_2$)$_n$N$R^9$(CH$_2$)$_n$—, which is optionally substituted with at least one $C_1$-$C_6$ alkyl or halo, and wherein each occurrence of n is independently selected from the group consisting of 1 and 2. In certain embodiments, one pair selected from the group consisting of $R^3$/$R^{3'}$, $R^4$/$R^{4'}$, and $R^3$/$R^4$ combine to form —(CH$_2$)$_n$S(CH$_2$)$_n$—, which is optionally substituted with at least one $C_1$-$C_6$ alkyl or halo, and wherein each occurrence of n is independently selected from the group consisting of 1 and 2. In certain embodiments, one pair selected from the group consisting of $R^3$/$R^3$, $R^4$/$R^{4'}$, and $R^3$/$R^4$ combine to form —(CH$_2$)$_n$S(=O)(CH$_2$)$_n$—, which is optionally substituted with at least one $C_1$-$C_6$ alkyl or halo, and wherein each occurrence of n is independently selected from the group consisting of 1 and 2. In certain embodiments, one pair selected from the group consisting of $R^3$/$R^{3'}$, $R^4$/$R^{4'}$, and $R^3$/$R^4$ combine to form —(CH$_2$)$_n$S(=O)$_2$(CH$_2$)$_n$—, which is optionally substituted with at least one $C_1$-$C_6$ alkyl or halo, and wherein each occurrence of n is independently selected from the group consisting of 1 and 2. In certain embodiments, $R^3$ and $R^{3'}$ are independently selected from the group consisting of H, methyl, ethyl, n-propyl, isopropyl, n-butyl, isobutyl, sec-butyl, t-butyl, hydroxymethyl, 2-hydroxy-ethyl, 2-methoxy-ethyl, methoxymethyl, 2-methyl-1-methoxy-prop-2-yl, 2-methyl-1-hydroxy-prop-2-yl, and trifluoroethyl. In certain embodiments, $R^4$ and $R^{4'}$ are independently selected from the group consisting of H, methyl, ethyl, n-propyl, isopropyl, n-butyl, isobutyl, sec-butyl, t-butyl, hydroxymethyl, 2-hydroxy-ethyl, 2-methoxy-ethyl, methoxymethyl, and 2-methyl-1-methoxy-prop-2-yl. In certain embodiments, $R^4$ is selected from the group consisting of H, methyl, ethyl, 2-hydroxy-ethyl, and 2-methoxy-ethyl. In certain embodiments, $R^3$ and $R^{3'}$ combine to form 1,1-methanediyl (i.e., an exocyclic double bond). In certain embodiments, $R^3$ and $R^{3'}$ combine to form 1,2-ethanediyl. In certain embodiments, $R^3$ and $R^{3'}$ combine to form 1,3-propanediyl. In certain embodiments, $R^3$ and $R^{3'}$ combine to form 1,4-butanediyl. In certain embodiments, $R^3$ and $R^{3'}$ combine to form 1,5-pentanediyl. In certain embodiments, $R^3$ and $R^{3'}$ combine to form 1,6-hexanediyl. In certain embodiments, $R^3$ and $R^4$ combine to form 1,2-ethanediyl. In certain embodiments, $R^3$ and $R^4$ combine to form 1,3-propanediyl. In certain embodiments, $R^3$ and $R^4$ combine to form 1,3-propanediyl. In certain embodiments, $R^3$ and $R^4$ combine to form (1- or 2-methyl)-1,4-butanediyl. In certain embodiments, $R^3$ and $R^4$ combine to form (1,1-, 1,2-, 1,3-, or 2,2-dimethyl)-1,3-propanediyl. In certain embodiments, $R^3$ and $R^4$ combine to form 1,5-pentanediyl. In certain embodiments, $R^3$ and $R^4$ combine to form 1,6-hexanediyl.

In certain embodiments, $R^5$ is H. In certain embodiments, $R^5$ is optionally substituted $C_1$-$C_6$ alkyl. In certain embodiments, $R^5$ is optionally substituted $C_3$-$C_8$ cycloalkyl.

In certain embodiments, $X^1$ is $CR^{6I}$. In certain embodiments, $X^1$ is N. In certain embodiments, $X^2$ is $CR^{6II}$. In certain embodiments, $X^2$ is N. In certain embodiments, $X^3$ is $CR^{6III}$. In certain embodiments, $X^3$ is N. In certain embodiments, $X^4$ is $CR^{6IV}$. In certain embodiments, $X^4$ is N. In certain embodiments, $X^3$ and $X^4$ combine to form —S—. In certain embodiments, $X^1$ and $X^2$ combine to form —S—.

In certain embodiments, none of $X^1$, $X^2$, $X^3$ and $X^4$ is N. In certain embodiments, only one from the group consisting of $X^1$, $X^2$, $X^3$ and $X^4$ is N. In certain embodiments, only two from the group consisting of $X^1$, $X^2$, $X^3$ and $X^4$ are N. In certain embodiments, $X^1$ is N. In certain embodiments, $X^2$ is N. In certain embodiments, $X^3$ is N. In certain embodiments, $X^4$ is N. In certain embodiments, if at least one N is present in the ring comprising $X^1$—$X^4$, the at least one N is optionally alkylated with $C_1$-$C_6$ alkyl if the adjacent carbon atom in the ring is substituted with —OH. In certain embodiments, $X^1$ is CH. In certain embodiments, $X^4$ is CH. In certain embodiments, $X^1$ is N. In certain embodiments, $X^4$ is N. In certain embodiments, $X^2$ is $CR^{6II}$, wherein $R^{6II}$ is not H. In certain embodiments, $X^3$ is $CR^{6III}$, wherein $R^{6III}$ is not H.

In certain embodiments, $R^{6I}$ is H. In certain embodiments, $R^{6I}$ is halo. In certain embodiments, $R^{6I}$ is —CN. In certain embodiments, $R^{6I}$ is pyrrolidinyl. In certain embodiments, $R^{6I}$ is optionally substituted $C_1$-$C_6$ alkyl (e.g., $C_1$-$C_6$ hydroxyalkyl, alkoxy-$C_1$-$C_6$ alkyl, and/or $C_1$-$C_6$ haloalkyl). In certain embodiments, $R^{6I}$ is optionally substituted $C_1$-$C_6$ alkenyl. In certain embodiments, $R^{6I}$ is optionally substituted $C_3$-$C_8$ cycloalkyl. In certain embodiments, $R^{6I}$ is optionally substituted heterocyclyl (e.g., morpholinyl). In certain embodiments, $R^{6I}$ is —OR. In certain embodiments, $R^{6I}$ is $C_1$-$C_6$ haloalkoxy. In certain embodiments, $R^{6I}$ is —N(R)(R). In certain embodiments, $R^{6I}$ is —$NO_2$. In certain embodiments, $R^{6I}$ is —S(=O)$_2$N(R)(R). In certain embodiments, $R^{6I}$ is acyl. In certain embodiments, $R^{6I}$ is $C_1$-$C_6$ alkoxycarbonyl.

In certain embodiments, $R^{6II}$ is H. In certain embodiments, $R^{6II}$ is halo. In certain embodiments, $R^{6II}$ is —CN. In certain embodiments, $R^{6II}$ is pyrrolidinyl. In certain embodiments, $R^{6II}$ is optionally substituted $C_1$-$C_6$ alkyl (e.g., $C_1$-$C_6$ hydroxyalkyl, alkoxy-$C_1$-$C_6$ alkyl, and/or $C_1$-$C_6$ haloalkyl). In certain embodiments, $R^{6II}$ is optionally substituted $C_1$-$C_6$ alkenyl. In certain embodiments, $R^{6II}$ is optionally substituted $C_3$-$C_8$ cycloalkyl. In certain embodiments, $R^{6II}$ is optionally substituted heterocyclyl (e.g., morpholinyl). In certain embodiments, $R^{6II}$ is —OR. In certain embodiments, $R^{6II}$ is $C_1$-$C_6$ haloalkoxy. In certain embodiments, $R^{6II}$ is —N(R)(R). In certain embodiments, $R^{6II}$ is —$NO_2$. In certain embodiments, $R^{6II}$ is —S(=O)$_2$N(R)(R). In certain embodiments, $R^{6II}$ is acyl. In certain embodiments, $R^{6II}$ is $C_1$-$C_6$ alkoxycarbonyl.

In certain embodiments, $R^{6III}$ is H. In certain embodiments, $R^{6III}$ is halo. In certain embodiments, $R^{6III}$ is —CN. In certain embodiments, $R^{6III}$ is pyrrolidinyl. In certain embodiments, $R^{6III}$ is optionally substituted $C_1$-$C_6$ alkyl (e.g., $C_1$-$C_6$ hydroxyalkyl, alkoxy-$C_1$-$C_6$ alkyl, and/or $C_1$-$C_6$ haloalkyl). In certain embodiments, $R^{6III}$ is optionally substituted $C_1$-$C_6$ alkenyl. In certain embodiments, $R^{6III}$ is optionally substituted $C_3$-$C_8$ cycloalkyl. In certain embodiments, $R^{6III}$ is optionally substituted heterocyclyl (e.g., morpholinyl). In certain embodiments, $R^{6III}$ is —OR. In certain embodiments, $R^{6III}$ is $C_1$-$C_6$ haloalkoxy. In certain embodiments, $R^{6III}$ is —N(R)(R). In certain embodiments, $R^{6III}$ is —$NO_2$. In certain embodiments, $R^{6III}$ is —S(=O)$_2$N(R)(R). In certain embodiments, $R^{6I}$ is acyl. In certain embodiments, $R^{6III}$ is $C_1$-$C_6$ alkoxycarbonyl.

In certain embodiments, $R^{6IV}$ is H. In certain embodiments, $R^{6IV}$ is halo. In certain embodiments, $R^{6IV}$ is —CN. In certain embodiments, $R^{6IV}$ is pyrrolidinyl. In certain embodiments, $R^{6IV}$ is optionally substituted $C_1$-$C_6$ alkyl (e.g., $C_1$-$C_6$ hydroxyalkyl, alkoxy-$C_1$-$C_6$ alkyl, and/or $C_1$-$C_6$ haloalkyl). In certain embodiments, $R^{6IV}$ is optionally substituted $C_1$-$C_6$ alkenyl. In certain embodiments, $R^{6IV}$ is optionally substituted $C_3$-$C_8$ cycloalkyl. In certain embodiments, $R^{6IV}$ is optionally substituted heterocyclyl (e.g., morpholinyl). In certain embodiments, $R^{6IV}$ is —OR. In certain embodiments, $R^{6IV}$ is $C_1$-$C_6$ haloalkoxy. In certain embodiments, $R^{6IV}$ is —N(R)(R). In certain embodiments, $R^{6IV}$ is —$NO_2$. In certain embodiments, $R^{6IV}$ is —S(=O)$_2$N(R)(R). In certain embodiments, $R^{6IV}$ is acyl. In certain embodiments, $R^{6IV}$ is $C_1$-$C_6$ alkoxycarbonyl.

In certain embodiments, $R^{6I}$ is selected from the group consisting of H, F, Cl, Br, I, CN, amino, methylamino, dimethylamino, methoxyethylamino, pyrrolidinyl, methoxy, ethoxy, n-propoxy, isopropoxyl, n-butoxy, sec-butoxy, isobutoxy, t-butoxy, 2-methoxy-ethoxy, 2-hydroxy-ethoxy, 3-methoxy-prop-1-yl, 3-hydroxy-prop-1-yl, 3-methoxy-prop-1-oxy, 3-hydroxy-prop-1-oxy, 4-methoxy-but-1-yl, 4-hydroxy-but-1-yl, 4-methoxy-but-1-oxy, 4-hydroxy-but-1-oxy, 2-hydroxy-ethoxy, 3-hydroxy-prop-1-yl, 4-hydroxy-but-1-yl, 3-hydroxy-2,2-dimethyl-prop-1-oxy, cyclopropyl-methoxy, 2,2,2-trifluoroethoxy, 2-(2-haloethoxy)-ethoxy, 2-(N-morpholino)-ethyl, 2-(N-morpholino)-ethoxy, 3-(N-morpholino)-prop-1-yl, 3-(N-morpholino)-prop-1-oxy, 4-(N-morpholino)-but-1-yl, 4-(N-morpholino)-butl-oxy, 2-amino-ethyl, 2-(NHC(=O)O$^t$Bu)-ethyl, 2-amino-ethoxy, 2-(NHC(=O)O$^t$Bu)-ethoxy, 3-amino-prop-1-yl, 3-(NHC(=O)O$^t$Bu)-prop-1-yl, 3-amino-prop-1-oxy, 3-(NHC(=O)O$^t$Bu)-prop-1-oxy, 4-amino-but-1-yl, 4-(NHC(=O)O$^t$Bu)-but-1-yl, 4-amino-but-1-oxy, and 4-(NHC(=O)O$^t$Bu)-but-1-oxy. In certain embodiments, $R^{6I}$ is selected from the group consisting of H, F, Cl, Br, I, CN, amino, methylamino, dimethylamino, methoxyethylamino, pyrrolidinyl, methoxy, ethoxy, n-propoxy, isopropoxyl, n-butoxy, sec-butoxy, isobutoxy, t-butoxy, 2-methoxy-ethoxy, 2-hydroxy-ethoxy, 3-methoxy-prop-1-yl, 3-hydroxy-prop-1-yl, 3-methoxy-prop-1-oxy, 3-hydroxy-prop-1-oxy, 4-methoxy-but-1-yl, 4-hydroxy-but-1-yl, 4-methoxy-but-1-oxy, 4-hydroxy-but-1-oxy, 2-hydroxy-ethoxy, 3-hydroxy-prop-1-yl, 4-hydroxy-but-1-yl, 3-hydroxy-2,2-dimethyl-prop-1-oxy, cyclopropyl-methoxy, 2,2,2-trifluoroethoxy, 2-(2-haloethoxy)-ethoxy, 2-(N-morpholino)-ethyl, 2-(N-morpholino)-ethoxy, 3-(N-morpholino)-prop-1-yl, 3-(N-morpholino)-prop-1-oxy, 4-(N-morpholino)-but-1-yl, 4-(N-morpholino)-butl-oxy, 2-amino-ethyl, 2-(NHC(=O)O$^t$Bu)-ethyl, 2-amino-ethoxy, 2-(NHC(=O)O$^t$Bu)-ethoxy, 3-amino-prop-1-yl, 3-(NHC(=O)O$^t$Bu)-prop-1-yl, 3-amino-prop-1-oxy, 3-(NHC(=O)O$^t$Bu)-prop-1-oxy, 4-amino-but-1-yl, 4-(NHC(=O)O$^t$Bu)-but-1-yl, 4-amino-but-1-oxy, and 4-(NHC(=O)O$^t$Bu)-but-1-oxy. In certain embodiments, $R^{6III}$ is selected from the group consisting of H, F, Cl, Br, I, CN, amino, methylamino, dimethylamino, methoxyethylamino, pyrrolidinyl, methoxy, ethoxy, n-propoxy, isopropoxyl, n-butoxy, sec-butoxy, isobutoxy, t-butoxy, 2-methoxy-ethoxy, 2-hydroxy-ethoxy, 3-methoxy-prop-1-yl, 3-hydroxy-prop-1-yl, 3-methoxy-prop-1-oxy, 3-hydroxy-prop-1-oxy, 4-methoxy-but-1-yl, 4-hydroxy-but-1-yl, 4-methoxy-but-1-oxy, 4-hydroxy-but-1-oxy, 2-hydroxy-ethoxy, 3-hydroxy-prop-1-yl, 4-hydroxy-but-1-yl, 3-hydroxy-2,2-dimethyl-prop-1-oxy, cyclopropyl-methoxy, 2,2,2-trifluoroethoxy, 2-(2-haloethoxy)-ethoxy, 2-(N-morpholino)-ethyl, 2-(N-morpholino)-ethoxy, 3-(N-morpholino)-prop-1-yl, 3-(N-morpholino)-prop-1-oxy, 4-(N-morpholino)-but-1-yl, 4-(N-morpholino)-butl-oxy, 2-amino-ethyl, 2-(NHC(=O)O$^t$Bu)-ethyl, 2-amino-ethoxy, 2-(NHC(=O)O$^t$Bu)-ethoxy, 3-amino-prop-1-yl, 3-(NHC(=O)O$^t$Bu)-prop-1-yl, 3-amino-prop-1-oxy, 3-(NHC(=O)O$^t$Bu)-prop-1-oxy, 4-amino-but-1-yl, 4-(NHC(=O)O$^t$Bu)-but-1-yl, 4-amino-but-1-oxy, and 4-(NHC(=O)O$^t$Bu)-but-1-oxy. In certain embodiments, $R^{6I}$V is selected from the group consisting of H, F, Cl, Br, I, CN, amino, methylamino, dimethylamino, methoxyethylamino, pyrrolidinyl, methoxy, ethoxy, n-propoxy, isopropoxyl, n-butoxy, sec-butoxy, isobutoxy, t-butoxy, 2-methoxy-ethoxy, 2-hydroxy-ethoxy, 3-methoxy-prop-1-yl, 3-hydroxy-prop-1-yl, 3-methoxy-prop-1-oxy, 3-hydroxy-prop-1-oxy, 4-methoxy-but-1-yl, 4-hydroxy-but-1-yl, 4-methoxy-but-1-oxy, 4-hydroxy-but-1-oxy, 2-hydroxy-ethoxy, 3-hydroxy-prop-1-yl, 4-hydroxy-but-1-yl, 3-hydroxy-2,2-dimethyl-prop-1-oxy, cyclopropyl-methoxy, 2,2,2-trifluoroethoxy, 2-(2-haloethoxy)-ethoxy, 2-(N-morpholino)-ethyl, 2-(N-morpholino)-ethoxy, 3-(N-morpholino)-prop-1-yl, 3-(N-morpholino)-prop-1-oxy, 4-(N-morpholino)-but-1-yl, 4-(N-morpholino)-butl-oxy, 2-amino-ethyl, 2-(NHC(=O)O$^t$Bu)-ethyl, 2-amino-ethoxy, 2-(NHC(=O)O$^t$Bu)-ethoxy, 3-amino-prop-1-yl, 3-(NHC(=O)O$^t$Bu)-prop-1-yl, 3-amino-prop-1-oxy, 3-(NHC(=O)O$^t$Bu)-prop-1-oxy, 4-amino-but-1-yl, 4-(NHC(=O)O$^t$Bu)-but-1-yl, 4-amino-but-1-oxy, and 4-(NHC(=O)O$^t$Bu)-but-1-oxy.

In certain embodiments, $X^1$ is $CR^{6I}$, $X^2$ is $CR^{6II}$, $X^3$ is $CR^{6III}$, and $X^4$ is $CR^6IV$. In certain embodiments, $R^{6I}$ is H, $R^{6II}$ is methoxy, $R^{6III}$ is 3-methoxy-propoxy, and $R^{6IV}$ is H. In certain embodiments, $R^{6I}$ is H, $R^{6II}$ is chloro, $R^{6III}$ is 3-methoxy-propoxy, and $R^{6IV}$ is H. In certain embodiments, $R^{6I}$ is H, $R^{6II}$ is isopropyl, $R^{6III}$ is 3-methoxy-propoxy, and $R^{6IV}$ is H. In certain embodiments, $R^{6I}$ is H, $R^{6II}$ is methoxy, $R^{6III}$ is methoxy, and $R^{6IV}$ is H. In certain embodiments, $R^{6I}$ is H, $R^{6II}$ is chloro, $R^{6III}$ is methoxy, and $R^{6IV}$ is H. In certain embodiments, $R^{6I}$ is H, $R^{6II}$ is cyclopropyl, $R^{6III}$ is methoxy, and $R^{6IV}$ is H.

In certain embodiments, $X^1$ is N, $X^2$ is $CR^{6II}$, $X^3$ is $CR^{6III}$, and $X^4$ is $CR^6IV$. In certain embodiments, $R^{6II}$ is methoxy, $R^{6III}$ is 3-methoxy-propoxy, and $R^{6IV}$ is H. In certain embodiments, $R^{6II}$ is chloro, $R^{6III}$ is 3-methoxy-propoxy, and $R^{6IV}$ is H. In certain embodiments, $R^{6II}$ is cyclopropyl, $R^{6III}$ is 3-methoxy-propoxy, and $R^{6IV}$ is H. In certain embodiments, $R^{6II}$ is methoxy, $R^{6III}$ is methoxy, and $R^{6IV}$ is H. In certain embodiments, $R^{6II}$ is chloro, $R^{6III}$ is methoxy, and $R^{6IV}$ is H. In certain embodiments, $R^{6II}$ is cyclopropyl, $R^{6III}$ is methoxy, and $R^{6I}$V is H.

In certain embodiments, each occurrence of R is independently selected from the group consisting of H, $C_1$-$C_6$ alkyl, R'-substituted $C_1$-$C_6$ alkyl, $C_1$-$C_6$ hydroxyalkyl, optionally substituted ($C_1$-$C_6$ alkoxy)-$C_1$-$C_6$ alkyl, and optionally substituted $C_3$-$C_8$ cycloalkyl. In certain embodiments, each occurrence of R' is independently selected from the group consisting of —NH$_2$, —NH($C_1$-$C_6$ alkyl), —N($C_1$-$C_6$ alkyl)($C_1$-$C_6$ alkyl), —NHC(=O)O$^t$Bu, —N($C_1$-$C_6$ alkyl)C(=O)O$^t$Bu, or a 5- or 6-membered heterocyclic group (such as, but not limited to, pyrrolidinyl, morpholinyl, piperidinyl, piperazinyl, and so forth), which is optionally N-linked.

In certain embodiments, $X^2$ is $CR^{6II}$, $X^3$ is $CR^{6III}$, and $R^{6II}$ and $R^{6III}$ combine to form a divalent group selected from the group consisting of —O(CHF)O—, —O(CF$_2$)O—, —O(CR$^9$R$^9$)O—, —O(CH$_2$)(CH$_2$)O— and —O(CH$_2$)(CR$^{11}$R$^{11}$)(CH$_2$)O—.

In certain embodiments, $R^7$ is H. In certain embodiments, $R^7$ is OH. In certain embodiments, $R^7$ is halo. In certain embodiments, $R^7$ is $C_1$-$C_6$ alkoxy. In certain embodiments, $R^7$ is optionally substituted $C_1$-$C_6$ alkyl (e.g., optionally substituted with 1-3 independently selected halo groups). In certain embodiments, $R^7$ is optionally substituted $C_3$-$C_8$ cycloalkyl. In certain embodiments, $R^7$ is H. In certain embodiments, $R^7$ is F. In certain embodiments, $R^7$ is methoxy. In certain embodiments, $R^7$ is ethoxy. In certain embodiments, $R^7$ is methyl. In certain embodiments, $R^7$ is ethyl. In certain embodiments, $R^7$ is n-propyl. In certain embodiments, $R^7$ is isopropyl.

In certain embodiments, $R^8$ is selected from the group consisting of H, optionally substituted $C_1$-$C_6$ alkyl, and optionally substituted $C_3$-$C_8$ cycloalkyl.

In certain embodiments, each occurrence of $R^9$ is independently selected from the group consisting of H and $C_1$-$C_6$ alkyl (e.g., methyl or ethyl).

In certain embodiments, $R^{10}$ is selected from the group consisting of optionally substituted $C_1$-$C_6$ alkyl and optionally substituted phenyl.

In certain embodiments, each occurrence of $R^{11}$ is independently selected from the group consisting of H, OH, $C_1$-$C_6$ alkyl, $C_1$-$C_6$ alkoxy, alkoxy-$C_1$-$C_6$ alkyl and alkoxy-$C_1$-$C_6$ alkoxy, wherein two $R^{11}$ groups bound to the same carbon atom are not simultaneously OH; or two $R^1$ groups combine with the carbon atom to which they are bound to form a moiety selected from the group consisting of C=O, C=CH$_2$ and oxetane-3,3-diyl.

In certain embodiments, the compounds of the invention, or a salt, solvate, stereoisomer (such as, in a non-limiting example, an enantiomer or diastereoisomer thereof), any mixture of one or more stereoisomers (such as, in a non-limiting example, mixtures in any proportion of enantiomers thereof, and/or mixtures in any proportion of diastereoisomers thereof), tautomer, and/or any mixture of tautomers thereof, are recited in Tables 1-3.

The compounds of the invention disclosed in the present application were screened to evaluate their potency and toxicity profiles. Several compounds having desirable potency and toxicity profiles were identified in these screens. For example, Example 22 was cleared relatively slowly from blood plasma in dogs, and, as measured in a Langendorff assay (Bell, et al., *Retrograde heart perfusion: The Langendorff technique of isolated heart perfusion*, J. Mol. Cell. Cardiol. 2011, 940-950; Guo, et al., *Validation of a guinea pig Langendorff heart model for assessing potential cardiovascular liability of drug candidates*, J. Pharmacol. Toxicol. Methods, 2009, 130-151), that compound showed no effect on any of the measured electrocardiogram parameters at any of the concentrations tested. These results suggest that Example 22 can be developed as an HBV therapeutic agent that is administered to human subjects in need thereof once per day, and that is unlikely to have undesirable cardiac side effects.

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or mixtures thereof, or in the case where two or more chiral center are present, all diastereomers or mixtures thereof.

In certain embodiments, the compounds of the invention exist as tautomers. All tautomers are included within the scope of the compounds recited herein.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$C $^{18}$F, $^{12}$I, $^{125}$I, $^{13}$N, $^{15}$N, $^{15}$O, $^{17}$O, $^{18}$O, $^{32}$P, and $^{35}$S. In certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

In all of the embodiments provided herein, examples of suitable optional substituents are not intended to limit the scope of the claimed invention. The compounds of the invention may contain any of the substituents, or combinations of substituents, provided herein.

Salts

The compounds described herein may form salts with acids or bases, and such salts are included in the present invention. The term "salts" embraces addition salts of free acids or bases that are useful within the methods of the invention. The term "pharmaceutically acceptable salt" refers to salts that possess toxicity profiles within a range that affords utility in pharmaceutical applications. In certain embodiments, the salts are pharmaceutically acceptable salts. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (or N-methylglucamine) and procaine. All of these salts may be prepared from the corresponding compound by reacting, for example, the appropriate acid or base with the compound.

Combination Therapies

In one aspect, the compounds of the invention are useful within the methods of the invention in combination with one or more additional agents useful for treating HBV infections. These additional agents may comprise compounds or compositions identified herein, or compounds (e.g., commercially available compounds) known to treat, prevent, or reduce the symptoms of HBV infections.

Non-limiting examples of one or more additional agents useful for treating HBV infections include: (a) reverse transcriptase inhibitors; (b) capsid inhibitors; (c) cccDNA formation inhibitors; (d) sAg secretion inhibitors; (e) oligomeric nucleotides targeted to the Hepatitis B genome; and (f) immunostimulators.

(a) Reverse Transcriptase Inhibitors

In certain embodiments, the reverse transcriptase inhibitor is a reverse-transcriptase inhibitor (NARTI or NRTI). In other embodiments, the reverse transcriptase inhibitor is a nucleotide analog reverse-transcriptase inhibitor (NtARTI or NtRTI).

Reported reverse transcriptase inhibitors include, but are not limited to, entecavir, clevudine, telbivudine, lamivudine, adefovir, and tenofovir, tenofovir disoproxil, tenofovir alafenamide, adefovir dipovoxil, (1R,2R,3R,5R)-3-(6-amino-9H-9-purinyl)-2-fluoro-5-(hydroxymethyl)-4-methylenecyclopentan-1-ol (described in U.S. Pat. No. 8,816,074, incorporated herein in its entirety by reference), emtricitabine, abacavir, elvucitabine, ganciclovir, lobucavir, famciclovir, penciclovir, and amdoxovir.

Reported reverse transcriptase inhibitors further include, but are not limited to, entecavir, lamivudine, and (1R,2R,3R,5R)-3-(6-amino-9H-9-purinyl)-2-fluoro-5-(hydroxymethyl)-4-methylenecyclopentan-1-ol.

Reported reverse transcriptase inhibitors further include, but are not limited to, a covalently bound phosphoramidate or phosphonamidate moiety of the above-mentioned reverse transcriptase inhibitors, or as described in for example U.S. Pat. No. 8,816,074, US Patent Application Publications No. US 2011/0245484 A1, and US 2008/0286230A1, all of which incorporated herein in their entireties by reference.

Reported reverse transcriptase inhibitors further include, but are not limited to, nucleotide analogs that comprise a phosphoramidate moiety, such as, for example, methyl ((((1R,3R,4R,5R)-3-(6-amino-9H-purin-9-yl)-4-fluoro-5-hydroxy-2-methylenecyclopentyl) methoxy)(phenoxy) phosphoryl)-(D or L)-alaninate and methyl ((((1R,2R,3R,4R)-3-fluoro-2-hydroxy-5-methylene-4-(6-oxo-1,6-dihydro-9H-purin-9-yl)cyclopentyl)methoxy)(phenoxy) phosphoryl)-(D or L)-alaninate. Also included are the individual diastereomers thereof, which include, for example, methyl ((R)-(((1R,3R,4R,5R)-3-(6-amino-9H-purin-9-yl)-4-fluoro-5-hydroxy-2-methylenecyclopentyl)methoxy)(phenoxy) phosphoryl)-(D or L)-alaninate and methyl ((S)-(((1R,3R,4R,5R)-3-(6-amino-9H-purin-9-yl)-4-fluoro-5-hydroxy-2-methylenecyclopentyl) methoxy)(phenoxy)phosphoryl)-(D or L)-alaninate.

Reported reverse transcriptase inhibitors further include, but are not limited to, compounds comprising a phosphonamidate moiety, such as, for example, tenofovir alafenamide, as well as those described in U.S. Patent Application Publication No. US 2008/0286230 A1, incorporated herein in its entirety by reference. Methods for preparing stereoselective phosphoramidate or phosphonamidate containing actives are described in, for example, U.S. Pat. No. 8,816,074, as well as U.S. Patent Application Publications No. US 2011/0245484 A1 and US 2008/0286230 A1, all of which incorporated herein in their entireties by reference.

(b) Capsid Inhibitors

As described herein, the term "capsid inhibitor" includes compounds that are capable of inhibiting the expression and/or function of a capsid protein either directly or indirectly. For example, a capsid inhibitor may include, but is not limited to, any compound that inhibits capsid assembly, induces formation of non-capsid polymers, promotes excess capsid assembly or misdirected capsid assembly, affects capsid stabilization, and/or inhibits encapsidation of RNA (pgRNA). Capsid inhibitors also include any compound that inhibits capsid function in a downstream event(s) within the replication process (e.g., viral DNA synthesis, transport of relaxed circular DNA (rcDNA) into the nucleus, covalently closed circular DNA (cccDNA) formation, virus maturation, budding and/or release, and the like). For example, in certain embodiments, the inhibitor detectably inhibits the expression level or biological activity of the capsid protein as measured, e.g., using an assay described herein. In certain embodiments, the inhibitor inhibits the level of rcDNA and downstream products of viral life cycle by at least 5%, at least 10%, at least 20%, at least 50%, at least 75%, or at least 90%.

Reported capsid inhibitors include, but are not limited to, compounds described in International Patent Applications Publication Nos WO 2013006394, WO 2014106019, and WO2014089296, all of which incorporated herein in their entireties by reference.

Reported capsid inhibitors also include, but are not limited to, the following compounds and pharmaceutically acceptable salts and/or solvates thereof: Bay-41-4109 (see Int'l Patent Application Publication No. WO 2013144129), AT-61 (see Int'l Patent Application Publication No. WO 1998033501; and King, et al., 1998, Antimicrob. Agents Chemother. 42(12):3179-3186), DVR-01 and DVR-23 (see Int'l Patent Application Publication No. WO 2013006394; and Campagna, et al., 2013, J. Virol. 87(12):6931, all of which incorporated herein in their entireties by reference.

In addition, reported capsid inhibitors include, but are not limited to, those generally and specifically described in U.S. Patent Application Publication Nos. US 2015/0225355, US 2015/0132258, US 2016/0083383, US 2016/0052921 and Int'l Patent Application Publication Nos. WO 2013096744, WO 2014165128, WO 2014033170, WO 2014033167, WO 2014033176, WO 2014131847, WO 2014161888, WO 2014184350, WO 2014184365, WO 2015059212, WO 2015011281, WO 2015118057, WO 2015109130, WO 2015073774, WO 2015180631, WO 2015138895, WO 2016089990, WO 2017015451, WO 2016183266, WO 2017011552, WO 2017048950, WO2017048954, WO 2017048962, WO 2017064156 and are incorporated herein in their entirety by reference.

(c) cccDNA Formation Inhibitors

Covalently closed circular DNA (cccDNA) is generated in the cell nucleus from viral rcDNA and serves as the transcription template for viral mRNAs. As described herein, the term "cccDNA formation inhibitor" includes compounds that are capable of inhibiting the formation and/or stability of cccDNA either directly or indirectly. For example, a cccDNA formation inhibitor may include, but is not limited to, any compound that inhibits capsid disassembly, rcDNA entry into the nucleus, and/or the conversion of rcDNA into cccDNA. For example, in certain embodiments, the inhibitor detectably inhibits the formation and/or stability of the cccDNA as measured, e.g., using an assay described herein. In certain embodiments, the inhibitor inhibits the formation and/or stability of cccDNA by at least 5%, at least 10%, at least 20%, at least 50%, at least 75%, or at least 90%.

Reported cccDNA formation inhibitors include, but are not limited to, compounds described in Int'l Patent Application Publication No. WO 2013130703, and are incorporated herein in their entirety by reference.

In addition, reported cccDNA formation inhibitors include, but are not limited to, those generally and specifically described in U.S. Patent Application Publication No. US 2015/0038515 A1, and are incorporated herein in their entirety by reference.

(d) sAg Secretion Inhibitors

As described herein, the term "sAg secretion inhibitor" includes compounds that are capable of inhibiting, either directly or indirectly, the secretion of sAg (S, M and/or L surface antigens) bearing subviral particles and/or DNA containing viral particles from HBV-infected cells. For example, in certain embodiments, the inhibitor detectably inhibits the secretion of sAg as measured, e.g., using assays known in the art or described herein, e.g., ELISA assay or by Western Blot. In certain embodiments, the inhibitor inhibits the secretion of sAg by at least 5%, at least 10%, at least 20%, at least 50%, at least 75%, or at least 90%. In certain embodiments, the inhibitor reduces serum levels of sAg in a patient by at least 5%, at least 10%, at least 20%, at least 50%, at least 75%, or at least 90%.

Reported sAg secretion inhibitors include compounds described in U.S. Pat. No. 8,921,381, as well as compounds described in U.S. Patent Application Publication Nos. US 2015/0087659 and US 2013/0303552, all of which are incorporated herein in their entireties by reference.

In addition, reported sAg secretion inhibitors include, but are not limited to, those generally and specifically described in Int'l Patent Application Publication Nos. WO 2015113990, WO 2015173164, US 2016/0122344, WO 2016107832, WO 2016023877, WO 2016128335, WO 2016177655, WO 2016071215, WO 2017013046, WO 2017016921, WO 2017016960, WO 2017017042, WO 2017017043, WO 2017102648, WO 2017108630, WO 2017114812, WO 2017140821 and are incorporated herein in their entirety by reference.

(e) Immunostimulators

The term "immunostimulator" includes compounds that are capable of modulating an immune response (e.g., stimulate an immune response (e.g., an adjuvant)). Immunostimulators include, but are not limited to, polyinosinic:polycytidylic acid (poly I:C) and interferons.

Reported immunostimulators include, but are not limited to, agonists of stimulator of IFN genes (STING) and interleukins. Reported immunostimulators further include, but are not limited to, HBsAg release inhibitors, TLR-7 agonists (such as, but not limited to, GS-9620, RG-7795), T-cell stimulators (such as, but not limited to, GS-4774), RIG-1 inhibitors (such as, but not limited to, SB-9200), and SMAC-mimetics (such as, but not limited to, Birinapant).

(f) Oligomeric Nucleotides

Reported oligomeric nucleotides targeted to the Hepatitis B genome include, but are not limited to, Arrowhead-ARC-520 (see U.S. Pat. No. 8,809,293; and Wooddell et al., 2013, Molecular Therapy 21(5):973-985, all of which incorporated herein in their entireties by reference).

In certain embodiments, the oligomeric nucleotides can be designed to target one or more genes and/or transcripts of the HBV genome. Oligomeric nucleotide targeted to the Hepatitis B genome also include, but are not limited to, isolated, double stranded, siRNA molecules, that each include a sense strand and an antisense strand that is hybridized to the sense strand. In certain embodiments, the siRNA target one or more genes and/or transcripts of the HBV genome.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to elsewhere herein may be applied to experimental data to generate a corresponding graph to aid in assessing the effects of the drug combination. The corresponding graphs associated with the equations referred to elsewhere herein are the concentration-effect curve, isobologram curve and combination index curve, respectively.

Synthesis

The present invention further provides methods of preparing the compounds of the present invention. Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It should be contemplated that the invention includes each and every one of the synthetic schemes described and/or depicted herein.

It is appreciated that where typical or preferred process conditions (i.e., reaction temperatures, times, mole ratios of reactants, solvents, pressures, and so forth) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene, et al., Protective Groups in Organic Synthesis, 2d. Ed. (Wiley & Sons, 1991), the entire disclosure of which is incorporated by reference herein for all purposes.

The reactions or the processes described herein can be carried out in suitable solvents that can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

In certain embodiments, a compound of the invention can be prepared, for example, according to the illustrative synthetic methods outlined in Scheme I:

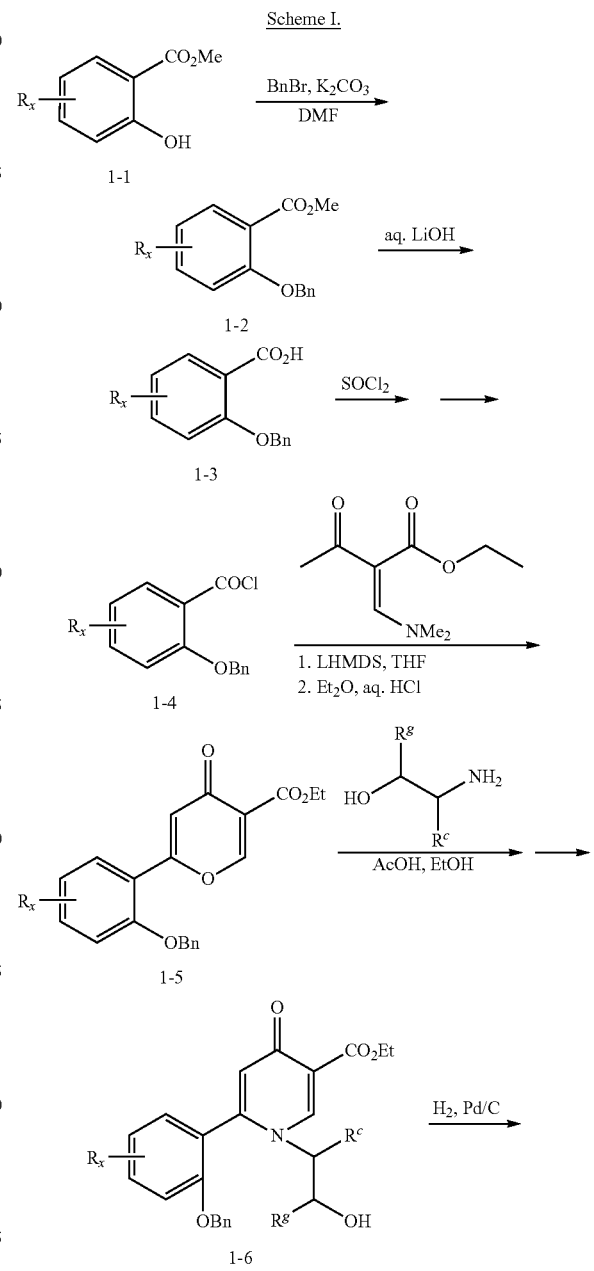

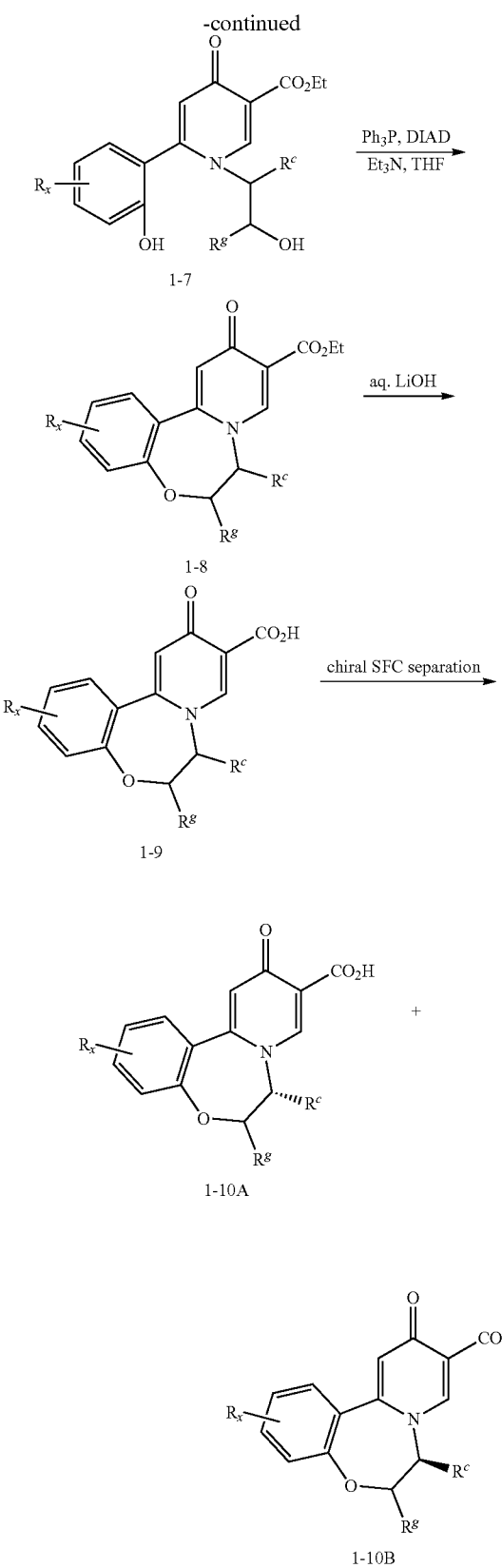
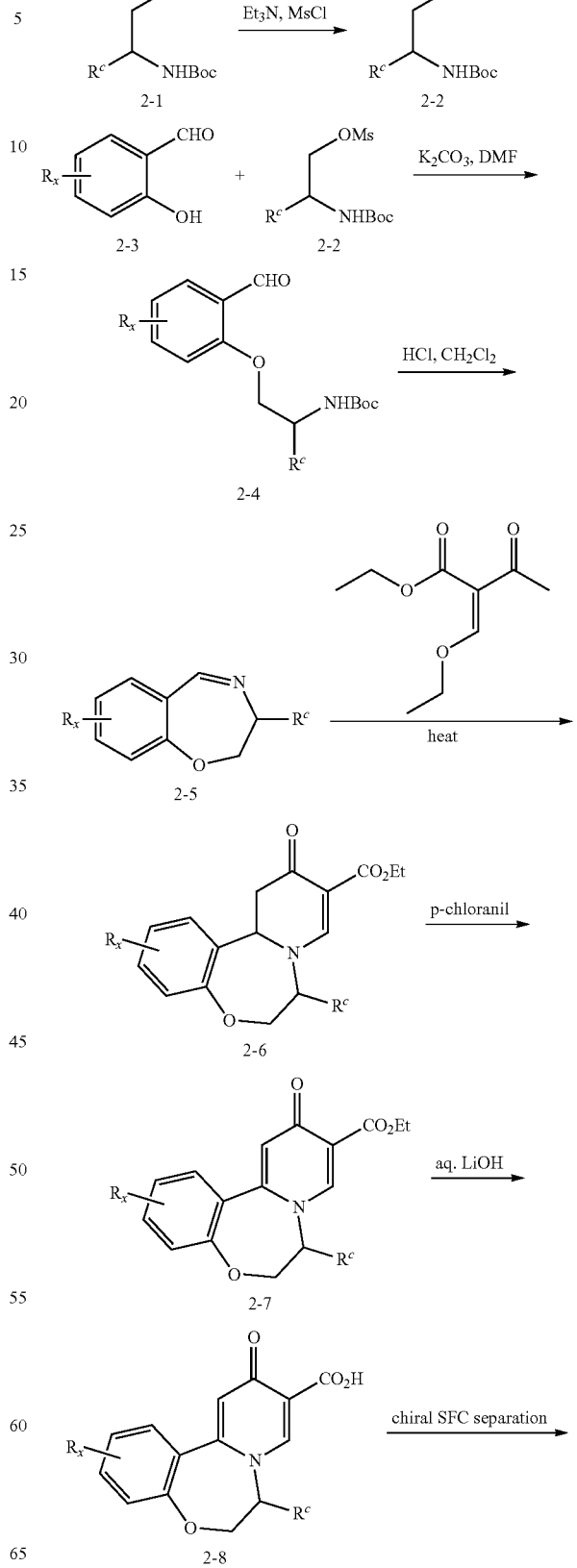
Scheme II.
In certain embodiments, a compound of the invention can be prepared, for example, according to the illustrative synthetic methods outlined in Scheme II:

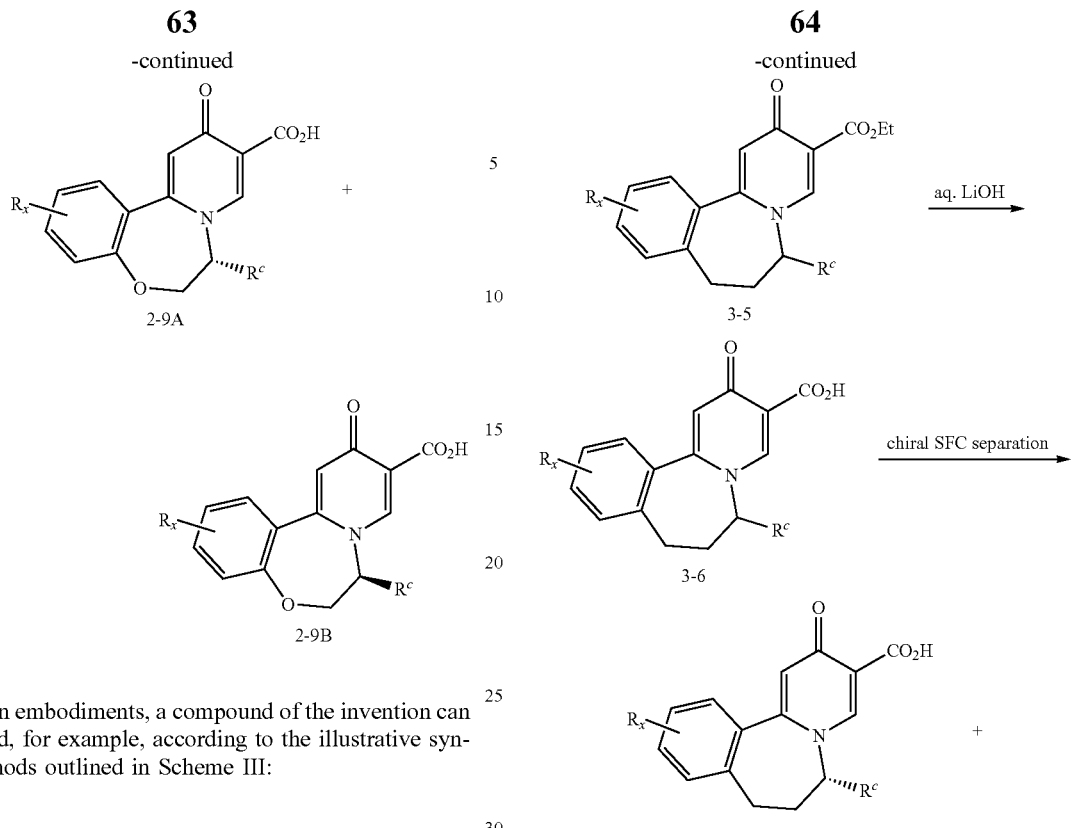
In certain embodiments, a compound of the invention can be prepared, for example, according to the illustrative synthetic methods outlined in Scheme III:
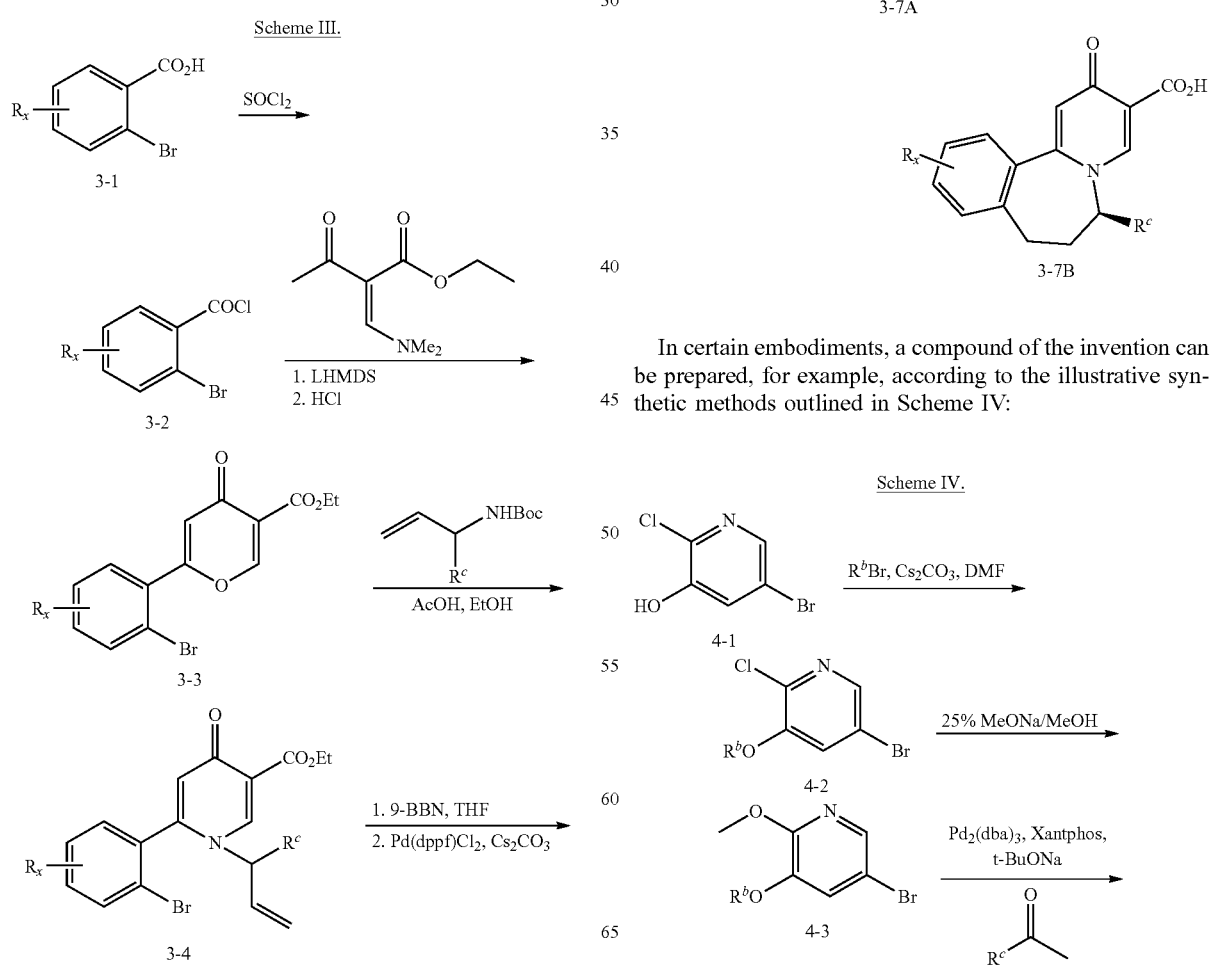
In certain embodiments, a compound of the invention can be prepared, for example, according to the illustrative synthetic methods outlined in Scheme IV:

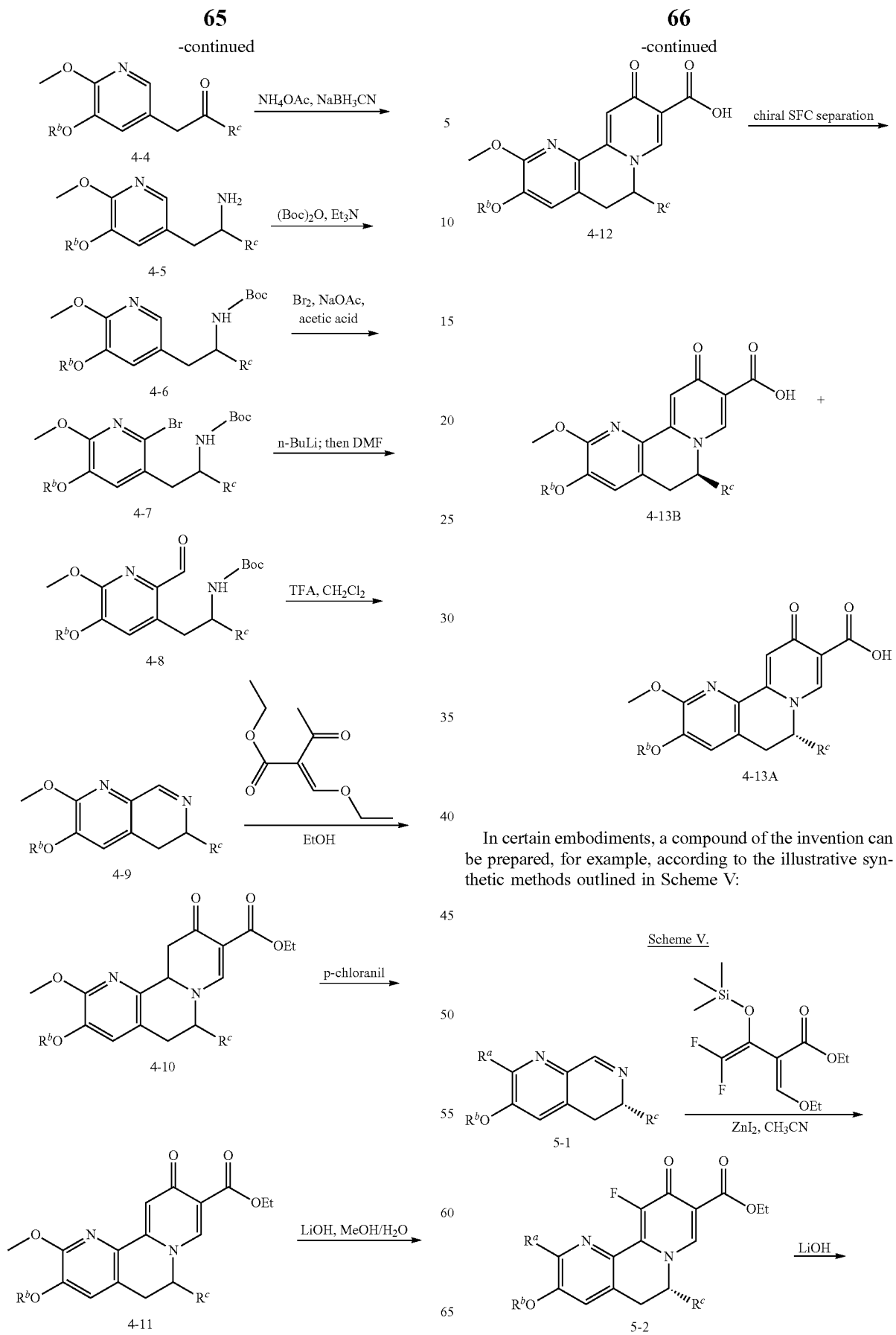
In certain embodiments, a compound of the invention can be prepared, for example, according to the illustrative synthetic methods outlined in Scheme V:
Scheme V.

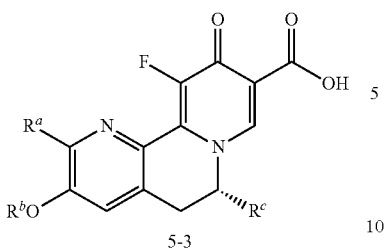
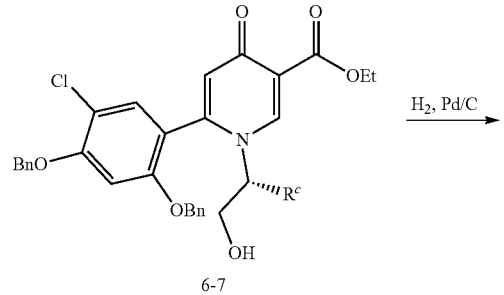
In certain embodiments, a compound of the invention can be prepared, for example, according to the illustrative synthetic methods outlined in Scheme VI:
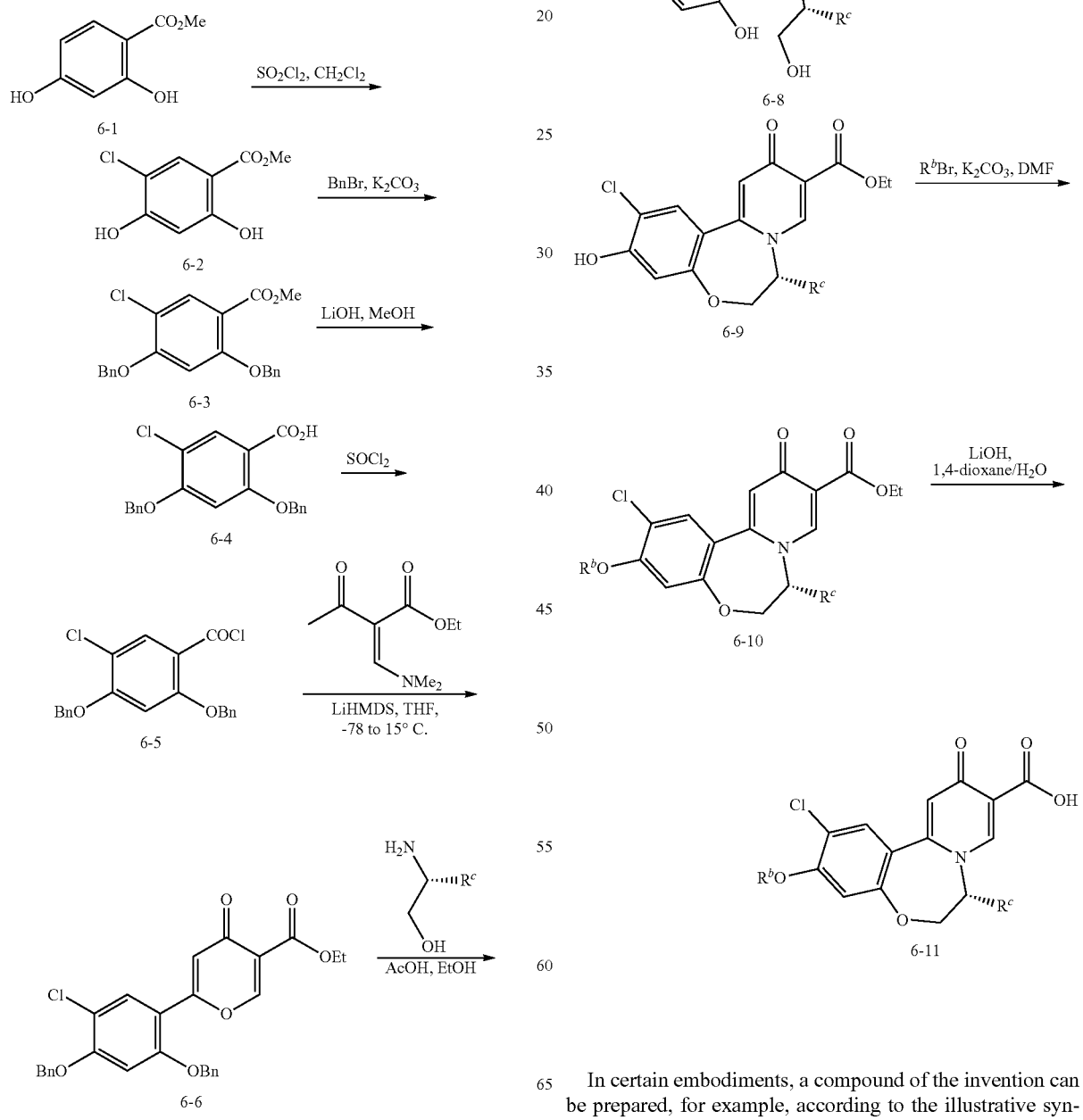
In certain embodiments, a compound of the invention can be prepared, for example, according to the illustrative synthetic methods outlined in Scheme VII:

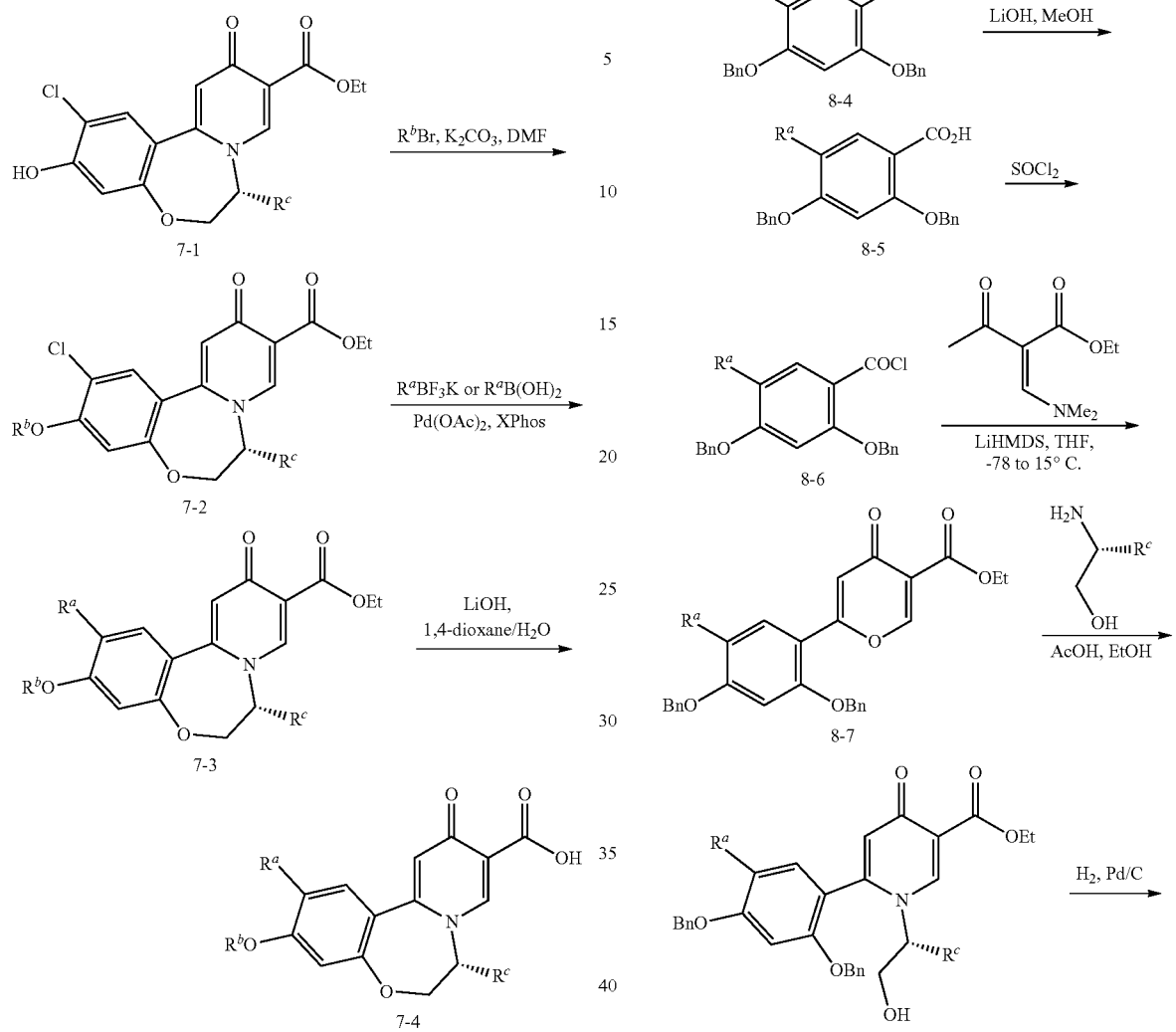
In certain embodiments, a compound of the invention can be prepared, for example, according to the illustrative synthetic methods outlined in Scheme VIII:
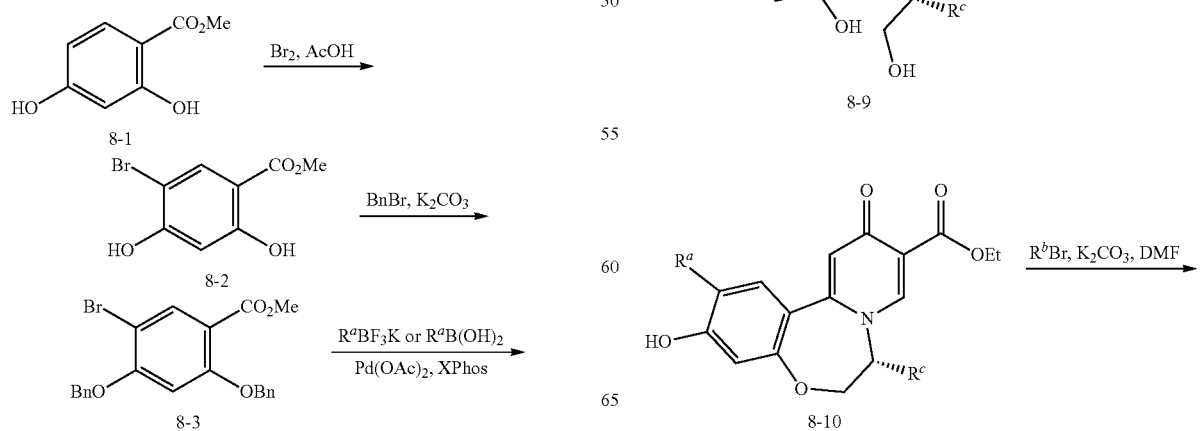

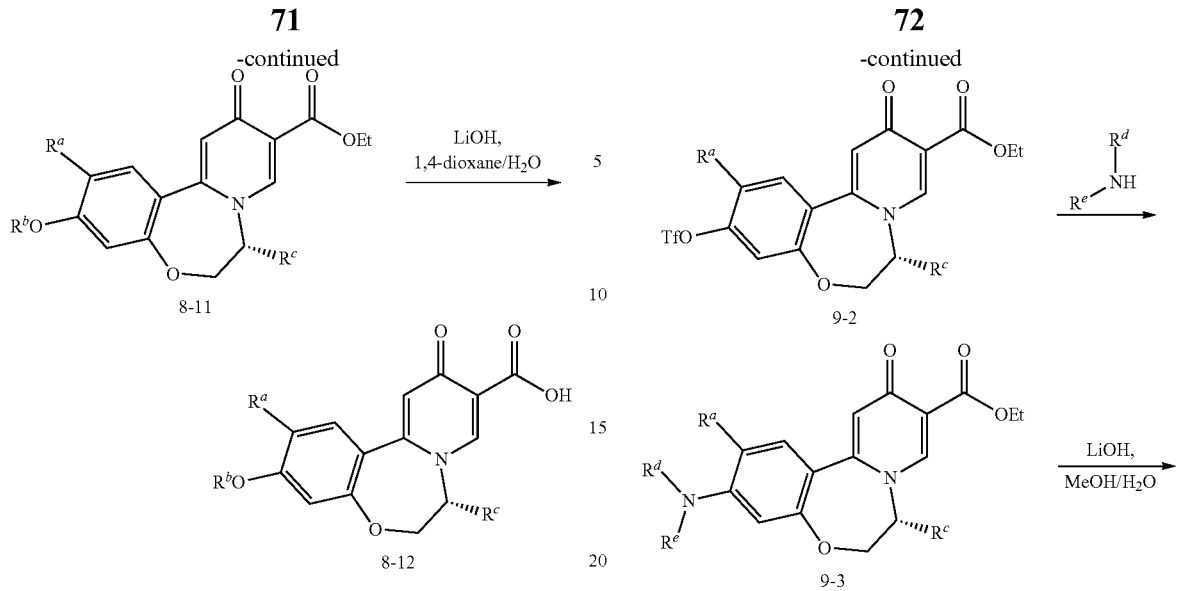
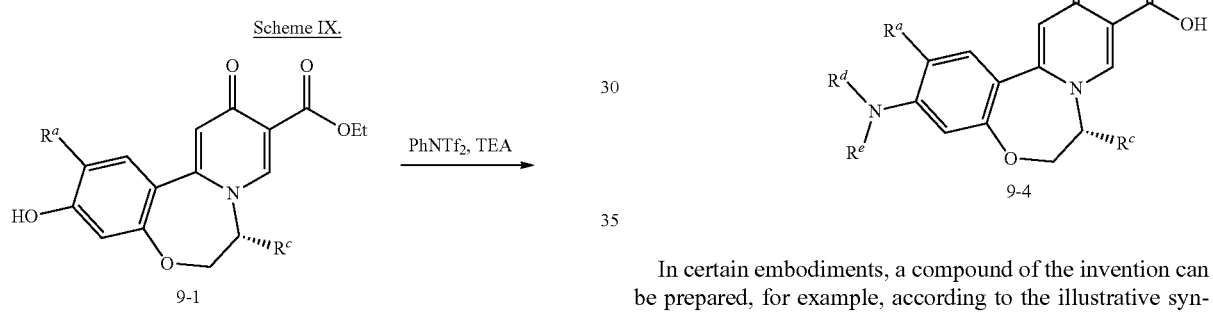
In certain embodiments, a compound of the invention can be prepared, for example, according to the illustrative synthetic methods outlined in Scheme IX:
In certain embodiments, a compound of the invention can be prepared, for example, according to the illustrative synthetic methods outlined in Scheme X:
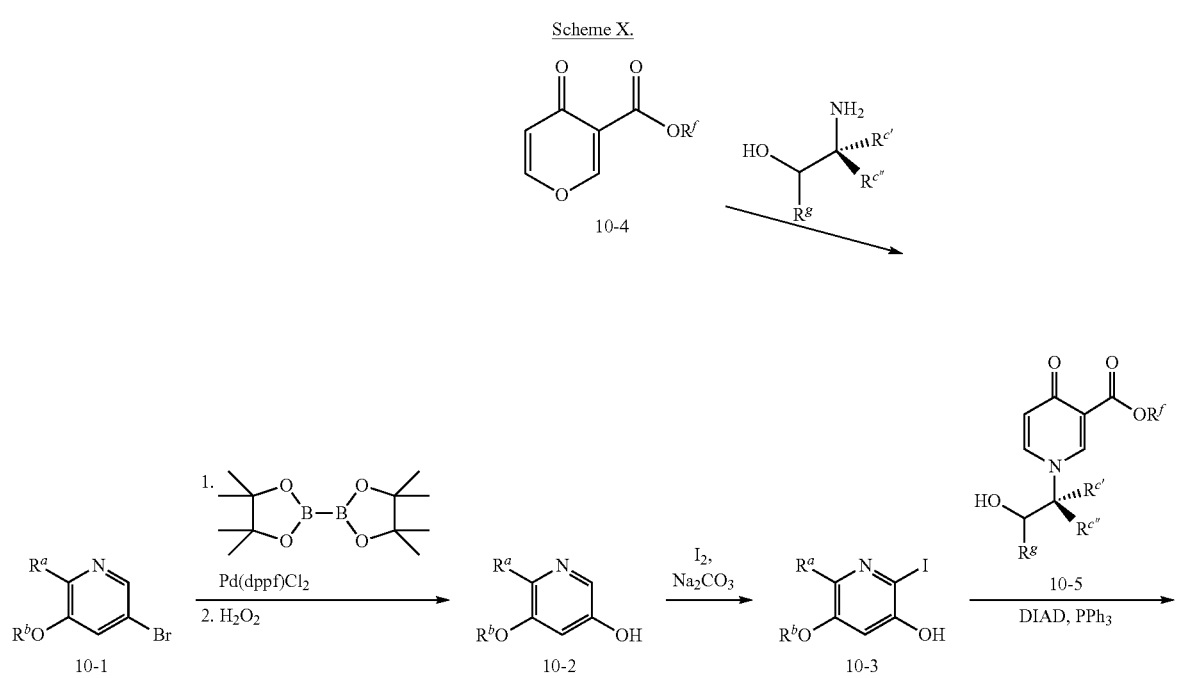

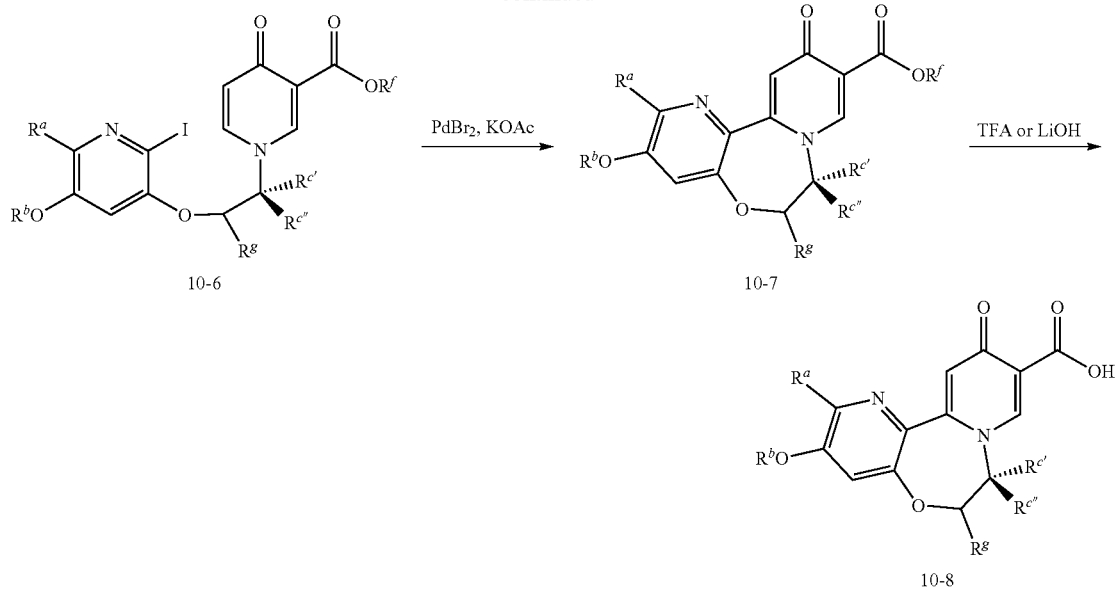
In certain embodiments, a compound of the invention can be prepared, for example, according to the illustrative synthetic methods outlined in Scheme XI:
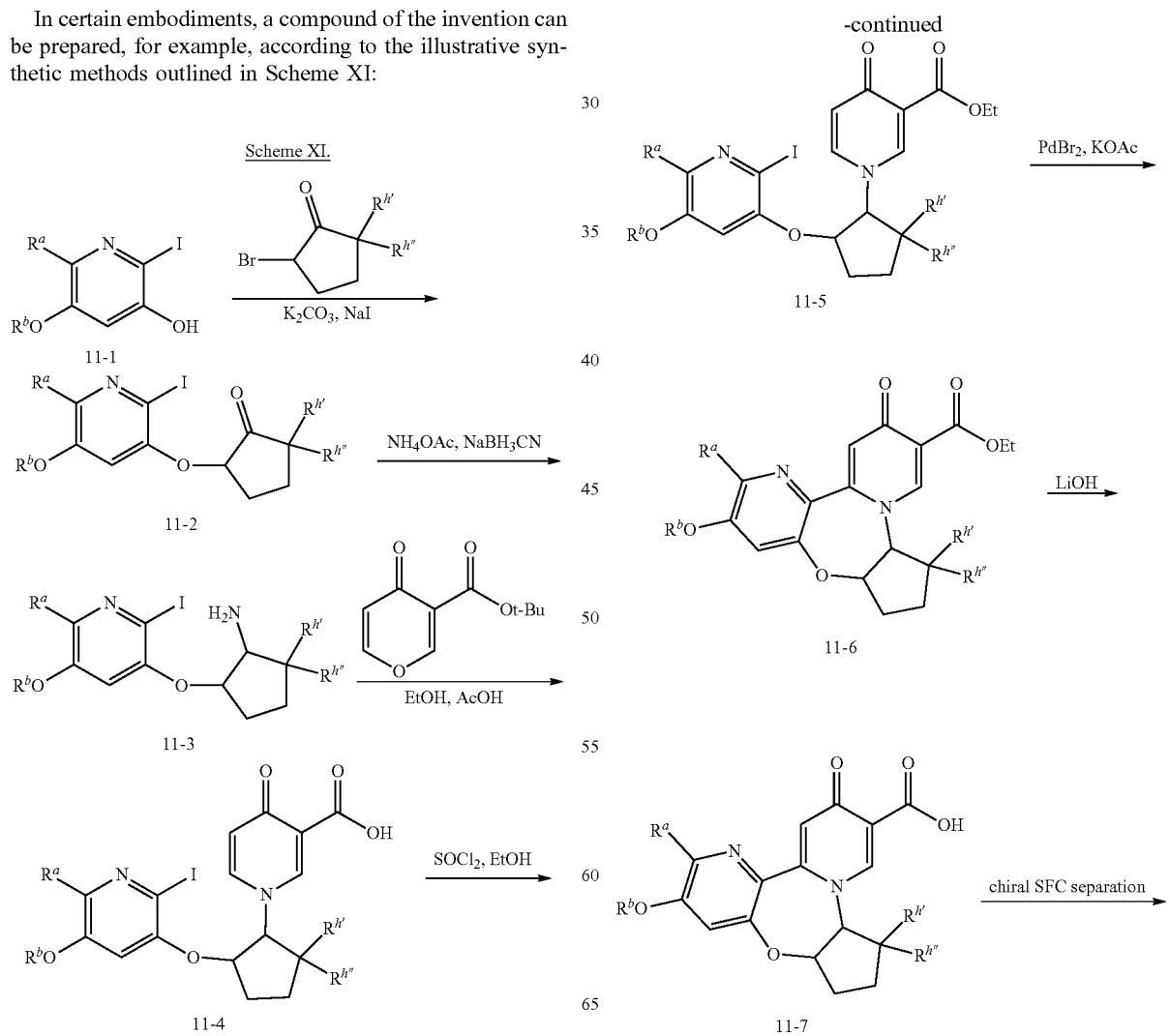

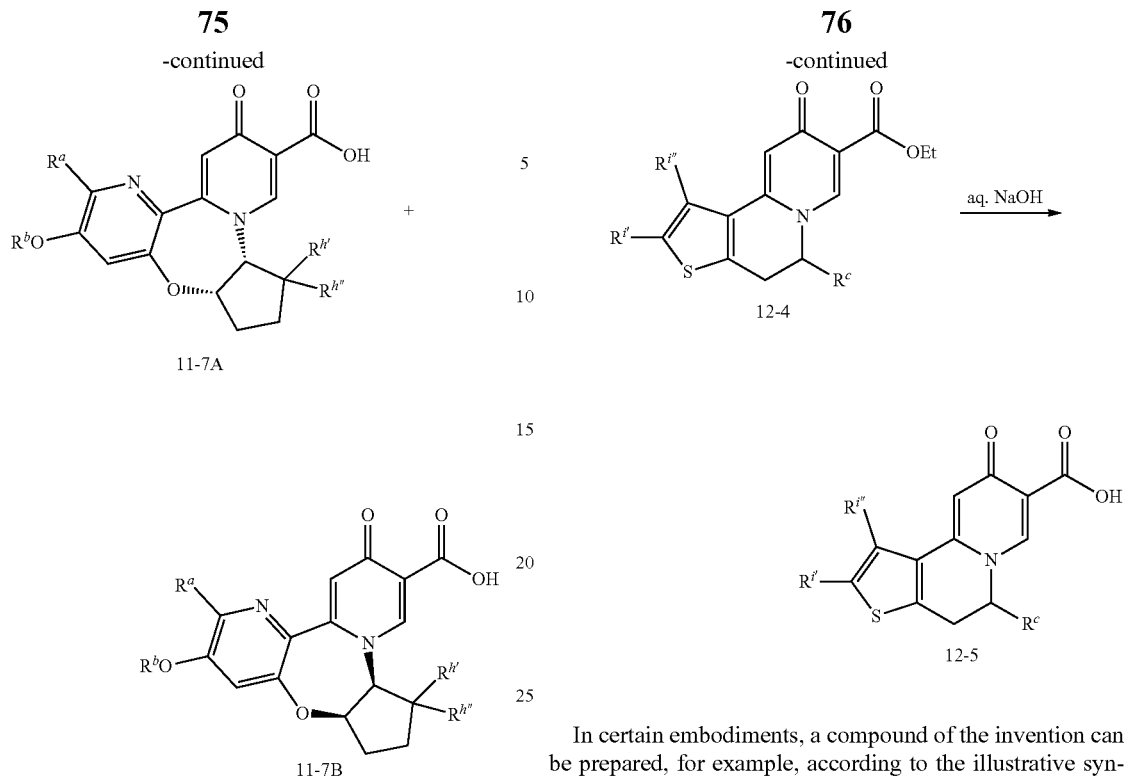
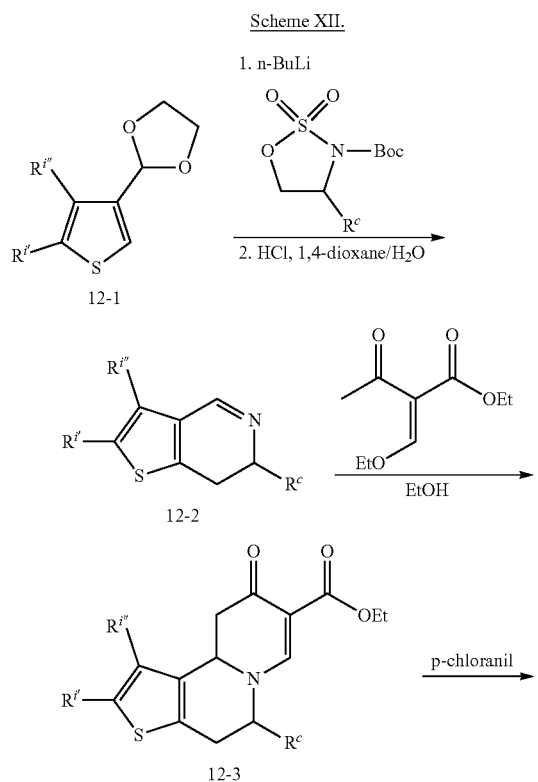
In certain embodiments, a compound of the invention can be prepared, for example, according to the illustrative synthetic methods outlined in Scheme XII:
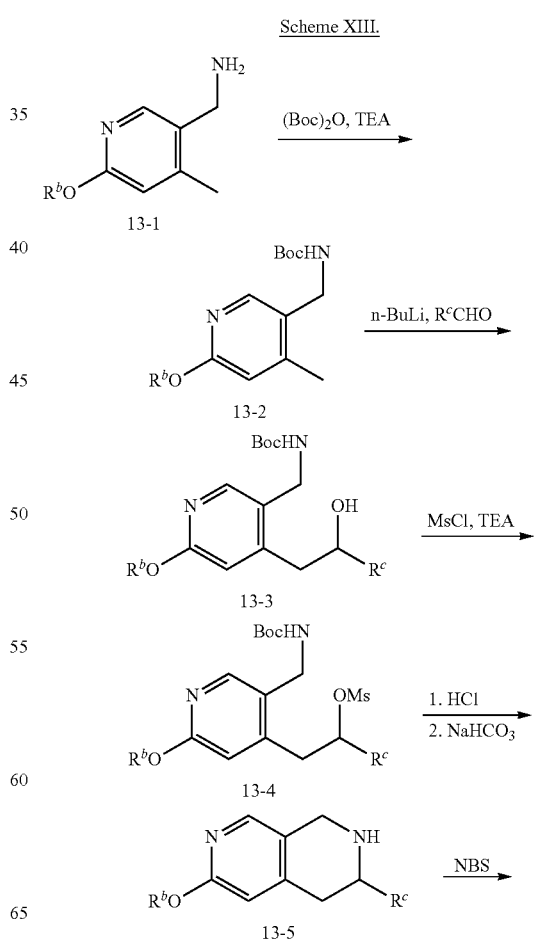
In certain embodiments, a compound of the invention can be prepared, for example, according to the illustrative synthetic methods outlined in Scheme XIII:

-continued
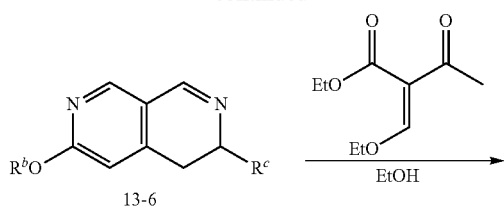
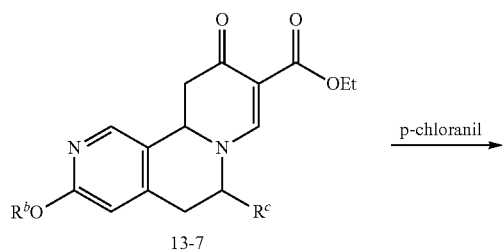
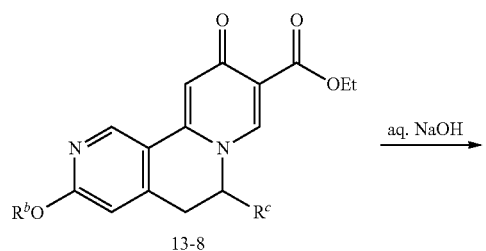
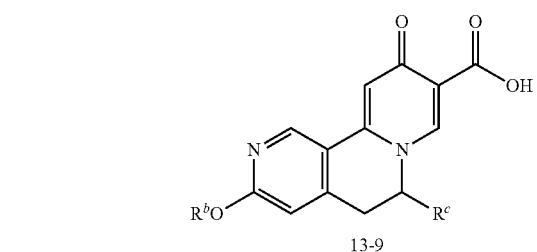
In certain embodiments, a compound of the invention can be prepared, for example, according to the illustrative synthetic methods outlined in Scheme XIV:
Scheme XIV.
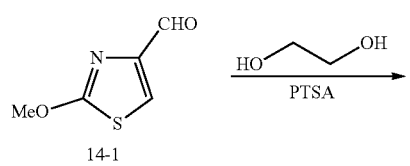
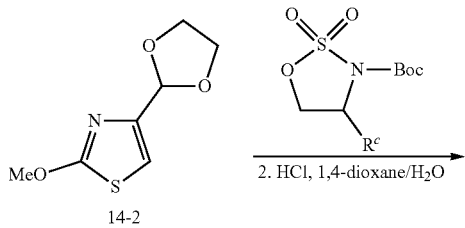
In certain embodiments, a compound of the invention can be prepared, for example, according to the illustrative synthetic methods outlined in Scheme XV:
Scheme XV.
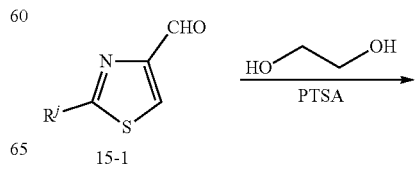

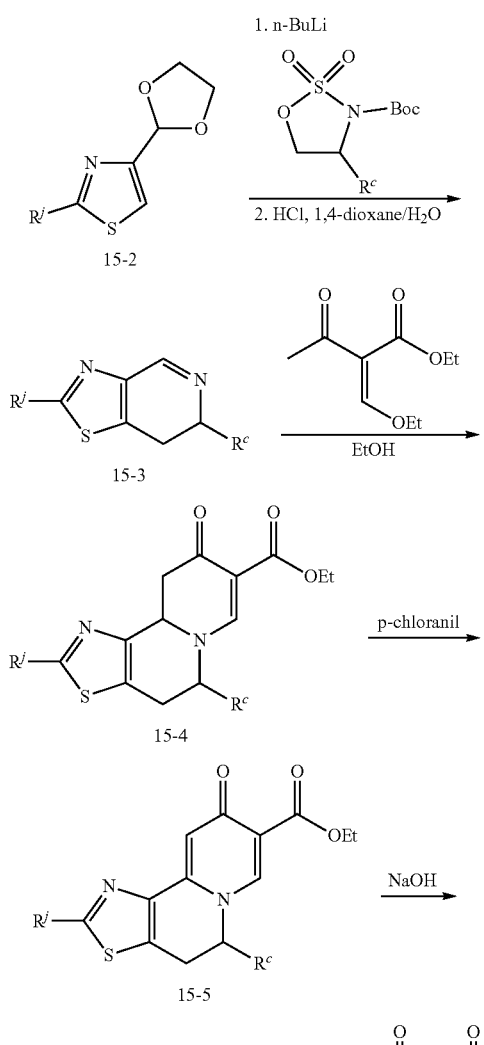
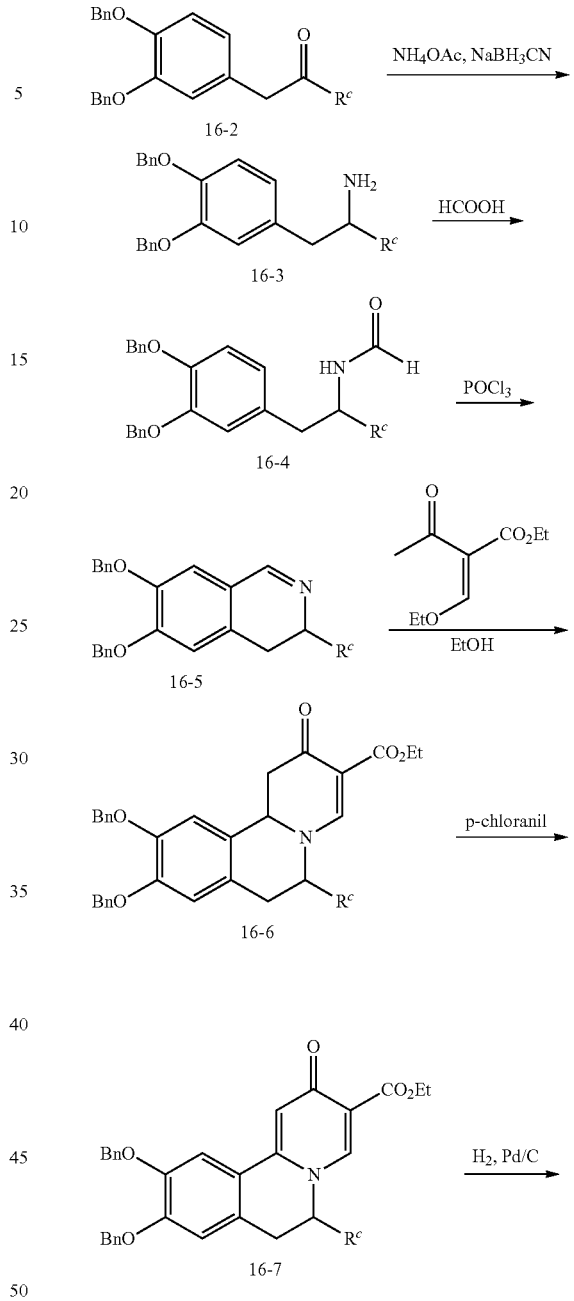
In certain embodiments, a compound of the invention can be prepared, for example, according to the illustrative synthetic methods outlined in Scheme XVI:
Scheme XVI.
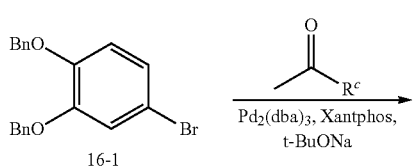
In certain embodiments, a compound of the invention can be prepared, for example, according to the illustrative synthetic methods outlined in Scheme XVII:

Scheme XVII.
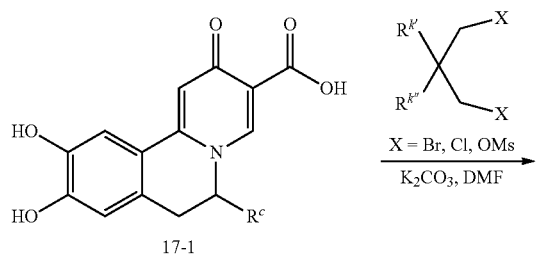
17-1
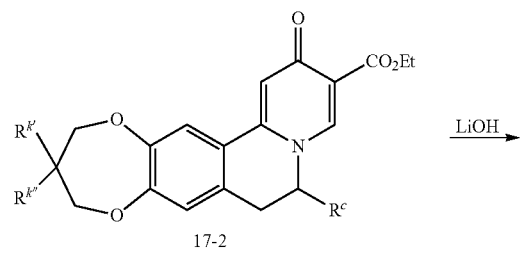
17-2
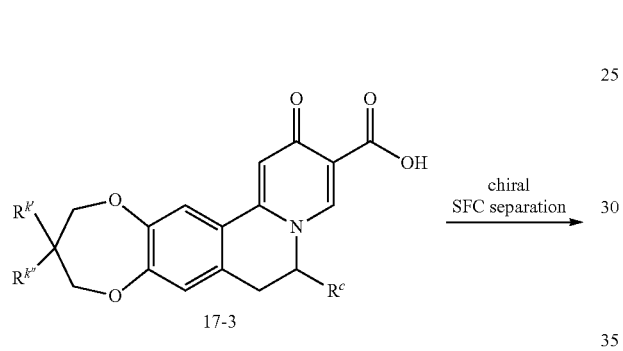
17-3
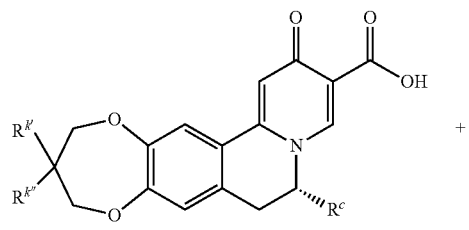
17-3A
+
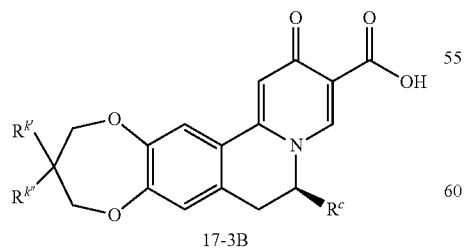
17-3B
In certain embodiments, a compound of the invention can be prepared, for example, according to the illustrative synthetic methods outlined in Scheme XVIII:
Scheme XVIII.
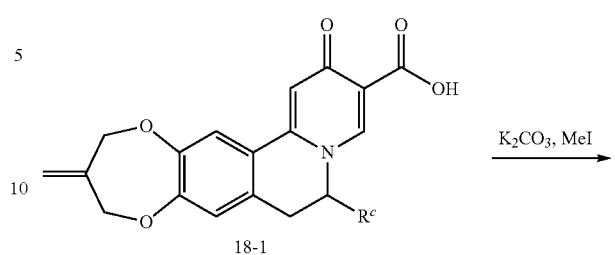
18-1
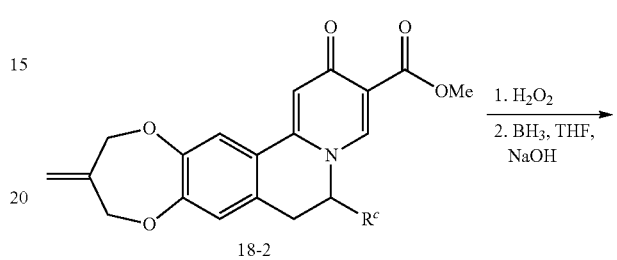
18-2
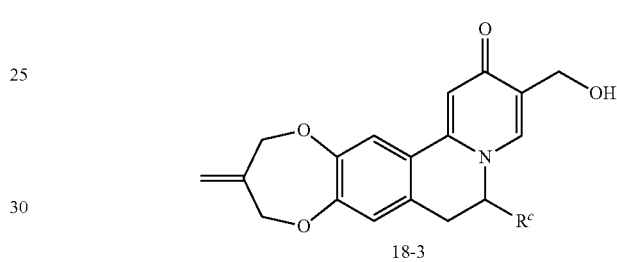
18-3
In certain embodiments, a compound of the invention can be prepared, for example, according to the illustrative synthetic methods outlined in Scheme XIX:
Scheme XIX.
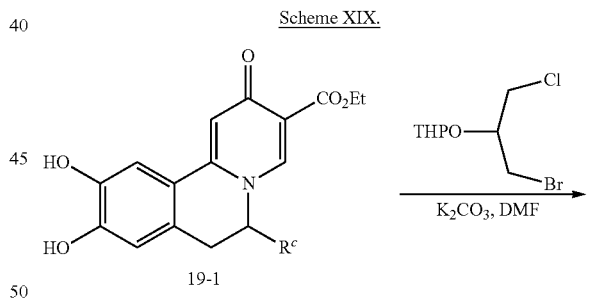
19-1
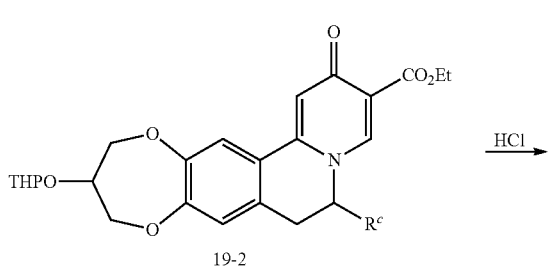
19-2

83
-continued
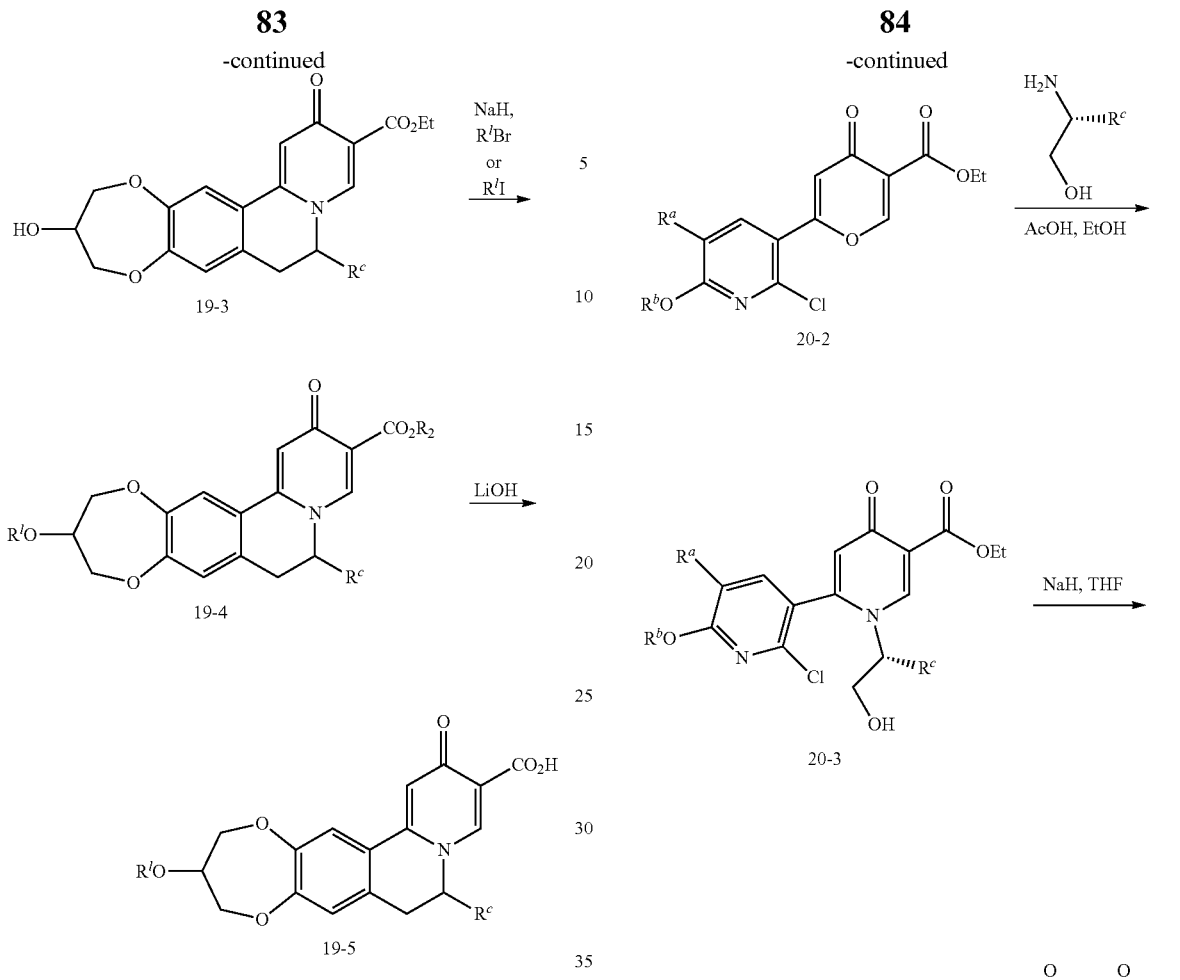
In certain embodiments, a compound of the invention can be prepared, for example, according to the illustrative synthetic methods outlined in Scheme XX:
Scheme XX.
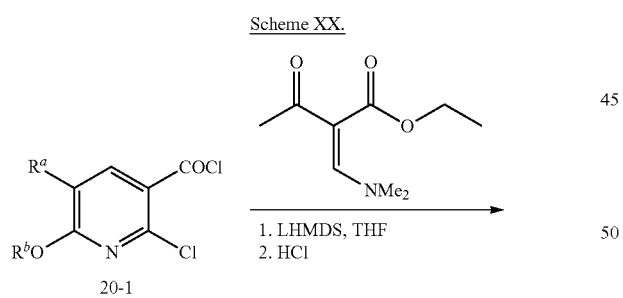
84
-continued
In certain embodiments, a compound of the invention can be prepared, for example, according to the illustrative synthetic methods outlined in Scheme XXI:
Scheme XXI.
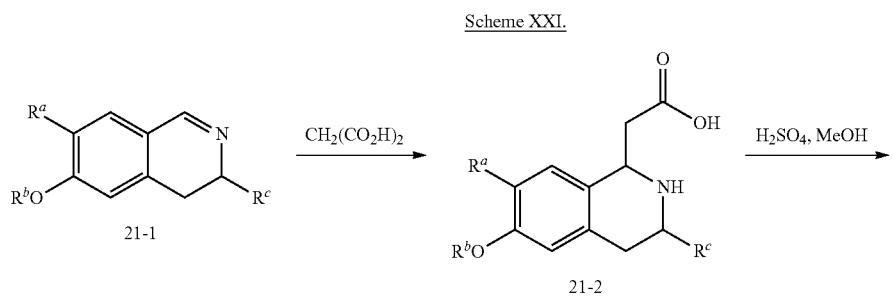

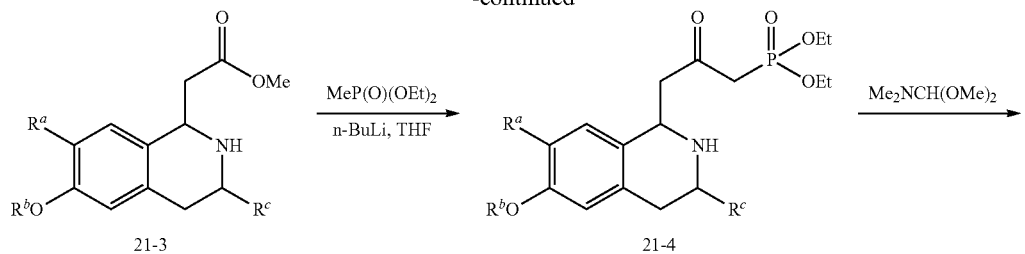
21-3 → 21-4
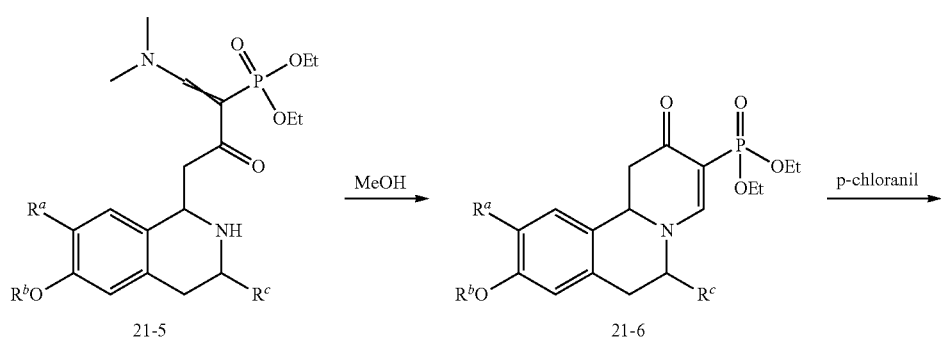
21-5 → 21-6
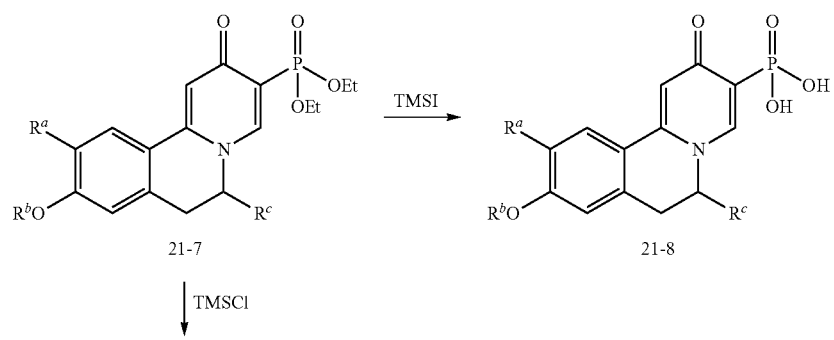
21-7 → 21-8
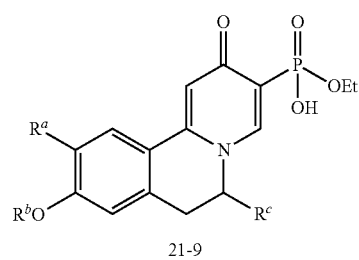
21-9

In certain embodiments, a compound of the invention can be prepared, for example, according to the illustrative synthetic methods outlined in Scheme XXII:
Scheme XXII.
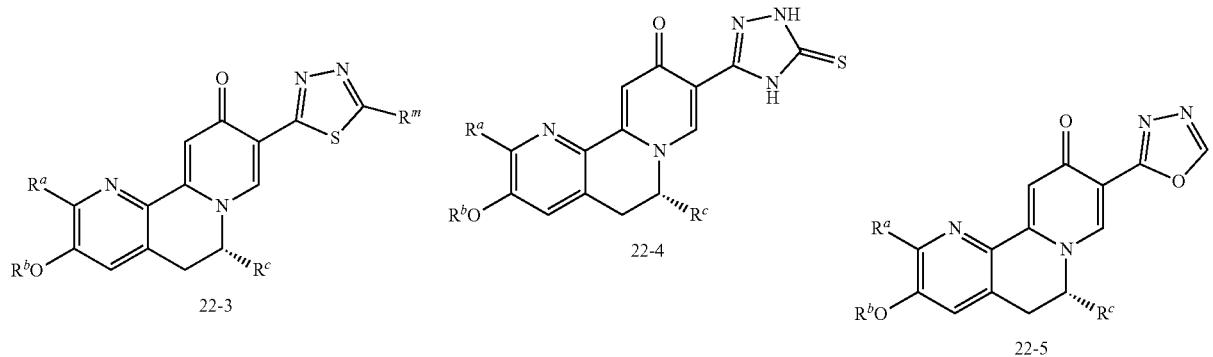
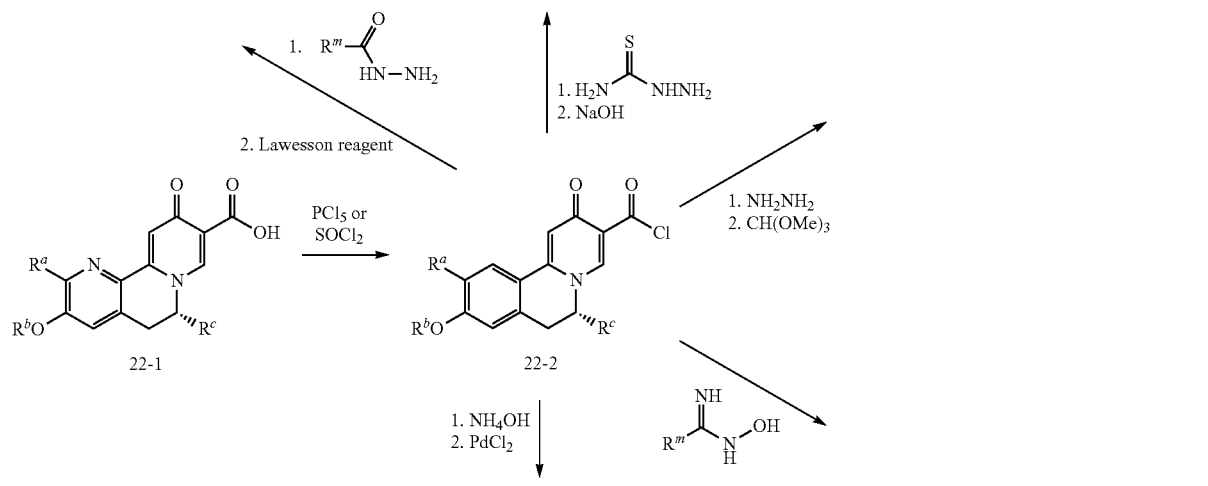
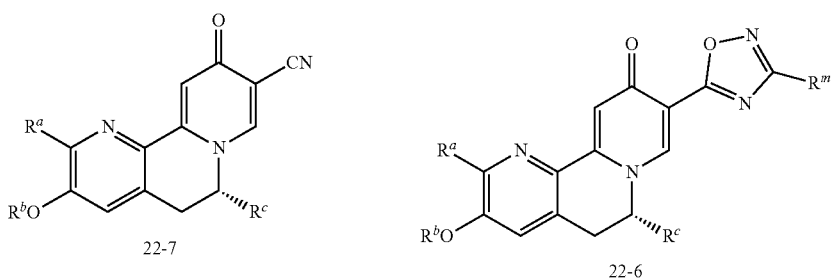

In certain embodiments, a compound of the invention can be prepared, for example, according to the illustrative synthetic methods outlined in Scheme XXIII:
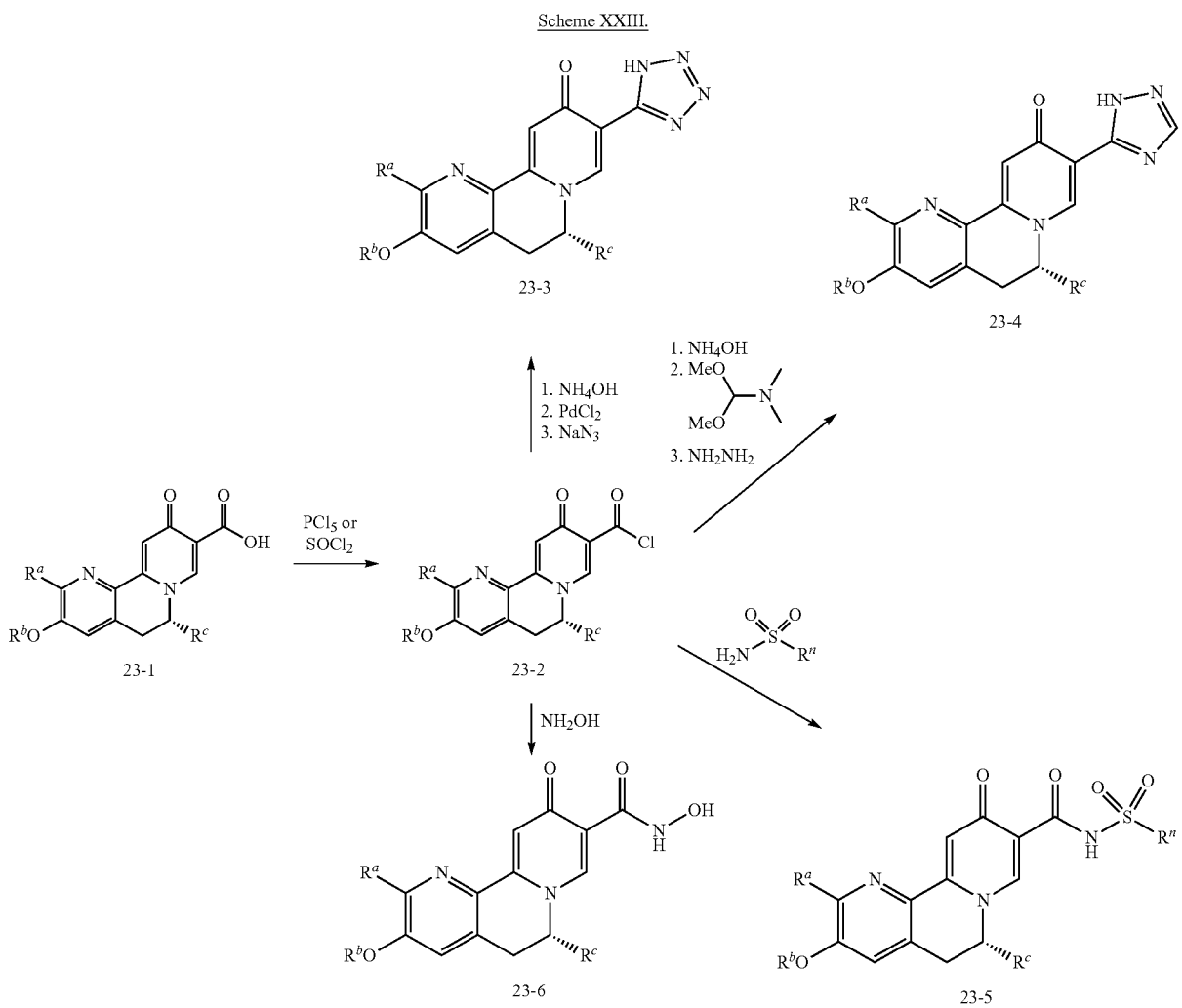
In certain embodiments, a compound of the invention can be prepared, for example, according to the illustrative synthetic methods outlined in Scheme XXIV:

Scheme XXIV.
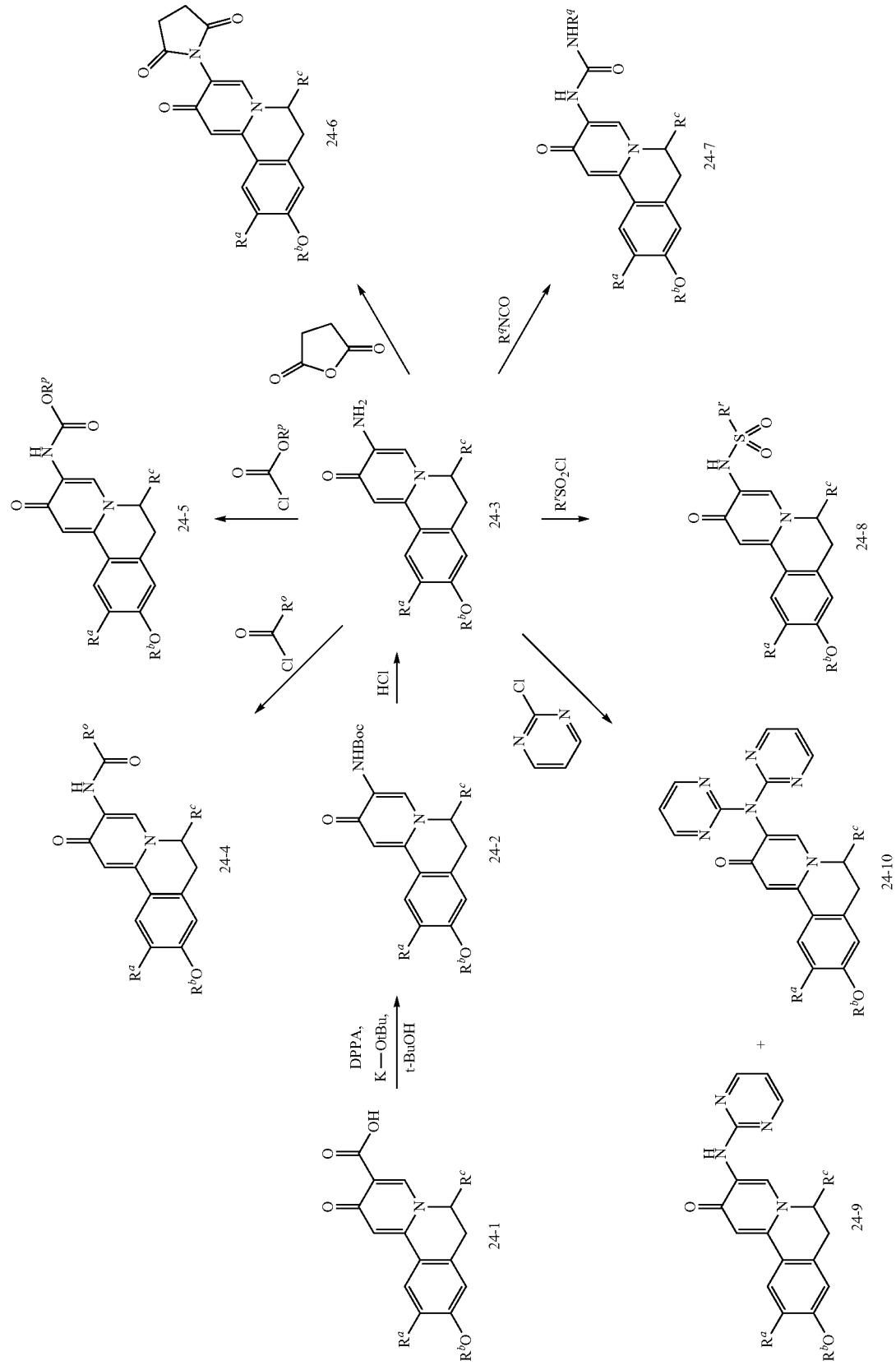

In certain embodiments, a compound of the invention can be prepared, for example, according to the illustrative synthetic methods outlined in Scheme XXV:
Scheme XXV.
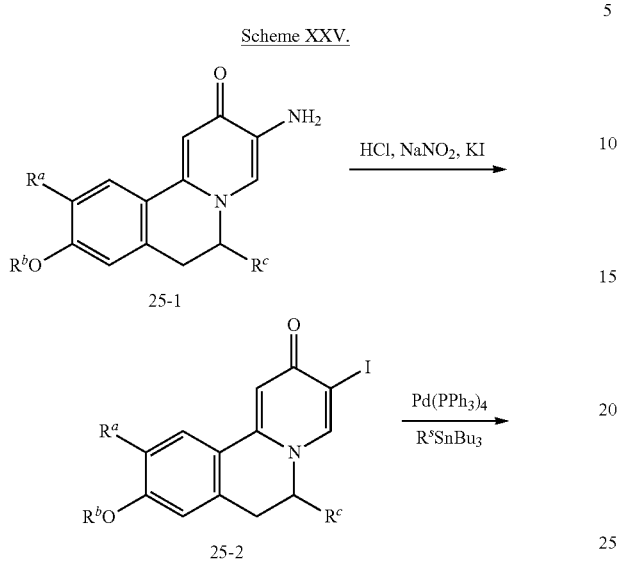
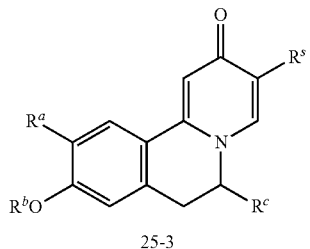
In certain embodiments, a compound of the invention can be prepared, for example, according to the illustrative synthetic methods outlined in Scheme XXVI:
Scheme XXVI.
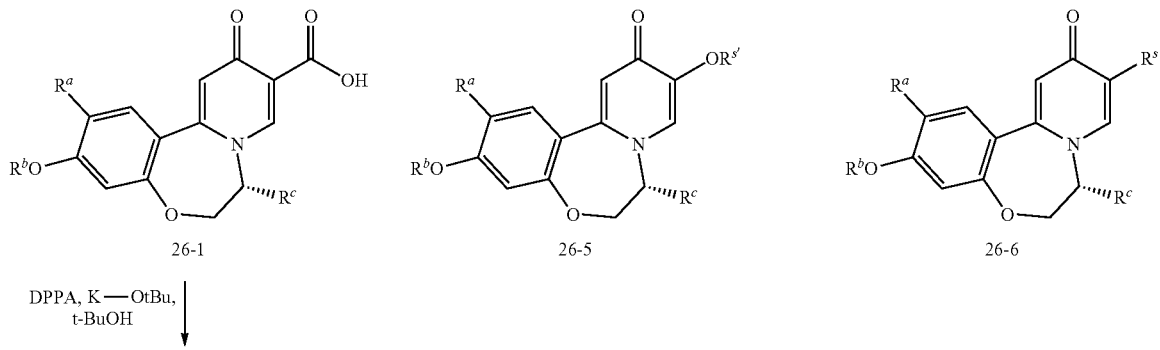
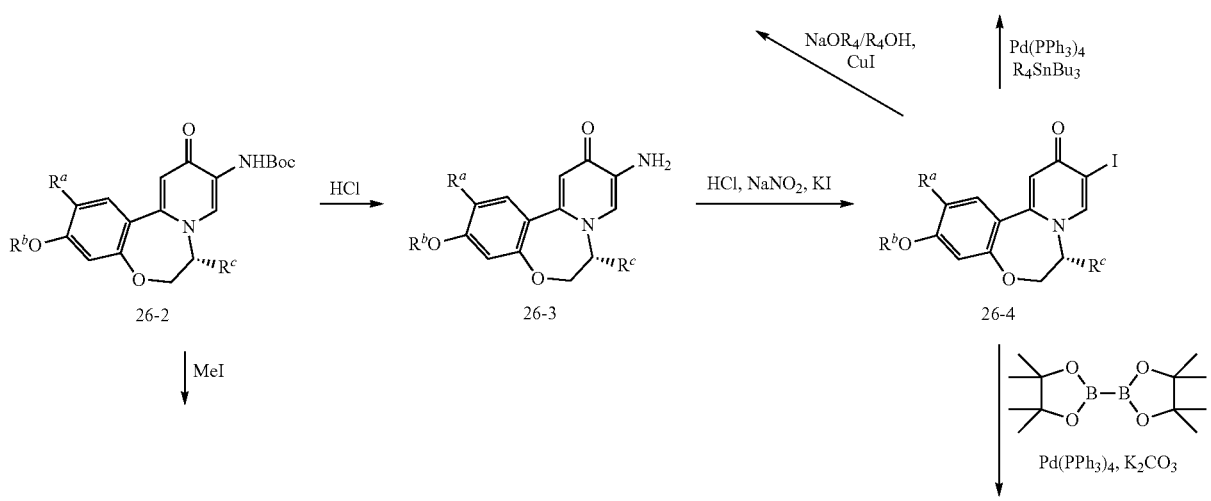

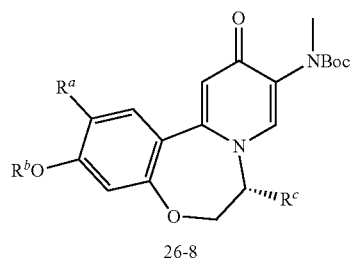

26-8

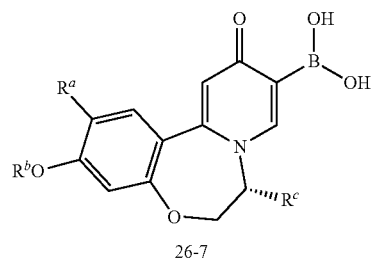

26-7

In certain embodiments, a compound of the invention can be prepared, for example, according to the illustrative synthetic methods outlined in Scheme XXVII:

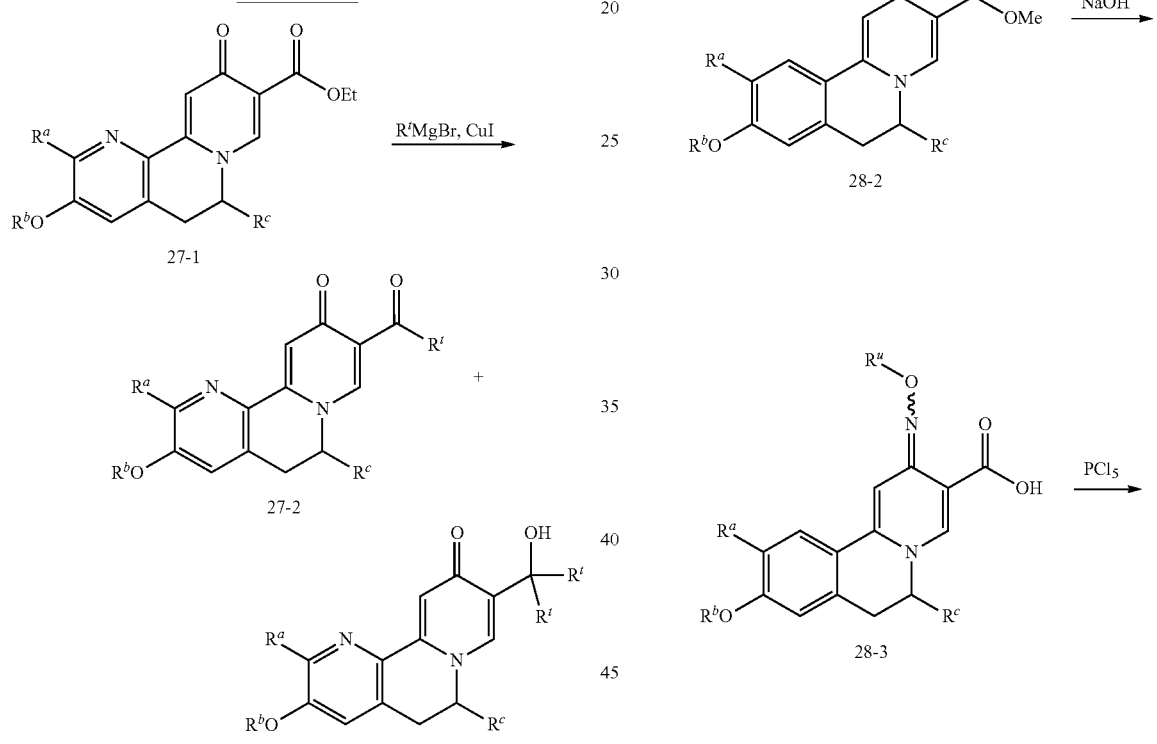

In certain embodiments, a compound of the invention can be prepared, for example, according to the illustrative synthetic methods outlined in Scheme XXVIII:

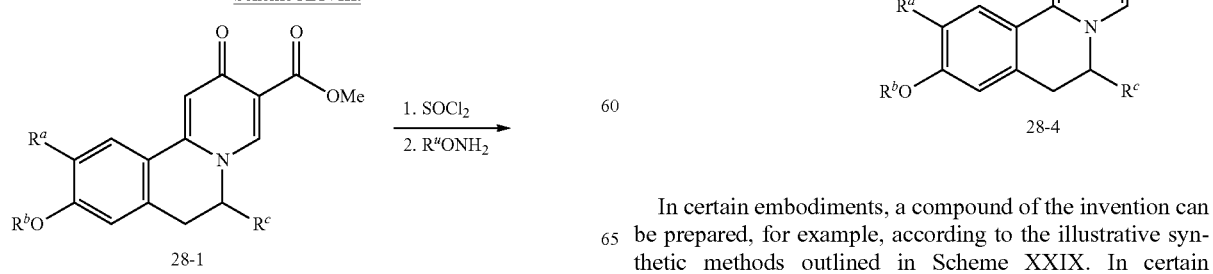

In certain embodiments, a compound of the invention can be prepared, for example, according to the illustrative synthetic methods outlined in Scheme XXIX. In certain embodiments, compound 29-3 is the E geometric isomer.

Scheme XXIX.
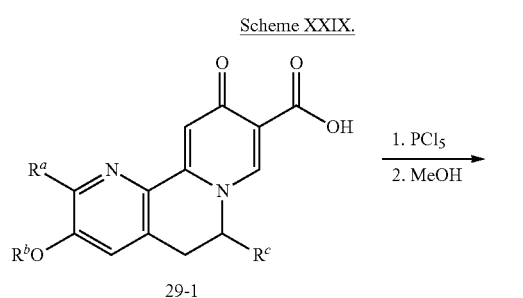
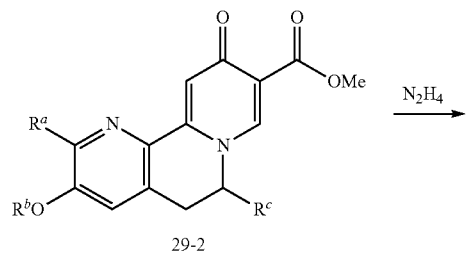
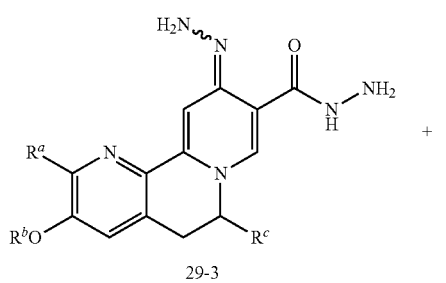
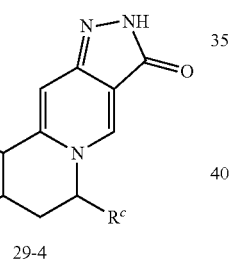
A compound of the invention can be prepared, for example, according to the illustrative synthetic methods outlined in Scheme XXX:
Scheme XXX.
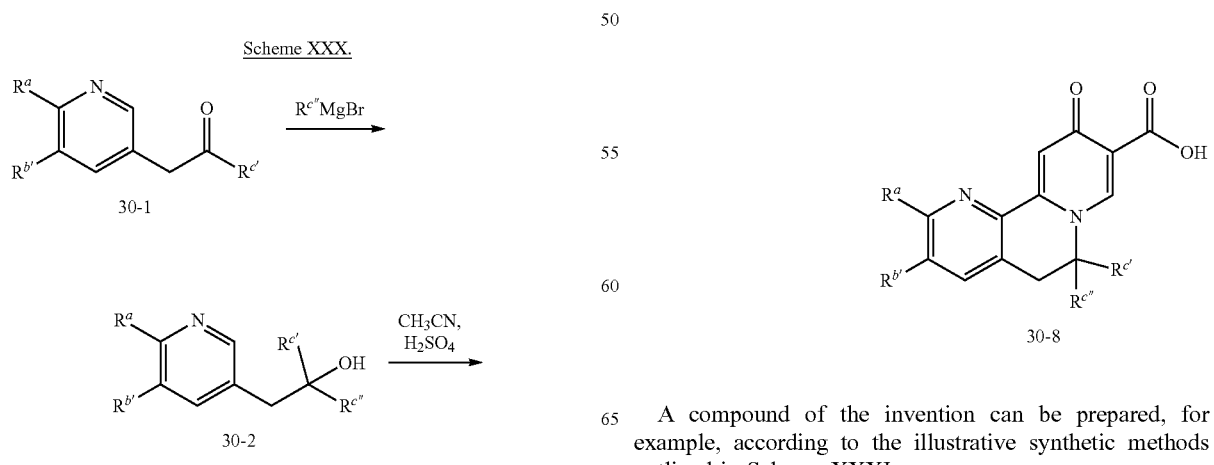
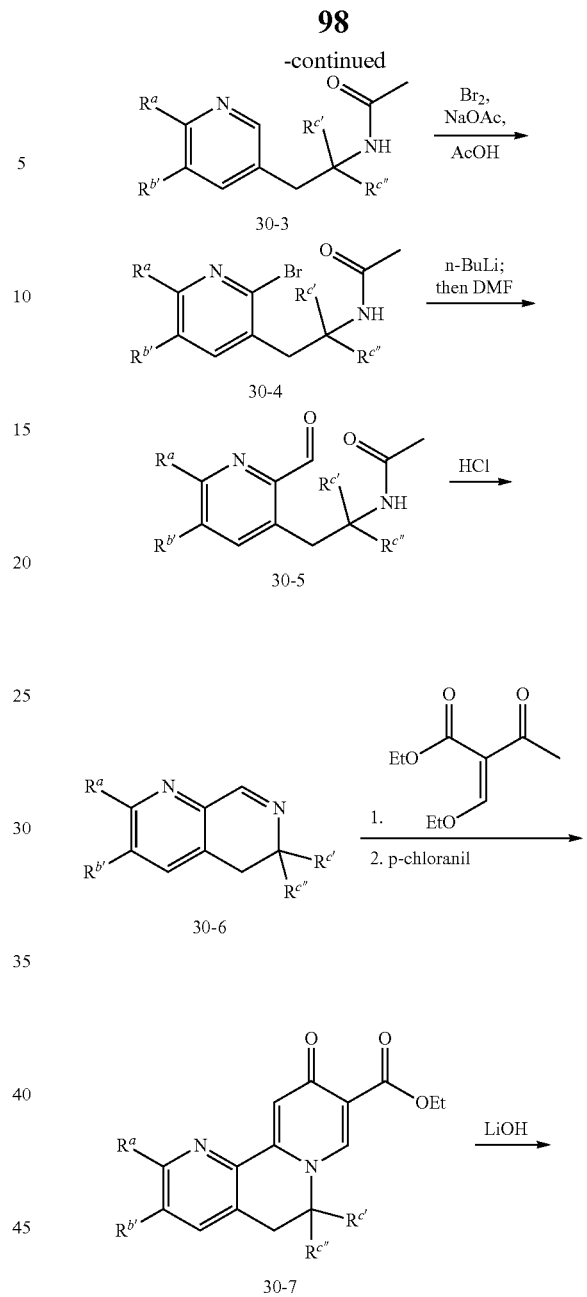
A compound of the invention can be prepared, for example, according to the illustrative synthetic methods outlined in Scheme XXXI:

Scheme XXXI.
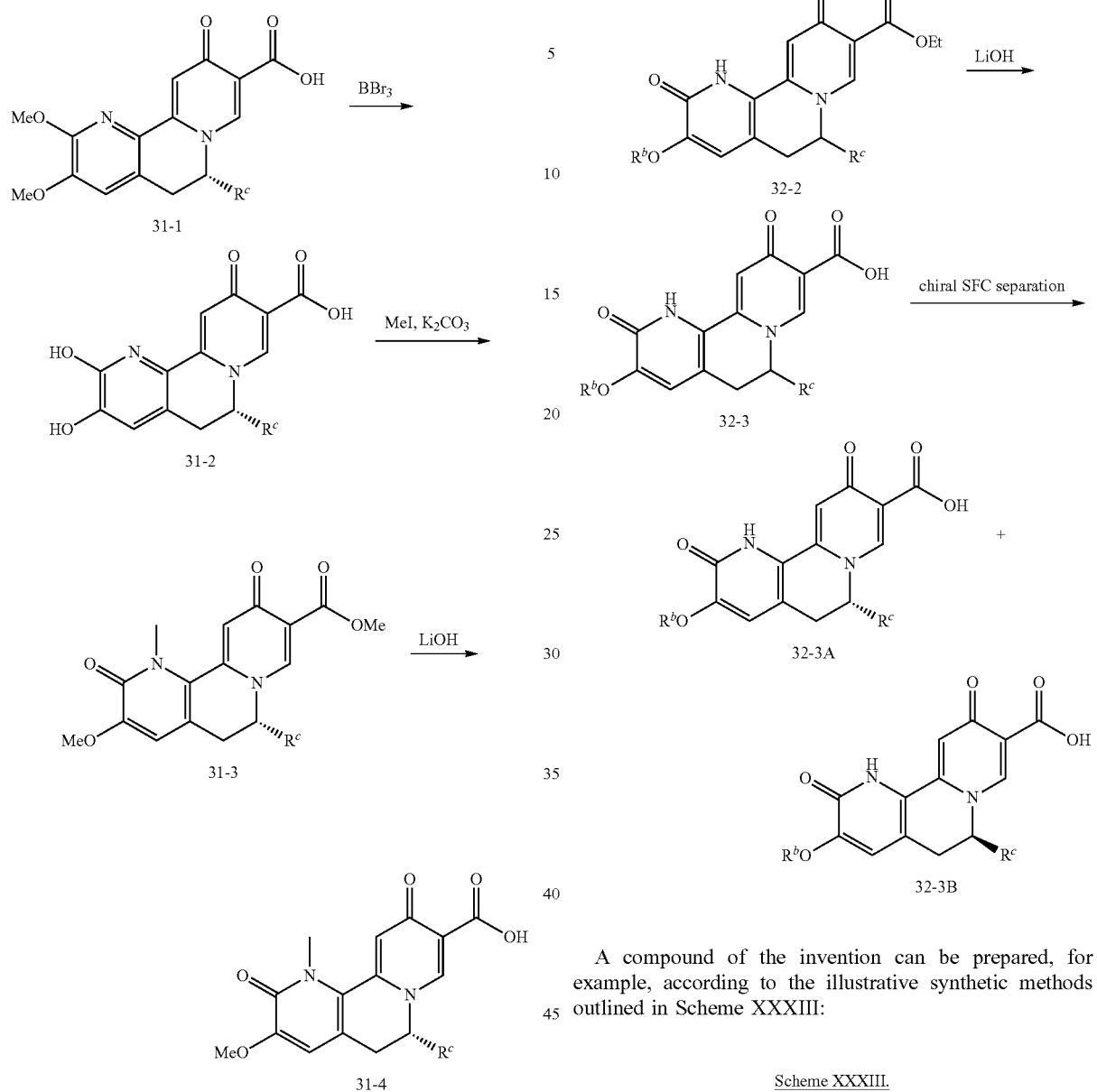
A compound of the invention can be prepared, for example, according to the illustrative synthetic methods outlined in Scheme XXXII:
Scheme XXXII.
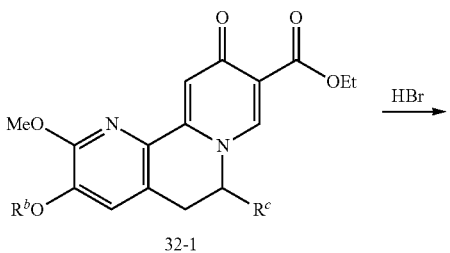
A compound of the invention can be prepared, for example, according to the illustrative synthetic methods outlined in Scheme XXXIII:
Scheme XXXIII.
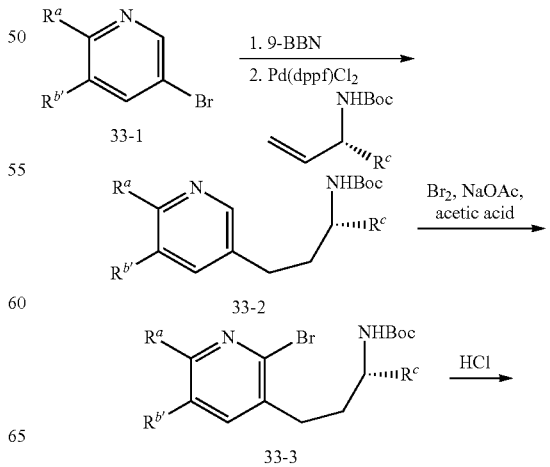

-continued
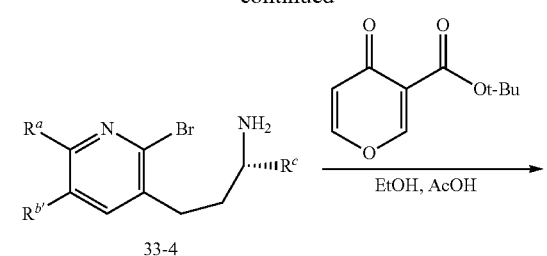
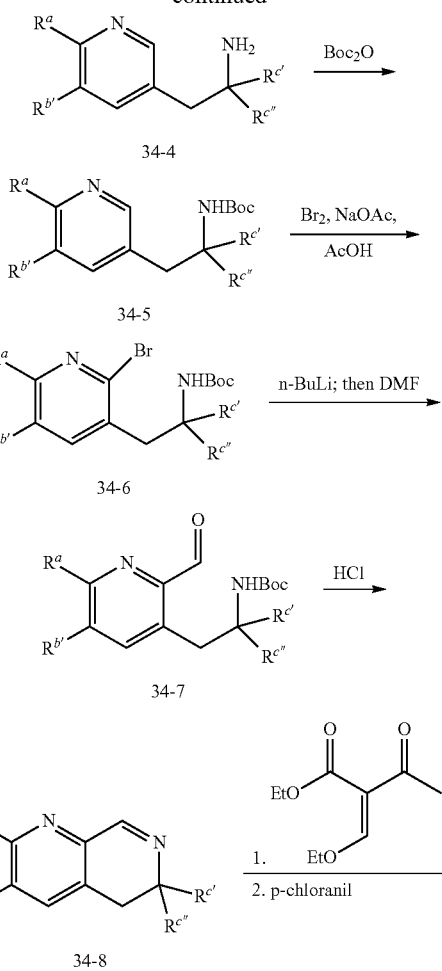
A compound of the invention can be prepared, for example, according to the illustrative synthetic methods outlined in Scheme XXXIV:
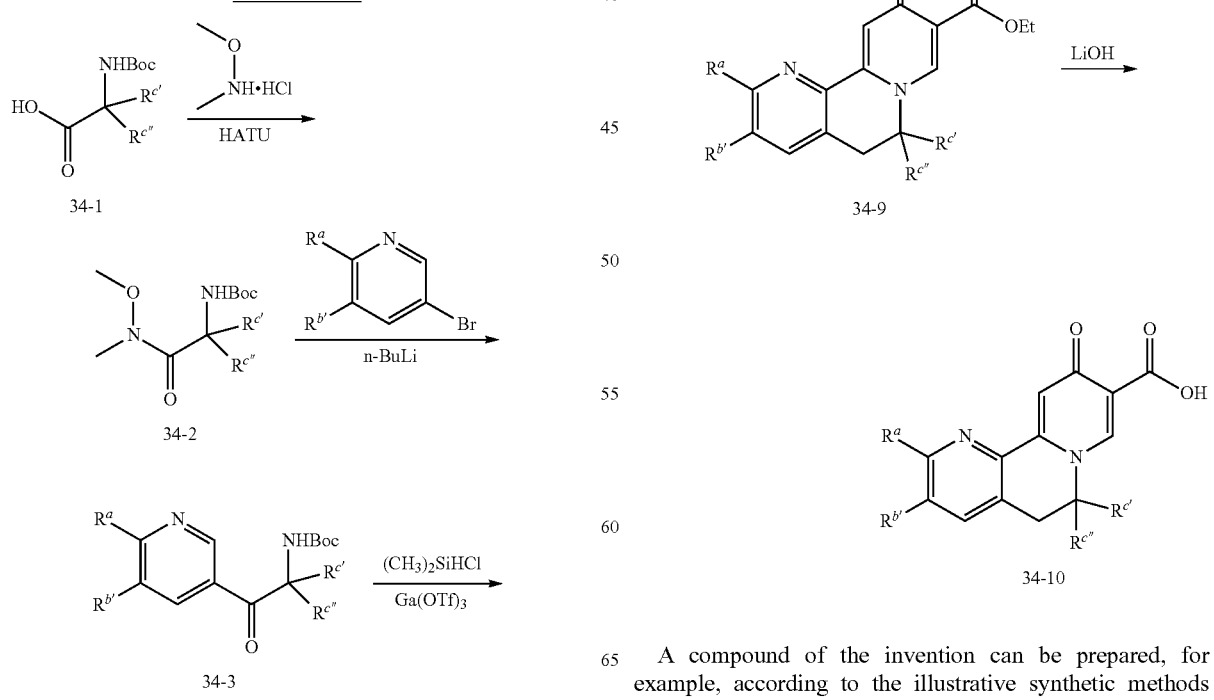
A compound of the invention can be prepared, for example, according to the illustrative synthetic methods outlined in Scheme XXXV:

Scheme XXXV.

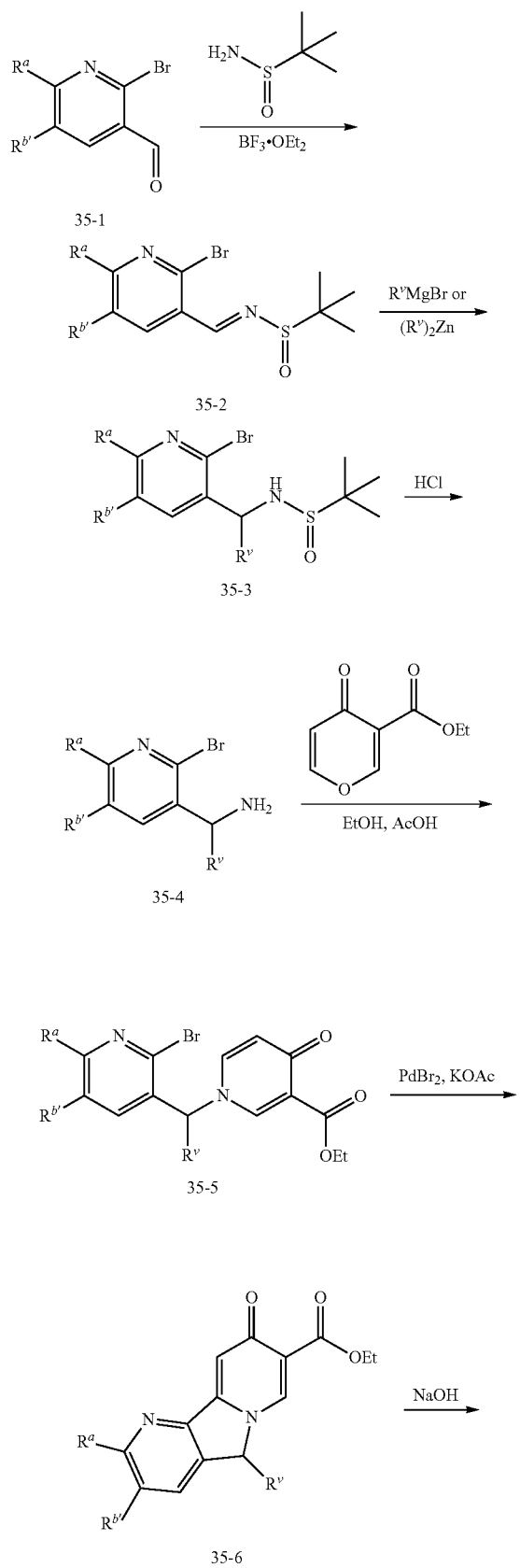

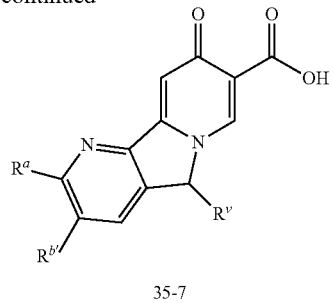

Methods

The invention provides a method of treating or preventing hepatitis virus infection in a subject. In certain embodiments, the infection comprises hepatitis B virus (HBV) infection. In other embodiments, the method comprises administering to the subject in need thereof a therapeutically effective amount of at least one compound of the invention. In yet other embodiments, the compound of the invention is the only antiviral agent administered to the subject. In yet other embodiments, the at least one compound is administered to the subject in a pharmaceutically acceptable composition. In yet other embodiments, the subject is further administered at least one additional agent useful for treating the hepatitis virus infection. In yet other embodiments, the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; and immunostimulator. In yet other embodiments, the subject is co-administered the at least one compound and the at least one additional agent. In yet other embodiments, the at least one compound and the at least one additional agent are coformulated.

The invention further provides a method of inhibiting and/or reducing HBV surface antigen (HBsAg) secretion either directly or indirectly in a subject. The invention further provides a method of reducing or minimizing levels of at least one selected from the group consisting of HBsAg, HBeAg, hepatitis B core protein, and pg RNA, in a HBV-infected subject. In certain embodiments, the method comprises administering to the subject in need thereof a therapeutically effective amount of at least one compound of the invention. In other embodiments, the at least one compound is administered to the subject in a pharmaceutically acceptable composition. In yet other embodiments, the compound of the invention is the only antiviral agent administered to the subject. In yet other embodiments, the subject is further administered at least one additional agent useful for treating HBV infection. In yet other embodiments, the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; and immunostimulator. In yet other embodiments, the subject is co-administered the at least one compound and the at least one additional agent. In yet other embodiments, the at least one compound and the at least one additional agent are coformulated.

In certain embodiments, the subject is a mammal. In other embodiments, the mammal is a human.

Pharmaceutical Compositions and Formulations

The invention provides pharmaceutical compositions comprising at least one compound of the invention or a salt or solvate thereof, which are useful to practice methods of the invention. Such a pharmaceutical composition may consist of at least one compound of the invention or a salt or solvate thereof, in a form suitable for administration to a subject, or the pharmaceutical composition may comprise at least one compound of the invention or a salt or solvate thereof, and one or more pharmaceutically acceptable carriers, one or more additional ingredients, or some combination of these. At least one compound of the invention may be present in the pharmaceutical composition in the form of a physiologically acceptable salt, such as in combination with a physiologically acceptable cation or anion, as is well known in the art.

In certain embodiments, the pharmaceutical compositions useful for practicing the method of the invention may be administered to deliver a dose of between 1 ng/kg/day and 100 mg/kg/day. In other embodiments, the pharmaceutical compositions useful for practicing the invention may be administered to deliver a dose of between 1 ng/kg/day and 1,000 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for nasal, inhalational, oral, rectal, vaginal, pleural, peritoneal, parenteral, topical, transdermal, pulmonary, intranasal, buccal, ophthalmic, epidural, intrathecal, intravenous or another route of administration. A composition useful within the methods of the invention may be directly administered to the brain, the brainstem, or any other part of the central nervous system of a mammal or bird. Other contemplated formulations include projected nanoparticles, microspheres, liposomal preparations, coated particles, polymer conjugates, resealed erythrocytes containing the active ingredient, and immunologically-based formulations.

In certain embodiments, the compositions of the invention are part of a pharmaceutical matrix, which allows for manipulation of insoluble materials and improvement of the bioavailability thereof, development of controlled or sustained release products, and generation of homogeneous compositions. By way of example, a pharmaceutical matrix may be prepared using hot melt extrusion, solid solutions, solid dispersions, size reduction technologies, molecular complexes (e.g., cyclodextrins, and others), microparticulate, and particle and formulation coating processes. Amorphous or crystalline phases may be used in such processes.

The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology and pharmaceutics. In general, such preparatory methods include the step of bringing the active ingredient into association with a carrier or one or more other accessory ingredients, and then, if necessary or desirable, shaping or packaging the product into a desired single-dose or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In certain embodiments, the compositions of the invention are formulated using one or more pharmaceutically acceptable excipients or carriers. In certain embodiments, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol, recombinant human albumin (e.g., RECOMBUMIN®), solubilized gelatins (e.g., GELOFUSINE®), and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), recombinant human albumin, solubilized gelatins, suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, isotonic agents, for example, sugars, sodium chloride, or polyalcohols such as mannitol and sorbitol, are included in the composition. Prolonged absorption of the injectable compositions may be brought about by including in the composition an agent that delays absorption, for example, aluminum monostearate or gelatin.

Formulations may be employed in admixtures with conventional excipients, i.e., pharmaceutically acceptable organic or inorganic carrier substances suitable for oral, parenteral, nasal, inhalational, intravenous, subcutaneous, transdermal enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or fragrance-conferring substances and the like. They may also be combined where desired with other active agents, e.g., other analgesic, anxiolytics or hypnotic agents. As used herein, "additional ingredients" include, but are not limited to, one or more ingredients that may be used as a pharmaceutical carrier.

The composition of the invention may comprise a preservative from about 0.005% to 2.0% by total weight of the composition. The preservative is used to prevent spoilage in the case of exposure to contaminants in the environment. Examples of preservatives useful in accordance with the invention include but are not limited to those selected from the group consisting of benzyl alcohol, sorbic acid, parabens, imidurea and combinations thereof. One such preservative is a combination of about 0.5% to 2.0% benzyl alcohol and 0.05% to 0.5% sorbic acid.

The composition may include an antioxidant and a chelating agent which inhibit the degradation of the compound. Antioxidants for some compounds are BHT, BHA, alpha-tocopherol and ascorbic acid in the exemplary range of about 0.01% to 0.3%, or BHT in the range of 0.03% to 0.1% by weight by total weight of the composition. The chelating agent may be present in an amount of from 0.01% to 0.5% by weight by total weight of the composition. Exemplary chelating agents include edetate salts (e.g. disodium edetate) and citric acid in the weight range of about 0.01% to 0.20%, or in the range of 0.02% to 0.10% by weight by total weight of the composition. The chelating agent is useful for chelating metal ions in the composition that may be detrimental to the shelf life of the formulation. While BHT and disodium edetate are exemplary antioxidant and chelating agent, respectively, for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethyl cellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, acacia, and ionic or non ionic surfactants. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, ionic and non-ionic surfactants, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying. Methods for mixing components include physical milling, the use of pellets in solid and suspension formulations and mixing in a transdermal patch, as known to those skilled in the art.

Administration/Dosing

The regimen of administration may affect what constitutes an effective amount. The therapeutic formulations may be administered to the patient either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, such as a mammal, such as a human, may be carried out using known procedures, at dosages and for periods of time effective to treat a disease or disorder contemplated herein. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 mg/kg to 100 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon a number of factors, such as, but not limited to, type and severity of the disease being treated, and type and age of the animal.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physician taking all other factors about the patient into account.

Compounds of the invention for administration may be in the range of from about 1 μg to about 7,500 mg, about 20 μg to about 7,000 mg, about 40 μg to about 6,500 mg, about 80 μg to about 6,000 mg, about 100 μg to about 5,500 mg, about 200 μg to about 5,000 mg, about 400 μg to about 4,000 mg, about 800 μg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments there-in-between.

In some embodiments, the dose of a compound of the invention is from about 0.5 μg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

The term "container" includes any receptacle for holding the pharmaceutical composition or for managing stability or water uptake. For example, in certain embodiments, the container is the packaging that contains the pharmaceutical composition, such as liquid (solution and suspension), semi-solid, lyophilized solid, solution and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, epidural, intrapleural, intraperitoneal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, emulsions, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic, generally recognized as safe (GRAS) pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation. Hard capsules comprising the active ingredient may be made using a physiologically degradable composition, such as gelatin. The capsules comprise the active ingredient, and may further comprise additional ingredients including, for example, an inert solid diluent such as calcium carbonate, calcium phosphate, or kaolin.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin from animal-derived collagen or from a hypromellose, a modified form of cellulose, and manufactured using optional mixtures of gelatin, water and plasticizers such as sorbitol or glycerol. Such soft capsules comprise the active ingredient, which may be mixed with water or an oil medium such as peanut oil, liquid paraffin, or olive oil.

For oral administration, the compounds of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY® film coating systems available from Colorcon, West Point, Pa. (e.g., OPADRY® OY Type, OYC Type, Organic Enteric OY-P Type, Aqueous Enteric OY-A Type, OY-PM Type and OPADRY® White, 32K18400). It is understood that similar type of film coating or polymeric products from other companies may be used.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form.

Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds useful within the methods of the invention, and a further layer providing for the immediate release of one or more compounds useful within the methods of the invention. Using a wax/pH-sensitive polymer mix, a gastric insoluble composition may be obtained in which the active ingredient is entrapped, ensuring its delayed release.

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Injectable formulations may also be prepared, packaged, or sold in devices such as patient-controlled analgesia (PCA) devices. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3-butane-diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form in a recombinant human albumin, a fluidized gelatin, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (i.e., U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In other embodiments, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. For example, it should be present in an amount from about 0.0005% to about 5% of the composition; for example, it should be present in an amount of from about 0.001% to about 1% of the composition. Such compounds may be synthetically- or naturally derived.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, may have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems:

In certain embodiments, the compositions and/or formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In certain embodiments of the invention, the compounds useful within the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials & Methods

The following procedures can be utilized in preparing and/or testing exemplary compounds of the invention. For those compounds for which absolute stereochemistries are disclosed herein, the assignment of chirality is based on X-ray crystallographic characterization of the compound, or use of an enantiomerically and/or diastereoisomerically pure chiral intermediate in the compound synthesis.

Example 1: 2-Chloro-7-isopropyl-3-methoxy-11-oxo-6,7-dihydro-11H-Benzo[f]pyrido[1,2-d][1,4]oxazepine-10-carboxylic acid

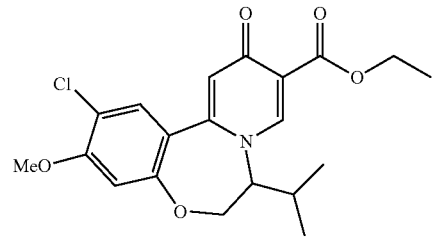 [SMILES: CCOC(=O)c1cn2c(cc1=O)-c1cc(Cl)c(OC)cc1OCC2C(C)C]

Methyl 2-(benzyloxy)-5-chloro-4-methoxybenzoate

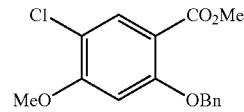 [SMILES: COC(=O)c1cc(Cl)c(OC)cc1OCc1ccccc1]

A mixture of methyl 5-chloro-2-hydroxy-4-methoxybenzoate (10.83 g, 50 mmol, prepared according to U.S. Pat. Appl. Publ. US20100168080), benzyl bromide (9.4 mL, 55 mmol) and potassium carbonate (13.8 g, 100 mmol) in DMF (100 ml) were stirred at room temperature overnight. The system was filtered, and solvents removed under vacuum. The residue was dissolved in dichloromethane (200 mL), washed with water and dried over sodium sulfate, and solvents removed to give methyl 2-(benzyloxy)-5-chloro-4-methoxybenzoate as a white solid that was used without further purification (13.8 g, 90% yield, m/z: 307 [M+H]$^+$ observed). $^1$H NMR (300 MHz, CDCl$_3$): δ 7.82 (d, J=2.5 Hz, 1H), 7.56-7.35 (m, 5H), 7.10 (d, J=2.5 Hz, 1H), 5.25 (s, 2H), 3.91 (s, 3H) and 3.82 (s, 3H).

2-(Benzyloxy)-5-chloro-4-methoxybenzoic acid

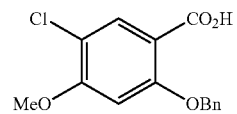

To a solution of methyl 2-(benzyloxy)-5-chloro-4-methoxybenzoate (12.28 g, 40 mmol) in dioxane (250 mL), aq. LiOH (40 mL of 2 M solution) was added and stirred at room temperature overnight. Solvents were removed under vacuum, and the contents were acidified with 1N aq. HCl (90 mL). The precipitate was filtered, washed with water (100 mL) and air-dried to furnish 2-(benzyloxy)-5-chloro-4-methoxybenzoic acid as a white solid, which was used without further purification (11.6 g, 98% yield, m/z: 293 [M+H]$^+$ observed). $^1$H NMR (300 MHz, CDCl$_3$): δ 12.60 (bs, 1H), 7.70 (s, 1H), 7.48-7.30 (m, 5H), 6.95 (s, 1H), 5.20 (s, 2H) and 3.85 (s, 3H).

2-(Benzyloxy)-5-chloro-4-methoxybenzoyl chloride

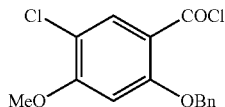

A mixture of 2-(benzyloxy)-5-chloro-4-methoxybenzoic acid (5.84 g, 20 mmol) and thionyl chloride (15 mL) was stirred at 80° C. for 4 h. The reaction mixture was concentrated under vacuum, and the crude was subjected to azeotropic distillation with toluene (2×20 mL) and then dried under high vacuum for 2 h to yield 2-(benzyloxy)-5-chloro-4-methoxybenzoyl chloride that was used without further purification (5.85 g, quantitative).

2-(2-(Benzyloxy)-5-chloro-4-methoxyphenyl)-4H-pyran-4-one

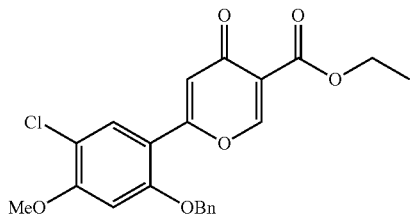 [SMILES: CCOC(=O)c1coc(-c2cc(Cl)c(OC)cc2OCc2ccccc2)cc1=O]

To a solution of LiHMDS (36 ml, 34 mL, 1.06 M in THF) in anhydrous THF (50 mL) at −78° C. (dry ice/acetone bath) under argon, a solution of ethyl (Z)-2-((dimethylamino)methylene)-3-oxobutanoate (2.78 g, 15 mmol) and 2-(benzyloxy)-5-chloro-4-methoxybenzoyl chloride (4.67 g, 15 mmol) in 50 mL anhydrous THF was added dropwise over 10 min. The dry ice/acetone bath was removed and the solution was warmed to room temperature over a 30 min period. Diethyl ether (100 mL) was added to the reaction mixture, followed by 3N aq. HCl (60 mL, 180 mmol) and stirred the contents overnight. Organic solvents were removed under vacuum at below 20° C. and the contents were treated with saturated aqueous bicarbonate solution until the aqueous layer reached basic pH, and the system was stirred vigorously for 10 min. The precipitate was filtered, washed with water, dissolved in dichloromethane, dried over sodium sulfate and concentrated to give dark orange residue (6.5 g). The residue was purified by normal phase SiO$_2$ chromatography (10% to 100% EtOAc/hexanes) to furnish 2-(2-(benzyloxy)-5-chloro-4-methoxyphenyl)-4H-pyran-4-one as an orange solid, which upon crystallization from methanol (30 mL) yielded 2-(2-(benzyloxy)-5-chloro-4-methoxyphenyl)-4H-pyran-4-one as a white solid (2.49 g, 40% yield, m/z: 415 [M+H]$^+$ observed). $^1$H NMR (400 MHz, CDCl$_3$): δ 8.54 (s, 1H), 7.74 (s, 1H), 7.45-7.32 (m, 5H), 7.20 (s, 1H), 6.57 (s, 1H), 5.25 (s, 2H), 4.37 (q, J=2.4 Hz, 2H), 3.85 (s, 3H) and 1.30 (t, J=2.4 Hz, 3H).

Ethyl 6-(2-(benzyloxy)-5-chloro-4-methoxyphenyl)-1-(1-hydroxy-3-methylbutan-2-yl)-4-oxo-1,4-dihydropyridine-3-carboxylate OH

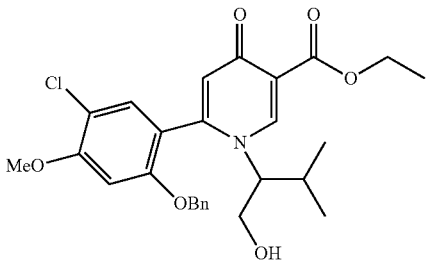 [SMILES: CCOC(=O)c1cn(C(CO)C(C)C)c(-c2cc(Cl)c(OC)cc2OCc2ccccc2)cc1=O]

To a mixture of 2-(2-(benzyloxy)-5-chloro-4-methoxyphenyl)-4H-pyran-4-one (208 mg, 0.5 mmol) in AcOH/EtOH (10 mL, 2:3 ratio), D,L-valinol (76 mg, 0.75 mmol) was added and the contents were refluxed for 4 h. The reaction mixture was concentrated under vacuum, and the residue was purified by normal phase SiO$_2$ chromatography (0% to 10% MeOH/CH$_2$Cl$_2$) to furnish ethyl 6-(2-(benzyloxy)-5-chloro-4-methoxyphenyl)-1-(1-hydroxy-3-methylbutan-2-yl)-4-oxo-1,4-dihydropyridine-3-carboxylate as an orange solid, which was collected upon crystallization from methanol (30 mL) yielded ethyl 6-(2-(benzyloxy)-5-chloro-4-methoxyphenyl)-1-(1-hydroxy-3-methylbutan-2-yl)-4-oxo-1,4-dihydropyridine-3-carboxylate as a white foam (125 mg, 50% yield, m/z: 500 [M+H]$^+$ observed). $^1$H NMR (300 MHz, CDCl$_3$): δ 8.36 (s, 1H), 7.63 (s, 1H), 7.40-7.28 (m, 5H), 7.15 (d, J=3.0 Hz, 1H), 6.10 (d, J=3.0 Hz, 1H), 5.20 (bs, 2H), 4.25 (q, J=2.0 Hz, 2H), 3.95 (s, 3H), 3.80-3.85 (m, 1H), 3.60-3.45 (m, 2H), 2.45-2.20 (m, 1H), 1.30 (t, J=2.0 Hz, 3H), 0.95-0.92 (dd, J=2.2 &1.0 Hz, 3H) and 0.75-0.67 (dd, J=6.0 & 2.2 Hz, 3H).

Ethyl 6-(5-chloro-2-hydroxy-4-methoxyphenyl)-1-(1-hydroxy-3-methylbutan-2-yl)-4-oxo-1,4-dihydropyridine-3-carboxylate

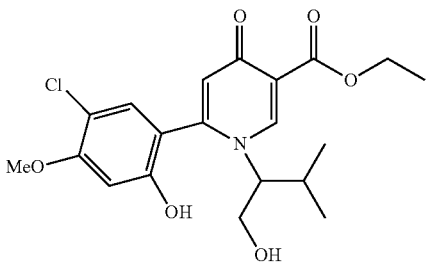 [SMILES: CCOC(=O)c1cn(C(CO)C(C)C)c(-c2cc(Cl)c(OC)cc2O)cc1=O]

A mixture of ethyl 6-(2-(benzyloxy)-5-chloro-4-methoxyphenyl)-1-(1-hydroxy-3-methyl butan-2-yl)-4-oxo-1,4-dihydropyridine-3-carboxylate (100 mg, 0.20 mmol) and 10% Pd/C (50 mg) in ethanol (10 mL) were hydrogenated at 2 psi for 5 min using Parr-shaker apparatus. The reaction mixture was filtered through celite, concentrated under vacuum to give ethyl 6-(5-chloro-2-hydroxy-4-methoxyphenyl)-1-(1-hydroxy-3-methylbutan-2-yl)-4-oxo-1,4-dihydropyridine-3- carboxylate, which was used without further purification (82 mg, 99% yield, m/z: 410 [M+H]+ observed). ¹H NMR (300 MHz, DMSO-d₆): δ 8.24 (s, 1H), 7.20 (s, 1H), 6.64 (s, 1H), 6.04 (s, 1H), 4.20 (q, J=2.4 Hz, 2H), 3.93-3.86 (m, 1H), 3.79 (s, 3H), 3.60-3.45 (m, 2H), 1.23 (t, J=2.4 Hz, 3H), 0.85-0.81 (m, 1H), 0.59 (s, 3H) and 0.52 (s, 3H).

Ethyl 2-chloro-7-isopropyl-3-methoxy-11-oxo-6,7-dihydro-11H-benzo[f]pyrido[1,2-d][1,4]oxazepine-10-carboxylate

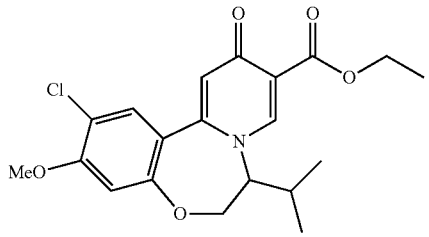 [SMILES: CCOC(=O)c1cn2c(cc1=O)-c1cc(Cl)c(OC)cc1OCC2C(C)C]

To a mixture of ethyl 6-(5-chloro-2-hydroxy-4-methoxy-phenyl)-1-(1-hydroxy-3-methylbutan-2-yl)-4-oxo-1,4-dihydropyridine-3-carboxylate (60 mg, 0.15 mmol) and Ph₃P (78 mg, 0.3 mmol) and triethylamine (0.2 mL) in anhydrous dichloromethane (20 mL) at 0° C., DIAD (60 uL, 0.3 mmol) was added dropwise and the contents were stirred at rt for 6 h under argon. Additional P Ph₃ (78 mg) and DIAD (60 uL, 0.3 mmol) were added and stirred for another 16 h. The reaction mixture was concentrated under vacuum, and the residue was purified by normal phase SiO₂ chromatography (0% to 10% MeOH/CH₂Cl₂) to furnish ethyl 2-chloro-7-isopropyl-3-methoxy-11-oxo-6,7-dihydro-11H-benzo[f]pyrido[1,2-d][1,4]oxazepine-10-carboxylate (27 mg, 50% yield, m/z: 392 [M+H]+ observed). ¹H NMR (300 MHz, CDCl₃): δ 8.14 (s, 1H), 7.50 (s, 1H), 6.67 (s, 1H), 6.59 (s, 1H), 4.70-4.50 (m, 2H), 4.43-4.35 (q, J=2.4 Hz, 2H), 3.93 (s, 3H), 3.75-3.66 (m, 1H), 2.10-1.98 (m, 1H), 1.40 (t, J=2.4 Hz, 3H), 1.65 (d, J=2.2 Hz, 3H) and 0.88 (d, J=2.2 Hz, 3H).

Example 2: 2-Chloro-7-isopropyl-3-methoxy-1-oxo-6,7-dihydro-11H-benzo[f]pyrido[1,2-d][1,4]oxazepine-10-carboxylic acid

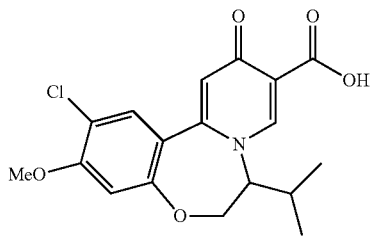 [SMILES: COc1cc2c(cc1Cl)-c1cc(=O)c(C(=O)O)cn1C(C(C)C)CO2]

To a mixture of ethyl 2-chloro-7-isopropyl-3-methoxy-11-oxo-6,7-dihydro-11H-benzo[f]pyrido[1,2-d][1,4]oxazepine-10-carboxylate (16 mg, 0.04 mmol) in dioxane (3 mL), aqueous LiOH (7 mg in 0.2 mL, 0.4 mmol) was added and stirred at room temperature overnight. The reaction mixture was concentrated under vacuum, and the residue was dissolved in water (2 mL), cooled to 10° C., acidified with 1N aq. HCl to pH 2-3. The precipitate was filtered and washed with 2 mL of water, and the precipitate was vacuum-dried to furnish 2-chloro-7-isopropyl-3-methoxy-11-oxo-6,7-dihydro-11H-benzo[f]pyrido[1,2-d][1,4]oxazepine-10-carboxylic acid as a white solid (13 mg, 87% yield, m/z: 364 [M+H]+ observed). ¹H NMR (300 MHz, DMSO-d₆): δ 8.76 (s, 1H), 7.73 (s, 1H), 7.00 (s, 1H), 6.86 (s, 1H), 4.68 (brd, J=1 Hz, 1H), 4.53 (brd, J=3.5 Hz, 1H), 3.89 (s, 3H), 3.33 (bs, 1H), 1.81 (bs, 1H), 0.95 (d, J=2.2 Hz, 3H) and 0.68 (d, J=2.2 Hz, 3H).

Example 3: (R)-2-Chloro-7-isopropyl-3-methoxy-11-oxo-6,7-dihydro-11H-benzo[f]pyrido[1,2-d][1,4]oxazepine-10-carboxylic acid

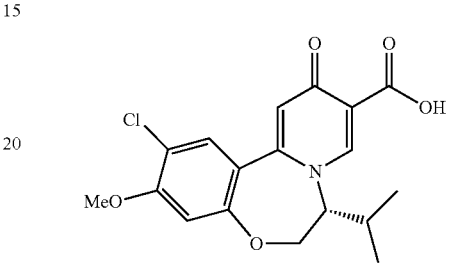

Example 4: (S)-2-Chloro-7-isopropyl-3-methoxy-11-oxo-6,7-dihydro-11H-benzo[f]pyrido[1,2-d][1,4]oxazepine-10-carboxylic acid

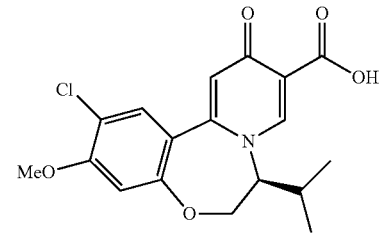 [SMILES: COc1cc2c(cc1Cl)-c1cc(=O)c(C(=O)O)cn1[C@@H](C(C)C)CO2]

100 mg of the mixture of enantiomers was separated by SFC (supercritical fluid chromatography) on an AD-H column using 40% EtOH (0.1% aq. NH₃) as a modifier to give (R)-2-chloro-7-isopropyl-3-methoxy-11-oxo-6,7-dihydro-11H-benzo[f]pyrido[1,2-d][1,4]oxazepine-10-carboxylic acid as a white solid (faster eluting enantiomer, 17.6 mg, 17%, m/z: 364 [M+H]+ observed) and (S)-2-chloro-7-isopropyl-3-methoxy-11-oxo-6,7-dihydro-11H-benzo[f]pyrido[1,2-d][1,4]oxazepine-10-carboxylic acid as a white solid (slower eluting enantiomer, 11 mg, 11%, m/z: 364 [M+H]+ observed).

Example 3: (R)-2-Chloro-7-isopropyl-3-methoxy-11-oxo-6,7-dihydro-11H-benzo[f]pyrido[1,2-d][1,4]oxazepine-10-carboxylic acid. m/z: 364 [M+H]+ observed). ¹H NMR (400 MHz, DMSO-d₆): δ 8.76 (s, 1H), 7.73 (s, 1H), 7.00 (s, 1H), 6.86 (s, 1H), 4.68 (brd, J=1 Hz, 1H), 4.53 (brd, J=3.5 Hz, 1H), 3.89 (s, 3H), 3.33 (bs, 1H), 1.81 (bs, 1H), 0.95 (d, J=2.2 Hz, 3H) and 0.68 (d, J=2.2 Hz, 3H).

Example 4: (S)-2-Chloro-7-isopropyl-3-methoxy-11-oxo-6,7-dihydro-11H-benzo[f]pyrido[1,2-d][1,4]oxazepine-10-carboxylic acid. m/z: 364 [M+H]+ observed). ¹H NMR (400 MHz, DMSO-d₆): δ 8.76 (s, 1H), 7.73 (s, 1H), 7.00 (s, 1H), 6.86 (s, 1H), 4.68 (brd, J=1 Hz, 1H), 4.53 (brd, J=3.5 Hz, 1H), 3.89 (s, 3H), 3.33 (bs, 1H), 1.81 (bs, 1H), 0.95 (d, J=2.2 Hz, 3H) and 0.68 (d, J=2.2 Hz, 3H).

The following example were prepared in a similar manner as (R)-2-chloro-7-isopropyl-3-methoxy-11-oxo-6,7-dihydro-11H-benzo[f]pyrido[1,2-d][1,4]oxazepine-10-carboxylic acid and (S)-2-chloro-7-isopropyl-3-methoxy-11-oxo-6,7-dihydro-11H-benzo[f]pyrido[1,2-d][1,4]oxazepine-10-carboxylic acid from 2-(2-(benzyloxy)-5-chloro-4-methoxyphenyl)-4H-pyran-4-one and an appropriate amine.

Example 5: 2-Chloro-7-isobutyl-3-methoxy-11-oxo-6,7-dihydro-11H-benzo[f]pyrido[1,2-d][1,4]oxazepine-10-carboxylic acid

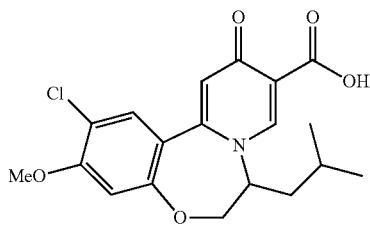 [SMILES: COc1cc2c(cc1Cl)-c1cc(=O)c(C(=O)O)cn1C(CC(C)C)CO2]

m/z: 378 [M+H]+ observed. 1H NMR (400 MHz, DMSO-d6): δ 8.74 (s, 1H), 7.78 (s, 1H), 6.99-6.98 (m, 2H), 4.62 (m, 3H), 3.93 (s, 3H), 1.61 (m, 2H), 1.46 (m, 2H), 0.81 (m, 6H).

Example 6: (S)-2-Chloro-7-isobutyl-3-methoxy-11-oxo-6,7-dihydro-11H-benzo[f]pyrido[1,2-d][1,4]oxazepine-10-carboxylic acid

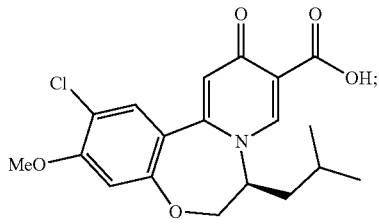 [SMILES: COc1cc2c(cc1Cl)-c1cc(=O)c(C(=O)O)cn1[C@@H](CC(C)C)CO2]

Example 7: (R)-2-Chloro-7-isobutyl-3-methoxy-1-oxo-6,7-dihydro-11H-benzo[f]pyrido[1,2-d][1,4]oxazepine-10-carboxylic acid

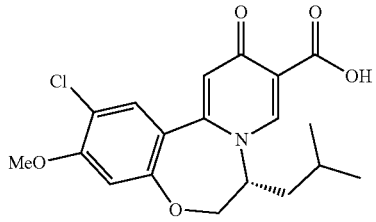 [SMILES: COc1cc2c(cc1Cl)-c1cc(=O)c(C(=O)O)cn1[C@H](CC(C)C)CO2]

84 mg of the mixture of enantiomers was separated by SFC (supercritical fluid chromatography) on an AS column using 35% EtOH (0.1% aq. NH3) as a modifier to give (S)-2-chloro-7-isobutyl-3-methoxy-11-oxo-6,7-dihydro-11H-benzo[f]pyrido[1,2-d][1,4]oxazepine-10-carboxylic acid as a white solid (faster eluting enantiomer, 42 mg, 50%, m/z: 378 [M+H]+ observed) and (R)-2-chloro-7-isobutyl-3-methoxy-11-oxo-6,7-dihydro-11H-benzo[f]pyrido[1,2-d][1,4]oxazepine-10-carboxylic acid as a white solid (slower eluting enantiomer, 40 mg, 47%, m/z: 378 [M+H]+ observed).

Example 6: (S)-2-Chloro-7-isobutyl-3-methoxy-11-oxo-6,7-dihydro-11H-benzo[f]pyrido[1,2-d][1,4]oxazepine-10-carboxylic acid. m/z: 378 [M+H]+ observed. 1H NMR (400 MHz, DMSO-d6): δ 8.74 (s, 1H), 7.78 (s, 1H), 6.99-6.98 (m, 2H), 4.62 (m, 3H), 3.93 (s, 3H), 1.61 (m, 2H), 1.46 (m, 1H), 0.81 (m, 6H).

Example 7: (R)-2-Chloro-7-isobutyl-3-methoxy-11-oxo-6,7-dihydro-11H-benzo[f]pyrido[1,2-d][1,4]oxazepine-10-carboxylic acid. m/z: 378 [M+H]+ observed. 1H NMR (400 MHz, DMSO-d6): δ 8.74 (s, 1H), 7.78 (s, 1H), 6.99-6.98 (m, 2H), 4.62 (m, 3H), 3.93 (s, 3H), 1.61 (m, 2H), 1.46 (m, 1H), 0.81 (m, 6H).

Example 8: 2-Chloro-7-ethyl-3-methoxy-11-oxo-6,7-dihydro-11H-benzo[f]pyrido[1,2-d][1,4]oxazepine-10-carboxylic acid

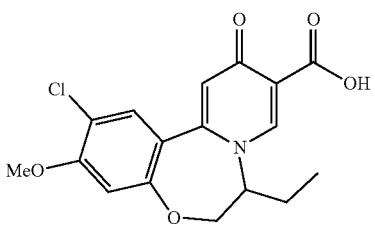 [SMILES: CCC1COc2cc(OC)c(Cl)cc2-c2cc(=O)c(C(=O)O)cn21]

m/z: 350 [M+H]+ observed. 1H NMR (400 MHz, DMSO-d6): δ 8.70 (s, 1H), 7.77 (s, 1H), 7.00 (s, 1H), 6.99 (s, 1H), 4.61 (m, 3H), 3.93 (s, 3H), 1.82 (m, 2H), 0.87-0.83 (t, J=7.2 Hz, 3H).

Example 9: 2-Chloro-7-(hydroxymethyl)-3-methoxy-1-oxo-6,7-dihydro-11H-benzo[f]pyrido[1,2-d][1,4]oxazepine-10-carboxylic acid

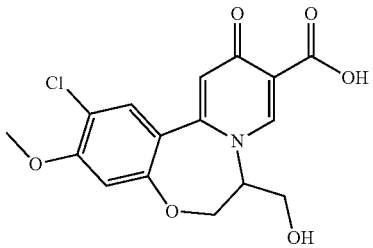 [SMILES: COc1cc2c(cc1Cl)-c1cc(=O)c(C(=O)O)cn1C(CO)CO2]

m/z: 352 [M+H]+ observed. 1H NMR (400 MHz, DMSO-d6): δ 16.31 (s, 1H), 8.94 (s, 1H), 7.76 (s, 1H), 7.04 (s, 1H), 6.95 (s, 1H), 5.47 (bs, 1H), 4.63-4.50 (m, 3H), 3.92 (s, 3H), 3.87-3.84 (m, 2H).

Example 10: 2-Chloro-7-cyclobutyl-3-methoxy-11-oxo-6,7-dihydro-11H-benzo[f]pyrido[1,2-d][1,4]oxazepine-10-carboxylic acid

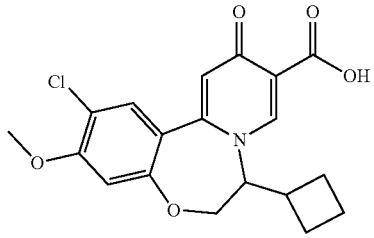 [SMILES: COc1cc2c(cc1Cl)-c1cc(=O)c(C(=O)O)cn1C(C1CCC1)CO2]

m/z: 376 [M+H]+ observed. ¹H NMR (400 MHz, DMSO-d₆): 16.30 (s, 1H), 8.50 (bs, 1H), 7.75 (s, 1H), 6.99 (s, 1H), 6.95 (s, 1H), 4.66 (m, 1H), 4.47 (t, J=12.0 Hz, 1H), 4.44 (m, 1H), 3.92 (s, 3H), 2.91 (m, 1H), 2.03 (m, 1H), 1.87-1.78 (m, 3H), 1.75-1.74 (m, 2H).

Example 11: 2-Chloro-7-(isopropoxymethyl)-3-methoxy-11-oxo-6,7-dihydro-11H-benzo[f]pyrido[1,2-d][1,4]oxazepine-10-carboxylic acid

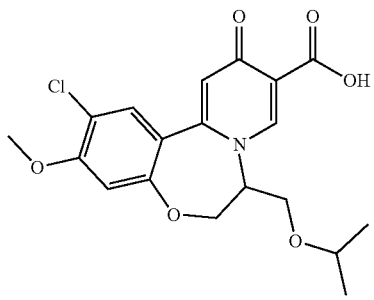 [SMILES: COc1cc2c(cc1Cl)-c1cc(=O)c(C(=O)O)cn1C(COC(C)C)CO2]

m/z: 394 [M+H]+ observed. ¹H NMR (400 MHz, CDCl₃): δ 15.60 (s, 1H), 8.92 (s, 1H), 7.49 (s, 1H), 6.74 (s, 2H), 4.72-4.66 (m, 1H), 4.47-4.41 (m, 2H), 3.95-3.93 (m, 4H), 3.84-3.80 (m, 1H), 3.70-3.64 (m, 1H), 1.27-1.25 (d, J=6.0 Hz, 3H), 1.20-1.18 (d, J=6.0 Hz, 3H).

Example 12: 6-(Tert-butyl)-2-chloro-3-methoxy-11-oxo-6,7-dihydro-11H-benzo[f]pyrido[1,2-d][1,4]oxazepine-10-carboxylic acid

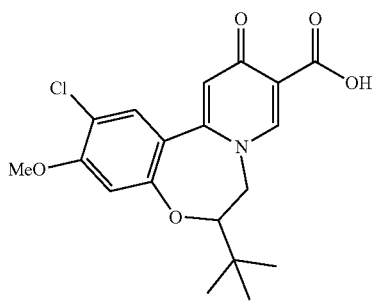 [SMILES: COc1cc2c(cc1Cl)-c1cc(=O)c(C(=O)O)cn1CC(C(C)(C)C)O2]

m/z: 378 [M+H]+ observed. ¹H NMR: (300 MHz, DMSO-d₆): δ 10.41 (s, 1H), 8.43 (s, 1H), 7.17 (s, 1H), 6.53 (s, 1H), 6.47 (s, 1H), 6.25 (m, 1H), 5.88 (m, 2H), 3.66 (s, 3H) and 0.74 (s, 9H).

Example 13: 11-Chloro-10-methoxy-2-oxo-5a,6,7,7a-tetrahydro-2H-benzo[f]cyclobuta[b]pyrido[1,2-d][1,4]oxazepine-3-carboxylic acid

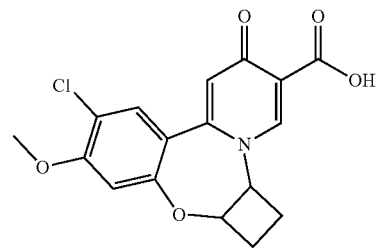 [SMILES: COc1cc2c(cc1Cl)-c1cc(=O)c(C(=O)O)cn1C1CCC1O2]

m/z: 348 [M+H]+ observed. ¹H NMR (400 MHz, DMSO-d₆): δ 8.75 (s 1H), 7.80 (s, 1H), 7.10 (s, 1H), 6.93 (s, 1H), 5.20-5.05 (m, 2H), 3.95 (s, 3H), 2.36-2.15 (m, 4H).

Example 14: 12-Chloro-11-methoxy-2-oxo-5a,7,8,8a-tetrahydro-2H,6H-benzo[f]cyclopenta[b]pyrido[1,2-d][1,4]oxazepine-3-carboxylic acid

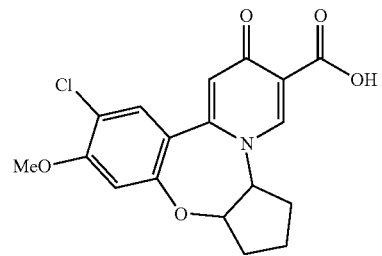 [SMILES: COc1cc2c(cc1Cl)-c1cc(=O)c(C(=O)O)cn1C1CCCC1O2]

m/z: 362 [M+H]+ observed. ¹H NMR (400 MHz, CDCl₃): δ 8.61 (s, 1H), 7.48 (s, 1H), 6.73-6.72 (m, 2H), 5.04-4.95 (m, 1H), 4.55-4.42 (m, 1H), 3.94 (s, 3H), 2.28-1.70 (m, 6H).

Example 15: 2-Fluoro-7-isopropyl-3-methoxy-11-oxo-6,7-dihydro-11H-benzo[f]pyrido[1,2-d][1,4]oxazepine-10-carboxylic acid

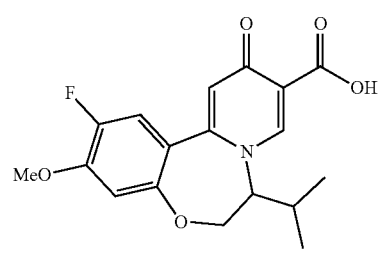 [SMILES: COc1cc2c(cc1F)-c1cc(=O)c(C(=O)O)cn1C(C(C)C)CO2]

2-((tert-Butoxycarbonyl)amino)-3-methylbutyl methanesulfonate

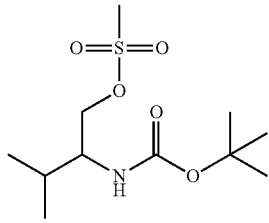 [SMILES: CC(C)C(COS(C)(=O)=O)NC(=O)OC(C)(C)C]

tert-butyl N-(1-hydroxy-3-methylbutan-2-yl)carbamate (600 mg, 2.95 mmol) and triethylamine (1.2 mL, 8.85 mmol) were dissolved in anhydrous THF (30 mL). Methanesulfonyl chloride (473 mg, 4.13 mmol) was added drop-wise and the mixture was stirred overnight at RT. The reaction was diluted with H$_2$O (25 mL) and extracted with EtOAc (2×25 mL). The combined organic fractions were washed with sat. aqueous brine solution (10 mL), dried over sodium sulfate and concentrated under vacuum to give crude tert-butyl N-[1-(methanesulfonyloxy)-3-methylbutan-2-yl]carbamate as a white solid that was used without further purification (0.73 g, 89% yield, m/z: 282 [M+H]$^+$ observed).

Tert-butyl (1-(4-fluoro-2-formyl-5-methoxyphenoxy)-3-methylbutan-2-yl)carbamate

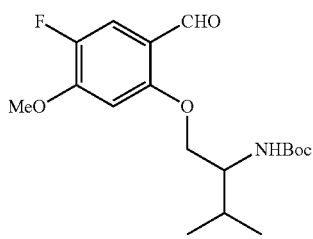 [SMILES: COc1cc(OCC(NC(=O)OC(C)(C)C)C(C)C)c(C=O)cc1F]

5-Fluoro-2-hydroxy-4-methoxybenzaldehyde (200 mg, 0.56 mmol) and cesium carbonate (840 mg, 2.59 mmol) were suspended in anhydrous DMF (5 mL) and stirred at rt for 15 minutes. Tert-butyl N-[1-(methanesulfonyloxy)-3-methylbutan-2-yl]carbamate (662 mg, 2.35 mmol) and potassium iodide (20 mg, 0.12 mmol) in DMF (1 mL) were added and the reaction mixture was heated at 55° C. for 36 hours. The reaction was diluted with H$_2$O (15 mL) and extracted with EtOAc (2×25 mL). The combined organic fractions were washed with sat. aqueous brine solution (10 mL), dried over sodium sulfate and concentrated under vacuum. The residue was purified by normal phase SiO$_2$ chromatography (5% to 45% EtOAc/hexanes) to furnish tert-butyl N-[1-(4-fluoro-2-formyl-5-methoxyphenoxy)-3-methylbutan-2-yl]carbamate as a light yellow solid (175 mg, 42% yield, m/z: 356 [M+H]$^+$ observed).

7-Fluoro-3-isopropyl-8-methoxy-2,3-dihydrobenzo [f][1,4]oxazepine hydrochloride

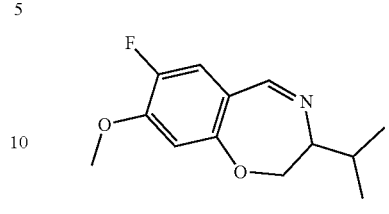

tert-butyl N-[1-(4-fluoro-2-formyl-5-methoxyphenoxy)-3-methylbutan-2-yl]carbamate (175 mg, 0.49 mmol) was dissolved in anhydrous CH$_2$Cl$_2$ (2 mL) and a hydrogen chloride solution (4M in 1,4-dioxane, 0.62 mL, 2.46 mmol) was added. The mixture was stirred at rt overnight. The mixture was concentrated under vacuum and further azeotroped with THF (2×5 mL), then dried over sodium sulfate and concentrated under vacuum to give 7-fluoro-3-isopropyl-8-methoxy-2,3-dihydro-1,4-benzoxazepine, hydrochloride salt as a light green solid that was used without further purification (0.11 g, 80% yield, m/z: 238 [M+H]$^+$ observed). $^1$H NMR (300 MHz, CDCl$_3$) δ ppm 8.51-8.67 (m, 1H) 7.35-7.49 (m, 1H) 6.69-6.78 (m, 1H) 4.63-4.79 (m, 1H) 4.02 (s, 5H) 1.96-2.12 (m, 1H) 1.12-1.31 (m, 6H).

Ethyl 2-fluoro-7-isopropyl-3-methoxy-11-oxo-6,7,12,12a-tetrahydro-11H-benzo[f]pyrido[1,2-d][1,4]oxazepine-10-carboxylate

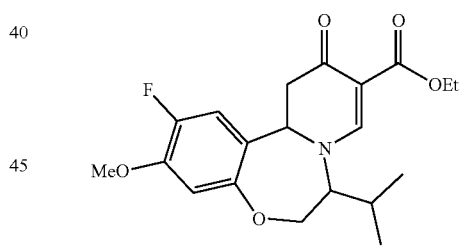

7-fluoro-3-isopropyl-8-methoxy-2,3-dihydro-1,4-benzoxazepine hydrochloride, (50 mg, 0.18 mmol) and ethyl (2E)-2-(ethoxymethylidene)-3-oxobutanoate (100 mg, 0.55 mmol) were dissolved in anhydrous EtOH (1 mL) and the mixture was heated at 115° C. in a microwave reactor for 2 hours. The mixture was concentrated to give the crude product ethyl 2-fluoro-7-isopropyl-3-methoxy-11-oxo-6,7,12,12a-tetrahydro-11H-benzo[f]pyrido[1,2-d][1,4]oxazepine-10-carboxylate as a yellow oil that was used in the next step without further purification (0.07 g, >100% yield, m/z: 378 [M+H]$^+$ observed).

Ethyl 2-fluoro-7-isopropyl-3-methoxy-11-oxo-6,7-dihydro-11H-benzo[f]pyrido[1,2-d][1,4]oxazepine-10-carboxylate

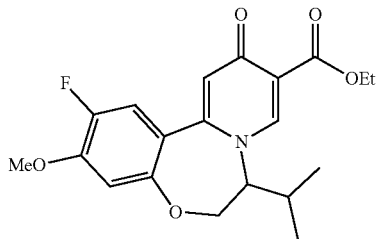 [SMILES: CCOC(=O)c1cn2c(cc1=O)-c1cc(F)c(OC)cc1OCC2C(C)C]

The crude ethyl 2-fluoro-7-isopropyl-3-methoxy-11-oxo-6,7,12,12a-tetrahydro-11H-benzo[f]pyrido[1,2-d][1,4]oxazepine-10-carboxylate (0.07 g, 0.19 mmol) was dissolved in 2-Me-THF (1 mL) and p-chloranil (54 mg, 0.22 mmol) was added. The mixture was heated at 70° C. for 3 hours. The reaction was diluted with EtOAc (15 mL) and washed with sat. aqueous sodium bicarbonate solution (15 mL), H$_2$O (10 mL), sat. aqueous brine solution (10 mL), dried over sodium sulfate and concentrated under vacuum. The residue was purified by reverse phase HPLC. The pure fractions were combined, extracted with EtOAc (3×30 mL) and concentrated under vacuum to afford ethyl 2-fluoro-7-isopropyl-3-methoxy-11-oxo-6,7-dihydro-11H-benzo[f]pyrido[1,2-d][1,4]oxazepine-10-carboxylate as a yellow solid (0.02 g, 25% yield, m/z: 376 [M+H]$^+$ observed). $^1$H NMR (400 MHz, CDCl$_3$) δ ppm 9.15-9.21 (m, 1H), 7.32 (s, 1H), 7.25 (s, 1H), 6.69 (d, J=7.33 Hz, 1H), 4.70 (bs, 2H), 4.42-4.56 (m, 2H), 4.06-4.23 (m, 1H), 3.97 (s, 3H), 2.07-2.18 (m, 1H), 1.43 (t, J=7.04 Hz, 3H), 1.15 (d, J=6.74 Hz, 3H), 0.86 (d, J=6.45 Hz, 3H).

2-Fluoro-7-isopropyl-3-methoxy-11-oxo-6,7-dihydro-11H-benzo[f]pyrido[1,2-d][1,4]oxazepine-10-carboxylic acid

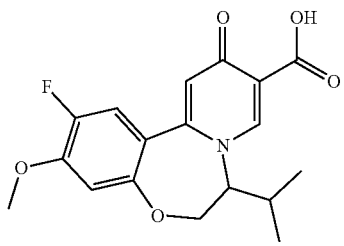 [SMILES: COc1cc2c(cc1F)-c1cc(=O)c(C(=O)O)cn1C(C(C)C)CO2]

Ethyl 2-fluoro-7-isopropyl-3-methoxy-11-oxo-6,7-dihydro-11H-benzo[f]pyrido[1,2-d][1,4]oxazepine-10-carboxylate (17 mg, 0.05 mmol) and lithium hydroxide monohydrate (6 mg, 0.14 mmol) were suspended in a THF/MeOH/H$_2$O mixture (3:1:1, 1 mL) and the reaction was stirred at rt for 2 hours. The reaction was acidified by the addition of aqueous 1N HCl (10 mL) and extracted with EtOAc (3×15 mL). The combined organic fractions were dried over sodium sulfate and concentrated under vacuum to give 2-fluoro-7-isopropyl-3-methoxy-11-oxo-6,7-dihydro-11H-benzo[f]pyrido[1,2-d][1,4]oxazepine-10-carboxylic acid (9 mg, 57% yield, m/z: 348 [M+H]$^+$ observed). $^1$H NMR (400 MHz, CDCl$_3$) δ ppm 8.58 (s, 1H), 7.24 (d, J=11.43 Hz, 1H), 6.90 (s, 1H), 6.70 (d, J=7.33 Hz, 1H), 4.53-4.66 (m, 2H), 3.95 (s, 4H), 2.07-2.18 (m, 1H), 1.09 (d, J=6.45 Hz, 3H), 0.86 (d, J=6.45 Hz, 3H).

The following example was prepared in a similar manner as 2-fluoro-7-isopropyl-3-methoxy-11-oxo-6,7-dihydro-11H-benzo[f]pyrido[1,2-d][1,4]oxazepine-10-carboxylic acid from 2-hydroxy-4-methoxybenzaldehyde and an appropriate mesylate.

Example 16: 7-Isopropyl-3-methoxy-11-oxo-6,7-dihydro-11H-benzo[f]pyrido[1,2-d][1,4]oxazepine-10-carboxylic acid

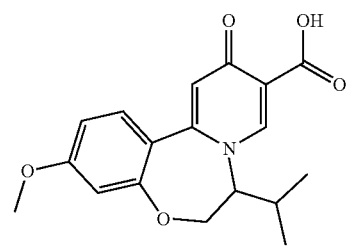 [SMILES: COc1ccc2c(c1)OCC(C(C)C)n1cc(C(=O)O)c(=O)cc1-2]

m/z: 330 [M+H]$^+$ observed). $^1$H NMR (300 MHz, CDCl$_3$) δ ppm 8.48-8.58 (m, 1H), 7.39-7.48 (m, 1H), 6.88-6.95 (m, 1H), 6.75-6.85 (m, 1H), 6.62 (br. s., 1H), 4.60 (bs, 2H), 3.87 (bs, 4H), 2.03-2.10 (m, 1H), 1.04-1.13 (m, 3H), 0.80-0.88 (m, 3H).

Example 17: (R)-7-Isopropyl-3-methoxy-11-oxo-6,7-dihydro-11H-benzo[f]pyrido[1,2-d][1,4]oxazepine-10-carboxylic acid

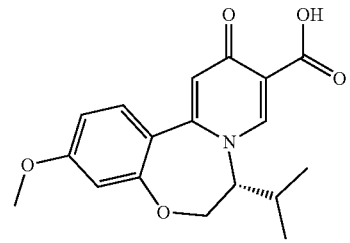 [SMILES: COc1ccc2c(c1)OC[C@@H](C(C)C)n1cc(C(=O)O)c(=O)cc1-2]

m/z: 330 [M+H]$^+$ observed). $^1$H NMR (300 MHz, CDCl$_3$) δ ppm 8.48-8.58 (m, 1H), 7.39-7.48 (m, 1H), 6.88-6.95 (m, 1H), 6.75-6.85 (m, 1H), 6.62 (br. s., 1H), 4.60 (bs, 2H), 3.87 (bs, 4H), 2.03-2.10 (m, 1H), 1.04-1.13 (m, 3H), 0.80-0.88 (m, 3H).

Example 18: (S)-7-Isopropyl-3-methoxy-1-oxo-6,7-dihydro-11H-benzo[f]pyrido[1,2-d][1,4]oxazepine-10-carboxylic acid

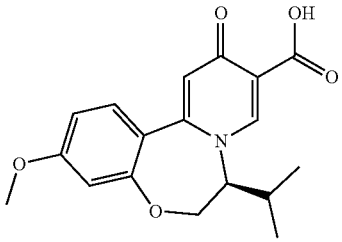 [SMILES: COc1ccc2c(c1)OC[C@H](C(C)C)n1cc(C(=O)O)c(=O)cc1-2]

m/z: 330 [M+H]$^+$ observed). $^1$H NMR (300 MHz, CDCl$_3$) δ ppm 8.48-8.58 (m, 1H), 7.39-7.48 (m, 1H), 6.88-6.95 (m, 1H), 6.75-6.85 (m, 1H), 6.62 (bs, 1H), 4.60 (bs, 2H), 3.87 (bs, 4H), 2.03-2.10 (m, 1H), 1.04-1.13 (m, 3H), 0.80-0.88 (m, 3H).

Example 19: 6-Isopropyl-10,11-dimethoxy-2-oxo-2,6,7,8-tetrahydrobenzo[c]pyrido[1,2-a]azepine-3-carboxylic acid

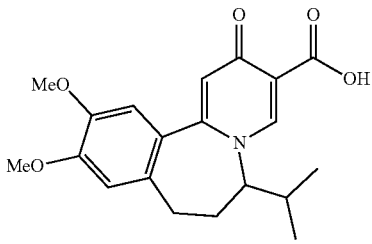 [SMILES: COc1cc2c(cc1OC)-c1cc(=O)c(C(=O)O)cn1C(C(C)C)CC2]

2-Bromo-4,5-dimethoxybenzoyl chloride

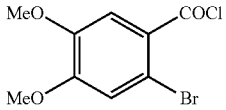 [SMILES: COc1cc(Br)c(C(=O)Cl)cc1OC]

A mixture of 2-bromo-4,5-dimethoxybenzoic acid (5.22 g, 20 mmol) and thionyl chloride (20 mL) were refluxed for 3 h. Excess thionyl chloride was removed under vacuum and the crude product was azeotroped from 50 mL toluene, followed by high vacuum drying for 2 h to give the desired product 2-bromo-4,5-dimethoxybenzoyl chloride as a clear oil that was used without further purification (5.6 g, quantitative yield).

Ethyl 6-(2-bromo-4,5-dimethoxyphenyl)-4-oxo-4H-pyran-3-carboxylate

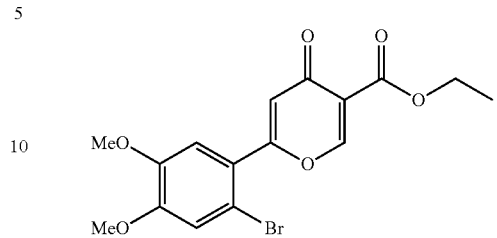

To a solution of LiHMDS (24 mmol, 22.6 mL, 1.06 M in THF) in anhydrous THF (30 mL) at −78° C. (dry ice/acetone bath) under argon, a solution of ethyl (Z)-2-((dimethylamino)methylene)-3-oxobutanoate (1.85 g, 10 mmol) and 2-bromo-4,5-dimethoxybenzoyl chloride (2.79 g, 10 mmol) in 50 mL anhydrous THF was added dropwise over 10 min. The dry ice/acetone bath was removed and the solution was warmed for 15 min period. Diethyl ether (100 mL) was added to the reaction mixture followed by 3N aq. HCl (30 mL, 90 mmol), and the contents were stirred overnight. The reaction mixture was poured slowly into a saturated aqueous bicarbonate solution (600 mL) with vigorous stirring, and additional solid sodium bicarbonate was added until the aqueous layer was reached basic pH. The resulting system was stirred vigorously for 10 min. The precipitate was filtered, washed with water, dissolved in dichloromethane, dried over sodium sulfate and concentrated to give a dark orange residue (6.5 g). Purification by normal phase SiO$_2$ chromatography (10% to 100% EtOAc/hexanes) yielded the desired product as an orange solid (2.1 g), which upon crystallization from methanol (20 mL) furnished ethyl 6-(2-bromo-4,5-dimethoxyphenyl)-4-oxo-4H-pyran-3-carboxylate as a light orange solid (1.56 g, 40% yield, m/z: 383/385 [M+H]$^+$ observed). $^1$H NMR (300 MHz, CDCl$_3$): δ 8.20 (s, 1H), 7.30 (s, 1H), 7.10 (s, 1H), 6.42 (s, 1H), 4.37 (q, J=2.4 Hz, 2H), 3.85 (m, 6H) and 1.35 (t, J=2.4 Hz, 3H).

Ethyl 6-(2-bromo-4,5-dimethoxyphenyl)-1-(4-methylpent-1-en-3-yl)-4-oxo-1,4-dihydro pyridine-3-carboxylate

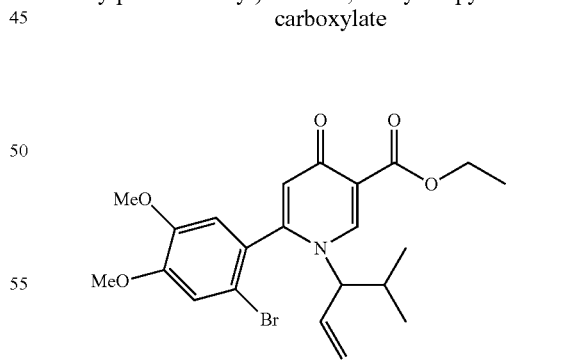

To a mixture of ethyl 6-(2-bromo-4,5-dimethoxyphenyl)-4-oxo-4H-pyran-3-carboxylate (383 mg, 1 mmol) in AcOH/EtOH (18 mL, 5:1 ratio), N-Boc-4-methylpent-1-en-3-amine (300 mg, 1.5 mmol) was added and refluxed at 120° C. for 12 h. The crude reaction mixture was concentrated under vacuum, and the residue was purified on normal phase SiO$_2$ chromatography (0% to 10% MeOH/CH$_2$Cl$_2$) to give ethyl 6-(2-bromo-4,5-dimethoxyphenyl)-1-(4-methylpent- 1-en-3-yl)-4-oxo-1,4-dihydropyridine-3-carboxylate as a yellow oil (139 mg, 30% yield, m/z: 464/466 [M+H]+ observed). ¹H NMR (300 MHz, CDCl₃): δ 8.28 (s, 1H), 7.11 (d, J=2.2 Hz, 1H), 6.70 (d, J=9.3 Hz, 1H), 6.42 (d, J=3.5 Hz, 1H), 6.05-5.85 (m, 1H), 5.45-4.85 (m, 2H), 4.41 (q, J=3.5 Hz, 2H), 3.95-3.70 (m, 7H), 2.20-2.05 (m, 1H), 1.41 (t, J=3.5 Hz, 3H) and 0.96-0.79 (m, 6H).

Ethyl 6-Isopropyl-10,11-dimethoxy-2-oxo-2,6,7,8-tetrahydrobenzo[c]pyrido[1,2-a]azepine-3-carboxylate

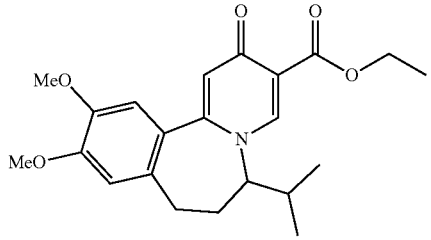 [SMILES: CCOC(=O)c1cn2c(cc1=O)-c1cc(OC)c(OC)cc1CCC2C(C)C]

To a stirred solution of ethyl 6-(2-bromo-4,5-dimethoxyphenyl)-1-(4-methylpent-1-en-3-yl)-4-oxo-1,4-dihydropyridine-3-carboxylate (93 mg, 0.2 mmol) in anhydrous THF (20 mL) under argon, 9-BBN (1.2 mL, 0.6 mmol, 0.5 M solution in THF) was added dropwise and the system was heated at 60° C. for 3 hours. Aqueous cesium carbonate (1 mL, 2 M solution, 2 mmol) and Pd(dppf)Cl₂ (16 mg, 0.020 mmol) were added and refluxed overnight. Solvents were removed and the crude product was purified on normal phase SiO₂ chromatography (0%-10% MeOH/CH₂Cl₂) to give ethyl 6-isopropyl-10,11-dimethoxy-2-oxo-2,6,7,8-tetrahydro benzo[c]pyrido[1,2-a]azepine-3-carboxylate as a white foam (40 mg, 52% yield, m/z: 386 [M+H]+ observed). ¹H NMR (300 MHz, CDCl₃): δ 8.20 (s, 1H), 7.18 (s, 1H), 6.97 (s, 1H), 6.94 (s, 1H), 5.60 (s, 1H), 5.27 (s, 1H), 4.38 (q, J=2.5 Hz, 2H), 4.10-3.93 (m, 7H), 1.90-1.75 (m, 2H), 1.70-1.60 (m, 1H), 1.30-1.20 (m, 1H), 1.39 (t, J=2.5 Hz, 3H), 0.90 (d, J=2.2 Hz, 3H) and 0.83 (d, J=2.2 Hz, 3H).

6-Isopropyl-10,11-dimethoxy-2-oxo-2,6,7,8-tetrahydrobenzo[c]pyrido[1,2-a]azepine-3-carboxylic acid

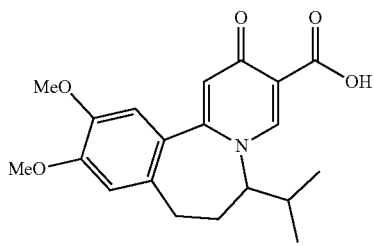 [SMILES: COc1cc2c(cc1OC)-c1cc(=O)c(C(=O)O)cn1C(C(C)C)CC2]

To a mixture of compound ethyl 6-isopropyl-10,11-dimethoxy-2-oxo-2,6,7,8-tetrahydrobenzo[c]pyrido[1,2-a]azepine-3-carboxylate (16 mg, 0.04 mmol) in dioxane (3 mL), aq. LiOH (3.5 mg in 0.2 mL, 0.2 mmol) was added and stirred at room temperature overnight. The reaction mixture was concentrated under vacuum, and the residue was dissolved in water (2 mL) and acidified with 1N aq. HCl to pH 2-3. The precipitate was filtered, washed with 2 mL of water and dried under high vacuum to furnish 6-isopropyl-10,11-dimethoxy-2-oxo-2,6,7,8-tetrahydrobenzo[c]pyrido[1,2-a]azepine-3-carboxylic acid as a white solid (9 mg, 60% yield, m/z: 358 [M+H]+ observed). ¹H NMR (300 MHz, DMSO-d6): δ 8.81 (s, 1H), 7.57 (bs, 2H), 7.26 (s, 1H), 5.87 (s, 1H), 5.36 (s, 1H), 5.00 (d, J=2.7 Hz, 1H), 3.91 (bs, 7H), 2.45 (bs, 1H), 1.71 (bs, 1H), 0.77 (bs, 6H).

Example 20: 6-Isopropyl-2-methoxy-3-(3-methoxypropoxy)-10-oxo-5,10-dihydro-6H-pyrido[1,2-h][1,7]naphthyridine-9-carboxylic acid

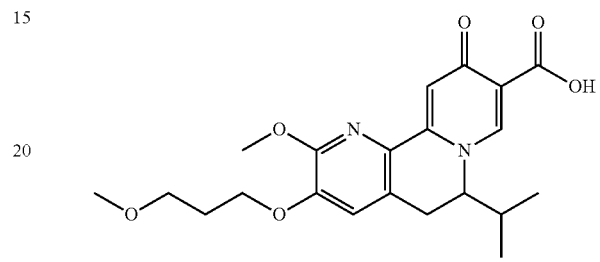

5-Bromo-2-chloro-3-(3-methoxypropoxy)pyridine

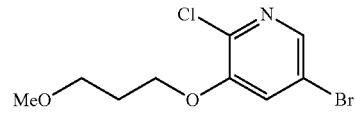 [SMILES: COCCCOc1cc(Br)cnc1Cl]

To a stirred solution of 5-bromo-2-chloropyridin-3-ol (7.1 g, 34.3 mmol) in DMF (50 mL) was added Cs₂CO₃ (16.7 g, 51.4 mmol) followed by 1-bromo-3-methoxypropane (6.29 g, 41.4 mmol) at room temperature, and the reaction mixture was stirred at rt for 4 h. The reaction was monitored by TLC. The reaction mixture was diluted with water (80 mL) and extracted in EtOAc (3×70 mL). The organic fractions were combined, dried over sodium sulfate, evaporated under vacuum, and the residue was purified by normal phase SiO₂ chromatography (0% to 30% EtOAc/hexanes) to furnish 5-bromo-2-chloro-3-(3-methoxypropoxy)pyridine as an off-white solid (6.11 g, 64% yield, m/z: 280/282 [M+H]+ observed). ¹H NMR (400 MHz, DMSO-d₆) δ 8.13 (d, J=1.2 Hz, 1H), 7.89 (d, J=1.2 Hz, 1H), 4.21-4.18 (t, J=6.4 Hz, 2H), 3.49-3.46 (t, J=6.4 Hz, 2H), 3.25 (s, 3H), 2.01-1.95 (m, 2H).

5-Bromo-2-methoxy-3-(3-methoxypropoxy)pyridine

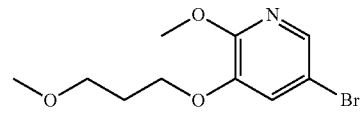

To a stirred solution of 5-bromo-2-chloro-3-(3-methoxypropoxy)pyridine (7 g, 25 mmol) was added NaOMe (25% solution in MeOH, 57 mL, 251 mmol), and the reaction mixture was heated at 80° C. for 3 h. The reaction was monitored by TLC and LCMS. The reaction mixture was cooled to room temperature and diluted with water (80 mL), then extracted with EtOAc (3×70 mL). The organic fractions were combined, dried over sodium sulfate and evaporated under vacuum to give 5-bromo-2-methoxy-3-(3-methoxypropoxy)pyridine as a yellow gum that was used without further purification (6.8 g, 98% yield, m/z: 276/278 [M+H]$^+$ observed). $^1$H NMR (400 MHz, DMSO-d$_6$) δ 7.77 (d, J=2.0 Hz, 1H), 7.48 (d, J=2.0 Hz, 1H), 4.05-4.02 (t, J=6.4 Hz, 2H), 3.82 (s, 3H), 3.44-3.41 (t, J=6.4 Hz, 2H), 3.22 (s, 3H), 1.96-1.91 (m, 2H).

1-(6-Methoxy-5-(3-methoxypropoxy)pyridin-3-yl)-3-methylbutan-2-one

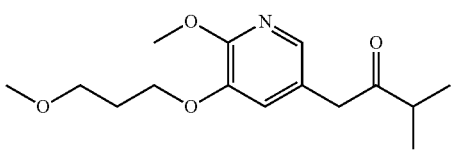 [SMILES: COCCCOc1cc(CC(=O)C(C)C)cnc1OC]

To a stirred solution of 5-bromo-2-methoxy-3-(3-methoxypropoxy)pyridine (1 g, 3.63 mmol) and 3-methylbutan-2-one (0.94 g, 10.9 mmol) in THF (10 mL) was added NaOtBu (1.15 g, 12 mmol). The reaction mixture was degassed at room temperature using an argon balloon for 30 min. Then Xantphos (42 mg, 0.072 mmol) was added to the reaction mixture followed by Pd$_2$(dba)$_3$ (33 mg, 0.036 mmol) at room temperature. The reaction mixture was warmed to 80° C. and stirred for 2 h. The reaction was monitored by TLC. The reaction mixture was cooled to room temperature, evaporated in vacuum, diluted with water (10 mL) and extracted with EtOAc (3×15 mL). The organic fractions were combined, dried over sodium sulfate, evaporated under vacuum and the residue was purified by normal phase SiO$_2$ chromatography (0% to 30% EtOAc/hexanes) to furnish 1-(6-methoxy-5-(3-methoxypropoxy)pyridin-3-yl)-3-methylbutan-2-one as a yellow oil (7.4 g, 73% yield from 10×1 g scale reactions, m/z: 282 [M+H]$^+$ observed). $^1$H NMR (400 MHz, CDCl$_3$) δ 7.51 (d, J=1.6 Hz, 1H), 6.93 (d, J=1.6 Hz, 1H), 4.09-4.05 (t, J=6.4 Hz, 2H), 3.98 (s, 3H), 3.64 (s, 2H), 3.55 (t, J=6.0 Hz, 2H), 3.33 (s, 3H), 2.73 (m, 1H), 2.11 (m, 2H), 1.13 (d, J=6.8 Hz, 6H).

1-(6-Methoxy-5-(3-methoxypropoxy)pyridin-3-yl)-3-methylbutan-2-amine

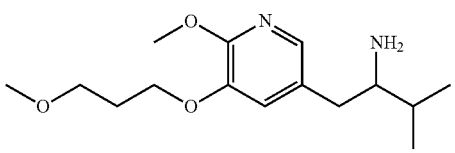 [SMILES: COCCCOc1cc(CC(N)C(C)C)cnc1OC]

To a stirred solution of 1-(6-methoxy-5-(3-methoxypropoxy)pyridin-3-yl)-3-methylbutan-2-one (7.4 g, 26.3 mmol) in MeOH (60 mL) at room temperature was added ammonium acetate (30.4 g, 395 mmol). The reaction mixture was cooled to 0° C., and NaCNBH$_3$ (3.26 g, 52.6 mmol) was added to the reaction mixture portion-wise and stirred at room temperature for 16 h. The reaction was monitored by TLC. The reaction mixture was evaporated under vacuum, diluted with ice cold water (80 mL) and extracted in EtOAc (3×100 mL). The organic fractions were dried over sodium sulfate and evaporated in vacuo to obtain 1-(6-methoxy-5-(3-methoxypropoxy)pyridin-3-yl)-3-methylbutan-2-amine as a brown oil that was used without further purification (8.2 g, >100% yield, m/z: 283 [M+H]$^+$ observed). $^1$H NMR (400 MHz, DMSO-d$_6$) δ 7.51 (s, 1H), 7.18 (s, 1H), 4.9 (bs, 2H), 4.01-3.98 (t, J=6.4 Hz, 2H), 3.81 (s, 3H), 3.46-3.43 (t, J=6.0 Hz, 2H), 3.23 (s, 3H), 2.95-2.91 (m, 1H), 2.85-2.81 (m, 1H), 2.69-2.65 (s, 1H), 1.97-1.91 (m, 2H), 1.70-1.66 (m, 1H), 0.85-0.95 (m, 6H).

Tert-butyl (1-(6-methoxy-5-(3-methoxypropoxy)pyridin-3-yl)-3-methylbutan-2-yl)carbamate

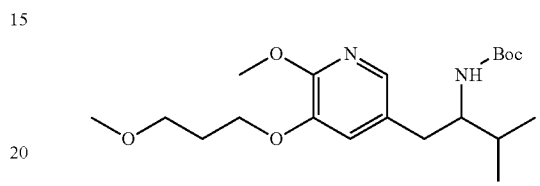

To a stirred solution of 1-(6-methoxy-5-(3-methoxypropoxy)pyridin-3-yl)-3-methylbutan-2-amine (8.2 g, 29 mmol) in CH$_2$Cl$_2$ (60 mL) was added triethylamine (10 mL, 73 mmol), followed by di-tert-butyl dicarbonate (7.6 g, 35 mmol) at 0° C. The reaction mixture was stirred at room temperature for 3 h, and the reaction was monitored by TLC. The reaction mixture was diluted with water (90 mL) and extracted in CH$_2$Cl$_2$ (3×50 mL). The combined organic fractions were dried over sodium sulfate and evaporated under vacuum, and the residue was purified by normal phase SiO$_2$ chromatography (0% to 20% EtOAc/hexanes) to furnish tert-butyl (1-(6-methoxy-5-(3-methoxypropoxy)pyridin-3-yl)-3-methylbutan-2-yl)carbamate as an off white solid (7.6 g, 68%, m/z: 383 [M+H]$^+$ observed). $^1$H NMR (400 MHz, CDCl$_3$) δ 7.49 (s, 1H), 6.98 (s, 1H), 4.34 (d, J=9.6 Hz, 1H), 4.11 (t, J=6.4 Hz, 2H), 3.99 (s, 3H), 3.68 (bs, 1H), 3.58 (t, J=6.4 Hz, 2H), 3.37 (s, 3H), 2.73 (dd, J=14.2, 6.1 Hz, 1H), 2.59 (dd, J=14.2, 8.4 Hz, 1H), 2.13 (m, 2H), 1.75 (m, 1H), 1.38 (s, 9H), 0.96 (dd, J=18.0, 6.8 Hz, 6H).

Tert-butyl (1-(2-bromo-6-methoxy-5-(3-methoxypropoxy)pyridin-3-yl)-3-methylbutan-2-yl)carbamate

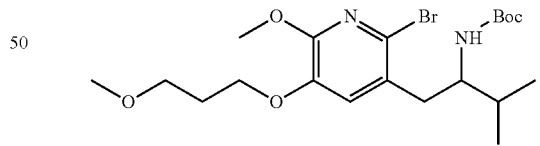

To a stirred solution of tert-butyl (1-(6-methoxy-5-(3-methoxypropoxy)pyridin-3-yl)-3-methylbutan-2-yl)carbamate (6.6 g, 17 mmol) in acetic acid (50 mL) at room temperature was added sodium acetate (1.41 g, 17.3 mmol) followed by bromine (0.88 mL, 17 mmol) and the reaction was stirred for 1 h. The reaction was monitored by TLC and LCMS. The reaction mixture was basified using saturated aqueous NaHCO$_3$ solution until reaching a pH of 10-12. The reaction mixture was extracted with CH$_2$Cl$_2$ (3×50 mL). The organic phase washed with saturated aqueous NaHCO$_3$ solution (75 mL), dried over sodium sulfate and evaporated under vacuum. The residue was purified by normal phase SiO₂ chromatography (0-15% EtOAc/hexanes) to afford tert-butyl (1-(2-bromo-6-methoxy-5-(3-methoxypropoxy) pyridin-3-yl)-3-methylbutan-2-yl)carbamate as brown gum (4.1 g, 52%, m/z: 461/463 [M+H]⁺ observed). ¹H NMR (400 MHz, CDCl₃) δ 7.02 (s, 1H), 4.44 (d, J=8.8 Hz, 1H), 4.10 (t, J=6.4 Hz, 2H), 3.96 (s, 3H), 3.78-3.74 (m, 1H), 3.57 (t, J=6.3 Hz, 2H), 3.34 (s, 3H), 2.85 (dd, J=14.2, 4.5 Hz, 1H), 2.66-2.6 (m, 1H), 2.11 (t, J=6.0 Hz, 2H), 1.85 (d, J=6.0 Hz, 1H), 1.37 (s, 9H), 1.05-0.91 (m, 6H).

Tert-butyl (1-(2-formyl-6-methoxy-5-(3-methoxypropoxy)pyridin-3-yl)-3-methylbutan-2-yl)carbamate)

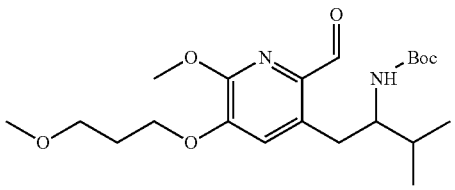 [SMILES: COCCCOc1cc(CC(NC(=O)OC(C)(C)C)C(C)C)c(C=O)nc1OC]

Tert-butyl (1-(2-bromo-6-methoxy-5-(3-methoxypropoxy)pyridin-3-yl)-3-methylbutan-2-yl) carbamate (500 mg, 1.08 mmol) was dissolved in anhydrous THF (25 mL), and the solids were completely dissolved by gently warming the solution with a heat gun. The reaction was cooled to −78° C. (dry ice/acetone bath) and n-BuLi (1.6M solution in hexanes, 1.69 mL, 2.71 mmol) was added dropwise. The mixture was stirred at −78° C. for 15 minutes. Dimethylformamide (0.12 mL, 1.63 mmol) was added dropwise and the reaction was stirred at −78° C. for 10 minutes, then warmed to room temperature and stirred for an additional 10 minutes. The reaction mixture was added dropwise to ice water (150 mL) with vigorous stirring. The precipitate was filtered to give a white solid. The filter cake was washed off with EtOAc (2×5 mL), and the residue was extracted with EtOAc (3×10 mL) to remove residual water. The EtOAc solution was dried with sodium sulfate and concentrated under vacuum to give tert-butyl (1-(2-formyl-6-methoxy-5-(3-methoxypropoxy) pyridin-3-yl)-3-methylbutan-2-yl)carbamate as a white solid that was used without further purification (455 mg, 92%, m/z: 411 [M+H]⁺ observed).

6-Isopropyl-2-methoxy-3-(3-methoxypropoxy)-5,6-dihydro-1,7-naphthyridine

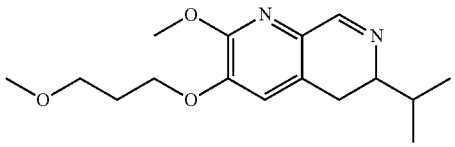 [SMILES: COCCCOc1cc2c(nc1OC)C=NC(C(C)C)C2]

Tert-butyl (1-(2-formyl-6-methoxy-5-(3-methoxypropoxy)pyridin-3-yl)-3-methylbutan-2-yl)carbamate (450 mg, 1.10 mmol) was dissolved in CH₂Cl₂ (10 mL) at room temperature and hydrogen chloride, (4M solution in 1,4-dioxane, 822 µL, 3.29 mmol) (4M/dioxane) was added. The reaction mixture was stirred at room temperature for 2 hours. The reaction mixture was concentrated, then treated with water (30 mL), and basified using saturated aqueous NaHCO₃ solution until pH 10-12. The mixture was extracted with CH₂Cl₂ (3×50 mL), the combined organic fractions was dried over anhydrous sodium sulfate, evaporated under vacuum and the residue was purified by normal phase SiO₂ chromatography (5-60% EtOAc/hexanes) to give 6-isopropyl-2-methoxy-3-(3-methoxypropoxy)-5,6-dihydro-1,7-naphthyridine as a yellow oil that was used without further purification (129 mg, 41%, m/z: 293 [M+H]⁺ observed).

Ethyl 6-isopropyl-2-methoxy-3-(3-methoxypropoxy)-10-oxo-5,10,11,11a-tetrahydro-6H-pyrido[1,2-h][1,7]naphthyridine-9-carboxylate

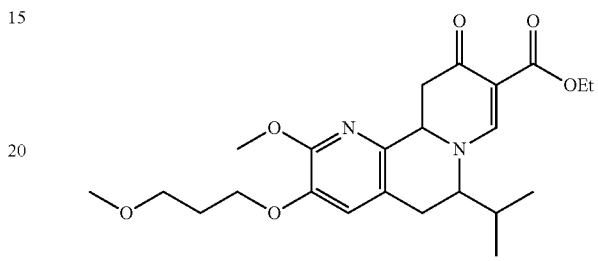

6-Isopropyl-2-methoxy-3-(3-methoxypropoxy)-5,6-dihydro-1,7-naphthyridine (129 mg, 0.441 mmol) and ethyl (2E)-2-(ethoxymethylidene)-3-oxobutanoate (247 mg, 1.32 mmol) were dissolved in anhydrous EtOH (3 mL), and the mixture was heated at 80° C. for 8 hours. LC/MS after 8 hours showed ~25% of imine starting material remaining. An additional 2 equivalents of ethyl (2E)-2-(ethoxymethylidene)-3-oxobutanoate (164 mg, 0.882 mmol) were added, and the mixture was further stirred at 80° C. for another 8 hours. The reaction mixture was concentrated under reduced pressure to give the ethyl 6-isopropyl-2-methoxy-3-(3-methoxypropoxy)-10-oxo-5,10,11,11a-tetrahydro-6H-pyrido[1,2-h][1,7]naphthyridine-9-carboxylate as a brown oil that was used without further purification (191 mg, 100%, m/z: 433 [M+H]⁺ observed).

Ethyl 6-isopropyl-2-methoxy-3-(3-methoxypropoxy)-10-oxo-5,10-dihydro-6H-pyrido[1,2-h][1,7]naphthyridine-9-carboxylate

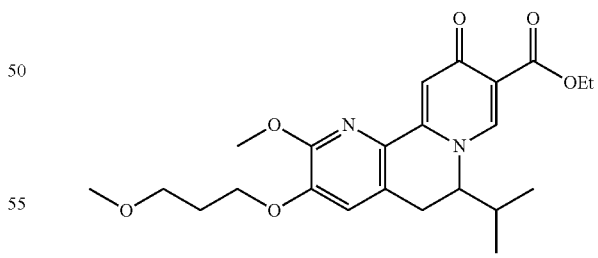

Ethyl 6-isopropyl-2-methoxy-3-(3-methoxypropoxy)-10-oxo-5,10,11,11a-tetrahydro-6H-pyrido[1,2-h][1,7]naphthyridine-9-carboxylate (191 mg, 0.441 mmol) from the step above and iodine (112 mg, 0.441 mmol) were dissolved in 2-MeTHF (3 mL) and stirred at 70° C. for 1 h. The reaction mixture was evaporated under vacuum and the residue was purified by normal phase SiO₂ chromatography (50-100% EtOAc/hexanes; then 0% to 7% MeOH/CH₂Cl₂) to give ethyl 6-isopropyl-2-methoxy-3-(3-methoxypropoxy)-10- oxo-5,10-dihydro-6H-pyrido[1,2-h][1,7]naphthyridine-9-carboxylate as a brown foam (90 mg, 47% yield over 3 steps, m/z: 431 [M+H]+ observed). ¹H NMR (400 MHz, DMSO-d₆) δ 8.36 (s, 1H), 7.36 (s, 1H), 6.95 (s, 1H), 4.22 (m, 3H), 4.11 (m, 2H), 3.95 (s, 3H), 3.48 (t, J=6.2 Hz, 2H), 3.32-3.23 (m, 4H), 3.14 (d, J=16.7 Hz, 1H), 2.00 (m, 2H), 1.70 (m, 1H), 1.27 (t, J=7.1 Hz, 3H), 0.88 (d, J=6.6 Hz, 3H), 0.72 (d, J=6.7 Hz, 3H).

6-Isopropyl-2-methoxy-3-(3-methoxypropoxy)-10-oxo-5,10-dihydro-6H-pyrido[1,2-h][1,7]naphthyridine-9-carboxylic acid

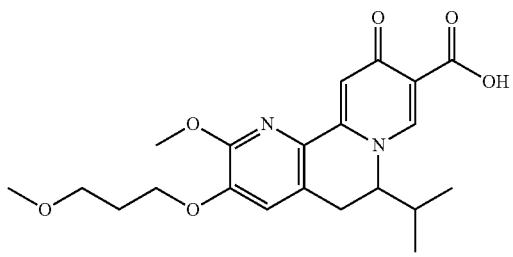

Ethyl 6-isopropyl-2-methoxy-3-(3-methoxypropoxy)-10-oxo-5H,6H-pyrido[1,2-h]1,7-naphthyridine-9-carboxylate, (230 mg, 0.53 mmol) and lithium hydroxide monohydrate (90 mg, 2.14 mmol) were suspended in THF/MeOH/H₂O mixture (3:1:1, 2 mL), and the reaction was stirred at room temperature for 1 hour. THF and MeOH were removed under reduced pressure and the crude residue was diluted with water (40 mL), extracted with 2×50 ml EtOAc (2×50 mL) to get rid of some impurities. The remaining aqueous solution was acidified to pH 2 with aqueous 1N HCl and extracted with EtOAc (3×50 mL). The combined organic fractions were dried with sodium sulfate, then concentrated under vacuum to give a crude light brown solid. The solid was further washed with EtOAc/hexanes mixture (4:1, 10 mL), filtered and dried to give 6-isopropyl-2-methoxy-3-(3-methoxypropoxy)-10-oxo-5,10-dihydro-6H-pyrido[1,2-h][1,7]naphthyridine-9-carboxylic acid as a light tan solid (105 mg, 49%, m/z: 403 [M+H]+ observed). ¹H NMR (400 MHz, DMSO-d₆) δ 16.52 (s, 1H), 8.82 (s, 1H), 7.42 (s, 1H), 7.37 (s, 1H), 4.51-4.47 (dd, J=5.6 Hz, J=8.8 Hz, 1H), 4.11 (m, 2H), 3.96 (s, 3H), 3.48 (t, J=6.4 Hz, 2H), 3.44-3.40 (m, 1H), 3.34 (s, 3H), 3.22 (m, 1H), 2.00 (m, 2H), 1.73 (m, 1H), 0.88 (d, J=6.4 Hz, 3H), 0.72 (d, J=6.4 Hz, 3H).

Example 21: (R)-6-Isopropyl-2-methoxy-3-(3-methoxypropoxy)-10-oxo-5,10-dihydro-6H-pyrido[1,2-h][1,7]naphthyridine-9-carboxylic acid

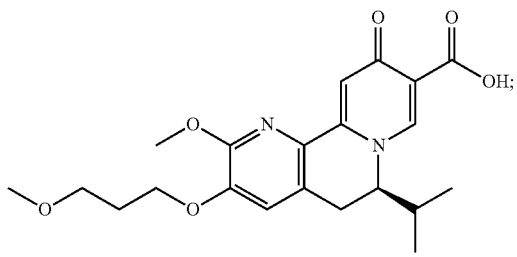 [SMILES: COCCCOc1cc2c(nc1OC)-c1cc(=O)c(C(=O)O)cn1[C@@H](C(C)C)C2]

Example 22: (S)-6-Isopropyl-2-methoxy-3-(3-methoxypropoxy)-10-oxo-5,10-dihydro-6H-pyrido[1,2-h][1,7]naphthyridine-9-carboxylic acid

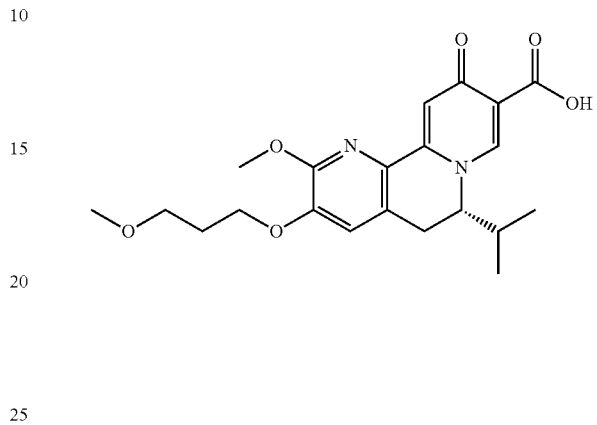

325 mg of the mixture of enantiomers was separated by SFC (supercritical fluid chromatography) on an CHIRALCEL OX-H column using liquid CO₂ and IPA:CH₃CN (1:1) and 0.1% diethylamine as modifier to give: (R)-6-isopropyl-2-methoxy-3-(3-methoxypropoxy)-10-oxo-5,10-dihydro-6H-pyrido[1,2-h][1,7]naphthyridine-9-carboxylic acid as a light brown solid (faster eluting enantiomer, 105 mg, 32%, m/z: 403 [M+H]+ observed) and (S)-6-isopropyl-2-methoxy-3-(3-methoxypropoxy)-10-oxo-5,10-dihydro-6H-pyrido[1,2-h][1,7]naphthyridine-9-carboxylic acid as a light brown solid (slower eluting enantiomer, 104 mg, 32%, m/z: 403 [M+H]+ observed).

Example 21: (R)-6-Isopropyl-2-methoxy-3-(3-methoxypropoxy)-10-oxo-5,10-dihydro-6H-pyrido[1,2-h][1,7]naphthyridine-9-carboxylic acid. m/z: 403 [M+H]+ observed). ¹H NMR (400 MHz, DMSO-d₆) δ 16.52 (s, 1H), 8.82 (s, 1H), 7.42 (s, 1H), 7.37 (s, 1H), 4.51-4.47 (dd, J=5.6 Hz, J=8.8 Hz, 1H), 4.11 (m, 2H), 3.96 (s, 3H), 3.48 (t, J=6.4 Hz, 2H), 3.44-3.40 (m, 1H), 3.34 (s, 3H), 3.22 (m, 1H), 2.00 (m, 2H), 1.73 (m, 1H), 0.88 (d, J=6.4 Hz, 3H), 0.72 (d, J=6.4 Hz, 3H).

Example 22: (S)-6-Isopropyl-2-methoxy-3-(3-methoxypropoxy)-10-oxo-5,10-dihydro-6H-pyrido[1,2-h][1,7]naphthyridine-9-carboxylic acid. m/z: 403 [M+H]+ observed). ¹H NMR (400 MHz, DMSO-d₆) δ 16.52 (s, 1H), 8.82 (s, 1H), 7.42 (s, 1H), 7.37 (s, 1H), 4.51-4.47 (dd, J=5.6 Hz, J=8.8 Hz, 1H), 4.11 (m, 2H), 3.96 (s, 3H), 3.48 (t, J=6.4 Hz, 2H), 3.44-3.40 (m, 1H), 3.34 (s, 3H), 3.22 (m, 1H), 2.00 (m, 2H), 1.73 (m, 1H), 0.88 (d, J=6.4 Hz, 3H), 0.72 (d, J=6.4 Hz, 3H).

The following examples were prepared in a similar manner as (R)-6-isopropyl-2-methoxy-3-(3-methoxypropoxy)-10-oxo-5,10-dihydro-6H-pyrido[1,2-h][1,7]naphthyridine-9-carboxylic acid and (S)-6-isopropyl-2-methoxy-3-(3-methoxypropoxy)-10-oxo-5,10-dihydro-6H-pyrido[1,2-h][1,7]naphthyridine-9-carboxylic acid from 5-bromo-2,3-dimethoxypyridine and an appropriate ketone.

Example 23: 6-Isopropyl-2,3-dimethoxy-10-oxo-5,10-dihydro-6H-pyrido[1,2-h][1,7]naphthyridine-9-carboxylic acid

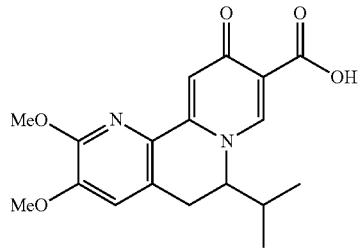 [SMILES: COc1cc2c(nc1OC)-c1cc(=O)c(C(=O)O)cn1C(C(C)C)C2]

m/z: 345 [M+H]+ observed. ¹H NMR (400 MHz, CDCl₃): δ 16.45 (s, 1H), 8.82 (s, 1H), 7.41 (s, 1H), 7.37 (s, 2H), 4.52-4.48 (m, 1H), 3.95 (s, 3H), 3.86 (s, 3H), 3.42-3.36 (m, 1H), 3.21-3.17 (m, 1H), 1.77-1.72 (m, 1H), 1.04-1.02 (d, J=4.8 Hz, 3H), 0.89-0.87 (d, J=6.8 Hz, 3H).

Example 24: 6-Isopropyl-2,3-dimethoxy-10-oxo-5,10-dihydro-6H-pyrido[1,2-h][1,7]naphthyridine-9-carboxylic acid (Single Enantiomer I)

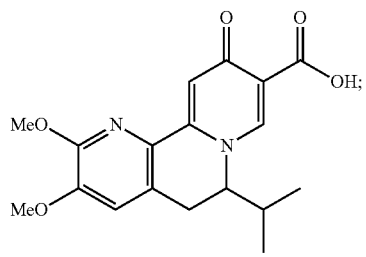 [SMILES: COc1cc2c(nc1OC)-c1cc(=O)c(C(=O)O)cn1C(C(C)C)C2]

Example 25: 6-Isopropyl-2,3-dimethoxy-10-oxo-5,10-dihydro-6H-pyrido[1,2-h][1,7]naphthyridine-9-carboxylic acid (Single Enantiomer II)

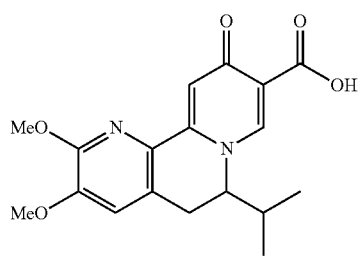 [SMILES: COc1cc2c(nc1OC)-c1cc(=O)c(C(=O)O)cn1C(C(C)C)C2]

425 mg of the mixture of enantiomers was separated by SFC (supercritical fluid chromatography) on an OX-H column using 45% i-PrOH:CH₃CN (1:1, 0.1% DEA) to give 6-isopropyl-2,3-dimethoxy-10-oxo-5,10-dihydro-6H-pyrido[1,2-h][1,7]naphthyridine-9-carboxylic acid (single enantiomer I) as an off-white solid (faster eluting enantiomer, 140 mg, 33%, m/z: 345 [M+H]+ observed) and 6-isopropyl-2,3-dimethoxy-10-oxo-5,10-dihydro-6H-pyrido[1,2-h][1,7] naphthyridine-9-carboxylic acid (single enantiomer II) as an off-white solid (slower eluting enantiomer, 100 mg, 24%, m/z: 345 [M+H]+ observed).

Example 24: 6-Isopropyl-2,3-dimethoxy-10-oxo-5,10-dihydro-6H-pyrido[1,2-h][1,7]naphthyridine-9-carboxylic acid (single enantiomer I). m/z: 370 [M+H]+ observed. ¹H NMR (400 MHz, CDCl₃): δ 16.45 (s, 1H), 8.82 (s, 1H), 7.41 (s, 1H), 7.37 (s, 2H), 4.52-4.48 (m, 1H), 3.95 (s, 3H), 3.86 (s, 3H), 3.42-3.36 (m, 1H), 3.21-3.17 (m, 1H), 1.77-1.72 (m, 1H), 1.04-1.02 (d, J=4.8 Hz, 3H), 0.89-0.87 (d, J=6.8 Hz, 3H).

Example 25: 6-Isopropyl-2,3-dimethoxy-10-oxo-5,10-dihydro-6H-pyrido[1,2-h][1,7]naphthyridine-9-carboxylic acid (single enantiomer II). m/z: 370 [M+H]+ observed. ¹H NMR (400 MHz, CDCl₃): δ 16.45 (s, 1H), 8.82 (s, 1H), 7.41 (s, 1H), 7.37 (s, 2H), 4.52-4.48 (m, 1H), 3.95 (s, 3H), 3.86 (s, 3H), 3.42-3.36 (m, 1H), 3.21-3.17 (m, 1H), 1.77-1.72 (m, 1H), 1.04-1.02 (d, J=4.8 Hz, 3H), 0.89-0.87 (d, J=6.8 Hz, 3H).

Example 26: (S)-11-Fluoro-6-isopropyl-2-methoxy-3-(3-methoxypropoxy)-10-oxo-5,10-dihydro-6H-pyrido[1,2-h][1,7]naphthyridine-9-carboxylic acid

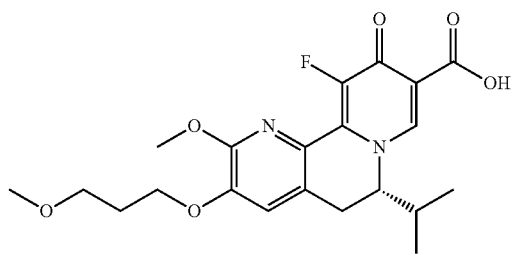 [SMILES: COCCCOc1cc2c(nc1OC)-c1c(F)c(=O)c(C(=O)O)cn1[C@H](C(C)C)C2]

Ethyl (S)-11-fluoro-6-isopropyl-2-methoxy-3-(3-methoxypropoxy)-10-oxo-5,10-dihydro-6H-pyrido[1,2-h][1,7]naphthyridine-9-carboxylate

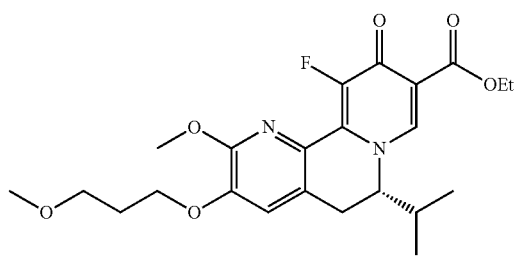 [SMILES: CCOC(=O)c1cn2c(c(F)c1=O)-c1nc(OC)c(OCCCOC)cc1C[C@H]2C(C)C]

A solution of zinc iodide (327 mg, 1.03 mmol) and (6S)-6-isopropyl-2-methoxy-3-(3-methoxypropoxy)-5,6-dihydro-1,7-naphthyridine (300 mg, 1 mmol) in dry acetonitrile (3 mL) was heated to 50° C. A solution of ethyl (2Z)-2-(ethoxymethylidene)-4,4-difluoro-3-[(trimethylsilyl)oxy]but-3-enoate (1.81 g, 6.16 mmol, prepared according to the procedure in WO2017140821) in DMF (4 mL) was added into above solution via a glass pipet under nitrogen. The reaction was stirred at 50° C. overnight. EtOAc (30 mL) and H₂O (30 mL) were added to reaction and the layers separated. The organic layer was washed with H₂O (2×20 mL), followed by sat. aqueous brine solution (20 mL). The organic layer was dried over sodium sulfate and concentrated under vacuum. The residue was purified by normal phase SiO₂ chromatography (0% to 6% MeOH/CH₂Cl₂) to furnish ethyl (6S)-11-fluoro-6-isopropyl-2-methoxy-3-(3-methoxypropoxy)-10-oxo-5H,6H-pyrido[1,2-h]1,7-naphthyridine-9-carboxylate as a brown solid (0.35 g, 76% yield, m/z: 449 [M+H]+ observed).

(S)-11-Fluoro-6-isopropyl-2-methoxy-3-(3-methoxypropoxy)-10-oxo-5,10-dihydro-6H-pyrido[1,2-h][1,7]naphthyridine-9-carboxylic acid

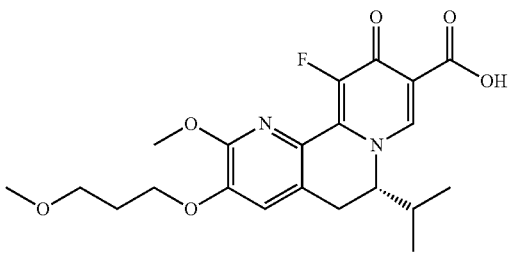 [SMILES: COCCCOc1cc2c(nc1OC)-c1c(F)c(=O)c(C(=O)O)cn1[C@H](C(C)C)C2]

Ethyl (6S)-11-fluoro-6-isopropyl-2-methoxy-3-(3-methoxypropoxy)-10-oxo-5H,6H-pyrido[1,2-h]1,7-naphthyridine-9-carboxylate (350 mg, 0.78 mmol), lithium hydroxide monohydrate (65 mg, 1.6 mmol) were dissolved in 1,4-dioxane:H₂O mixture (5 mL, 1:1). The reaction was stirred at rt for 2 h. CH₂Cl₂ (10 mL) and H₂O (10 mL) were added and layers separated. The aqueous layer was washed with CH₂Cl₂ (2×10 mL). The pH of the aqueous layer was adjusted to 5 using 1N HCl. CH₂Cl₂ (10 mL) was added and the layers separated. The aqueous layer was washed with CH₂Cl₂ (3×10 mL). The combined organic layers were dried over sodium sulfate and concentrated under vacuum. The residue was purified by normal phase SiO₂ chromatography (0% to 5% MeOH/CH₂Cl₂) to furnish (6S)-11-fluoro-6-isopropyl-2-methoxy-3-(3-methoxypropoxy)-10-oxo-5H,6H-pyrido[1,2-h]1,7-naphthyridine-9-carboxylic acid as a light brown solid (53 mg, 16% yield, m/z: 421 [M+H]+ observed). ¹H NMR (400 MHz, CDCl₃): δ 8.48 (s, 1H), 6.96 (s, 1H), 4.25-4.11 (m, 2H), 4.01-4.03 (m, 4H), 3.56 (tt, J=6.1, 3.0 Hz, 2H), 3.47-3.37 (m, 1H), 3.35 (s, 3H), 3.06 (dd, J=16.5, 1.7 Hz, 1H), 2.14 (p, J=6.2 Hz, 2H), 1.85 (dt, J=9.9, 6.7 Hz, 1H), 0.95 (d, J=6.7 Hz, 3H), 0.81 (d, J=6.7 Hz, 3H).

Example 27: (R)-2-Chloro-7-isopropyl-3-(3-methoxypropoxy)-11-oxo-6,7-dihydro-11H-benzo[f]pyrido[1,2-d][1,4]oxazepine-10-carboxylic acid

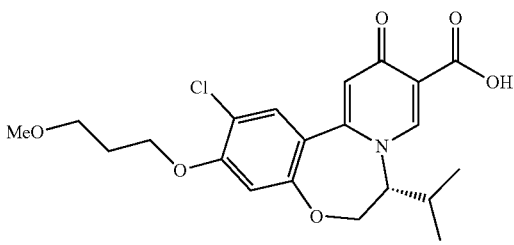 [SMILES: COCCCOc1cc2c(cc1Cl)-c1cc(=O)c(C(=O)O)cn1[C@H](C(C)C)CO2]

Methyl 5-chloro-2,4-dihydroxybenzoate

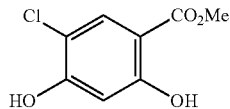

To a stirred solution of methyl 2,4-dihydroxybenzoate (8 g, 48 mmol) in CH₂Cl₂ (500 mL) at 0° C. was added sulfuryl chloride (4 mL, 49 mmol). The reaction mixture was warmed to room temperature and stirred for 36 h. The reaction was followed by TLC. Saturated aqueous NaHCO₃ solution (150 mL) was added, and the reaction mixture was extracted with CH₂Cl₂ (2×500 mL). The combined organic phase was washed with saturated aqueous brine solution (2×200 mL), dried over sodium sulfate, filtered and concentrated under vacuum. The residue was purified by normal phase SiO₂ chromatography (10% to 30% EtOAc/petroleum ether) to afford methyl 5-chloro-2,4-dihydroxybenzoate as a white solid (3.8 g, 40% yield, m/z: 203 [M+H]+ observed).

Methyl 2,4-bis(benzyloxy)-5-chlorobenzoate

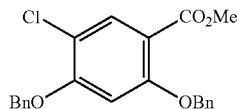

A solution of methyl 5-chloro-2,4-dihydroxybenzoate (3.8 g, 19 mmol), benzyl bromide (4.9 mL, 41.27 mmol) and potassium carbonate (6.2 g, 45 mmol) in anhydrous DMF (10 mL) was stirred at 60° C. for 12 h. The reaction was followed by TLC. The mixture was poured into ice-water (120 mL) and extracted with EtOAc (2×200 mL). The combined organic fractions were washed with saturated aqueous brine solution (2×50 mL), dried over sodium sulfate, filtered and concentrated under vacuum. The residue was purified by normal phase SiO₂ chromatography (0% to 10% EtOAc/petroleum ether) to afford methyl 2,4-bis(benzyloxy)-5-chlorobenzoate as a white solid (6.0 g, 84% yield).

2,4-Bis(benzyloxy)-5-chlorobenzoic acid

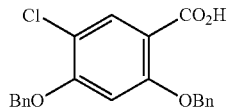

A solution of methyl 2,4-bis(benzyloxy)-5-chlorobenzoate (5 g, 13 mmol) and lithium hydroxide monohydrate (2.74 g, 65.3 mmol) in MeOH (50 mL) and H₂O (30 mL) was stirred at 70° C. for 4 h. The reaction was monitored by TLC. The reaction mixture was concentrated in vacuum. 2N aqueous HCl solution was added to reach pH=3 to yield a precipitate, which was filtered, washed with water (10 mL) and dried to give 2,4-bis(benzyloxy)-5-chlorobenzoic acid as a white solid. That solid was used without further purification (4 g, 83% yield, m/z: 369 [M+H]+ observed).

2,4-Bis(benzyloxy)-5-chlorobenzoyl chloride

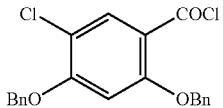

A mixture of 2,4-bis(benzyloxy)-5-chlorobenzoic acid (4 g, 11 mmol) in thionyl chloride (50 mL, 0.69 mol) was stirred at 80° C. for 2 h. The reaction was followed by TLC. The reaction mixture was concentrated under vacuum to give 2,4-bis(benzyloxy)-5-chlorobenzoyl chloride as a yellow oil that was used without further purification (4 g, 95% yield).

Ethyl 6-(2,4-bis(benzyloxy)-5-chlorophenyl)-4-oxo-4H-pyran-3-carboxylate

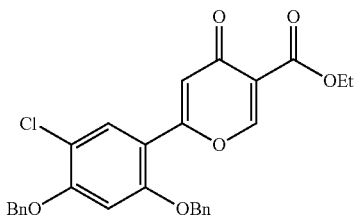 [SMILES: CCOC(=O)c1coc(-c2cc(Cl)c(OCc3ccccc3)cc2OCc2ccccc2)cc1=O]

To a solution of ethyl (Z)-2-((dimethylamino)methylene)-3-oxobutanoate (1.9 g, 10 mmol) in anhydrous THF (50 mL) at −78° C. (dry ice/acetone bath) was added LiHMDS (1 M solution in THF, 25 mL, 25 mmol). After stirring for 30 min, 2,4-bis(benzyloxy)-5-chlorobenzoyl chloride (4 g, 10 mmol) was added over 10 min to the mixture while keeping the temperature at −78° C. Following complete addition, the reaction mixture was warmed to room temperature and stirred for 2 h. The reaction was followed by TLC. 2N aqueous HCl solution (20 mL) was added to the mixture, and the aqueous phase was extracted with EtOAc (2×400 mL). The combined organic fractions were washed with saturated aqueous brine solution (2×150 mL), dried over sodium sulfate, filtered and concentrated under vacuum. The residue was purified by normal phase SiO$_2$ chromatography (10% to 40% EtOAc/petroleum ether) to afford ethyl 6-(2,4-bis(benzyloxy)-5-chlorophenyl)-4-oxo-4H-pyran-3-carboxylate as a yellow solid (3.5 g, 69% yield, m/z: 491 [M+H]$^+$ observed). $^1$H NMR (400 MHz, DMSO-d$_6$) δ 8.76 (s, 1H), 7.83 (s, 1H), 7.50-7.37 (m, 10H), 7.23 (s, 1H), 6.91 (s, 1H), 5.35-5.30 (m, 4H), 4.26-4.20 (q, J=10.8, 7.2 Hz, 2H), 1.28-1.25 (t, J=7.2 Hz, 3H).

Ethyl (R)-6-(2,4-bis(benzyloxy)-5-chlorophenyl)-1-(1-hydroxy-3-methylbutan-2-yl)-4-oxo-1,4-dihydropyridine-3-carboxylate

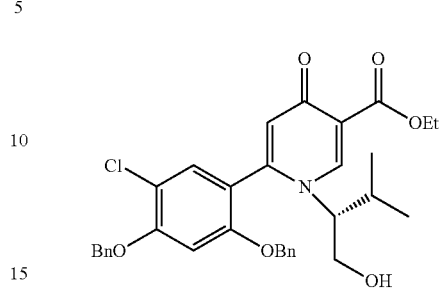

To a solution of ethyl 6-(2,4-bis(benzyloxy)-5-chlorophenyl)-4-oxo-4H-pyran-3-carboxylate (10 g, 20 mmol) in glacial AcOH (85 mL) and EtOH (100 mL) at room temperature was added (R)-2-amino-3-methylbutan-1-ol (2.71 g, 26.3 mmol). The reaction mixture was warmed to 80° C. and stirred for 16 h. The reaction was monitored by TLC. The reaction mixture was cooled to room temperature and concentrated under reduced pressure. The residue was diluted with CH$_2$Cl$_2$ (500 mL), washed with saturated aqueous NaHCO$_3$ solution (500 mL), and the aqueous layer was extracted with CH$_2$Cl$_2$ (500 mL). The combined organic fractions were dried over sodium sulfate, filtered and concentrated under reduced vacuum. The residue was purified by normal phase SiO$_2$ chromatography (0% to 10% MeOH/CH$_2$Cl$_2$) to afford ethyl (R)-6-(2,4-bis(benzyloxy)-5-chlorophenyl)-1-(1-hydroxy-3-methylbutan-2-yl)-4-oxo-1,4-dihydropyridine-3-carboxylate as a yellow solid (7.5 g, 64% yield, m/z: 576 [M+H]$^+$ observed).

Ethyl (R)-6-(5-chloro-2,4-dihydroxyphenyl)-1-(1-hydroxy-3-methylbutan-2-yl)-4-oxo-1,4-dihydropyridine-3-carboxylate

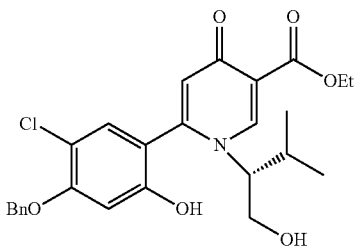 [SMILES: CCOC(=O)c1cn([C@@H](CO)C(C)C)c(-c2cc(Cl)c(OCc3ccccc3)cc2O)cc1=O]

To a solution of ethyl (R)-6-(2,4-bis(benzyloxy)-5-chlorophenyl)-1-(1-hydroxy-3-methylbutan-2-yl)-4-oxo-1,4-dihydropyridine-3-carboxylate (3.0 g, 5.2 mmol) in EtOH (100 mL) was added palladium on carbon (10% on carbon, 1 g, 94 mmol). The suspension was degassed under vacuum and back-filled with hydrogen-gas 2 times. The mixture was stirred under H$_2$ (15 psi) at room temperature for 15 min. The reaction was followed by TLC. The reaction mixture was filtered, washed with EtOH (3×50 mL) and the filtrate concentrated under reduced pressure. The residue was dissolved in THF (50 mL) and concentrated under vacuum (repeated 3 times) to give ethyl (R)-6-(5-chloro-2,4-dihydroxyphenyl)-1-(1-hydroxy-3-methylbutan-2-yl)-4-oxo-1, 4-dihydropyridine-3-carboxylate as a yellow solid that was used without further purification (1.72 g, 83% yield, m/z: 396 [M+H]+ observed).

Ethyl (R)-2-chloro-3-hydroxy-7-isopropyl-11-oxo-6,7-dihydro-11H-benzo[f]pyrido[1,2-d][1,4]oxazepine-10-carboxylate

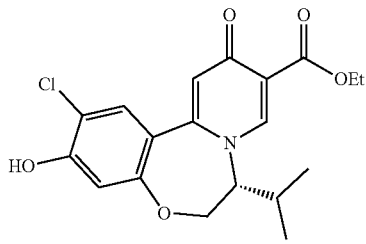 [SMILES: CCOC(=O)c1cn2c(cc1=O)-c1cc(Cl)c(O)cc1OC[C@H]2C(C)C]

To a solution of ethyl (R)-6-(5-chloro-2,4-dihydroxyphenyl)-1-(1-hydroxy-3-methylbutan-2-yl)-4-oxo-1,4-dihydropyridine-3-carboxylate (3.3 g, 8.3 mmol) and PPh₃ (10.9 g, 41.8 mmol) in THF (600 mL) was added dropwise a solution of diethyl azodicarboxylate (40% wt in toluene, 3 mL, 42 mmol, 5 eq) in THF (70 mL) at −10° C. under N₂. The mixture was stirred at −10° C. for 2 h and followed by TLC. Water (100 mL) was added to the reaction mixture, and the aqueous phase was extracted with EtOAc (2×200 mL). The combined organic phase was washed with saturated aqueous brine solution (2×150 mL), dried over sodium sulfate, filtered and concentrated under vacuum. The residue was purified by normal phase SiO₂ chromatography (30% to 100% EtOAc/hexanes; then 0% to 10% MeOH/CH₂Cl₂) to afford ethyl (R)-2-chloro-3-hydroxy-7-isopropyl-11-oxo-6,7-dihydro-11H-benzo[f]pyrido[1,2-d][1,4]oxazepine-10-carboxylate as a light yellow solid (2.0 g, 64% yield, m/z: 378 [M+H]+ observed). ¹H NMR (400 MHz, DMSO-d₆) δ 11 (s, 1H), 8.35 (s, 1H), 7.54 (s, 1H), 6.64 (s, 1H), 6.40 (s, 1H), 4.57-4.53 (m, 2H), 4.23-4.18 (m, 3H), 1.74 (m, 1H), 1.28-1.24 (t, J=6.8 Hz, 3H), 0.93-0.91 (d, J=6.4 Hz, 3H), 0.70-0.69 (d, J=6.4 Hz, 3H).

Ethyl (R)-2-chloro-7-isopropyl-3-(3-methoxypropoxy)-11-oxo-6,7-dihydro-1H-benzo[f]pyrido[1,2-d][1,4]oxazepine-10-carboxylate

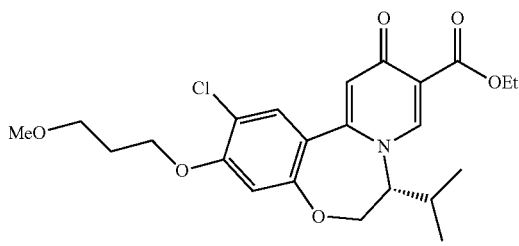 [SMILES: CCOC(=O)c1cn2c(cc1=O)-c1cc(Cl)c(OCCCOC)cc1OC[C@H]2C(C)C]

To a solution of ethyl (R)-2-chloro-3-hydroxy-7-isopropyl-11-oxo-6,7-dihydro-11H-benzo[f]pyrido[1,2-d][1,4]oxazepine-10-carboxylate (3.5 g, 9.3 mmol) and K₂CO₃ (2.56 g, 18.6 mmol) in DMF (50 mL) was added 1-bromo-3-methoxypropane (2.82 g, 18.6 mmol), and the mixture was stirred at 80° C. for 2 hr. The reaction was followed by TLC. The reaction mixture was diluted with water (50 mL) and extracted with EtOAc (3×50 mL). The combined organic fractions were washed with sat. aq. brine solution (50 mL), dried over sodium sulfate, filtered and concentrated under reduced pressure. The residue was purified by normal phase SiO₂ chromatography (0% to 10% EtOAc/MeOH) to afford ethyl (R)-2-chloro-7-isopropyl-3-(3-methoxypropoxy)-11-oxo-6,7-dihydro-11H-benzo[f]pyrido[1,2-d][1,4]oxazepine-10-carboxylate as a white solid (3.9 g, 94% yield, m/z: 450 [M+H]+ observed). ¹H NMR (400 MHz, DMSO-d₆) δ 8.36 (s, 1H), 7.63 (s, 1H), 6.87 (s, 1H), 6.44 (s, 1H), 4.62-4.59 (m, 2H), 4.24-4.12 (m, 5H), 3.50-3.47 (t, J=6.4 Hz, 2H), 3.25 (s, 3H), 2.01-1.94 (m, 2H), 1.75 (m, 1H), 1.28-1.25 (t, J=7.2 Hz, 3H), 0.94-0.93 (d, J=6.4 Hz, 3H), 0.71-0.70 (d, J=6.40, 3H).

(R)-2-Chloro-7-isopropyl-3-(3-methoxypropoxy)-11-oxo-6,7-dihydro-1H-benzo[f]pyrido[1,2-d][1,4]oxazepine-10-carboxylic acid

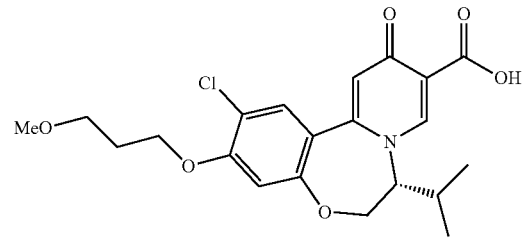 [SMILES: COCCCOc1cc2c(cc1Cl)-c1cc(=O)c(C(=O)O)cn1[C@H](C(C)C)CO2]

To a solution of ethyl (R)-2-chloro-7-isopropyl-3-(3-methoxypropoxy)-11-oxo-6,7-dihydro-11H-benzo[f]pyrido[1,2-d][1,4]oxazepine-10-carboxylate (3.3 g, 7.35 mmol) in 1,4-dioxane (10 mL) and H₂O (10 mL) was added lithium hydroxide monohydrate (1.54 g, 36.7 mmol). The reaction mixture was stirred at room temperature for 1 h and followed by TLC. The reaction mixture was concentrated under reduced pressure, and 1N aq. HCl solution was added to reach pH=2-3. The mixture was extracted with EtOAc (3×20 mL), and the combined organic fractions were washed with sat. aq. brine solution (20 mL), dried over sodium sulfate, filtered and concentrated under reduced pressure to give (R)-2-chloro-7-isopropyl-3-(3-methoxypropoxy)-11-oxo-6,7-dihydro-11H-benzo[f]pyrido[1,2-d][1,4]oxazepine-10-carboxylic acid as a light yellow solid (5.25 g, 85% yield from 2×3.3 g scale reactions, m/z: 422 [M+H]+ observed). ¹H NMR (400 MHz, CDCl₃) δ 15.64 (s, 1H), 8.39 (s, 1H), 7.45 (s, 1H), 6.78 (s, 1H), 6.59 (s, 1H), 4.55-4.46 (m, 2H), 4.11-4.08 (m, 2H), 3.82-3.78 (m, 1H), 3.55-3.52 (m, 2H), 3.30 (s, 3H), 2.09-2.03 (m, 3H), 1.02-1.01 (d, J=6.4 Hz, 3H), 0.80-0.79 (d, J=6.4 Hz, 3H).

The following examples were prepared in a similar manner as (R)-2-chloro-7-isopropyl-3-(3-methoxypropoxy)-11-oxo-6,7-dihydro-11H-benzo[f]pyrido[1,2-d][1,4]oxazepine-10-carboxylic acid from ethyl 2-chloro-3-hydroxy-7-isopropyl-11-oxo-6,7-dihydro-11H-benzo[f]pyrido[1,2-d][1,4]oxazepine-10-carboxylate and an appropriate bromide.

Example 28: (S)-2-Chloro-7-isopropyl-3-(3-methoxypropoxy)-11-oxo-6,7-dihydro-11H-benzo[f]pyrido[1,2-d][1,4]oxazepine-10-carboxylic acid

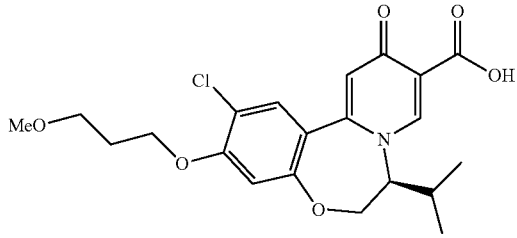 [SMILES: COCCCOc1cc2c(cc1Cl)-c1cc(=O)c(C(=O)O)cn1[C@@H](C(C)C)CO2]

m/z: 422 [M+H]+ observed. ¹H NMR (400 MHz, CDCl₃) δ 15.64 (s, 1H), 8.39 (s, 1H), 7.45 (s, 1H), 6.78 (s, 1H), 6.59 (s, 1H), 4.55-4.46 (m, 2H), 4.11-4.08 (m, 2H), 3.82-3.78 (m, 1H), 3.55-3.52 (m, 2H), 3.30 (s, 3H), 2.09-2.03 (m, 3H), 1.02-1.01 (d, J=6.4 Hz, 3H), 0.80-0.79 (d, J=6.4 Hz, 3H).

Example 29: 2-Chloro-7-isopropyl-3-(2-methoxyethoxy)-11-oxo-6,7-dihydro-11H-benzo[f]pyrido[1,2-d][1,4]oxazepine-10-carboxylic acid

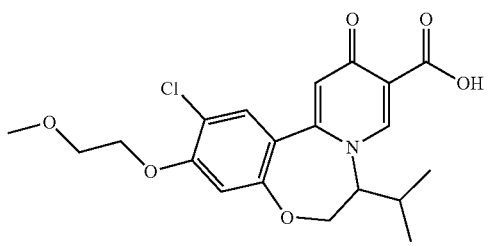 [SMILES: COCCOc1cc2c(cc1Cl)-c1cc(=O)c(C(=O)O)cn1C(C(C)C)CO2]

m/z: 408 [M+H]+ observed. ¹H NMR (400 MHz, DMSO-d₆): δ 8.73 (bs, 1H), 7.77 (s, 1H), 6.98 (bs, 1H), 6.92 (s, 1H), 4.70 (s, 2H), 4.52 (s, 1H), 4.28 (m, 2H), 3.71 (t, J=4.4 Hz, 2H), 3.34 (s, 3H), 1.82 (bs, 1H), 0.99 (d, J=6.4 Hz, 3H), 0.71 (d, J=6.4 Hz, 3H).

Example 30: (R)-2-Chloro-7-isopropyl-3-(2-methoxyethoxy)-11-oxo-6,7-dihydro-11H-benzo[f]pyrido[1,2-d][1,4]oxazepine-10-carboxylic acid

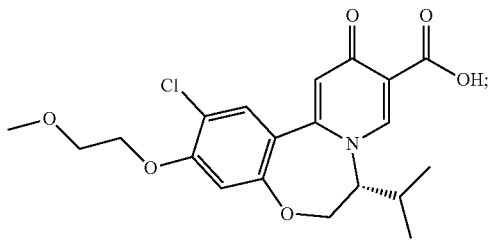 [SMILES: COCCOc1cc2c(cc1Cl)-c1cc(=O)c(C(=O)O)cn1[C@H](C(C)C)CO2]

Example 31: (S)-2-Chloro-7-isopropyl-3-(2-methoxyethoxy)-11-oxo-6,7-dihydro-11H-benzo[f]pyrido[1,2-d][1,4]oxazepine-10-carboxylic acid

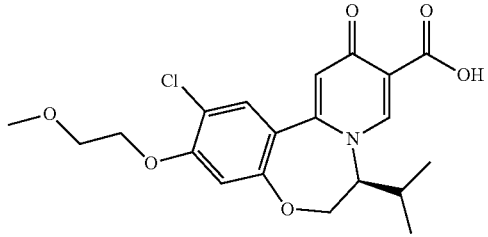 [SMILES: COCCOc1cc2c(cc1Cl)-c1cc(=O)c(C(=O)O)cn1[C@@H](C(C)C)CO2]

66 mg of the mixture of enantiomers was separated by SFC (supercritical fluid chromatography) on an AD-3 column using 40% EtOH (0.1% aq. NH₃) as a modifier to give (R)-2-chloro-7-isopropyl-3-(2-methoxyethoxy)-11-oxo-6,7-dihydro-11H-benzo[f]pyrido[1,2-d][1,4]oxazepine-10-carboxylic acid as a white solid (faster eluting enantiomer, 17.9 mg, 26%, m/z: 408 [M+H]+ observed) and (S)-2-chloro-7-isopropyl-3-(2-methoxyethoxy)-11-oxo-6,7-dihydro-11H-benzo[f]pyrido[1,2-d][1,4]oxazepine-10-carboxylic acid as a white solid (slower eluting enantiomer, 20.5 mg, 31%, m/z: 408 [M+H]+ observed).

Example 30: (R)-2-Chloro-7-isopropyl-3-(2-methoxyethoxy)-11-oxo-6,7-dihydro-11H-benzo[f]pyrido[1,2-d][1,4]oxazepine-10-carboxylic acid. m/z: 408 [M+H]+ observed. ¹H NMR (400 MHz, DMSO-d₆): δ 8.73 (bs, 1H), 7.77 (s, 1H), 6.98 (bs, 1H), 6.92 (s, 1H), 4.70 (s, 2H), 4.52 (s, 1H), 4.28 (m, 2H), 3.71 (t, J=4.4 Hz, 2H), 3.34 (s, 3H), 1.82 (bs, 1H), 0.99 (d, J=6.4 Hz, 3H), 0.71 (d, J=6.4 Hz, 3H).

Example 31: (S)-2-Chloro-7-isopropyl-3-(2-methoxyethoxy)-11-oxo-6,7-dihydro-11H-benzo[f]pyrido[1,2-d][1,4]oxazepine-10-carboxylic acid. m/z: 378 [M+H]+ observed. ¹H NMR (400 MHz, DMSO-d₆): δ 8.73 (bs, 1H), 7.77 (s, 1H), 6.98 (bs, 1H), 6.92 (s, 1H), 4.70 (s, 2H), 4.52 (s, 1H), 4.28 (m, 2H), 3.71 (t, J=4.4 Hz, 2H), 3.34 (s, 3H), 1.82 (bs, 1H), 0.99 (d, J=6.4 Hz, 3H), 0.71 (d, J=6.4 Hz, 3H).

Example 32. Ethyl 2-chloro-3-hydroxy-7-isopropyl-11-oxo-6,7-dihydro-11H-benzo[f]pyrido[1,2-d][1,4]oxazepine-10-carboxylate

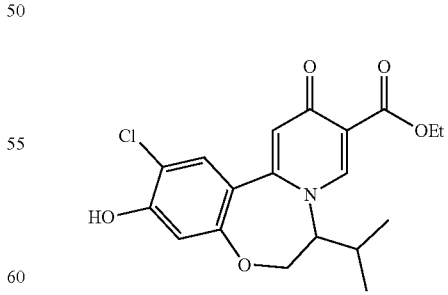

m/z: 378 [M+H]+ observed. ¹H NMR (400 MHz, DMSO-d₆) δ 11 (s, 1H), 8.35 (s, 1H), 7.54 (s, 1H), 6.64 (s, 1H), 6.40 (s, 1H), 4.57-4.53 (m, 2H), 4.23-4.18 (m, 3H), 1.74 (m, 1H), 1.28-1.24 (t, J=6.8 Hz, 3H), 0.93-0.91 (d, J=6.4 Hz, 3H), 0.70-0.69 (d, J=6.4 Hz, 3H).

Example 33: 2-Chloro-7-isopropyl-3-(3-methoxypropoxy)-11-oxo-6,7-dihydro-11H-benzo[f]pyrido[1,2-d][1,4]oxazepine-10-carboxylic acid

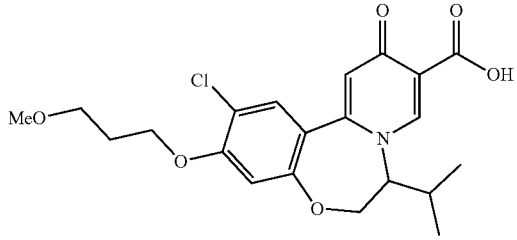 [SMILES: COCCCOc1cc2c(cc1Cl)-c1cc(=O)c(C(=O)O)cn1C(C(C)C)CO2]

m/z: 422 [M+H]+ observed. $^1$H NMR (400 MHz, CDCl$_3$) δ 15.64 (s, 1H), 8.39 (s, 1H), 7.45 (s, 1H), 6.78 (s, 1H), 6.59 (s, 1H), 4.55-4.46 (m, 2H), 4.11-4.08 (m, 2H), 3.82-3.78 (m, 1H), 3.55-3.52 (m, 2H), 3.30 (s, 3H), 2.09-2.03 (m, 3H), 1.02-1.01 (d, J=6.4 Hz, 3H), 0.80-0.79 (d, J=6.4 Hz, 3H).

Example 34: (R)-2-Chloro-7-isopropyl-11-oxo-3-(2,2,2-trifluoroethoxy)-6,7-dihydro-11H-benzo[f]pyrido[1,2-d][1,4]oxazepine-10-carboxylic acid

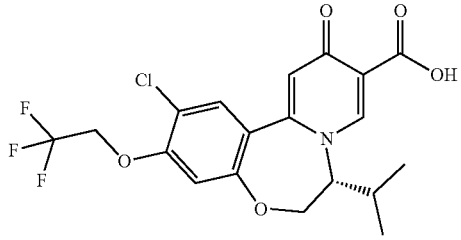 [SMILES: CC(C)[C@@H]1COc2cc(OCC(F)(F)F)c(Cl)cc2-c2cc(=O)c(C(=O)O)cn21]

m/z: 432 [M+H]+ observed. $^1$H NMR (400 MHz, DMSO-d$_6$): δ 8.80 (s, 1H), 7.82 (s, 1H), 7.07 (s, 2H), 4.97 (m, 2H), 4.72 (m, 2H), 4.57 (d, J=10 Hz, 1H), 1.81 (m, 1H), 0.98 (d, J=6.8 Hz, 3H), 0.71 (d, J=6.4 Hz, 3H).

Example 35: (R)-2-Chloro-3-(cyclopropylmethoxy)-7-isopropyl-11-oxo-6,7-dihydro-11H-benzo[f]pyrido[1,2-d][1,4]oxazepine-10-carboxylic acid

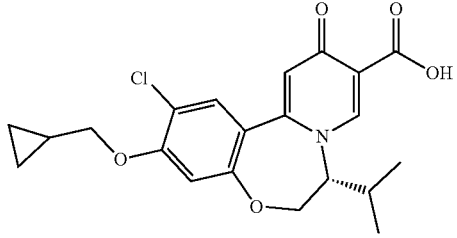 [SMILES: CC(C)[C@@H]1COc2cc(OCC3CC3)c(Cl)cc2-c2cc(=O)c(C(=O)O)cn21]

m/z: 404 [M+H]+ observed. $^1$H NMR (400 MHz, DMSO-d$_6$): δ 8.78 (s, 1H), 7.74 (s, 1H), 7.02 (s, 1H), 6.84 (s, 1H), 4.69 (m, 2H), 4.54 (br d, J=10.8 Hz, 1H), 4.00 (m, 2H), 1.82 (br s, 1H), 1.26 (m, 1H), 0.97 (d, J=6.4 Hz, 3H), 0.70 (d, J=6.4 Hz, 3H), 0.59 (m, 2H), 0.37 (m, 2H).

Example 36: (R)-2-Chloro-3-(3-hydroxypropoxy)-7-isopropyl-11-oxo-6,7-dihydro-11H-benzo[f]pyrido[1,2-d][1,4]oxazepine-10-carboxylic acid

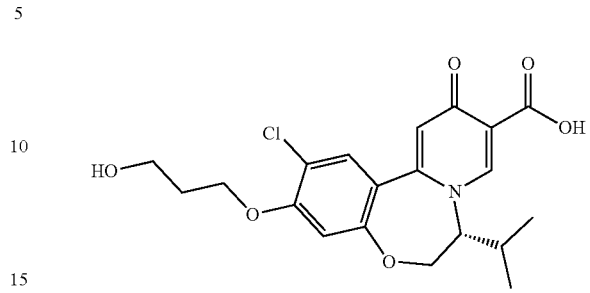

m/z: 408 [M+H]+ observed. $^1$H NMR (400 MHz, DMSO-d$_6$): δ 8.78 (s, 1H), 7.74 (s, 1H), 7.02 (s, 1H), 6.88 (s, 1H), 4.71 (m, 2H), 4.54 (bd, J=104. Hz, 2H), 4.20 (m, 2H), 3.58 (t, J=6 Hz, 2H), 1.88 (m, 3H), 0.98 (d, J=6.8 Hz, 3H), 0.70 (d, J=6.4 Hz, 3H).

Example 37: (R)-2-Chloro-3-(3-hydroxy-2,2-dimethylpropoxy)-7-isopropyl-11-oxo-6,7-dihydro-11H-benzo[f]pyrido[1,2-d][1,4]oxazepine-10-carboxylic acid

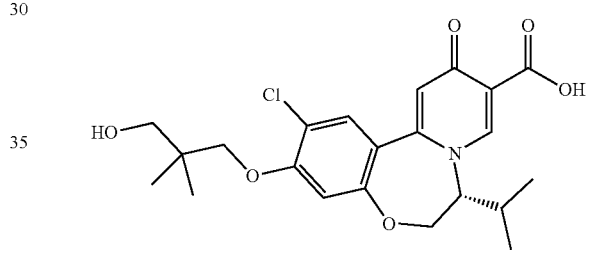

m/z: 436 [M+H]+ observed. $^1$H NMR (400 MHz, DMSO-d$_6$): δ 8.78 (s, 1H), 7.74 (s, 1H), 7.02 (s, 1H), 6.85 (s, 1H), 4.69 (m, 2H), 4.54 (m, 1H), 3.83 (m, 2H), 3.30 (m, 2H), 1.84 (s, 1H), 0.97 (m, 9H), 0.70 (d, J=6.8 Hz, 3H).

Example 38: (R)-2-Chloro-7-isopropyl-3-(4-methoxybutoxy)-11-oxo-6,7-dihydro-11H-benzo[f]pyrido[1,2-d][1,4]oxazepine-10-carboxylic acid

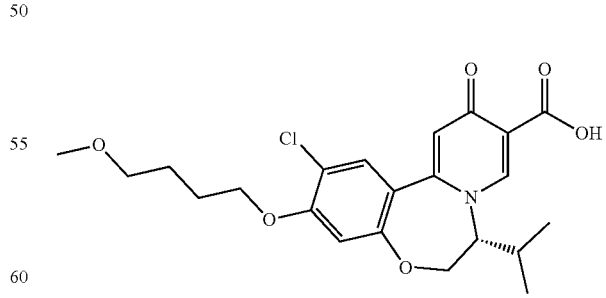

m/z: 436 [M+H]+ observed. $^1$H NMR (400 MHz, DMSO-d$_6$): δ 8.78 (s, 1H), 7.74 (s, 1H), 7.02 (s, 1H), 6.87 (s, 1H), 4.69 (m, 2H), 4.55 (bd, J=10.4 Hz, 1H), 4.14 (m, 2H), 3.39 (t, J=6.4 Hz, 2H), 3.23 (s, 3H), 1.79 (m, 3H), 1.68 (m, 2H), 0.97 (d, J=6.4 Hz, 3H), 0.71 (d, J=6.8 Hz, 3H).

Example 39: (R)-2-Chloro-3-(4-hydroxybutoxy)-7-isopropyl-11-oxo-6,7-dihydro-11H-benzo[f]pyrido[1,2-d][1,4]oxazepine-10-carboxylic acid

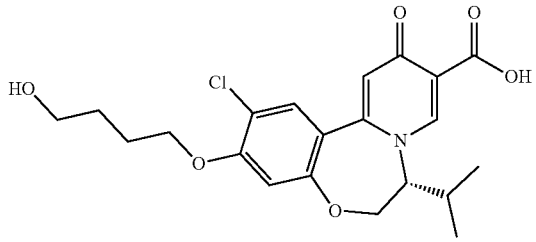 [SMILES: CC(C)[C@@H]1COc2cc(OCCCCO)c(Cl)cc2-c2cc(=O)c(C(=O)O)cn21]

m/z: 422 [M+H]⁺ observed. ¹H NMR (400 MHz, DMSO-d₆): δ 8.78 (s, 1H), 7.74 (s, 1H), 7.02 (s, 1H), 6.88 (s, 1H), 4.70 (s, 2H), 4.55 (m, 1H), 4.18-4.09 (m, 2H), 3.46 (t, J=6.4 Hz, 3H), 1.78 (m, 3H), 1.60 (m, 2H), 0.97 (d, J=6.4 Hz, 3H), 0.70 (d, J=6.4 Hz, 3H).

Example 40: (R)-2-Chloro-7-isopropyl-3-(3-morpholinopropoxy)-11-oxo-6,7-dihydro-11H-benzo[f]pyrido[1,2-d][1,4]oxazepine-10-carboxylic acid

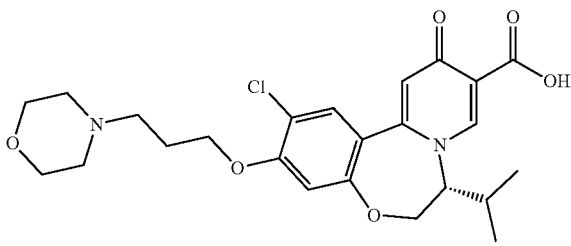 [SMILES: CC(C)[C@@H]1COc2cc(OCCCN3CCOCC3)c(Cl)cc2-c2cc(=O)c(C(=O)O)cn21]

m/z: 477 [M+H]⁺ observed. ¹H NMR (400 MHz, DMSO-d₆): δ 10.03 (s, 1H), 8.79 (s, 1H), 7.77 (s, 1H), 7.02 (s, 1H), 6.90 (s, 1H), 4.71 (m, 2H), 4.58 (bd, J=10 Hz, 1H), 4.22 (m, 2H), 4.01 (bd, J=12 Hz, 2H), 3.67 (m, =11.6 Hz, 2H), 3.51 (bd, J=12 Hz, 2H), 3.30 (t, J=7.2 Hz, 2H), 3.13 (m, 2H), 2.20 (m, 2H), 1.83 (bs, 1H), 0.98 (d, J=6.4 Hz, 3H), 0.73-0.71 (d, J=6.4 Hz, 3H).

Example 41: (R)-3-(2-(2-Bromoethoxy)ethoxy)-2-chloro-7-isopropyl-11-oxo-6,7-dihydro-11H-benzo[f]pyrido[1,2-d][1,4]oxazepine-10-carboxylic acid

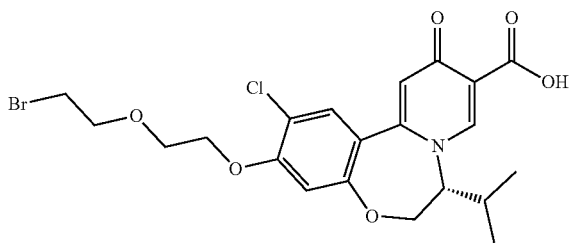 [SMILES: CC(C)[C@@H]1COc2cc(OCCOCCBr)c(Cl)cc2-c2cc(=O)c(C(=O)O)cn21]

m/z: 499, 501 [M+H]⁺ observed. ¹H NMR (300 MHz, CDCl₃): δ 8.56 (s, 1H), 7.52 (s, 1H), 6.97 (s, 1H), 6.69 (s, 1H), 4.68-4.50 (m, 2H), 4.26-4.24 (m, 1H) 3.98-3.96 (m, 6H), 3.51 (t, J=6.0 Hz, 2H), 2.06-2.10 (m, 1H), 1.09 (d, J=6.5 Hz, 3H), 0.86 (d, J=6.5 Hz, 3H).

Example 42: (R)-3-(3-((tert-Butoxycarbonyl)amino)propoxy)-2-chloro-7-isopropyl-11-oxo-6,7-dihydro-11H-benzo[f]pyrido[1,2-d][1,4]oxazepine-10-carboxylic acid

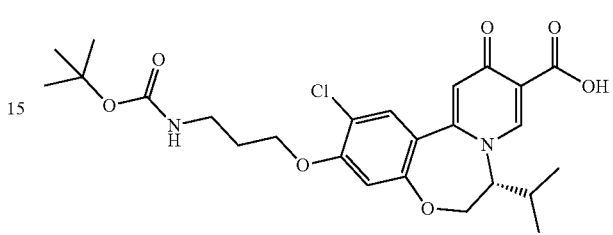

m/z: 507 [M+H]⁺ observed. ¹H NMR (300 MHz, CDCl₃): δ 8.48 (s, 1H), 7.50 (d, J=1.2 Hz, 1H), 6.85 (s, 1H), 6.62 (s, 1H), 5.01 (d, J=5.3 Hz, 1H), 4.65 (dd, J=12.7, 5.7 Hz, 2H), 4.56 (dd, J=12.6, 2.9 Hz, 1H), 4.18-4.05 (m, 2H), 3.38 (q, J=6.2 Hz, 2H), 2.13-2.00 (m, 2H), 1.43 (s, 9H), 1.25-1.24 (m, 1H), 1.09 (d, J=6.5 Hz, 3H), 0.86 (d, J=6.5 Hz, 3H).

Example 43: (R)-2-Chloro-7-(2-hydroxyethyl)-3-(3-methoxypropoxy)-11-oxo-6,7-dihydro-11H-benzo[f]pyrido[1,2-d][1,4]oxazepine-10-carboxylic acid

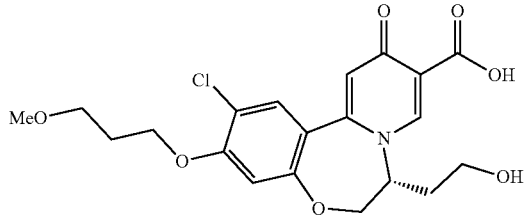 [SMILES: COCCCOc1cc2c(cc1Cl)-c1cc(=O)c(C(=O)O)cn1[C@H](CCO)CO2]

m/z: 424 [M+H]⁺ observed. ¹H NMR (400 MHz, DMSO-d₆): δ 16.36 (s, 1H), 8.67 (s, 1H), 7.74 (s, 1H), 6.96 (s, 2H), 4.81-4.72 (m, 2H), 4.61-4.50 (m, 2H), 4.17 (t, J=6.0 Hz, 2H), 3.49-3.46 (m, 2H), 3.37-3.42 (m, 1H), 3.24 (s, 3H), 1.98 (m, 2H), 1.95-1.85 (m, 2H), 1.32 (s, 1H) Example 44: (R)-2-Cyclopropyl-3-isobutoxy-7-isopropyl-11-oxo-6,7-dihydro-11H-benzo[f]pyrido[1,2-d][1,4]oxazepine-10-carboxylic acid

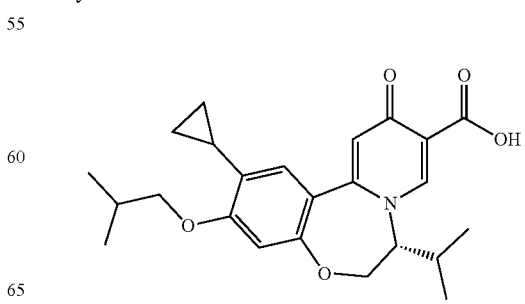

Ethyl (R)-2-chloro-3-isobutoxy-7-isopropyl-11-oxo-6,7-dihydro-11H-benzo[f]pyrido[1,2-d][1,4]oxazepine-10-carboxylate

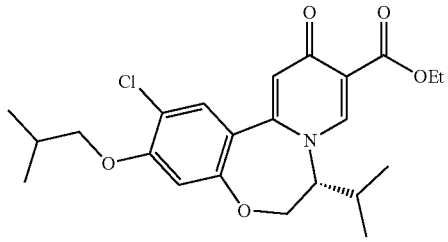 [SMILES: CCOC(=O)c1cn2c(cc1=O)-c1cc(Cl)c(OCC(C)C)cc1OC[C@H]2C(C)C]

Ethyl (R)-2-chloro-3-hydroxy-7-isopropyl-11-oxo-6,7-dihydro-11H-benzo[f]pyrido[1,2-d][1,4]oxazepine-10-carboxylate (200 mg, 0.53 mmol), $K_2CO_3$ (219 mg, 1.59 mmol) and isobutyl bromide (73 mg, 0.53 mmol) were dissolved in DMF (1 mL) and heated to 80° C. for 16 hours. The reaction was diluted with EtOAc (50 mL) and washed with $H_2O$ (2×15 mL). The organic layer was dried over sodium sulfate, filtered and concentrated under vacuum. The residue was purified by normal phase $SiO_2$ chromatography (0% to 10% MeOH/$CH_2Cl_2$) to afford (R)-2-chloro-3-isobutoxy-7-isopropyl-11-oxo-6,7-dihydro-11H-benzo[f]pyrido[1,2-d][1,4]oxazepine-10-carboxylate as a yellow solid (130 mg, 57% yield, m/z: 434 [M+H]$^+$ observed). $^1$H NMR (400 MHz, CDCl$_3$) δ 8.14 (s, 1H), 7.47 (s, 1H), 6.65 (s, 1H), 6.56 (s, 1H), 4.55 (m, 2H), 4.37 (m, 2H), 3.79 (m, 3H), 2.17 (m, 1H), 2.02 (m, 1H), 1.38 (t, J=7.2 Hz, 3H), 1.05 (m, 9H), 0.86 (d, J=6.8 Hz, 3H).

Ethyl (R)-2-cyclopropyl-3-isobutoxy-7-isopropyl-11-oxo-6,7-dihydro-11H-benzo[f]pyrido[1,2-d][1,4]oxazepine-10-carboxylate

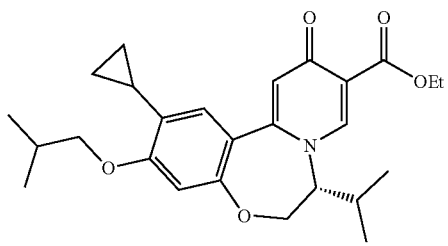 [SMILES: CCOC(=O)c1cn2c(cc1=O)-c1cc(C3CC3)c(OCC(C)C)cc1OC[C@H]2C(C)C]

In a microwave vial, $Cs_2CO_3$ (98 mg, 0.30 mmol), (R)-2-chloro-3-isobutoxy-7-isopropyl-11-oxo-6,7-dihydro-11H-benzo[f]pyrido[1,2-d][1,4]oxazepine-10-carboxylate (45 mg, 0.10 mmol) and potassium cyclopropyltrifluoroborate (22 mg, 0.15 mmol) were added. A mixture of toluene/$H_2O$ (0.6 mL, 5:1) was added. The solution was purged with argon for 1 min, followed by the addition of Xphos (9.5 mg, 0.021 mmol) and palladium(II)acetate (2 mg, 0.01 mmol). The microwave vial was sealed. The reaction was stirred at 110° C. for 60 min with microwave irradiation. LCMS showed complete conversion. The vial was opened and the reaction mixture concentrated under vacuum. The residue was purified by normal phase $SiO_2$ chromatography (0% to 7% MeOH/$CH_2Cl_2$) to afford ethyl (R)-2-cyclopropyl-3-isobutoxy-7-isopropyl-11-oxo-6,7-dihydro-11H-benzo[f]pyrido[1,2-d][1,4]oxazepine-10-carboxylate as as a yellow solid (35 mg, 77% yield, m/z: 440 [M+H]$^+$ observed).

(R)-2-Cyclopropyl-3-isobutoxy-7-isopropyl-11-oxo-6,7-dihydro-11H-benzo[f]pyrido[1,2-d][1,4]oxazepine-10-carboxylic acid

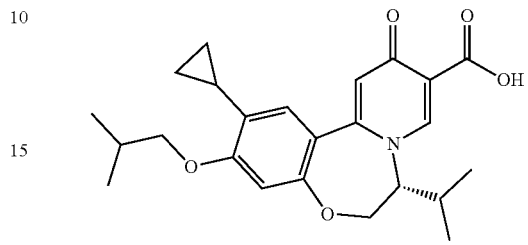

Ethyl (R)-2-cyclopropyl-3-isobutoxy-7-isopropyl-11-oxo-6,7-dihydro-11H-benzo[f]pyrido[1,2-d][1,4]oxazepine-10-carboxylate as (30 mg, 0.068 mmol) and lithium hydroxide monohydrate (5.1 mg, 0.12 mmol) were dissolved in dioxane/$H_2O$ (1 mL, 1:1) and stirred at rt for 16 h. The pH was changed to 5 by the dropwise addition of 1N HCl. A white sticky solid formed. The aqueous layer was extracted with EtOAc (4×5 mL). The combined organic phase was washed dried over sodium sulfate, filtered and concentrated under vacuum. The residue was purified by reverse phase HPLC to afford (R)-2-cyclopropyl-3-isobutoxy-7-isopropyl-11-oxo-6,7-dihydro-11H-benzo[f]pyrido[1,2-d][1,4]oxazepine-10-carboxylic acid as white solid (15 mg, 55% yield, m/z: 412 [M+H]$^+$ observed). $^1$H NMR (400 MHz, DMSO-d$_6$) δ 8.77 (s, 1H), 7.04 (s, 1H), 6.97 (s, 1H), 6.66 (s, 1H), 4.62 (m, 2H), 4.48 (m, 1H), 3.84 (m, 2H), 2.06 (m, 2H), 1.78 (bs, 1H), 1.03 (d, J=6.8 Hz, 6H), 0.96 (d, J=6.4 Hz, 3H), 0.89 (m, 2H), 0.77 (m, 2H), 0.67 (d, J=6.8 Hz, 3H).

The following example were prepared in a similar manner as (R)-2-cyclopropyl-3-isobutoxy-7-isopropyl-11-oxo-6,7-dihydro-11H-benzo[f]pyrido[1,2-d][1,4]oxazepine-10-carboxylic acid from Ethyl (R)-2-chloro-3-hydroxy-7-isopropyl-11-oxo-6,7-dihydro-11H-benzo[f]pyrido[1,2-d][1,4]oxazepine-10-carboxylate and an appropriate bromide, followed by a suitable organoboron species.

Example 45: (R)-2-Cyclopropyl-7-isopropyl-3-(3-methoxypropoxy)-11-oxo-6,7-dihydro-11H-benzo[f]pyrido[1,2-d][1,4]oxazepine-10-carboxylic acid

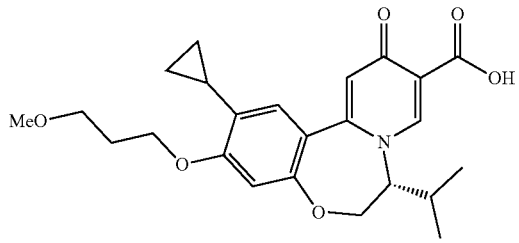 [SMILES: COCCCOc1cc2c(cc1C1CC1)-c1cc(=O)c(C(=O)O)cn1[C@H](C(C)C)CO2]

m/z: 428 [M+H]$^+$ observed. $^1$H NMR (300 MHz, CDCl$_3$): δ 8.47 (d, J=1.7 Hz, 1H), 6.93 (d, J=1.6 Hz, 1H), 6.81 (d, J=1.6 Hz, 1H), 6.54 (d, J=1.5 Hz, 1H), 4.55 (dd, J=11.3, 4.5 Hz, 2H), 4.11 (td, J=6.2, 1.4 Hz, 2H), 3.97-3.81 (m, 1H), 3.66-3.49 (m, 2H), 3.36 (d, J=1.6 Hz, 3H), 2.21-1.91 (m, Example 46: (R)-7-Isopropyl-3-(3-methoxypropoxy)-2-methyl-11-oxo-6,7-dihydro-11H-benzo[f]pyrido[1,2-d][1,4]oxazepine-10-carboxylic acid

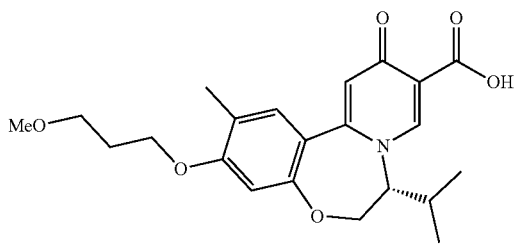 [SMILES: COCCCOc1cc2c(cc1C)-c1cc(=O)c(C(=O)O)cn1[C@H](C(C)C)CO2]

m/z: 402 [M+H]+ observed. ¹H NMR (300 MHz, CDCl₃): δ 8.49 (s, 1H), 7.21 (s, 1H), 6.85 (s, 1H), 6.53 (d, J=1.4 Hz, 1H), 4.54 (td, J=12.4, 11.5, 4.5 Hz, 2H), 4.15-4.03 (m, 2H), 3.98-3.85 (m, 1H), 3.57 (td, J=6.0, 1.3 Hz, 2H), 3.36 (d, J=1.3 Hz, 3H), 2.20 (s, 3H), 2.17-1.92 (m, 3H), 1.05 (d, J=6.6 Hz, 3H), 0.86-0.77 (m, 3H).

Example 47: (R)-2-Ethyl-7-isopropyl-3-(3-methoxypropoxy)-11-oxo-6,7-dihydro-11H-benzo[f]pyrido[1,2-d][1,4]oxazepine-10-carboxylic acid

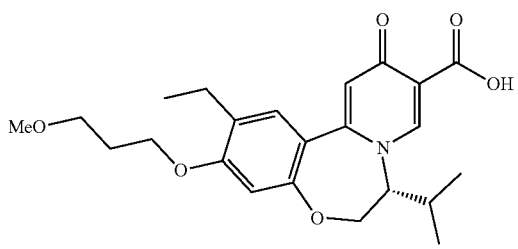 [SMILES: CCc1cc2c(cc1OCCCOC)OC[C@@H](C(C)C)n1cc(C(=O)O)c(=O)cc1-2]

m/z: 416 [M+H]+ observed. ¹H NMR (300 MHz, CDCl₃): δ 8.56 (s, 1H), 7.26 (s, 1H), 7.04 (s, 1H), 6.55 (s, 1H), 4.64 (dd, J=12.8, 5.7 Hz, 1H), 4.58-4.47 (m, 1H), 4.09 (t, J=6.1 Hz, 2H), 3.96 (s, 1H), 3.59 (dd, J=6.6, 5.4 Hz, 2H), 3.37 (d, J=1.2 Hz, 3H), 2.71-2.55 (m, 2H), 2.18-2.03 (m, 3H), 1.21 (td, J=7.4, 1.2 Hz, 3H), 1.08 (d, J=6.4 Hz, 3H), 0.84 (d, J=6.5 Hz, 3H).

Example 48: (R)-7-Isopropyl-3-(3-methoxypropoxy)-11-oxo-2-vinyl-6,7-dihydro-11H-benzo[f]pyrido[1,2-d][1,4]oxazepine-10-carboxylic acid

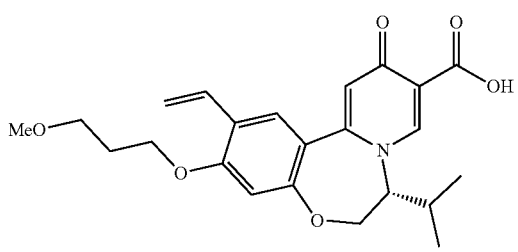 [SMILES: C=Cc1cc2c(cc1OCCCOC)OC[C@@H](C(C)C)n1cc(C(=O)O)c(=O)cc1-2]

m/z: 414 [M+H]+ observed. ¹H NMR (300 MHz, CDCl₃): δ 8.45 (s, 1H), 7.55 (s, 1H), 7.01-6.84 (m, 2H), 6.59 (s, 1H), 5.75 (dd, J=17.7, 1.2 Hz, 1H), 5.32 (dd, J=11.2, 1.2 Hz, 1H), 4.65-4.49 (m, 2H), 4.13 (t, J=6.3 Hz, 2H), 3.86 (m, 1H), 3.58 (t, J=6.0 Hz, 2H), 3.37 (s, 3H), 2.16-2.08 (m, J=6.1 Hz, 3H), 1.08 (d, J=6.5 Hz, 3H), 0.86 (d, J=6.6 Hz, 3H).

Example 49: (R)-3-(Cyclopropylmethoxy)-7-isopropyl-2-methyl-11-oxo-6,7-dihydro-11H-benzo[f]pyrido[1,2-d][1,4]oxazepine-10-carboxylic acid

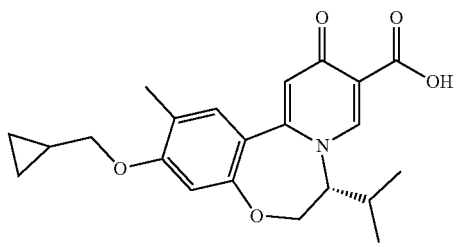 [SMILES: Cc1cc2c(cc1OCC1CC1)OC[C@@H](C(C)C)n1cc(C(=O)O)c(=O)cc1-2]

m/z: 384 [M+H]+ observed. ¹H NMR (300 MHz, CDCl₃): δ 8.47 (s, 1H), 7.24 (s, 1H), 6.85 (s, 1H), 6.48 (s, 1H), 4.54 (td, J=12.5, 11.1, 4.3 Hz, 2H), 3.96-3.80 (m, 3H), 2.23 (d, J=0.9 Hz, 3H), 2.08 (bs, 1H), 1.35-1.21 (m, 1H), 1.05 (d, J=6.5 Hz, 3H), 0.82 (d, J=6.5 Hz, 3H), 0.73-0.60 (m, 2H), 0.39 (dd, J=6.0, 4.6 Hz, 2H).

Example 50: (R)-3-(Cyclopropylmethoxy)-2-ethyl-7-isopropyl-11-oxo-6,7-dihydro-11H-benzo[f]pyrido[1,2-d][1,4]oxazepine-10-carboxylic acid

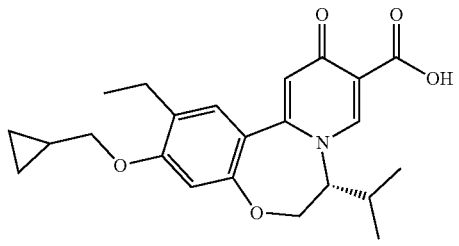 [SMILES: CCc1cc2c(cc1OCC1CC1)OC[C@@H](C(C)C)n1cc(C(=O)O)c(=O)cc1-2]

m/z: 398 [M+H]+ observed. ¹H NMR (300 MHz, CDCl₃): δ 8.61 (s, 1H), 7.26 (s, 1H), 7.12 (s, 1H), 6.49 (s, 1H), 4.65 (dd, J=13.5, 5.7 Hz, 1H), 4.52 (d, J=12.7 Hz, 1H), 4.03-3.98 (m, 1H), 3.86 (d, J=6.7 Hz, 2H), 2.66 (hept, J=7.5 Hz, 2H), 2.11-2.00 (m, 1H), 1.24 (td, J=7.5, 1.4 Hz, 3H), 1.09 (d, J=6.4 Hz, 3H), 0.85 (d, J=6.4 Hz, 3H), 0.66 (dd, J=7.2, 5.5 Hz, 2H), 0.44-0.32 (m, 2H).

Example 51: (R)-3-Isobutoxy-7-isopropyl-2-methyl-11-oxo-6,7-dihydro-11H-benzo[f]pyrido[1,2-d][1,4]oxazepine-10-carboxylic acid

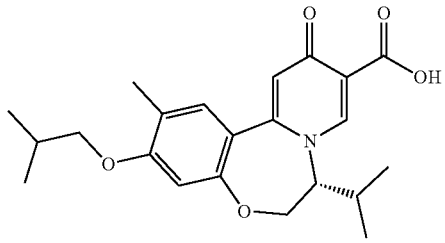 [SMILES: Cc1cc2c(cc1OCC(C)C)OC[C@@H](C(C)C)n1cc(C(=O)O)c(=O)cc1-2]

m/z: 386 [M+H]+ observed. ¹H NMR (300 MHz, CDCl₃): δ 8.68 (s, 1H), 7.25 (s, 1H), 7.13 (s, 1H), 6.51 (s, 1H), 4.68 (dd, J=13.0, 5.1 Hz, 1H), 4.55 (d, J=12.6 Hz, 1H), 4.10 (d, J=10.5 Hz, 1H), 3.84-3.69 (m, 2H), 2.23 (s, 3H), 2.12 (dd, J=13.0, 6.6 Hz, 2H), 1.25-1.05 (m, 9H), 0.82 (d, J=6.5 Hz, 3H).

Example 52: (R)-2-Ethyl-3-isobutoxy-7-isopropyl-11-oxo-6,7-dihydro-11H-benzo[f]pyrido[1,2-d][1,4]oxazepine-10-carboxylic acid

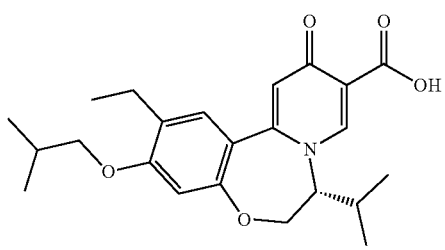 [SMILES: CCc1cc2c(cc1OCC(C)C)OC[C@@H](C(C)C)n1cc(C(=O)O)c(=O)cc1-2]

m/z: 400 [M+H]+ observed. ¹H NMR (300 MHz, CDCl₃): δ 8.62 (s, 1H), 7.25 (d, J=4.5 Hz, 1H), 7.08 (s, 1H), 6.51 (s, 1H), 4.64 (s, 1H), 4.56 (s, 1H), 4.03 (s, 1H), 3.84-3.69 (m, 2H), 2.75-2.54 (m, 2H), 2.15 (dp, J=13.0, 6.5 Hz, 2H), 1.23 (t, J=7.5 Hz, 3H), 1.08 (t, J=7.2 Hz, 9H), 0.84 (d, J=6.4 Hz, 3H).

Example 53: (R)-3-(3-((tert-Butoxycarbonyl)amino)propoxy)-2-cyclopropyl-7-isopropyl-11-oxo-6,7-dihydro-11H-benzo[f]pyrido[1,2-d][1,4]oxazepine-10-carboxylic acid

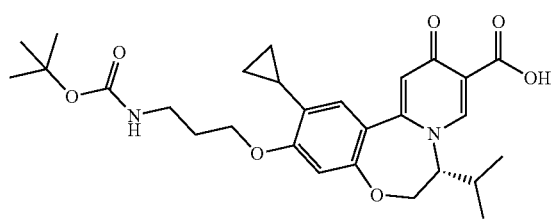 [SMILES: CC(C)[C@@H]1COc2cc(OCCCNC(=O)OC(C)(C)C)c(C3CC3)cc2-c2cc(=O)c(C(=O)O)cn21]

m/z: 513 [M+H]+ observed. ¹H NMR (300 MHz, CDCl₃): δ 8.47 (s, 1H), 6.98 (s, 1H), 6.82 (s, 1H), 6.52 (s, 1H), 5.00-5.02 (m, 1H), 4.56 (qd, J=12.4, 4.4 Hz, 2H), 4.18-4.04 (m, 2H), 3.94-3.84 (m, 1H), 3.39 (q, J=4.5, 2.8 Hz, 2H), 2.11-1.94 (m, 3H), 1.65 (d, J=7.5 Hz, 1H), 1.43 (s, 9H), 1.31-1.19 (m, 2H), 1.11-0.92 (m, 4H), 0.83 (d, J=6.5 Hz, 3H), 0.63 (ddd, J=9.4, 6.4, 3.7 Hz, 1H).

Example 54: (R)-2-Cyclopropyl-7-isopropyl-11-oxo-3-(2,2,2-trifluoroethoxy)-6,7-dihydro-11H-benzo[f]pyrido[1,2-d][1,4]oxazepine-10-carboxylic acid

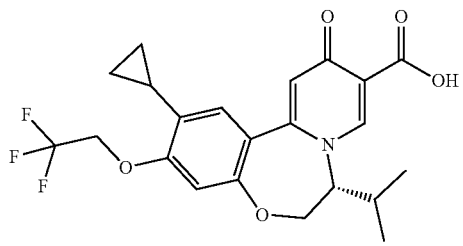 [SMILES: CC(C)[C@@H]1COc2cc(OCC(F)(F)F)c(C3CC3)cc2-c2cc(=O)c(C(=O)O)cn21]

m/z: 438 [M+H]+ observed. ¹H NMR (300 MHz, CDCl₃): δ 8.55 (s, 1H), 7.03-6.98 (m, 2H), 6.51 (s, 1H), 4.63-4.52 (m, 2H), 4.42 (q, J=7.9 Hz, 2H), 3.94 (s, 1H), 2.08 (s, 2H), 1.04 (m 5H), 0.90-0.81 (m, 3H), 0.71-0.65 (m, 2H).

Example 55: (R)-3-(2-Ethoxyethoxy)-7-isopropyl-2-methyl-11-oxo-6,7-dihydro-11H-benzo[f]pyrido[1,2-d][1,4]oxazepine-10-carboxylic acid

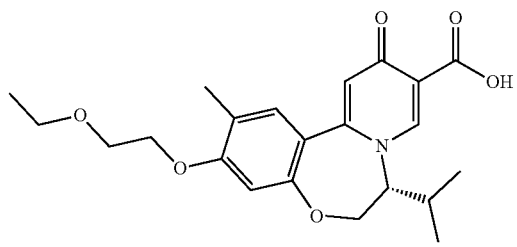 [SMILES: CCOCCOc1cc2c(cc1C)-c1cc(=O)c(C(=O)O)cn1[C@H](C(C)C)CO2]

m/z: 402 [M+H]+ observed. (400 MHz, DMSO-d₆): δ 8.76 (s, 1H), 7.45 (s, 1H), 6.96 (s, 1H), 6.68 (s, 1H), 4.65 (d, J=3.2 Hz, 2H), 4.52 (bd, J=11.2 Hz, 1H), 4.17 (m, 2H), 3.72 (t, J=4.4 Hz, 2H), 3.51 (m, 2H), 2.14 (s, 3H), 1.81 (bs, 1H), 1.13 (t, J=6.8 Hz, 3H), 0.96 (d, J=6.4 Hz, 3H), 0.67 (d, J=6.4 Hz, 3H).

Example 56: (R)-2-Ethyl-3-(3-hydroxypropoxy)-7-isopropyl-11-oxo-6,7-dihydro-11H-benzo[f]pyrido[1,2-d][1,4]oxazepine-10-carboxylic acid

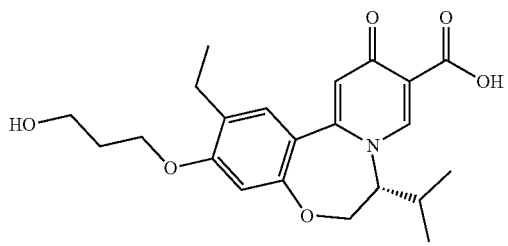 [SMILES: CCc1cc2c(cc1OCCCO)OC[C@@H](C(C)C)n1cc(C(=O)O)c(=O)cc1-2]

m/z: 402 [M+H]⁺ observed. (400 MHz, DMSO-d₆): δ 8.76 (s, 1H), 7.40 (s, 1H), 6.99 (s, 1H), 6.66 (s, 1H), 4.66 (d, J=3.6 Hz, 2H), 4.52 (bd, J=12 Hz, 1H) 4.09 (m, 2H), 3.58 (t, J=6.4 Hz, 2H), 2.53 (m, 2H), 1.88 (m, 2H), 1.80 (m, 1H), 1.15 (t, J=7.2 Hz, 3H), 0.98-0.96 (d, J=6.4 Hz, 3H), 0.69-0.68 (d, J=6.4 Hz, 3H).

Example 57: (R)-3-(2-Ethoxyethoxy)-2-ethyl-7-isopropyl-11-oxo-6,7-dihydro-111H-benzo[f]pyrido[1,2-d][1,4]oxazepine-10-carboxylic acid

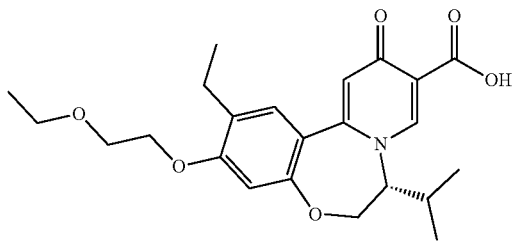 [SMILES: CCOCCOc1cc2c(cc1CC)-c1cc(=O)c(C(=O)O)cn1[C@H](C(C)C)CO2]

m/z: 416 [M+H]⁺ observed. (400 MHz, DMSO-d₆): δ 8.76 (s, 1H), 7.40 (s, 1H), 6.99 (s, 1H), 6.68 (s, 1H), 4.65 (d, J=3.2 Hz, 2H), 4.52 (bd, J=10.4 Hz, 1H), 4.16 (m, 2H), 3.72 (t, J=4.4 Hz, 2H), 3.52 (q, J=14, 7.2, 2H), 2.55 (m, 2H), 1.81 (s, 1H), 1.11 (m, 6H), 0.94 (d, J=6.4 Hz, 3H), 0.68 (d, J=6.4 Hz, 3H).

Example 58: (R)-2-Ethyl-7-isopropyl-11-oxo-3-(2,2,2-trifluoroethoxy)-6,7-dihydro-11H-benzo[f]pyrido[1,2-d][1,4]oxazepine-10-carboxylic acid

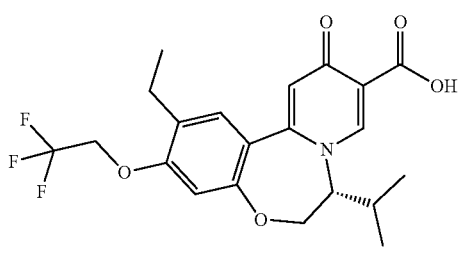 [SMILES: CCc1cc2c(cc1OCC(F)(F)F)OC[C@@H](C(C)C)n1cc(C(=O)O)c(=O)cc1-2]

m/z: 426 [M+H]⁺ observed. (400 MHz, DMSO-d₆): δ 8.78 (s, 1H), 7.48 (s, 1H), 7.03 (s, 1H), 6.83 (s, 1H), 4.87 (m, 2H), 4.68 (d, J=3.2 Hz, 2H), 4.55 (bd, J=10.4 Hz, 1H), 2.58 (m, 2H), 1.77 (bs, 1H), 1.16 (t, J=7.2 Hz, 3H), 0.97 (d, J=6.8 Hz, 3H), 0.69 (d, J=6.8 Hz, 3H).

Example 59: (R)-7-Isopropyl-2-methyl-11-oxo-3-(2,2,2-trifluoroethoxy)-6,7-dihydro-11H-benzo[f]pyrido[1,2-d][1,4]oxazepine-10-carboxylic acid

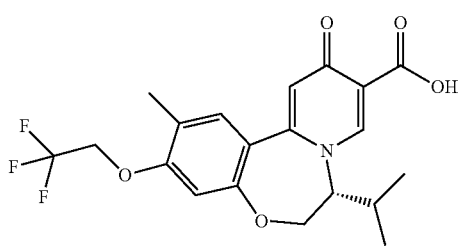 [SMILES: Cc1cc2c(cc1OCC(F)(F)F)OC[C@@H](C(C)C)n1cc(C(=O)O)c(=O)cc1-2]

Methyl 5-bromo-2,4-dihydroxybenzoate

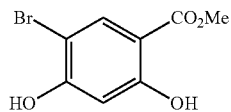

To a stirred solution of methyl 2,4-dihydroxybenzoate (10 g, 60 mmol) in AcOH (150 mL) was added a solution of Br₂ (3 mL, 60 mmol) in AcOH (50 mL) drop-wise. The reaction mixture was stirred at 10° C. for 12 h. The pH of the reaction mixture was adjusted to 8 by the addition of saturated aqueous NaHCO₃ (300 mL) and the reaction was extracted with EtOAc (2×200 mL). The combined organic phase was washed with saturated aqueous brine solution (300 mL), dried over sodium sulfate, filtered and concentrated under vacuum. The residue was washed with 100 mL (CH₂Cl₂: petroleum ether=10:1) to give methyl 5-bromo-2,4-dihydroxybenzoate as a white solid (9.5 g, 65% yield, m/z: 246, 248 [M+H]⁺ observed).

Methyl 2,4-bis(benzyloxy)-5-bromobenzoate

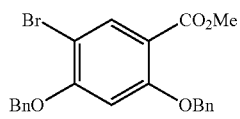

To a stirred solution of 5-bromo-2,4-dihydroxybenzoate (8.0 g, 33 mmol) in CH₃CN (80 mL) was added K₂CO₃ (18 g, 130 mmol), followed by benzyl bromide (9.7 mL, 81 mmol). The mixture was stirred at 80° C. for 12 h. The reaction mixture was quenched by the addition of H₂O (200 mL) and extracted with EtOAc (2×300 mL). The combined organic layers were washed with brine (300 mL), dried over Na₂SO₄, filtered and concentrated under vacuum. The residue was washed with 100 mL (PE:EA=20:1) to give methyl 2,4-bis(benzyloxy)-5-bromobenzoate as a white solid (12 g, 87% yield, m/z: 426, 428 [M+H]⁺ observed). ¹H NMR (400 MHz, CD₃Cl) δ8.11 (s, 1H), 7.39 (m, 10H), 6.54 (s, 1H), 5.12 (s, 2H), 5.11 (s, 2H), 3.88 (s, 3H).

Methyl 2,4-bis(benzyloxy)-5-methylbenzoate

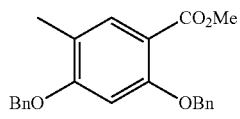

To a stirred solution of 2,4-bis(benzyloxy)-5-bromobenzoate (2.0 g, 4.7 mmol) in 1,4-dioxane (20 mL) and H₂O (4 mL) was added trimethylboroxine solution (4 M in THF, 2 mL, 8 mmol), Pd(OAc)₂ (74 mg, 0.33 mmol), SPhos (289 mg, 0.7 mmol) and K₂CO₃ (2.6 g, 19 mmol). The mixture was stirred at 90° C. for 16 hours. The reaction mixture was diluted H₂O (20 mL) and extracted with EtOAc (3×15 mL). The combined organic layers were separated, dried over Na₂SO₄, filtered and concentrated under vacuum. The residue was purified by normal phase SiO₂ chromatography (5% to 20% EtOAc/petroleum ether) to afford methyl 2,4-bis (benzyloxy)-5-methylbenzoate as a light yellow solid (1.5 g, 88% yield, m/z: 363 [M+H]+ observed). ¹H NMR (400 MHz, CD₃Cl) δ 7.72 (s, 1H), 7.41 (m, 10H), 6.52 (s, 1H), 5.13 (s, 2H), 5.06 (s, 2H), 3.88 (s, 3H), 2.21 (s, 3H).

2,4-Bis(benzyloxy)-5-methylbenzoic acid

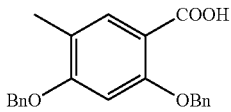

To a stirred solution of methyl 2,4-bis(benzyloxy)-5-methylbenzoate (1 g, 4.7 mmol) in THF (10 mL), MeOH (10 mL) and H₂O (10 mL) was added lithium hydroxide monohydrate (590 mg, 14 mmol). The mixture was stirred at 60° C. for 4 hours. The reaction mixture was concentrated under vacuum to remove the organic solvents. The aqueous solution was acidified with 1N HCl (10 mL) to pH=3. The resulting white solid was collected by filtration and washed with H₂O (2×10 mL) to give 2,4-bis(benzyloxy)-5-methylbenzoic acid (0.9 g, 94% yield, m/z: 349 [M+H]+ observed). ¹H NMR (400 MHz, DMSO-d₆) δ 12.17 (s, 1H), 7.46 (m, 11H), 6.89 (s, 1H), 5.20 (s, 2H), 5.15 (s, 2H), 2.11 (s, 3H).

2,4-Bis(benzyloxy)-5-methylbenzoyl chloride

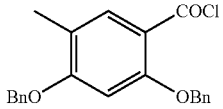

A mixture of 2,4-bis(benzyloxy)-5-methylbenzoic acid (0.9 g, 2.58 mmol) in thionyl chloride (2.6 mL, 36 mmol) was stirred at 80° C. for 2 hours. The mixture was concentrated under vacuum to remove the organic solvent to give 2,4-bis(benzyloxy)-5-methylbenzoyl chloride as a light yellow solid that was used without further purification (0.9 g, 96% yield).

Ethyl 6-(2,4-bis(benzyloxy)-5-methylphenyl)-4-oxo-4H-pyran-3-carboxylate

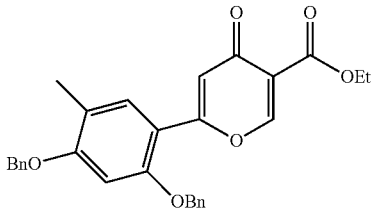 [SMILES: CCOC(=O)c1coc(-c2cc(C)c(OCc3ccccc3)cc2OCc2ccccc2)cc1=O]

To a solution of at −78° C. (dry ice/acetone bath) was added the mixture of 2,4-bis (benzyloxy)-5-methylbenzoyl chloride (0.9 g, 2.5 mmol) and ethyl (Z)-2-((dimethylamino)methylene)-3-oxobutanoate (455 mg, 2.45 mmol) in THF (6 mL) at −78° C. was added LiHMDS (1 M in THF, 5.9 mL, 5.9 mmol). The reaction mixture warmed to 0° C. over 30 min. Then MTBE (2.5 mL) and 3N HCl (7.5 mL) was added to the mixture and the solution was stirred at room temperature for 1.5 hours. The pH of the reaction mixture was adjusted to 8 by addition of saturated aqueous NaHCO₃ (20 mL) and extracted with EtOAc (3×20 mL). The combined organic layers were washed with brine (30 mL), dried over Na₂SO₄, filtered and concentrated under vacuum. The residue was purified by normal phase SiO₂ chromatography (5% to 50% EtOAc/petroleum ether) to afford ethyl 6-(2,4-bis(benzyloxy)-5-methylphenyl)-4-oxo-4H-pyran-3-carboxylate as a yellow solid (0.85 g, 73% yield, m/z: 471 [M+H]+ observed). ¹H NMR (400 MHz, CD₃Cl) δ 8.54 (s, 1H), 7.50 (s, 1H), 7.40 (m, 10H), 7.16 (s, 1H), 6.53 (s, 1H), 5.14 (s, 2H), 5.04 (s, 2H), 4.44 (q, J=14.4, 7.2 Hz, 2H), 2.23 (s, 3H), 1.40-1.37 (t, J=7.2 Hz, 3H).

Ethyl (R)-6-(2,4-bis(benzyloxy)-5-methylphenyl)-1-(1-hydroxy-3-methylbutan-2-yl)-4-oxo-1,4-dihydropyridine-3-carboxylate

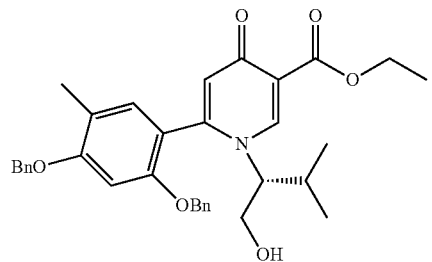 [SMILES: CCOC(=O)c1cn([C@@H](CO)C(C)C)c(-c2cc(C)c(OCc3ccccc3)cc2OCc2ccccc2)cc1=O]

To a solution of ethyl 6-(2,4-bis(benzyloxy)-5-methylphenyl)-4-oxo-4H-pyran-3-carboxylate (0.5 g, 1.1 mmol) in EtOH (1.5 mL) and glacial AcOH (1.0 mL) was added (R)-2-amino-3-methylbutan-1-ol (0.16 g, 1.6 mmol, 1.50 eq). The mixture was stirred at 90° C. for 4 hours. The pH of the reaction mixture was adjusted to 8 by addition of saturated aqueous NaHCO₃ (15 mL) and extracted with EtOAc (3×30 mL). The combined organic layers were separated, dried over Na₂SO₄, filtered and concentrated under vacuum. The residue was purified by normal phase SiO₂ chromatography (20% to 50% EtOAc/petroleum ether) to afford ethyl (R)-6-(2,4-bis(benzyloxy)-5-methylphenyl)-1-(1-hydroxy-3-methylbutan-2-yl)-4-oxo-1,4-dihydropyridine-3-carboxylate as a light yellow solid that was used without further purification (0.4 g, 68% yield, m/z: 557 [M+H]+ observed).

Ethyl (R)-6-(2,4-dihydroxy-5-methylphenyl)-1-(1-hydroxy-3-methylbutan-2-yl)-4-oxo-1,4-dihydropyridine-3-carboxylate

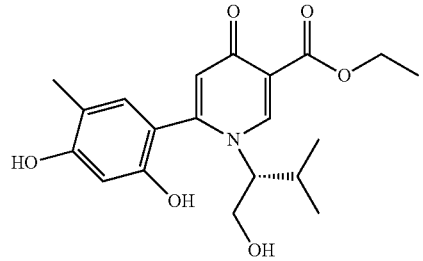 [SMILES: CCOC(=O)c1cn([C@@H](CO)C(C)C)c(-c2cc(C)c(O)cc2O)cc1=O]

To a mixture of ethyl (R)-6-(2,4-bis(benzyloxy)-5-methylphenyl)-1-(1-hydroxy-3-methylbutan-2-yl)-4-oxo-1,4-dihydropyridine-3-carboxylate (300 mg, 0.54 mmol) in absolute EtOH (20 mL) was added palladium on carbon (10% on carbon, 100 mg, 9.3 mmol). The mixture was stirred at room temperature for 15 min under H$_2$ (15 Psi). The reaction was followed by TLC. The reaction mixture was filtered, washed with EtOH (3×50 mL) and the filtrate concentrated under reduced pressure. The residue was diluted with H$_2$O (20 mL) and extracted with EtOAc (3×30 mL). The combined organic fractions were dried over sodium sulfate, filtered and concentrated under vacuum to yield ethyl (R)-6-(2,4-dihydroxy-5-methylphenyl)-1-(1-hydroxy-3-methylbutan-2-yl)-4-oxo-1,4-dihydropyridine-3-carboxylate a yellow solid that was used without further purification (0.19 g, 94% yield, m/z: 376 [M+H]$^+$ observed).

Ethyl (R)-3-hydroxy-7-isopropyl-2-methyl-11-oxo-6,7-dihydro-11H-benzo[f]pyrido[1,2-d][1,4]oxazepine-10-carboxylate

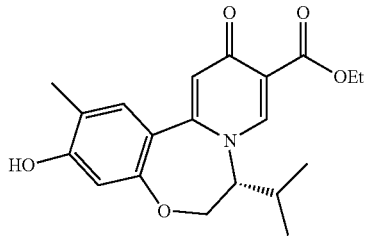 [SMILES: CCOC(=O)c1cn2c(cc1=O)-c1cc(C)c(O)cc1OC[C@H]2C(C)C]

To a solution of ethyl (R)-6-(2,4-dihydroxy-5-methylphenyl)-1-(1-hydroxy-3-methylbutan-2-yl)-4-oxo-1,4-dihydropyridine-3-carboxylate (0.19 g, 0.51 mmol) in THF (70 mL) was added PPh$_3$ (0.66 g, 2.5 mmol), followed by diethyl azodicarboxylate (40% wt in toluene, 0.2 mL, 2.5 mmol) (440 mg, 2.53 mmol, 5.00 eq). The reaction mixture was stirred at rt for 12 hours. The mixture was concentrated under vacuum and the residue was diluted with H$_2$O (50 mL). The mixture was extracted with EtOAc (2×200 mL). The combined organic layers were separated, dried over Na$_2$SO$_4$, filtered and concentrated under vacuum. The residue was purified by normal phase SiO$_2$ chromatography (10% to 50% EtOAc/petroleum ether) to afford ethyl (R)-3-hydroxy-7-isopropyl-2-methyl-11-oxo-6,7-dihydro-11H-benzo[f]pyrido[1,2-d][1,4]oxazepine-10-carboxylate as a yellow solid that was used without further purification (0.12 g, 66% yield, m/z: 358 [M+H]$^+$ observed).

Ethyl (R)-7-isopropyl-2-methyl-11-oxo-3-(2,2,2-trifluoroethoxy)-6,7-dihydro-11H-benzo[f]pyrido[1,2-d][1,4]oxazepine-10-carboxylate

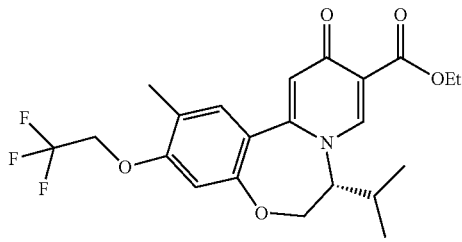 [SMILES: CCOC(=O)c1cn2c(cc1=O)-c1cc(C)c(OCC(F)(F)F)cc1OC[C@H]2C(C)C]

To the mixture of ethyl (R)-3-hydroxy-7-isopropyl-2-methyl-11-oxo-6,7-dihydro-11H-benzo[f]pyrido[1,2-d][1,4]oxazepine-10-carboxylate (0.12 g, 0.34 mmol) in DMF (4 mL) was added 2-bromo-1,1,1-trifluoroethane (0.11 g, 0.66 mmol) and K$_2$CO$_3$ (0.12 g, 0.84 mmol). The reaction mixture was stirred at 80° C. for 2 hours. Then the reaction mixture was diluted with H$_2$O (50 mL) and extracted with EtOAc (3×60 mL). The combined organic layers were separated, dried over Na$_2$SO$_4$, filtered and concentrated under vacuum to afford ethyl (R)-7-isopropyl-2-methyl-11-oxo-3-(2,2,2-trifluoroethoxy)-6,7-dihydro-11H-benzo[f]pyrido[1,2-d][1,4]oxazepine-10-carboxylate as a light yellow solid that was used without further purification (0.11 g, 74% yield, m/z: 440 [M+H]$^+$ observed).

(R)-7-Isopropyl-2-methyl-11-oxo-3-(2,2,2-trifluoroethoxy)-6,7-dihydro-11H-benzo[f]pyrido[1,2-d][1,4]oxazepine-10-carboxylic acid

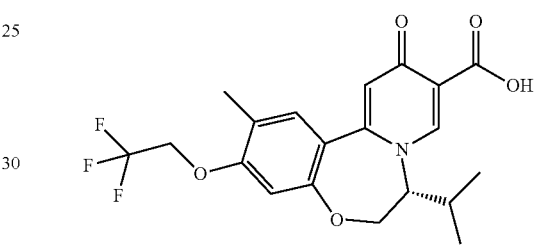

To a solution of ethyl (R)-7-isopropyl-2-methyl-11-oxo-3-(2,2,2-trifluoroethoxy)-6,7-dihydro-11H-benzo[f]pyrido[1,2-d][1,4]oxazepine-10-carboxylate (110 mg, 0.25 mmol) in dioxane (3 mL) and H$_2$O (2 mL) was added lithium hydroxide monohydrate (52 mg, 1.25 mmol). The reaction mixture was stirred at rt for 16 hours. The mixture was concentrated under vacuum. The residue was diluted with H$_2$O (10 mL), acidified to pH 2 with 1N HCl solution (10 mL) and the mixture was extracted with CH$_2$Cl$_2$ (3×20 mL). The combined organic layers were separated, dried over Na$_2$SO$_4$, filtered and concentrated under vacuum. The residue was purified by reverse phase HPLC to afford (R)-7-isopropyl-2-methyl-11-oxo-3-(2,2,2-trifluoroethoxy)-6,7-dihydro-11H-benzo[f]pyrido[1,2-d][1,4]oxazepine-10-carboxylic acid as white solid (49 mg, 48% yield, m/z: 412 [M+H]$^+$ observed). $^1$H NMR (400 MHz, DMSO-d$_6$) δ 8.78 (s, 1H), 7.53 (s, 1H), 6.99 (s, 1H), 6.84 (s, 1H), 4.88 (m, 2H), 4.68 (d, J=3.2 Hz, 2H), 4.54 (d, J=10.4 Hz, 1H), 2.16 (s, 3H), 1.77 (bs, 1H), 0.97 (d, J=6.4 Hz, 3H), 0.69 (d, J=6.4 Hz, 3H).

The following example were prepared in a similar manner as (R)-7-isopropyl-2-methyl-11-oxo-3-(2,2,2-trifluoroethoxy)-6,7-dihydro-11H-benzo[f]pyrido[1,2-d][1,4]oxazepine-10-carboxylic acid from methyl 2,4-bis(benzyloxy)-5-bromobenzoate and an appropriate organoboron species.

Example 60: (R)-3-(3-Hydroxypropoxy)-7-isopropyl-2-methyl-11-oxo-6,7-dihydro-11H-benzo[f]pyrido[1,2-d][1,4]oxazepine-10-carboxylic acid

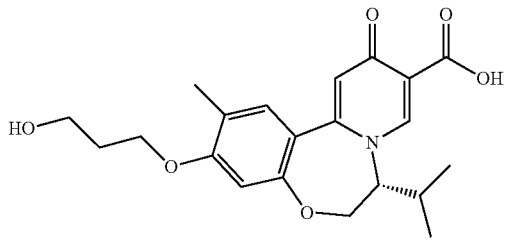 [SMILES: Cc1cc2c(cc1OCCCO)OC[C@@H](C(C)C)n1cc(C(=O)O)c(=O)cc1-2]

m/z: 388 [M+H]+ observed. ¹H NMR (300 MHz, CDCl₃): δ 8.76 (s, 1H), 7.44 (s, 1H), 6.95 (s, 1H), 6.65 (s, 1H), 4.66 (d, J=3.6 Hz, 2H), 4.52 (d, J=11.2 Hz, 1H), 4.09 (m, 2H), 3.58 (t, J=6.0 Hz, 2H), 2.13 (s, 3H), 1.89 (m, 3H), 1.81 (bs, 1H), 0.97 (d, J=6.4 Hz, 3H), 0.69 (d, J=6.4 Hz, 3H).

Example 61: (R)-2-Chloro-7-isopropyl-3-((3-methoxypropyl)amino)-11-oxo-6,7-dihydro-11H-benzo[f]pyrido[1,2-d][1,4]oxazepine-10-carboxylic acid

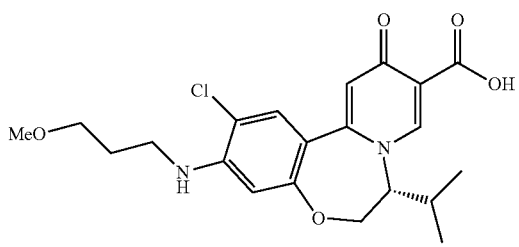 [SMILES: COCCCNc1cc2c(cc1Cl)-c1cc(=O)c(C(=O)O)cn1[C@H](C(C)C)CO2]

Ethyl (R)-2-chloro-7-isopropyl-3-((3-methoxypropyl)amino)-11-oxo-6,7-dihydro-11H-benzo[f]pyrido[1,2-d][1,4]oxazepine-10-carboxylate

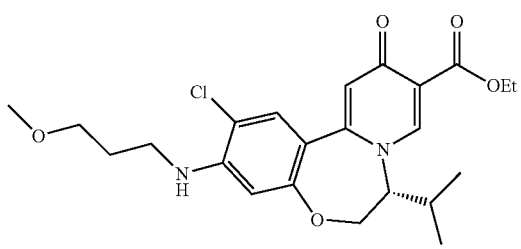 [SMILES: CCOC(=O)c1cn2c(cc1=O)-c1cc(Cl)c(NCCCOC)cc1OC[C@H]2C(C)C]

To a solution of ethyl (R)-2-chloro-3-hydroxy-7-isopropyl-11-oxo-6,7-dihydro-11H-benzo[f]pyrido[1,2-d][1,4]oxazepine-10-carboxylate (1 g, 2.7 mmol) and N-phenyl-bis(trifluoromethanesulfonimide) (1.14 g, 3.18 mmol) in CH₂Cl₂ (20 mL) was added TEA (0.74 mL, 5.3 mmol, 2.00 eq). The reaction mixture was stirred for 16 h at rt. The reaction mixture was diluted H₂O (20 mL) and extracted with CH₂Cl₂ (3×10 mL). The combined organic layers were separated, dried over Na₂SO₄, filtered and concentrated under vacuum. The residue was purified by normal phase SiO₂ chromatography (0% to 10% MeOH/CH₂Cl₂) to afford ethyl (R)-2-chloro-7-isopropyl-11-oxo-3-(((trifluoromethyl)sulfonyl)oxy)-6,7-dihydro-11H-benzo[f]pyrido[1,2-d][1,4]oxazepine-10-carboxylate as a white solid (1 g, 74% yield) that was used directly in the next step.

A solution of ethyl (R)-2-chloro-7-isopropyl-11-oxo-3-(((trifluoromethyl)sulfonyl)oxy)-6,7-dihydro-11H-benzo[f]pyrido[1,2-d][1,4]oxazepine-10-carboxylate (700 mg, 1.37 mmol), 3-methoxypropan-1-amine (184 mg, 2.06 mmol) and cesium carbonate (895 mg, 2.75 mmol) in toluene (30 mL) was flushed with nitrogen (3 times). Then palladium(II) acetate (62 mg, 0.275 mmol), BINAP (513 mg, 0.825 mmol) and bis(dibenzylideneacetone)palladium(0) (79 mg, 0.138 mmol) were added and the reaction mixture was heated at 100° C. for 16 h. The reaction mixture was concentrated under vacuum. The residue was purified by normal phase SiO₂ chromatography (0% to 5% MeOH/CH₂Cl₂) to afford ethyl (R)-2-chloro-7-isopropyl-3-((3-methoxypropyl)amino)-11-oxo-6,7-dihydro-11H-benzo[f]pyrido[1,2-d][1,4]oxazepine-10-carboxylate as a light yellow oil (200 mg, 32% yield, m/z: 449 [M+H]+ observed).

(R)-2-Chloro-7-isopropyl-3-((3-methoxypropyl)amino)-11-oxo-6,7-dihydro-11H-benzo[f]pyrido[1,2-d][1,4]oxazepine-10-carboxylic acid

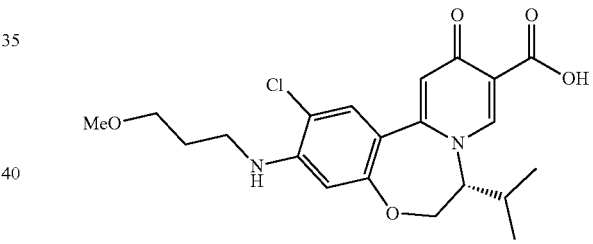

To a mixture of ethyl (R)-2-chloro-7-isopropyl-3-((3-methoxypropyl)amino)-11-oxo-6,7-dihydro-11H-benzo[f]pyrido[1,2-d][1,4]oxazepine-10-carboxylate (100 mg, 0.216 mmol) in MeOH (2 mL) and H₂O (2 mL) was added lithium hydroxide monohydrate (37 mg, 0.89 mmol) and stirred at rt for 10 hr. The reaction mixture was concentrated under vacuum. The residue was purified by reverse phase HPLC to afford (R)-2-chloro-7-isopropyl-3-((3-methoxypropyl)amino)-11-oxo-6,7-dihydro-11H-benzo[f]pyrido[1,2-d][1,4]oxazepine-10-carboxylic acid as white solid (19 mg, 20% yield, m/z: 421 [M+H]+ observed). ¹H NMR (400 MHz, DMSO-d₆) δ 8.73 (s, 1H), 7.55 (s, 1H), 6.92 (s, 1H), 6.33 (s, 1H), 6.21 (bs, 1H), 4.63 (d, J=3.2 Hz, 2H), 4.52 (m, 1H), 3.40 (t, J=6 Hz, 2H), 3.25 (m, 5H), 1.89 (bs, 1H), 1.79 (m, 2H), 0.98 (d, J=6.4 Hz, 3H), 0.69 (d, J=6.4 Hz, 3H).

The following example were prepared in a similar manner as (R)-2-chloro-7-isopropyl-3-((3-methoxypropyl)amino)-11-oxo-6,7-dihydro-11H-benzo[f]pyrido[1,2-d][1,4]oxazepine-10-carboxylic acid from ethyl (R)-2-chloro-3-hydroxy-7-isopropyl-11-oxo-6,7-dihydro-11H-benzo[f]pyrido[1,2-d][1,4]oxazepine-10-carboxylate and an appropriate amine.

Example 62: (R)-2-Chloro-7-isopropyl-3-morpholino-11-oxo-6,7-dihydro-11H-benzo[f]pyrido[1,2-d][1,4]oxazepine-10-carboxylic acid

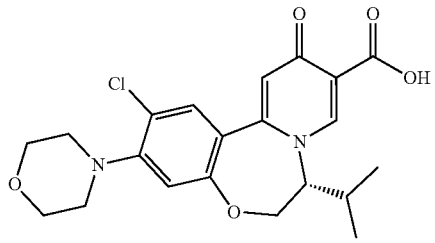 [SMILES: CC(C)[C@@H]1COc2cc(N3CCOCC3)c(Cl)cc2-c2cc(=O)c(C(=O)O)cn21]

m/z: 419 [M+H]⁺ observed. ¹H NMR (300 MHz, DMSO-$d_6$): δ 8.78 (s, 1H), 7.71 (s, 1H), 7.03 (s, 1H), 6.77 (s, 1H), 4.69 (d, J=3.6 Hz, 2H), 4.55 (bd, J=10.4 Hz, 1H), 3.74 (t, J=4.4 Hz, 4H), 3.13 (m, 2H), 3.04 (m, 2H), 1.83 (bs, 1H), 0.98 (d, J=6.8 Hz, 3H), 0.72 (d, J=6.4 Hz, 3H).

Example 63: (R)-2-Chloro-7-isopropyl-3-((3-methoxypropyl)(methyl)amino)-11-oxo-6,7-dihydro-11H-benzo[f]pyrido[1,2-d][1,4]oxazepine-10-carboxylic acid

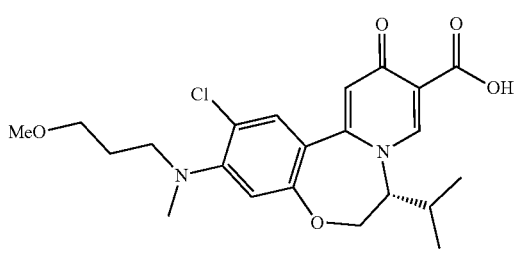 [SMILES: COCCCN(C)c1cc2c(cc1Cl)-c1cc(=O)c(C(=O)O)cn1[C@H](C(C)C)CO2]

m/z: 435 [M+H]⁺ observed. ¹H NMR (300 MHz, DMSO-$d_6$): δ 8.77 (s, 1H), 7.65 (s, 1H), 7.00 (s, 1H), 6.73 (s, 1H), 4.67 (m, J=3.6 Hz, 2H), 4.55 (bd, J=9.6 Hz, 1H), 3.32 (t, J=6 Hz, 2H), 3.2 (m, 5H), 2.80 (s, 3H), 1.80 (m, 3H), 0.99 (d, J=6 Hz, 3H), 0.71 (d, J=6.8 Hz, 3H).

Example 64: (R)-2-Chloro-7-isopropyl-3-((2-methoxyethyl)amino)-11-oxo-6,7-dihydro-11H-benzo[f]pyrido[1,2-d][1,4]oxazepine-10-carboxylic acid

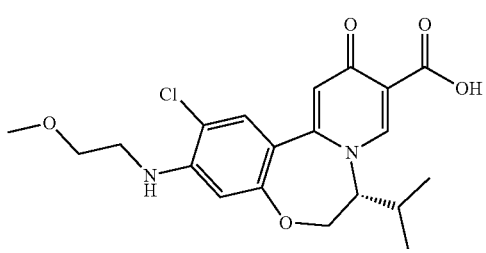 [SMILES: COCCNc1cc2c(cc1Cl)-c1cc(=O)c(C(=O)O)cn1[C@H](C(C)C)CO2]

m/z: 407 [M+H]⁺ observed. ¹H NMR (300 MHz, DMSO-$d_6$): δ 8.73 (s, 1H), 7.56 (s, 1H), 6.93 (s, 1H), 6.42 (s, 1H), 6.00 (bs, 1H), 4.63 (m, 2H), 4.51 (bd, J=10.8 Hz, 1H), 3.50 (t, J=5.2 Hz, 2H), 3.36 (m, 2H), 3.27 (s, 3H), 1.89 (bs, 1H), 0.98 (d, J=6.4 Hz, 3H), 0.70 (d, J=6.4 Hz, 3H).

Example 65: (R)-2-Chloro-7-isopropyl-3-((2-methoxyethyl)(methyl)amino)-11-oxo-6,7-dihydro-11H-benzo[f]pyrido[1,2-d][1,4]oxazepine-10-carboxylic acid

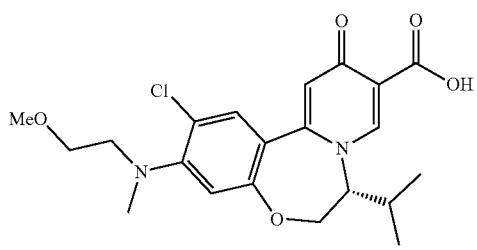 [SMILES: COCCN(C)c1cc2c(cc1Cl)-c1cc(=O)c(C(=O)O)cn1[C@H](C(C)C)CO2]

m/z: 421 [M+H]⁺ observed. ¹H NMR (300 MHz, DMSO-$d_6$): δ 8.78 (s, 1H), 7.64 (s, 1H), 7.02 (s, 1H), 6.73 (s, 1H), 4.68 (d, J=3.2 Hz, 2H), 4.55 (d, J=10.8 Hz, 1H), 3.57 (t, J=6 Hz, 2H), 3.37 (t, J=6 Hz, 2H), 3.21 (s, 3H), 2.86 (s, 3H), 1.84 (bs, 1H), 0.98 (d, J=6.4 Hz, 3H), 0.71 (d, J=6.4 Hz, 3H).

Example 66: (R)-7-(Tert-butyl)-2-chloro-3-(3-methoxypropoxy)-11-oxo-6,7-dihydro-11H-dipyrido[1,2-d:2',3'-f][1,4]oxazepine-10-carboxylic acid

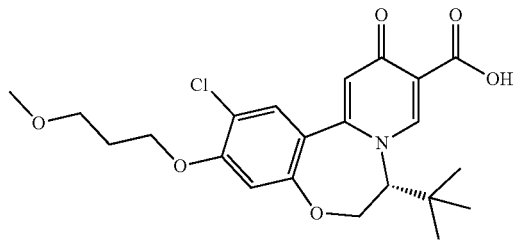 [SMILES: COCCCOc1cc2c(cc1Cl)-c1cc(=O)c(C(=O)O)cn1[C@H](C(C)(C)C)CO2]

6-Chloro-5-(3-methoxypropoxy)pyridin-3-ol

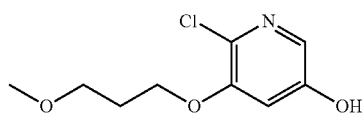

A solution of 5-bromo-2-chloro-3-(3-methoxypropoxy)pyridine (10 g, 36 mmol), bis(pinacolato)diboron (10.9 g, 42.8 mmol), Pd(dppf)Cl₂·CH₂Cl₂ (1.45 g, 1.78 mmol) and potassium acetate (10.5 g, 107 mmol) in dioxane (100 mL) was purged with nitrogen and then heated for 16 hours at 85° C. The solution was diluted with EtOAc (150 mL) and washed with aqueous sat. NaHCO₃ solution (200 mL). The organic phase was dried over magnesium sulfate, filtered and concentrated under reduced vacuum. To a stirred solution of crude 2-chloro-3-(3-methoxypropoxy)-5-(4,4,5,5-tetramethyl-1,3,2-dioxaborolan-2-yl)pyridine in THF (100 mL) at room temperature was added 30% hydrogen peroxide (30% (w/w) in H₂O, 3.6 mL, 120 mmol) dropwise and stirring was continued for 4 hours. Additional hydrogen peroxide (30% (w/w) in H₂O, 3.6 mL, 120 mmol) was added and the reaction mixture stirred overnight. Upon completion, the solution was concentrated under reduced vacuum to remove THF. The aqueous mixture was diluted with EtOAc (100 mL), washed with aqueous sat. NaHCO₃ solution (100 mL) and then aqueous sat. brine solution (100 mL). The organic layer was dried over magnesium sulfate, filtered and concentrated under reduced vacuum. The residue was purified by normal phase SiO₂ chromatography (25% to 75% EtOAc/hexanes) to afford 6-chloro-5-(3-methoxypropoxy) pyridin-3-ol as a yellow oil (3.3 g, 42% yield, m/z: 218 [M+H]⁺ observed).

6-Chloro-2-iodo-5-(3-methoxypropoxy)pyridin-3-ol

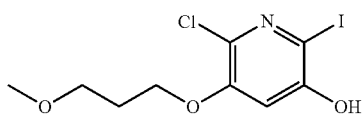

To a solution of 6-chloro-5-(3-methoxypropoxy)pyridin-3-ol (1.5 g, 6.9 mmol) and sodium carbonate (1.5 g, 14 mmol) in H₂O (75 mL) was added iodine (1.8 g, 6.9 mmol). The reaction mixture was stirred at rt for 2 hours then the pH was adjusted to to 7.5-8 with sat. aqueous ammonium chloride (~50 mL). The solution was extracted with EtOAc (2×100 mL) and the combined organic fractions were dried on magnesium sulfate, filtered and concentrated under reduced vacuum. The residue was purified by normal phase SiO₂ chromatography (25% to 100% EtOAc/hexanes) to afford 6-chloro-2-iodo-5-(3-methoxypropoxy)pyridin-3-ol as a yellow solid (2 g, 85% yield, m/z: 344 [M+H]⁺ observed).

Tert-butyl (R)-1-(1-hydroxy-3,3-dimethylbutan-2-yl)-4-oxo-1,4-dihydropyridine-3-carboxylate

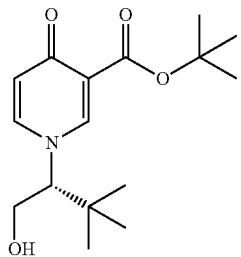 [SMILES: CC(C)(C)OC(=O)c1cn([C@@H](CO)C(C)(C)C)ccc1=O]

A solution of tert-butyl 4-oxopyran-3-carboxylate (1.5 g, 7.7 mmol) and (R)-2-amino-3,3-dimethyl-1-butanol (2.1 mL, 16 mmol) in anhydrous ethanol (30 mL) was refluxed overnight. The reaction mixture was concentrated under reduced vacuum. The residue was purified by normal phase SiO₂ chromatography (0% to 15% MeOH/CH₂Cl₂) to afford tert-butyl (R)-1-(1-hydroxy-3,3-dimethylbutan-2-yl)-4-oxo-1,4-dihydropyridine-3-carboxylate as a yellow solid (650 mg, 29% yield).

Tert-butyl (R)-1-(1-((6-chloro-2-iodo-5-(3-methoxypropoxy)pyridin-3-yl)oxy)-3,3-dimethylbutan-2-yl)-4-oxo-1,4-dihydropyridine-3-carboxylate

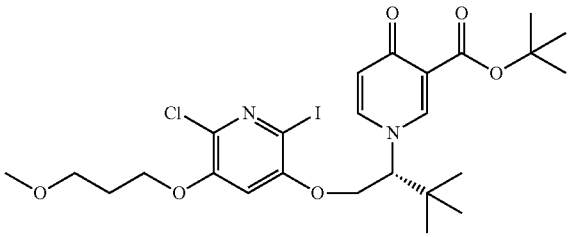 [SMILES: COCCCOc1cc(OC[C@H](n2ccc(=O)c(C(=O)OC(C)(C)C)c2)C(C)(C)C)c(I)nc1Cl]

To a solution of 6-chloro-2-iodo-5-(3-methoxypropoxy)pyridin-3-ol (760 mg, 2.2 mmol), tert-butyl (R)-1-(1-hydroxy-3,3-dimethylbutan-2-yl)-4-oxo-1,4-dihydropyridine-3-carboxylate (650 mg, 2.2 mmol) and triphenylphosphine (1.2 g, 4.4 mmol) in toluene (25 mL) was slowly added diisopropyl azodicarboxylate (1.3 mL, 6.6 mmol). The solution was heated to 55° C. for 2 hours then concentrated under reduced vacuum. The residue was purified by normal phase SiO₂ chromatography (0% to 15% MeOH/CH₂Cl₂) to afford tert-butyl (R)-1-(1-((6-chloro-2-iodo-5-(3-methoxypropoxy)pyridin-3-yl)oxy)-3,3-dimethylbutan-2-yl)-4-oxo-1,4-dihydropyridine-3-carboxylate as a yellow solid (575 mg, 42%, m/z: 621 [M+H]⁺ observed).

Tert-butyl (R)-7-(tert-butyl)-2-chloro-3-(3-methoxypropoxy)-11-oxo-6,7-dihydro-11H-dipyrido[1,2-d:2',3'-f][1,4]oxazepine-10-carboxylate

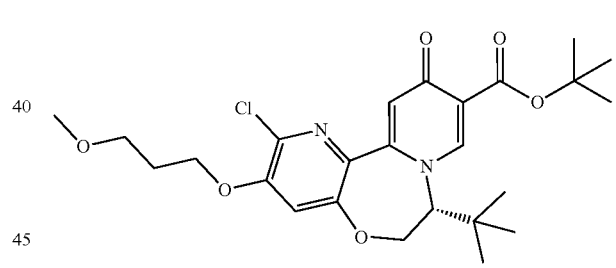

A solution of tert-butyl (R)-1-(1-((6-chloro-2-iodo-5-(3-methoxypropoxy)pyridin-3-yl)oxy)-3,3-dimethylbutan-2-yl)-4-oxo-1,4-dihydropyridine-3-carboxylate (580 mg, 0.93 mmol), palladium bromide (120 mg, 0.45 mmol) and potassium acetate (180 mg, 1.9 mmol) in N,N-dimethylacetamide (10 mL) was purged with nitrogen and stirred for 16 h at 120° C. in a sealed reaction vessel. Additional PdBr₂ (25 mg, 0.1 mmol) was added and heating was continued for another 24 h. Upon completion, the desired product and the t-butyl ester hydrolysis product were both observed. The solution was poured into H₂O (100 mL) and extracted with EtOAc (5×75 mL). The combined extracts were washed with sat. aqueous brine solution (2×100 mL), dried over magnesium sulfate, filtered and concentrated under reduced vacuum. The residue was purified by normal phase SiO₂ chromatography (0% to 5% MeOH/CH₂Cl₂) to afford a mixture of desired tert-butyl (R)-7-(tert-butyl)-2-chloro-3-(3-methoxypropoxy)-11-oxo-6,7-dihydro-11H-dipyrido[1,2-d:2',3'-f][1,4]oxazepine-10-carboxylate and the ester hydrolysis product (R)-7-(tert-butyl)-2-chloro-3-(3-methoxypropoxy)-11-oxo- 6,7-dihydro-11H-dipyrido[1,2-d:2',3'-f][1,4]oxazepine-10-carboxylic acid. The mixture was used in the next step without further purification (85 mg, 19% yield, m/z: 493 [M+H]+ observed).

(R)-7-(Tert-butyl)-2-chloro-3-(3-methoxypropoxy)-11-oxo-6,7-dihydro-11H-dipyrido[1,2-d:2',3'-f][1,4]oxazepine-10-carboxylic acid

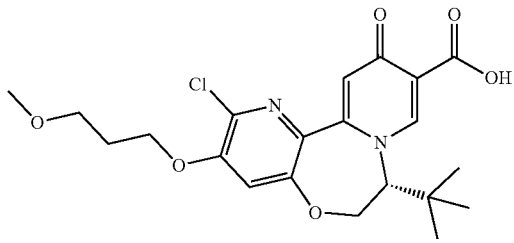 [SMILES: COCCCOc1cc2c(nc1Cl)-c1cc(=O)c(C(=O)O)cn1[C@H](C(C)(C)C)CO2]

A solution of tert-butyl (R)-7-(tert-butyl)-2-chloro-3-(3-methoxypropoxy)-11-oxo-6,7-dihydro-11H-dipyrido[1,2-d:2',3'-f][1,4]oxazepine-10-carboxylate (85 mg crude, 0.17 mmol) in dichloromethane/trifluoroacetic acid solution (2:1, 10 mL) was stirred overnight at rt. The solution was concentrated under reduced vacuum and azeotroped with toluene (3×) to remove all residual trifluoroacetic acid. The residue was purified by normal phase SiO2 chromatography (0% to 15% MeOH/CH2Cl2), followed by precipitation from methanol (2 mL) to afford (R)-7-(tert-butyl)-2-chloro-3-(3-methoxypropoxy)-11-oxo-6,7-dihydro-11H-dipyrido[1,2-d:2',3'-f][1,4]oxazepine-10-carboxylic acid as a white solid (4.2 mg, 6% yield, m/z: 437 [M+H]+ observed). 1H NMR (300 MHz, CDCl3): δ 8.39 (s, 1H), 8.13 (s, 1H), 6.83 (s, 1H), 4.99 (dd, J=14.0, 4.9 Hz, 1H), 4.48-4.32 (m, 1H), 4.18 (q, J=6.2, 5.6 Hz, 3H), 3.59 (t, J=5.8 Hz, 2H), 3.36 (s, 3H), 2.14 (p, J=6.1 Hz, 2H), 1.05 (s, 9H).

Example 67: (R)-7-(Tert-butyl)-2-cyclopropyl-3-(3-methoxypropoxy)-11-oxo-6,7-dihydro-11H-dipyrido[1,2-d:2',3'-f][1,4]oxazepine-10-carboxylic acid

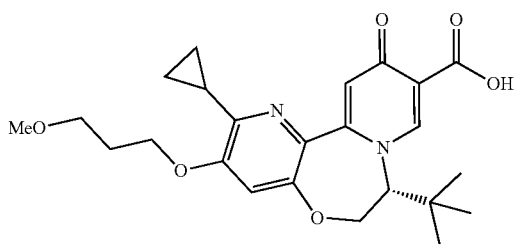 [SMILES: COCCCOc1cc2c(nc1C1CC1)-c1cc(=O)c(C(=O)O)cn1[C@H](C(C)(C)C)CO2]

Ethyl(7R)-7-tert-butyl-2-cyclopropyl-3-(3-methoxypropoxy)-11-oxo-6,7-dihydrodipyrido[5,3-b:1',3'-e][1,4]oxazepine-10-carboxylate

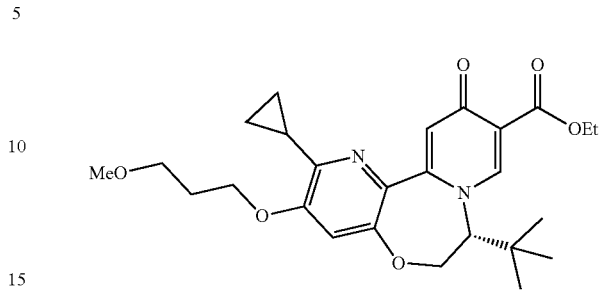

To a mixture of ethyl(7R)-7-tert-butyl-2-chloro-3-(3-methoxypropoxy)-11-oxo-6,7-dihydrodipyrido[5,3-b:1',3'-e][1,4]oxazepine-10-carboxylate (200 mg, 0.43 mmol) and potassium cyclopropyltrifluoroborate (96 mg, 0.65 mmol) in toluene (3 mL) and H2O (3 mL) was added cesium carbonate (562 mg, 1.72 mmol) of Cs2CO3, palladium(II) acetate (10 mg, 0.043 mol) and XPhos 61.52 mg (62 mg, 0.129 mmol). The mixture was stirred at 120° C. for 16 hr. The reaction mixture was diluted with H2O (10 mL) and extracted with EtOAc (3×5 mL). The combined organic layers were washed with sat. aqueous brine solution (2.5 mL), dried over sodium sulfate, filtered and concentrated under reduced pressure. The residue was purified by preparative TLC to give ethyl(7R)-7-tert-butyl-2-cyclopropyl-3-(3-methoxypropoxy)-11-oxo-6,7-dihydrodipyrido[5,3-b:1',3'-e][1,4]oxazepine-10-carboxylate as a yellow solid (140 mg, 59% yield, m/z: 471 [M+H]+ observed).

(7R)-7-Tert-butyl-2-cyclopropyl-3-(3-methoxypropoxy)-11-oxo-6,7-dihydrodipyrido[5,3-b:1',3'-e][1,4]oxazepine-10-carboxylic acid

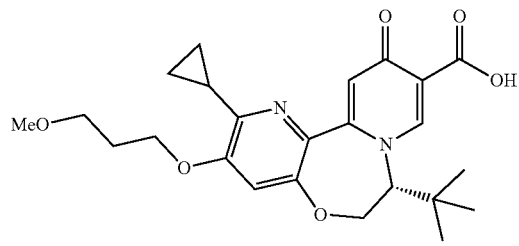 [SMILES: COCCCOc1cc2c(nc1C1CC1)-c1cc(=O)c(C(=O)O)cn1[C@H](C(C)(C)C)CO2]

To a mixture of ethyl (7R)-7-tert-butyl-2-cyclopropyl-3-(3-methoxypropoxy)-11-oxo-6,7-dihydrodipyrido[5,3-b:1',3'-e][1,4]oxazepine-10-carboxylate (150 mg, 0.32 mmol) in THF (1 mL) and H2O (1 mL) was added lithium hydroxide monohydrate (67 mg, 1.6 mmol) in one portion under N2. The mixture was stirred at 20° C. for 16 hr. The reaction mixture was adjusted to pH 7 with aqueous sodium carbonate solution and extracted with 3×5 mL of EtOAc (3×5 mL). The mixture was dried over sodium sulfate, filtered and concentrated under reduced pressure. The residue was purified by reverse phase HPLC to afford the (7R)-7-tert-butyl-2-cyclopropyl-3-(3-methoxypropoxy)-11-oxo-6,7-dihydrodipyrido[5,3-b:1',3'-e][1,4]oxazepine-10-carboxylic acid as a yellow solid (37 mg, 26% yield, m/z: 443 [M+H]+ observed). 1H NMR (400 MHz, DMSO-d6) δ 8.61 (s, 1H), 7.81 (s, 1H), 7.02 (s, 1H), 4.94-4.87 (m, 2H), 4.55-4.52 (d, J=13.6 Hz, 1H), 4.18-4.15 (t, J=6.4 Hz, 2H), 3.65-3.62 (t, J=6 Hz, 2H), 3.26 (s, 3H), 2.43-2.40 (m, 1H), 2.05-1.98 (m, 2H), 1.04-0.86 (m, 13H).

The following example were prepared in a similar manner as (R)-7-(tert-butyl)-2-chloro-3-(3-methoxypropoxy)-11-oxo-6,7-dihydro-11H-dipyrido[1,2-d:2',3'-f][1,4]oxazepine-10-carboxylic acid from 6-chloro-2-iodo-5-(3-methoxypropoxy)pyridin-3-ol, tert-butyl 4-oxopyran-3-carboxylate and an appropriate amine.

Example 68: (R)-2-Chloro-7-isopropyl-3-(3-methoxypropoxy)-11-oxo-6,7-dihydro-11H-dipyrido[1,2-d:2',3'-f][1,4]oxazepine-10-carboxylic acid

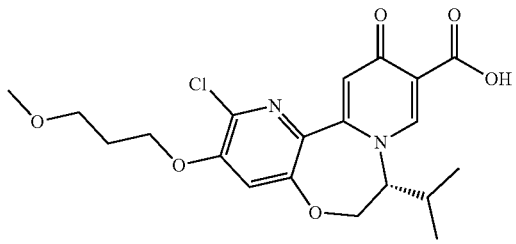 [SMILES: COCCCOc1cc2c(nc1Cl)-c1cc(=O)c(C(=O)O)cn1[C@H](C(C)C)CO2]

m/z: 423 [M+H]$^+$ observed. $^1$H NMR (400 MHz, DMSO-d$_6$): δ 8.78 (s, 1H), 7.51 (s, 1H), 7.32 (s, 1H), 4.90 (dd, J=11.8, 5.2 Hz, 1H), 4.79 (dd, J=11.1, 5.1 Hz, 1H), 4.67 (d, J=13.7 Hz, 1H), 4.24 (t, J=5.8 Hz, 2H), 3.49 (t, J=6.2 Hz, 2H), 3.26 (s, 3H), 2.04-1.96 (q, J=6.2 Hz, 2H), 1.94-1.84 (m, 1H), 1.07 (d, J=6.5 Hz, 3H), 0.75 (d, J=6.6 Hz, 3H).

Example 69: 2'-Chloro-3'-(3-methoxypropoxy)-1'-oxo-6'H,11'H-spiro[cyclohexane-1,7'-dipyrido[1,2-d:2',3'-f][1,4]oxazepine]-10'-carboxylic acid

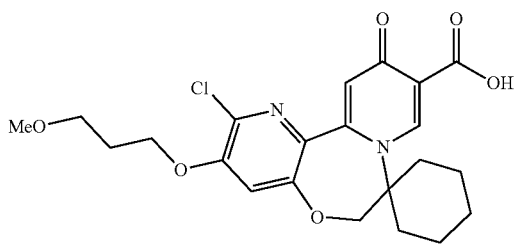

1-[1-(Hydroxymethyl)cyclohexyl]-4-oxo-pyridine-3-carboxylic acid

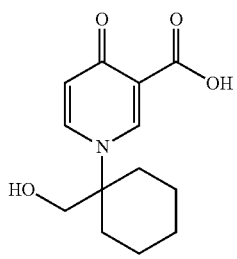

To a solution of of tert-butyl 4-oxopyran-3-carboxylate (1.67 g, 8.51 mmol) in EtOH (6 mL) and AcOH (4 mL) was added 1-amino-1-(hydroxyethyl)cyclohexane (1 g, 7.7 mmol). The mixture was stirred at 90° C. for 16 hr. The reaction mixture was concentrated under reduced pressure to give 1-[1-(hydroxy methyl)cyclohexyl]-4-oxo-pyridine-3-carboxylic acid as a white solid (1.1 g, 51% yield, m/z: 252 [M+H]$^+$ observed).

1-[1-(hydroxymethyl)cyclohexyl]-4-oxo-pyridine-3-carboxylate

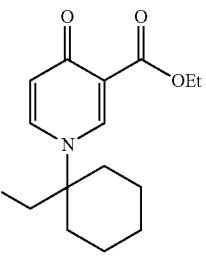

To a mixture of 1-[1-(hydroxymethyl)cyclohexyl]-4-oxo-pyridine-3-carboxylic acid (1 g, 4 mmol) of in EtOH (10 mL) was added sulfuric acid (5 mL, 94 mmol). The mixture was stirred at 60° C. for 5 hr. The reaction mixture was concentrated under reduced pressure. The residue was purified by reverse phase HPLC to afford 1-[1-(hydroxymethyl)cyclohexyl]-4-oxo-pyridine-3-carboxylate as a yellow oil (1.1 g, 99% yield, m/z: 280 [M+H]$^+$ observed).

Ethyl 1-[1-[[6-chloro-2-iodo-5-(3-methoxypropoxy)-3-pyridyl]oxymethyl]cyclohexyl]-4-oxo-pyridine-3-carboxylate

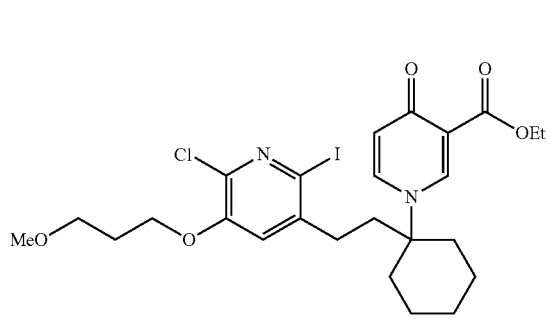

To a solution of 6-chloro-2-iodo-5-(3-methoxypropoxy)pyridin-3-ol (1 g, 2.9 mmol), ethyl 1-[1-(hydroxymethyl)cyclohexyl]-4-oxo-pyridine-3-carboxylate (988 mg, 3.53 mmol) and PPh$_3$ (1.73 g, 5.89 mmol) in THF (25 mL) was added a solution of diisopropyl azodicarboxylate (1.2 mL, 5.82 mmol) in THF (6 mL) dropwise at 25° C. under N$_2$. The reaction mixture was stirred at 45° C. for 20 h under N$_2$. The reaction mixture was concentrated under reduced pressure. The residue was purified by normal phase SiO$_2$ chromatography (0% to 10% MeOH/CH$_2$Cl$_2$) to afford ethyl 1-[1-[[6-chloro-2-iodo-5-(3-methoxypropoxy)-3-pyridyl]oxy methyl]cyclohexyl]-4-oxo-pyridine-3-carboxylate as a white solid (700 mg, 39% yield, m/z: 605 [M+H]$^+$ observed).

Ethyl 2-chloro-3-(3-methoxypropoxy)-11-oxo-spiro [6H-dipyrido[5,3-b:3',1'-d][1,4]oxazepine-7,1'-cyclohexane]-10-carboxylate

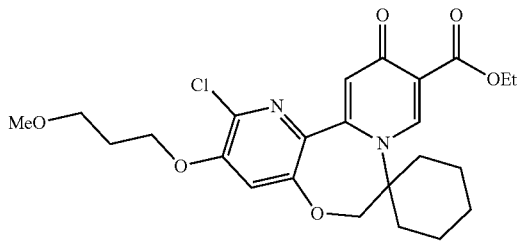 [SMILES: CCOC(=O)c1cn2c(cc1=O)-c1nc(Cl)c(OCCCOC)cc1OCC21CCCCC1]

To a mixture of ethyl 1-[1-[[6-chloro-2-iodo-5-(3-methoxypropoxy)-3-pyridyl]oxymethyl]cyclohexyl]-4-oxopyridine-3-carboxylate (950 mg, 1.6 mmol) and potassium acetate (308 mg, 3.14 mmol) in N,N-dimethylacetamide (25 mL) was added palladium(II) bromide (126 mg, 0.472 mmol) under $N_2$. The mixture was heated to 120° C. and stirred for 16 hours under $N_2$. The mixture was diluted with $H_2O$ (200 mL) and extracted with EtOAc (2×150 mL). The combined organic layers were concentrated under reduced pressure. The residue was purified by reverse phase HPLC to afford ethyl 2-chloro-3-(3-methoxypropoxy)-11-oxo-spiro[6H-dipyrido[5,3-b:3',1'-d][1,4]oxazepine-7,1'-cyclohexane]-10-carboxylate as a light yellow solid (140 mg, 19% yield, m/z: 477 [M+H]+ observed. 1H NMR (400 MHz, CDCl3) δ 8.51 (s, 1H), 7.53 (s, 1H), 6.75 (s, 1H), 4.40 (s, 1H), 4.36-4.31 (m, 2H), 4.10-4.07 (t, J=6.0 Hz, 2H), 3.54-3.51 (t, J=6.0 Hz, 2H), 3.30 (s, 3H), 2.09-2.05 (m, 2H), 1.93 (m, 2H), 1.86-1.80 (m, 5H), 1.75-1.56 (m, 4H), 1.33-1.31 (m, 3H).

2-Chloro-3-(3-methoxypropoxy)-11-oxo-spiro[6H-dipyrido[5,3-b:3',1'-d][1,4]oxazepine-7,1'-cyclohexane]-10-carboxylic acid

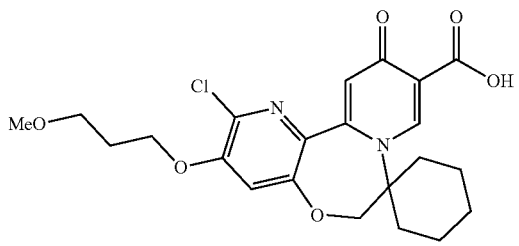

To a mixture of ethyl 2-chloro-3-(3-methoxypropoxy)-11-oxo-spiro[6H-dipyrido[5,3-b:3',1'-d][1,4]oxazepine-7,1'-cyclohexane]-10-carboxylate (140 mg, 0.29 mmol) in $H_2O$ (4 mL) and (4 mL) was added lithium hydroxide monohydrate (37 mg, 0.882 mmol). The mixture was stirred for 16 hours at 25° C. The mixture was acidized with 1 N hydrogen chloride solution until pH to 2 and extracted with EtOAc (2×10 mL). The combined organic layers were concentrated under reduced pressure. The residue was purified by reverse phase HPLC to afford 2-chloro-3-(3-methoxypropoxy)-11-oxo-spiro[6H-dipyrido[5,3-b:3',1'-d][1,4]oxaze pine-7,1'-cyclohexane]-10-carboxylic acid as a light solid (46 mg, 34% yield, m/z: 449 [M+H]+ observed). 1H NMR (400 MHz, DMSO-d6) δ 8.77 (s, 1H), 7.53 (s, 1H), 7.33 (s, 1H), 4.69 (s, 2H), 4.26-4.23 (t, J=6.0 Hz, 2H), 3.51-3.48 (t, J=6.0 Hz, 2H), 3.26 (s, 3H), 2.07-1.98 (m, 6H), 1.71 (m, 2H), 1.61-1.59 (m, 3H), 1.35 (m, 1H).

The following examples were prepared in a similar manner as 2-chloro-3-(3-methoxypropoxy)-11-oxo-spiro[6H-dipyrido[5,3-b:3',1'-d][1,4]oxazepine-7,1'-cyclohexane]-10-carboxylic acid from tert-butyl 4-oxopyran-3-carboxylate and an appropriate amino alcohol.

Example 70: 2'-Chloro-3'-(3-methoxypropoxy)-11'-oxo-6'H,11'H-spiro[cyclopentane-1,7'-dipyrido[1,2-d:2',3'-f][1,4]oxazepine]-10'-carboxylic acid

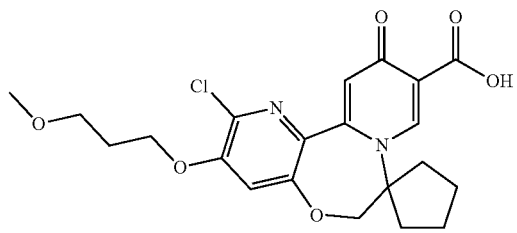 [SMILES: COCCCOc1cc2c(nc1Cl)-c1cc(=O)c(C(=O)O)cn1C1(CCCC1)CO2]

m/z: 435 [M+H]+ observed. 1H NMR (400 MHz, DMSO-d6): δ 8.63 (s, 1H), 7.41 (s, 1H), 7.22 (s, 1H), 4.65 (s, 2H), 4.25 (t, J=8.0 Hz, 2H), 3.50 (t, J=8.0 Hz, 2H), 3.26 (s, 3H), 2.15 (m, 2H), 2.01 (m, 4H), 1.69 (m, 4H).

Example 71: 2-Chloro-3-(3-methoxypropoxy)-1-oxo-6H,11H-spiro[dipyrido[1,2-d:2',3'-f][1,4]oxazepine-7,3'-oxetane]-10-carboxylic acid

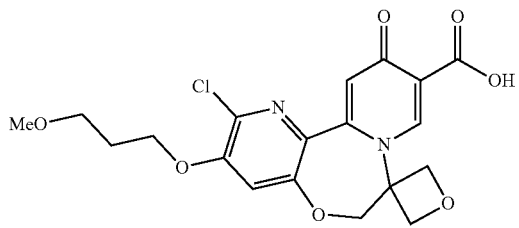 [SMILES: COCCCOc1cc2c(nc1Cl)-c1cc(=O)c(C(=O)O)cn1C1(COC1)CO2]

m/z: 423 [M+H]+ observed. 1H NMR (400 MHz, DMSO-d6): δ 8.67 (s, 1H), 7.54 (s, 1H), 6.88 (s, 1H), 5.11 (m, 2H), 4.79 (s, 2H), 4.27-4.22 (m, 4H), 3.49-3.46 (t, J=6.4 Hz, 2H), 3.24 (s, 3H), 2.03-1.97 (m, 2H).

Example 72: 2'-Chloro-3'-(3-methoxypropoxy)-3,3-dimethyl-11'-oxo-6'H,11'H-spiro[cyclobutane-1,7'-dipyrido[1,2-d:2',3'-f][1,4]oxazepine]-10'-carboxylic acid

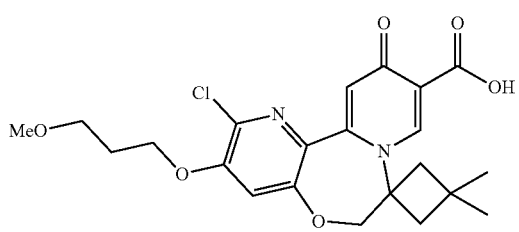 [SMILES: COCCCOc1cc2c(nc1Cl)-c1cc(=O)c(C(=O)O)cn1C1(CO2)CC(C)(C)C1]

m/z: 449 [M+H]+ observed. ¹H NMR (400 MHz, CDCl₃): δ 15.90 (s, 1H), 8.65 (s, 1H), 7.17 (s, 1H), 7.02 (s, 1H), 4.63 (s, 2H), 4.23-4.20 (t, J=6 Hz, 2H), 3.62 (t, J=6 Hz, 2H), 3.39 (s, 3H), 2.38-2.14 (m, 4H), 2.06-2.02 (m, 2H), 1.19 (s, 3H), 1.09 (s, 3H).

Example 73: 2'-Chloro-3'-(3-methoxypropoxy)-3-methyl-11'-oxo-6'H,11'H-spiro[cyclobutane-1,7'-dipyrido[1,2-d:2',3'-f][1,4]oxazepine]-10'-carboxylic acid

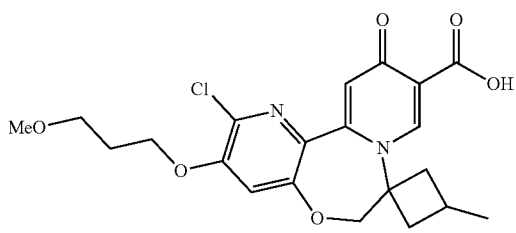 [SMILES: COCCCOc1cc2c(nc1Cl)-c1cc(=O)c(C(=O)O)cn1C1(CO2)CC(C)C1]

m/z: 435 [M+H]+ observed. ¹H NMR (mixture of cis/trans, 400 MHz, DMSO-d₆): δ 8.73 (s, 0.5H), 8.50 (s, 0.5H), 7.52-7.48 (m, 1H), 6.94-6.91 (m, 1H), 4.83-4.78 (m, 2H), 4.27-4.23 (m, 2H), 3.26 (s, 3H), 2.20 (m, 2H), 2.05-1.98 (m, 2H), 1.82-1.80 (m, 1H), 1.30-1.25 (m, 2H), 1.38-1.23 (m, 1H), 1.05-0.96 (m, 3H), 0.89-0.85 (m, 1H).

Example 74: 2-Chloro-3-(3-methoxypropoxy)-11-oxo-2',3',5',6'-tetrahydro-6H,11H-spiro[dipyrido[1,2-d:2',3'-f][1,4]oxazepine-7,4'-thiopyran]-10-carboxylic acid

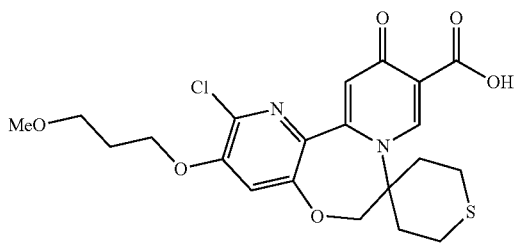

m/z: 467 [M+H]+ observed. ¹H NMR (400 MHz, DMSO-d₆): δ 8.73 (s, 1H), 7.58 (s, 1H), 7.33 (s, 1H), 4.78 (s, 2H), 4.27-4.24 (t, J=6 Hz, 2H), 3.52-3.49 (t, J=6 Hz, 2H), 3.26 (s, 3H), 3.08-3.02 (t, J=13.2 Hz, 2H), 2.77-2.73 (d, J=14.4, 2H), 2.37 (s, 2H), 2.33-2.30 (d, J=13.2 Hz, 2H), 2.05-2.00 (7, J=6 Hz, 2H).

Example 75: (R)-2-Chloro-7-isopropyl-3-methoxy-11-oxo-6,7-dihydro-11H-dipyrido[1,2-d:2',3'-f][1,4]oxazepine-10-carboxylic acid

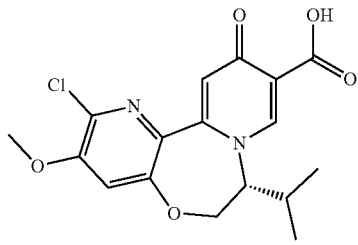 [SMILES: COc1cc2c(nc1Cl)-c1cc(=O)c(C(=O)O)cn1[C@H](C(C)C)CO2]

m/z: 365 [M+H]+ observed. ¹H NMR (400 MHz, DMSO-d₆): δ 8.78 (s, 1H), 7.52 (s, 1H), 7.32 (s, 1H), 4.91 (dd, J=12.0, 4.0 Hz, 1H), 4.85 (m, 1H), 4.69 (d, J=16.0 Hz, 1H), 3.97 (s, 3H), 1.85 (m, 1H), 1.15 (d, J=8.0 Hz, 3H), 0.75 (d, J=8.0 Hz, 3H).

Example 76: (R)-2-Cyclopropyl-3-isobutoxy-7-isopropyl-11-oxo-6,7-dihydro-11H-dipyrido[1,2-d:2',3'-f][1,4]oxazepine-10-carboxylic acid

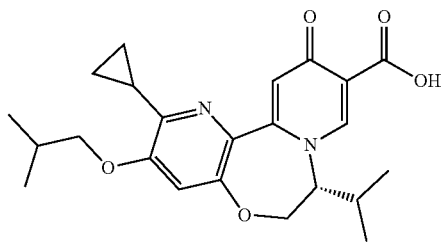 [SMILES: CC(C)COc1cc2c(nc1C1CC1)-c1cc(=O)c(C(=O)O)cn1[C@H](C(C)C)CO2]

m/z: 413 [M+H]+ observed. ¹H NMR (400 MHz, CDCl₃): δ 8.48-8.43 (m, 1H), 8.28-8.22 (m, 1H), 6.96 (s, 1H), 4.89 (d, J=12.3 Hz, 1H), 4.63 (d, J=13.4 Hz, 1H), 3.98 (d, J=9.3 Hz, 1H), 3.81-3.67 (m, 2H), 2.47 (s, 1H), 2.09 (s, 2H), 1.15-1.14 (m, 5H), 1.08-1.05 (m, 8H), 0.91 (d, J=6.6 Hz, 3H).

Example 77: (R)-3-(Benzyloxy)-2-chloro-7-isopropyl-11-oxo-6,7-dihydro-11H-dipyrido[1,2-d:2',3'-f][1,4]oxazepine-10-carboxylic acid

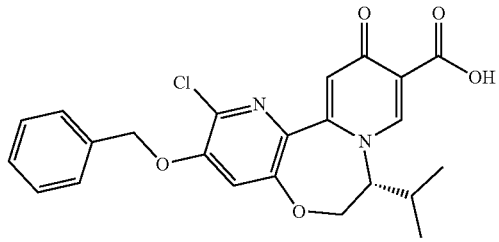 [SMILES: CC(C)[C@@H]1COc2cc(OCc3ccccc3)c(Cl)nc2-c2cc(=O)c(C(=O)O)cn21]

m/z: 441 [M+H]+ observed. ¹H NMR (400 MHz, CDCl₃): δ 8.51 (s, 1H), 8.27 (s, 1H), 7.53-7.34 (m, 5H), 6.99 (s, 1H), 5.13-5.03 (m, 2H), 4.95 (s, 1H), 4.78-4.59 (m, 2H), 4.07 (dd, J=11.3, 5.2 Hz, 1H), 2.03 (dd, J=12.0, 6.1 Hz, 1H), 1.15 (d, J=6.5 Hz, 3H), 0.94 (d, J=6.6 Hz, 3H).

Example 78: (R)-2-Chloro-3-hydroxy-7-isopropyl-11-oxo-6,7-dihydro-11H-dipyrido[1,2-d:2',3'-f][1,4]oxazepine-10-carboxylic acid

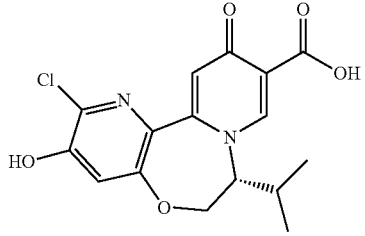 [SMILES: CC(C)[C@@H]1COc2cc(O)c(Cl)nc2-c2cc(=O)c(C(=O)O)cn21]

m/z: 351 [M+H]+ observed. ¹H NMR (400 MHz, CDCl₃): δ 8.48 (s, 1H), 8.14 (s, 1H), 7.03 (s, 1H), 5.04 (dd, J=13.4, 5.2 Hz, 1H), 4.77 (d, J=13.4 Hz, 1H), 4.04 (dd, J=11.2, 5.1 Hz, 1H), 2.06 (dt, J=11.8, 6.4 Hz, 1H), 1.17 (d, J=6.5 Hz, 3H), 0.95 (d, J=6.6 Hz, 3H).

Example 79: (R)-2-Chloro-3-isobutoxy-7-isopropyl-11-oxo-6,7-dihydro-11H-dipyrido[1,2-d:2',3'-f][1,4]oxazepine-10-carboxylic acid

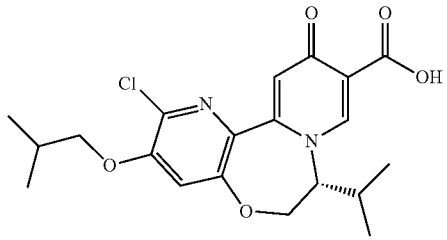 [SMILES: CC(C)COc1cc2c(nc1Cl)-c1cc(=O)c(C(=O)O)cn1[C@H](C(C)C)CO2]

m/z: 407 [M+H]+ observed. ¹H NMR (400 MHz, CDCl₃): δ 8.44 (s, 1H), 8.24 (s, 1H), 6.99 (s, 1H), 4.92 (m, 1H), 4.68 (d, J=13.3 Hz, 1H), 3.94 (m, 1H), 3.79 (ddd, J=27.2, 8.5, 6.5 Hz, 2H), 2.28-2.08 (m, 1H), 2.02-2.01 (m, 1H), 1.16 (d, J=6.6 Hz, 3H), 1.07 (dd, J=6.7, 1.8 Hz, 6H), 0.95 (d, J=6.6 Hz, 3H).

Example 80: (R)-2-Chloro-7-(2-hydroxyethyl)-3-(3-methoxypropoxy)-11-oxo-6,7-dihydro-11H-dipyrido[1,2-d:2',3'-f][1,4]oxazepine-10-carboxylic acid

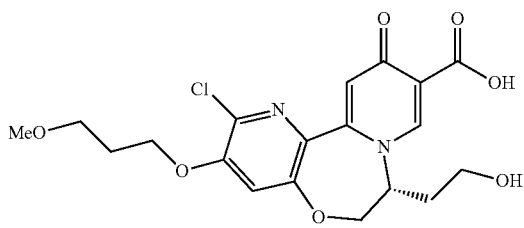 [SMILES: COCCCOc1cc2c(nc1Cl)-c1cc(=O)c(C(=O)O)cn1[C@H](CCO)CO2]

m/z: 425 [M+H]+ observed. ¹H NMR (400 MHz, DMSO-d₆): δ 16.51 (s, 1H), 8.67 (s, 1H), 7.47 (s, 1H), 7.33 (s, 1H), 5.15-5.13 (m, 1H), 4.77-4.75 (m, 2H), 4.65 (d, J=13.6 Hz, 1H), 4.23 (t, J=12.0 Hz, 2H), 3.50-3.47 (m, 3H), 3.25 (s, 3H), 2.03-1.98 (m, 2H), 1.93-1.88 (m, 1H), 1.79-1.73 (m, 2H).

Example 81: 6-Chloro-7-(3-methoxypropoxy)-12,12-dimethyl-3-oxo-9a,11,12,12a-tetrahydro-3H,10H-cyclopenta[b]dipyrido[1,2-d:2',3'-f][1,4]oxazepine-2-carboxylic acid

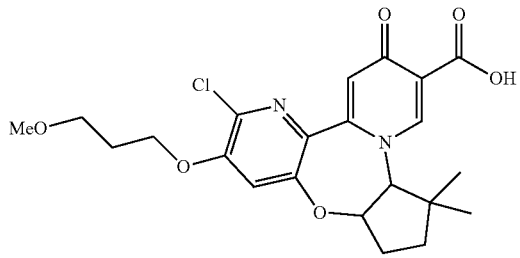 [SMILES: COCCCOc1cc2c(nc1Cl)-c1cc(=O)c(C(=O)O)cn1C1C(CCC1(C)C)O2]

5-((6-Chloro-2-iodo-5-(3-methoxypropoxy)pyridin-3-yl)oxy)-2,2-dimethylcyclopentan-1-one

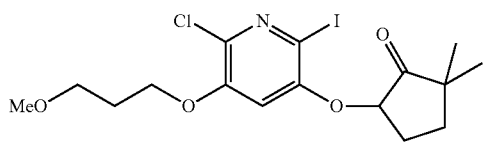 [SMILES: COCCCOc1cc(OC2CCC(C)(C)C2=O)c(I)nc1Cl]

To a mixture of 6-chloro-2-iodo-5-(3-methoxypropoxy) pyridin-3-ol (7 g, 20 mmol) and 5-bromo-2,2-dimethyl-cyclopentanone (4.2 g, 22 mmol in acetone (100 mL) was added potassium carbonate (5.7 g, 41 mmol) and sodium iodide (1.5 g, 10 mmol) in one portion under N₂. The mixture was stirred at 60° C. for 16 hours. The mixture was diluted with water (100 mL) and the aqueous phase was extracted with ethyl acetate (2×100 mL). The combined organic phase was washed with sat. aqueous brine solution (100 mL), dried with anhydrous sodium sulfate, filtered and concentrated in vacuum. The residue was purified by normal phase SiO₂ chromatography (10% to 40% EtOAc/petroleum ether) to afford 5-((6-chloro-2-iodo-5-(3-methoxypropoxy) pyridin-3-yl)oxy)-2,2-dimethylcyclopentan-1-one as a yellow solid (6.8 g, 74% yield, m/z: 454 [M+H]+ observed).

5-[[6-Chloro-2-iodo-5-(3-methoxypropoxy)-3-pyridyl]oxy]-2,2-dimethyl-cyclopentanamine

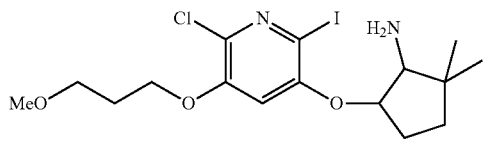 [SMILES: COCCCOc1cc(OC2CCC(C)(C)C2N)c(I)nc1Cl]

To a mixture of 5-((6-chloro-2-iodo-5-(3-methoxy-propoxy)pyridin-3-yl)oxy)-2,2-dimethylcyclopentan-1-one (6.8 g, 15 mmol) in EtOH (80 mL) was added ammonium acetate (17.3 g, 224 mmol) and sodium cyanoborohydride (1.9 g, 30 mmol) in one portion under N₂. The mixture was stirred at 90° C. for 16 hours. The mixture was diluted with H₂O (10 mL) and the pH was adjusted to 10-11 by the addition of 1 M sodium hydroxide solution. The residue was extracted with CH₂Cl₂ (3×50 mL). The combined organic phase was washed with sat. aqueous brine solution (15 mL), dried over anhydrous sodium sulfate, filtered and concentrated under vacuum. The residue was purified by normal phase SiO$_2$ chromatography (10% to 100% EtOAc/petroleum ether) to afford 5-[[6-chloro-2-iodo-5-(3-methoxypropoxy)-3-pyridyl]oxy]-2,2-dimethyl-cyclopentanamine as a yellow oil (3.7 g, 54% yield, m/z: 455 [M+H]$^+$ observed).

Ethyl 1-(5-((6-chloro-2-iodo-5-(3-methoxypropoxy) pyridin-3-yl)oxy)-2,2-dimethylcyclopentyl)-4-oxo-1, 4-dihydropyridine-3-carboxylate

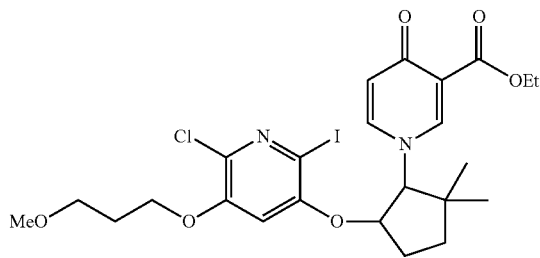 [SMILES: CCOC(=O)c1cn(C2C(Oc3cc(OCCCOC)c(Cl)nc3I)CCC2(C)C)ccc1=O]

A mixture of 5-[[6-chloro-2-iodo-5-(3-methoxypropoxy)-3-pyridyl]oxy]-2,2-dimethyl-cyclopentanamine (6.4 g, 15 mmol) and tert-butyl 4-oxopyran-3-carboxylate (3.52 g, 18 mmol) in EtOH (25 mL) and AcOH (25 mL) was stirred at 100° C. for 16 hours. The mixture was concentrated in vacuum to afford 1-[5-[[6-chloro-2-iodo-5-(3-methoxypropoxy)-3-pyridyl]oxy]-2,2-dimethyl-cyclopentyl]-4-oxo-pyridine-3-carboxylic acid as a yellow solid that was used in the next step without further purification (4.2 g, 62%).

To a mixture of 1-[5-[[6-chloro-2-iodo-5-(3-methoxypropoxy)-3-pyridyl]oxy]-2,2-dimethyl-cyclopentyl]-4-oxo-pyridine-3-carboxylic acid (4.2 g, 7.3 mmol) in EtOH (100 mL) was added thionyl chloride (2.7 mL, 36.5 mmol) over 5 min under N$_2$. The mixture was stirred at 60° C. for 16 hours. The mixture was concentrated in vacuum. The residue was purified by normal phase SiO$_2$ chromatography (10% to 100% EtOAc/petroleum ether) to afford ethyl 1-[5-[[6-chloro-2-iodo-5-(3-methoxypropoxy)-3-pyridyl]oxy]-2,2-dimethyl-cyclopentyl]-4-oxo-pyridine-3-carboxylate as a yellow oil (3.0 g, 68% yield, m/z: 605 [M+H]$^+$ observed). $^1$H NMR (mixture of rotamers, 400 MHz, CDCl$_3$) δ 8.33-8.32 (m, 1H), 7.80-7.77 (m, 1H), 6.74 (m, 1H), 6.40-6.38 (m, 1H), 5.31 (m, 1H), 4.32-4.27 (m, 2H), 4.11-4.08 (m, 2H), 3.93 (m, 1H), 3.56-3.53 (m, 2H), 3.33 (s, 3H), 2.07-1.94 (m, 6H), 1.33-1.31 (m, 3H), 1.29-1.22 (m, 6H).

Ethyl 19-chloro-15-(3-methoxypropoxy)-23,23-dimethyl-13-oxo-28-oxa-24,25-diazatetracyclooctadeca-4(16),5(14),6(17),15(19),18(24)-pentaene-17-carboxylate

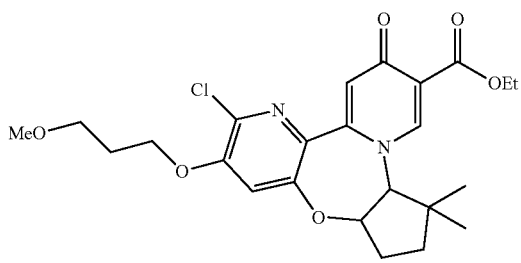

To a mixture of ethyl 1-[5-[[6-chloro-2-iodo-5-(3-methoxypropoxy)-3-pyridyl]oxy]-2,2-dimethyl-cyclopentyl]-4-oxo-pyridine-3-carboxylate (3 g, 4.96 mmol) in N,N-dimethylacetamide (50 mL) was added potassium acetate (0.975 g, 9.93 mmol) and palladium(II) bromide (660 mg, 2.5 mmol) under N$_2$. The mixture was stirred at 120° C. for 16 hours. The mixture was filtered and the residue was diluted with H$_2$O (20 mL). The aqueous phase was extracted with ethyl acetate (2×20 mL). The combined organic phase was washed with sat. aqueous brine solution (10 mL), dried with anhydrous sodium sulfate, filtered and concentrated in vacuum. The residue was purified by reverse phase HPLC to afford ethyl 19-chloro-15-(3-methoxypropoxy)-23,23-dimethyl-13-oxo-28-oxa-24,25-diazatetracyclooctadeca-4(16),5(14),6(17), 15(19),18(24)-pentaene-17-carboxylate as a yellow solid (0.5 g, 21% yield, m/z: 477 [M+H]$^+$ observed).

6-Chloro-7-(3-methoxypropoxy)-12,12-dimethyl-3-oxo-9a,11,12,12a-tetrahydro-3H, 1 OH-cyclopenta [b]dipyrido[1,2-d:2',3'-f][1,4]oxazepine-2-carboxylic acid

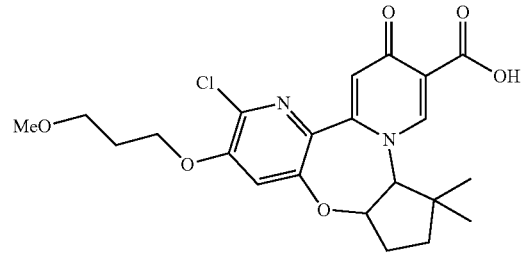 [SMILES: COCCCOc1cc2c(nc1Cl)-c1cc(=O)c(C(=O)O)cn1C1C(CCC1(C)C)O2]

To a mixture of ethyl 19-chloro-15-(3-methoxypropoxy)-23,23-dimethyl-13-oxo-28-oxa-24,25-diazatetracycloocta-deca-4(16),5(14),6(17),15(19),18(24)-pentaene-17-carboxylate (50 mg, 0.105 mmol) in H$_2$O (1 mL) and THF (1 mL) was added lithium hydroxide monohydrate (13 mg, 0.314 mmol) in one portion at 25° C. under N$_2$. The mixture was stirred at 25° C. for 1 hr. The mixture was diluted 1 M hydrogen chloride solution to pH 4 and the aqueous phase was extracted with EtOAc (2×20 mL). The combined organic phase was washed with sat. aqueous brine solution (10 mL), dried with anhydrous sodium sulfate, filtered and concentrated in vacuum. The residue was purified by reverse phase HPLC to afford 6-chloro-7-(3-methoxypropoxy)-12,12-dimethyl-3-oxo-9a, 11,12,12a-tetrahydro-3H, 1 OH-cyclopenta[b]dipyrido[1,2-d:2',3'-f][1,4]oxazepine-2-carboxylic acid as a yellow solid (11 mg, 23% yield, m/z: 449 [M+H]$^+$ observed). $^1$H NMR (400 MHz, DMSO-d$_6$) δ 15.99 (s, 1H), 8.80 (s, 1H), 7.55 (s, 1H), 6.99 (s, 1H), 5.46-5.40 (m, 1H), 4.99-4.97 (d, J=9.2 Hz, 1H), 4.33-4.29 (m, 1H), 4.24-4.22 (m, 1H), 3.52-3.49 (t, J=6 Hz, 2H), 3.26 (s, 3H), 2.16-2.00 (m, 4H), 1.35-1.28 (m, 1H), 1.12-1.05 (m, 1H), 1.02 (s, 3H), 0.33 (s, 3H).

Example 82: 6-Chloro-7-(3-methoxypropoxy)-12,12-dimethyl-3-oxo-9a,11,12,12a-tetrahydro-3H,10H-cyclopenta[b]dipyrido[1,2-d:2',3'-f][1,4]oxazepine-2-carboxylic acid (Single Enantiomer I)

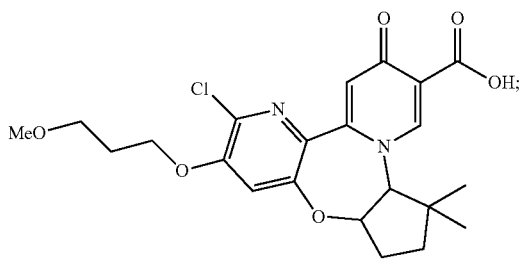 [SMILES: COCCCOc1cc2c(nc1Cl)-c1cc(=O)c(C(=O)O)cn1C1C(CCC1(C)C)O2]

Example 83: 6-Chloro-7-(3-methoxypropoxy)-12,12-dimethyl-3-oxo-9a,11,12,12a-tetrahydro-3H,10H-cyclopenta[b]dipyrido[1,2-d:2',3'-f][1,4]oxazepine-2-carboxylic acid (Single Enantiomer II)

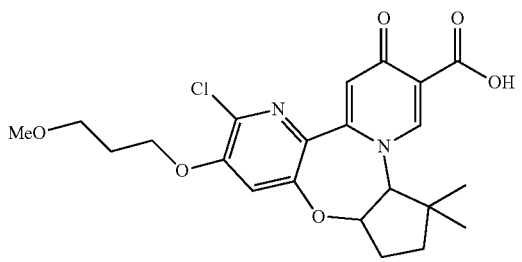 [SMILES: COCCCOc1cc2c(nc1Cl)-c1cc(=O)c(C(=O)O)cn1C1C(CCC1(C)C)O2]

150 mg of the mixture of enantiomers was separated by SFC (supercritical fluid chromatography) on an OD-3 column using 30% MeOH (0.05% diethylamine as a modifier) to give 6-chloro-7-(3-methoxypropoxy)-12,12-dimethyl-3-oxo-9a, 11,12,12a-tetrahydro-3H, 10H-cyclopenta[b]dipyrido[1,2-d:2',3'-f][1,4]oxazepine-2-carboxylic acid (single enantiomer I) as a white solid (faster eluting enantiomer, 36 mg, 24%, m/z: 449 [M+H]$^+$ observed) and 6-chloro-7-(3-methoxypropoxy)-12,12-dimethyl-3-oxo-9a, 11,12,12a-tetrahydro-3H, 10H-cyclopenta[b]dipyrido[1,2-d:2',3'-f][1,4]oxazepine-2-carboxylic acid (single enantiomer II) as a white solid (slower eluting enantiomer, 33 mg, 22%, m/z: 449[M+H]$^+$ observed).

Example 82: 6-Chloro-7-(3-methoxypropoxy)-12,12-dimethyl-3-oxo-9a,11,12,12a-tetrahydro-3H,10H-cyclopenta[b]dipyrido[1,2-d:2',3'-f][1,4]oxazepine-2-carboxylic acid (single enantiomer I). m/z: 449 [M+H]$^+$ observed). $^1$H NMR (400 MHz, DMSO-d$_6$) δ 15.99 (s, 1H), 8.80 (s, 1H), 7.55 (s, 1H), 6.99 (s, 1H), 5.46-5.40 (m, 1H), 4.99-4.97 (d, J=9.2 Hz, 1H), 4.33-4.29 (m, 1H), 4.24-4.22 (m, 1H), 3.52-3.49 (t, J=6 Hz, 2H), 3.26 (s, 3H), 2.16-2.00 (m, 4H), 1.35-1.28 (m, 1H), 1.12-1.05 (m, 1H), 1.02 (s, 3H), 0.33 (s, 3H).

Example 83: 6-Chloro-7-(3-methoxypropoxy)-12,12-dimethyl-3-oxo-9a,11,12,12a-tetrahydro-3H,10H-cyclopenta[b]dipyrido[1,2-d:2',3'-f][1,4]oxazepine-2-carboxylic acid (single enantiomer II). m/z: 449 [M+H]$^+$ observed). $^1$H NMR (400 MHz, DMSO-d$_6$) δ 15.99 (s, 1H), 8.80 (s, 1H), 7.55 (s, 1H), 6.99 (s, 1H), 5.46-5.40 (m, 1H), 4.99-4.97 (d, J=9.2 Hz, 1H), 4.33-4.29 (m, 1H), 4.24-4.22 (m, 1H), 3.52-3.49 (t, J=6 Hz, 2H), 3.26 (s, 3H), 2.16-2.00 (m, 4H), 1.35-1.28 (m, 1H), 1.12-1.05 (m, 1H), 1.02 (s, 3H), 0.33 (s, 3H).

Example 84: 5-Isopropyl-9-oxo-4,9-dihydro-5H-thieno[3,2-a]quinolizine-8-carboxylic acid

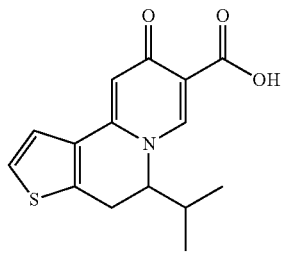 [SMILES: CC(C)C1Cc2sccc2-c2cc(=O)c(C(=O)O)cn21]

6-Isopropyl-6,7-dihydrothieno[3,2-c]pyridine

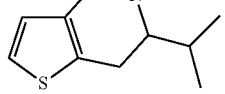

A solution of 2-(thiophen-3-yl)-1,3-dioxolane (0.97 g, 6.2 mmol) in anhydrous THF (5 mL) was cooled to −78° C. (dry ice/acetone bath), followed by the drop-wise addition of n-BuLi (2.5 M in THF, 2.7 mL, 6.8 mmol). The mixture was stirred at −78° C. for 2 h. Tert-butyl 4-isopropyl-1,2,3-oxathiazolidine-3-carboxylate 2,2-dioxide (prepared according to the procedure by Guo, et al., 2010, J. Org. Chem. 75:937) (1.5 g, 5.7 mmol) in THF (7 mL) was added drop-wise at −78° C. and the resulting mixture was slowly warmed up to rt and stirred for 16 h. The reaction mixture was concentrated under vacuum. The residue was diluted with HCl (4N in 1,4-dioxane, 20 mL), H$_2$O (2 mL) at rt and stirred for 1 h. The reaction mixture was diluted with CH$_2$Cl$_2$ (30 mL) and basified with 1M aqueous Na$_2$CO$_3$ solution (10 mL). The reaction mixture was extracted with CH$_2$Cl$_2$ (2×20 mL), washed with H$_2$O (15 mL) and sat. aqueous brine solution (10 mL), dried over sodium sulfate, filtered and concentrated under vacuum. The residue was purified by normal phase SiO$_2$ chromatography (20% to 80% EtOAc/hexanes) to afford 6-isopropyl-6,7-dihydrothieno[3,2-c]pyridine as a colorless oil (300 mg, 27% yield, m/z: 180 [M+H]$^+$ observed). $^1$H NMR (400 MHz, CDCl$_3$) δ 8.33-8.32 (d, J=3.2 Hz, 1H), 7.10-7.08 (d, J=6.0 Hz, 1H), 7.03-7.02 (d, J=5.2 Hz, 1H), 3.46-3.40 (m, 1H), 2.91-2.86 (dd, J=16.8, 6.8 Hz, 1H), 2.73-2.65 (t, J=16.0 Hz, 1H), 2.14-2.09 (m, 1H), 1.09-1.07 (d, J=6.8 Hz, 3H), 1.06-1.04 (d, J=6.8 Hz, 3H).

Ethyl 5-isopropyl-9-oxo-4,9,10, a-tetrahydro-5H-thieno[3,2-a]quinolizine-8-carboxylate

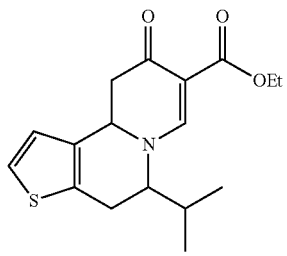 [SMILES: CCOC(=O)C1=CN2C(CC1=O)c1ccsc1CC2C(C)C]

To a solution of 6-isopropyl-6,7-dihydrothieno[3,2-c]pyridine (380 mg, 2.12 mmol) in ethanol (20 mL) was added ethyl (2E)-2-acetyl-3-ethoxy-2-propenoate (1.18 g, 6.36 mmol) and the reaction mixture was stirred at 100° C. for 16 h. The reaction mixture was concentrated under vacuum. The residue was purified by normal phase SiO$_2$ chromatography (0% to 5% MeOH/CH$_2$Cl$_2$) to afford ethyl 5-isopropyl-9-oxo-4,9,10,10a-tetrahydro-5H-thieno[3,2-a]quinolizine-8-carboxylate as a light brown syrup (250 mg, 37% yield, m/z: 320 [M+H]$^+$ observed). $^1$H NMR (400 MHz, CDCl$_3$): 8.28 (s, 1H), 7.20-7.19 (d, J=5.2 Hz, 1H), 6.79-6.78 (d, J=5.2 Hz, 1H), 4.74-4.70 (dd, J=3.2, 15.6 Hz, 1H), 4.29-4.24 (q, J=6.8 Hz, 2H), 3.55-3.50 (m, 1H), 3.22-3.18 (m, 2H), 2.85-2.80 (dd, J=4.4, 15.6 Hz, 1H), 2.58-2.50 (m, 1H), 1.88-1.82 (m, 1H), 1.35-1.31 (t, J=7.2 Hz, 3H), 0.97-0.95 (d, J=6.8 Hz, 3H), 0.92-0.90 (d, J=6.8 Hz, 3H).

Ethyl 5-isopropyl-9-oxo-4,9-dihydro-SH-thieno[3,2-a]quinolizine-8-carboxylate

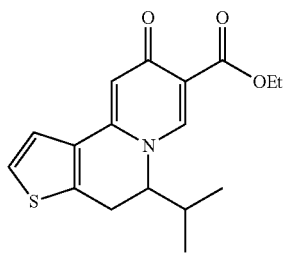 [SMILES: CCOC(=O)c1cn2c(cc1=O)-c1ccsc1CC2C(C)C]

To a stirred solution of ethyl 5-isopropyl-9-oxo-4,9,10,10a-tetrahydro-5H-thieno[3,2-a]quinolizine-8-carboxylate (250 mg, 0.783 mmol) in 1,2-dimethoxyethane (10 mL) was added p-chloranil (193 mg, 0.783 mmol). The reaction mixture was stirred at 100° C. for 2 h. The reaction mixture was cooled to rt and resulting precipitate was filtered and washed with EtOAc (2×25 mL). The filtrate was washed with H$_2$O (10 mL) and sat. aqueous brine solution (10 mL). The organic layer was dried over sodium sulfate, filtered and concentrated under vacuum. The residue was purified by normal phase SiO$_2$ chromatography (0% to 5% MeOH/CH$_2$Cl$_2$) to afford ethyl 5-isopropyl-9-oxo-4,9-dihydro-5H-thieno[3,2-a]quinolizine-8-carboxylate as a brown syrup (180 mg, 73% yield, m/z: 318 [M+H]$^+$ observed). $^1$H NMR (400 MHz, DMSO-D6): δ 8.38 (s, 1H), 7.54-7.53 (d, J=5.2 Hz, 1H), 7.49-7.48 (d, J=5.2 Hz, 1H), 6.66 (s, 1H), 4.21-4.15 (q, J=6.4 Hz, 2H), 3.40-3.34 (m, 3H), 1.88-1.84 (m, 1H), 1.22-1.20 (t, J=4.0 Hz, 3H), 0.85-0.84 (d, J=6.8 Hz, 3H), 0.69-0.68 (d, J=6.8 Hz, 3H).

5-Isopropyl-9-oxo-4,9-dihydro-5H-thieno[3,2-a]quinolizine-8-carboxylic acid

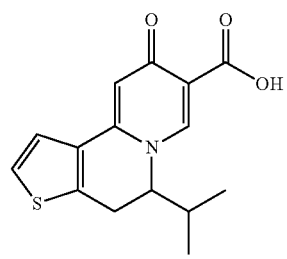 [SMILES: CC(C)C1Cc2sccc2-c2cc(=O)c(C(=O)O)cn21]

To a solution of ethyl 5-isopropyl-9-oxo-4,9-dihydro-5H-thieno[3,2-a]quinolizine-8-carboxylate carboxylate (180 mg, 0.56 mmol) in 1,4-dioxane (2 mL) was added 10% aqueous NaOH solution (1.5 mL) at rt and stirred for 2 hours. The reaction mixture was cooled to 0° C., acidified with aqueous 2N HCl solution to pH 2 and stirred for 1 h at rt. The resulted solids were filtered, washed with H$_2$O (5 mL) and diethyl ether (5 mL) to give 5-isopropyl-9-oxo-4,9-dihydro-5H-thieno[3,2-a]quinolizine-8-carboxylic acid as a light brown solid (90 mg, 55% yield, m/z: 290 [M+H]$^+$ observed). $^1$H NMR (400 MHz, DMSO-d6): δ 8.82 (s, 1H), 7.67-7.66 (d, J=5.2 Hz, 1H), 7.56-7.55 (d, J=5.2 Hz, 1H), 7.18 (s, 1H), 4.61-4.58 (t, J=7.2 Hz, 1H), 3.47-3.43 (m, 2H), 1.82-1.76 (m, 1H), 0.87-0.85 (d, J=6.8 Hz, 3H), 0.67-0.66 (d, J=6.8 Hz, 3H).

Example 85: 2-Chloro-5-isopropyl-9-oxo-4,9-dihydro-5H-thieno[3,2-a]quinolizine-8-carboxylic acid

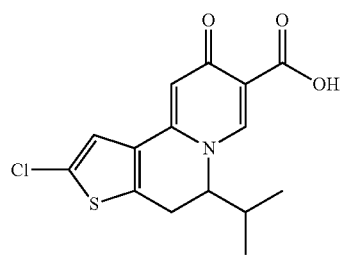 [SMILES: CC(C)C1Cc2sc(Cl)cc2-c2cc(=O)c(C(=O)O)cn21]

m/z: 324 [M+H]$^+$ observed. $^1$H NMR (300 MHz, DMSO-d6): δ 8.71 (s, 1H), 8.27 (s, 1H), 8.06 (s. 1H), 5.07 (m, 1H), 3.97 (m, 2H), 1.83 (m, 1H), 0.67 (d, J=6.8 Hz, 3H), 0.49 (d, J=6.8 Hz, 3H).

Example 86: 6-isopropyl-3-methoxy-10-oxo-5,10-dihydro-6H-pyrido[2,1-a][2,7]naphthyridine-9-carboxylic acid

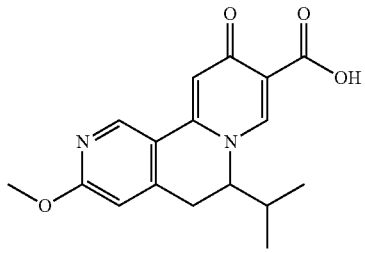 [SMILES: COc1cc2c(cn1)-c1cc(=O)c(C(=O)O)cn1C(C(C)C)C2]

Tert-butyl ((6-methoxy-4-methylpyridin-3-yl)methyl)carbamate

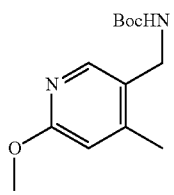 [SMILES: COc1cc(C)c(CNC(=O)OC(C)(C)C)cn1]

To a solution of (6-methoxy-4-methylpyridin-3-yl)methanamine (1 g, 6.6 mmol) in CH$_2$Cl$_2$ (10 mL) was added di-tert-butyl decarbonate (1.72 g, 7.88 mmol) and triethylamine (1.28 mL, 9.20 mmol) at 0° C. The mixture was warmed to rt and stirred for 12 h. H$_2$O (10 mL) was added to the mixture and extracted with CH$_2$Cl$_2$ (2×15 mL), washed with sat. aqueous brine solution (15 mL), dried over sodium sulfate, filtered and concentrated under vacuum. The residue was purified by normal phase SiO$_2$ chromatography (0% to 15% EtOAc/hexanes) to afford tert-butyl ((6-methoxy-4-methylpyridin-3-yl)methyl)carbamate as a white solid (1.3 g, 78% yield, m/z: 253 [M+H]$^+$ observed).

Tert-butyl ((4-(2-hydroxy-3-methylbutyl)-6-methoxypyridin-3-yl)methyl) carbamate

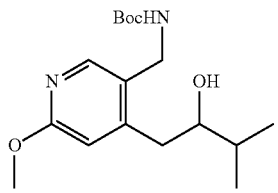 [SMILES: COc1cc(CC(O)C(C)C)c(CNC(=O)OC(C)(C)C)cn1]

To a solution of tert-butyl ((6-methoxy-4-methylpyridin-3-yl)methyl) (1.1 g, 4.36 mmol) in THF (10 mL) at −78° C. (dry ice/acetone bath) was added n-BuLi (2.5 M in hexanes, 5 mL, 12 mmol) and stirred for 1 hour at −78° C. Isovelaraldehyde (1.3 mL, 12 mmol) was added at −78° C. and the reaction mixture stirred for 30 min. The temperature was slowly raised to rt and stirred for 4 h. Sat. aqueous NH$_4$Cl solution (10 mL) was added to the reaction mixture at 0° C. The aqueous phase was extracted with EtOAc (2×15 mL) and washed with sat. aqueous brine solution (15 mL). The combined organic extracts were dried over sodium sulfate, filtered and concentrated under vacuum. The residue was purified by normal phase SiO$_2$ chromatography (0% to 30% EtOAc/hexanes) to afford tert-butyl ((4-(2-hydroxy-3-methylbutyl)-6-methoxypyridin-3-yl)methyl)carbamate as a white solid (0.8 g, 57% yield, m/z: 325 [M+H]$^+$ observed). $^1$H NMR (400 MHz, DMSO-d$_6$): δ 7.90 (s, 1H), 7.18 (m, 1H), 6.65 (s, 1H), 4.50-4.49 (d, J=6.0 Hz, 1H), 4.16-4.03 (m, 2H), 3.78 (s, 3H), 3.40-3.39 (m, 1H), 2.68-2.64 (m, 1H), 1.65-1.60 (m, 1H), 1.36 (s, 9H), 0.90-0.89 (d, J=2.4 Hz, 3H), 0.88-0.87 (d, J=2.4 Hz, 3H).

1-(5-(((tert-Butoxycarbonyl)amino)methyl)-2-methoxypyridin-4-yl)-3-methylbutan-2-yl methanesulfonate

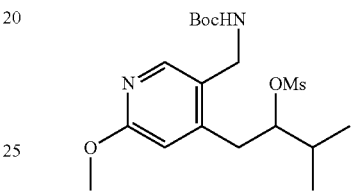

To a solution of t-butyl (4-(2-hydroxy-3-methylbutyl)-6-methoxypyridin-3-yl)methyl carbamate (0.2 g, 0.62 mmol) in CH$_2$Cl$_2$ (3 mL) was added trimethylamine (0.13 mL, 0.92 mmol) and methanesulfonyl chloride (0.07 mL, 0.92 mmol) at 0° C. The resultant mixture was stirred for 3 hours at 0° C. H$_2$O (5 mL) was added, extracted with EtOAc (2×15 mL), washed with sat. aqueous brine solution (10 mL), dried over sodium sulfate, filtered and concentrated under vacuum. The residue was purified by normal phase SiO$_2$ chromatography (0% to 30% EtOAc/hexanes) to afford 1-(5-(((tert-butoxycarbonyl)amino)methyl)-2-methoxypyridin-4-yl)-3-methylbutan-2-yl methanesulfonate as a pale yellow syrup (190 mg, 77% yield). $^1$H NMR (400 MHz, CDCl$_3$): δ 8.05 (s, 1H), 6.63 (s, 1H), 4.84-4.77 (m, 2H), 4.29-4.28 (d, J=5.2 Hz, 2H), 3.91 (s, 3H), 2.98-2.92 (m, 2H), 2.66 (s, 3H), 2.10-2.09 (m, 1H), 1.44 (s, 9H), 1.07-1.05 (d, J=7.2 Hz, 6H).

3-Isopropyl-6-methoxy-1,2,3,4-tetrahydro-2,7-naphthyridine

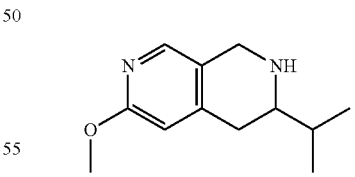

To a solution of 1-(5-(((tert-butoxycarbonyl)amino)methyl)-2-methoxypyridin-4-yl)-3-methylbutan-2-yl methanesulfonate (190 mg, 0.47 mmol) in dioxane (3 mL) was added 6N HCl (3 mL) at 0° C. The reaction mixture was warmed to rt and stirred for 3 h. Sat. aqueous NaHCO$_3$ solution (10 mL) was added to the mixture dropwise to adjust the pH to 8-9 and stirred for 2 h. The mixture was extracted with EtOAc (2×15 mL), washed with sat. aqueous brine solution (10 mL), dried over sodium sulfate, filtered and concentrated under vacuum. The residue was purified by normal phase SiO₂ chromatography (0% to 10% MeOH/ CH₂Cl₂) to afford 3-isopropyl-6-methoxy-1,2,3,4-tetrahydro-2,7-naphthyridine as a colorless oil (85 mg, 88% yield). ¹H NMR (400 MHz, DMSO-d₆): δ 7.82 (s, 1H), 6.51 (s, 1H), 3.91-3.87 (d, J=15.6 Hz, 1H), 3.73-3.71 (m, 5H), 2.65-2.61 (m, 1H), 2.41-2.38 (m, 1H), 1.63-1.58 (m, 1H), 0.94-0.83 (m, 6H).

3-Isopropyl-6-methoxy-3,4-dihydro-2,7-naphthyridine

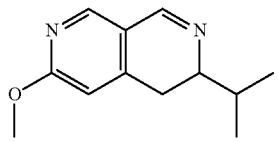

To a solution of 1,2,3,4-tetrahydro-3-isopropyl-6-methoxy-2,7-naphthyridine (80 mg, 0.39 mmol) in CH₂Cl₂ (2 mL) at 0° C. was added N-bromosuccinamide (140 mg, 0.77 mmol) and the reaction mixture stirred for 2 h. Sat. aqueous NaHCO₃ solution (3 mL) was added to mixture and extracted with EtOAc (2×10 mL). The combined organic layer was washed with sat. aqueous brine solution (10 mL), dried over sodium sulfate, filtered and concentrated under vacuum. The residue was purified by normal phase SiO₂ chromatography (0% to 50% EtOAc/hexanes) to afford 3-isopropyl-6-methoxy-3,4-dihydro-2,7-naphthyridine as a colorless oil (55 mg, 69% yield, m/z: 205 [M+H]⁺ observed).

Ethyl 6-isopropyl-3-methoxy-10-oxo-5,10,11,11a-tetrahydro-6H-pyrido[2,1-a][2,7]naphthyridine-9-carboxylate

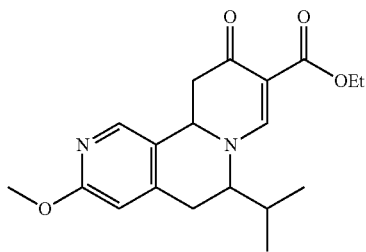 [SMILES: CCOC(=O)C1=CN2C(CC1=O)c1cnc(OC)cc1CC2C(C)C]

A mixture of 3-isopropyl-6-methoxy-3,4-dihydro-2,7-naphthyridine (50 mg, 0.24 mmol) and ethyl (2E)-2-acetyl-3-ethoxy-2-propenoate (0.14 g, 0.73 mmol) in EtOH (4 mL) was stirred at 100° C. for 12 h. The reaction mixture was concentrated under vacuum to give ethyl 6-isopropyl-3-methoxy-10-oxo-5,10,11,11a-tetrahydro-6H-pyrido[2,1-a][2,7]naphthyridine-9-carboxylate as a brown oil which was used without further purification (90 mg, >100%, m/z: 345 [M+H]⁺ observed).

Ethyl 6-isopropyl-3-methoxy-10-oxo-5,10-dihydro-6H-pyrido[2,1-a][2,7]naphthyridine-9-carboxylate

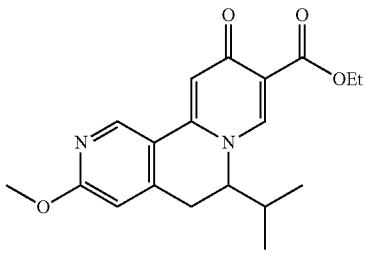 [SMILES: CCOC(=O)c1cn2c(cc1=O)-c1cnc(OC)cc1CC2C(C)C]

To a solution of ethyl 6-isopropyl-3-methoxy-10-oxo-5,10,11,11a-tetrahydro-6H-pyrido[2,1-a][2,7]naphthyridine-9-carboxylate (85 mg, 0.25 mmol) in 1,2-dimethoxyethane (2 mL) was added p-chloranil (71 mg, 0.29 mmol) and the reaction mixture stirred at 100° C. for 4 h. The reaction mixture was concentrated under vacuum to give to give ethyl 6-isopropyl-3-methoxy-10-oxo-5,10,11,11a-tetrahydro-6H-pyrido[2,1-a][2,7]naphthyridine-9-carboxylate which was used without further purification (90 mg, >100%).

6-Isopropyl-3-methoxy-O-oxo-5,10-dihydro-6H-pyrido[2,1-a][2,7]naphthyridine-9-carboxylic acid

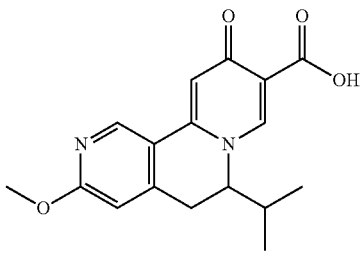 [SMILES: COc1cc2c(cn1)-c1cc(=O)c(C(=O)O)cn1C(C(C)C)C2]

To a solution of ethyl 6-isopropyl-3-methoxy-10-oxo-5,10,11,11a-tetrahydro-6H-pyrido[2,1-a][2,7]naphthyridine-9-carboxylate (85 mg, 0.25 mmol) in MeOH (2 mL) was added a 10% aqueous NaOH (2 mL) and stirred at rt for 4 h. The reaction mixture was washed with diethyl ether (2×4 mL) and the pH of the aqueous layer adjusted to 1-2 with 2M HCl. The resultant solids were filtered, washed with diethyl ether (2×4 mL) and recrystallized from EtOH to give pure 6-isopropyl-3-methoxy-10-oxo-5,10-dihydro-6H-pyrido[2,1-a][2,7]naphthyridine-9-carboxylic acid as a white solid (20 mg, 26% yield, m/z: 315 [M+H]⁺ observed). ¹H NMR (400 MHz, CDCl₃) δ 8.87 (s, 1H), 8.79 (s, 1H), 7.47 (s, 1H), 6.95 (s, 1H), 4.51-4.47 (m, 1H), 3.91 (s, 3H), 3.35-3.30 (m, 2H), 1.54-1.48 (m, 1H), 0.85-0.83 (d, J=6.8 Hz, 3H), 0.70-0.68 (d, J=6.8 Hz, 3H).

Example 87: 5-Isopropyl-2-methoxy-9-oxo-4,9-dihydro-5H-thiazolo[4,5-a]quinolizine-8-carboxylic acid

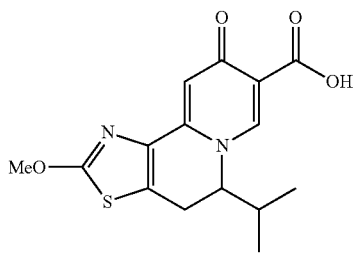 [SMILES: COc1nc2c(s1)CC(C(C)C)n1cc(C(=O)O)c(=O)cc1-2]

4-(1,3-Dioxolan-2-yl)-2-methoxythiazole

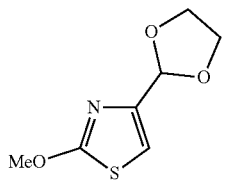 [SMILES: COc1nc(C2OCCO2)cs1]

A mixture of 2-methoxythiazole-4-carbaldehyde (500 mg, 3.49 mmol) in benzene (20 mL), triethyl orthoformate (0.70 ml, 4.2 mmol), ethylene glycol (1.2 ml, 21 mmol) and p-toluenesulfonic acid monohydrate (6 mg, 0.034 mmol) was heated to 40° C. for 2 h. The reaction mixture was cooled to rt and quenched with aqueous NaHCO$_3$ (10 mL) and extracted with EtOAc (2×20 mL). The combined organic extracts were washed with sat. aqueous brine solution (10 mL), dried over sodium sulfate and concentrated under vacuum. The residue was purified by normal phase SiO$_2$ chromatography (5% to 20% EtOAc/hexanes) to afford 4-(1,3-dioxolan-2-yl)-2-methoxythiazole as a colorless oil (450 mg, 69% yield). $^1$H NMR (400 MHz, CDCl$_3$): δ 6.78 (s, 1H), 5.81 (s, 1H), 4.15-4.12 (m, 2H), 4.09 (s, 3H), 4.04-4.00 (m, 2H).

6-Isopropyl-6,7-dihydrothiazolo[4,5-c]pyridin-2-ol

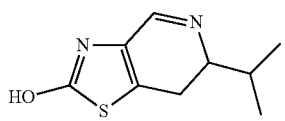

To a stirred solution of 4-(1,3-dioxolan-2-yl)-2-methoxythiazole (0.45 g, 2.4 mmol) in dry THF (10 mL) at −78° C. (dry ice/acetone bath) was added n-BuLi (2.5 M in hexanes, 1.2 mL, 2.9 mmol) drop-wise and the mixture allowed to stir for 2 h. t-Butyl 4-isopropyl-1,2,3-oxathiazolidine-3-carboxylate 2,2-dioxide (640 mg, 2.4 mmol) in THF (5 mL) was added drop-wise and the resulting mixture was slowly warmed to rt and stirred for 16 h. The reaction mixture was concentrated under reduced pressure and treated with HCl (4N in 1,4-dioxane, 20 mL), followed by H$_2$O (1.5 mL) at rt and allowed to stir for 1 h. The reaction mixture was diluted with CH$_2$Cl$_2$ (20 mL) and basified with 1M aqueous Na$_2$CO$_3$ solution. The layers were separated and the aqueous portion was extracted with CH$_2$Cl$_2$ (2×20 mL), washed with H$_2$O (15 mL), sat. aqueous brine solution (10 mL), dried over sodium sulfate and concentrated under vacuum. The residue was purified by normal phase SiO$_2$ chromatography (5% to 50% EtOAc/hexanes) to afford 6-isopropyl-6,7-dihydrothiazolo[4,5-c]pyridin-2-ol as a colorless oil (330 mg, 70% yield). $^1$H NMR (400 MHz, CDCl$_3$): δ 7.26 (s, 1H), 3.79-3.75 (m, 1H), 3.66-3.62 (m, 1H), 3.51-3.43 (m, 1H), 2.13-2.06 (m, 1H), 1.05-1.04 (d, J=6.8 Hz, 3H), 1.03-1.01 (d, J=6.8 Hz, 3H).

2-Hydroxy-5-isopropyl-9-oxo-5,9,10,10a-tetrahydro-4H-thiazolo[4,5-a]quinolizine-8-carboxylate

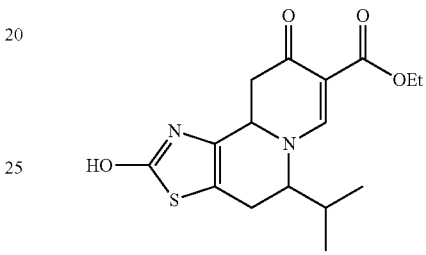

To a solution of 6-isopropyl-6,7-dihydrothiazolo[4,5-c]pyridin-2-ol (330 mg, 1.68 mmol) in ethanol (20 mL) was added ethyl (2E)-2-acetyl-3-ethoxy-2-propenoate (880 mg, 4.7 mmol) at rt and resultant mixture was stirred at 100° C. for 16 h. The solvent was removed under vacuum and the residue was purified by normal phase SiO$_2$ chromatography (0% to 5% MeOH/CH$_2$Cl$_2$) to afford 2-hydroxy-5-isopropyl-9-oxo-5,9,10,10a-tetrahydro-4H-thiazolo[4,5-a]quinolizine-8-carboxylate as a light brown solid (120 mg, 21% yield, m/z: 337 [M+H]$^+$ observed). $^1$H NMR (400 MHz, DMSO-d$_6$): 11.24 (s, 1H), 8.32 (s, 1H), 4.53-4.49 (d, J=14.8 Hz, 1H), 4.08-4.02 (q, J=7.2 Hz, 2H), 3.89-3.85 (dd, J=10.0, 4.8, 1H), 2.85-2.78 (m, 1H), 2.74-2.64 (m, 2H), 1.84-1.82 (m, 1H), 1.18-1.14 (t, J=7.2 Hz, 4H), 0.90-0.88 (d, J=6.8 Hz, 3H), 0.80-0.78 (d, J=6.4 Hz, 3H).

Ethyl 2-hydroxy-5-isopropyl-9-oxo-4,9-dihydro-5H-thiazolo[4,5-a]quinolizine-8-carboxylate

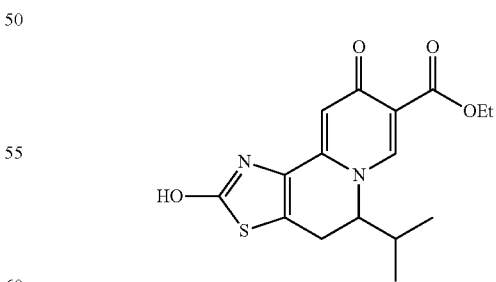

To a solution of 2-hydroxy-5-isopropyl-9-oxo-5,9,10,10a-tetrahydro-4H-thiazolo[4,5-a]quinolizine-8-carboxylate (120 mg, 0.36 mmol) in 1,2-dimethoxyethane (20 mL) was added p-chloranil (88 mg, 0.36 mmol) and the mixture was stirred at 100° C. for 2 h. The reaction was cooled to rt. The resulting solids collection by filtration and washed with EtOAc (25 mL). The filtrate was washed with H$_2$O (10 mL), sat. aqueous brine solution (10 mL), dried over sodium sulfate and concentrated under vacuum. The residue was purified by normal phase SiO$_2$ chromatography (0% to 5% MeOH/CH$_2$Cl$_2$) to afford ethyl 2-hydroxy-5-isopropyl-9-oxo-4,9-dihydro-5H-thiazolo[4,5-a]quinolizine-8-carboxylate as a light yellow solid (60 mg, 50% yield, m/z: 335 [M+H]$^+$ observed). $^1$H NMR (400 MHz, DMSO-d$_6$): 11.87 (s, 1H), 8.36 (s, 1H), 6.49 (s, 1H), 5.73 (s, 1H), 4.43 (m, 1H), 4.29 (m, 1H), 4.17-4.16 (q, 2H), 1.99-1.97 (m, 1H), 1.27-1.21 (t, J=6.8 Hz, 3H), 0.89-0.87 (d, J=6.4 Hz, 3H), 0.72-0.70 (d, J=6.8 Hz, 3H).

Ethyl 5-isopropyl-2-methoxy-9-oxo-4,9-dihydro-5H-thiazolo[4,5-a]quinolizine-8-carboxylate

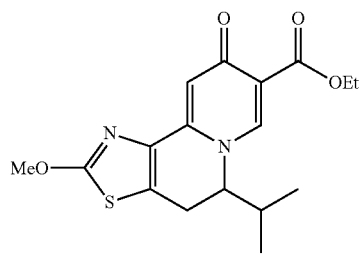 [SMILES: CCOC(=O)c1cn2c(cc1=O)-c1nc(OC)sc1CC2C(C)C]

To a solution of ethyl 2-hydroxy-5-isopropyl-9-oxo-4,9-dihydro-5H-thiazolo[4,5-a]quinolizine-8-carboxylate (60 mg, 0.18 mmol) in acetone (10 mL) was added potassium carbonate (160 mg, 1.2 mmol), followed by drop-wise addition of methyl iodide (0.12 mL, 1.9 mmol). The reaction mixture was stirred at rt for 24 h. The reaction mixture was diluted with EtOAc (2×20 mL), washed with H$_2$O (10 mL) and sat. aqueous brine solution (10 mL). The organic layer was dried over sodium sulfate and concentrated under vacuum. The residue was purified by normal phase SiO$_2$ chromatography (0% to 10% MeOH/CH$_2$Cl$_2$) to afford ethyl 5-isopropyl-2-methoxy-9-oxo-4,9-dihydro-5H-thiazolo[4,5-a]quinolizine-8-carboxylate as a light yellow solid (30 mg, 48% yield, m/z: 349 [M+H]$^+$ observed).

5-Isopropyl-2-methoxy-9-oxo-4,9-dihydro-5H-thiazolo[4,5-a]quinolizine-8-carboxylic acid

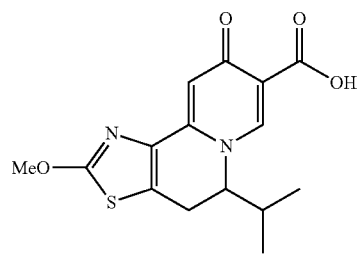 [SMILES: COc1nc2c(s1)CC(C(C)C)n1cc(C(=O)O)c(=O)cc1-2]

To a solution of ethyl 5-isopropyl-2-methoxy-9-oxo-4,9-dihydro-5H-thiazolo[4,5-a]quinolizine-8-carboxylate (30 mg, 0.086 mmol) in 1,4-dioxane (2 mL) was added 10% aqueous NaOH solution (1.5 mL) at rt and stirred for 2 h. The reaction the mixture was cooled to 0° C., acidified with aqueous 2N HCl to pH 1-2 and stirred for 1 h at rt. The resulting solids were filtered, washed with H$_2$O (5 mL), followed by diethyl ether (5 mL) and dried to give 5-isopropyl-2-methoxy-9-oxo-4,9-dihydro-5H-thiazolo[4,5-a]quinolizine-8-carboxylic acid as pale yellow solid (20 mg, 73% yield, m/z: 321 [M+H]$^+$ observed). $^1$H NMR (400 MHz, DMSO-d$_6$): δ 16.02 (bs, 1H), 8.81 (s, 1H), 6.95 (s, 1H), 4.52-4.50 (d, J=9.2 Hz, 1H), 3.38 (s, 3H), 3.20 (s, 2H), 2.09-2.07 (m, 1H), 0.92-0.91 (d, J=6.4 Hz, 3H), 0.77-0.76 (d, J=6.4 Hz, 3H).

Example 88: 5-Isopropyl-2-(methoxymethyl)-9-oxo-4,9-dihydro-5H-thiazolo[4,5-a]quinolizine-8-carboxylic acid

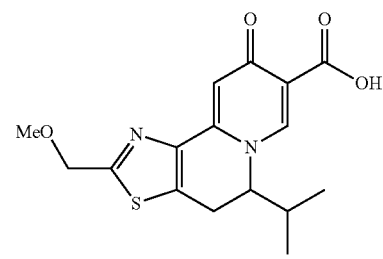 [SMILES: COCc1nc2c(s1)CC(C(C)C)n1cc(C(=O)O)c(=O)cc1-2]

4-(1,3-Dioxolan-2-yl)-2-(methoxymethyl)thiazole

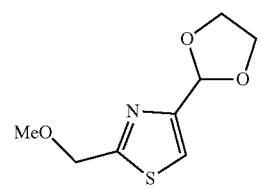 [SMILES: COCc1nc(C2OCCO2)cs1]

A mixture of 2-(methoxymethyl)thiazole-4-carbaldehyde (700 mg, 4.46 mmol) in benzene (20 mL), triethyl orthoformate (0.9 ml, 5.4 mmol), ethylene glycol (1.2 ml, 20.75 mmol) and p-toluene sulfonic acid monohydrate (8 mg, 0.044 mmol) was heated to 40° C. for 2 h. The reaction mixture was cooled to rt and quenched with aqueous NaHCO$_3$ (15 mL) and extracted with EtOAc (2×30 mL). The combined organic extracts were washed with sat. aqueous brine solution (10 mL), dried over sodium sulfate and concentrated under vacuum. The residue was purified by normal phase SiO$_2$ chromatography (5% to 25% EtOAc/hexanes) to afford 4-(1,3-dioxolan-2-yl)-2-(methoxymethyl)thiazole as a colorless oil (600 mg, 67% yield). $^1$H NMR (400 MHz, CDCl$_3$): δ 7.41 (s, 1H), 5.98 (s, 1H), 4.74 (s, 3H), 4.16-4.13 (m, 2H), 4.06-4.02 (m, 2H), 3.49 (s, 2H).

6-isopropyl-2-(methoxymethyl)-6,7-dihydrothiazolo[4,5-c]pyridine

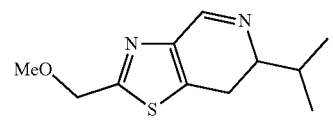

To a stirred solution of 4-(1,3-dioxolan-2-yl)-2-methoxythiazole (0.6 g, 3 mmol) in dry THF (10 mL) at −78° C. was added drop wise n-BuLi (2.5 M in hexanes, 1.43 mL, 3.58 mmol) and the mixture stirred for 2 h at −78° C. t-Butyl 4-isopropyl-1,2,3-oxathiazolidine-3-carboxylate 2,2-dioxide (800 mg, 3 mmol) in THF (5 mL) was added drop-wise, and then the resulting mixture was slowly warmed up to 20° C. and stirred for 16 h. The reaction mixture was concentrated under reduced pressure and treated with HCl (4N in 1,4-dioxane, 24 mL), followed by H$_2$O (2 mL) at rt and allowed to stir for 1 h. The reaction mixture was diluted with CH$_2$Cl$_2$ (30 mL) and basified with 1M aqueous Na$_2$CO$_3$ solution. The layers were separated and the aqueous portion was extracted with CH$_2$Cl$_2$ (2×20 mL), washed with H$_2$O (15 mL), sat. aqueous brine solution (10 mL), dried over sodium sulfate and concentrated under vacuum. The residue was purified by normal phase SiO$_2$ chromatography (5% to 50% EtOAc/hexanes) to afford 6-isopropyl-2-(methoxymethyl)-6,7-dihydrothiazolo[4,5-c]pyridine as a colorless oil (290 mg, 43% yield, m/z: 225 [M+H]$^+$ observed). $^1$H NMR (400 MHz, CDCl$_3$): δ 8.45 (s, 1H), 4.70 (s, 2H), 3.53-3.51 (m, 1H), 3.49 (s, 3H), 3.99-3.93 (m, 1H), 2.80-2.72 (m, 1H), 2.14-2.09 (m, 1H), 1.09-1.07 (d, J=6.8 Hz, 3H), 1.07-1.05 (d, J=6.8 Hz, 3H).

Ethyl 5-isopropyl-2-(methoxymethyl)-9-oxo-4,9,10,10a-tetrahydro-5H-thiazolo[4,5-a]quinolizine-8-carboxylate

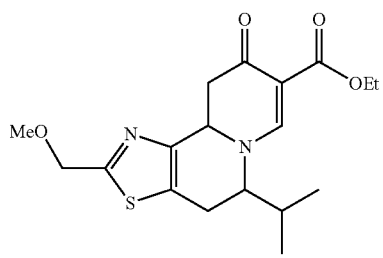 [SMILES: CCOC(=O)C1=CN2C(CC1=O)c1nc(COC)sc1CC2C(C)C]

To a stirred solution of 6-isopropyl-2-(methoxymethyl)-6,7-dihydrothiazolo[4,5-c]pyridine (290 mg, 1.3 mmol) in ethanol (20 mL) was added ethyl (2E)-2-acetyl-3-ethoxy-2-propenoate (722 mg, 3.88 mmol) at 20° C. and the resultant mixture was stirred at 100° C. for 16 h. The solvent was removed under vacuum and the residue was purified by normal phase SiO$_2$ chromatography (50% to 100% EtOAc/hexanes) to afford ethyl 5-isopropyl-2-(methoxymethyl)-9-oxo-4,9,10,10a-tetrahydro-5H-thiazolo[4,5-a]quinolizine-8-carboxylate as a light brown syrup (250 mg, 53% yield, m/z: 365 [M+H]$^+$ observed). $^1$H NMR (400 MHz, CDCl$_3$): 8.27 (s, 1H), 4.78 (m, 1H), 4.75 (s, 2H), 4.27-4.25 (q, J=7.2 Hz, 2H), 3.49 (m, 5H), 3.19-3.09 (m, 3H), 1.86-1.83 (m, 1H), 1.33-1.31 (t, J=7.2 Hz, 3H), 0.97-0.95 (d, J=6.8 Hz, 3H), 0.93-0.92 (d, J=6.8 Hz, 3H).

Ethyl 5-isopropyl-2-(methoxymethyl)-9-oxo-4,9-dihydro-5H-thiazolo[4,5-a]quinolizine-8-carboxylate

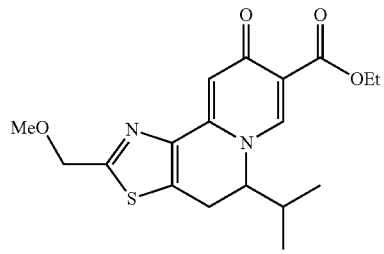 [SMILES: CCOC(=O)c1cn2c(cc1=O)-c1nc(COC)sc1CC2C(C)C]

To a stirred solution of ethyl 5-isopropyl-2-(methoxymethyl)-9-oxo-4,9,10,10a-tetrahydro-5H-thiazolo[4,5-a]quinolizine-8-carboxylate (250 mg, 0.69 mmol) in 1,2-dimethoxyethane (20 mL) was added p-chloranil (170 mg, 0.69 mmol) and the mixture was stirred at 100° C. for 2 h. The reaction was cooled to rt. The resulting solids collection by filtration and washed with EtOAc (25 mL). The filtrate was washed with H$_2$O (10 mL), sat. aqueous brine solution (10 mL), dried over sodium sulfate and concentrated under vacuum. The residue was purified by normal phase SiO$_2$ chromatography (0% to 5% MeOH/CH$_2$Cl$_2$) to afford ethyl 5-isopropyl-2-(methoxymethyl)-9-oxo-4,9-dihydro-5H-thiazolo[4,5-a]quinolizine-8-carboxylate as a light yellow solid (150 mg, 60% yield, m/z: 363 [M+H]$^+$ observed). $^1$H NMR (400 MHz, DMSO-d$_6$): 8.41 (s, 1H), 6.63 (s, 1H), 4.71 (s, 2H), 4.41-4.37 (q, J=6.8 Hz, 2H), 4.21-4.16 (m, 3H), 3.40 (s, 3H), 1.84-1.79 (m, 1H), 1.22-1.20 (t, J=7.2 Hz, 3H), 0.85-0.84 (d, J=6.8 Hz, 3H), 0.71-0.69 (d, J=6.4 Hz, 3H).

5-Isopropyl-2-(methoxymethyl)-9-oxo-4,9-dihydro-5H-thiazolo[4,5-a]quinolizine-8-carboxylic acid

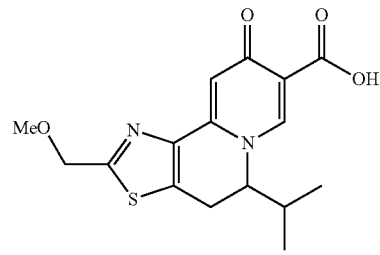 [SMILES: COCc1nc2c(s1)CC(C(C)C)n1cc(C(=O)O)c(=O)cc1-2]

To a solution of ethyl 5-isopropyl-2-(methoxymethyl)-9-oxo-4,9-dihydro-5H-thiazolo[4,5-a]quinolizine-8-carboxylate (150 mg, 0.41 mmol) in 1,4-dioxane (3 mL) was added 10% aqueous NaOH solution (2.0 mL) at rt and stirred for 2 h. The reaction the mixture was cooled to 0° C., acidified with aqueous 2N HCl to pH 1-2 and stirred for 1 h at rt. The crude mixture was extracted with EtOAc (2×20 mL). The combined organic layers were dried over sodium sulfate, filtered and concentrated under vacuum. The residue was purified by preparative TLC to give 5-isopropyl-2-(methoxymethyl)-9-oxo-4,9-dihydro-5H-thiazolo[4,5-a]quinolizine-8-carboxylic acid as a pale yellow solid (70 mg, 51% yield, m/z: 335.0 [M+H]$^+$ observed). $^1$H NMR (400 MHz, DMSO-d$_6$): δ 16.18 (bs, 1H), 8.88 (s, 1H), 7.03 (s, 1H), 4.74 (s, 2H), 4.69-4.65 (m, 1H), 3.64-3.59 (m, 1H), 3.52-3.46 (m, 1H), 3.42 (s, 3H), 1.89-1.82 (m, 1H), 0.87-0.86 (d, J=6.8 Hz, 3H), 0.70-0.68 (d, J=6.8 Hz, 3H).

Example 89: Ethyl 6-(tert-butyl)-9,10-dihydroxy-2-oxo-6,7-dihydro-2H-pyrido[2,1-a]isoquinoline-3-carboxylate

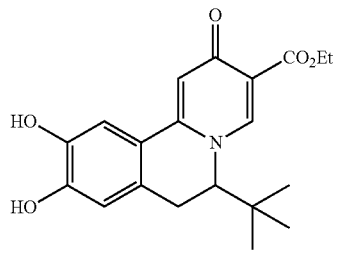 [SMILES: CCOC(=O)c1cn2c(cc1=O)-c1cc(O)c(O)cc1CC2C(C)(C)C]

1-(3,4-Bis(benzyloxy)phenyl)-3,3-dimethylbutan-2-one

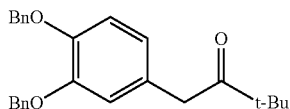 [SMILES: CC(C)(C)C(=O)Cc1ccc(OCc2ccccc2)c(OCc2ccccc2)c1]

To a solution of (((4-bromo-1,2-phenylene)bis(oxy))bis(methylene))dibenzene (50 g, 0.14 mol) and 3,3-dimethyl-2-butanone (51 mL, 0.41 mol) in 1,4-dioxane (600 mL) was added sodium tert-butoxide (43 g, 0.448 mol), Xantphos (7.86 g, 13.5 mmol) and tris(dibenzylideneacetone)dipalladium(0) (6.22 g, 6.79 mmol). The mixture was stirred at 100° C. for 3 hrs. The mixture was filtered through Celite®, washed with ethyl acetate (3×80 mL) and concentrated under vacuum. The residue was purified by normal phase SiO$_2$ chromatography (0% to 20% petroleum ether/EtOAc) to afford 1-(3,4-bis(benzyloxy) phenyl)-3,3-dimethylbutan-2-one as a yellow solid (31.5 g, 60% yield, m/z: 389 [M+H]$^+$ observed). $^1$H NMR (400 MHz, CDCl$_3$): δ 7.48-7.42 (m, 4H), 7.40-7.28 (m, 6H), 6.89 (d, J=8.0 Hz, 1H), 6.82 (s, 1H), 6.72-6.69 (m, 1H), 5.15 (d, J=4.8 Hz, 4H), 3.70 (s, 2H), 1.14 (s, 9H).

1-(3,4-Bis(benzyloxy)phenyl)-3,3-dimethylbutan-2-amine

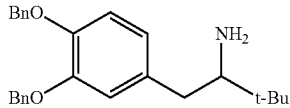 [SMILES: CC(C)(C)C(N)Cc1ccc(OCc2ccccc2)c(OCc2ccccc2)c1]

To a solution of 1-(3,4-bis(benzyloxy)phenyl)-3,3-dimethylbutan-2-one (13.5 g, 34.8 mmol) in MeOH (40 mL) was added NH$_4$OAc (26.8 g, 348 mol) and the mixture was stirred at rt for 12 hr. The reaction mixture was cooled to 0° C. and sodium cyanoborohydride (3.5 g, 55.7 mmol) was added and contents of the flask was stirred at 40° C. for 30 hr. The mixture was concentrated under vacuum. The residue was diluted H$_2$O (100 mL), extracted with CH$_2$Cl$_2$ (3×300 mL) and washed with sat. aqueous brine solution (2×100 mL). The combined organic layers were dried over Na$_2$SO$_4$, filtered and concentrated under vacuum to give 1-(3,4-bis(benzyloxy)phenyl)-3,3-dimethylbutan-2-amine as a yellow oil that was used without further purification (13.7 g, >100% yield, m/z: 390 [M+H]$^+$ observed).

N-(1-(3,4-bis(benzyloxy)phenyl)-3,3-dimethylbutan-2-yl)formamide

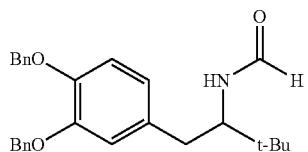 [SMILES: CC(C)(C)C(Cc1ccc(OCc2ccccc2)c(OCc2ccccc2)c1)NC=O]

To a solution of 1-(3,4-bis(benzyloxy)phenyl)-3,3-dimethylbutan-2-amine (13.7 g, 35.2 mmol) in 1,4-dioxane (140 mL) was added formic acid (40 mL, 1.06 mol). The mixture was stirred at 120° C. for 50 hrs. The reaction mixture was concentrated under vacuum. The residue was purified by normal phase SiO$_2$ chromatography (10% to 50% petroleum ether/EtOAc) to afford N-(1-(3,4-bis(benzyloxy)phenyl)-3,3-dimethylbutan-2-yl)formamide as a yellow solid (6.2 g, 42% yield, m/z: 418 [M+H]$^+$ observed). $^1$H NMR (400 MHz, CDCl$_3$, mixture of rotamers): δ 7.94-7.28 (m, 10H), 6.90-6.78 (m, 1H), 6.72-6.66 (m, 2H), 5.88-5.06 (m, 5H), 4.21-2.87 (m, 2H), 2.34-2.22 (m, 1H), 0.99 (d, J=3.6 Hz, 9H).

6,7-Bis(benzyloxy)-3-(tert-butyl)-3,4-dihydroisoquinoline

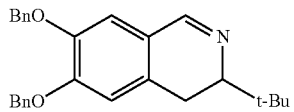 [SMILES: CC(C)(C)C1Cc2cc(OCc3ccccc3)c(OCc3ccccc3)cc2C=N1]

To a solution of N-(1-(3,4-bis(benzyloxy)phenyl)-3,3-dimethylbutan-2-yl)formamide (10 g, 24 mmol) in CH$_2$Cl$_2$ (120 mL) was added phosphorus(V) oxychloride (6 mL, 65 mmol) dropwise and the mixture was stirred at 40° C. for 12 hr. The mixture was poured into aqueous ammonium hydroxide solution (10%, 60 mL). The reaction mixture was extracted with CH$_2$Cl$_2$ (3×80 mL). The combined organic layers were dried over Na$_2$SO$_4$, filtered and concentrated under vacuum to afford 6,7-bis(benzyloxy)-3-(tert-butyl)-3,4-dihydroisoquinoline as a yellow gum that was used without further purification (9.2 g, >100% yield, m/z: 400 [M+H]$^+$ observed).

Ethyl 9,10-bis(benzyloxy)-6-(tert-butyl)-2-oxo-6,7-dihydro-2H-pyrido[2,1-a]isoquinoline-3-carboxylate

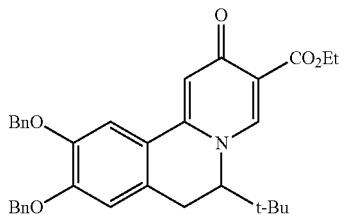 [SMILES: CCOC(=O)c1cn2c(cc1=O)-c1cc(OCc3ccccc3)c(OCc3ccccc3)cc1CC2C(C)(C)C]

A mixture of 6,7-bis(benzyloxy)-3-(tert-butyl)-3,4-dihydroisoquinoline (9.2 g, 23 mmol) and ethyl (E)-2-(ethoxymethylene)-3-oxobutanoate (18.6 g, 83.9 mmol) in EtOH (80.00 mL) was stirred at 100° C. for 60 hr. The reaction mixture was concentrated under vacuum to give ethyl 9,10-bis(benzyloxy)-6-(tert-butyl)-2-oxo-1,6,7,11 b-tetrahydro-2H-pyrido[2,1-a]isoquinoline-3-carboxylate as brown gum that was used in the next step without further purification (30.7 g, >100% yield, m/z: 540 [M+H]$^+$ observed).

To a solution of crude ethyl 9,10-bis(benzyloxy)-6-(tert-butyl)-2-oxo-1,6,7,11 b-tetrahydro-2H-pyrido[2,1-a]isoquinoline-3-carboxylate (12.4 g) in 1,2-dimethoxyethane (180 mL) was added p-chloranil (6 g, 24 mmol). The mixture was stirred at 70° C. for 3 hr and concentrated to −120 mL under vacuum. The reaction mixture was cooled to 5° C. The mixture, filtered and washed with cooled 1,2-dimethoxyethane (3×8 mL) to give a first crop of the desired product. The filtrate was concentrated to about 80 mL and cooled to 0° C. The mixture was filtered and filter solid was washed with cooled DME (6 mL*3) to give a second crop of the desired product. The 2 crops were combined to give ethyl 9,10-bis(benzyloxy)-6-(tert-butyl)-2-oxo-6,7-dihydro-2H-pyrido[2,1-a]isoquinoline-3-carboxylate as a yellow solid (7 g, 54% yield, m/z: 538 [M+H]$^+$ observed). $^1$H NMR (400 MHz, CDCl$_3$): δ 8.73 (s, 1H), 7.51 (d, J=2.4 Hz, 2H), 7.49-7.44 (m, 4H), 7.42-7.28 (m, 6H), 7.22 (s, 1H), 5.29-5.18 (m, 4H), 4.57 (bd, J=6.4 Hz, 1H), 4.30 (dd, J=14 Hz, 7.2 Hz, 2H), 3.42-3.34 (m, 1H), 3.27-3.21 (m, 1H), 1.30 (m, 3H), 0.71 (s, 9H).

Ethyl 6-(tert-butyl)-9,10-dihydroxy-2-oxo-6,7-dihydro-2H-pyrido[2,1-a]isoquinoline-3-carboxylate

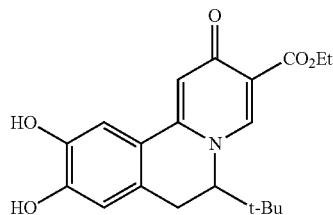 [SMILES: CCOC(=O)c1cn2c(cc1=O)-c1cc(O)c(O)cc1CC2C(C)(C)C]

A mixture of ethyl 9,10-bis(benzyloxy)-6-(tert-butyl)-2-oxo-6,7-dihydro-2H-pyrido[2,1-a]isoquinoline-3-carboxylate (2 g, 3.7 mmol) and palladium on carbon (10%, 300 mg, 37 mmol) under H$_2$ (30 psi) in EtOH (50 mL) was stirred at rt for 6 hrs. The reaction mixture was filtered through Celite® and washed with ethanol (5×30 mL). The filtrate was concentrated under vacuum to give ethyl 6-(tert-butyl)-9,10-dihydroxy-2-oxo-6,7-dihydro-2H-pyrido[2,1-a]isoquinoline-3-carboxylate as a brown solid (1.16 g, 87% yield, m/z: 538 [M+H]$^+$ observed). $^1$H NMR (400 MHz, DMSO-d$_6$): δ 10.14 (br s, 1H), 9.66 (br s, 1H), 8.73 (s, 1H), 7.33 (bs, 1H), 7.21 (s, 1H), 6.81 (s, 1H), 4.54 (bd, J=6.4 Hz, 1H), 4.29 (m, 2H), 3.32 (m, 1H), 3.14 (m, 1H), 1.29 (m, 3H), 0.73 (s, 9H).

Example 90: 6-(Tert-butyl)-2-oxo-6,7,11,12-tetrahydro-2H,10H-[1,4]dioxepino[2,3-g]pyrido[2,1-a]isoquinoline-3-carboxylic acid

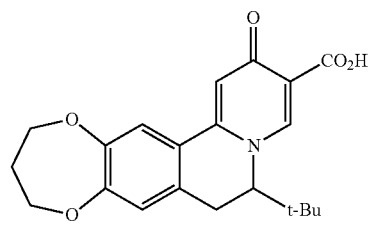 [SMILES: CC(C)(C)C1Cc2cc3c(cc2-c2cc(=O)c(C(=O)O)cn21)OCCCO3]

To a mixture of ethyl 6-(tert-butyl)-9,10-dihydroxy-2-oxo-6,7-dihydro-2H-pyrido[2,1-a]isoquinoline-3-carboxylate (500 mg, 1.4 mmol) and K$_2$CO$_3$ (680 mg, 4.9 mmol) in EtOH (20 mL) was added 1,3-dibromopropane (0.28 mL, 2.80 mmol). The mixture was stirred at 100° C. for 12 hr. The reaction mixture was concentrated under vacuum. To the residue was added H$_2$O (80 mL) and extracted with and CH$_2$Cl$_2$ (500 mL). The pH was adjusted to 1 with 1N HCl. The organic phase was washed sat. aqueous brine solution (2×100 mL), dried over sodium sulfate, filtered and concentrated under vacuum to afford ethyl 6-(tert-butyl)-2-oxo-6,7,11,12-tetrahydro-2H, 10H-[1,4]dioxepino[2,3-g]pyrido[2,1-a]isoquinoline-3-carboxylate as brown solid that was used in the next step without further purification in the next step (600 mg, >100% yield, m/z: 398 [M+H]$^+$ observed).

To a mixture of crude ethyl 6-(tert-butyl)-2-oxo-6,7,11,12-tetrahydro-2H, 10H-[1,4]dioxepino[2,3-g]pyrido[2,1-a]isoquinoline-3-carboxylate and 6-(tert-butyl)-2-oxo-6,7,11,12-tetrahydro-2H, 10H-[1,4]dioxepino[2,3-g]pyrido[2,1-a]isoquinoline-3-carboxylic acid (516.6 mg) in a mixture of H$_2$O (10 mL) and THF (10 mL) was added LiOH.H$_2$O (200. mg, 4.8 mmol). The mixture was stirred at rt for 12 hrs. The pH of the reaction mixture was adjusted to 1 using aqueous HCl (2N) at 0° C. The mixture was extracted with CH$_2$Cl$_2$ (3×100 mL). The combined organic phase was washed with saturated aqueous brine solution (2×60 mL), dried over sodium sulfate, filtered and concentrated under vacuum. The residue was purified by normal phase SiO$_2$ chromatography (0% to 10% MeOH/CH$_2$Cl$_2$) and further recrystallized from toluene/EtOH (1:1, 2 mL) to furnish 6-(tert-butyl)-2-oxo-6,7,11,12-tetrahydro-2H, 10H-[1,4]dioxepino[2,3-g]pyrido[2,1-a]isoquinoline-3-carboxylic acid as a white solid (90 mg, 17% yield, m/z: 370 [M+H]$^+$ observed). $^1$H NMR (400 MHz, DMSO-d$_6$): δ 8.71 (s, 1H), 7.64 (s, 1H), 7.29 (s, 1H), 7.03 (s, 1H), 4.57 (d, J=5.6 Hz, 1H), 4.32-4.09 (m, 4H), 3.36-3.21 (m, 2H), 2.19-2.09 (m, 2H), 0.71 (s, 9H).

Example 91: 6-(Tert-butyl)-2-oxo-6,7,11,12-tetrahydro-2H,10H-[1,4]dioxepino[2,3-g]pyrido[2,1-a]isoquinoline-3-carboxylic acid (Single Enantiomer I)

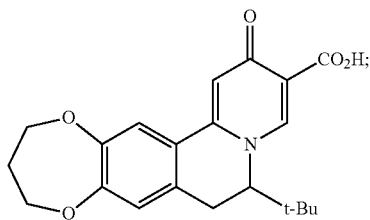 [SMILES: CC(C)(C)C1Cc2cc3c(cc2-c2cc(=O)c(C(=O)O)cn21)OCCCO3]

Example 92: 6-(Tert-butyl)-2-oxo-6,7,11,12-tetrahydro-2H,10H-[1,4]dioxepino[2,3-g]pyrido[2,1-a]isoquinoline-3-carboxylic acid (Single Enantiomer II)

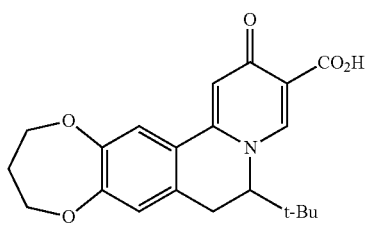 [SMILES: CC(C)(C)C1Cc2cc3c(cc2-c2cc(=O)c(C(=O)O)cn21)OCCCO3]

45 mg of the mixture of enantiomers was separated by SFC (supercritical fluid chromatography) on an OD column using 40% CH$_3$CN to give 6-(tert-butyl)-2-oxo-6,7,11,12-tetrahydro-2H, 10H-[1,4]dioxepino[2,3-g]pyrido[2,1-a]isoquinoline-3-carboxylic acid (single enantiomer I) as a white solid (faster eluting enantiomer, 10.1 mg, 22%, m/z: 370 [M+H]$^+$ observed) and 6-(tert-butyl)-2-oxo-6,7,11,12-tetrahydro-2H, 1 OH-[1,4]dioxepino[2,3-g]pyrido[2,1-a]isoquinoline-3-carboxylic acid (single enantiomer II) as a white solid (slower eluting enantiomer, 10.4 mg, 22%, m/z: 370 [M+H]$^+$ observed).

Example 91: 6-(Tert-butyl)-2-oxo-6,7,11,12-tetrahydro-2H,10H-[1,4]dioxepino[2,3-g]pyrido[2,1-a]isoquinoline-3-carboxylic acid (single enantiomer I). m/z: 370 [M+H]$^+$ observed). $^1$H NMR (400 MHz, DMSO-d$_6$): δ 8.71 (s, 1H), 7.64 (s, 1H), 7.29 (s, 1H), 7.03 (s, 1H), 4.57 (d, J=5.6 Hz, 1H), 4.32-4.09 (m, 4H), 3.36-3.21 (m, 2H), 2.19-2.09 (m, 2H), 0.71 (s, 9H).

Example 92: 6-(Tert-butyl)-2-oxo-6,7,11,12-tetrahydro-2H,10H-[1,4]dioxepino[2,3-g]pyrido[2,1-a]isoquinoline-3-carboxylic acid (single enantiomer II). m/z: 370 [M+H]$^+$ observed). $^1$H NMR (400 MHz, DMSO-d$_6$): δ 8.71 (s, 1H), 7.64 (s, 1H), 7.29 (s, 1H), 7.03 (s, 1H), 4.57 (d, J=5.6 Hz, 1H), 4.32-4.09 (m, 4H), 3.36-3.21 (m, 2H), 2.19-2.09 (m, 2H), 0.71 (s, 9H).

The following examples were prepared in a similar manner as (R)-6-(tert-butyl)-2-oxo-6,7,11,12-tetrahydro-2H,10H-[1,4]dioxepino[2,3-g]pyrido[2,1-a]isoquinoline-3-carboxylic acid and (S)-6-(tert-butyl)-2-oxo-6,7,11,12-tetrahydro-2H, 1 OH-[1,4]dioxepino[2,3-g]pyrido[2,1-a]isoquinoline-3-carboxylic acid from ethyl 6-(tert-butyl)-9,10-dihydroxy-2-oxo-6,7-dihydro-2H-pyrido[2,1-a]isoquinoline-3-carboxylate and an appropriate di-bromide, di-mesylate or di-chloride.

Example 93: 6'-(Tert-butyl)-2'-oxo-6',7'-dihydro-2'H,10'H,12'H-spiro[oxetane-3,11'-[1,4]dioxepino[2,3-g]pyrido[2,1-a]isoquinoline]-3'-carboxylic acid

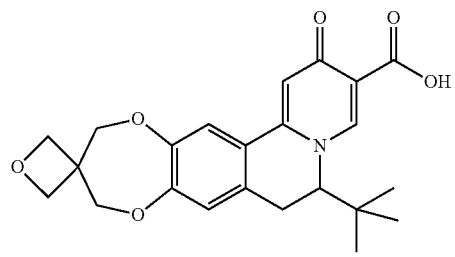 [SMILES: CC(C)(C)C1Cc2cc3c(cc2-c2cc(=O)c(C(=O)O)cn21)OCC1(COC1)CO3]

m/z: 412 [M+H]$^+$ observed. $^1$H NMR (400 MHz, DMSO-d$_6$): 8.71 (s, 1H), 7.66 (s, 1H), 7.32-7.27 (m, 1H), 7.06 (s, 1H), 4.59-4.33 (m, 9H), 3.29 (m, 1H), 3.28-3.20 (m, 1H), 0.70 (s, 9H).

Example 94: 6'-(Tert-butyl)-2'-oxo-6',7'-dihydro-2'H,10'H,12'H-spiro[oxetane-3,11'-[1,4]dioxepino[2,3-g]pyrido[2,1-a]isoquinoline]-3'-carboxylic acid (Single Enantiomer I)

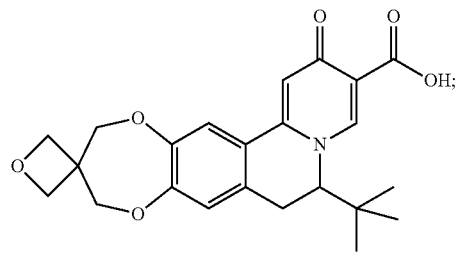 [SMILES: CC(C)(C)C1Cc2cc3c(cc2-c2cc(=O)c(C(=O)O)cn21)OCC1(COC1)CO3]

Example 95: 6'-(Tert-butyl)-2'-oxo-6',7'-dihydro-2'H,10'H,12'H-spiro[oxetane-3,11'-[1,4]dioxepino[2,3-g]pyrido[2,1-a]isoquinoline]-3'-carboxylic acid (Single Enantiomer II)

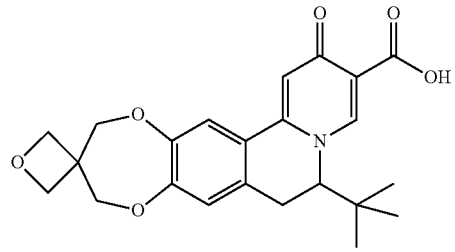 [SMILES: CC(C)(C)C1Cc2cc3c(cc2-c2cc(=O)c(C(=O)O)cn21)OCC1(COC1)CO3]

174 mg of the mixture of enantiomers was separated by SFC (supercritical fluid chromatography) on an OD-3 column using 40% EtOH (0.1% aq. NH$_3$) to give 6'-(tert-butyl)-2'-oxo-6',7'-dihydro-2'H, 10'H, 12'H-spiro[oxetane-3,11'-[1, 4]dioxepino[2,3-g]pyrido[2,1-a]isoquinoline]-3'-carboxylic acid (single enantiomer I) as an yellow solid (faster eluting enantiomer, 37 mg, 21%, m/z: 412 [M+H]$^+$ observed) and 6'-(tert-butyl)-2'-oxo-6',7'-dihydro-2'H, 10'H, 12'H-spiro[oxetane-3,11'-[1,4]dioxepino[2,3-g]pyrido[2,1-a]isoquinoline]-3'-carboxylic acid (single enantiomer II) as an off-white solid (slower eluting enantiomer, 20 mg, 11%, m/z: 412 [M+H]$^+$ observed).

Example 94: 6'-(Tert-butyl)-2'-oxo-6',7'-dihydro-2'H,10'H,12'H-spiro[oxetane-3,11'-[1,4]dioxepino[2,3-g]pyrido[2,1-a]isoquinoline]-3'-carboxylic acid (single enantiomer I). m/z: 412 [M+H]$^+$ observed. $^1$H NMR (400 MHz, DMSO-d$_6$): 8.71 (s, 1H), 7.66 (s, 1H), 7.32-7.27 (m, 1H), 7.06 (s, 1H), 4.59-4.33 (m, 9H), 3.29 (m, 1H), 3.28-3.20 (m, 1H), 0.70 (s, 9H).

Example 95: 6'-(Tert-butyl)-2'-oxo-6',7'-dihydro-2'H, 10'H,12'H-spiro[oxetane-3,11'-[1,4]dioxepino[2,3-g]pyrido[2,1-a]isoquinoline]-3'-carboxylic acid (single enantiomer II). m/z: 412 [M+H]$^+$ observed. $^1$H NMR (400 MHz, DMSO-d$_6$): 8.71 (s, 1H), 7.66 (s, 1H), 7.32-7.27 (m, 1H), 7.06 (s, 1H), 4.59-4.33 (m, 9H), 3.29 (m, 1H), 3.28-3.20 (m, 1H), 0.70 (s, 9H).

Example 96: 6-(Tert-butyl)-11-(methoxymethyl)-2-oxo-6,7,11,12-tetrahydro-2H,10H-[1,4]dioxepino[2,3-g]pyrido[2,1-a]isoquinoline-3-carboxylic acid

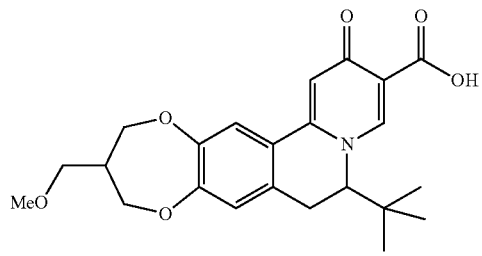 [SMILES: COCC1COc2cc3c(cc2OC1)-c1cc(=O)c(C(=O)O)cn1C(C(C)(C)C)C3]

m/z: 414 [M+H]$^+$ observed. $^1$H NMR (400 MHz, CDCl$_3$): δ 8.44 (s, 1H), 7.28 (s, 1H), 7.01 (s, 1H), 6.80 (s, 1H), 4.38-4.16 (m, 4H), 4.00-3.98 (m, 1H), 3.52-3.47 (m, 2H), 3.38 (s, 3H), 3.38-3.30 (m, 1H), 3.17-3.13 (m, 1H), 2.62-2.60 (m, 1H), 0.81 (s, 9H).

Example 97: 6-(Tert-butyl)-11-(2-methoxyethoxy)-2-oxo-6,7,11,12-tetrahydro-2H,10H-[1,4]dioxepino[2,3-g]pyrido[2,1-a]isoquinoline-3-carboxylic acid

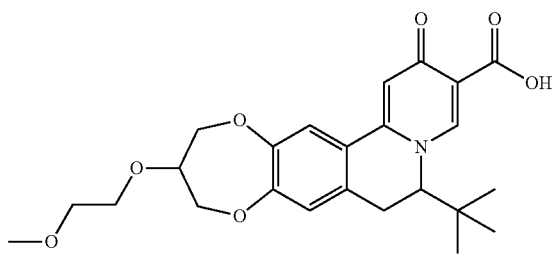 [SMILES: COCCOC1COc2cc3c(cc2OC1)-c1cc(=O)c(C(=O)O)cn1C(C(C)(C)C)C3]

m/z: 444 [M+H]$^+$ observed. $^1$H NMR (400 MHz, DMSO-d$_6$): δ 8.73-8.66 (m, 1H), 7.63-7.57 (m, 1H), 7.32-7.27 (m, 1H), 7.02-6.96 (m, 1H), 4.52-4.58 (m, 1H) 4.43-4.01 (m, 4H), 3.63-3.71 (m, 2H), 3.59 (bs, 1H), 3.46 (m, 2H), 3.30-3.19 (m, 5H), 0.72 (s, 9H).

Example 98: 6-(Tert-butyl)-11-methylene-2-oxo-6,7,11,12-tetrahydro-2H,10H-[1,4]dioxepino[2,3-g]pyrido[2,1-a]isoquinoline-3-carboxylic acid

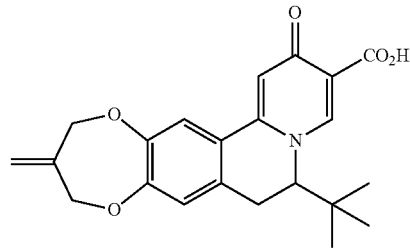 [SMILES: C=C1COc2cc3c(cc2OC1)-c1cc(=O)c(C(=O)O)cn1C(C(C)(C)C)C3]

m/z: 382 [M+H]$^+$ observed. $^1$H NMR (400 MHz, DMSO-d$_6$): δ 8.70 (s, 1H), 7.64 (s, 1H), 7.30 (s, 1H), 7.01 (s, 1H), 5.20 (bd, J=14.0 Hz, 2H), 4.90-4.72 (m, 4H), 4.56 (bd, J=5.6 Hz, 1H), 3.30 (bs, 1H), 3.27-3.20 (m, 1H), 0.72 (s, 9H).

Example 99: 6-(Tert-butyl)-11,11-bis(methoxymethyl)-2-oxo-6,7,11,12-tetrahydro-2H,10H-[1,4]dioxepino[2,3-g]pyrido[2,1-a]isoquinoline-3-carboxylic

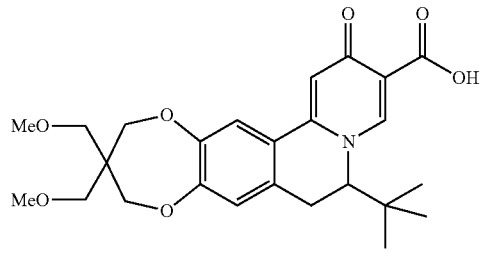 [SMILES: COCC1(COC)COc2cc3c(cc2OC1)-c1cc(=O)c(C(=O)O)cn1C(C(C)(C)C)C3]

m/z: 458 [M+H]$^+$ observed. $^1$H NMR (400 MHz, DMSO-d$_6$): δ 8.68 (s, 1H), 7.59 (s, 1H), 7.26 (s, 1H), 6.99 (s, 1H), 4.55-4.53 (d, 1H), 4.10-4.00 (m, 4H), 3.39-3.37 (d, 4H), 3.26 (s, 6H), 3.24 (s, 1H), 3.22 (s, 1H), 0.69 (s, 9H).

Example 100: 6-(Tert-butyl)-1-methyl-2-oxo-6,7,11,12-tetrahydro-2H,10H-[1,4]dioxepino[2,3-g]pyrido[2,1-a]isoquinoline-3-carboxylic acid

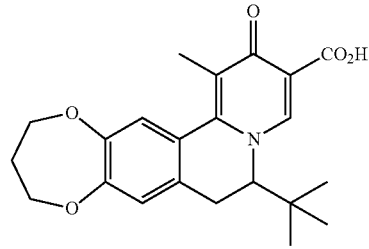 [SMILES: Cc1c2n(cc(C(=O)O)c1=O)C(C(C)(C)C)Cc1cc3c(cc1-2)OCCCO3]

m/z: 384 [M+H]$^+$ observed. $^1$H NMR (400 MHz, DMSO-d$_6$): δ 8.68 (s, 1H), 7.39 (s, 1H), 7.10 (s, 1H), 4.59-4.53 (m, 1H), 4.32-4.15 (m, 4H), 3.26-3.14 (m, 2H), 2.32 (s, 3H), 2.20-2.15 (m, 2H), 0.66 (s, 9H).

Example 101: 6-(Tert-butyl)-3-(hydroxymethyl)-1-methylene-6,7,11,12-tetrahydro-2H,10H-[1,4]dioxepino[2,3-g]pyrido[2,1-a]isoquinolin-2-one

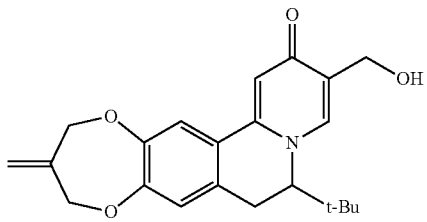 [SMILES: C=C1COc2cc3c(cc2OC1)-c1cc(=O)c(CO)cn1C(C(C)(C)C)C3]

Methyl 6-(tert-butyl)-11-methylene-2-oxo-6,7,11,12-tetrahydro-2H,10H-[1,4]dioxepino[2,3-g]pyrido[2,1-a]isoquinoline-3-carboxylate

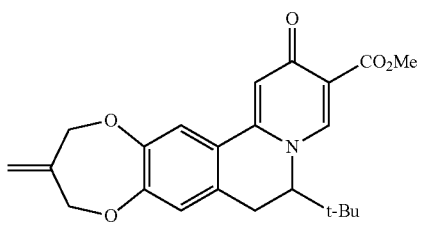 [SMILES: C=C1COc2cc3c(cc2OC1)-c1cc(=O)c(C(=O)OC)cn1C(C(C)(C)C)C3]

To a suspension of 6-(tert-butyl)-11-methylene-2-oxo-6,7,11,12-tetrahydro-2H, 1 OH-[1,4]dioxepino[2,3-g]pyrido[2,1-a]isoquinoline-3-carboxylic acid (1.3 g, 3.30 mmol) and iodomethane (1.0 mL, 16 mmol) in CH$_3$CN (80 mL) was added potassium carbonate (800 mg, 5.8 mmol). The mixture was stirred at rt for 12 hr. Then, additional CH$_3$CN (50 mL) and iodomethane (1.0 mL, 16 mmol) were added and the mixture was stirred at rt for another 12 hr. The mixture was filtered through Celite® and the filtrate was concentrated under vacuum. The residue was purified by normal phase SiO$_2$ chromatography (0% to 10% MeOH/CH$_2$Cl$_2$) to afford methyl 6-(tert-butyl)-11-methylene-2-oxo-6,7,11,12-tetrahydro-2H, 10H-[1,4]dioxepino[2,3-g]pyrido[2,1-a]isoquinoline-3-carboxylate as a yellow solid (1.2 g, 92% yield, m/z: 396 [M+H]$^+$ observed).

6-(Tert-butyl)-3-(hydroxymethyl)-11-methylene-6,7,11,12-tetrahydro-2H,10H-[1,4]dioxepino[2,3-g]pyrido[2,1-a]isoquinolin-2-one

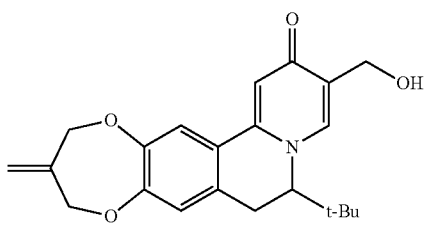 [SMILES: C=C1COc2cc3c(cc2OC1)-c1cc(=O)c(CO)cn1C(C(C)(C)C)C3]

To a solution of methyl 6-(tert-butyl)-11-methylene-2-oxo-6,7,11,12-tetrahydro-2H, 1 OH-[1,4]dioxepino[2,3-g]pyrido[2,1-a]isoquinoline-3-carboxylate (100 mg, 0.25 mmol) in THF (5 mL) was added H$_2$O$_2$ (30 wt % in H$_2$O, 0.07 mL, 0.76 mmol) at 0° C. The mixture was stirred at rt for 2 hr. Borane tetrahydrofuran complex solution (1 M in THF, 0.3 mL, 0.3 mmol) and aqueous NaOH solution (2.5 M, 0.3 mL, 0.76 mmol) were added at 0° C. The mixture was stirred at rt for 5 hrs. H$_2$O (2 mL) was added to quench the reaction. CH$_2$Cl$_2$ (30 mL) and H$_2$O (10 mL) were added. The pH was adjusted to 3 with 1N HCl (0.5 mL). The mixture was separated and the organic phase was washed a sat. aqueous sodium sulfite solution (15 mL), sat. aqueous brine solution (2×15 mL), dried over sodium sulfate, filtered and concentrated under vacuum. The residue was purified by prep-TLC (10% MeOH/CH$_2$Cl$_2$) to afford 6-(tert-butyl)-3-(hydroxy methyl)-11-methylene-6,7,11,12-tetrahydro-2H, 1 OH-[1,4]dioxepino[2,3-g]pyrido[2,1-a]isoquinolin-2-one as a light yellow solid (20 mg, 21% yield, m/z: 368 [M+H]$^+$ observed). $^1$H NMR (400 MHz, DMSO-d$_6$) δ 8.02 (s, 1H), 7.43 (s, 1H), 7.04-6.98 (m, 2H), 5.21 (d, J=12.8 Hz, 2H), 4.89-4.74 (m, 4H), 4.51-4.39 (m, 3H), 3.26 (br s, 1H), 3.22-3.18 (m, 1H), 0.73 (s, 9H).

Example 102: 6-(Tert-butyl)-11-methoxy-2-oxo-6,7,11,12-tetrahydro-2H,10H-[1,4]dioxepino[2,3-g]pyrido[2,1-a]isoquinoline-3-carboxylic acid

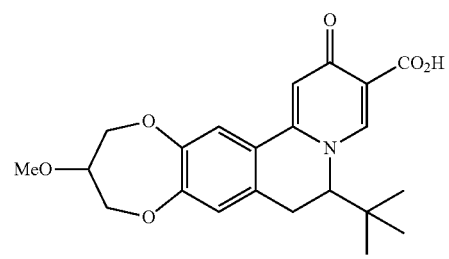 [SMILES: COC1COc2cc3c(cc2OC1)-c1cc(=O)c(C(=O)O)cn1C(C(C)(C)C)C3]

Ethyl 6-(tert-butyl)-2-oxo-11-((tetrahydro-2H-pyran-2-yl)oxy)-6,7,11,12-tetrahydro-2H,10H-[1,4]dioxepino[2,3-g]pyrido[2,1-a]isoquinoline-3-carboxylate

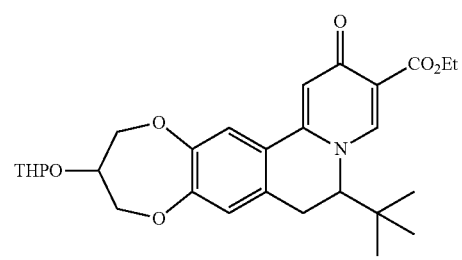

To a solution of ethyl 6-(tert-butyl)-9,10-dihydroxy-2-oxo-6,7-dihydro-2H-pyrido[2,1-a]isoquinoline-3-carboxylate (800 mg, 2.2 mmol) in DMF (15 mL) was added K$_2$CO$_3$ (1.24 g, 8.96 mmol), then the mixture was heated to 100° C. To this mixture was added a solution of 2-((1-bromo-3-chloropropan-2-yl)oxy)tetrahydro-2H-pyran (prepared according to the procedure by Drevermann, et al., 2007, Helv. Chim. Acta 90:1006) (803 mg, 3.14 mmol) in DMF (1 mL) drop-wise. The mixture was stirred at 120° C. for 12 hrs. The mixture was poured into ice water (60 mL) and diluted with CH$_2$Cl$_2$ (300 mL). The pH was adjusted to 6 with sat. aqueous 1N HCl (12 mL). The mixture was separated and the organic phase was washed with sat. aqueous brine solution (2×50 mL), dried over sodium sulfate, filtered and concentrated under vacuum. The residue was purified by normal phase SiO$_2$ chromatography (0% to 10% MeOH/CH$_2$Cl$_2$) to afford ethyl 6-(tert-butyl)-2-oxo-11-((tetrahydro-2H-pyran-2-yl)oxy)-6,7,11,12-tetrahydro-2H, 10H-[1,4]dioxepino[2,3-g]pyrido[2,1-a]isoquinoline-3-carboxylate as a brown solid (790 mg, 71% yield, m/z: 498 [M+H]$^+$ observed). $^1$H NMR (400 MHz, CDCl$_3$) δ 8.20-8.14 (m, 1H), 7.27-7.20 (m, 1H), 6.91-6.82 (m, 1H), 6.80-6.71 (m, 1H), 4.92-4.71 (m, 1H), 4.60-4.24 (m, 8H), 3.97-3.80 (m, 3H), 3.57 (bs, 1H), 3.40-3.25 (m, 1H), 3.10 (bd, J=16.8 Hz, 1H), 1.85 (m, 2H), 1.75 (m, 3H), 1.65 (m, 2H), 0.80 (br s, 9H).

Ethyl 6-(tert-butyl)-11-hydroxy-2-oxo-6,7,11,12-tetrahydro-2H,10 OH-[1,4]dioxepino[2,3-g]pyrido[2,1-a]isoquinoline-3-carboxylate; 6-(tert-butyl)-11-hydroxy-2-oxo-6,7,11,12-tetrahydro-2H, 1 OH-[1,4]dioxepino[2,3-g]pyrido[2,1-a]isoquinoline-3-carboxylic acid

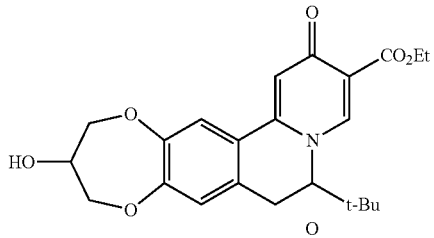

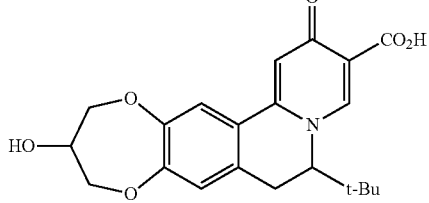

A solution of ethyl 6-(tert-butyl)-2-oxo-11-((tetrahydro-2H-pyran-2-yl)oxy)-6,7,11,12-tetrahydro-2H, 10H-[1,4]dioxepino[2,3-g]pyrido[2,1-a]isoquinoline-3-carboxylate (440 mg, 0.88 mmol) in aqueous HCl (1 N, 4.40 mL, 4.4 mmol) and THF (15 mL) was stirred at rt for 12 hrs. The mixture was diluted with CH$_2$Cl$_2$ (80 mL) and H$_2$O (20 mL). The mixture was separated and the organic phase was washed H$_2$O (40 mL), sat. aqueous brine solution (2×40 mL), dried over sodium sulfate, filtered and concentrated under vacuum to give a mixture of ethyl 6-(tert-butyl)-11-hydroxy-2-oxo-6,7,11,12-tetrahydro-2H, 10H-[1,4]dioxepino[2,3-g]pyrido[2,1-a]isoquinoline-3-carboxylate and 6-(tert-butyl)-11-hydroxy-2-oxo-6,7,11,12-tetrahydro-2H, 10H-[1,4]dioxepino[2,3-g]pyrido[2,1-a]isoquinoline-3-carboxylic acid as a yellow solid used in the next step without further purification (351 mg, 96% yield, m/z: 414 [M+H]$^+$ observed).

Methyl 6-(tert-butyl)-11-methoxy-2-oxo-6,7,11,12-tetrahydro-2H,1 OH-[1,4]dioxepino[2,3-g]pyrido[2,1-a]isoquinoline-3-carboxylate

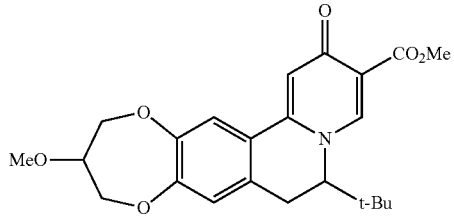 [SMILES: COC(=O)c1cn2c(cc1=O)-c1cc3c(cc1CC2C(C)(C)C)OCC(OC)CO3]

To a solution of ethyl 6-(tert-butyl)-11-hydroxy-2-oxo-6,7,11,12-tetrahydro-2H, 1 OH-[1,4]dioxepino[2,3-g]pyrido[2,1-a]isoquinoline-3-carboxylate and 6-(tert-butyl)-11-hydroxy-2-oxo-6,7,11,12-tetrahydro-2H, 1 OH-[1,4]dioxepino[2,3-g]pyrido[2,1-a]isoquinoline-3-carboxylic acid (300 mg) in DMF (4 mL) at 0° C. was added NaH (60% in mineral oil, 100 mg, 2.5 mmol). The ice bath was removed and the mixture was stirred at rt for 1 hr. Iodomethane (0.3 mL, 4.82 mmol) was added and the mixture was stirred at rt for 12 hrs. The mixture was cooled to 0° C. and aqueous HCl (1N, 0.5 mL) was added to quench the reaction. The mixture was concentrated under vacuum. The residue was purified by preparative TLC to give methyl 6-(tert-butyl)-11-methoxy-2-oxo-6,7,11,12-tetrahydro-2H, 10H-[1,4]dioxepino[2,3-g]pyrido[2,1-a]isoquinoline-3-carboxylate as a yellow solid (170 mg, 57% yield, m/z: 414 [M+H]$^+$ observed).

6-(Tert-butyl)-11-methoxy-2-oxo-6,7,11,12-tetrahydro-2H,10H-[1,4]dioxepino[2,3-g]pyrido[2,1-a]isoquinoline-3-carboxylic acid A solution of methyl 6-(tert-butyl)-11-methoxy-2-oxo-6,7,11,12-tetrahydro-2H, 10H-[1,4]dioxepino[2,3-g]pyrido[2,1-a]isoquinoline-3-carboxylate (170 mg, 0.411 mmol) in H$_2$O (2 mL) and THF (1 mL) was added lithium hydroxide monohydrate (86 mg, 2.06 mmol). The mixture was stirred at rt for 12 hrs. The mixture was cooled to 0° C. and aqueous HCl (1N, 2 mL) was added to adjust the pH to 1. The resulting precipitate was collected by filtration to give 127 mg of crude product. The crude solid was recrystallized from toluene:EtOH (1.2 mL: 1 mL) to afford 6-(tert-butyl)-11-methoxy-2-oxo-6,7,11,12-tetrahydro-2H, 10H-[1,4]dioxepino[2,3-g]pyrido[2,1-a]isoquinoline-3-carboxylic acid as a white solid (38 mg, 23% yield, m/z: 400 [M+H]$^+$ observed). $^1$H NMR (400 MHz, DMSO-d6) δ 8.70 (s, 1H), 7.61 (s, 1H), 7.30 (bs, 1H), 7.01 (s, 1H), 4.56 (bd, J=5.2 Hz, 1H), 4.42-4.13 (m, 4H) 3.95-3.85 (m, 1H), 3.34 (d, J=10.4 Hz, 3H), 3.29 (bd, J=6.8 Hz, 1H), 3.26-3.19 (m, 1H), 0.71 (s, 9H).

Example 103: 6-(Tert-butyl)-11-hydroxy-2-oxo-6,7,11,12-tetrahydro-2H,10H-[1,4]dioxepino[2,3-g]pyrido[2,1-a]isoquinoline-3-carboxylic acid

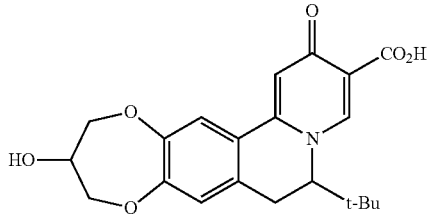 [SMILES: CC(C)(C)C1Cc2cc3c(cc2-c2cc(=O)c(C(=O)O)cn21)OCC(O)CO3]

A solution of ethyl 6-(tert-butyl)-11-hydroxy-2-oxo-6,7,11,12-tetrahydro-2H, 1 OH-[1,4]dioxepino[2,3-g]pyrido[2,1-a]isoquinoline-3-carboxylate and 6-(tert-butyl)-11-hydroxy-2-oxo-6,7,11,12-tetrahydro-2H, 1 OH-[1,4]dioxepino[2,3-g]pyrido[2,1-a]isoquinoline-3-carboxylic acid (600 mg, 1.45 mmol) in THF (6 mL) and H$_2$O (10 mL) was added lithium hydroxide monohydrate (305 mg, 7.26 mmol). The mixture was stirred at rt for 16 hrs. The mixture was cooled to 0° C. and aqueous 1N HCl was added to adjust the pH to 3. The mixture was extracted with CH$_2$Cl$_2$ (100 mL) and the organic phase was washed with sat. aqueous brine solution (2×20 mL), dried over sodium sulfate, filtered and concentrated under vacuum. The residue was purified by normal phase SiO$_2$ chromatography (0% to 20% MeOH/CH$_2$Cl$_2$) to afford 6-(tert-butyl)-11-hydroxy-2-oxo-6,7,11,12-tetrahydro-2H, 1 OH-[1,4]dioxepino[2,3-g]pyrido[2,1-a]isoquinoline-3-carboxylic acid as a yellow solid (96 mg, 17% yield, m/z: 386 [M+H]$^+$ observed). $^1$H NMR (400 MHz, DMSO-d6) δ 8.70 (s, 1H), 7.61 (s, 1H), 7.29 (s, 1H), 7.00 (s, 1H), 4.57-4.55 (m, 1H), 4.44-4.25 (m, 2H), 4.20-4.11 (m, 1H), 4.09-3.95 (m, 2H), 3.35-3.28 (m, 1H), 3.27-3.18 (m, 1H), 0.71 (m, 9H).

Example 104: 2-Chloro-7-isopropyl-3-methoxy-11-oxo-6,7-dihydro-11H-dipyrido[1,2-d:3',2'-f][1,4]oxazepine-10-carboxylic acid

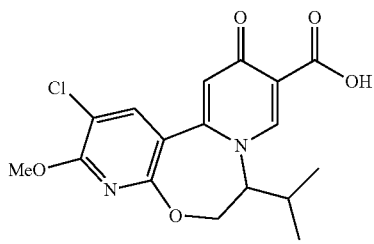 [SMILES: COc1nc2c(cc1Cl)-c1cc(=O)c(C(=O)O)cn1C(C(C)C)CO2]

Ethyl 6-(2,5-dichloro-6-methoxypyridin-3-yl)-4-oxo-4H-pyran-3-carboxylate

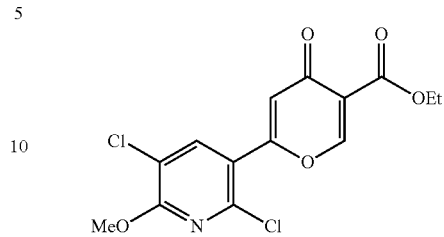

To a solution of LiHMDS (1M solution in THF, 22.6 mL, 24 mmol) in dry THF (30 ml) at −78° C. (dry ice/acetone bath) under argon, a solution of ethyl (Z)-2-((dimethylamino) methylene)-3-oxobutanoate (1.85 g, 10 mmol) and 2,5-dichloro-6-methoxynicotinoyl chloride (2.4 g, 10 mmol, prepared from 2,5,6-trichloronicotinic acid by the methods in WO2008130527 and WO2010146351) in 50 mL THF was added dropwise over 10 min. The dry ice/acetone bath was removed and the solution warmed to rt over a 30 min. Diethyl ether (100 mL) was added to the reaction mixture followed by aqueous HCl (3N, 30 ml, 90 mmol) and the contents were stirred overnight. The organic solvents were removed under vacuum keep the bath temperature below 30° C. and the solids were treated with sat. aqueous sodium bicarbonate solution until to adjust the pH to 7-8 and stirred vigorously for 10 min. The precipitate was filtered, washed with H$_2$O (25 mL), dissolved in CH$_2$Cl$_2$ (50 mL), dried over sodium sulfate and concentrated under vacuum to give dark orange residue (6.5 g). The residue was purified by normal phase SiO$_2$ chromatography (10% to 100% EtOAc/hexanes), followed by recrystallization from methanol (20 mL) afforded ethyl 6-(2,5-dichloro-6-methoxypyridin-3-yl)-4-oxo-4H-pyran-3-carboxylate as a white solid (0.76 g, 20% yield, m/z: 344 [M+H]$^+$ observed). $^1$H NMR (300 MHz, CDCl$_3$) δ 8.56 (s, 1H), 7.85 (d, J=1.5 Hz, 1H), 6.87 (d, J=1.5 Hz, 1H), 4.43-4.35 (m, 2H), 4.11 (s, 3H), 1.41-1.37 (m, 3H).

Ethyl 2',5'-dichloro-1-(1-hydroxy-3-methylbutan-2-yl)-6'-methoxy-4-oxo-1,4-dihydro-[2,3'-bipyridine]-5-carboxylate

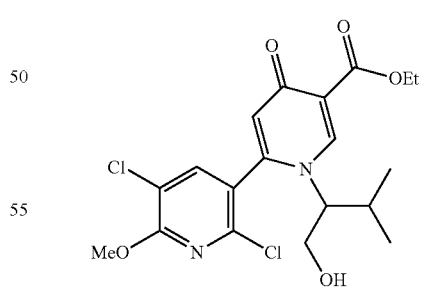

To a mixture of ethyl 6-(2,5-dichloro-6-methoxypyridin-3-yl)-4-oxo-4H-pyran-3-carboxylate (138 mg, 0.402 mmol) in AcOH/EtOH (2:3, 10 mL) was added DL-valinol (62 mg, 0.6 mmol). The reaction was heated at 100° C. for 8 h. The reaction mixture was concentrated under vacuum and the residue was purified by normal phase SiO$_2$ chromatography (0% to 10% MeOH/CH$_2$Cl$_2$) to afford ethyl 2',5'-dichloro-1-(1-hydroxy-3-methylbutan-2-yl)-6'-methoxy-4-oxo-1,4- dihydro-[2,3'-bipyridine]-5-carboxylate as a white foam (100 mg, 58% yield, m/z: 429 [M+H]+ observed). ¹H NMR (300 MHz, CDCl₃) δ 8.70 (s, 1H), 7.49 (s, 1H), 6.26 (s, 1H), 4.40-4.25 (m, 2H), 4.15 (s, 3H), 4.00-3.95 (m, 2H), 3.25 (m, 1H), 2.45 (m, 1H), 1.37 (m, 3H) and 1.05-0.85 (m, 6H).

2-Chloro-7-isopropyl-3-methoxy-11-oxo-6,7-dihydro-11H-dipyrido[1,2-d:3',2'-f][1,4]oxazepine-10-carboxylic acid

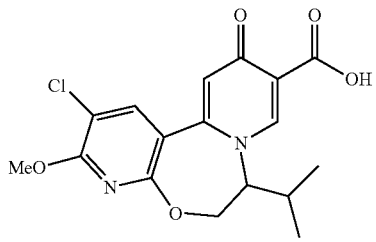 [SMILES: COc1nc2c(cc1Cl)-c1cc(=O)c(C(=O)O)cn1C(C(C)C)CO2]

To a solution of ethyl 2',5'-dichloro-1-(1-hydroxy-3-methylbutan-2-yl)-6'-methoxy-4-oxo-1,4-dihydro-[2,3'-bipyridine]-5-carboxylate (86 mg, 0.2 mmol) in anhydrous THF (10 mL) at 0° C. was added sodium hydride (60% in mineral oil, 9 mg, 0.4 mmol). The reaction mixture was stirred at room temperature for 30 min and then refluxed for 4 h. The organic solvent was removed under reduced pressure and the reaction mixture was neutralized with aqueous HCl (1N, 5 mL), extracted with ethyl acetate (2×10 mL), washed with H₂O, dried over sodium sulfate and concentrated under vacuum. The residue was purified by reverse phase HPLC to afford 2-chloro-7-isopropyl-3-methoxy-11-oxo-6,7-dihydro-11H-dipyrido[1,2-d:3',2'-f][1,4]oxazepine-10-carboxylic acid as white solid (25 mg, 34% yield, m/z: 365 [M+H]+ observed). ¹H NMR (300 MHz, DMSO-d₆) δ 8.54 (s, 1H), 7.45 (s, 1H), 6.94 (s, 1H), 5.53-5.43 (m, 2H), 4.08 (s, 3H), 4.04-3.98 (m, 1H), 2.05 (m, 1H) and 1.05-0.95 (m, 6H).

Example 105: Diethyl (6-(tert-butyl)-10-chloro-9-(3-methoxypropoxy)-2-oxo-6,7-dihydro-2H-pyrido[2,1-a]isoquinolin-3-yl)phosphonate

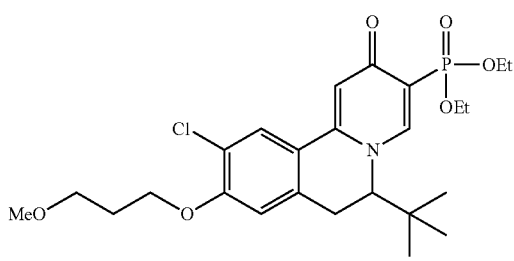 [SMILES: CCOP(=O)(OCC)c1cn2c(cc1=O)-c1cc(Cl)c(OCCCOC)cc1CC2C(C)(C)C]

2-(3-(Tert-butyl)-7-chloro-6-(3-methoxypropoxy)-1,2,3,4-tetrahydroisoquinolin-1-yl)acetic acid

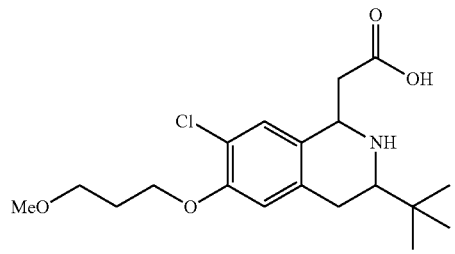 [SMILES: COCCCOc1cc2c(cc1Cl)C(CC(=O)O)NC(C(C)(C)C)C2]

A mixture of 3-(tert-butyl)-7-chloro-6-(3-methoxypropoxy)-3,4-dihydroisoquinoline (3.5 g, 11 mmol, prepared according to the procedure in WO2015113990A1) and malonic acid (1.18 g, 11.3 mmol) was heated at 120° C. for 30 min. The reaction mixture was cooled to rt, diluted with CH₂Cl₂ (50 mL) and washed with H₂O (3×30 mL). The organic phase was dried over anhydrous sodium sulfate and evaporated in vacuum to obtain crude 2-(3-(tert-butyl)-7-chloro-6-(3-methoxypropoxy)-1,2,3,4-tetrahydroisoquinolin-1-yl)acetic acid as a brown solid that was used without further purification (2.0 g, 48% yield, m/z: 370 [M+H]+ observed).

Methyl 2-(3-(tert-butyl)-7-chloro-6-(3-methoxypropoxy)-1,2,3,4-tetrahydroisoquinolin-1-yl)acetate

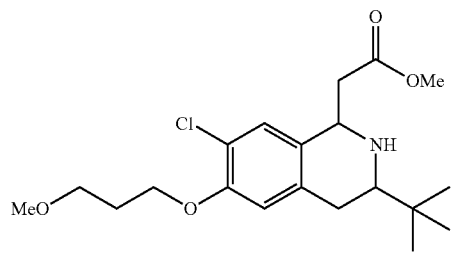 [SMILES: COCCCOc1cc2c(cc1Cl)C(CC(=O)OC)NC(C(C)(C)C)C2]

To a stirred solution of 2-(3-(tert-butyl)-7-chloro-6-(3-methoxypropoxy)-1,2,3,4-tetrahydroisoquinolin-1-yl)acetic acid (2.0 g, 5.4 mmol) in MeOH (20 mL) at 0° C. was added conc. sulfuric acid (2 mL) and stirred at 70° C. for 16 h. The reaction mixture was evaporated in vacuum and basified using aqueous ammonium hydroxide solution to adjust the pH to 8-9. The mixture was extracted with EtOAc (3×25 mL). The combined organic phase was dried over anhydrous sodium sulfate and evaporated in vacuum. The residue was purified by normal phase SiO₂ chromatography (5% to 15% EtOAc/hexanes) to afford methyl 2-(3-(tert-butyl)-7-chloro-6-(3-methoxypropoxy)-1,2,3,4-tetrahydroisoquinolin-1-yl)acetate as a brown solid (1 g, 48% yield, m/z: 384 [M+H]+ observed).

Diethyl (3-(3-(tert-butyl)-7-chloro-6-(3-methoxypropoxy)-1,2,3,4-tetrahydroisoquinolin-1-yl)-2-oxopropyl)phosphonate

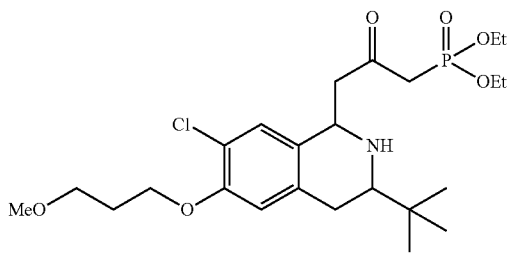 [SMILES: CCOP(=O)(CC(=O)CC1NC(C(C)(C)C)Cc2cc(OCCCOC)c(Cl)cc21)OCC]

To a stirred solution of diethyl methylphosphonate (0.11 mL, 0.782 mmol) in dry THF (2 mL) was added n-BuLi (2.5 M in hexanes, 0.3 mL, 0.756 mmol) at −78° C. (dry ice/acetone bath) and the mixture was stirred for 30 min. Then methyl 2-(3-(tert-butyl)-7-chloro-6-(3-methoxypropoxy)-1,2,3,4-tetrahydroisoquinolin-1-yl)acetate (0.1 g, 0.27 mmol) in THF (0.5 mL) was added to the reaction mixture and stirred at −78° C. for 15 min. The temperature was raised to rt over 2 h. The reaction mixture was diluted with H$_2$O (5 mL) and extracted in EtOAc (3×10 mL). The organic phase was dried over anhydrous sodium sulfate and evaporated in vacuum to obtain crude diethyl (3-(3-(tert-butyl)-7-chloro-6-(3-methoxypropoxy)-1,2,3,4-tetrahydroisoquinolin-1-yl)-2-oxopropyl)phosphonate as a brown gum that was used without further purification (115 mg, 88% yield, m/z: 504 [M+H]$^+$ observed).

Diethyl (4-(3-(tert-butyl)-7-chloro-6-(3-methoxypropoxy)-1,2,3,4-tetrahydroisoquinolin-1-yl)-1-(dimethylamino)-3-oxobut-1-en-2-yl)phosphonate

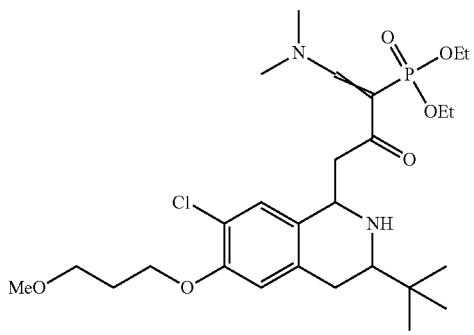 [SMILES: CCOP(=O)(OCC)C(=CN(C)C)C(=O)CC1NC(C(C)(C)C)Cc2cc(OCCCOC)c(Cl)cc21]

To a stirred solution of diethyl (3-(3-(tert-butyl)-7-chloro-6-(3-methoxypropoxy)-1,2,3,4-tetrahydroisoquinolin-1-yl)-2-oxopropyl)phosphonate (0.31 g, 0.62 mmol) in toluene (1.5 mL) at rt was added N,N-dimethylformamide dimethyl acetal (0.12 mL, 0.924 mmol) and the reaction mixture was stirred at 100° C. for 12 h. The reaction mixture was evaporated in vacuum to obtain crude diethyl (4-(3-(tert-butyl)-7-chloro-6-(3-methoxypropoxy)-1,2,3,4-tetrahydroisoquinolin-1-yl)-1-(dimethylamino)-3-oxobut-1-en-2-yl)phosphonate as a brown gum that was used without further purification (0.3 g, 72% yield, m/z: 559 [M+H]$^+$ observed).

Diethyl (6-(tert-butyl)-10-chloro-9-(3-methoxypropoxy)-2-oxo-1,6,7,11b-tetrahydro-2H-pyrido[2,1-a]isoquinolin-3-yl)phosphonate

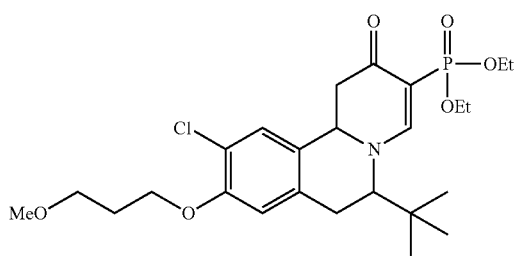 [SMILES: CCOP(=O)(OCC)C1=CN2C(CC1=O)c1cc(Cl)c(OCCCOC)cc1CC2C(C)(C)C]

A solution of diethyl (4-(3-(tert-butyl)-7-chloro-6-(3-methoxypropoxy)-1,2,3,4-tetrahydroisoquinolin-1-yl)-1-(dimethylamino)-3-oxobut-1-en-2-yl)phosphonate (0.29 g, 0.52 mmol) in MeOH (3 mL) was stirred at rt for 16 h. The reaction was evaporated in vacuum to obtain crude diethyl (6-(tert-butyl)-10-chloro-9-(3-methoxypropoxy)-2-oxo-1,6,7,11b-tetrahydro-2H-pyrido[2,1-a]isoquinolin-3-yl)phosphonate as a brown gum that was used without further purification (190 mg, 71% yield, m/z: 514 [M+H]$^+$ observed).

Diethyl (6-(tert-butyl)-10-chloro-9-(3-methoxypropoxy)-2-oxo-6,7-dihydro-2H-pyrido[2,1-a]isoquinolin-3-yl)phosphonate

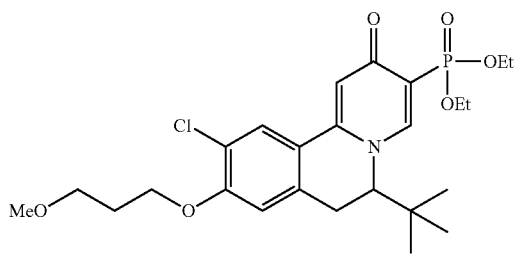 [SMILES: CCOP(=O)(OCC)c1cn2c(cc1=O)-c1cc(Cl)c(OCCCOC)cc1CC2C(C)(C)C]

To a stirred solution of diethyl (6-(tert-butyl)-10-chloro-9-(3-methoxypropoxy)-2-oxo-1,6,7,11 b-tetrahydro-2H-pyrido[2,1-a]isoquinolin-3-yl)phosphonate (0.14 g, 0.27 mmol) in DME (2 mL) at rt was added p-chloranil (0.134 g, 0.545 mmol) and the reaction mixture was stirred at 85° C. for 2 h. The reaction was evaporated in vacuum. The residue was purified by reverse phase HPLC to afford diethyl (6-(tert-butyl)-10-chloro-9-(3-methoxypropoxy)-2-oxo-6,7-dihydro-2H-pyrido[2,1-a]isoquinolin-3-yl)phosphonate as a grey solid (13 mg, 10% yield, m/z: 512 [M+H]$^+$ observed). $^1$H NMR (400 MHz, DMSO-d$_6$) δ 8.08 (d, J=13.2 Hz, 1H), 7.99 (s, 1H), 7.25 (s, 1H), 6.81 (d, 1H), 4.38 (s, 1H), 4.22-4.14 (m, 2H), 4.08-4.01 (m, 4H), 3.51 (t, J=6 Hz, 2H), 3.33 (s, 2H), 3.26 (s, 3H), 2.01 (t, J=6 Hz, 2H), 1.24 (t, J=7.2 Hz, 6H), 0.72 (s, 9H).

Example 106: Ethyl hydrogen (6-(tert-butyl)-10-chloro-9-(3-methoxypropoxy)-2-oxo-6,7-dihydro-2H-pyrido[2,1-a]isoquinolin-3-yl)phosphonate

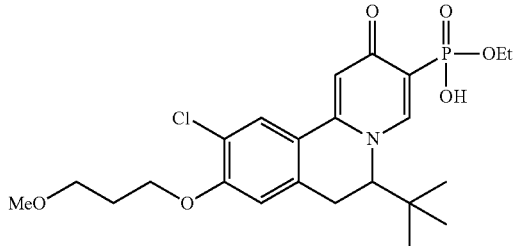 [SMILES: CCOP(=O)(O)c1cn2c(cc1=O)-c1cc(Cl)c(OCCCOC)cc1CC2C(C)(C)C]

To a stirred solution of diethyl (6-(tert-butyl)-10-chloro-9-(3-methoxypropoxy)-2-oxo-6,7-dihydro-2H-pyrido[2,1-a]isoquinolin-3-yl)phosphonate (0.15 g, 0.29 mmol) in CH$_2$Cl$_2$ (4 mL) was added chlorotrimethylsilane (0.08 ml, 0.6 mmol) at 0° C. and stirred at rt for 16 h. The reaction was evaporated in vacuum to obtain crude. The residue was purified by reverse phase HPLC to afford ethyl hydrogen (6-(tert-butyl)-10-chloro-9-(3-methoxypropoxy)-2-oxo-6,7-dihydro-2H-pyrido[2,1-a]isoquinolin-3-yl)phosphonate as a brown solid (20 mg, 15% yield, m/z: 484 [M+H]$^+$ observed). $^1$H NMR (400 MHz, DMSO-d$_6$) δ 8.17-8.14 (d, J=11.6 Hz, 1H), 8.00 (s, 1H), 7.26 (s, 1H), 6.96 (s, 1H), 4.38 (s, 1H), 4.19-4.15 (m, 2H), 3.70-3.67 (m, 3H), 3.53-3.50 (m, 2H), 3.33 (s, 3H), 2.04-1.98 (t, J=6.4 Hz, 2H), 1.24 (s, 1H), 1.09-1.05 (t, J=7.2 Hz, 3H), 0.72 (s, 9H).

Example 107: (6-(Tert-butyl)-10-chloro-9-(3-methoxypropoxy)-2-oxo-6,7-dihydro-2H-pyrido[2,1-a]isoquinolin-3-yl)phosphonic acid

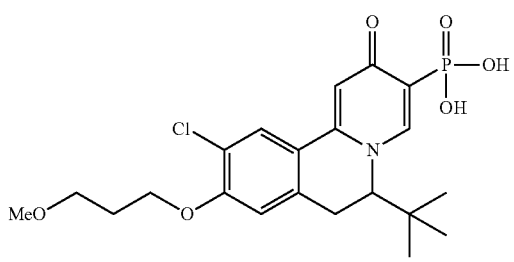 [SMILES: COCCCOc1cc2c(cc1Cl)-c1cc(=O)c(P(=O)(O)O)cn1C(C(C)(C)C)C2]

To a stirred solution of diethyl (6-(tert-butyl)-10-chloro-9-(3-methoxypropoxy)-2-oxo-6,7-dihydro-2H-pyrido[2,1-a]isoquinolin-3-yl)phosphonate (0.250 g, 0.49 mmol) in CH$_2$Cl$_2$ (10 mL) was added iodotrimethylsilane (0.35 mL, 2.44 mmol) at rt and the reaction was stirred for 6 h. The reaction was evaporated in vacuum. The residue was purified by reverse phase HPLC to afford (6-(tert-butyl)-10-chloro-9-(3-methoxypropoxy)-2-oxo-6,7-dihydro-2H-pyrido[2,1-a]isoquinolin-3-yl)phosphonic acid as an off-white solid (20 mg, 15% yield, m/z: 456 [M+H]$^+$ observed). $^1$H NMR (400 MHz, DMSO-d$_6$) δ 8.23-8.19 (d, J=11.2 Hz, 1H), 7.98 (s, 1H), 7.26 (s, 1H), 6.96 (s, 1H), 4.39 (s, 1H), 4.24-4.12 (m, 2H), 3.52-3.49 (t, J=6 Hz, 2H), 3.31-3.25 (m, 5H), 2.02-1.99 (t, J=6 Hz, 2H), 0.70 (s, 9H).

Example 108: (S)-6-Isopropyl-2-methoxy-3-(3-methoxypropoxy)-9-(5-methyl-1,3,4-thiadiazol-2-yl)-5,6-dihydro-10H-pyrido[1,2-h][1,7]naphthyridin-10-one

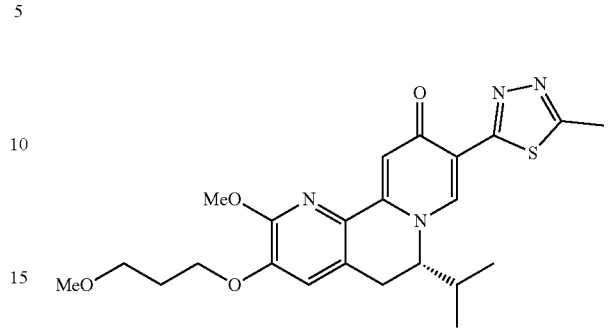

(6S)-6-isopropyl-2-methoxy-3-(3-methoxypropoxy)-10-oxo-5H,6H-pyrido[1,2-h]1,7-naphthyridine-9-carboxylic acid (60 mg, 0.15 mmol) was dissolved in CH$_2$Cl$_2$ (2 mL) and stirred at 0° C. Phosphorus pentachloride (38 mg, 0.18 mmol) was added and the mixture stirred at 0° C. for 15 min. Acetohydrazide (22 mg, 0.30 mmol) in (1 mL) was added into the above solution dropwise and the reaction stirred at rt for 3 h. The solvent was removed under vacuum. Lawesson reagent (30 mg, 0.07 mmol) was added, followed by 1,4-dioxane (4 mL). The reaction was heated to 100° C. for 1 h. Additional Lawesson reagent (30 mg, 0.07 mmol) was added. The reaction was stirred at 100° C. for 3 days. The reaction mixture was concentrated under vacuum. The residue was purified by reverse phase HPLC to afford 1-[1-(hydroxymethyl) cyclohexyl]-4-oxo-pyridine-3-carboxylate, followed by normal phase SiO$_2$ chromatography (0% to 10% MeOH/CH$_2$Cl$_2$) to afford (6S)-6-isopropyl-2-methoxy-3-(3-methoxypropoxy)-9-(5-methyl-1,3,4-thiadiazol-2-yl)-5H,6H-pyrido[1,2-h]1,7-naphthyridin-10-one as a light yellow solid (3.1 mg, 5% yield, m/z: 457 [M+H]$^+$ observed). $^1$H NMR (400 MHz, CDCl$_3$) δ 8.73 (s, 1H), 7.59 (s, 1H), 6.91 (s, 1H), 4.14-4.09 (m, 2H), 4.08 (s, 3H), 3.91 (dd, J=9.6, 5.4 Hz, 1H), 3.58 (td, J=6.0, 1.6 Hz, 2H), 3.40 (dd, J=16.3, 5.7 Hz, 1H), 3.36 (s, 3H), 3.06 (dd, J=16.5, 1.5 Hz, 1H), 2.80 (s, 3H), 2.15 (p, J=6.2 Hz, 2H), 2.03-1.92 (m, 1H), 0.97 (d, J=6.7 Hz, 3H), 0.86 (d, J=6.8 Hz, 3H).

Example 109: (S)-6-Isopropyl-2-methoxy-3-(3-methoxypropoxy)-9-(5-thioxo-4,5-dihydro-1H-1,2,4-triazol-3-yl)-5,6-dihydro-10H-pyrido[1,2-h][1,7]naphthyridin-10-one

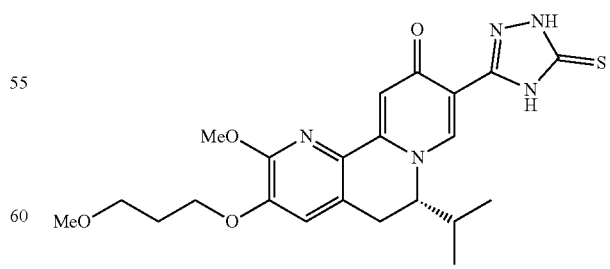

(6S)-6-isopropyl-2-methoxy-3-(3-methoxypropoxy)-10-oxo-5H,6H-pyrido[1,2-h]1,7-naphthyridine-9-carboxylic acid (60 mg, 0.15 mmol) was dissolved in CH$_2$Cl$_2$ (2 mL) and the mixture was stirred at 0° C. Phosphorus pentachloride (37 mg, 0.18 mmol) was added and reaction was stirred at 0° C. for 15 min. Hydrazinecarbothioamide (19 mg, 0.21 mmol) was added into the above solution, followed by CH₃CN/THF mixture (1:1, 2 mL) to solubilize the thiohydrazide. The reaction was stirred at room temperature for 2 h. The solvent was removed under vacuum. Sodium hydroxide (30 mg, 0.75 mmol) was added, followed by H₂O (3 mL) and the reaction was stirred at 100° C. for 16 h. The mixture was cooled to rt and 1N HCl was added to adjust the pH to 4-5. The aqueous solution was extracted with CH₂Cl₂ (3×5 mL). The combined organic fractions were dried over sodium sulfate and concentrated under vacuum. The residue was purified by reverse phase HPLC to afford (6S)-6-isopropyl-2-methoxy-3-(3-methoxypropoxy)-9-(5-sulfanylidene-1,4-dihydro-1,2,4-triazol-3-yl)-5H,6H-pyrido[1,2-h]1,7-naphthyridin-10-one as a yellow solid (13 mg, 18% yield, m/z: 458 [M+H]⁺ observed). ¹H NMR (400 MHz, CDCl₃) δ 8.73 (s, 1H), 7.74 (s, 1H), 6.91 (s, 1H), 4.29 (s, 1H), 4.16 (s, 2H), 4.00 (s, 3H), 3.57-3.59 (m, 3H), 3.37 (s, 3H), 3.08 (d, J=16.6 Hz, 1H), 2.23-2.06 (m, 2H), 2.01-1.80 (m, 1H), 0.93 (d, J=6.6 Hz, 3H), 0.81 (dd, J=17.1, 6.7 Hz, 3H).

Example 110: (S)-6-Isopropyl-2-methoxy-3-(3-methoxypropoxy)-9-(1,3,4-oxadiazol-2-yl)-5,6-dihydro-10-pyrido[1,2-h][1,7]naphthyridin-10-one

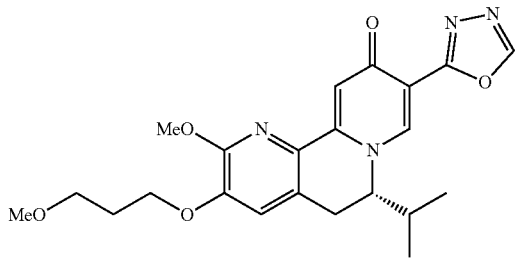 [SMILES: COCCCOc1cc2c(nc1OC)-c1cc(=O)c(-c3nnco3)cn1[C@H](C(C)C)C2]

To a solution of (6S)-6-isopropyl-2-methoxy-3-(3-methoxypropoxy)-10-oxo-5H,6H-pyrido[1,2-h]1,7-naphthyridine-9-carboxylic acid (60 mg, 0.15 mmol) in CH₂Cl₂ (2 mL) at 0° C. was added phosphorus pentachloride (47 mg, 0.22 mmol). The reaction was stirred for 10 minutes. A solution hydrazine monohydrate (11 mg, 0.22 mmol) in CH₂Cl₂ (0.5 mL) was added to the reaction dropwise. The mixture was stirred for 2 h. Check LCMS. The mixture was concentrated under vacuum. Trimethyl orthoformate (0.8 mL, 7.5 mmol) was added and the reaction was stirred at 135° C. for 16 h. The solvent was removed under vacuum. The residue was purified by reverse phase HPLC to afford (6S)-6-isopropyl-2-methoxy-3-(3-methoxypropoxy)-9-(1,3,4-oxadiazol-2-yl)-5H,6H-pyrido[1,2-h]1,7-naphthyridin-10-one as a yellow solid (5 mg, 8% yield, m/z: 427 [M+H]⁺ observed). ¹H NMR (400 MHz, CDCl₃) δ 8.56 (s, 1H), 8.48 (s, 1H), 7.78 (s, 1H), 6.91 (s, 1H), 4.18 (d, J=5.0 Hz, 2H), 4.07 (s, 3H), 3.94 (s, 1H), 3.58 (t, J=5.9 Hz, 2H), 3.43 (d, J=12.9 Hz, 1H), 3.36 (s, 3H), 3.08 (d, J=16.4 Hz, 1H), 2.24-2.08 (m, 2H), 1.99 (d, J=7.4 Hz, 1H), 0.98 (d, J=6.6 Hz, 3H), 0.86 (d, J=6.6 Hz, 3H).

Example 111: (S)-6-isopropyl-2-methoxy-3-(3-methoxypropoxy)-9-(3-methyl-1,2,4-oxadiazol-5-yl)-5,6-dihydro-10H-pyrido[1,2-h][1,7]naphthyridin-10-one

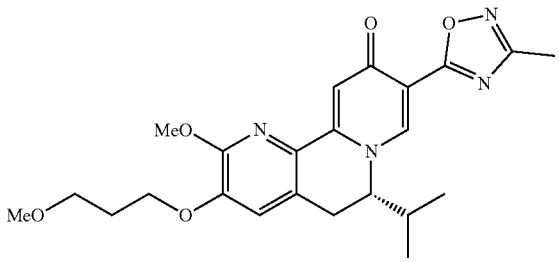 [SMILES: COCCCOc1cc2c(nc1OC)-c1cc(=O)c(-c3nc(C)no3)cn1[C@H](C(C)C)C2]

To a solution of (6S)-6-isopropyl-2-methoxy-3-(3-methoxypropoxy)-10-oxo-5H,6H-pyrido[1,2-h]1,7-naphthyridine-9-carboxylic acid (60 mg, 0.15 mmol) in CH₂Cl₂ (3 mL) at 0° C. was added phosphorus pentachloride (37 mg, 0.18 mmol). The reaction was stirred at 0° C. for 15 minutes. N-hydroxyethanimidamide (13 mg, 0.18 mmol) was added to the reaction, followed by THF (2 mL). The reaction was stirred at room temperature for 16 h. The solvent was removed under vacuum and the crude mixture was re-dissolved in DMF (2 mL). The reaction was heated to 110° C. for 24 h. The DMF was removed under vacuum. The residue was purified by normal phase SiO₂ chromatography (0% to 5% MeOH/CH₂Cl₂) to afford (6S)-6-isopropyl-2-methoxy-3-(3-methoxypropoxy)-9-(3-methyl-1,2,4-oxadiazol-5-yl)-5H, 6H-pyrido[1,2-h]1,7-naphthyridin-10-one as a white solid (13 mg, 19% yield, m/z: 441[M+H]⁺ observed). ¹H NMR (400 MHz, CDCl₃) δ 8.29 (s, 1H), 7.51 (s, 1H), 6.89 (s, 1H), 4.16 (td, J=6.5, 4.5 Hz, 2H), 4.04 (s, 3H), 3.82 (dd, J=9.4, 5.3 Hz, 1H), 3.57 (td, J=6.1, 1.6 Hz, 2H), 3.43-3.37 (m, 1H), 3.36 (s, 3H), 3.04 (dd, J=16.6, 1.5 Hz, 1H), 2.47 (s, 3H), 2.14 (p, J=6.3 Hz, 2H), 1.94 (dt, J=9.5, 6.7 Hz, 1H), 0.96 (d, J=6.7 Hz, 3H), 0.85 (d, J=6.7 Hz, 3H).

Example 112: (S)-6-Isopropyl-2-methoxy-3-(3-methoxypropoxy)-9-(3-phenyl-1,2,4-oxadiazol-5-yl)-5,6-dihydro-10H-pyrido[1,2-h][1,7]naphthyridin-10-one

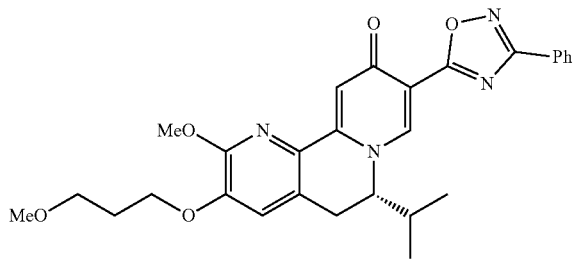 [SMILES: COCCCOc1cc2c(nc1OC)-c1cc(=O)c(-c3nc(-c4ccccc4)no3)cn1[C@H](C(C)C)C2]

To a solution of (6S)-6-isopropyl-2-methoxy-3-(3-methoxypropoxy)-10-oxo-5H,6H-pyrido[1,2-h]1,7-naphthyridine-9-carboxylic acid (60 mg, 0.15 mmol) in CH₂Cl₂ (3 mL) at 0° C. was added phosphorus pentachloride (37 mg, 0.18 mmol). The reaction was stirred at 0° C. for 15 minutes. N-hydroxybenzenecarboximidamide (24 mg, 0.18 mmol) was added to the reaction, followed by THF (2 mL). The reaction was stirred at room temperature for 16 h. The solvent was removed under vacuum and the crude mixture was re-dissolved in DMF (2 mL). The reaction was heated to 110° C. for 24 h. The DMF was removed under vacuum. The residue was purified by reverse phase HPLC to afford (S)-6-isopropyl-2-methoxy-3-(3-methoxypropoxy)-9-(3-phenyl-1,2,4-oxadiazol-5-yl)-5,6-dihydro-10H-pyrido[1,2-h][1,7]naphthyridin-10-one as a white solid (4 mg, 5% yield, m/z: 503 [M+H]$^+$ observed). $^1$H NMR (400 MHz, CDCl$_3$) δ 8.70 (s, 1H), 8.10 (dd, J=7.9, 1.8 Hz, 2H), 7.99 (s, 1H), 7.53-7.42 (m, 3H), 6.93 (s, 1H), 4.18 (tt, J=6.6, 3.3 Hz, 3H), 4.04 (s, 3H), 3.66-3.52 (m, 3H), 3.38 (d, J=0.5 Hz, 3H), 3.13 (d, J=16.7 Hz, 1H), 2.15 (p, J=6.3 Hz, 2H), 2.07-1.95 (m, 1H), 1.01 (d, J=6.6 Hz, 3H), 0.87 (d, J=6.7 Hz, 3H).

Example 113: (S)-6-Isopropyl-2-methoxy-3-(3-methoxypropoxy)-10-oxo-5,10-dihydro-6H-pyrido [1,2-h][1,7]naphthyridine-9-carbonitrile

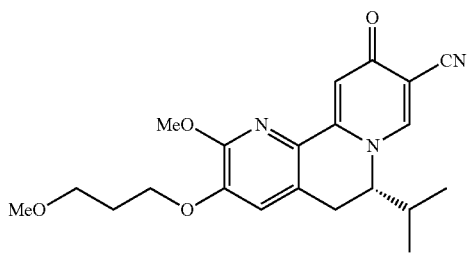 [SMILES: COCCCOc1cc2c(nc1OC)-c1cc(=O)c(C#N)cn1[C@H](C(C)C)C2]

To a solution of 6-isopropyl-2-methoxy-3-(3-methoxypropoxy)-10-oxo-5H,6H-pyrido[1,2-h]1,7-naphthyridine-9-carboxylic acid (20 mg, 0.05 mmol) in CH$_2$Cl$_2$ (1 mL) at 0° C. was added phosphorus pentachloride (12 mg, 0.06 mmol). The reaction was at 0° C. stirred for 15 minutes. Ammonium hydroxide (28-23% in H$_2$O, 0.02 mL, 0.15 mmol) was added to reaction and the mixture was stirred at rt for 2 h. The solvent was removed under reduced pressure. The residue was purified by normal phase SiO$_2$ chromatography (0% to 5% MeOH/CH$_2$Cl$_2$) to afford the crude amide. The amide was dissolved in a mixture of CH$_3$CN/H$_2$O (1:1, 5 mL). Palladium chloride (4.4 mg, 0.02 mmol) was added and the reaction was stirred at 50° C. for 24 h. The solvent was removed under vacuum. The residue was purified by normal phase SiO$_2$ chromatography (0% to 5% MeOH/CH$_2$Cl$_2$) to afford (S)-6-isopropyl-2-methoxy-3-(3-methoxypropoxy)-10-oxo-5,10-dihydro-6H-pyrido[1,2-h][1,7]naphthyridine-9-carbonitrile as a white solid (2.3 mg, 12% yield, m/z: 384 [M+H]$^+$ observed). $^1$H NMR (400 MHz, CDCl$_3$) δ 7.88-7.74 (m, 1H), 7.40 (s, 1H), 6.89 (s, 1H), 4.15 (td, J=6.5, 4.6 Hz, 2H), 4.01 (s, 3H), 3.78 (dd, J=9.7, 4.8 Hz, 1H), 3.56 (td, J=6.1, 1.7 Hz, 2H), 3.45-3.37 (m, 1H), 3.35 (s, 3H), 3.03 (dd, J=16.6, 1.6 Hz, 1H), 2.24-2.04 (m, 2H), 1.91 (dt, J=9.6, 6.7 Hz, 1H), 0.96 (d, J=6.7 Hz, 3H), 0.84 (d, J=6.7 Hz, 3H).

Example 114: 6-(Tert-butyl)-10-chloro-9-(3-methoxypropoxy)-3-(5-oxo-4,5-dihydro-1H-tetrazol-1-yl)-6,7-dihydro-2H-pyrido [2,1-a]isoquinolin-2-one

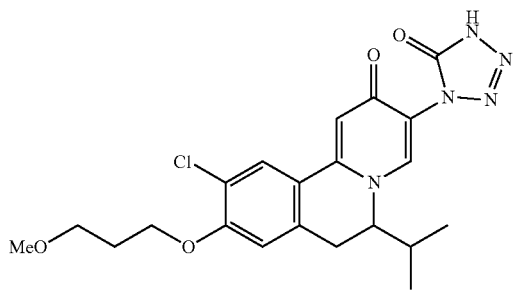 [SMILES: COCCCOc1cc2c(cc1Cl)-c1cc(=O)c(-n3nn[nH]c3=O)cn1C(C(C)C)C2]

A stream of argon gas was bubbled through a solution of 6-(tert-butyl)-10-chloro-9-(3-methoxypropoxy)-2-oxo-6,7-dihydro-2H-pyrido[2,1-a]isoquinoline-3-carboxylic acid (84 mg, 0.2 mmol, synthesized by the procedure described in the patent WO2015113990) in anhydrous CH$_2$Cl$_2$ (5 mL) for 5 min. Triethylamine (0.42 mL, 3 mmol), followed by diphenyl phosphoryl azide (0.3 mL, 1.5 mmol) were added and stirred at rt overnight. The reaction mixture was concentrated under vacuum. The residue was purified by reverse phase HPLC to afford 6-(tert-butyl)-10-chloro-9-(3-methoxypropoxy)-3-(5-oxo-4,5-dihydro-1H-tetrazol-1-yl)-6,7-dihydro-2H-pyrido[2,1-a]isoquinolin-2-one as a grey solid (20 mg, 22% yield, m/z: 460 [M+H]$^+$ observed). $^1$H NMR (300 MHz, CDCl$_3$) δ 8.82 (s, 1H), 8.05 (s, 1H), 7.73 (s, 1H), 7.41 (s, 1H), 6.80 (s, 1H), 4.22-4.15 (m, 2H), 4.05 (d, J=6.6 Hz, 1H), 3.64-3.59 (m, 2H), 3.49-3.42 (m, 1H), 3.37 (s, 3H), 3.24-3.18 (m, 1H), 2.18-2.09 (m, 2H), and 0.83 (bs, 9H).

Example 115: (S)-6-Isopropyl-2-methoxy-3-(3-methoxypropoxy)-9-(1H-tetrazol-5-yl)-5,6-dihydro-10H-pyrido[1,2-h][1,7]naphthyridin-10-one

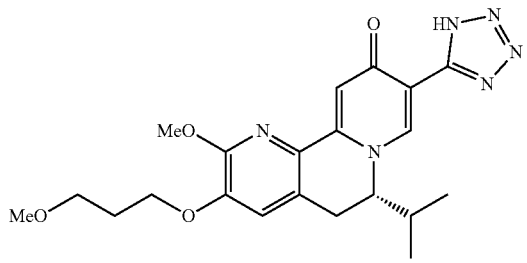 [SMILES: COCCCOc1cc2c(nc1OC)-c1cc(=O)c(-c3nnn[nH]3)cn1[C@H](C(C)C)C2]

To a solution of (6S)-6-isopropyl-2-methoxy-3-(3-methoxypropoxy)-10-oxo-5H,6H-pyrido[1,2-h]1,7-naphthyridine-9-carboxylic acid (70 mg, 0.17 mmol) in CH$_2$Cl$_2$ (3 mL) at 0° C. was added phosphorus pentachloride (43 mg, 0.21 mmol). The reaction was stirred at 0° C. for 15 minutes. Ammonium hydroxide (28-30% in H$_2$O, 0.07 mL, 0.52 mmol) was added to the reaction and the mixture was stirred at rt for 2 h. The solvent was evaporated under vacuum.

The residue was purified by normal phase SiO$_2$ chromatography (0% to 5% MeOH/CH$_2$Cl$_2$) and concentrated under vacuum. The crude amide product was dissolved in CH$_3$CN:H$_2$O (1:1, 5 mL), followed by the addition of palladium chloride (15 mg, 0.09 mmol) and the reaction was stirred at 50° C. for 24 h. The solvent was removed under vacuum. The residue was purified by normal phase SiO₂ chromatography (0% to 5% MeOH/CH₂Cl₂) and concentrated under vacuum. The crude cyano product was dissolved in toluene (1 mL), followed by the addition of sodium azide (113 mg, 1.74 mmol) and triethylamine hydrochloride (239 mg, 1.74 mmol). The reaction was refluxed for 16 h. The pH of the reaction was acidified with 1N HCl to 4-5. The reaction mixture was extracted with EtOAc (3×5 mL). The combined organic fractions were dried over sodium sulfate and concentrated under vacuum. The residue was purified by normal phase SiO₂ chromatography (0% to 5% MeOH/CH₂Cl₂) to afford 6-isopropyl-2-methoxy-3-(3-methoxypropoxy)-9-(1H-1,2,3,4-tetrazol-5-yl)-5H,6H-pyrido[1,2-h]1,7-naphthyridin-10-one as a light brown solid (17 mg, 23% yield, m/z: 427 [M+H]⁺ observed). ¹H NMR (400 MHz, CDCl₃) δ 8.69 (s, 1H), 7.60 (s, 1H), 6.92 (s, 1H), 4.24-4.09 (m, 2H), 4.07 (s, 3H), 3.97 (dd, J=9.5, 5.4 Hz, 1H), 3.58 (td, J=6.1, 1.3 Hz, 2H), 3.43 (dd, J=16.4, 5.6 Hz, 1H), 3.36 (s, 3H), 3.08 (dd, J=16.6, 1.5 Hz, 1H), 2.15 (p, J=6.3 Hz, 2H), 2.02-1.92 (m, 1H), 0.98 (d, J=6.6 Hz, 3H), 0.85 (d, J=6.7 Hz, 3H).

Example 116: (S)-6-Isopropyl-2-methoxy-3-(3-methoxypropoxy)-9-(1H-1,2,4-triazol-5-yl)-5,6-dihydro-10H-pyrido[1,2-h][1,7]naphthyridin-10-one

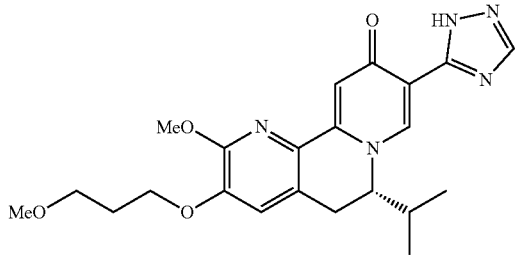 [SMILES: COCCCOc1cc2c(nc1OC)-c1cc(=O)c(-c3ncn[nH]3)cn1[C@H](C(C)C)C2]

To a solution of (6S)-6-isopropyl-2-methoxy-3-(3-methoxypropoxy)-10-oxo-5H,6H-pyrido[1,2-h]1,7-naphthyridine-9-carboxylic acid (60 mg, 0.15 mmol) in CH₂Cl₂ (3 mL) at 0° C. was added phosphorus pentachloride (37 mg, 0.18 mmol) and the reaction was stirred for 30 min. Ammonium hydroxide (28-30% in H₂O, 0.07 mL, 0.52 mmol) was added and the reaction stirred at rt for overnight. H₂O (5 mL) was added and the layers separated. The organic phase was dried over sodium sulfate and concentrated under vacuum. The crude amide product was dissolved in N, N-dimethylformamide dimethyl acetal (1 mL) and stirred at 90° C. for 30 min. The N, N-dimethylformamide dimethyl acetal was removed under vacuum. Glacial acetic acid (2 mL) was added to reaction mixture followed by hydrazine monohydrate (0.03 mL, 0.75 mmol). The reaction was stirred at 95° C. for 30 minutes. The acetic acid was removed under vacuum. The residue was purified by normal phase SiO₂ chromatography (0% to 5% MeOH/CH₂Cl₂) to afford (6S)-6-isopropyl-2-methoxy-3-(3-methoxypropoxy)-9-(2H-1,2,4-triazol-3-yl)-5H,6H-pyrido[1,2-h]1,7-naphthyridin-10-one as a white solid (12 mg, 20% yield, m/z: 426 [M+H]⁺ observed). ¹H NMR (400 MHz, CDCl₃) δ 13.48 (s, 1H), 8.50 (s, 1H), 7.99 (s, 1H), 7.56 (s, 1H), 6.91 (s, 1H), 4.25-4.12 (m, 2H), 4.08 (s, 3H), 3.88 (dd, J=9.6, 5.4 Hz, 1H), 3.58 (td, J=6.1, 1.6 Hz, 2H), 3.36 (d, J=0.5 Hz, 4H), 3.05 (dd, J=16.4, 1.5 Hz, 1H), 2.15 (p, J=6.2 Hz, 2H), 1.97 (dt, J=9.3, 6.7 Hz, 1H), 0.96 (d, J=6.7 Hz, 3H), 0.85 (d, J=6.7 Hz, 3H).

Example 117: (S)—N-Hydroxy-6-isopropyl-2-methoxy-3-(3-methoxypropoxy)-10-oxo-5,10-dihydro-6H-pyrido[1,2-h][1,7]naphthyridine-9-carboxamide

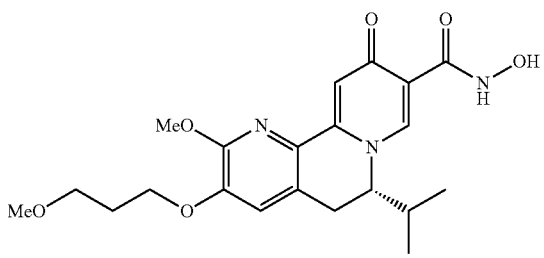 [SMILES: COCCCOc1cc2c(nc1OC)-c1cc(=O)c(C(=O)NO)cn1[C@H](C(C)C)C2]

(6S)-6-Isopropyl-2-methoxy-3-(3-methoxypropoxy)-10-oxo-5H,6H-pyrido[1,2-h]1,7-naphthyridine-9-carboxylic acid (50 mg, 0.12 mmol) was dissolved in a mixture of CH₂Cl₂:thionyl chloride (1:1, 2 mL). The reaction was stirred at 40° C. for 30 min. The solvent was evaporated under vacuum. Residual thionyl chloride was removed by azeotropic evaporation from toluene (2×2 mL) to give a yellow foam. The yellow foam in CH₂Cl₂ (1 mL) was added dropwise to a pre-formed mixture of hydroxylamine hydrochloride (0.03 mL, 0.62 mmol) in CH₂Cl₂ (1 mL) and triethylamine (0.3 mL, 2 mmol). The reaction was stirred at 40° C. for 2 h. The solvent was removed under vacuum. The residue was purified by normal phase SiO₂ chromatography (0% to 6% MeOH/CH₂Cl₂) to afford (6S)—N-hydroxy-6-isopropyl-2-methoxy-3-(3-methoxypropoxy)-10-oxo-5H,6H-pyrido[1,2-h]1,7-naphthyridine-9-carboxamide as a white solid (14 mg, 27% yield, m/z: 418 [M+H]⁺ observed). ¹H NMR (400 MHz, CDCl₃) δ 12.67 (s, 1H), 8.37 (s, 1H), 7.44 (s, 1H), 6.89 (s, 1H), 4.15 (td, J=6.5, 4.5 Hz, 2H), 4.03 (s, 3H), 3.88 (dd, J=9.4, 5.4 Hz, 1H), 3.57 (td, J=6.1, 1.2 Hz, 2H), 3.43-3.25 (m, 4H), 3.02 (dd, J=16.5, 1.5 Hz, 1H), 2.14 (p, J=6.2 Hz, 2H), 1.96-1.80 (m, 1H), 0.93 (d, J=6.7 Hz, 3H), 0.80 (d, J=6.7 Hz, 3H).

Example 118: (S)-6-Isopropyl-2-methoxy-3-(3-methoxypropoxy)-N-(methylsulfonyl)-10-oxo-5,10-dihydro-6H-pyrido[1,2-h][1,7]naphthyridine-9-carboxamide

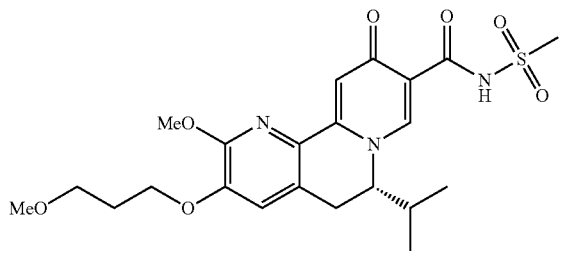 [SMILES: COCCCOc1cc2c(nc1OC)-c1cc(=O)c(C(=O)NS(C)(=O)=O)cn1[C@H](C(C)C)C2]

(6S)-6-Isopropyl-2-methoxy-3-(3-methoxypropoxy)-10-oxo-5H,6H-pyrido[1,2-h]1,7-naphthyridine-9-carboxylic acid (50 mg, 0.12 mmol) in a mixture of CH₂Cl₂:thionyl chloride (1:1, 2 mL) solution. The reaction was stirred at 40° C. for 30 min. The solvent was removed under vacuum. Residual thionyl chloride was removed by azeotropic evaporation from toluene (2×2 mL) to give a yellow foam. The yellow foam in CH$_2$Cl$_2$ (1 mL) was added dropwise to a pre-formed mixture of methanesulfonamide (18 mg, 0.19 mmol) in CH$_2$Cl$_2$ (1 mL) and triethylamine (0.3 mL, 2 mmol). The reaction was stirred at 40° C. for 2 h. The solvent was removed under vacuum. The residue was purified by normal phase SiO$_2$ chromatography (0% to 6% MeOH/CH$_2$Cl$_2$) to afford (6S)-6-isopropyl-N-methanesulfonyl-2-methoxy-3-(3-methoxypropoxy)-10-oxo-5H,6H-pyrido[1,2-h]1,7-naphthyridine-9-carboxamide as a white solid (9 mg, 15% yield, m/z: 480 [M+H]$^+$ observed). $^1$H NMR (400 MHz, CDCl$_3$) δ 13.87 (s, 1H), 8.44 (s, 1H), 7.54 (s, 1H), 6.91 (s, 1H), 4.17 (td, J=6.5, 4.8 Hz, 2H), 4.05 (s, 3H), 3.92 (dd, J=9.6, 5.3 Hz, 1H), 3.57 (td, J=6.1, 1.7 Hz, 2H), 3.36 (m, 7H), 3.06 (dd, J=16.8, 1.6 Hz, 1H), 2.14 (q, J=6.1 Hz, 2H), 2.07-1.69 (m, 1H), 0.97 (d, J=6.7 Hz, 3H), 0.81 (d, J=6.7 Hz, 3H).

Example 119: Tert-butyl N-[6-tert-butyl-10-chloro-9-(3-methoxypropoxy)-2-oxo-6H,7H-pyrido[2,1-a]isoquinolin-3-yl]carbamate

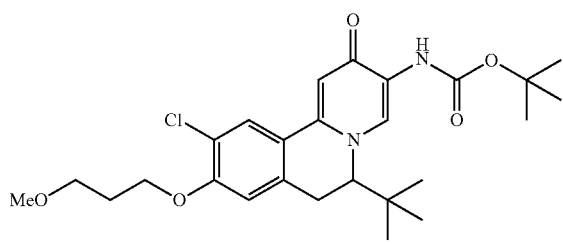 [SMILES: COCCCOc1cc2c(cc1Cl)-c1cc(=O)c(NC(=O)OC(C)(C)C)cn1C(C(C)(C)C)C2]

To a solution of 6-tert-butyl-10-chloro-9-(3-methoxypropoxy)-2-oxo-6H,7H-pyrido[2,1-a]isoquinoline-3-carboxylic acid (250 mg, 0.60 mmol) in tert-butyl alcohol (5 mL) were added potassium t-butoxide (81 mg, 0.71 mmol) and diphenylphosphoryl azide (200 mg, 0.71 mmol) under nitrogen atmosphere. The mixture was refluxed for 12 h, then cooled to room temperature, and diluted with EtOAc (15 mL). The organic phase was washed with sat. aqueous NaHCO$_3$ solution (15 mL), then sat. aqueous brine, dried over magnesium sulfate and concentrated under reduced pressure to give a yellowish oil. The residue was purified by normal phase SiO$_2$ chromatography (0% to 5% MeOH/CH$_2$Cl$_2$) to afford tert-butyl N-[6-tert-butyl-10-chloro-9-(3-methoxypropoxy)-2-oxo-6H,7H-pyrido[2,1-a]isoquinolin-3-yl]carbamate as a white solid (0.21 g, 73% yield, m/z: 491 [M+H]$^+$ observed). $^1$H NMR (300 MHz, CDCl$_3$) δ 8.37 (s, 1H), 7.67 (d, J=15.7 Hz, 2H), 6.83-6.64 (m, 2H), 4.15 (d, J=6.8 Hz, 2H), 3.85 (d, J=6.3 Hz, 1H), 3.59 (t, J=5.6 Hz, 2H), 3.47-3.23 (m, 4H), 3.22-3.03 (m, 1H), 2.22-1.92 (m, 2H), 1.54-1.27 (m, 9H), 0.99-0.53 (m, 9H).

Example 120: 3-Amino-6-tert-butyl-10-chloro-9-(3-methoxypropoxy)-6H,7H-pyrido[2,1-a]isoquinolin-2-one hydrochloride

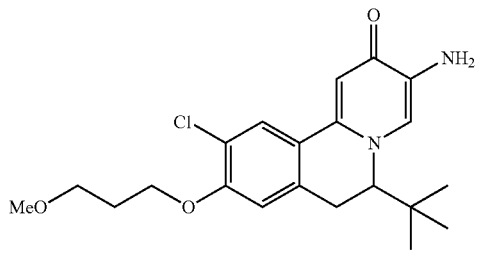 [SMILES: COCCCOc1cc2c(cc1Cl)-c1cc(=O)c(N)cn1C(C(C)(C)C)C2]

Tert-butyl N-[6-tert-butyl-10-chloro-9-(3-methoxypropoxy)-2-oxo-6H,7H-pyrido[2,1-a]isoquinolin-3-yl]carbamate (200 mg, 0.41 mmol) was dissolved in anhydrous CH$_2$Cl$_2$ (4 mL) and hydrogen chloride solution (4N in 1,4-dioxane, 0.41 mL, 1.63 mmol) was added. The mixture was stirred at rt overnight. The resulting precipitate was filtered, washed with CH$_2$Cl$_2$ (2×5 mL), then dried to give 3-amino-6-tert-butyl-10-chloro-9-(3-methoxypropoxy)-6H,7H-pyrido[2,1-a]isoquinolin-2-one, HCl salt as a dark pink solid (0.16 g, 99% yield, m/z: 391 [M+H]$^+$ observed). $^1$H NMR (300 MHz, DMSO-d$_6$) δ ppm 7.79-7.89 (m, 1H), 7.66-7.77 (m, 1H), 7.49-7.61 (m, 1H), 7.26-7.37 (m, 1H), 5.66-6.00 (m, 2H), 4.43-4.53 (m, 1H), 4.05-4.24 (m, 2H), 3.30-3.55 (m, 4H), 3.22 (d, J=1.47 Hz, 3H), 1.91-2.05 (m, 2H), 0.71 (bs, 9H).

Example 121: N-[6-Tert-butyl-10-chloro-9-(3-methoxypropoxy)-2-oxo-6H,7H-pyrido[2,1-a]isoquinolin-3-yl]acetamide

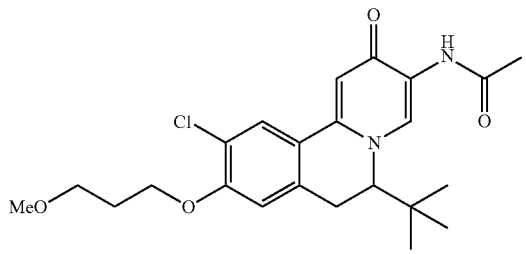 [SMILES: COCCCOc1cc2c(cc1Cl)-c1cc(=O)c(NC(C)=O)cn1C(C(C)(C)C)C2]

3-amino-6-tert-butyl-10-chloro-9-(3-methoxypropoxy)-6H, 7H-pyrido[2,1-a]isoquinolin-2-one, hydrochloride salt (15 mg, 0.04 mmol) and triethylamine (0.01 mL, 0.08 mmol) were dissolved in anhydrous CH$_2$Cl$_2$ (1 mL) and cooled to 0° C. Acetyl chloride (0.003 mL, 0.04 mmol) was added dropwise and the mixture was warmed to rt and stirred overnight. The solution was concentrated under vacuum and the crude residue was purified by preparative TLC to give N-[6-tert-butyl-10-chloro-9-(3-methoxypropoxy)-2-oxo-6H,7H-pyrido[2,1-a]isoquinolin-3-yl]acetamide as a white solid (11 mg, 72% yield, m/z: 433 [M+H]$^+$ observed). $^1$H NMR (300 MHz, CDCl$_3$) δ ppm 8.84 (s, 1H), 8.48 (s, 1H), 7.66 (s, 1H), 6.83 (s, 1H), 6.76 (s, 1H), 4.16 (d, J=7.04 Hz, 2H), 3.85-3.92 (m, 1H), 3.60 (d, J=0.88 Hz, 2H), 3.36 (d, J=1.47 Hz, 4H), 3.08-3.18 (m, 1H), 2.20 (s, 3H), 2.12 (t, J=6.01 Hz, 2H), 0.80 (s, 9H).

Example 122: Methyl N-[6-tert-butyl-10-chloro-9-(3-methoxypropoxy)-2-oxo-6H,7H-pyrido[2,1-a]isoquinolin-3-yl]carbamate

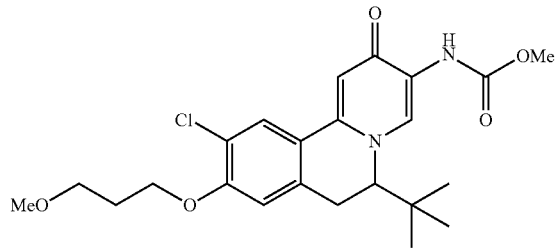 [SMILES: COCCCOc1cc2c(cc1Cl)-c1cc(=O)c(NC(=O)OC)cn1C(C(C)(C)C)C2]

3-Amino-6-tert-butyl-10-chloro-9-(3-methoxypropoxy)-6H, 7H-pyrido[2,1-a]isoquinolin-2-one, hydrochloride salt (15 mg, 0.04 mmol) and triethylamine (0.02 mL, 0.11 mmol) were dissolved in CH$_2$Cl$_2$ (1 mL) and cooled to 0° C. Methyl chloroformate (0.005 mL, 0.04 mmol) was added dropwise and the mixture was warmed to rt and stirred overnight. The reaction was concentrated under reduced pressure. The residue was purified by preparative TLC to give methyl N-[6-tert-butyl-10-chloro-9-(3-methoxypropoxy)-2-oxo-6H,7H-pyrido[2,1-a]isoquinolin-3-yl]carbamate as a tan solid (14 mg, 89% yield, m/z: 449 [M+H]$^+$ observed). $^1$H NMR (300 MHz, CDCl$_3$) δ ppm 8.42 (s, 1H), 7.83-7.91 (m, 1H), 7.61-7.68 (m, 1H), 6.77-6.83 (m, 1H), 6.72-6.77 (m, 1H), 4.11-4.22 (m, 2H), 3.83-3.90 (m, 1H), 3.76 (s, 3H), 3.56-3.65 (m, 2H), 3.36 (s, 4H), 3.06-3.16 (m, 1H), 2.12 (s, 2H), 0.81 (s, 9H).

The following examples were prepared in a similar manner as methyl N-[6-tert-butyl-10-chloro-9-(3-methoxypropoxy)-2-oxo-6H,7H-pyrido[2,1-a]isoquinolin-3-yl]carbamate from 3-amino-6-tert-butyl-10-chloro-9-(3-methoxypropoxy)-6H,7H-pyrido[2,1-a]isoquinolin-2-one, hydrochloride salt and an appropriate chloroformate.

Example 123: Pyridin-2-ylmethyl (6-(tert-butyl)-10-chloro-9-(3-methoxypropoxy)-2-oxo-6,7-dihydro-2H-pyrido[2,1-a]isoquinolin-3-yl)carbamate

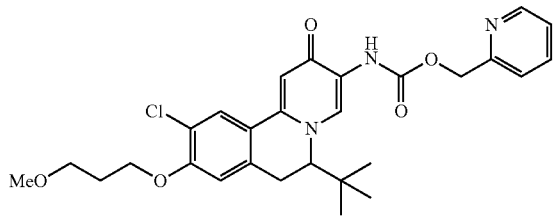 [SMILES: COCCCOc1cc2c(cc1Cl)-c1cc(=O)c(NC(=O)OCc3ccccn3)cn1C(C(C)(C)C)C2]

m/z: 526 [M+H]$^+$ observed. $^1$H NMR (300 MHz, CDCl$_3$) δ ppm 8.58-8.63 (m, 1H), 8.43-8.48 (m, 1H), 8.05-8.11 (m, 1H), 7.70-7.78 (m, 1H), 7.69 (s, 1H), 7.39-7.45 (m, 1H), 7.21-7.26 (m, 1H), 6.85 (s, 1H), 6.77 (s, 1H), 5.34 (d, J=6.45 Hz, 2H), 4.14-4.24 (m, 2H), 3.86-3.92 (m, 1H), 3.58-3.65 (m, 2H), 3.38 (s, 4H), 3.10-3.19 (m, 1H), 2.14 (s, 2H), 0.82 (s, 9H).

Example 124: Neopentyl (6-(tert-butyl)-10-chloro-9-(3-methoxypropoxy)-2-oxo-6,7-dihydro-2H-pyrido[2,1-a]isoquinolin-3-yl)carbamate

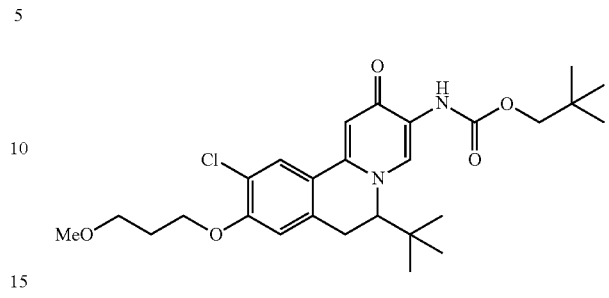

m/z: 505 [M+H]$^+$ observed. $^1$H NMR (300 MHz, CDCl$_3$) δ ppm 8.43 (s, 1H), 7.85-7.90 (m, 1H), 7.64-7.68 (m, 1H), 6.79-6.82 (m, 1H), 6.73-6.77 (m, 1H), 4.11-4.21 (m, 2H), 3.79-3.90 (m, 3H), 3.57-3.63 (m, 2H), 3.36 (s, 4H), 3.08-3.17 (m, 1H), 2.07-2.17 (m, 2H), 0.96 (s, 9H), 0.81 (s, 9H).

Example 125: 1-[6-Tert-butyl-10-chloro-9-(3-methoxypropoxy)-2-oxo-6H,7H-pyrido[2,1-a]isoquinolin-3-yl]pyrrolidine-2,5-dione

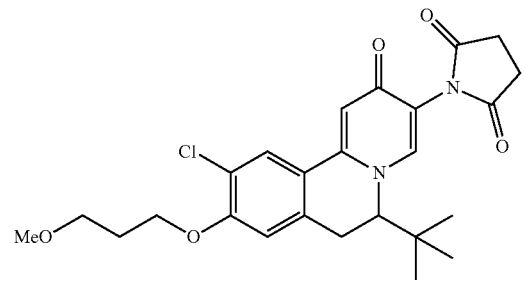 [SMILES: COCCCOc1cc2c(cc1Cl)-c1cc(=O)c(N3C(=O)CCC3=O)cn1C(C(C)(C)C)C2]

Succinic anhydride (6 mg, 0.06 mmol) was dissolved in CH$_2$Cl$_2$ (1 mL) and cooled to 0° C. 3-amino-6-tert-butyl-10-chloro-9-(3-methoxypropoxy)-6H, 7H-pyrido[2,1-a]isoquinolin-2-one, hydrochloride salt (25 mg, 0.06 mmol) and triethylamine (0.003 mL, 0.18 mmol) in CH$_2$Cl$_2$ (0.5 mL) was added dropwise and the reaction was warmed to rt and stirred overnight. Reaction was concentrated under reduced pressured. The residue was purified by preparative TLC to give methyl N-[6-tert-butyl-10-chloro-9-(3-methoxypropoxy)-2-oxo-6H,7H-pyrido[2,1-a]isoquinolin-3-yl]carbamate as a white foam (10 mg, 43% yield, m/z: 473 [M+H]$^+$ observed). $^1$H NMR (300 MHz, CDCl$_3$) δ ppm 7.65-7.68 (m, 1H), 7.38-7.41 (m, 1H), 6.85-6.88 (m, 1H), 6.75-6.78 (m, 1H), 4.12-4.23 (m, 2H), 3.79-3.84 (m, 1H), 3.61 (d, J=1.17 Hz, 2H), 3.39-3.47 (m, 1H), 3.37 (s, 3H), 3.09-3.18 (m, 1H), 2.93-3.06 (m, 2H), 2.74-2.88 (m, 2H), 2.13 (s, 2H), 1.76-0.83 (m, 9H).

Example 126: 3-Tert-butyl-1-[6-tert-butyl-10-chloro-9-(3-methoxypropoxy)-2-oxo-6H,7H-pyrido[2,1-a]isoquinolin-3-yl]urea

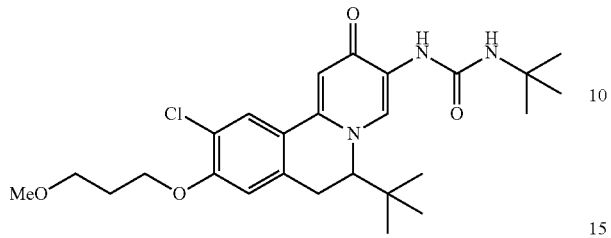

3-Amino-6-tert-butyl-10-chloro-9-(3-methoxypropoxy)-6H,7H-pyrido[2,1-a]isoquinolin-2-one, hydrochloride salt (15 mg, 0.04 mmol), tert-butyl isocyanate (0.004 mL, 0.04 mmol) and triethylamine (0.005 mL, 0.04 mmol) were dissolved in anhydrous THF (2 mL) and the mixture was heated at 80° C. for 6 hours. The reaction was concentrated. The residue was purified by normal phase SiO$_2$ chromatography (50% to 100% EtOAc/hexanes) to furnish 3-tert-butyl-1-[6-tert-butyl-10-chloro-9-(3-methoxypropoxy)-2-oxo-6H,7H-pyrido[2,1-a]isoquinolin-3-yl]urea as a tan solid (5 mg, 25% yield, m/z: 491 [M+H]$^+$ observed). $^1$H NMR (300 MHz, CDCl$_3$): δ ppm 8.94-8.99 (m, 1H), 8.75-8.79 (m, 1H), 7.55 (s, 1H), 7.37-7.42 (m, 1H), 6.71-6.78 (m, 2H), 4.11-4.23 (m, 2H), 3.89-3.96 (m, 1H), 3.57-3.65 (m, 2H), 3.37 (s, 4H), 3.06-3.15 (m, 1H), 2.07-2.18 (m, 2H), 1.47 (s, 9H), 0.81 (s, 9H).

Example 127: N-[6-Tert-butyl-10-chloro-9-(3-methoxypropoxy)-2-oxo-6H,7H-pyrido[2,1-a]isoquinolin-3-yl]-2,2,2-trifluoroethanesulfonamide

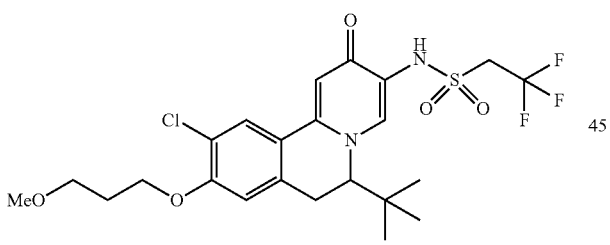

3-Amino-6-tert-butyl-10-chloro-9-(3-methoxypropoxy)-6H,7H-pyrido[2,1-a]isoquinolin-2-one, hydrochloride salt (20 mg, 0.05 mmol) and triethylamine (0.01 mL, 0.09 mmol) were dissolved in CH$_2$Cl$_2$ (1 mL) and cooled to 0° C. 2,2,2-trifluoroethanesulfonyl chloride (0.007 mL, 0.06 mmol) was added dropwise and the mixture was stirred overnight at rt. Reaction was concentrated under reduce pressure. The residue was purified by reverse phase HPLC to afford N-[6-tert-butyl-10-chloro-9-(3-methoxypropoxy)-2-oxo-6H,7H-pyrido[2,1-a]isoquinolin-3-yl]-2,2,2-trifluoroethanesulfonamide as a white solid (5 mg, 18% yield, m/z: 537 [M+H]$^+$ observed). $^1$H NMR (300 MHz, CDCl$_3$) δ ppm 7.96-8.00 (m, 1H), 7.74 (s, 1H), 7.29 (s, 1H), 6.81 (s, 1H), 4.20 (d, J=5.86 Hz, 2H), 4.00-4.06 (m, 2H), 3.87-3.98 (m, 2H), 3.62 (s, 2H), 3.40-3.48 (m, 1H), 3.38 (s, 3H), 3.16-3.26 (m, 1H), 2.14 (t, J=6.01 Hz, 2H), 0.83 (s, 9H).

The following example was prepared in a similar manner as N-[6-tert-butyl-10-chloro-9-(3-methoxypropoxy)-2-oxo-6H,7H-pyrido[2,1-a]isoquinolin-3-yl]-2,2,2-trifluoroethanesulfonamide from 3-amino-6-tert-butyl-10-chloro-9-(3-methoxypropoxy)-6H,7H-pyrido[2,1-a]isoquinolin-2-one, hydrochloride salt and an appropriate sulfonyl chloride.

Example 128: N-(6-(Tert-butyl)-10-chloro-9-(3-methoxypropoxy)-2-oxo-6,7-dihydro-2H-pyrido[2,1-a]isoquinolin-3-yl)-1,1,1-trifluoromethanesulfonamide

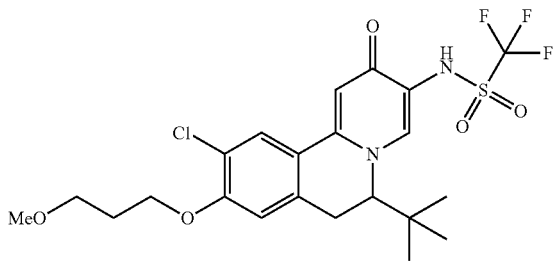 [SMILES: COCCCOc1cc2c(cc1Cl)-c1cc(=O)c(NS(=O)(=O)C(F)(F)F)cn1C(C(C)(C)C)C2]

m/z: 523 [M+H]$^+$ observed. $^1$H NMR (300 MHz, CDCl$_3$) δ 8.03 (s, 1H), 7.72 (s, 1H), 7.29 (s, 1H), 6.81 (s, 1H), 4.29-4.12 (m, 2H), 4.05 (d, J=6.7 Hz, 1H), 3.63 (t, J=5.9 Hz, 2H), 3.46 (dd, J=16.8, 6.7 Hz, 1H), 3.38 (d, J=0.8 Hz, 3H), 3.23 (d, J=16.8 Hz, 1H), 2.14 (p, J=6.1 Hz, 2H), 0.82 (s, 9H).

Example 129: 6-(Tert-butyl)-10-chloro-9-(3-methoxypropoxy)-3-(pyrimidin-2-ylamino)-6,7-dihydro-2H-pyrido[2,1-a]isoquinolin-2-one

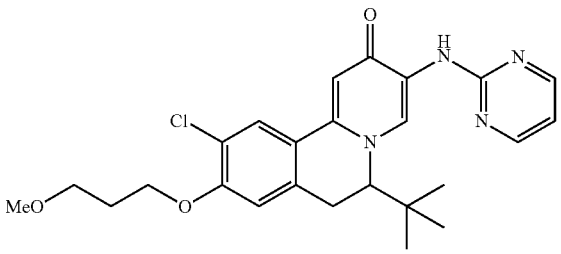 [SMILES: COCCCOc1cc2c(cc1Cl)-c1cc(=O)c(Nc3ncccn3)cn1C(C(C)(C)C)C2]

Example 130: 6-(Tert-butyl)-10-chloro-3-(di(pyrimidin-2-yl)amino)-9-(3-methoxypropoxy)-6,7-dihydro-2H-pyrido[2,1-a]isoquinolin-2-one

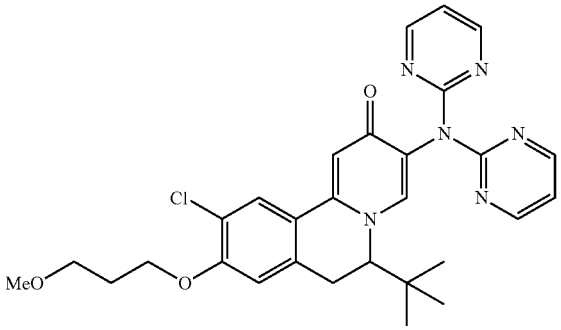 [SMILES: COCCCOc1cc2c(cc1Cl)-c1cc(=O)c(N(c3ncccn3)c3ncccn3)cn1C(C(C)(C)C)C2]

3-Amino-6-tert-butyl-10-chloro-9-(3-methoxypropoxy)-6H,7H-pyrido[2,1-a]isoquinolin-2-one, hydrochloride salt (20 mg, 0.05 mmol) and 2-chloro-pyrimidine (4 mg, 0.12 mmol) were melted and heated neat at 90° C. for 3 minutes. The mixture was purified by reverse phase HPLC to afford:

Example 129: 6-(Tert-butyl)-10-chloro-9-(3-methoxypropoxy)-3-(pyrimidin-2-ylamino)-6,7-dihydro-2H-pyrido[2,1-a]isoquinolin-2-one as a tan solid (8 mg, 37% yield, m/z: 469 [M+H]$^+$ observed). $^1$H NMR (300 MHz, CDCl$_3$) δ ppm 9.02-9.08 (m, 1H), 8.44 (d, J=4.98 Hz, 3H), 7.69 (s, 1H), 6.91 (s, 1H), 6.78 (s, 1H), 6.72 (s, 1H), 4.18 (d, J=6.45 Hz, 2H), 4.00 (d, J=6.45 Hz, 1H), 3.57-3.67 (m, 2H), 3.40-3.50 (m, 1H), 3.38 (s, 3H), 3.17 (d, J=16.42 Hz, 1H), 2.14 (t, J=6.01 Hz, 2H), 0.85 (s, 9H) and Example 130: 6-(Tert-butyl)-10-chloro-3-(di(pyrimidin-2-yl)amino)-9-(3-methoxypropoxy)-6,7-dihydro-2H-pyrido[2,1-a]isoquinolin-2-one as a light green solid (2 mg, 8% yield, m/z: 547 [M+H]$^+$ observed). $^1$H NMR (300 MHz, CDCl$_3$) δ ppm 8.59 (d, J=4.98 Hz, 4H), 8.01-8.05 (m, 1H), 7.92-7.95 (m, 1H), 7.81-7.85 (m, 1H), 6.99-7.08 (m, 2H), 6.78-6.83 (m, 1H), 4.15-4.26 (m, 2H), 3.95-4.02 (m, 1H), 3.59-3.67 (m, 2H), 3.48-3.58 (m, 1H), 3.39 (s, 3H), 3.18-3.28 (m, 1H), 2.10-2.21 (m, 2H), 0.84 (s, 9H).

Example 131: 6-Tert-butyl-10-chloro-3-iodo-9-(3-methoxypropoxy)-6H,7H-pyrido[2,1-a]isoquinolin-2-one

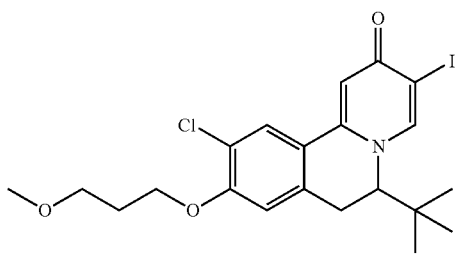 [SMILES: COCCCOc1cc2c(cc1Cl)-c1cc(=O)c(I)cn1C(C(C)(C)C)C2]

3-Amino-6-tert-butyl-10-chloro-9-(3-methoxypropoxy)-6H,7H-pyrido[2,1-a]isoquinolin-2-one, hydrochloride salt (40 mg, 0.09 mmol) was dissolved in HCl (12 N in H$_2$O, 2 mL) and the mixture was cooled to 0° C. Sodium nitrite (7 mg, 0.10 mmol) was added slowly and the mixture was stirred at 0° C. for 15 min, followed by the addition of a solution of potassium iodide (160 mg, 0.94 mmol) in H$_2$O (1 mL). The reaction mixture was gradually warmed to rt and stirred for 16 h. The reaction was concentrated under reduced pressure. The residue was purified by normal phase SiO$_2$ chromatography (0% to 5% MeOH/CH$_2$Cl$_2$) to furnish 6-tert-butyl-10-chloro-3-iodo-9-(3-methoxypropoxy)-6H,7H-pyrido[2,1-a]isoquinolin-2-one as a dark yellow solid (30 mg, 64% yield, m/z: 502 [M+H]$^+$ observed). $^1$H NMR (300 MHz, CDCl$_3$): δ ppm 7.84-7.90 (m, 1H), 7.68-7.74 (m, 1H), 6.79 (bs, 2H), 4.19 (bs, 2H), 3.83 (bs, 1H), 3.62 (bs, 2H), 3.38 (bs, 4H), 3.14 (d, J=15.24 Hz, 2H), 2.13 (bs, 2H), 0.82 (bs, 9H).

Example 132: 6-Tert-butyl-10-chloro-9-(3-methoxypropoxy)-3-(pyrimidin-2-yl)-6H,7H-pyrido[2,1-a]isoquinolin-2-one

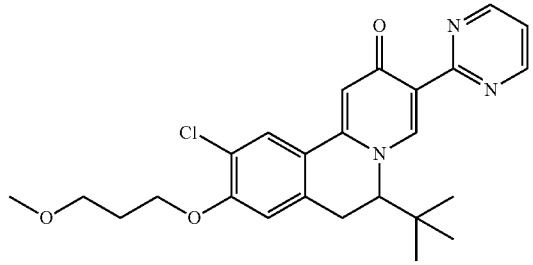 [SMILES: COCCCOc1cc2c(cc1Cl)-c1cc(=O)c(-c3ncccn3)cn1C(C(C)(C)C)C2]

6-Tert-butyl-10-chloro-3-iodo-9-(3-methoxypropoxy)-6H,7H-pyrido[2,1-a]isoquinolin-2-one (30 mg, 0.06 mmol), 2-(tributylstannyl)pyrimidine (0.03 mL, 0.08 mmol), and palladium-tetrakis(triphenylphosphine) (14 mg, 0.01 mmol) were dissolved in 1,4-dioxane (1 mL) in a microwave reaction vial. The vessel was flushed with nitrogen gas, then sealed and heated at 90° C. in a microwave reactor for 1 hour. The reaction was concentrated under reduced pressure. The residue was purified by reverse phase HPLC to afford 6-tert-butyl-10-chloro-9-(3-methoxypropoxy)-3-(pyrimidin-2-yl)-6H,7H-pyrido[2,1-a]isoquinolin-2-one as a white solid (1.2 mg, 4% yield, m/z: 454 [M+H]$^+$ observed). $^1$H NMR (300 MHz, CDCl$_3$) δ ppm 8.81-8.90 (m, 2H), 8.35-8.43 (m, 1H), 7.75-7.79 (m, 1H), 7.18-7.25 (m, 1H), 7.00-7.06 (m, 1H), 6.79 (s, 1H), 4.15-4.25 (m, 2H), 4.04-4.11 (m, 1H), 3.59-3.67 (m, 2H), 3.40-3.49 (m, 1H), 3.39 (s, 3H), 3.15-3.24 (m, 1H), 2.15 (s, 2H), 0.86 (s, 9H).

The following example was prepared in a similar manner as 6-tert-butyl-10-chloro-9-(3-methoxypropoxy)-3-(pyrimidin-2-yl)-6H,7H-pyrido[2,1-a]isoquinolin-2-one from 6-tert-butyl-10-chloro-3-iodo-9-(3-methoxypropoxy)-6H,7H-pyrido[2,1-a]isoquinolin-2-one and an appropriate organotin reagent.

Example 133: 6-(Tert-butyl)-10-chloro-9-(3-methoxypropoxy)-3-(pyridin-2-yl)-6,7-dihydro-2H-pyrido[2,1-a]isoquinolin-2-one

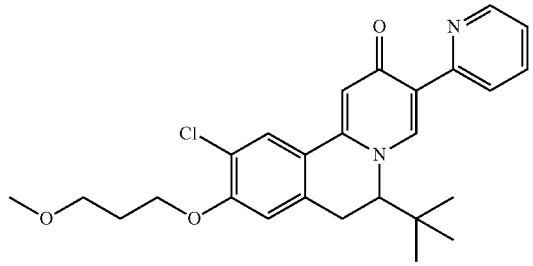 [SMILES: COCCCOc1cc2c(cc1Cl)-c1cc(=O)c(-c3ccccn3)cn1C(C(C)(C)C)C2]

m/z: 453 [M+H]$^+$ observed. $^1$H NMR (300 MHz, CDCl$_3$) δ ppm 8.83-8.90 (m, 1H), 8.51-8.62 (m, 2H), 7.76 (s, 2H), 7.17-7.25 (m, 1H), 6.92-6.97 (m, 1H), 6.79 (s, 1H), 4.15-4.25 (m, 2H), 4.03-4.13 (m, 1H), 3.63 (s, 2H), 3.39 (s, 4H), 3.13-3.23 (m, 1H), 2.15 (t, J=6.16 Hz, 2H), 0.85 (s, 9H).

235

Example 134: Tert-butyl (R)-(2-chloro-7-isopropyl-3-(3-methoxypropoxy)-11-oxo-6,7-dihydro-11H-benzo[f]pyrido[1,2-d][1,4]oxazepin-10-yl)carbamate

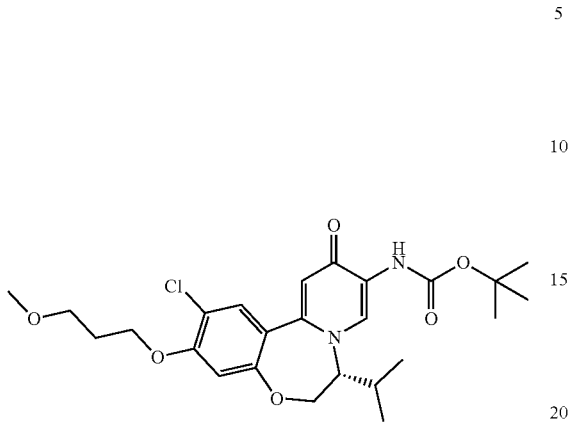

To a solution of (R)-2-chloro-7-isopropyl-3-(3-methoxypropoxy)-11-oxo-6,7-dihydro-11H-benzo[f]pyrido[1,2-d][1,4]oxazepine-10-carboxylic acid (300 mg, 0.71 mmol) in tert-butyl alcohol (5 mL) were added potassium t-butoxide (98 mg, 0.85 mmol) and diphenyl phosphoryl azide (0.18 mL, 0.85 mmol) under nitrogen atmosphere. The mixture was refluxed for 12 h, cooled to room temperature, and diluted with EtOAc (10 mL). The organic phase was washed with sat. aqueous NaHCO$_3$ solution (10 mL), then sat. aqueous brine solution (10 mL), dried over magnesium sulfate and concentrated under reduced pressure to a give a yellowish oil. The residue was purified by normal phase SiO$_2$ chromatography (0% to 5% MeOH/CH$_2$Cl$_2$) to furnish tert-butyl (R)-(2-chloro-7-isopropyl-3-(3-methoxypropoxy)-11-oxo-6,7-dihydro-11H-benzo[f]pyrido[1,2-d][1,4]oxazepin-10-yl)carbamate as an off-white foam (0.18 g, 53% yield, m/z: 493 [M+H]$^+$ observed). $^1$H NMR (300 MHz, CDCl$_3$): δ ppm 8.38 (s, 1H), 7.75 (s, 1H), 7.51 (s, 1H), 6.60 (d, J=2.64 Hz, 2H), 4.53 (s, 2H), 4.09-4.20 (m, 2H), 3.65-3.73 (m, 1H), 3.61 (s, 2H), 3.37 (s, 3H), 2.12 (t, J=6.01 Hz, 2H), 1.95-2.05 (m, 1H), 1.46-1.57 (m, 9H), 1.03 (d, J=6.45 Hz, 3H), 0.87 (d, J=6.74 Hz, 3H).

Example 135: (R)-2-Chloro-7-isopropyl-3-(3-methoxypropoxy)-10-(pyrimidin-2-yl)-6,7-dihydro-11H-benzo[f]pyrido[1,2-d][1,4]oxazepin-11-one

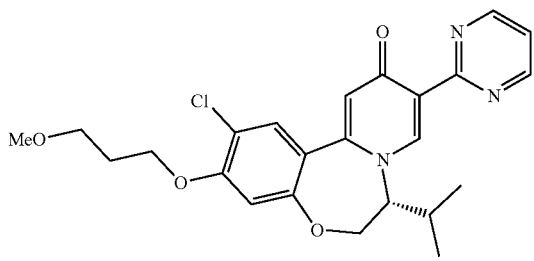 [SMILES: COCCCOc1cc2c(cc1Cl)-c1cc(=O)c(-c3ncccn3)cn1[C@H](C(C)C)CO2]

236

Example 136: (R)-2-Chloro-7-isopropyl-3-(3-methoxypropoxy)-6,7-dihydro-11H-benzo[f]pyrido[1,2-d][1,4]oxazepin-11-one

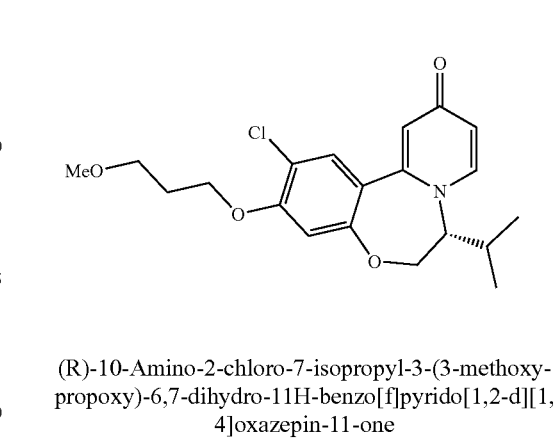

(R)-10-Amino-2-chloro-7-isopropyl-3-(3-methoxypropoxy)-6,7-dihydro-11H-benzo[f]pyrido[1,2-d][1,4]oxazepin-11-one Tert-butyl (R)-(2-chloro-7-isopropyl-3-(3-methoxypropoxy)-11-oxo-6,7-dihydro-11H-benzo[f]pyrido[1,2-d][1,4]oxazepin-10-yl)carbamate (180 mg, 0.37 mmol) was dissolved in 4 ml anhydrous CH$_2$Cl$_2$ (4 mL) and a solution of hydrogen chloride (4N in 1,4-dioxane, 0.46 mL, 1.8 mmol) was added. The mixture was stirred at rt overnight. The resulting precipitate was filtered, washed with CH$_2$Cl$_2$ (5 mL), then dried to give (R)-10-amino-2-chloro-7-isopropyl-3-(3-methoxypropoxy)-6,7-dihydro-11H-benzo[f]pyrido[1,2-d][1,4]oxazepin-11-one, hydrochloride salt as a tan solid (155 mg, 99% yield, m/z: 393 [M+H]$^+$ observed).

(R)-2-Chloro-10-iodo-7-isopropyl-3-(3-methoxypropoxy)-6,7-dihydro-11H-benzo[f]pyrido[1,2-d][1,4]oxazepin-11-one

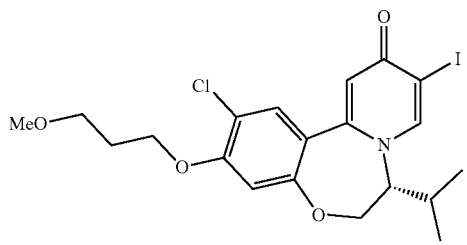 [SMILES: COCCCOc1cc2c(cc1Cl)-c1cc(=O)c(I)cn1[C@H](C(C)C)CO2]

(R)-10-Amino-2-chloro-7-isopropyl-3-(3-methoxypropoxy)-6,7-dihydro-11H-benzo[f]pyrido[1,2-d][1,4]oxazepin-11-one, hydrochloride salt (81 mg, 0.19 mmol) was suspended in concentrated aqueous HCl solution (2 mL), cooled to 0° C., and sodium nitrite (17 mg, 0.25 mmol)

in H₂O (0.5 mL) was added dropwise. The mixture was stirred at 0° C. for 15 min, then a solution of potassium iodide (313 mg, 1.89 mmol) in H₂O (1 mL) was added dropwise. The reaction mixture was stirred at rt for 16 h. After concentration under vacuum, the residue was purified by normal phase SiO₂ chromatography (0% to 5% MeOH/CH₂Cl₂) to furnish (R)-2-chloro-10-iodo-7-isopropyl-3-(3-methoxypropoxy)-6,7-dihydro-11H-benzo[f]pyrido[1,2-d][1,4]oxazepin-11-one as a tan solid (95 mg, 100% yield, m/z: 504 [M+H]⁺ observed).

(R)-2-Chloro-7-isopropyl-3-(3-methoxypropoxy)-10-(pyrimidin-2-yl)-6,7-dihydro-11H-benzo[f]pyrido[1,2-d][1,4]oxazepin-11-one (R)-2-Chloro-7-isopropyl-3-(3-methoxypropoxy)-6,7-dihydro-11H-benzo[f]pyrido[1,2-d][1,4]oxazepin-11-one (R)-2-Chloro-10-iodo-7-isopropyl-3-(3-methoxypropoxy)-6,7-dihydro-11H-benzo[f]pyrido[1,2-d][1,4]oxazepin-11-one (36 mg, 0.07 mmol), 2-(tributylstannyl)pyrimidine (0.04 mL, 0.14 mmol), and palladium-tetrakis(triphenylphosphine) (8 mg, 0.01 mmol) were dissolved in 1,4-dioxane (1 mL) in a microwave reaction vial. The vessel was flushed with nitrogen gas, then sealed and heated at 90° C. in a microwave reactor for 1 hour. The reaction was concentrated under vacuum.

The residue was purified by reverse phase HPLC to afford (R)-2-chloro-7-isopropyl-3-(3-methoxypropoxy)-10-(pyrimidin-2-yl)-6,7-dihydro-11H-benzo[f]pyrido[1,2-d][1,4]oxazepin-11-one as a white solid (3.1 mg, 10% yield), and and (R)-2-chloro-7-isopropyl-3-(3-methoxypropoxy)-6,7-dihydro-11H-benzo[f]pyrido[1,2-d][1,4]oxazepin-11-one as an yellow oil (2.4 mg, 5% yield, m/z).

Example 135: (R)-2-Chloro-7-isopropyl-3-(3-methoxypropoxy)-10-(pyrimidin-2-yl)-6,7-dihydro-11H-benzo[f]pyrido[1,2-d][1,4]oxazepin-11-one; m/z: 456 [M+H]⁺, ¹H NMR (300 MHz, CDCl₃) δ ppm 8.84 (d, J=4.98 Hz, 2H), 8.22 (s, 1H), 7.57 (s, 1H), 7.15-7.21 (m, 1H), 6.79 (s, 1H), 6.60 (s, 1H), 4.52-4.65 (m, 2H), 4.09-4.19 (m, 2H), 3.70-3.79 (m, 1H), 3.60 (s, 2H), 3.37 (s, 3H), 2.05-2.17 (m, 3H), 1.03-1.10 (m, 3H), 0.89-0.95 (m, 3H).

Example 136: (R)-2-Chloro-7-isopropyl-3-(3-methoxypropoxy)-6,7-dihydro-11H-benzo[f]pyrido[1,2-d][1,4]oxazepin-11-one; m/z: 378 [M+H]⁺, ¹H NMR (300 MHz, CDCl₃) δ ppm 7.41 (s, 1H), 7.21 (m, 1H), 6.5 (s, 2H)k 6.24-6.28 (m, 1H)k 4.52-4.65 (m, 2H)k 4.09-4.19 (m, 2H), 3.43-3.60 (m, 3H), 3.25 (s, 3H), 2.05-2.10 (m, 2H), 1.85-1.99 (m, 1H), 0.90-1.0 (m, 3H), 0.75-0.85 (m, 3H).

The following examples were prepared in a similar manner as (R)-2-chloro-7-isopropyl-3-(3-methoxypropoxy)-10-(pyrimidin-2-yl)-6,7-dihydro-11H-benzo[f]pyrido[1,2-d][1,4]oxazepin-11-one from (R)-2-chloro-10-iodo-7-isopropyl-3-(3-methoxypropoxy)-6,7-dihydro-11H-benzo[f]pyrido[1,2-d][1,4]oxazepin-11-one and an appropriate organotin reagent.

Example 137: (R)-2-Chloro-7-isopropyl-3-(3-methoxypropoxy)-10-(3-methylpyridin-2-yl)-6,7-dihydro-11H-benzo[f]pyrido[1,2-d][1,4]oxazepin-11-one

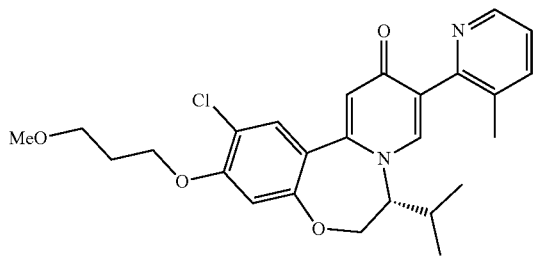 [SMILES: COCCCOc1cc2c(cc1Cl)-c1cc(=O)c(-c3ncccc3C)cn1[C@H](C(C)C)CO2]

m/z: 469 [M+H]⁺ observed. ¹H NMR (300 MHz, CDCl₃) δ ppm 8.45-8.50 (m, 1H), 7.60 (d, J=2.35 Hz, 3H), 7.18-7.25 (m, 1H), 6.72 (s, 1H), 6.61 (s, 1H), 4.55-4.67 (m, 2H), 4.11-4.20 (m, 2H), 3.67-3.75 (m, 1H), 3.62 (s, 2H), 3.38 (s, 3H), 2.39 (s, 3H), 2.10-2.18 (m, 2H), 2.01-2.08 (m, 1H), 1.06 (d, J=6.45 Hz, 3H), 0.90 (d, J=6.45 Hz, 3H).

Example 138: (R)-2-Chloro-7-isopropyl-3-(3-methoxypropoxy)-10-(pyridin-2-yl)-6,7-dihydro-11H-benzo[f]pyrido[1,2-d][1,4]oxazepin-11-one

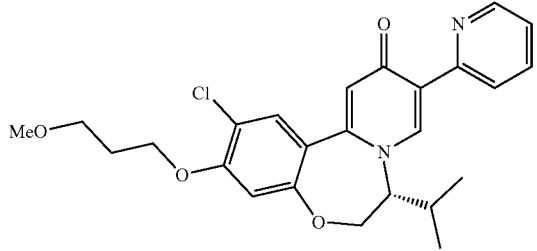 [SMILES: COCCCOc1cc2c(cc1Cl)-c1cc(=O)c(-c3ccccn3)cn1[C@H](C(C)C)CO2]

m/z: 455 [M+H]⁺ observed. ¹H NMR (300 MHz, CDCl₃) δ ppm 8.81-8.89 (m, 1H), 8.51-8.61 (m, 2H), 7.74-7.82 (m, 1H), 7.58 (s, 1H), 7.19-7.26 (m, 1H), 6.77 (s, 1H), 6.62 (s, 1H), 4.60 (d, J=2.64 Hz, 2H), 4.15 (d, J=2.35 Hz, 2H), 3.82-3.93 (m, 1H), 3.62 (s, 2H), 3.38 (s, 3H), 2.13 (s, 3H), 1.08 (d, J=6.74 Hz, 3H), 0.91 (d, J=6.45 Hz, 3H).

Example 139: (R)-2-Chloro-7-isopropyl-10-methoxy-3-(3-methoxypropoxy)-6,7-dihydro-11H-benzo[f]pyrido[1,2-d][1,4]oxazepin-11-one

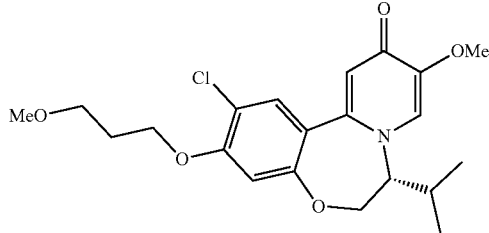 [SMILES: COCCCOc1cc2c(cc1Cl)-c1cc(=O)c(OC)cn1[C@H](C(C)C)CO2]

(R)-2-chloro-10-iodo-7-isopropyl-3-(3-methoxypropoxy)-6,7-dihydro-11H-benzo[f]pyrido[1,2-d][1,4]

oxazepin-11-one (25 mg, 0.05 mmol), copper(I) iodide (1.42 mg, 0.01 mmol) and sodium methoxide (11 mg, 0.20 mmol) were suspended in MeOH (1 mL) and the mixture was heated at 100° C. in a microwave reactor for 10 minutes. Aqueous ammonium chloride solution (1M, 5 mL) was added and the mixture was extracted with EtOAc (3×10 mL). The combined organic phase was dried over anhydrous magnesium sulfate and concentrated under reduced pressure. The reaction was concentrated under vacuum. The residue was purified by reverse phase HPLC to afford (R)-2-chloro-7-isopropyl-10-methoxy-3-(3-methoxypropoxy)-6,7-dihydro-11H-benzo[f]pyrido[1,2-d][1,4]oxazepin-11-one as a white foam (2.8 mg, 14% yield, m/z: 408[M+H]$^+$ observed). $^1$H NMR (300 MHz, CDCl$_3$) δ 7.50 (s, 1H), 7.32 (s, 1H), 7.04 (s, 1H), 6.59 (s, 1H), 4.74-4.61 (m, 1H), 4.56 (d, J=12.8 Hz, 1H), 4.13 (d, J=2.6 Hz, 2H), 3.87 (s, 4H), 3.60 (t, J=6.0 Hz, 2H), 3.37 (d, J=1.4 Hz, 3H), 2.12 (p, J=6.3 Hz, 3H), 1.08 (d, J=6.6 Hz, 3H), 0.84 (d, J=6.5 Hz, 3H).

Example 140: (R)-(2-Chloro-7-isopropyl-3-(3-methoxypropoxy)-11-oxo-6,7-dihydro-11H-benzo[f]pyrido[1,2-d][1,4]oxazepin-10-yl)boronic acid

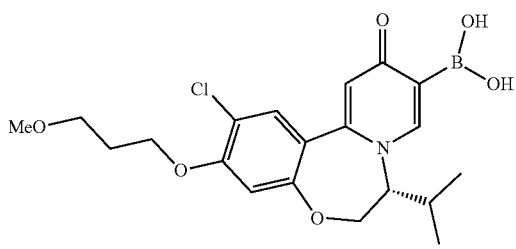 [SMILES: COCCCOc1cc2c(cc1Cl)-c1cc(=O)c(B(O)O)cn1[C@H](C(C)C)CO2]

(R)-2-Chloro-10-iodo-7-isopropyl-3-(3-methoxypropoxy)-6,7-dihydro-11H-benzo[f]pyrido[1,2-d][1,4]oxazepin-11-one (27 mg, 0.054 mmol), bis(pinacolato)diboron (31.30 mg, 0.12 mmol), palladium-tetrakis(triphenylphosphine) (3.10 mg, 0.003 mmol) and potassium carbonate (17 mg, 0.12 mmol) were suspended in a mixture of 1,4-dioxane/water (4:1, 1 mL) and the reaction was heated at 70° C. in a microwave reactor for 10 minutes. The reaction was filtered through Celite® and concentrated under reduced pressure. The residue was purified by reverse phase HPLC to afford (R)-(2-chloro-7-isopropyl-3-(3-methoxypropoxy)-11-oxo-6,7-dihydro-11H-benzo[f]pyrido[1,2-d][1,4]oxazepin-10-yl)boronic acid as a white foam (2.5 mg, 11% yield, m/z: 422[M+H]$^+$ observed). $^1$H NMR (300 MHz, MeOH-d$_4$) δ 7.95 (s, 1H), 7.72 (s, 1H), 7.18 (s, 1H), 6.83 (s, 1H), 4.85-4.76 (m, 1H), 4.69-4.57 (m, 1H), 4.43 (s, 1H), 4.19 (t, J=6.1 Hz, 2H), 3.61 (t, J=6.1 Hz, 2H), 3.38-3.32 (m, 3H), 2.18-1.95 (m, 3H), 1.11 (d, J=6.5 Hz, 3H), 0.77 (d, J=6.6 Hz, 3H).

Example 141: Tert-butyl (R)-(2-chloro-7-isopropyl-3-(3-methoxypropoxy)-11-oxo-6,7-dihydro-11H-benzo[f]pyrido[1,2-d][1,4]oxazepin-10-yl)(methyl)carbamate

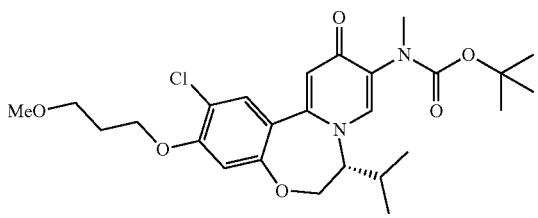 [SMILES: COCCCOc1cc2c(cc1Cl)-c1cc(=O)c(N(C)C(=O)OC(C)(C)C)cn1[C@H](C(C)C)CO2]

Tert-butyl (R)-(2-chloro-7-isopropyl-3-(3-methoxypropoxy)-11-oxo-6,7-dihydro-11H-benzo[f]pyrido[1,2-d][1,4]oxazepin-10-yl)carbamate (15 mg, 0.03 mmol) was dissolved in anhydrous DMF (1 mL) and cooled to 0° C. Sodium hydride (60% dispersion in mineral oil, 1.6 mg, 0.04 mmol) was added under an argon stream and the mixture was stirred at 0° C. for 20 minutes. Methyl iodide (0.002 mL, 0.03 mmol) was added and the reaction was warmed to rt and stirred overnight. The mixture was purified by reverse phase HPLC. The pure fractions were combined, washed with sat. aqueous NaHCO$_3$ solution (20 mL), and extracted with EtOAc (3×25 mL). The combined organic fractions were dried over sodium sulfate and concentrated under vacuum to give tert-butyl (R)-(2-chloro-7-isopropyl-3-(3-methoxypropoxy)-11-oxo-6,7-dihydro-11H-benzo[f]pyrido[1,2-d][1,4]oxazepin-10-yl)(methyl)carbamate as a white foam (11 mg, 72% yield, m/z: 507[M+H]$^+$ observed). $^1$H NMR (300 MHz, CDCl$_3$) δ ppm 7.51-7.54 (m, 1H), 7.35-7.44 (m, 1H), 6.66 (s, 1H), 6.61 (s, 1H), 4.51-4.60 (m, 2H), 4.11-4.19 (m, 2H), 3.61 (t, J=5.86 Hz, 3H), 3.38 (s, 3H), 3.18 (s, 3H), 2.09-2.17 (m, 2H), 1.96-2.05 (m, 1H), 1.45 (bs, 9H), 1.05 (d, J=6.74 Hz, 3H), 0.89 (d, J=6.45 Hz, 3H).

Example 142: 9-Acetyl-6-isopropyl-2-methoxy-3-(3-methoxypropoxy)-5,6-dihydro-10H-pyrido[1,2-h][1,7]naphthyridin-10-one

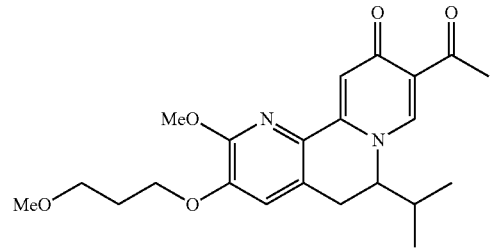 [SMILES: COCCCOc1cc2c(nc1OC)-c1cc(=O)c(C(C)=O)cn1C(C(C)C)C2]

Example 143: 9-(2-Hydroxypropan-2-yl)-6-isopropyl-2-methoxy-3-(3-methoxypropoxy)-5,6-dihydro-10H-pyrido[1,2-h][1,7]naphthyridin-10-one

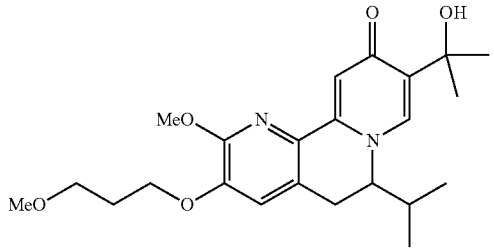 [SMILES: COCCCOc1cc2c(nc1OC)-c1cc(=O)c(C(C)(C)O)cn1C(C(C)C)C2]

Ethyl 6-isopropyl-2-methoxy-3-(3-methoxypropoxy)-10-oxo-5H,6H-pyrido[1,2-h]1,7-naphthyridine-9-carboxylate (59 mg, 0.14 mmol) and copper(I) iodide (57 mg, 0.30 mmol) were suspended in THF (2 mL), then cooled to −78° C. (dry ice/acetone bath) and methylmagnesium bromide solution (3M in in diethyl ether, 0.05 mL, 0.14 mmol) was added dropwise. The mixture was stirred at −78° C. for 1 hour, then another additional equivalent of methylmagnesium bromide solution (3M in in diethyl ether, 0.05 mL, 0.14 mmol) was added. The reaction was further stirred at −78° C. for another 4 hours. The mixture was then warmed to 0° C. and quenched with sat. aqueous ammonium chloride solution (50 mL). The aqueous layer was extracted with EtOAc (3×50 mL). The combined organic fractions were washed with H$_2$O (20 mL), sat. aqueous brine solution (20 mL), dried over sodium sulfate and concentrated under vacuum. The residue was purified by reverse phase HPLC to afford 9-acetyl-6-isopropyl-2-methoxy-3-(3-methoxypropoxy)-5,6-dihydro-10H-pyrido[1,2-h][1,7]naphthyridin-10-one as a yellow oil (1.6 mg, 3% yield), and 9-(2-hydroxypropan-2-yl)-6-isopropyl-2-methoxy-3-(3-methoxypropoxy)-5,6-dihydro-10H-pyrido[1,2-h][1,7]naphthyridin-10-one as an yellow foam (6.4 mg, 11% yield).

Example 142: 9-Acetyl-6-isopropyl-2-methoxy-3-(3-methoxypropoxy)-5,6-dihydro-10H-pyrido[1,2-h][1,7]naphthyridin-10-one; m/z: 401 [M+H]$^+$, $^1$H NMR (400 MHz, CDCl$_3$) δ 8.14 (s, 1H), 7.45 (s, 1H), 6.88 (s, 1H), 4.23-4.09 (m, 2H), 4.06 (d, J=0.4 Hz, 3H), 3.77 (dd, J=9.4, 5.0 Hz, 1H), 3.57 (td, J=6.1, 1.5 Hz, 2H), 3.37-3.30 (m, 4H), 3.05-2.96 (m, 1H), 2.77 (d, J=0.4 Hz, 3H), 2.14 (p, J=6.2 Hz, 2H), 1.95-1.82 (m, 1H), 0.94 (d, J=6.7 Hz, 3H), 0.81 (d, J=6.8 Hz, 3H).

Example 143: 9-(2-Hydroxypropan-2-yl)-6-isopropyl-2-methoxy-3-(3-methoxypropoxy)-5,6-dihydro-10H-pyrido[1,2-h][1,7]naphthyridin-10-one; m/z: 417 [M+H]$^+$, $^1$H NMR (400 MHz, CDCl$_3$) δ 7.34 (s, 1H), 7.25-7.22 (m, 1H), 6.89-6.84 (m, 1H), 4.20-4.06 (m, 3H), 4.04 (s, 3H), 3.72-3.64 (m, 1H), 3.57 (td, J=6.1, 1.3 Hz, 2H), 3.39-3.28 (m, 4H), 2.99 (dd, J=16.4, 1.6 Hz, 1H), 2.13 (p, J=6.2 Hz, 2H), 1.90 (dp, J=9.4, 6.6 Hz, 1H), 1.56 (s, 3H), 1.29-1.19 (m, 2H), 0.93 (d, J=6.7 Hz, 3H), 0.79 (d, J=6.7 Hz, 3H).

Example 144: Methyl 6-tert-butyl-10-chloro-2-(hydroxyimino)-9-(3-methoxypropoxy)-6H,7H-pyrido[2,1-a]isoquinoline-3-carboxylate

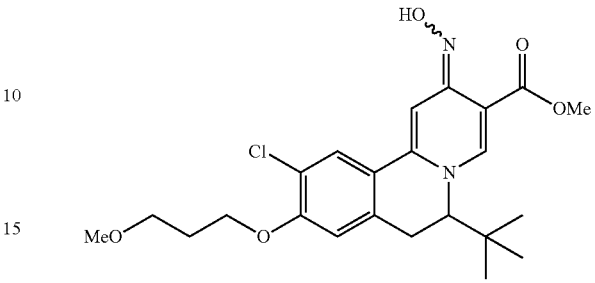

Methyl 6-tert-butyl-10-chloro-9-(3-methoxypropoxy)-2-oxo-6H, 7H-pyrido[2,1-a]isoquinoline-3-carboxylate (0.15 g, 0.35 mmol, prepared according to the procedure in WO2015113990A1) was suspended in thionyl chloride (1.3 mL, 17.3 mmol) and the mixture was heated at 70° C. for 2 hours. The volatile was removed under reduced pressure and the sample was azeotroped with toluene (2×5 mL). The crude chloro-pyridinium salt was dissolved in DMF (3 mL) and cooled to 0° C. Hydroxylamine (50% solution in H$_2$O, 0.04 mL, 0.4 mmol) was added dropwise and the reaction was gradually warmed to rt and stirred overnight. The residue was purified by reverse phase HPLC to afford methyl 6-tert-butyl-10-chloro-2-(hydroxyimino)-9-(3-methoxypropoxy)-6H,7H-pyrido[2,1-a]isoquinoline-3-carboxylate as a yellow solid (0.11 g, 71% yield, m/z: 449 [M+H]$^+$ observed). $^1$H NMR (400 MHz, DMSO-d$_6$) δ 11.49 (s, 1H), 8.79 (s, 1H), 8.19 (s, 1H), 7.63 (s, 1H), 7.31 (s, 1H), 4.63 (d, J=5.2 Hz, 1H), 4.17 (tt, J=9.7, 6.4 Hz, 2H), 3.87 (s, 3H), 3.47 (t, J=6.1 Hz, 2H), 3.42-3.30 (m, 2H), 3.22 (s, 3H), 2.06-1.91 (m, 2H), 0.70 (s, 9H).

Example 145: 6-Tert-butyl-10-chloro-2-(hydroxyimino)-9-(3-methoxypropoxy)-6H,7H-pyrido[2,1-a]isoquinoline-3-carboxylic acid

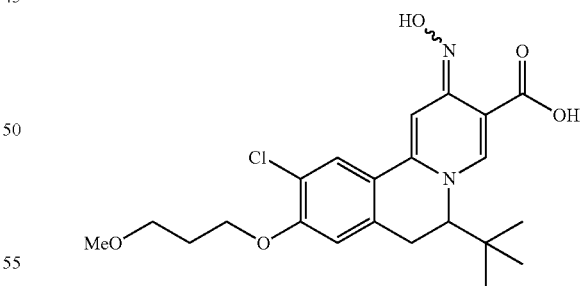

Methyl 10-chloro-2-(hydroxyimino)-6-isopropyl-9-(3-methoxypropoxy)-6H,7H-pyrido[2,1-a]isoquinoline-3-carboxylate (0.07 g, 0.16 mmol) was dissolved in 1,4-dioxane (2 mL) and a solution of sodium hydroxide (0.01 g, 0.32 mmol) in H$_2$O (1 mL) was added. The reaction was stirred at rt for 12 hours. The reaction was diluted with H$_2$O (5 mL) and the solution was acidified with 1N HCl (20 mL). The aqueous layer was extracted with EtOAc (2×15 mL). The combined organic fractions were evaporated under reduced pressure. The residue was purified by reverse phase HPLC to afford 6-tert-butyl-10-chloro-2-(hydroxyimino)-9-(3-methoxypropoxy)-6H,7H-pyrido[2,1-a]isoquinoline-3-carboxylic acid as a white solid (0.03 g, 40% yield, m/z: 435 [M+H]⁺ observed). ¹H NMR (300 MHz, CDCl₃) δ ppm 8.37-8.43 (m, 1H), 7.81 (bs, 1H), 7.45 (bs, 1H), 6.79-6.85 (m, 1H), 4.17-4.26 (m, 2H), 4.10-4.16 (m, 1H), 3.60-3.66 (m, 2H), 3.39 (bs, 3H), 3.18-3.28 (m, 2H), 2.10-2.20 (m, 2H), 0.81 (bs, 9H).

Example 146: 6-(Tert-butyl)-2-chloro-3-(3-methoxypropoxy)-5,6-dihydro-9H-isoxazolo[3',4':4,5]pyrido[2,1-a]isoquinolin-9-one

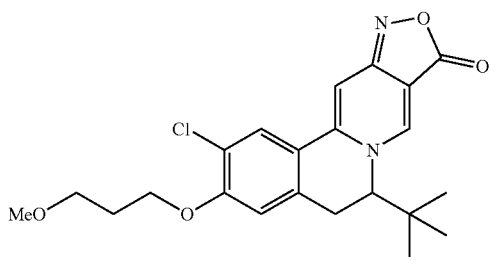 [SMILES: COCCCOc1cc2c(cc1Cl)-c1cc3noc(=O)c-3cn1C(C(C)(C)C)C2]

6-tert-butyl-10-chloro-2-(hydroxyimino)-9-(3-methoxypropoxy)-6H, 7H-pyrido[2,1-a]isoquinoline-3-carboxylic acid (30 mg, 0.07 mmol) was dissolved in anhydrous CH₂Cl₂ (1 mL) and the mixture was cooled to 0° C. Phosphorus pentachloride (16 mg, 0.08 mmol) was added portion-wise and the mixture was stirred at 0° C. until all solids dissolved (10 minutes). The reaction was gradually warmed to rt and stirred for 18 hours. The reaction mixture was concentrated under reduced pressure. The residue was purified by reverse phase HPLC to afford 6-(tert-butyl)-2-chloro-3-(3-methoxypropoxy)-5,6-dihydro-9H-isoxazolo[3',4':4,5]pyrido[2,1-a]isoquinolin-9-one as a white solid (8 mg, 27% yield, m/z: 417 [M+H]⁺ observed). ¹H NMR (300 MHz, CDCl₃) δ 8.05-7.95 (m, 1H), 7.72 (d, J=1.5 Hz, 1H), 7.03 (d, J=1.4 Hz, 1H), 6.79 (s, 1H), 4.19 (q, J=6.5, 6.0 Hz, 2H), 3.96 (d, J=6.3 Hz, 1H), 3.62 (tt, J=6.1, 1.8 Hz, 2H), 3.48-3.27 (m, 4H), 3.20 (d, J=16.6 Hz, 1H), 2.14 (tt, J=7.0, 3.5 Hz, 2H), 0.82 (d, J=1.6 Hz, 9H).

The following examples were prepared in a similar manner as 6-(tert-butyl)-2-chloro-3-(3-methoxypropoxy)-5,6-dihydro-9H-isoxazolo[3',4':4,5]pyrido[2,1-a]isoquinolin-9-one from methyl 6-tert-butyl-10-chloro-9-(3-methoxypropoxy)-2-oxo-6H,7H-pyrido[2,1-a]isoquinoline-3-carboxylate and an appropriate alkyl or alkoxy/hydroxyl amine.

Example 147: 6-(Tert-butyl)-10-methoxy-9-(3-methoxypropoxy)-2-(methylimino)-6,7-dihydro-2H-pyrido[2,1-a]isoquinoline-3-carboxylic acid

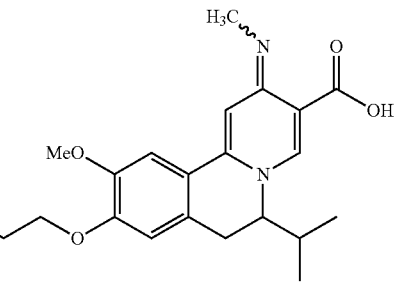

m/z: 415 [M+H]⁺ observed. ¹H NMR (300 MHz, CDCl₃) δ ppm 9.58-9.72 (bs, 1H), 8.50 (bs, 1H), 6.94-7.00 (m, 1H), 6.77 (s, 1H), 6.67 (s, 1H), 4.03-4.12 (m, 2H), 3.88-3.96 (m, 1H), 3.84 (s, 3H), 3.45 (s, 2H), 3.18-3.29 (m, 4H), 2.88-3.05 (m, 4H), 2.02 (t, J=6.16 Hz, 2H), 1.61-1.74 (m, 1H), 0.80 (d, J=6.45 Hz, 3H), 0.67 (d, J=6.74 Hz, 3H).

Example 148: Methyl 6-isopropyl-10-methoxy-2-(methoxyimino)-9-(3-methoxy propoxy)-6,7-dihydro-2H-pyrido[2,1-a]isoquinoline-3-carboxylate

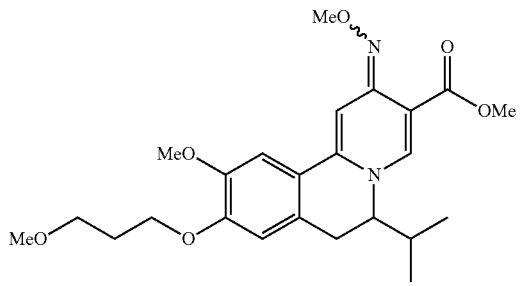 [SMILES: COCCCOc1cc2c(cc1OC)-c1cc(=NOC)c(C(=O)OC)cn1C(C(C)C)C2]

m/z: 445 [M+H]⁺ observed. ¹H NMR (300 MHz, CDCl₃) δ ppm 7.66 (s, 1H) 7.19 (s, 1H) 7.07 (s, 1H) 6.67 (s, 1H) 4.15 (d, J=1.17 Hz, 2H) 3.97 (s, 3H) 3.93 (s, 3H) 3.85 (s, 3H) 3.54-3.62 (m, 2H) 3.40-3.47 (m, 1H) 3.37 (s, 3H) 3.14-3.24 (m, 1H) 2.86-2.94 (m, 1H) 2.14 (s, 2H) 1.67-1.74 (m, 1H) 0.87 (dd, J=6.60, 4.84 Hz, 6H).

Example 149: 6-(Tert-butyl)-10-methoxy-2-(methoxyimino)-9-(3-methoxypropoxy)-6,7-dihydro-2H-pyrido[2,1-a]isoquinoline-3-carboxylic acid

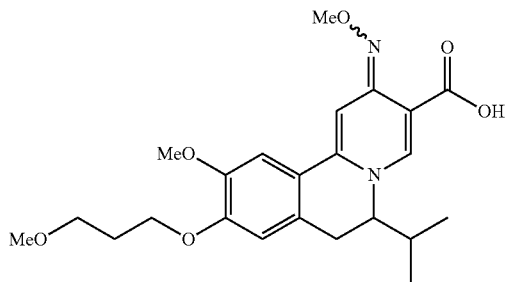 [SMILES: COCCCOc1cc2c(cc1OC)-c1cc(=NOC)c(C(=O)O)cn1C(C(C)C)C2]

m/z: 431 [M+H]+ observed. ¹H NMR (300 MHz, CDCl₃) δ ppm 8.60-8.68 (m, 1H), 7.23-7.25 (m, 1H), 7.20-7.23 (m, 1H), 6.81 (s, 1H), 4.21 (d, J=1.76 Hz, 2H), 4.03-4.13 (m, 1H), 3.88-4.00 (m, 6H), 3.59 (d, J=1.17 Hz, 2H), 3.37-3.43 (m, 4H), 3.03-3.14 (m, 1H), 2.16 (t, J=6.16 Hz, 2H), 1.75-1.89 (m, 1H), 0.94 (d, J=6.74 Hz, 3H), 0.81 (d, J=6.74 Hz, 3H).

Example 150: Ethyl 2-chloro-11-(hydroxyimino)-7-isopropyl-3-methoxy-6,7-dihydro-11H-benzo[f]pyrido[1,2-d][1,4]oxazepine-10-carboxylate

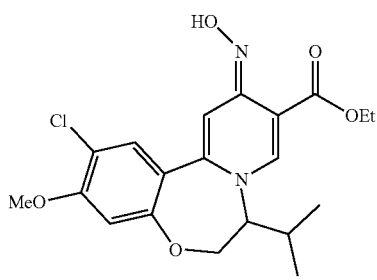 [SMILES: CCOC(=O)c1cn2c(c/c1=N\O)-c1cc(Cl)c(OC)cc1OCC2C(C)C]

m/z: 407 [M+H]+ observed. ¹H NMR (300 MHz, CHLOROFORM-d) δ ppm 12.19-12.58 (m, 1H) 8.68 (d, J=9.38 Hz, 1H) 7.81 (s, 1H) 7.37-7.60 (m, 2H) 6.71-6.85 (m, 1H) 4.82-5.08 (m, 2H) 4.57-4.79 (m, 2H) 4.28 (s, 3H) 2.09-2.39 (m, 1H) 1.53-1.78 (m, 3H) 1.31 (br. s., 3H) 1.05 (br. s., 3H)

Example 151: 2-Chloro-7-isopropyl-3-methoxy-6,7-dihydro-10H-benzo[f]isoxazolo[3',4':4,5]pyrido[1,2-d][1,4]oxazepin-10-one

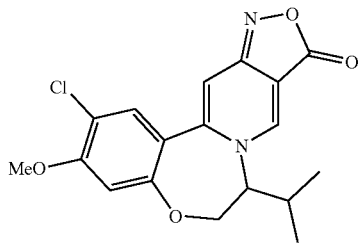 [SMILES: COc1cc2c(cc1Cl)-c1cc3noc(=O)c-3cn1C(C(C)C)CO2]

m/z: 361 [M+H]+ observed). ¹H NMR (300 MHz, CDCl₃) δ 8.06 (d, J=3.6 Hz, 1H), 7.49 (d, J=3.8 Hz, 1H), 6.77 (d, J=3.5 Hz, 1H), 6.65 (d, J=3.7 Hz, 1H), 4.54 (d, J=4.6 Hz, 2H), 3.94 (d, J=4.0 Hz, 3H), 3.80 (d, J=10.5 Hz, 1H), 2.04 (s, 1H), 1.06 (dd, J=6.4, 3.6 Hz, 3H), 0.88 (dd, J=6.9, 3.5 Hz, 3H).

Example 152: (6S,10)-10-Hydrazinylidene-6-isopropyl-2-methoxy-3-(3-methoxy propoxy)-5H,6H-pyrido[1,2-h]1,7-naphthyridine-9-carbohydrazide

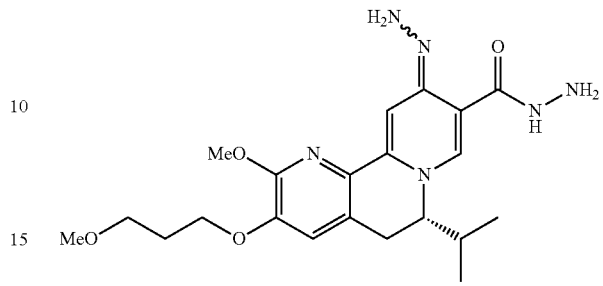

Example 153: (S)-6-Isopropyl-2-methoxy-3-(3-methoxypropoxy)-5,10-dihydropyrazolo[3',4':4,5]pyrido[1,2-h][1,7]naphthyridin-9(6H)-one

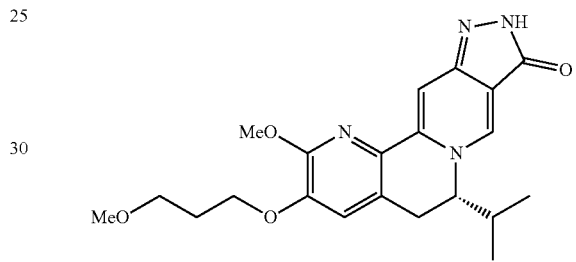

To a solution of (6S)-6-isopropyl-2-methoxy-3-(3-methoxypropoxy)-10-oxo-5H,6H-pyrido[1,2-h]1,7-naphthyridine-9-carboxylic acid (60 mg, 0.15 mmol) in CH₂Cl₂ (3 mL) at 0° C. was added phosphorus pentachloride (47 mg, 0.22 mmol). The reaction was stirred for 10 min. The reaction mixture was transferred via pipet into a stirring solution of methanol in another round bottom flask. The reaction was stirred for 5 min, then quenched by adding sat. sodium bicarbonate solution (10 mL). The aqueous layer was extracted with CH₂Cl₂ (2×15 mL). The combined organic fractions were dried over sodium sulfate and concentrated under vacuum to give crude methyl (S)-6-isopropyl-2-methoxy-3-(3-methoxypropoxy)-10-oxo-5,10-dihydro-6H-pyrido[1,2-h][1,7]naphthyridine-9-carboxylate.

The methyl (S)-6-isopropyl-2-methoxy-3-(3-methoxypropoxy)-10-oxo-5,10-dihydro-6H-pyrido[1,2-h][1,7]naphthyridine-9-carboxylate was dissolved in EtOH (2 mL) and hydrazine monohydrate (0.03 mL, 0.75 mmol) was added. The reaction was refluxed for 10 h. The solvent was removed under vacuum. The residue was purified by normal phase SiO₂ chromatography (0% to 5% MeOH/CH₂Cl₂) to furnish:

Example 152: (6S,10)-10-Hydrazinylidene-6-isopropyl-2-methoxy-3-(3-methoxypropoxy)-5H,6H-pyrido[1,2-h]1,7-naphthyridine-9-carbohydrazide as a white solid (28 mg, 44% yield, m/z: 431 [M+H]+ observed). ¹H NMR (400 MHz, CDCl₃) δ 11.25-11.20 (m, 1H), 8.38 (s, 1H), 7.44 (s, 1H), 6.88 (s, 1H), 4.20-4.09 (m, 2H), 4.02 (d, J=0.4 Hz, 3H), 3.89-3.80 (m, 1H), 3.55 (td, J=6.1, 1.4 Hz, 2H), 3.34 (d, J=0.4 Hz, 4H), 3.01 (dd, J=16.5, 1.5 Hz, 1H), 2.12 (p, J=6.2 Hz, 2H), 1.90 (dt, J=9.4, 6.7 Hz, 1H), 0.93 (d, J=6.7 Hz, 3H), 0.79 (d, J=6.8 Hz, 3H) and Example 153: (S)-6-Isopropyl-2-methoxy-3-(3-methoxypropoxy)-5,10-dihydropyrazolo[3',4':4,5]pyrido[1,2-h][1,7]naphthyridin-9(6H)-one as an yellow solid (5 mg, 8% yield, m/z: 399 [M+H]+ observed). ¹H NMR (400 MHz, CDCl₃) δ 9.24 (s, 1H), 8.18 (s, 1H), 7.95 (s, 1H), 6.90 (s, 1H), 4.16 (td, J=6.6, 4.5 Hz, 2H), 4.08 (s, 3H), 3.83 (dd, J=9.4, 4.8 Hz, 1H), 3.58 (td, J=6.1, 1.6 Hz, 2H), 3.36 (s, 4H), 3.04 (dd, J=16.3, 1.7 Hz, 1H), 2.15 (p, J=6.2 Hz, 2H), 2.04-1.84 (m, 1H), 0.97 (d, J=6.7 Hz, 3H), 0.79 (d, J=6.7 Hz, 3H).

Example 154: (6S)—N'-Acetyl-6-isopropyl-2-methoxy-3-(3-methoxypropoxy)-10-oxo-5H,6H-pyrido[1,2-h]1,7-naphthyridine-9-carbohydrazide

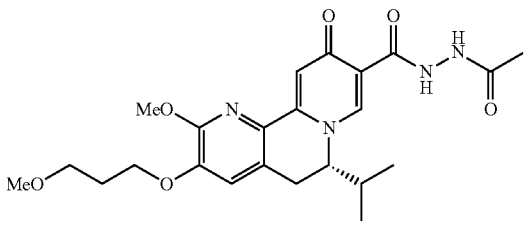 [SMILES: COCCCOc1cc2c(nc1OC)-c1cc(=O)c(C(=O)NNC(C)=O)cn1[C@H](C(C)C)C2]

To a solution of (6S)-6-isopropyl-2-methoxy-3-(3-methoxypropoxy)-10-oxo-5H,6H-pyrido[1,2-h]1,7-naphthyridine-9-carboxylic acid (60 mg, 0.15 mmol) in CH₂Cl₂ (3 mL) at 0° C. was added phosphorus pentachloride (37 mg, 0.18 mmol) and the reaction was stirred for 15 min. Acetohydrazide (0.002 mL, 0.30 mmol) in THF (1 mL) was added into above solution dropwise. The reaction was stirred for 3 h at rt. The solvent was removed under vacuum. The residue was purified by normal phase SiO₂ chromatography (0% to 5% MeOH/CH₂Cl₂) to furnish (6S,10E)-10-hydrazinylidene-6-isopropyl-2-methoxy-3-(3-methoxypropoxy)-5H,6H-pyrido[1,2-h]1,7-naphthyridine-9-carbohydrazide as a white solid (5.5 mg, 8% yield, m/z: 459 [M+H]+ observed). ¹H NMR (400 MHz, CDCl₃) 9.27 (s, 1H), 7.93 (s, 1H), 6.98 (s, 1H), 4.21 (t, J=6.5 Hz, 2H), 3.99 (s, 3H), 3.76 (d, J=11.2 Hz, 1H), 3.58 (td, J=6.1, 1.9 Hz, 2H), 3.37-3.38 (m, 4H), 3.13 (d, J=16.6 Hz, 1H), 2.13-2.15 (d, J=12.3 Hz, 5H), 1.95-1.98 (m, 1H), 0.96 (d, J=6.7 Hz, 3H), 0.80 (d, J=6.7 Hz, 3H).

Example 155: 6-Isopropyl-2-methoxy-3-(3-methoxypropoxy)-6-methyl-10-oxo-5,10-dihydro-6H-pyrido[1,2-h][1,7]naphthyridine-9-carboxylic acid

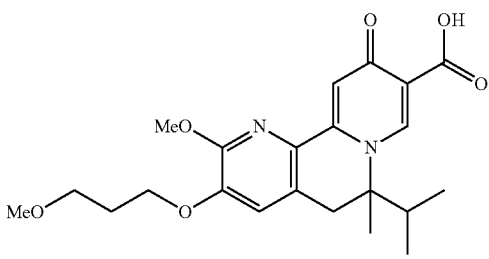 [SMILES: COCCCOc1cc2c(nc1OC)-c1cc(=O)c(C(=O)O)cn1C(C)(C(C)C)C2]

1-[6-Methoxy-5-(3-methoxypropoxy)pyridin-3-yl]-2,3-dimethylbutan-2-ol

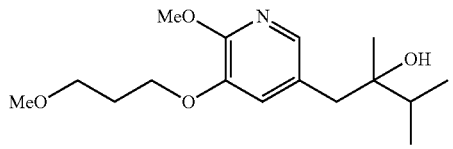 [SMILES: COCCCOc1cc(CC(C)(O)C(C)C)cnc1OC]

Methylmagnesium bromide solution (3.0M in diethyl ether, 3.6 mL, 11 mmol) was added to anhydrous THF (15 mL) and the mixture was cooled to 0° C. 1-[6-methoxy-5-(3-methoxypropoxy)pyridin-3-yl]-3-methylbutan-2-one (1 g, 3.6 mmol) in anhydrous THF (1 mL) was added dropwise. The resulting mixture slowly warmed to rt over 2 h and stirred for 30 min. The mixture was then cooled to 0° C. and quenched with sat. aqueous ammonium chloride solution (50 mL) and extracted with EtOAc (3×30 mL). The combined organic fractions were washed with H₂O, then washed with sat. aqueous brine solution, dried over sodium sulfate and concentrated under vacuum to give 1-[6-methoxy-5-(3-methoxypropoxy) pyridin-3-yl]-2,3-dimethylbutan-2-ol (1.03 g, 97.4%) as a yellow oil that was used without further purification (1.03 g, 97% yield, m/z: 298 [M+H]+ observed). ¹H NMR (400 MHz, CDCl₃) δ 7.54 (d, J=1.9 Hz, 1H), 7.05 (d, J=1.9 Hz, 1H), 4.10 (td, J=6.8, 5.8 Hz, 2H), 3.99 (s, 3H), 3.56 (t, J=6.1 Hz, 2H), 3.35 (s, 3H), 2.71 (d, J=13.7 Hz, 1H), 2.61 (d, J=13.9 Hz, 1H), 2.10 (p, J=6.3 Hz, 2H), 1.71 (h, J=6.8 Hz, 1H), 1.03 (s, 3H), 0.99 (dd, J=6.8, 2.7 Hz, 6H).

N-{1-[6-Methoxy-5-(3-methoxypropoxy)pyridin-3-yl]-2,3-dimethylbutan-2-yl}acetamide

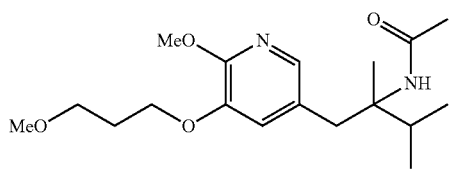 [SMILES: COCCCOc1cc(CC(C)(NC(C)=O)C(C)C)cnc1OC]

1-[6-methoxy-5-(3-methoxypropoxy)pyridin-3-yl]-2,3-dimethylbutan-2-ol, (520 mg, 1.8 mmol) was dissolved in acetonitrile (5 mL) and concentrated sulfuric acid (0.48 mL, 8.8 mmol) was added dropwise at 0° C. After stirring at room temperature for 18 hours the reaction mixture was diluted with H₂O (30 mL) and extracted with EtOAc (3×30 mL). The combined organic fractions were dried over sodium sulfate and concentrated under vacuum. The residue was purified by normal phase SiO₂ chromatography (10% to 100% EtOAc/hexanes) to afford N-{1-[6-methoxy-5-(3-methoxypropoxy)pyridin-3-yl]-2,3-dimethylbutan-2-yl}acetamide as a clear oil (228 mg, 39% yield, m/z: 339 [M+H]+ observed).

N-{1-[2-Bromo-6-methoxy-5-(3-methoxypropoxy)
pyridin-3-yl]-2,3-dimethylbutan-2-yl}acetamide

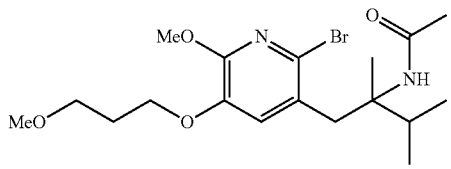 [SMILES: COCCCOc1cc(CC(C)(NC(C)=O)C(C)C)c(Br)nc1OC]

N-{1-[6-methoxy-5-(3-methoxypropoxy)pyridin-3-yl]-2,3-dimethylbutan-2-yl}acetamide (130 mg, 0.38 mmol) and sodium acetate (37 mg, 0.45 mmol) were suspended in glacial acetic acid (2 mL), then cooled to 0° C. and bromine (0.02 mL, 0.38 mmol) was added drop-wise. The mixture was stirred for 3 hours at rt. The mixture was added drop-wise to a solution of ice water with vigorous stirring. The precipitate was filtered and dried to give N-{1-[2-bromo-6-methoxy-5-(3-methoxypropoxy)pyridin-3-yl]-2,3-dimethylbutan-2-yl}acetamide that was used without further purification as a white solid (95 mg, 60% yield, m/z: 416/420 [M+H]$^+$ observed).

N-{1-[2-Formyl-6-methoxy-5-(3-methoxypropoxy)
pyridin-3-yl]-2,3-dimethylbutan-2-yl}acetamide

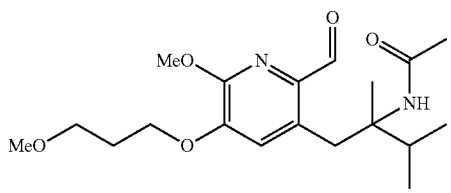 [SMILES: COCCCOc1cc(CC(C)(NC(C)=O)C(C)C)c(C=O)nc1OC]

N-{1-[2-bromo-6-methoxy-5-(3-methoxypropoxy)pyridin-3-yl]-2,3-dimethylbutan-2-yl)}acetamide (67 mg, 0.13 mmol) was dissolved in anhydrous THF (2 mL), then cooled to −78° C. (dry ice/acetone bath) and n-butyllithium (1.6 M in hexanes, 0.20 mL, 0.32 mmol) was added drop-wise. The reaction mixture was stirred at −78° C. for 60 min. Dimethylformamide (0.02 mL, 0.19 mmol) was a subsequently added drop-wise and the reaction was stirred at −78° C. for 10 minutes, then warmed to rt and stirred for an additional 30 minutes. The reaction was diluted with H$_2$O (5 mL) and extracted with EtOAc (3×15 mL). The combined organic fractions were washed with H$_2$O (5 mL), sat. aqueous brine solution (5 mL), dried over sodium sulfate and concentrated under vacuum to give a crude N-{1-[2-formyl-6-methoxy-5-(3-methoxypropoxy)pyridin-3-yl]-2,3-dimethylbutan-2-yl}acetamide that was used without further purification as a yellow oil (47 mg, 60% yield, m/z: 367 [M+H]$^+$ observed).

6-Isopropyl-2-methoxy-3-(3-methoxypropoxy)-6-methyl-5H-1,7-naphthyridine

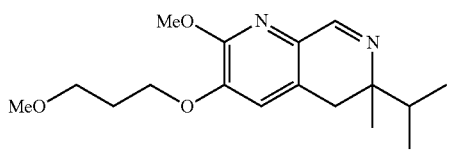 [SMILES: COCCCOc1cc2c(nc1OC)C=NC(C)(C(C)C)C2]

To a solution of N-{1-[2-formyl-6-methoxy-5-(3-methoxypropoxy)pyridin-3-yl]-2,3-dimethylbutan-2-yl}acetamide (47 mg, 0.08 mmol) in CH$_2$C$_2$ (0.5 mL) was added hydrogen chloride solution (4M in 1,4-dioxane, 0.58 mL, 2.3 mmol). The reaction mixture was stirred at rt for 2 hours. The volatiles were evaporated under vacuum, then the residue was dissolved in H$_2$O and the solution was adjusted to pH 10-12 with sat. aqueous sodium bicarbonate solution. The aqueous layer was then extracted with CH$_2$Cl$_2$ (3×20 mL). The combined organic phase was dried over anhydrous sodium sulfate and evaporated in vacuum. The residue was purified by normal phase SiO$_2$ chromatography (5% to 60% EtOAc/hexanes) to afford 6-isopropyl-2-methoxy-3-(3-methoxypropoxy)-6-methyl-5H-1,7-naphthyridine as a yellow oil (26 mg, 83% yield, m/z: 307 [M+H]$^+$ observed). $^1$H NMR (400 MHz, CDCl$_3$): δ 8.21 (s, 1H), 6.83 (s, 1H), 4.14 (t, J=6.5 Hz, 2H), 4.01 (s, 3H), 3.56 (t, J=5.9 Hz, 2H), 3.35 (s, 3H), 2.87 (d, J=16.5 Hz, 1H), 2.49 (d, J=16.4 Hz, 1H), 2.12 (p, J=6.3 Hz, 2H), 1.96 (p, J=6.7 Hz, 1H), 1.08 (s, 3H), 0.98 (dd, J=19.2, 6.9 Hz, 6H).

Ethyl 6-isopropyl-2-methoxy-3-(3-methoxypropoxy)-6-methyl-10-oxo-5,10-dihydro-6H-pyrido
[1,2-h][1,7]naphthyridine-9-carboxylate

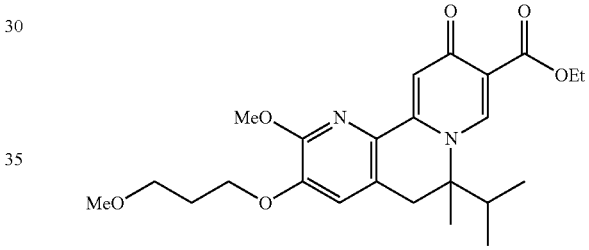

6-isopropyl-2-methoxy-3-(3-methoxypropoxy)-6-methyl-5H-1,7-naphthyridine (26 mg, 0.08 mmol) and ethyl (2E)-2-(ethoxymethylidene)-3-oxobutanoate (47 mg, 0.25 mmol) were dissolved in anhydrous EtOH (1 mL) in a sealed tube. The reaction vessel was flushed with air, then sealed and heated at 90° C. overnight. The reaction mixture was concentrated under reduced pressure to give crude ethyl 6-isopropyl-2-methoxy-3-(3-methoxypropoxy)-6-methyl-10-oxo-5,10,11,11a-tetrahydro-6H-pyrido[1,2-h][1,7]naphthyridine-9-carboxylate as a brown oil that was used without further purification (23 mg, 61% yield).

The crude mixture from above and p-chloranil (23 mg, 0.09 mmol) were dissolved in 2-MeTHF (1 mL) and stirred at 75° C. for 1 h. The reaction mixture was concentrated under vacuum. The residue was purified by reverse phase HPLC to afford ethyl 6-isopropyl-2-methoxy-3-(3-methoxypropoxy)-6-methyl-10-oxo-5,10-dihydro-6H-pyrido[1,2-h][1,7]naphthyridine-9-carboxylate as a tan solid (25 mg, 66% yield, m/z: 445 [M+H]$^+$ observed). $^1$H NMR (400 MHz, CDCl$_3$) δ 8.42 (s, 1H), 7.58 (s, 1H), 6.85 (s, 1H), 4.40 (q, J=7.1 Hz, 2H), 4.20-4.07 (m, 2H), 4.05 (s, 3H), 3.57 (t, J=5.9 Hz, 2H), 3.36 (s, 3H), 3.12 (d, J=16.5 Hz, 1H), 3.01 (d, J=16.4 Hz, 1H), 2.13 (q, J=6.0 Hz, 2H), 2.10-2.05 (m, 1H), 1.63 (s, 3H), 1.40 (t, J=7.1 Hz, 3H), 0.87 (d, J=6.8 Hz, 3H), 0.72 (d, J=6.8 Hz, 3H).

6-Isopropyl-2-methoxy-3-(3-methoxypropoxy)-6-methyl-10-oxo-5H-pyrido[1,2-h]1,7-naphthyridine-9-carboxylic acid Example 157: 6-Isopropyl-2-methoxy-3-(3-methoxypropoxy)-6-methyl-10-oxo-5,10-dihydro-6H-pyrido[1,2-h][1,7]naphthyridine-9-carboxylic acid (Single Enantiomer II)

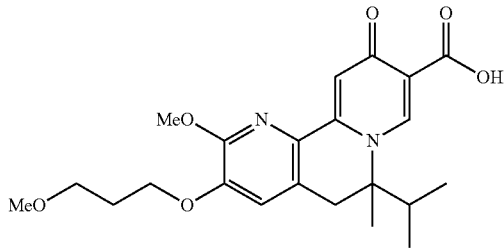 [SMILES: COCCCOc1cc2c(nc1OC)-c1cc(=O)c(C(=O)O)cn1C(C)(C(C)C)C2]

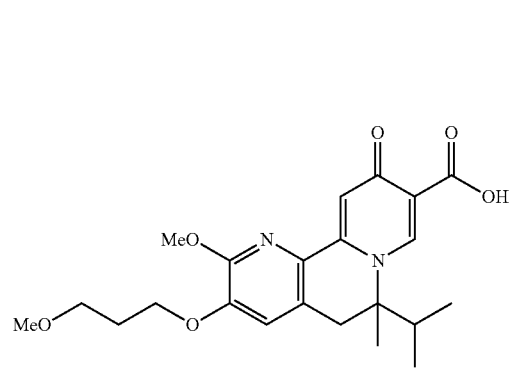

Ethyl 6-isopropyl-2-methoxy-3-(3-methoxypropoxy)-6-methyl-10-oxo-5H-pyrido[1,2-h]1,7-naphthyridine-9-carboxylate (25 mg, 0.06 mmol) and lithium hydroxide monohydrate (9 mg, 0.2 mmol) were suspended in a THF:MeOH:H$_2$O mixture (3:1:1, 2 mL) and the reaction was stirred at rt for 2 hours. The volatile organics were removed under reduced pressure, H$_2$O (3 mL) was added and the aqueous solution was extracted with EtOAc (3×10 mL). The remaining aqueous solution was acidified to pH 2 with aqueous 1M HCl solution, then extracted with EtOAc (2×10 mL). The organics were dried with sodium sulfate and concentrated to give 6-isopropyl-2-methoxy-3-(3-methoxypropoxy)-6-methyl-10-oxo-5H-pyrido[1,2-h]1,7-naphthyridine-9-carboxylic acid as a light brown oil (6.6 mg, 28%, m/z: 417 [M+H]$^+$ observed). $^1$H NMR (400 MHz, CDCl$_3$) δ 8.65 (s, 1H), 7.73 (d, J=1.2 Hz, 1H), 6.89 (s, 1H), 4.22-4.12 (m, 2H), 4.06 (d, J=1.1 Hz, 3H), 3.58 (td, J=6.0, 1.6 Hz, 2H), 3.36 (s, 3H), 3.18 (d, J=16.5 Hz, 1H), 3.07 (d, J=16.6 Hz, 1H), 2.17-2.13 (m, 2H), 2.12-2.08 (m, 1H), 1.69 (s, 3H), 0.89 (d, J=6.8 Hz, 3H), 0.71 (d, J=6.8 Hz, 3H).

Example 156: 6-Isopropyl-2-methoxy-3-(3-methoxypropoxy)-6-methyl-10-oxo-5,10-dihydro-6H-pyrido[1,2-h][1,7]naphthyridine-9-carboxylic acid (Single Enantiomer I)

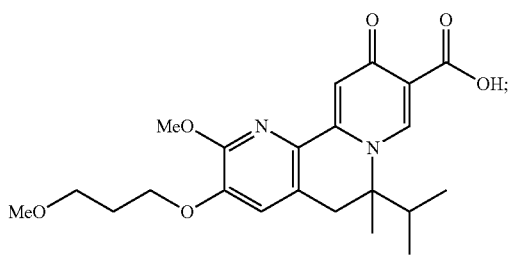 [SMILES: COCCCOc1cc2c(nc1OC)-c1cc(=O)c(C(=O)O)cn1C(C)(C(C)C)C2]

23 mg of the mixture of enantiomers were separated by SFC (supercritical fluid chromatography) on a CHIRALPAK AD column using 30% IPA (0.2% diethylamine as modifier) to give 6-isopropyl-2-methoxy-3-(3-methoxypropoxy)-6-methyl-10-oxo-5,10-dihydro-6H-pyrido[1,2-h][1,7]naphthyridine-9-carboxylic acid (single enantiomer I) as a yellow oil (faster eluting enantiomer, 8.3 mg, 36%, m/z: 417 [M+H]$^+$ observed) and 6-isopropyl-2-methoxy-3-(3-methoxypropoxy)-6-methyl-10-oxo-5,10-dihydro-6H-pyrido[1,2-h][1,7]naphthyridine-9-carboxylic acid (single enantiomer II) as a tan solid (slower eluting enantiomer, 7.7 mg, 33%, m/z: 417 [M+H]$^+$ observed).

Example 156: 6-Isopropyl-2-methoxy-3-(3-methoxypropoxy)-6-methyl-10-oxo-5,10-dihydro-6H-pyrido[1,2-h][1,7]naphthyridine-9-carboxylic acid (single enantiomer I). m/z: 417 [M+H]$^+$ observed. $^1$H NMR (400 MHz, CDCl$_3$) δ 8.65 (s, 1H), 7.73 (d, J=1.2 Hz, 1H), 6.89 (s, 1H), 4.22-4.12 (m, 2H), 4.06 (d, J=1.1 Hz, 3H), 3.58 (td, J=6.0, 1.6 Hz, 2H), 3.36 (s, 3H), 3.18 (d, J=16.5 Hz, 1H), 3.07 (d, J=16.6 Hz, 1H), 2.17-2.13 (m, 2H), 2.12-2.08 (m, 1H), 1.69 (s, 3H), 0.89 (d, J=6.8 Hz, 3H), 0.71 (d, J=6.8 Hz, 3H).

Example 157: 6-Isopropyl-2-methoxy-3-(3-methoxypropoxy)-6-methyl-10-oxo-5,10-dihydro-6H-pyrido[1,2-h][1,7]naphthyridine-9-carboxylic acid (single enantiomer II). m/z: 417 [M+H]$^+$ observed. $^1$H NMR (400 MHz, CDCl$_3$) δ 8.65 (s, 1H), 7.73 (d, J=1.2 Hz, 1H), 6.89 (s, 1H), 4.22-4.12 (m, 2H), 4.06 (d, J=1.1 Hz, 3H), 3.58 (td, J=6.0, 1.6 Hz, 2H), 3.36 (s, 3H), 3.18 (d, J=16.5 Hz, 1H), 3.07 (d, J=16.6 Hz, 1H), 2.17-2.13 (m, 2H), 2.12-2.08 (m, 1H), 1.69 (s, 3H), 0.89 (d, J=6.8 Hz, 3H), 0.71 (d, J=6.8 Hz, 3H).

The following examples were prepared in a similar manner as (S)-6-isopropyl-2-methoxy-3-(3-methoxypropoxy)-6-methyl-10-oxo-5,10-dihydro-6H-pyrido[1,2-h][1,7]naphthyridine-9-carboxylic acid and (R)-6-isopropyl-2-methoxy-3-(3-methoxypropoxy)-6-methyl-10-oxo-5,10-dihydro-6H-pyrido[1,2-h][1,7]naphthyridine-9-carboxylic acid using an appropriate ketone and Grignard reagent.

Example 158: 6-(Tert-butyl)-2-methoxy-3-(3-methoxypropoxy)-6-methyl-10-oxo-5,10-dihydro-6H-pyrido[1,2-h][1,7]naphthyridine-9-carboxylic acid

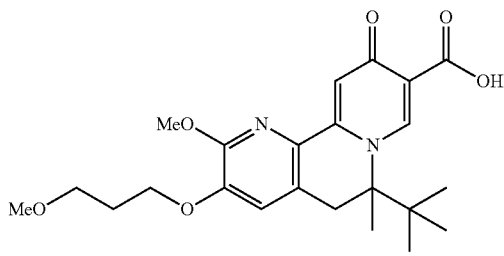 [SMILES: COCCCOc1cc2c(nc1OC)-c1cc(=O)c(C(=O)O)cn1C(C)(C(C)(C)C)C2]

m/z: 431 [M+H]⁺ observed. ¹H NMR (400 MHz, CDCl₃) δ 8.65 (s, 1H), 7.75 (s, 1H), 6.83 (s, 1H), 4.24-4.09 (m, 2H), 4.05 (s, 3H), 3.58 (td, J=6.1, 1.5 Hz, 2H), 3.36 (s, 3H), 3.26 (s, 2H), 2.15 (p, J=6.3 Hz, 2H), 1.81 (s, 3H), 0.83 (s, 9H).

Example 159: 6-(Tert-butyl)-2-methoxy-3-(3-methoxypropoxy)-6-methyl-10-oxo-5,10-dihydro-6H-pyrido[1,2-h][1,7]naphthyridine-9-carboxylic acid (Single Enantiomer I)

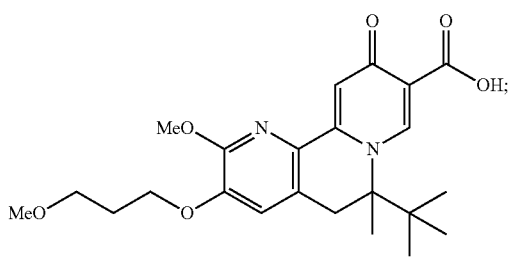 [SMILES: COCCCOc1cc2c(nc1OC)-c1cc(=O)c(C(=O)O)cn1C(C)(C(C)(C)C)C2]

5 mg of the mixture of enantiomers was separated by SFC (supercritical fluid chromatography) on a CHIRALPAK AD column using 25% IPA (0.1% diethylamine as modifier) to give 6-(tert-butyl)-2-methoxy-3-(3-methoxypropoxy)-6-methyl-10-oxo-5,10-dihydro-6H-pyrido[1,2-h][1,7]naphthyridine-9-carboxylic acid (single enantiomer I) as a light brown solid (faster eluting enantiomer, 1.5 mg, 30%, m/z: 431 [M+H]⁺ observed) and 6-(tert-butyl)-2-methoxy-3-(3-methoxypropoxy)-6-methyl-10-oxo-5,10-dihydro-6H-pyrido[1,2-h][1,7]naphthyridine-9-carboxylic acid (single enantiomer II) as a light brown solid (slower eluting enantiomer, 1.3 mg, 26%, m/z: 431 [M+H]⁺ observed)

Example 159: 6-(Tert-butyl)-2-methoxy-3-(3-methoxypropoxy)-6-methyl-10-oxo-5,10-dihydro-6H-pyrido[1,2-h][1,7]naphthyridine-9-carboxylic acid (single enantiomer I). m/z: 431 [M+H]⁺ observed. ¹H NMR (400 MHz, CDCl₃) δ 8.65 (s, 1H), 7.75 (s, 1H), 6.83 (s, 1H), 4.24-4.09 (m, 2H), 4.05 (s, 3H), 3.58 (td, J=6.1, 1.5 Hz, 2H), 3.36 (s, 3H), 3.26 (s, 2H), 2.15 (p, J=6.3 Hz, 2H), 1.81 (s, 3H), 0.83 (s, 9H).

Example 160: 6-(Tert-butyl)-2-methoxy-3-(3-methoxypropoxy)-6-methyl-10-oxo-5,10-dihydro-6H-pyrido[1,2-h][1,7]naphthyridine-9-carboxylic acid (single enantiomer II). m/z: 431 [M+H]⁺ observed. ¹H NMR (400 MHz, CDCl₃) δ 8.65 (s, 1H), 7.75 (s, 1H), 6.83 (s, 1H), 4.24-4.09 (m, 2H), 4.05 (s, 3H), 3.58 (td, J=6.1, 1.5 Hz, 2H), 3.36 (s, 3H), 3.26 (s, 2H), 2.15 (p, J=6.3 Hz, 2H), 1.81 (s, 3H), 0.83 (s, 9H).

Example 161: Ethyl 6,6-diethyl-2-methoxy-3-(3-methoxypropoxy)-10-oxo-5,10-dihydro-6H-pyrido[1,2-h][1,7]naphthyridine-9-carboxylate

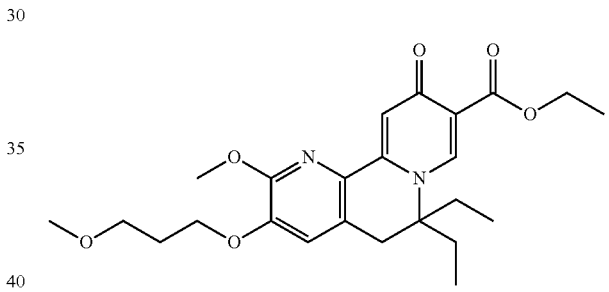

Example 160: 6-(Tert-butyl)-2-methoxy-3-(3-methoxypropoxy)-6-methyl-10-oxo-5,10-dihydro-6H-pyrido[1,2-h][1,7]naphthyridine-9-carboxylic acid (Single Enantiomer II)

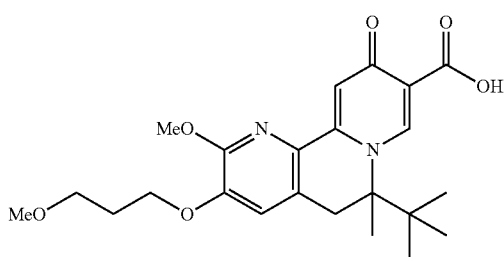 [SMILES: COCCCOc1cc2c(nc1OC)-c1cc(=O)c(C(=O)O)cn1C(C)(C(C)(C)C)C2]

Example 162: 6,6-Diethyl-2-methoxy-3-(3-methoxypropoxy)-10-oxo-5,10-dihydro-6H-pyrido[1,2-h][1,7]naphthyridine-9-carboxylic acid

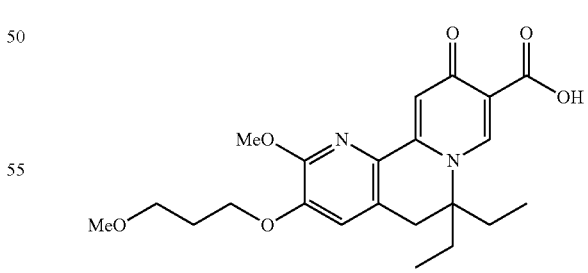

m/z: 417 [M+H]⁺ observed. ¹H NMR (400 MHz, CDCl₃) δ 8.60 (s, 1H), 7.77 (s, 1H), 6.89 (s, 1H), 4.17 (t, J=6.5 Hz, 2H), 4.06 (s, 3H), 3.57 (t, J=5.9 Hz, 2H), 3.36 (s, 3H), 3.07 (s, 2H), 2.14 (p, J=6.2 Hz, 2H), 1.96 (q, J=7.4 Hz, 4H), 0.92 (t, J=7.4 Hz, 6H).

Example 163: 6-Ethyl-6-isopropyl-2-methoxy-3-(3-methoxypropoxy)-10-oxo-5,10-dihydro-6H-pyrido[1,2-h][1,7]naphthyridine-9-carboxylic acid

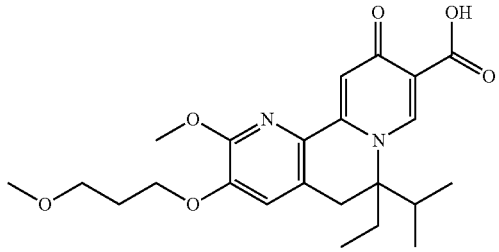 [SMILES: CCC1(C(C)C)Cc2cc(OCCCOC)c(OC)nc2-c2cc(=O)c(C(=O)O)cn21]

m/z: 431 [M+H]$^+$ observed. $^1$H NMR (400 MHz, CDCl$_3$) δ 8.55 (s, 1H), 7.79 (d, J=0.7 Hz, 1H), 6.89 (s, 1H), 4.23-4.12 (m, 2H), 4.06 (d, J=0.7 Hz, 3H), 3.58 (t, J=5.9 Hz, 2H), 3.36 (d, J=0.7 Hz, 3H), 3.23 (d, J=16.6 Hz, 1H), 2.97 (d, J=16.6 Hz, 1H), 2.31 (p, J=6.9 Hz, 1H), 2.22-2.10 (m, 3H), 0.97 (t, J=7.3 Hz, 3H), 0.89 (dd, J=13.4, 6.8 Hz, 6H).

Example 164: (6S)-2,3-Dihydroxy-6-isopropyl-10-oxo-5H,6H-pyrido[1,2-h]1,7-naphthyridine-9-carboxylic acid

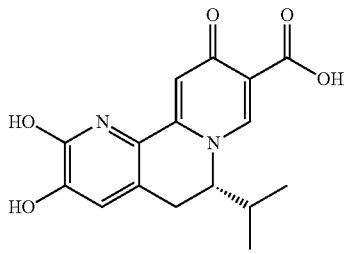 [SMILES: CC(C)[C@@H]1Cc2cc(O)c(O)nc2-c2cc(=O)c(C(=O)O)cn21]

(6S)-6-isopropyl-2,3-dimethoxy-10-oxo-5H,6H-pyrido[1,2-h]1,7-naphthyridine-9-carboxylic acid (150 mg, 0.44 mmol) was dissolved in anhydrous CH$_2$Cl$_2$ (3 mL) and cooled to 0° C. Boron tribromide solution (1M in CH$_2$Cl$_2$, 1.7 mL, 1.7 mmol) was added drop-wise and the mixture was stirred at 0° C. for 2 hours, then warmed to rt and heated at 50° C. for 1 hour. Methanol (2 mL) was added to the reaction and the mixture was concentrated to afford (6S)-2,3-dihydroxy-6-isopropyl-10-oxo-5H,6H-pyrido[1,2-h]1,7-naphthyridine-9-carboxylic acid as a yellow solid which was used in the next step without further purification (135 mg, 97%, m/z: 317 [M+H]$^+$ observed). $^1$H NMR (300 MHz, DMSO-d$_6$) δ ppm 10.25-10.33 (m, 1H) 8.73-8.80 (m, 1H) 7.24-7.35 (m, 1H) 6.87-6.98 (m, 1H) 4.38-4.48 (m, 1H) 3.32 (br. s., 2H) 3.12-3.27 (m, 1H) 2.94-3.07 (m, 1H) 1.75-1.90 (m, 1H) 0.88 (d, J=6.45 Hz, 3H) 0.69 (d, J=6.45 Hz, 3H).

Methyl (6S)-6-isopropyl-3-methoxy-1-methyl-2,10-dioxo-5H,6H-pyrido[1,2-h]1,7-naphthyridine-9-carboxylate

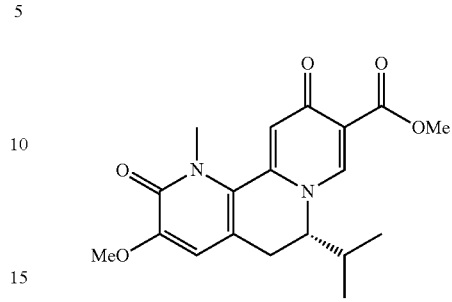

(6S)-2,3-Dihydroxy-6-isopropyl-10-oxo-5H,6H-pyrido[1,2-h]1,7-naphthyridine-9-carboxylic acid (90 mg, 0.26 mmol) and potassium carbonate (177 mg, 1.28 mmol) were suspended in DMF (3 mL) and the mixture was heated to 90° C. in an oil bath. Methyl iodide (0.8 mL, 1.3 mmol) in DMF (0.5 mL) was added dropwise and the mixture was stirred at 90° C. for 2 hours. The reaction was filtered through Celite® and the filtrate was concentrated under reduced pressure. The residue was purified by reverse phase HPLC to afford methyl (6S)-6-isopropyl-3-methoxy-1-methyl-2,10-dioxo-5H,6H-pyrido[1,2-h]1,7-naphthyridine-9-carboxylate as a white solid (70 mg, 76% yield, m/z: 359 [M+H]$^+$ observed). $^1$H NMR (400 MHz, CDCl$_3$) δ 8.71 (s, 1H), 7.16 (s, 1H), 6.53 (s, 1H), 4.14 (dd, J=9.8, 5.0 Hz, 1H), 3.95 (d, J=14.4 Hz, 6H), 3.72 (s, 3H), 3.31 (dd, J=17.4, 5.3 Hz, 1H), 2.97 (d, J=17.4 Hz, 1H), 2.16-2.05 (m, 1H), 0.99 (dd, J=23.3, 6.7 Hz, 6H).

Example 165: (S)-6-Isopropyl-3-methoxy-1-methyl-2,10-dioxo-2,5,6,10-tetrahydro-1H-pyrido[1,2-h][1,7]naphthyridine-9-carboxylic acid

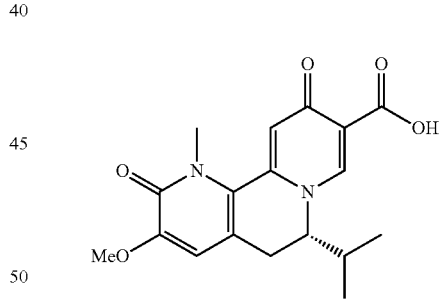

Methyl (6S)-6-isopropyl-3-methoxy-1-methyl-2,10-dioxo-5H,6H-pyrido[1,2-h]1,7-naphthyridine-9-carboxylate (10 mg, 0.03 mmol) and lithium hydroxide monohydrate (10 mg, 0.14 mmol) were suspended in a 1,4-dioxane/water mixture (1:1, 1 mL) and the reaction was stirred at rt overnight. The reaction was concentrated under reduced pressure and the crude residue was taken up in H$_2$O (5 mL), then extracted with EtOAc (2×10 mL) to get rid of impurities. The remaining aqueous solution was acidified to pH 2 with aqueous 1M HCl solution, then extracted with EtOAc (2×10 mL). The combined organic fractions were dried with sodium sulfate, then concentrated to give (S)-6-isopropyl-3-methoxy-1-methyl-2,10-dioxo-2,5,6,10-tetrahydro-1H-pyrido[1,2-h][1,7]naphthyridine-9-carboxylic acid as a white solid (5.6 mg, 58% yield, m/z: 345 [M+H]$^+$ observed).

¹H NMR (400 MHz, CDCl₃) δ 8.52 (s, 1H), 6.90 (d, J=1.2 Hz, 1H), 6.51 (s, 1H), 4.00-3.83 (m, 4H), 3.74 (d, J=1.2 Hz, 3H), 3.20 (dd, J=17.1, 5.2 Hz, 1H), 2.95 (d, J=17.2 Hz, 1H), 2.13-2.03 (m, 1H), 1.05-0.94 (m, 6H).

Ethyl 6-isopropyl-3-(3-methoxypropoxy)-2,10-dioxo-2,5,6,10-tetrahydro-1H-pyrido[1,2-h][1,7]naphthyridine-9-carboxylate

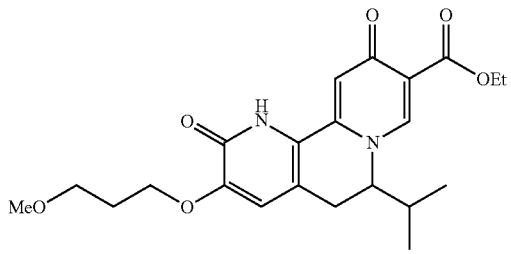 [SMILES: CCOC(=O)c1cn2c(cc1=O)-c1[nH]c(=O)c(OCCCOC)cc1CC2C(C)C]

A mixture of ethyl 6-isopropyl-2-methoxy-3-(3-methoxypropoxy)-10-oxo-5,10-dihydro-6H-pyrido[1,2-h][1,7]naphthyridine-9-carboxylate (1 g, 2.3 mmol) in hydrobromic acid (40% aqueous solution, 10 mL) was stirred at rt for 16 hours. The pH of the reaction mixture was adjusted to 8 with sat. aqueous NaHCO₃ (30 mL). The aqueous phase was extracted with CH₂Cl₂ (5×40 mL). The combined organic layers were concentrated under reduced pressure to give ethyl 6-isopropyl-3-(3-methoxypropoxy)-2,10-dioxo-5,6-dihydro-1H-pyrido[1,2-h][1,7]naphthyridine-9-carboxylate as a dark brown solid that was used in the next step without further purification (750 mg, 78% yield, m/z: 417 [M+H]⁺ observed).

6-isopropyl-3-(3-methoxypropoxy)-2,10-dioxo-2,5,6,10-tetrahydro-1H-pyrido[1,2-h][1,7]naphthyridine-9-carboxylic acid

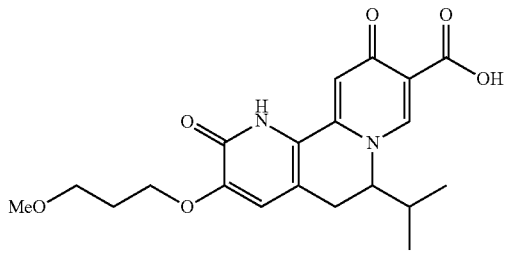 [SMILES: COCCCOc1cc2c([nH]c1=O)-c1cc(=O)c(C(=O)O)cn1C(C(C)C)C2]

To a solution of ethyl 6-isopropyl-3-(3-methoxypropoxy)-2,10-dioxo-5,6-dihydro-1H-pyrido[1,2-h][1,7]naphthyridine-9-carboxylate (700 mg, 1.68 mmol) in THF (7 mL) and H₂O (7 mL) was added lithium hydroxide monohydrate (70 mg, 1.7 mmol). The mixture was stirred at rt for 16 hr. The reaction mixture was extracted with CH₂Cl₂ (5×30 mL). The combined organic phase was concentrated in vacuum and the pH was adjusted to 3 with 1N HCl (4 mL). The resulting solid was filtered and washed with CH₃CN (3×3 mL) to afford 6-isopropyl-3-(3-methoxypropoxy)-2,10-dioxo-2,5,6,10-tetrahydro-1H-pyrido[1,2-h][1,7]naphthyridine-9-carboxylic acid as a white solid that was used in the next step without further purification (240 mg, 37% yield, m/z: 389 [M+H]⁺ observed).

Example 166: 6-Isopropyl-3-(3-methoxypropoxy)-2,10-dioxo-2,5,6,10-tetrahydro-1H-pyrido[1,2-h][1,7]naphthyridine-9-carboxylic acid (Single Enantiomer I)

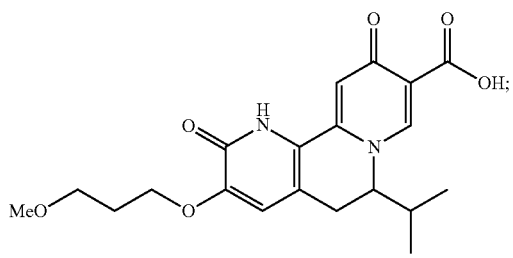 [SMILES: COCCCOc1cc2c([nH]c1=O)-c1cc(=O)c(C(=O)O)cn1C(C(C)C)C2]

Example 167: 6-Isopropyl-3-(3-methoxypropoxy)-2,10-dioxo-2,5,6,10-tetrahydro-1H-pyrido[1,2-h][1,7]naphthyridine-9-carboxylic acid (Single Enantiomer II)

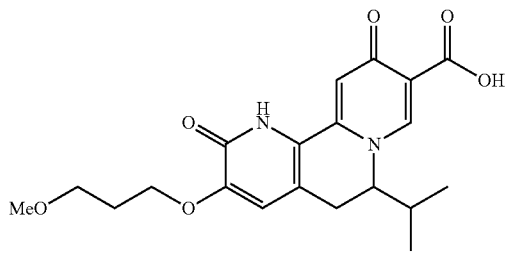 [SMILES: COCCCOc1cc2c([nH]c1=O)-c1cc(=O)c(C(=O)O)cn1C(C(C)C)C2]

240 mg of the mixture of 6-isopropyl-3-(3-methoxypropoxy)-2,10-dioxo-2,5,6,10-tetrahydro-1H-pyrido[1,2-h][1,7]naphthyridine-9-carboxylic acid enantiomers was separated by SFC (supercritical fluid chromatography) on a CHIRALCEL® OJ-3 column using 35% MeOH (0.1% NH₄OH as modifier) to give 6-isopropyl-3-(3-methoxypropoxy)-2,10-dioxo-2,5,6,10-tetrahydro-1H-pyrido[1,2-h][1,7]naphthyridine-9-carboxylic acid (single enantiomer I) as an yellow solid (faster eluting enantiomer, 84 mg, 35%, m/z: 389 [M+H]⁺ observed) and 6-isopropyl-3-(3-methoxypropoxy)-2,10-dioxo-2,5,6,10-tetrahydro-1H-pyrido[1,2-h][1,7]naphthyridine-9-carboxylic acid (single enantiomer II) as an yellow solid (slower eluting enantiomer, 92 mg, 38%, m/z: 389 [M+H]⁺ observed).

Example 166: 6-Isopropyl-3-(3-methoxypropoxy)-2,10-dioxo-2,5,6,10-tetrahydro-1H-pyrido[1,2-h][1,7]naphthyridine-9-carboxylic acid (single enantiomer I). m/z: 389 [M+H]⁺ observed. ¹H NMR (400 MHz, DMSO-d₆) δ 8.78 (s, 1H), 7.30 (s, 1H), 7.21 (s, 1H), 4.47-4.44 (m, 1H), 4.12-4.02 (m, 2H), 3.49-3.46 (t, J=6 Hz, 2H), 3.25 (m, 4H), 3.11-3.07 (m, 1H), 2.02-1.95 (m, 2H), 1.84-1.78 (m, 1H), 0.89-0.87 (d, J=6.4 Hz, 3H), 0.70-0.68 (d, J=6.8 Hz, 3H).

Example 167: 6-Isopropyl-3-(3-methoxypropoxy)-2,10-dioxo-2,5,6,10-tetrahydro-1H-pyrido[1,2-h][1,7]naphthyridine-9-carboxylic acid (single enantiomer II). m/z: 389 [M+H]⁺ observed. ¹H NMR (400 MHz, DMSO-d₆) δ 8.78 (s, 1H), 7.30 (s, 1H), 7.21 (s, 1H), 4.47-4.44 (m, 1H), 4.12-4.02 (m, 2H), 3.49-3.46 (t, J=6 Hz, 2H), 3.25 (m, 4H), 3.11-3.07 (m, 1H), 2.02-1.95 (m, 2H), 1.84-1.78 (m, 1H), 0.89-0.87 (d, J=6.4 Hz, 3H), 0.70-0.68 (d, J=6.8 Hz, 3H).

Example 168: (S)-7-Isopropyl-2-methoxy-3-(3-methoxypropoxy)-11-oxo-5,6,7,11-tetrahydrodipyrido[1,2-a:2',3'-c]azepine-10-carboxylic acid

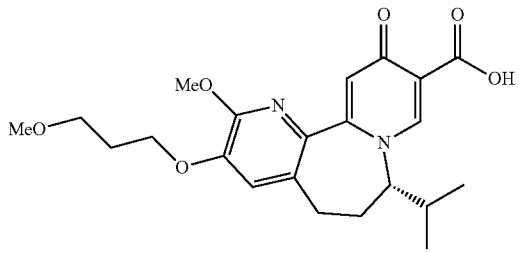 [SMILES: COCCCOc1cc2c(nc1OC)-c1cc(=O)c(C(=O)O)cn1[C@H](C(C)C)CC2]

Tert-butyl N-[(3S)-1-[6-methoxy-5-(3-methoxypropoxy)pyridin-3-yl]-4-methylpentan-3-yl]carbamate

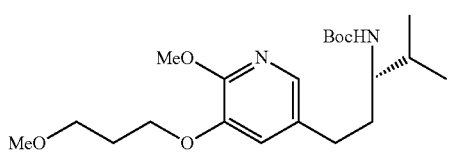 [SMILES: COCCCOc1cc(CC[C@@H](NC(=O)OC(C)(C)C)C(C)C)cnc1OC]

In a dry microwave vial, tert-butyl N-[(3R)-4-methylpent-1-en-3-yl]carbamate (289 mg, 1.45 mmol) was dissolved in THF (1 mL), followed by the addition of 9-borabicyclo[3.3.1]nonane (0.5 M in THF, 5.8 mL, 2.90 mmol) at 0° C. The reaction was warmed up to room temperature and stirred for 2 h. The solution was purged with nitrogen gas for 1 minute. 5-Bromo-2-methoxy-3-(3-methoxypropoxy)pyridine (400 mg, 1.45 mmol) was dissolved in THF (0.5 mL) and added into above solution via syringe. [1,1'-Bis(diphenylphosphino) ferrocene]dichloropalladium(II) (118 mg, 0.14 mmol), cesium carbonate (0.94 g, 2.90 mmol) and H$_2$O (0.5 mL) were added to the mixture. The reaction was stirred at room temperature for 16 h. The solvent was removed under reduced pressure. The residue was purified by normal phase SiO$_2$ chromatography (0% to 50% EtOAc/hexanes) to furnish tert-butyl N-[(3 S)-1-[6-methoxy-5-(3-methoxypropoxy)pyridin-3-yl]-4-methylpentan-3-yl]carbamate as a light yellow oil (0.28 g, 49% yield, m/z: 397 [M+H]$^+$ observed).

Tert-butyl N-[(3S)-1-[2-bromo-6-methoxy-5-(3-methoxypropoxy)pyridin-3-yl]-4-methylpentan-3-yl]carbamate

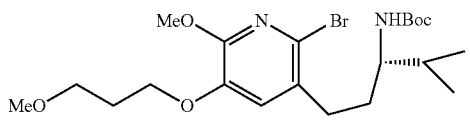 [SMILES: COCCCOc1cc(CC[C@H](NC(=O)OC(C)(C)C)C(C)C)c(Br)nc1OC]

Sodium acetate (57 mg, 0.69 mmol), tert-butyl N-[(3S)-1-[6-methoxy-5-(3-methoxypropoxy)pyridin-3-yl]-4-methylpentan-3-yl]carbamate (280 mg, 0.71 mmol) and bromine (0.04 mL, 0.71 mmol) were dissolved in glacial acetic acid (2 mL) and the reaction was stirred at room temperature for 2 h. The reaction was quenched by the addition of sat. aqueous sodium bicarbonate solution (5 mL). The reaction mixture was extracted with CH$_2$Cl$_2$ (2×5 mL). The combined organic layer was dried over sodium sulfate and concentrated under reduced pressure. The residue was purified by normal phase SiO$_2$ chromatography (0% to 40% EtOAc/hexanes) to furnish tert-butyl N-[(3 S)-1-[2-bromo-6-methoxy-5-(3-methoxypropoxy)pyridin-3-yl]-4-methylpentan-3-yl]carbamate as a light yellow solid (210 mg, 63% yield, m/z: 474/476 [M+H]$^+$ observed).

(3S)-1-[2-Bromo-6-methoxy-5-(3-methoxypropoxy)pyridin-3-yl]-4-methylpentan-3-amine

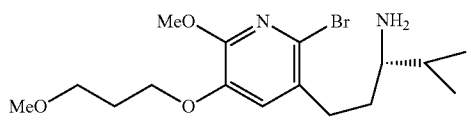 [SMILES: COCCCOc1cc(CC[C@H](N)C(C)C)c(Br)nc1OC]

To a solution of tert-butyl N-[(3 S)-1-[2-bromo-6-methoxy-5-(3-methoxypropoxy)pyridin-3-yl]-4-methylpentan-3-yl]carbamate (210 mg, 0.44 mmol) in CH$_2$Cl$_2$ (2 mL) was added a solution of HCl (4N in 1,4-dioxane, 0.2 mL, 0.88 mmol) was added and stirred at room temperature for 16 h.

The reaction was quenched by adding 1N aqueous sodium hydroxide solution (2 mL). The aqueous layer was extracted with CH$_2$Cl$_2$ (3×2 mL). The combined organic layer was dried over sodium sulfate and concentrated under reduced pressure to give (3 S)-1-[2-bromo-6-methoxy-5-(3-methoxypropoxy)pyridin-3-yl]-4-methylpentan-3-amine as a yellow solid that was used in the next step without further purification (0.13 g, 78% yield, m/z: 374/376 [M+H]$^+$ observed).

1-[(3S)-1-[2-Bromo-6-methoxy-5-(3-methoxypropoxy)pyridin-3-yl]-4-methylpentan-3-yl]-4-oxopyridine-3-carboxylic acid

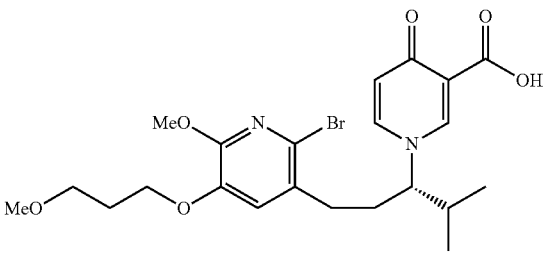 [SMILES: COCCCOc1cc(CC[C@@H](C(C)C)n2ccc(=O)c(C(=O)O)c2)c(Br)nc1OC]

(3S)-1-[2-Bromo-6-methoxy-5-(3-methoxypropoxy)pyridin-3-yl]-4-methylpentan-3-amine (20 mg, 0.05 mmol) and tert-butyl 4-oxopyran-3-carboxylate (10 mg, 0.05 mmol) were dissolved in ethanol/acetic acid (1:1, 0.2 mL) and heated to 90° C. for 4 h. The solvent was removed under reduced pressure. The residue was purified by reverse phase HPLC to afford 1-[(3S)-1-[2-bromo-6-methoxy-5-(3-methoxypropoxy)pyridin-3-yl]-4-methylpentan-3-yl]-4-oxopyridine-3-carboxylic acid as a white solid (11 mg, 44% yield, m/z: 497 [M+H]$^+$ observed).

(S)-7-Isopropyl-2-methoxy-3-(3-methoxypropoxy)-11-oxo-5,6,7,11-tetrahydrodipyrido[1,2-a:2',3'-c]azepine-10-carboxylic acid

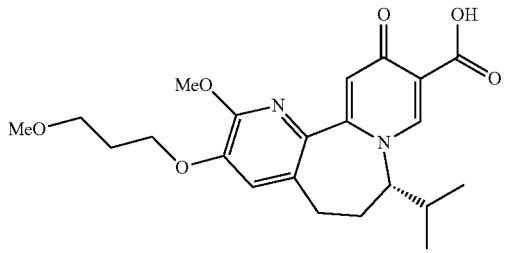 [SMILES: COCCCOc1cc2c(nc1OC)-c1cc(=O)c(C(=O)O)cn1[C@H](C(C)C)CC2]

1-[(3S)-1-[2-bromo-6-methoxy-5-(3-methoxypropoxy)pyridin-3-yl]-4-methylpentan-3-yl]-4-oxopyridine-3-carboxylic acid (27 mg, 0.05 mmol) and potassium acetate (12 mg, 0.12 mmol) were dissolved in dimethylacetamide (2 mL) in a microwave flask and sealed. The solution was purged with nitrogen for 2 min, followed by the addition of (chloro[(tri-tert-butylphosphine)-2-(2-aminobiphenyl)]palladium(II)) (3 mg, 0.01 mmol). The reaction was heated at 125° C. in microwave reactor for 1 h. The crude mixture was purified by reverse phase HPLC to afford (S)-7-isopropyl-2-methoxy-3-(3-methoxypropoxy)-11-oxo-5,6,7,11-tetrahydrodipyrido[1,2-a:2',3'-c]azepine-10-carboxylic acid as a white solid (5 mg, 24% yield, m/z: 417 [M+H]$^+$ observed). $^1$H NMR (300 MHz, CDCl$_3$) δ 8.64 (s, 1H), 7.18 (s, 1H), 6.94 (s, 1H), 4.18 (t, J=6.5 Hz, 2H), 4.05 (d, J=1.0 Hz, 3H), 3.59-3.60 (m, 3H), 3.37 (t, J=1.1 Hz, 3H), 2.69 (bs, 1H), 2.49 (bs, 3H), 2.15 (m, 3H), 1.02-0.86 (m, 6H).

The following example was prepared in a similar manner as (S)-7-isopropyl-2-methoxy-3-(3-methoxypropoxy)-11-oxo-5,6,7,11-tetrahydrodipyrido[1,2-a:2',3'-c]azepine-10-carboxylic acid from 8-bromo-3,4-dihydro-2H-[1,4]dioxepino[2,3-b]pyridine and tert-butyl N-[(3R)-4-methylpent-1-en-3-yl]carbamate.

Example 169: (S)-6-Isopropyl-2-oxo-2,6,7,8,12,13-hexahydro-11I-[1,4]dioxepino[2',3':5,6]pyrido[2,3-c]pyrido[1,2-a]azepine-3-carboxylic acid

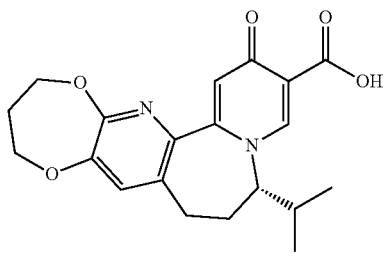 [SMILES: CC(C)[C@@H]1CCc2cc3c(nc2-c2cc(=O)c(C(=O)O)cn21)OCCCO3]

m/z: 371 [M+H]$^+$ observed. $^1$H NMR (400 MHz, CDCl$_3$): δ 8.55 (s, 1H), 7.12 (s, 1H), 6.99 (s, 1H), 4.39 (d, J=30.7 Hz, 4H), 3.51 (bs, 1H), 2.83-1.75 (m, 6H), 1.36 (d, J=13.0 Hz, 1H), 0.97-0.78 (m, 6H).

Example 170: (S)-6-Isopropyl-2-oxo-2,6,7,8,11,12-hexahydro-[1,4]dioxino[2',3':5,6]pyrido[2,3-c]pyrido[1,2-a]azepine-3-carboxylic acid e

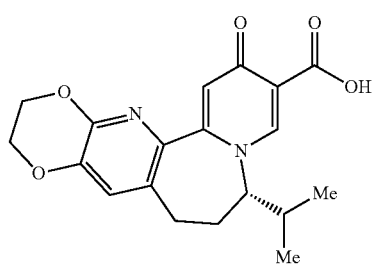 [SMILES: CC(C)[C@@H]1CCc2cc3c(nc2-c2cc(=O)c(C(=O)O)cn21)OCCO3]

Example 171: 2'-Methoxy-3'-(3-methoxypropoxy)-10'-oxo-5',10'-dihydrospiro[cyclobutane-1,6'-pyrido[1,2-h][1,7]naphthyridine]-9'-carboxylic acid

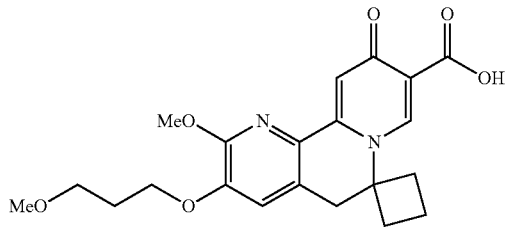 [SMILES: COCCCOc1cc2c(nc1OC)-c1cc(=O)c(C(=O)O)cn1C1(CCC1)C2]

Tert-butyl N-[1-[methoxy(methyl)carbamoyl]cyclobutyl]carbamate

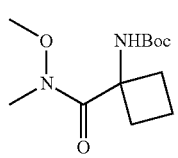 [SMILES: CON(C)C(=O)C1(NC(=O)OC(C)(C)C)CCC1]

1-(tert-Butoxycarbonylamino)cyclobutanecarboxylic acid (3 g, 13.9 mmol), HATU (6.36 g, 16.7 mmol) and N,O-dimethylhydroxylamine hydrochloride (1.5 g, 15.3 mmol) were dissolved in DMF (45 mL). Then N,N-diisopropylethylamine (9.71 mL, 55.8 mmol) was added. The reaction was stirred at rt for 16 h. The mixture was diluted with EtOAc (100 mL) and poured into H$_2$O (200 mL). The aqueous phase was separated and extracted with EtOAc (2×50 mL). The combined organics were dried over sodium sulfate, filtered and concentrated under vacuum. The residue was purified by normal phase SiO$_2$ chromatography (5% to 50% EtOAc/petroleum ether) to give tert-butyl N-[1-[methoxy(methyl)carbamoyl]cyclobutyl]carbamate as a light yellow solid (2 g, 56%, m/z: 259 [M+H]$^+$ observed).

Tert-butyl N-[1-[6-methoxy-5-(3-methoxypropoxy)pyridine-3-carbonyl]cyclo butyl]carbamate

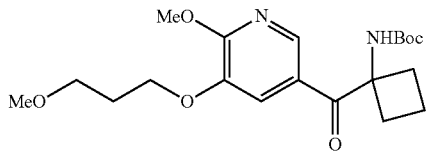 [SMILES: COCCCOc1cc(C(=O)C2(NC(=O)OC(C)(C)C)CCC2)cnc1OC]

To a mixture of 5-bromo-2-methoxy-3-(3-methoxypropoxy)pyridine (3 g, 11 mmol) in THF (30 mL) was added n-BuLi (2.5M in hexanes, 6.1 mL, 15 mmol) dropwise at −70° C. under $N_2$. The mixture was stirred at −70° C. for 1 h. Then a mixture of tert-butyl N-[1-[methoxy(methyl) carbamoyl]cyclobutyl]carbamate (0.37 mL, 5.76 mmol) in THF (10 mL) was added dropwise at −70° C. under $N_2$. The mixture was stirred at −70° C. for 3 h. The mixture was quenched with sat. aqueous ammonium chloride solution (200 mL) and extracted with EtOAc (3×100 mL). The combined organic layers were dried over sodium sulfate, filtered and concentrated under reduced pressure. The residue was purified by normal phase $SiO_2$ chromatography (10% to 35% EtOAc/petroleum ether) to give tert-butyl N-[1-[6-methoxy-5-(3-methoxy propoxy)pyridine-3-carbonyl]cyclobutyl]carbamate as a yellow oil (500 mg, 22%, m/z: 395 $[M+H]^+$ observed).

1-[[6-Methoxy-5-(3-methoxypropoxy)-3-pyridyl]methyl]cyclobutanamine

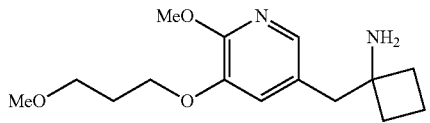 [SMILES: COCCCOc1cc(CC2(N)CCC2)cnc1OC]

To a mixture of tert-butyl N-[1-[6-methoxy-5-(3-methoxypropoxy)pyridine-3-carbonyl]cyclobutyl]carbamate (500 mg, 1.3 mmol) and gadolinium(III) trifluoromethanesulfonate (524 mg, 1.01 mmol) in 1,2-dichloroethane (10 mL) was added chlorodimethylsilane (600 mg, 6.3 mmol). The reaction was stirred at 80° C. for 16 hours. The pH of the reaction was adjusted to 8-9 with sat. aqueous sodium bicarbonate solution. The aqueous layer was extracted with $CH_2Cl_2$ (3×50 mL). The combined organics were dried over over sodium sulfate, filtered and concentrated under vacuum to give 1-[[6-methoxy-5-(3-methoxypropoxy)-3-pyridyl]methyl]cyclobutanamine as a yellow oil that was used in the next step without further purification (360 mg, 99%, m/z: 281 $[M+H]^+$ observed).

Tert-butyl N-[1-[[6-methoxy-5-(3-methoxypropoxy)-3-pyridyl]methyl]cyclobutyl]carbamate

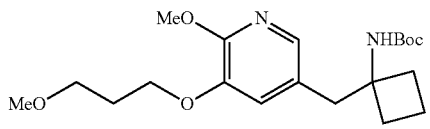 [SMILES: COCCCOc1cc(CC2(NC(=O)OC(C)(C)C)CCC2)cnc1OC]

To a mixture of 1-[[6-methoxy-5-(3-methoxypropoxy)-3-pyridyl]methyl]cyclobutanamine (360 mg, 1.28 mmol) and triethylamine (0.45 mL, 3.2 mmol) in $CH_2Cl_2$ (10 mL) was added di-tert-butyl dicarbonate (336.3 mg, 1.54 mmol). The reaction was stirred at rt for 16 hours. The reaction was quenched by adding $H_2O$ (20 mL). The aqueous layer was extracted with $CH_2Cl_2$ (3×10 mL). The combined organics were dried over sodium sulfate, filtered and concentrated under reduced pressure. The residue was purified by normal phase $SiO_2$ chromatography (25% to 50% EtOAc/petroleum ether) to give tert-butyl N-[1-[[6-methoxy-5-(3-methoxypropoxy)-3-pyridyl]methyl]cyclobutyl]carbamate as a yellow solid (220 mg, 45%, m/z: 381 $[M+H]^+$ observed).

Tert-butyl N-[1-[[2-bromo-6-methoxy-5-(3-methoxypropoxy)-3-pyridyl]methyl]cyclobutyl]carbamate

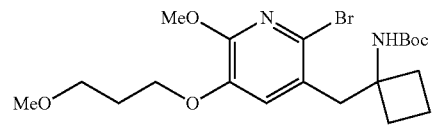 [SMILES: COCCCOc1cc(CC2(NC(=O)OC(C)(C)C)CCC2)c(Br)nc1OC]

To a mixture of tert-butyl N-[1-[[6-methoxy-5-(3-methoxypropoxy)-3-pyridyl]methyl]cyclobutyl]carbamate (220 mg, 0.58 mmol) in $CH_2Cl_2$ (1 mL) and sat. aqueous $NaHCO_3$ solution (1 mL) at 0° C. under $N_2$ was added a solution of bromine (0.03 mL, 0.64 mmol) in $CH_2Cl_2$ (1 mL) dropwise. The mixture was stirred at rt for 16 hours. The reaction mixture was quenched by the addition of sat. aqueous sodium bicarbonate solution (20 mL) and extracted with $CH_2Cl_2$ (3×10 mL). The combined organic layers were dried over sodium sulfate, filtered and concentrated under reduced pressure. The residue purified by normal phase $SiO_2$ chromatography (5% to 35% EtOAc/petroleum ether) to give tert-butyl N-[1-[[2-bromo-6-methoxy-5-(3-methoxypropoxy)-3-pyridyl]methyl]cyclobutyl]carbamate as a yellow oil (110 mg, 42%, m/z: 458/460 $[M+H]^+$ observed). $^1$H NMR (400 MHz, $CDCl_3$): δ 7.14 (s, 1H), 4.49 (s, 1H), 4.13-4.10 (m, 3H), 3.98 (s, 3H), 3.58-3.55 (m, 2H), 3.36 (s, 3H), 3.12 (m, 1H), 2.28-2.25 (m, 2H), 2.19-2.09 (m, 2H), 1.82-1.79 (m, 2H), 1.57-1.47 (m, 2H), 1.37 (s, 9H).

Tert-butyl (1-((2-formyl-6-methoxy-5-(3-methoxypropoxy)pyridin-3-yl)methyl)cyclobutyl) carbamate

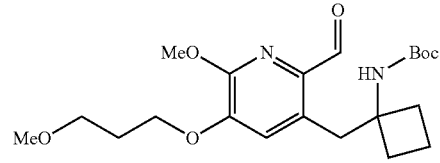 [SMILES: COCCCOc1cc(CC2(NC(=O)OC(C)(C)C)CCC2)c(C=O)nc1OC]

Tert-butyl N-(1-{[2-bromo-6-methoxy-5-(3-methoxypropoxy)pyridin-3-yl]methyl}cyclobutyl) carbamate (110 mg, 0.24 mmol) was dissolved in anhydrous THF (5 mL). The reaction was cooled to −78° C. and n-BuLi (1.6 M solution in hexanes, 0.45 mL, 0.72 mmol) was added dropwise. The reaction mixture was stirred at −78° C. for 15 minutes. Dimethylformamide (0.02 mL, 0.29 mmol) was added dropwise and the reaction was stirred at −78° C. for 10 minutes, then warmed to room temperature and stirred for an additional 10 minutes. The reaction mixture was quenched with H₂O (5 mL) with vigorous stirring. The reaction was extracted with EtOAc (3×5 mL). The combined organics were dried with sodium sulfate and concentrated under vacuum to give tert-butyl N-(1-{[2-formyl-6-methoxy-5-(3-methoxypropoxy)pyridin-3-yl]methyl}cyclobutyl)carbamate as a yellow oil that was used in the next step without further purification (98 mg, 100.0%, m/z: 409 [M+H]⁺ observed).

2'-Methoxy-3'-(3-methoxypropoxy)-5'H-spiro[cyclobutane-1,6'-[1,7]naphthyridine]

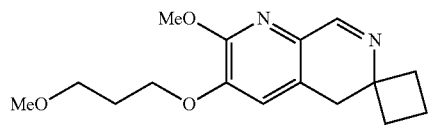 [SMILES: COCCCOc1cc2c(nc1OC)C=NC1(CCC1)C2]

To a solution of tert-butyl N-(1-{[2-formyl-6-methoxy-5-(3-methoxypropoxy)pyridin-3-yl]methyl}cyclobutyl)carbamate (98 mg, 0.24 mmol) in CH₂Cl₂ (5 mL) was added hydrogen chloride (4N solution in 1,4-dioxane, 0.12 mL, 0.48 mmol). The reaction mixture was stirred at room temperature for 5 hours. The reaction mixture was concentrated under vacuum, then treated with H₂O (5 mL) and basified with sat. aqueous sodium bicarbonate solution until pH 10-12. The mixture was extracted with CH₂Cl₂ (3×5 mL). The combined organics were dried over anhydrous sodium sulfate and evaporated under vacuum. The residue was purified by normal phase SiO₂ chromatography (0-6% MeOH/CH₂Cl₂) to give 2-methoxy-3-(3-methoxypropoxy)-5H-spiro[1,7-naphthyridine-6,1'-cyclobutane] as a colorless oil that was used in the next step without further purification (25 mg, 36%, m/z: 291 [M+H]⁺ observed).

Ethyl 2'-methoxy-3'-(3-methoxypropoxy)-10'-oxo-5',10',11',11a'-tetrahydrospiro[cyclobutane-1,6'-pyrido[1,2-h[1,7]naphthyridine]-9'-carboxylate

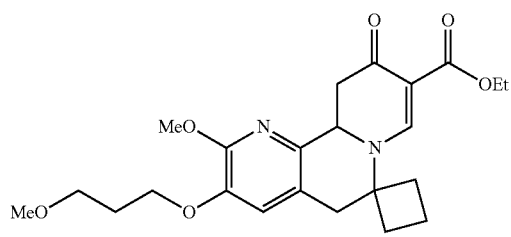 [SMILES: CCOC(=O)C1=CN2C(CC1=O)c1nc(OC)c(OCCCOC)cc1CC21CCC1]

2-Methoxy-3-(3-methoxypropoxy)-5H-spiro[1,7-naphthyridine-6,1'-cyclobutane] (25 mg, 0.09 mmol) and ethyl (2E)-2-(ethoxymethylidene)-3-oxobutanoate (48 mg, 0.26 mmol) were dissolved in anhydrous ethanol (3 mL) and the reaction mixture was heated at 80° C. for 16 hours. The reaction mixture was concentrated under reduced pressure to give ethyl 2'-methoxy-3'-(3-methoxypropoxy)-10'-oxo-11',11'a-dihydro-5'H-spiro[cyclobutane-1,6'-pyrido[1,2-h]1,7-naphthyridine]-9'-carboxylate as a brown foam that was used in the next step without further purification (37 mg, 100%, m/z: 431 [M+H]⁺ observed).

Ethyl 2'-methoxy-3'-(3-methoxypropoxy)-10'-oxo-5',10'-dihydrospiro[cyclobutane-1,6'-pyrido[1,2-h][1,7]naphthyridine]-9'-carboxylate

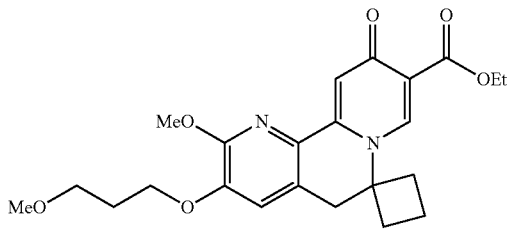 [SMILES: CCOC(=O)c1cn2c(cc1=O)-c1nc(OC)c(OCCCOC)cc1CC21CCC1]

ethyl 2'-methoxy-3'-(3-methoxypropoxy)-10'-oxo-11',11'a-dihydro-5'H-spiro[cyclobutane-1,6'-pyrido[1,2-h]1,7-naphthyridine]-9'-carboxylate (37 mg, 0.09 mmol) and p-chloranil (25.4 mg, 0.10 mmol) were dissolved in 2-MeTHF (3 mL) and stirred at 70° C. for 1 h. The reaction mixture was evaporated under vacuum. The residue was purified by normal phase SiO₂ chromatography (0% to 7% MeOH/CH₂Cl₂) to give ethyl 2'-methoxy-3'-(3-methoxypropoxy)-10'-oxo-5'H-spiro[cyclobutane-1,6'-pyrido[1,2-h]1,7-naphthyridine]-9'-carboxylate as a yellow solid that was used in the next step without further purification (8 mg, 22%, m/z: 431 [M+H]⁺ observed).

2'-Methoxy-3'-(3-methoxypropoxy)-10'-oxo-5',1'-dihydrospiro[cyclobutane-1,6'-pyrido[1,2-h][1,7]naphthyridine]-9'-carboxylic acid

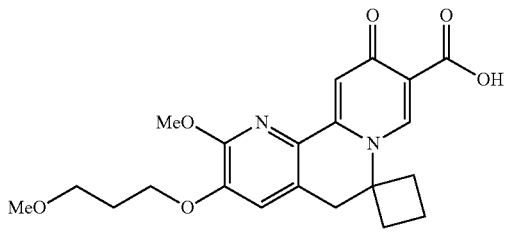 [SMILES: COCCCOc1cc2c(nc1OC)-c1cc(=O)c(C(=O)O)cn1C1(CCC1)C2]

To a solution of ethyl 2'-methoxy-3'-(3-methoxypropoxy)-10'-oxo-5'H-spiro[cyclobutane-1,6'-pyrido[1,2-h]1,7-naphthyridine]-9'-carboxylate (8 mg, 0.02 mmol) in 1,4-dioxane/H₂O (2:1 mixture, 2 mL) was added lithium hydroxide monohydrate (1.2 mg, 0.03 mmol). The reaction was stirred at rt for 6 hours. The pH of the reaction was adjusted to 5-6 by the addition of 1N HCl. EtOAc (2 mL) and H₂O (2 mL) were added to the reaction mixture. The aqueous layer was extracted with EtOAc (2×2 mL). The combined organic phase was dried over sodium sulfate and the solvent removed under vacuum. The residue was purified by normal phase SiO₂ chromatography (0% to 4% MeOH/CH₂Cl₂) to afford 2'-methoxy-3'-(3-methoxypropoxy)-10'-oxo-5'H-spiro[cyclobutane-1,6'-pyrido[1,2-h]1,7-naphthyridine]-9'-carboxylic acid as a white solid (5 mg, 66%, m/z: 401 [M+H]⁺ observed). ¹H NMR (400 MHz, CDCl₃) δ 8.53 (s, 1H), 7.74 (d, J=0.6 Hz, 1H), 7.00 (s, 1H), 4.55 (q, J=8.1 Hz, 1H), 4.19 (q, J=6.4 Hz, 2H), 4.06 (d, J=0.7 Hz, 3H), 3.65 (td, J=7.1, 3.3 Hz, 1H), 3.58 (dp, J=8.3, 2.9 Hz, 2H), 3.36 (d, J=0.7 Hz, 3H), 2.38-2.07 (m, 5H), 1.83 (tdd, J=15.6, 10.7, 7.4 Hz, 2H), 1.70 (dt, J=12.9, 7.9 Hz, 1H).

Example 172: (R)-5-Isopropyl-2-methoxy-9-oxo-5,9-dihydropyrido[2,3-a]indolizine-8-carboxylic acid

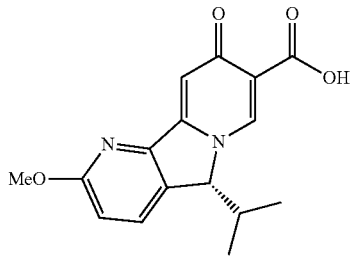 [SMILES: COc1ccc2c(n1)-c1cc(=O)c(C(=O)O)cn1[C@@H]2C(C)C]

(R,E)-N-((2-Bromo-6-methoxypyridine-3-yl)methylene)-2-methylpropane-2-sulfinamide

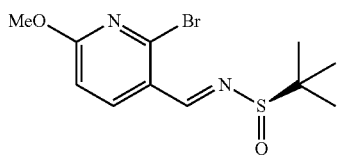 [SMILES: COc1ccc(/C=N/[S@](=O)C(C)(C)C)c(Br)n1]

To a solution of 2-bromo-6-methoxy-nicotinaldehyde (1.0 g, 4.6 mmol) and (R)-(+)-2-methyl-2-propanesulfinamide (0.84 g, 6.9 mmol) in CH$_2$Cl$_2$ (100 mL) was added boron trifluoride-diethyl ether complex (1.7 mL, 14 mmol) and the resulting mixture was stirred at rt for 24 h. The reaction mixture was then cooled to 0° C. and treated with aqueous sodium bicarbonate solution (100 mL). After stirring for 30 min the biphasic mixture was filtered through a plug of Celite®. The organic layer was separated, washed with sat. aqueous brine solution (100 mL), dried over anhydrous sodium sulfate and the solvent was removed under reduced pressure. The residue was purified by normal phase SiO$_2$ chromatography (0 to 10% EtOAc/hexanes) to give (R,E)-N-((2-bromo-6-methoxypyridine-3-yl)methylene)-2-methylpropane-2-sulfinamide as white solid (1.1 g, 75% yield, m/z: 318/320 [M+H]$^+$ observed). $^1$H NMR (300 MHz, CDCl$_3$): δ 8.85 (s, 1H), 8.22 (d, J=9 Hz, 1H), 6.80 (d, J=6 Hz, 1H), 4.03 (s, 3H), 1.27 (s, 9H).

(R)—N—((R)-1-(2-bromo-6-methoxypyridine-3-yl)-2-methylpropyl)-2-methylpropane-2-sulfinamide

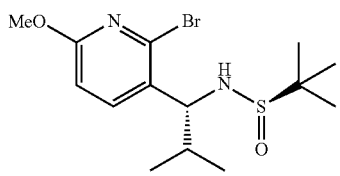 [SMILES: COc1ccc([C@H](N[S@](=O)C(C)(C)C)C(C)C)c(Br)n1]

To a solution of diisopropyl zinc (1.0 M solution in toluene, 10.1 mL, 10.2 mmol) was added dropwise isopropyl magnesium chloride (2.0 M solution in THF, 4 mL, 8 mmol) and the mixture allowed to stir at rt under argon for 20 min to give the triorganozincate reagent. The triorganozincate solution was transferred via cannula to a flask containing (R,E)-N-((2-bromo-6-methoxypyridine-3-yl)methylene)-2-methylpropane-2-sulfinamide (2.16 g, 6.79 mmol) in THF (50 mL) at −78° C. and the mixture allowed to stir for further 3 h. Saturated aqueous ammonium chloride solution (50 mL) and EtOAc (50 mL) were added to the mixture and stirred at rt for 1 h. The biphasic mixture was filtered through a pad of Celite® and the organic layer separated, washed with sat. aqueous brine solution (100 mL) and dried over anhydrous sodium sulfate. The organic solvent was distilled off under reduced pressure and the resultant residue was purified by normal phase SiO$_2$ chromatography (10 to 20% EtOAc/CH$_2$Cl$_2$) to give the major diastereomer (R)—N—((R)-1-(2-bromo-6-methoxypyridine-3-yl)-2-methylpropyl)-2-methylpropane-2-sulfinamide as white solid (0.92 g, 37% yield, m/z: 362/364 [M+H]$^+$ observed). $^1$H NMR (300 MHz, CDCl$_3$): δ 7.50 (d, J=6 Hz, 1H), 6.74 (d, J=9 Hz, 1H), 4.39 (t, J=6 Hz, 1H), 3.94 (s, 3H), 3.69 (d, J=9 Hz, 1H), 2.22-2.15 (m, 1H), 1.23 (s, 9H), 1.04 (d, J=6 Hz, 3H), 0.91 (d, J=6 Hz, 3H).

(R)-1-(2-Bromo-6-methoxypyridine-3-yl)-2-methylpropane-1-amine

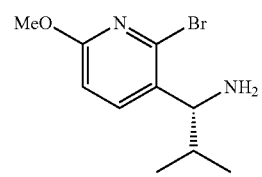

To a stirred solution of (R)—N—((R)-1-(2-bromo-6-methoxypyridine-3-yl)-2-methylpropyl)-2-methylpropane-2-sulfinamide (0.92 g, 2.5 mmol) in MeOH (50 mL) was added HCl solution (4N in 1,4-dioxane, 10 mL) and the mixture allowed to stir at rt for 15 h. The mixture was then concentrated to dryness under reduced pressure and the residue treated with aqueous saturated sodium bicarbonate solution (25 mL), extracted with EtOAc (2×30 mL) and the organic layer dried over anhydrous sodium sulfate. The organic solvent was removed under reduced pressure to give (R)-1-(2-bromo-6-methoxypyridine-3-yl)-2-methylpropane-1-amine as a yellow oil that was used in the next step without further purification (0.75 g, >100% yield, m/z: 258/260 [M+H]$^+$ observed). $^1$H NMR (300 MHz, CDCl$_3$): δ 7.67 (d, J=9 Hz, 1H), 6.74 (d, J=6 Hz, 1H), 4.07 (d, J=6 Hz, 1H), 3.94 (s, 3H), 1.96-1.89 (m, 1H), 1.52 (bs, 2H), 1.01 (d, J=6 Hz, 3H), 0.89 (d, J=6 Hz, 3H).

(R)-Ethyl-1-(1-(2-bromo-6-methoxypyridine-3-yl)-2-methylpropyl)-4-oxo-1,4-dihydro pyridine-3-carboxylate

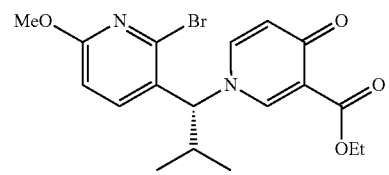

A mixture of (R)-1-(2-bromo-6-methoxypyridine-3-yl)-2-methylpropane-1-amine (0.65 g, 2.5 mmol) and ethyl-4-oxo-4H-pyran-3-carboxylate (0.42 g, 2.50 mmol, prepared according to WO201713046) in EtOH (20 mL) was stirred at 90° C. for 1 h. Acetic acid (3 mL) was then added and the mixture allowed to stir at 90° C. for further 6 h. The reaction mixture was then concentrated to dryness under reduced pressure and the residue treated with EtOAc (30 mL) and aqueous saturated sodium bicarbonate solution (25 mL). The organic layer was separated, dried over anhydrous sodium sulfate, and the solvent distilled off under reduced pressure and the resultant residue was purified by normal phase SiO$_2$ chromatography (0 to 10% MeOH/CH$_2$Cl$_2$) to give (R)-ethyl-1-(1-(2-bromo-6-methoxypyridine-3-yl)-2-methylpropyl)-4-oxo-1,4-dihydro pyridine-3-carboxylate as yellow oil (0.79 g, 77% yield, m/z: 408/410 [M+H]$^+$ observed). $^1$H NMR (300 MHz, CDCl$_3$): δ 8.26 (d, J=3 Hz, 1H), 7.67 (d, J=6 Hz, 1H), 7.32 (dd, J=6, 2 Hz, 1H), 6.86 (d, J=9 Hz, 1H), 6.48 (d, J=6 Hz, 1H), 4.83 (d, J=12 Hz, 1H), 4.38 (q, J=6 Hz, 2H), 3.97 (s, 3H), 2.60-2.51 (m, 1H), 1.39 (t, J=6 Hz, 3H), 1.01 (dd, J=9 Hz & 6 Hz, 6H).

Example 173: (R)-ethyl-5-isopropyl-2-methoxy-9-oxo-5,9-dihydropyrido[2,3-a]indolizine-8-carboxylate

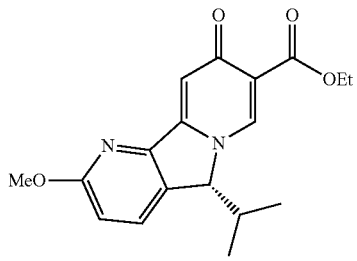

To a solution of (R)-ethyl-1-(1-(2-bromo-6-methoxypyridine-3-yl)-2-methylpropyl)-4-oxo-1,4-dihydro pyridine-3-carboxylate (0.79 g, 1.9 mmol) in dry N,N-dimethyl acetamide (10 mL) was added potassium acetate (0.38 g, 3.8 mmol) and degassed for 10 minutes with argon gas. Palladium (II) bromide (0.051 mg, 0.19 mmol) was added under argon atmosphere and the degassing continued for 20 minutes. The reaction mixture was then stirred at 120° C. for 30 h. The reaction mixture was cooled to rt, diluted with H$_2$O (30 mL) and extracted with EtOAc (3×10 mL), washed with sat. aqueous brine solution (10 mL), dried over sodium sulfate, filtered and concentrated under reduced pressure. The residue was purified by normal phase SiO$_2$ chromatography (0 to 15% MeOH in EtOAc) to afford a yellow oil. The semi pure yellow oil was purified twice by preparative TLC (9:1 CH$_2$Cl$_2$/MeOH, followed by 9:1 EtOAc/MeOH) to give (R)-ethyl-5-isopropyl-2-methoxy-9-oxo-5,9-dihydropyrido[2,3-a]indolizine-8-carboxylate as an off-white solid (100 mg, 16% yield, m/z: 329 [M+H]$^+$ observed). $^1$H NMR (300 MHz, CDCl$_3$): δ 8.47 (s, 1H), 7.71 (d, J=9 Hz, 1H), 7.09 (s, 1H), 6.89 (d, J=9 Hz, 1H), 5.16 (d, J=6 Hz, 1H), 4.44-4.37 (m, 2H), 4.03 (s, 3H), 2.61-2.55 (m, 1H), 1.41 (t, J=9 Hz, 3H), 1.24 (d, J=6 Hz, 3H), 0.60 (d, J=6 Hz, 3H).

Example 172: (R)-5-Isopropyl-2-methoxy-9-oxo-5,9-dihydropyrido[2,3-a]indolizine-8-carboxylic acid

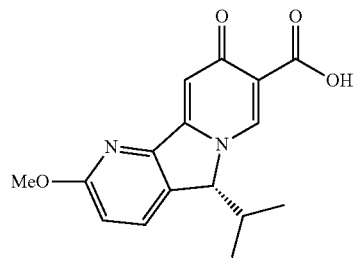 [SMILES: CCOC(=O)c1cn2c(cc1=O)-c1nc(OC)ccc1[C@H]2C(C)C]

To a solution of (R)-ethyl-5-isopropyl-2-methoxy-9-oxo-5,9-dihydropyrido[2,3-a]indolizine-8-carboxylate (50 mg, 0.15 mmol) in MeOH (3 mL) was added a solution of sodium hydroxide (0.018 g, 0.45 mmol) in H$_2$O (3 mL) and the mixture allowed to stir at rt for 4 h. The solvent was removed under reduced pressure and the resulting residue was diluted with H$_2$O (3 mL) and extracted with EtOAc (2×2 mL). The EtOAc extracts were discarded and the pH of the aqueous layer was adjusted to 5 using 1N HCl that resulted in the formation of a white precipitate. The white solid was collected by filtration, washed with H$_2$O (3 mL) and dried under vacuum to give (R)-5-isopropyl-2-methoxy-9-oxo-5,9-dihydropyrido[2,3-a]indolizine-8-carboxylic acid as a white solid (23 mg, 51% yield, m/z: 301 [M+H]$^+$ observed). $^1$H NMR (300 MHz, CDCl$_3$): δ 16.17 (s, 1H), 8.85 (s, 1H), 7.79 (d, J=9 Hz, 1H), 7.31 (s, 1H), 6.89 (d, J=9 Hz, 1H), 5.32 (d, J=3 Hz, 1H), 4.07 (s, 3H), 2.78-2.65 (m, 1H), 1.30 (d, J=6 Hz, 3H), 0.57 (d, J=6 Hz, 3H).

Example 174: Biological Examples

HBsAg Assay

Inhibition of HBsAg was determined in HepG2.2.15 cells. Cells were maintained in culture medium containing 10% fetal calf serum, G414, Glutamine, penicillin/streptomycin. Cells were seeded in 96-well collagen-coated plate at a density of 30,000 cells/well. Serially diluted compounds were added to cells next day at the final DMSO concentration of 0.5%. Cells were incubated with compounds for 2-3 days, after which medium was removed. Fresh medium containing compounds was added to cells for additional 3-4 days. At day 6 after exposure of compounds, supernatant was collected, the HBsAg immunoassay (microplate-based chemiluminescence immunoassay kits, CLIA, Autobio Diagnosics Co., Zhengzhou, China, Catalog # CL0310-2) was used to determine the level of HBsAg according to manufactory instruction. Dose-response curves were generated and the EC$_{50}$ value (effective concentrations that achieved 50% inhibitory effect) were determined using XLfit software. In addition, cells were seeded at a density of 5,000 cells/well for determination of cell viability in the presence and absence of compounds by using CellTiter-Glo reagent (Promega). Tables 1-3 show EC$_{50}$ values obtained by the HBsAg assay for selected compounds.

TABLE 1

| Ex. No. | Structure | Nomenclature | sAg EC$_{50}$, μM |
|---|---|---|---|
| 1 | 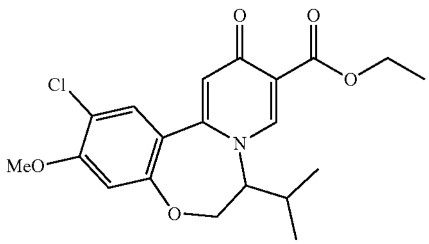 [SMILES: CCOC(=O)c1cn2c(cc1=O)-c1cc(Cl)c(OC)cc1OCC2C(C)C] | ethyl 2-chloro-7-isopropyl-3-methoxy-11-oxo-6,7-dihydro-11H-benzo[f]pyrido[1,2-d][1,4]oxazepine-10-carboxylate | 0.91 |
| 2 | 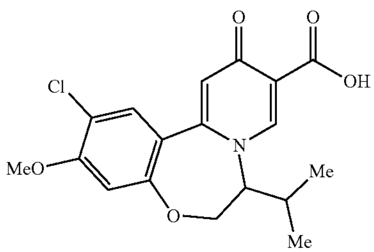 | 2-chloro-7-isopropyl-3-methoxy-11-oxo-6,7-dihydro-11H-benzo[f]pyrido[1,2-d][1,4]oxazepine-10-carboxylic acid | 0.076 |
| 3 | 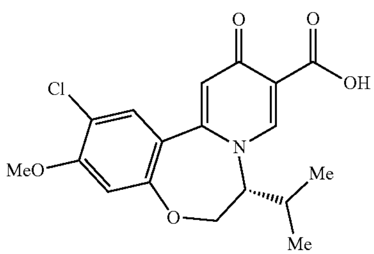 | (R)-2-chloro-7-isopropyl-3-methoxy-11-oxo-6,7-dihydro-11H-benzo[f]pyrido[1,2-d][1,4]oxazepine-10-carboxylic acid | 0.032 |
| 4 | 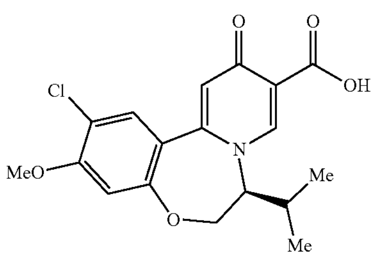 [SMILES: COc1cc2c(cc1Cl)-c1cc(=O)c(C(=O)O)cn1[C@@H](C(C)C)CO2] | (S)-2-chloro-7-isopropyl-3-methoxy-11-oxo-6,7-dihydro-11H-benzo[f]pyrido[1,2-d][1,4]oxazepine-10-carboxylic acid | 3.4 |
| 5 | 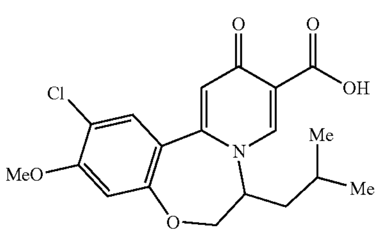 [SMILES: COc1cc2c(cc1Cl)-c1cc(=O)c(C(=O)O)cn1C(CC(C)C)CO2] | 2-chloro-7-isobutyl-3-methoxy-11-oxo-6,7-dihydro-11H-benzo[f]pyrido[1,2-d][1,4]oxazepine-10-carboxylic acid | 0.91 |
| 6 | 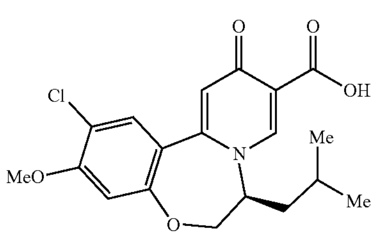 [SMILES: COc1cc2c(cc1Cl)-c1cc(=O)c(C(=O)O)cn1[C@@H](CC(C)C)CO2] | (S)-2-chloro-7-isobutyl-3-methoxy-11-oxo-6,7-dihydro-11H-benzo[f]pyrido[1,2-d][1,4]oxazepine-10-carboxylic acid | 3.8 |

TABLE 1-continued

| Ex. No. | Structure | Nomenclature | sAg EC$_{50}$, μM |
|---|---|---|---|
| 7 | 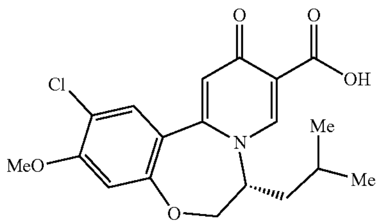 [SMILES: COc1cc2c(cc1Cl)-c1cc(=O)c(C(=O)O)cn1[C@H](CC(C)C)CO2] | (R)-2-chloro-7-isobutyl-3-methoxy-11-oxo-6,7-dihydro-11H-benzo[f]pyrido[1,2-d][1,4]oxazepine-10-carboxylic acid | 0.61 |
| 8 | 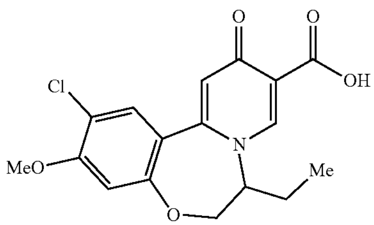 [SMILES: CCC1COc2cc(OC)c(Cl)cc2-c2cc(=O)c(C(=O)O)cn21] | 2-chloro-7-ethyl-3-methoxy-11-oxo-6,7-dihydro-11H-benzo[f]pyrido[1,2-d][1,4]oxazepine-10-carboxylic acid | 0.42 |
| 9 | 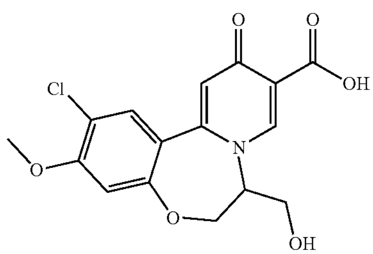 [SMILES: COc1cc2c(cc1Cl)-c1cc(=O)c(C(=O)O)cn1C(CO)CO2] | 2-chloro-7-(hydroxymethyl)-3-methoxy-11-oxo-6,7-dihydro-11H-benzo[f]pyrido[1,2-d][1,4]oxazepine-10-carboxylic acid | 8.6 |
| 10 | 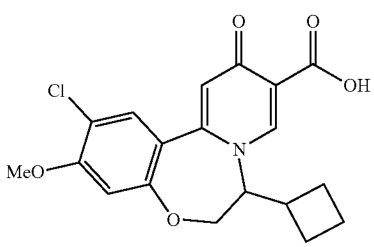 [SMILES: COc1cc2c(cc1Cl)-c1cc(=O)c(C(=O)O)cn1C(C1CCC1)CO2] | 2-chloro-7-cyclobutyl-3-methoxy-11-oxo-6,7-dihydro-11H-benzo[f]pyrido[1,2-d][1,4]oxazepine-10-carboxylic acid | 0.24 |
| 11 | 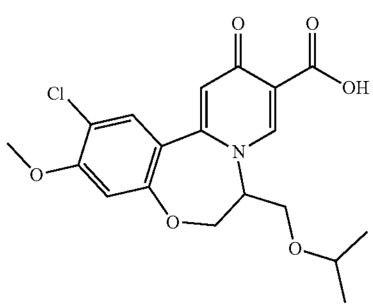 [SMILES: COc1cc2c(cc1Cl)-c1cc(=O)c(C(=O)O)cn1C(COC(C)C)CO2] | 2-Chloro-7-(isopropoxymethyl)-3-methoxy-11-oxo-6,7-dihydro-11H-benzo[f]pyrido[1,2-d][1,4]oxazepine-10-carboxylic acid | 12 |
| 12 | 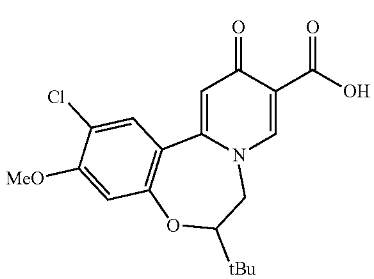 [SMILES: COc1cc2c(cc1Cl)-c1cc(=O)c(C(=O)O)cn1CC(C(C)(C)C)O2] | 6-(tert-butyl)-2-chloro-3-methoxy-11-oxo-6,7-dihydro-11H-benzo[f]pyrido[1,2-d][1,4]oxazepine-10-carboxylic acid | 47 |

TABLE 1-continued

| Ex. No. | Structure | Nomenclature | sAg EC$_{50}$, μM |
|---|---|---|---|
| 15 | 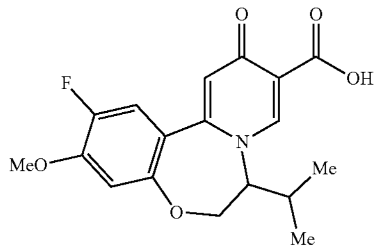 | 2-fluoro-7-isopropyl-3-methoxy-11-oxo-6,7-dihydro-11H-benzo[f]pyrido[1,2-d][1,4]oxazepine-10-carboxylic acid | 0.90 |
| 16 | 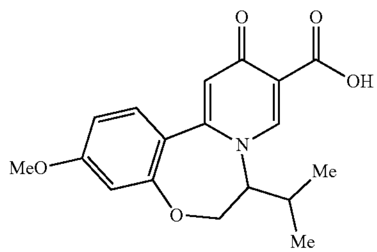 [SMILES: COc1ccc2c(c1)OCC(C(C)C)n1cc(C(=O)O)c(=O)cc1-2] | 7-isopropyl-3-methoxy-11-oxo-6,7-dihydro-11H-benzo[f]pyrido[1,2-d][1,4]oxazepine-10-carboxylic acid | 3.5 |
| 17 | 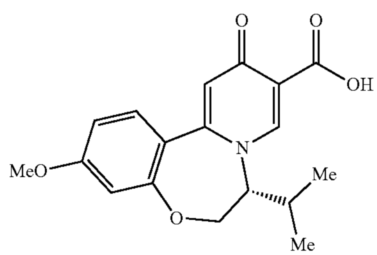 [SMILES: COc1ccc2c(c1)OC[C@@H](C(C)C)n1cc(C(=O)O)c(=O)cc1-2] | (R)-7-isopropyl-3-methoxy-11-oxo-6,7-dihydro-11H-benzo[f]pyrido[1,2-d][1,4]oxazepine-10-carboxylic acid | 0.88 |
| 18 | 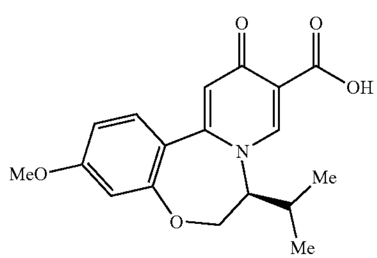 [SMILES: COc1ccc2c(c1)OC[C@H](C(C)C)n1cc(C(=O)O)c(=O)cc1-2] | (S)-7-isopropyl-3-methoxy-11-oxo-6,7-dihydro-11H-benzo[f]pyrido[1,2-d][1,4]oxazepine-10-carboxylic acid | 29 |
| 19 | 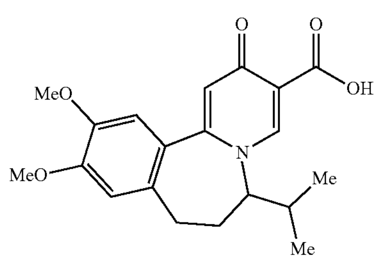 [SMILES: COc1cc2c(cc1OC)-c1cc(=O)c(C(=O)O)cn1C(C(C)C)CC2] | 6-isopropyl-10,11-dimethoxy-2-oxo-2,6,7,8-tetrahydrobenzo[c]pyrido[1,2-a]azepine-3-carboxylic acid | 0.027 |
| 33 | 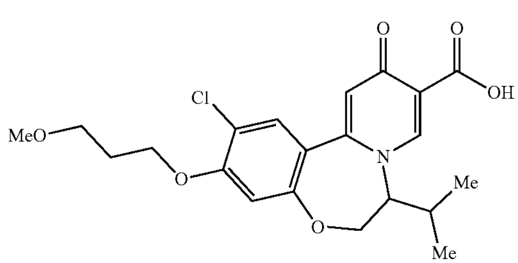 [SMILES: COCCCOc1cc2c(cc1Cl)-c1cc(=O)c(C(=O)O)cn1C(C(C)C)CO2] | 2-chloro-7-isopropyl-3-(3-methoxypropoxy)-11-oxo-6,7-dihydro-11H-benzo[f]pyrido[1,2-d][1,4]oxazepine-10-carboxylic acid | 0.029 |

TABLE 1-continued

| Ex. No. | Structure | Nomenclature | sAg EC$_{50}$, μM |
|---|---|---|---|
| 27 | 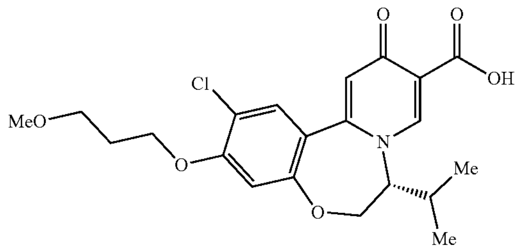 [SMILES: COCCCOc1cc2c(cc1Cl)-c1cc(=O)c(C(=O)O)cn1[C@H](C(C)C)CO2] | (R)-2-chloro-7-isopropyl-3-(3-methoxypropoxy)-11-oxo-6,7-dihydro-11H-benzo[f]pyrido[1,2-d][1,4]oxazepine-10-carboxylic acid | 0.011 |
| 28 | 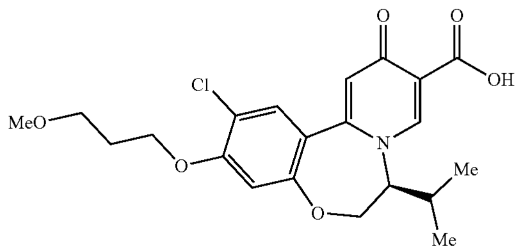 [SMILES: COCCCOc1cc2c(cc1Cl)-c1cc(=O)c(C(=O)O)cn1[C@@H](C(C)C)CO2] | (S)-2-chloro-7-isopropyl-3-(3-methoxypropoxy)-11-oxo-6,7-dihydro-11H-benzo[f]pyrido[1,2-d][1,4]oxazepine-10-carboxylic acid | 0.46 |
| 29 | 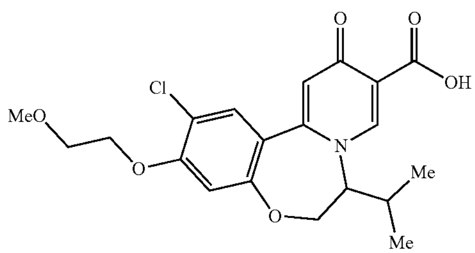 [SMILES: COCCOc1cc2c(cc1Cl)-c1cc(=O)c(C(=O)O)cn1C(C(C)C)CO2] | 2-chloro-7-isopropyl-3-(2-methoxyethoxy)-11-oxo-6,7-dihydro-11H-benzo[f]pyrido[1,2-d][1,4]oxazepine-10-carboxylic acid | 0.065 |
| 30 | 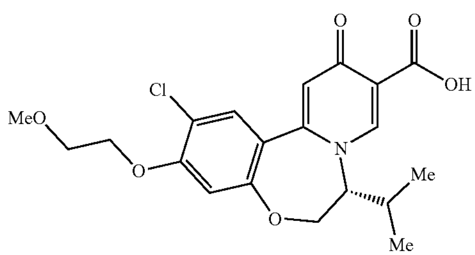 [SMILES: COCCOc1cc2c(cc1Cl)-c1cc(=O)c(C(=O)O)cn1[C@H](C(C)C)CO2] | (R)-2-chloro-7-isopropyl-3-(2-methoxyethoxy)-11-oxo-6,7-dihydro-11H-benzo[f]pyrido[1,2-d][1,4]oxazepine-10-carboxylic acid | 0.053 |
| 31 | 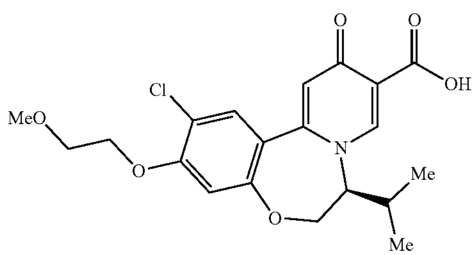 [SMILES: COCCOc1cc2c(cc1Cl)-c1cc(=O)c(C(=O)O)cn1[C@@H](C(C)C)CO2] | (S)-2-chloro-7-isopropyl-3-(2-methoxyethoxy)-11-oxo-6,7-dihydro-11H-benzo[f]pyrido[1,2-d][1,4]oxazepine-10-carboxylic acid | 0.8 |
| 32 | 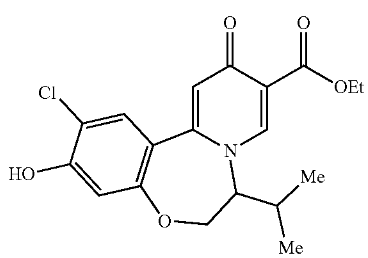 [SMILES: CCOC(=O)c1cn2c(cc1=O)-c1cc(Cl)c(O)cc1OCC2C(C)C] | ethyl 2-chloro-3-hydroxy-7-isopropyl-11-oxo-6,7-dihydro-11H-benzo[f]pyrido[1,2-d][1,4]oxazepine-10-carboxylate | 22 |

TABLE 1-continued

| Ex. No. | Structure | Nomenclature | sAg EC$_{50}$, μM |
|---|---|---|---|
| 34 | 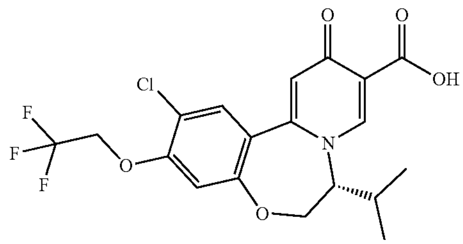 [SMILES: CC(C)[C@@H]1COc2cc(OCC(F)(F)F)c(Cl)cc2-c2cc(=O)c(C(=O)O)cn21] | (R)-2-chloro-7-isopropyl-11-oxo-3-(2,2,2-trifluoroethoxy)-6,7-dihydro-11H-benzo[f]pyrido[1,2-d][1,4]oxazepine-10-carboxylic acid | 0.086 |
| 35 | 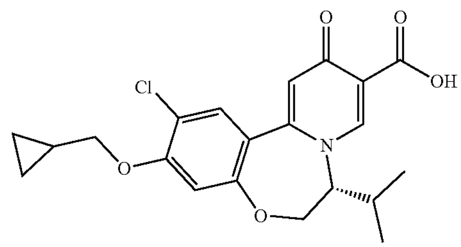 [SMILES: CC(C)[C@@H]1COc2cc(OCC3CC3)c(Cl)cc2-c2cc(=O)c(C(=O)O)cn21] | (R)-2-chloro-3-(cyclopropylmethoxy)-7-isopropyl-11-oxo-6,7-dihydro-11H-benzo[f]pyrido[1,2-d][1,4]oxazepine-10-carboxylic acid | 0.033 |
| 36 | 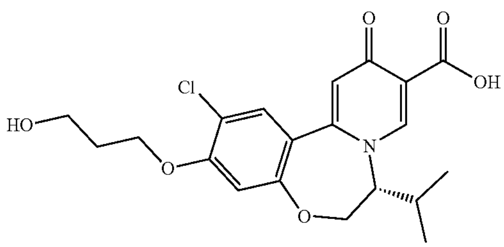 [SMILES: CC(C)[C@@H]1COc2cc(OCCCO)c(Cl)cc2-c2cc(=O)c(C(=O)O)cn21] | (R)-2-chloro-3-(3-hydroxypropoxy)-7-isopropyl-11-oxo-6,7-dihydro-11H-benzo[f]pyrido[1,2-d][1,4]oxazepine-10-carboxylic acid | 0.019 |
| 37 | 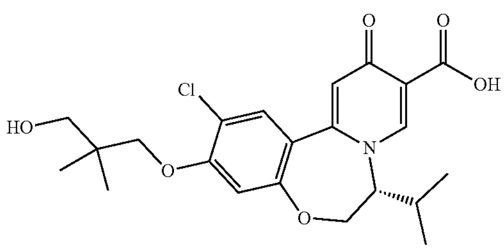 [SMILES: CC(C)[C@@H]1COc2cc(OCC(C)(C)CO)c(Cl)cc2-c2cc(=O)c(C(=O)O)cn21] | (R)-2-chloro-3-(3-hydroxy-2,2-dimethylpropoxy)-7-isopropyl-11-oxo-6,7-dihydro-11H-benzo[f]pyrido[1,2-d][1,4]oxazepine-10-carboxylic acid | 0.012 |
| 38 | 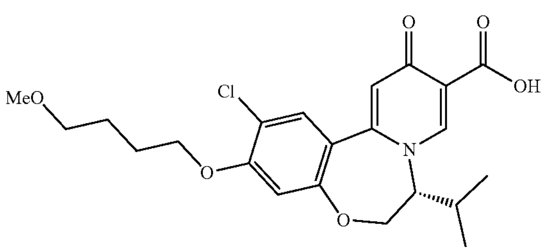 [SMILES: COCCCCOc1cc2c(cc1Cl)-c1cc(=O)c(C(=O)O)cn1[C@H](C(C)C)CO2] | (R)-2-chloro-7-isopropyl-3-(4-methoxybutoxy)-11-oxo-6,7-dihydro-11H-benzo[f]pyrido[1,2-d][1,4]oxazepine-10-carboxylic acid | 0.017 |
| 39 | 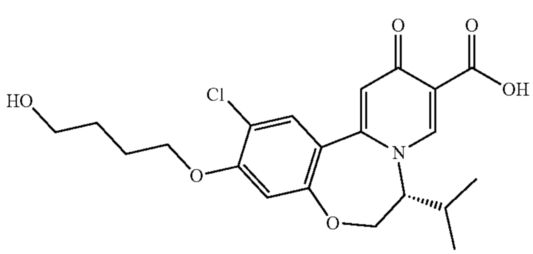 [SMILES: CC(C)[C@@H]1COc2cc(OCCCCO)c(Cl)cc2-c2cc(=O)c(C(=O)O)cn21] | (R)-2-chloro-3-(4-hydroxybutoxy)-7-isopropyl-11-oxo-6,7-dihydro-11H-benzo[f]pyrido[1,2-d][1,4]oxazepine-10-carboxylic acid | 0.014 |

TABLE 1-continued

| Ex. No. | Structure | Nomenclature | sAg EC$_{50}$, μM |
|---|---|---|---|
| 40 | 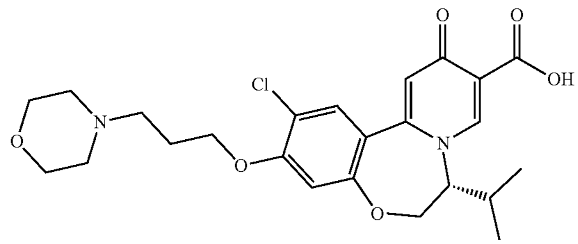 [SMILES: CC(C)[C@@H]1COc2cc(OCCCN3CCOCC3)c(Cl)cc2-c2cc(=O)c(C(=O)O)cn21] | (R)-2-chloro-7-isopropyl-3-(3-morpholinopropoxy)-11-oxo-6,7-dihydro-11H-benzo[f]pyrido[1,2-d][1,4]oxazepine-10-carboxylic acid | 0.14 |
| 41 | 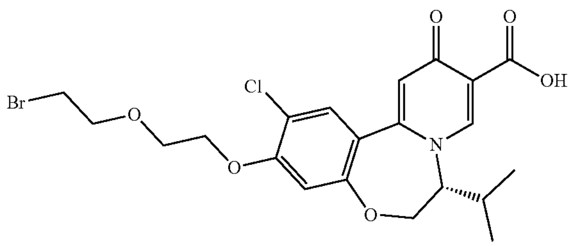 [SMILES: CC(C)[C@@H]1COc2cc(OCCOCCBr)c(Cl)cc2-c2cc(=O)c(C(=O)O)cn21] | (R)-3-(2-(2-bromoethoxy)ethoxy)-2-chloro-7-isopropyl-11-oxo-6,7-dihydro-11H-benzo[f]pyrido[1,2-d][1,4]oxazepine-10-carboxylic acid | 0.1 |
| 42 | 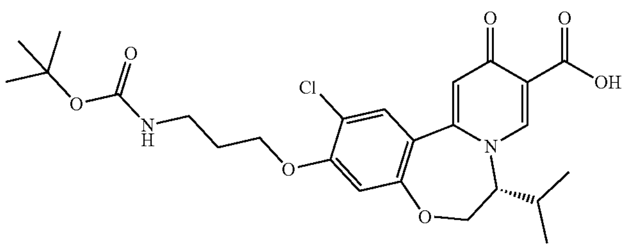 [SMILES: CC(C)[C@@H]1COc2cc(OCCCNC(=O)OC(C)(C)C)c(Cl)cc2-c2cc(=O)c(C(=O)O)cn21] | (R)-3-(3-((tert-butoxycarbonyl)amino)propoxy)-2-chloro-7-isopropyl-11-oxo-6,7-dihydro-11H-benzo[f]pyrido[1,2-d][1,4]oxazepine-10-carboxylic acid | 0.042 |
| 43 | 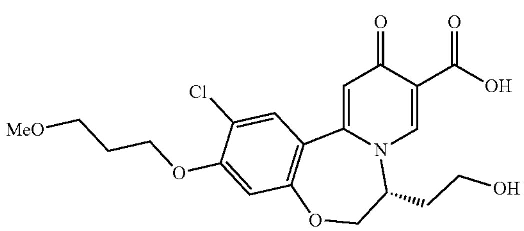 [SMILES: COCCCOc1cc2c(cc1Cl)-c1cc(=O)c(C(=O)O)cn1[C@H](CCO)CO2] | (R)-2-chloro-7-(2-hydroxyethyl)-3-(3-methoxypropoxy)-11-oxo-6,7-dihydro-11H-benzo[f]pyrido[1,2-d][1,4]oxazepine-10-carboxylic acid | 0.35 |
| 44 | 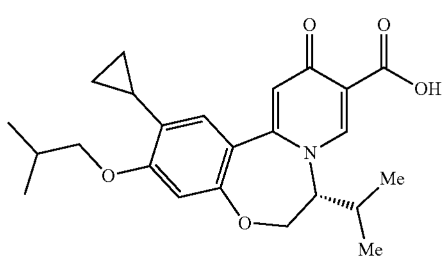 [SMILES: CC(C)COc1cc2c(cc1C1CC1)-c1cc(=O)c(C(=O)O)cn1[C@H](C(C)C)CO2] | (R)-2-cyclopropyl-3-isobutoxy-7-isopropyl-11-oxo-6,7-dihydro-11H-benzo[f]pyrido[1,2-d][1,4]oxazepine-10-carboxylic acid | 0.006 |
| 13 | 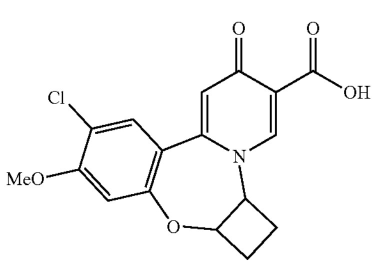 [SMILES: COc1cc2c(cc1Cl)-c1cc(=O)c(C(=O)O)cn1C1CCC1O2] | 11-chloro-10-methoxy-2-oxo-5a,6,7,7a-tetrahydro-2H-benzo[f]cyclobuta[b]pyrido[1,2-d][1,4]oxazepine-3-carboxylic acid | 1.8 |

TABLE 1-continued

| Ex. No. | Structure | Nomenclature | sAg EC$_{50}$, μM |
|---|---|---|---|
| 14 | 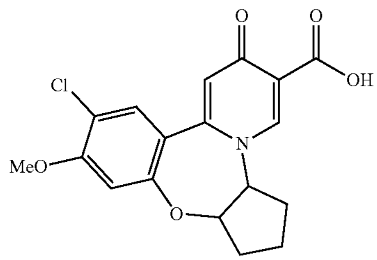 [SMILES: COc1cc2c(cc1Cl)-c1cc(=O)c(C(=O)O)cn1C1CCCC1O2] | 12-chloro-11-methoxy-2-oxo-5a,7,8,8a-tetrahydro-2H,6H-benzo[f]cyclopenta[b]pyrido[1,2-d][1,4]oxazepine-3-carboxylic acid | 0.56 |
| 75 | 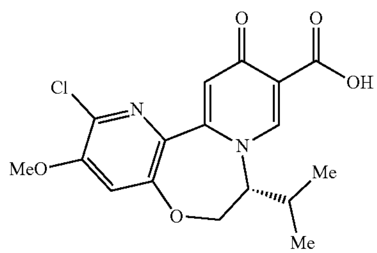 [SMILES: COc1cc2c(nc1Cl)-c1cc(=O)c(C(=O)O)cn1[C@H](C(C)C)CO2] | (R)-2-chloro-7-isopropyl-3-methoxy-11-oxo-6,7-dihydro-11H-dipyrido[1,2-d:2',3'-f][1,4]oxazepine-10-carboxylic acid | 0.026 |
| 70 | 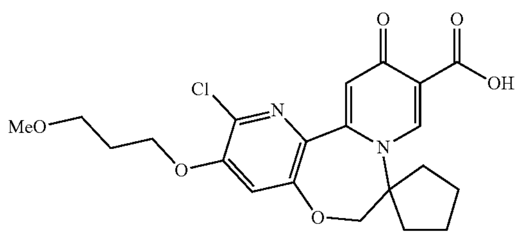 [SMILES: COCCCOc1cc2c(nc1Cl)-c1cc(=O)c(C(=O)O)cn1C1(CCCC1)CO2] | 2'-chloro-3'-(3-methoxypropoxy)-11'-oxo-6'H,11'H-spiro[cyclopentane-1,7'-dipyrido[1,2-d:2',3'-f][1,4]oxazepine]-10'-carboxylic acid | 0.041 |
| 69 | 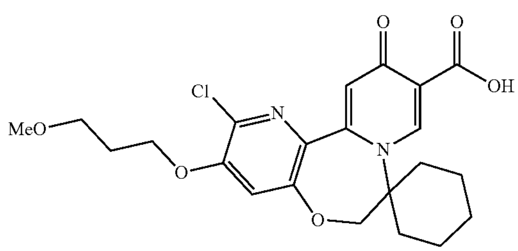 [SMILES: COCCCOc1cc2c(nc1Cl)-c1cc(=O)c(C(=O)O)cn1C1(CCCCC1)CO2] | 2'-chloro-3'-(3-methoxypropoxy)-11'-oxo-6'H,11'H-spiro[cyclohexane-1,7'-dipyrido[1,2-d:2',3'-f][1,4]oxazepine]-10'-carboxylic acid | 0.021 |
| 71 | 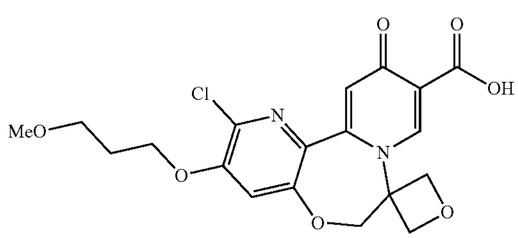 [SMILES: COCCCOc1cc2c(nc1Cl)-c1cc(=O)c(C(=O)O)cn1C1(COC1)CO2] | 2-chloro-3-(3-methoxypropoxy)-11-oxo-6H,11H-spiro[dipyrido[1,2-d:2',3'-f][1,4]oxazepine-7,3'-oxetane]-10-carboxylic acid | 30 |
| 72 | 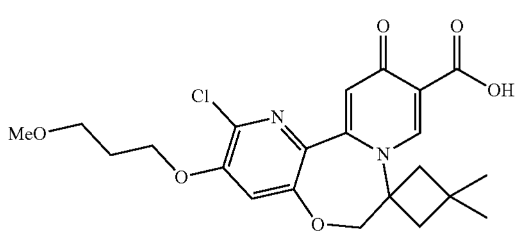 [SMILES: COCCCOc1cc2c(nc1Cl)-c1cc(=O)c(C(=O)O)cn1C1(CO2)CC(C)(C)C1] | 2'-chloro-3'-(3-methoxypropoxy)-3,3-dimethyl-11'-oxo-6'H,11'H-spiro[cyclobutane-1,7'-dipyrido[1,2-d:2',3'-f][1,4]oxazepine]-10'-carboxylic acid | 0.18 |

TABLE 1-continued

| Ex. No. | Structure | Nomenclature | sAg EC$_{50}$, μM |
|---|---|---|---|
| 73 | 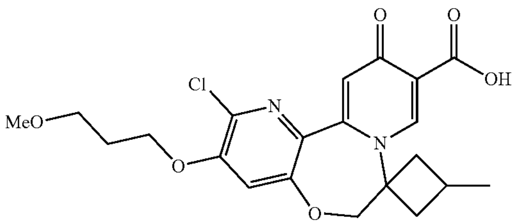 [SMILES: COCCCOc1cc2c(nc1Cl)-c1cc(=O)c(C(=O)O)cn1C1(CO2)CC(C)C1] | 2'-chloro-3'-(3-methoxypropoxy)-3-methyl-11'-oxo-6'H,11'H-spiro[cyclobutane-1,7'-dipyrido[1,2-d:2',3'-f][1,4]oxazepine]-10'-carboxylic acid | 0.26 |
| 74 | 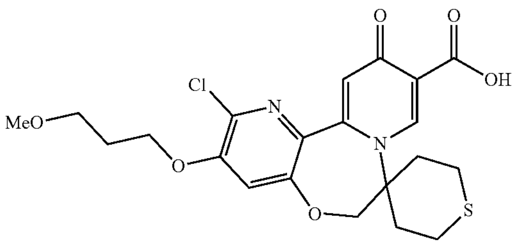 [SMILES: COCCCOc1cc2c(nc1Cl)-c1cc(=O)c(C(=O)O)cn1C1(CCSCC1)CO2] | 2-chloro-3-(3-methoxypropoxy)-11-oxo-2',3',5',6'-tetrahydro-6H,11H-spiro[dipyrido[1,2-d:2',3'-f][1,4]oxazepine-7,4'-thiopyran]-10-carboxylic acid | 5.0 |
| 76 | 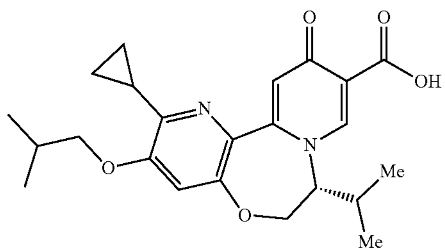 [SMILES: CC(C)COc1cc2c(nc1C1CC1)-c1cc(=O)c(C(=O)O)cn1[C@H](C(C)C)CO2] | (R)-2-cyclopropyl-3-isobutoxy-7-isopropyl-11-oxo-6,7-dihydro-11H-dipyrido[1,2-d:2',3'-f][1,4]oxazepine-10-carboxylic acid | 0.86 |
| 77 | 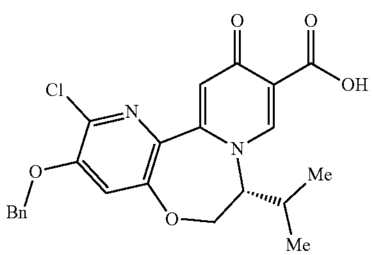 [SMILES: CC(C)[C@@H]1COc2cc(OCc3ccccc3)c(Cl)nc2-c2cc(=O)c(C(=O)O)cn21] | (R)-3-(benzyloxy)-2-chloro-7-isopropyl-11-oxo-6,7-dihydro-11H-dipyrido[1,2-d:2',3'-f][1,4]oxazepine-10-carboxylic acid | 3.2 |
| 78 | 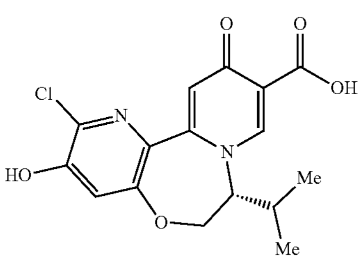 [SMILES: CC(C)[C@@H]1COc2cc(O)c(Cl)nc2-c2cc(=O)c(C(=O)O)cn21] | (R)-2-chloro-3-hydroxy-7-isopropyl-11-oxo-6,7-dihydro-11H-dipyrido[1,2-d:2',3'-f][1,4]oxazepine-10-carboxylic acid | 5 |
| 79 | 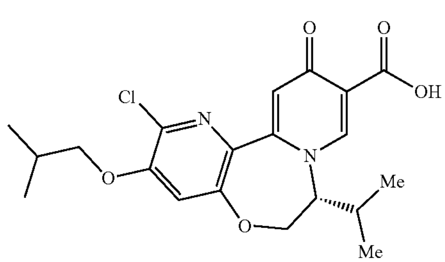 [SMILES: CC(C)COc1cc2c(nc1Cl)-c1cc(=O)c(C(=O)O)cn1[C@H](C(C)C)CO2] | (R)-2-chloro-3-isobutoxy-7-isopropyl-11-oxo-6,7-dihydro-11H-dipyrido[1,2-d:2',3'-f][1,4]oxazepine-10-carboxylic acid | 0.79 |

TABLE 1-continued

| Ex. No. | Structure | Nomenclature | sAg EC$_{50}$, μM |
|---|---|---|---|
| 80 | 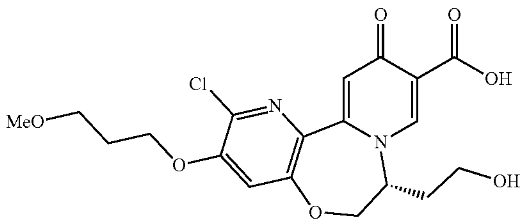 [SMILES: COCCCOc1cc2c(nc1Cl)-c1cc(=O)c(C(=O)O)cn1[C@H](CCO)CO2] | (R)-2-chloro-7-(2-hydroxyethyl)-3-(3-methoxypropoxy)-11-oxo-6,7-dihydro-11H-dipyrido[1,2-d:2',3'-f][1,4]oxazepine-10-carboxylic acid | 0.26 |
| 81 | 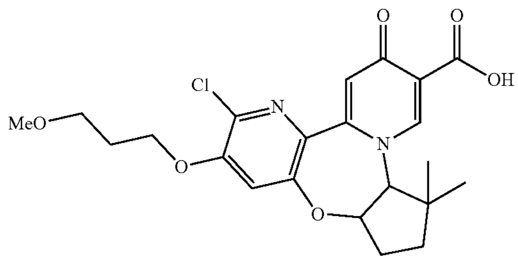 [SMILES: COCCCOc1cc2c(nc1Cl)-c1cc(=O)c(C(=O)O)cn1C1C(CCC1(C)C)O2] | 6-chloro-7-(3-methoxypropoxy)-12,12-dimethyl-3-oxo-9a,11,12,12a-tetrahydro-3H,10H-cyclopenta[b]dipyrido[1,2-d:2',3'-f][1,4]oxazepine-10-carboxylic acid | 0.011 |
| 82 | 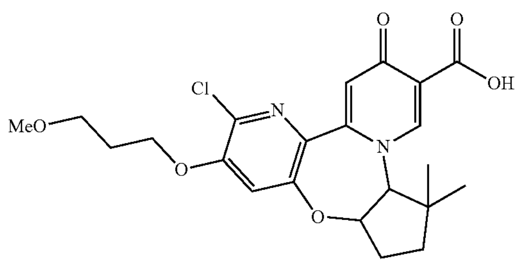 [SMILES: COCCCOc1cc2c(nc1Cl)-c1cc(=O)c(C(=O)O)cn1C1C(CCC1(C)C)O2] | 6-chloro-7-(3-methoxypropoxy)-12,12-dimethyl-3-oxo-9a,11,12,12a-tetrahydro-3H,10H-cyclopenta[b]dipyrido[1,2-d:2',3'-f][1,4]oxazepine-2-carboxylic acid (single enantiomer I) | 0.008 |
| 83 | 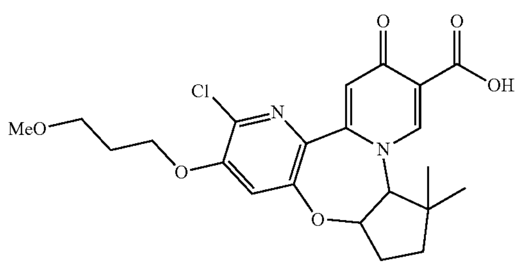 [SMILES: COCCCOc1cc2c(nc1Cl)-c1cc(=O)c(C(=O)O)cn1C1C(CCC1(C)C)O2] | 6-chloro-7-(3-methoxypropoxy)-12,12-dimethyl-3-oxo-9a,11,12,12a-tetrahydro-3H,10H-cyclopenta[b]dipyrido[1,2-d:2',3'-f][1,4]oxazepine-2-carboxylic acid (single enantiomer II) | 1 |
| 45 | 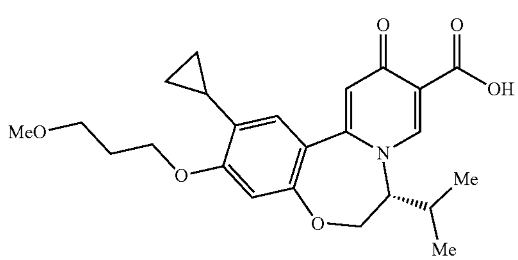 [SMILES: COCCCOc1cc2c(cc1C1CC1)-c1cc(=O)c(C(=O)O)cn1[C@H](C(C)C)CO2] | (R)-2-cyclopropyl-7-isopropyl-3-(3-methoxypropoxy)-11-oxo-6,7-dihydro-11H-benzo[f]pyrido[1,2-d][1,4]oxazepine-10-carboxylic acid | 0.006 |
| 46 | 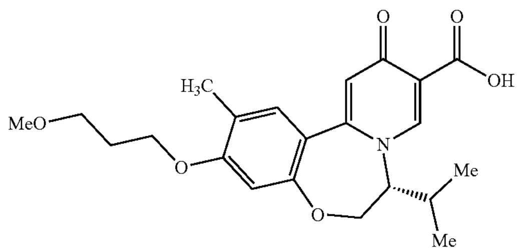 [SMILES: COCCCOc1cc2c(cc1C)-c1cc(=O)c(C(=O)O)cn1[C@H](C(C)C)CO2] | (R)-7-isopropyl-3-(3-methoxypropoxy)-2-methyl-11-oxo-6,7-dihydro-11H-benzo[f]pyrido[1,2-d][1,4]oxazepine-10-carboxylic acid | 0.039 |

TABLE 1-continued

| Ex. No. | Structure | Nomenclature | sAg EC$_{50}$, μM |
|---|---|---|---|
| 47 | 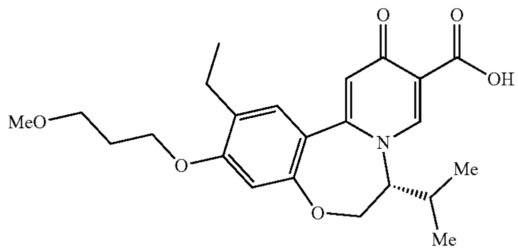 [SMILES: CCc1cc2c(cc1OCCCOC)OC[C@@H](C(C)C)n1cc(C(=O)O)c(=O)cc1-2] | (R)-2-ethyl-7-isopropyl-3-(3-methoxypropoxy)-11-oxo-6,7-dihydro-11H-benzo[f]pyrido[1,2-d][1,4]oxazepine-10-carboxylic acid | 0.006 |
| 48 | 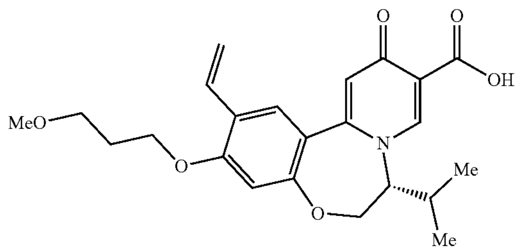 [SMILES: C=Cc1cc2c(cc1OCCCOC)OC[C@@H](C(C)C)n1cc(C(=O)O)c(=O)cc1-2] | (R)-7-isopropyl-3-(3-methoxypropoxy)-11-oxo-2-vinyl-6,7-dihydro-11H-benzo[f]pyrido[1,2-d][1,4]oxazepine-10-carboxylic acid | 0.004 |
| 49 | 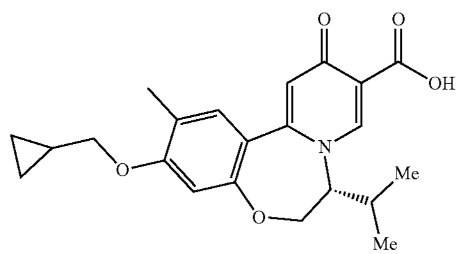 [SMILES: Cc1cc2c(cc1OCC1CC1)OC[C@@H](C(C)C)n1cc(C(=O)O)c(=O)cc1-2] | (R)-3-(cyclopropylmethoxy)-7-isopropyl-2-methyl-11-oxo-6,7-dihydro-11H-benzo[f]pyrido[1,2-d][1,4]oxazepine-10-carboxylic acid | 0.049 |
| 50 | 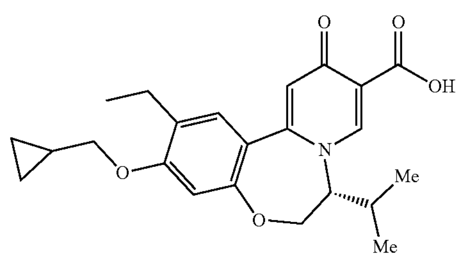 [SMILES: CCc1cc2c(cc1OCC1CC1)OC[C@@H](C(C)C)n1cc(C(=O)O)c(=O)cc1-2] | (R)-3-(cyclopropylmethoxy)-2-ethyl-7-isopropyl-11-oxo-6,7-dihydro-11H-benzo[f]pyrido[1,2-d][1,4]oxazepine-10-carboxylic acid | 0.011 |
| 51 | 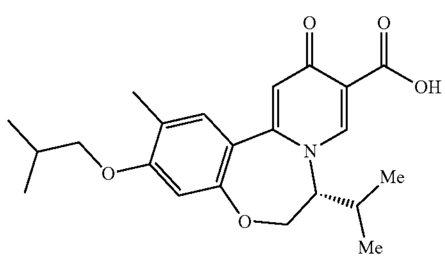 [SMILES: Cc1cc2c(cc1OCC(C)C)OC[C@@H](C(C)C)n1cc(C(=O)O)c(=O)cc1-2] | (R)-3-isobutoxy-7-isopropyl-2-methyl-11-oxo-6,7-dihydro-11H-benzo[f]pyrido[1,2-d][1,4]oxazepine-10-carboxylic acid | 0.015 |
| 52 | 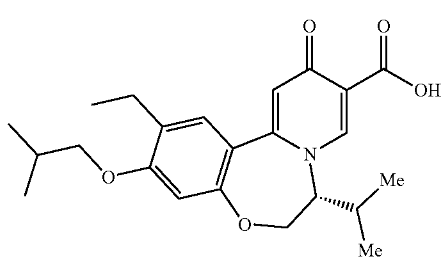 [SMILES: CCc1cc2c(cc1OCC(C)C)OC[C@@H](C(C)C)n1cc(C(=O)O)c(=O)cc1-2] | (R)-2-ethyl-3-isobutoxy-7-isopropyl-11-oxo-6,7-dihydro-11H-benzo[f]pyrido[1,2-d][1,4]oxazepine-10-carboxylic acid | 0.007 |

TABLE 1-continued

| Ex. No. | Structure | Nomenclature | sAg EC$_{50}$, μM |
|---|---|---|---|
| 53 | 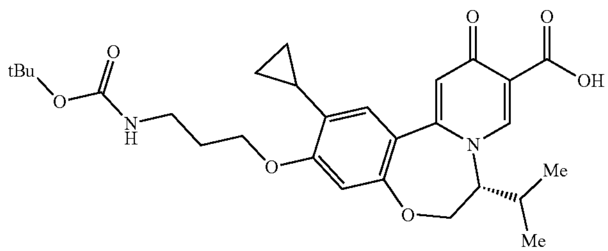 [SMILES: CC(C)[C@@H]1COc2cc(OCCCNC(=O)OC(C)(C)C)c(C3CC3)cc2-c2cc(=O)c(C(=O)O)cn21] | (R)-3-(3-((tert-butoxycarbonyl)amino)propoxy)-2-cyclopropyl-7-isopropyl-11-oxo-6,7-dihydro-11H-benzo[f]pyrido[1,2-d][1,4]oxazepine-10-carboxylic acid | 0.013 |
| 54 | 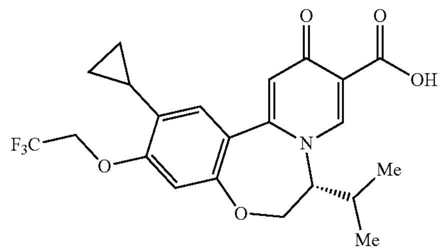 [SMILES: CC(C)[C@@H]1COc2cc(OCC(F)(F)F)c(C3CC3)cc2-c2cc(=O)c(C(=O)O)cn21] | (R)-2-cyclopropyl-7-isopropyl-11-oxo-3-(2,2,2-trifluoroethoxy)-6,7-dihydro-11H-benzo[f]pyrido[1,2-d][1,4]oxazepine-10-carboxylic acid | 0.012 |
| 55 | 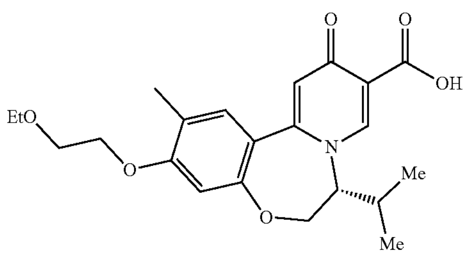 [SMILES: CCOCCOc1cc2c(cc1C)-c1cc(=O)c(C(=O)O)cn1[C@H](C(C)C)CO2] | (R)-3-(2-ethoxyethoxy)-7-isopropyl-2-methyl-11-oxo-6,7-dihydro-11H-benzo[f]pyrido[1,2-d][1,4]oxazepine-10-carboxylic acid | 0.13 |
| 56 | 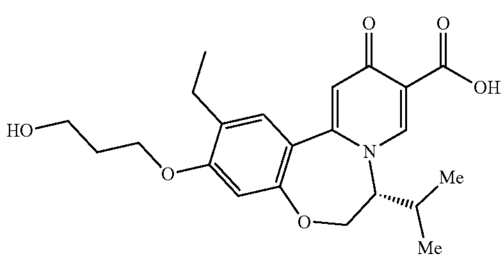 [SMILES: CCc1cc2c(cc1OCCCO)OC[C@@H](C(C)C)n1cc(C(=O)O)c(=O)cc1-2] | (R)-2-ethyl-3-(3-hydroxypropoxy)-7-isopropyl-11-oxo-6,7-dihydro-11H-benzo[f]pyrido[1,2-d][1,4]oxazepine-10-carboxylic acid | 0.026 |
| 57 | 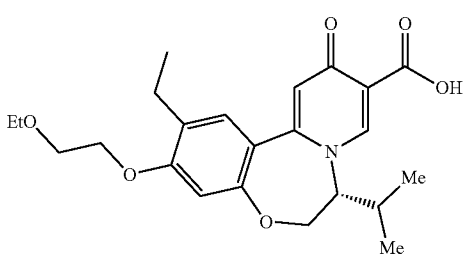 [SMILES: CCOCCOc1cc2c(cc1CC)-c1cc(=O)c(C(=O)O)cn1[C@H](C(C)C)CO2] | (R)-3-(2-ethoxyethoxy)-2-ethyl-7-isopropyl-11-oxo-6,7-dihydro-11H-benzo[f]pyrido[1,2-d][1,4]oxazepine-10-carboxylic acid | 0.034 |
| 58 | 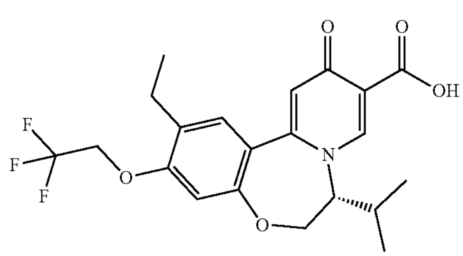 [SMILES: CCc1cc2c(cc1OCC(F)(F)F)OC[C@@H](C(C)C)n1cc(C(=O)O)c(=O)cc1-2] | (R)-2-ethyl-7-isopropyl-11-oxo-3-(2,2,2-trifluoroethoxy)-6,7-dihydro-11H-benzo[f]pyrido[1,2-d][1,4]oxazepine-10-carboxylic acid | 0.021 |

TABLE 1-continued

| Ex. No. | Structure | Nomenclature | sAg EC$_{50}$, μM |
|---|---|---|---|
| 59 | 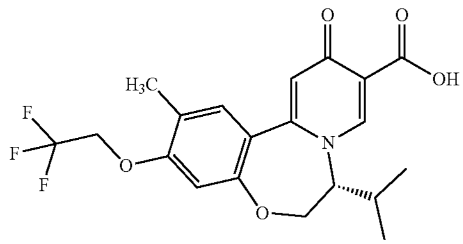 [SMILES: Cc1cc2c(cc1OCC(F)(F)F)OC[C@@H](C(C)C)n1cc(C(=O)O)c(=O)cc1-2] | (R)-7-isopropyl-2-methyl-11-oxo-3-(2,2,2-trifluoroethoxy)-6,7-dihydro-11H-benzo[f]pyrido[1,2-d][1,4]oxazepine-10-carboxylic acid | 0.089 |
| 60 | 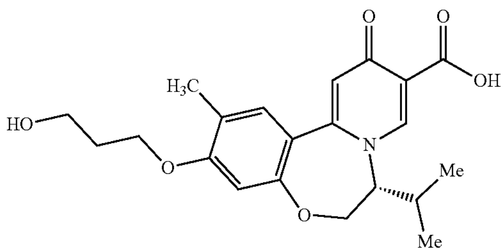 [SMILES: Cc1cc2c(cc1OCCCO)OC[C@@H](C(C)C)n1cc(C(=O)O)c(=O)cc1-2] | (R)-3-(3-hydroxypropoxy)-7-isopropyl-2-methyl-11-oxo-6,7-dihydro-11H-benzo[f]pyrido[1,2-d][1,4]oxazepine-10-carboxylic acid | 0.057 |
| 61 | 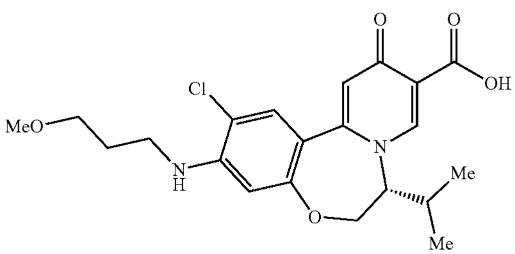 [SMILES: COCCCNc1cc2c(cc1Cl)-c1cc(=O)c(C(=O)O)cn1[C@H](C(C)C)CO2] | (R)-2-chloro-7-isopropyl-3-((3-methoxypropyl)amino)-11-oxo-6,7-dihydro-11H-benzo[f]pyrido[1,2-d][1,4]oxazepine-10-carboxylic acid | 0.023 |
| 62 | 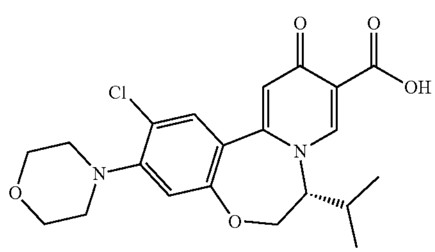 [SMILES: CC(C)[C@@H]1COc2cc(N3CCOCC3)c(Cl)cc2-c2cc(=O)c(C(=O)O)cn21] | (R)-2-chloro-7-isopropyl-3-morpholino-11-oxo-6,7-dihydro-11H-benzo[f]pyrido[1,2-d][1,4]oxazepine-10-carboxylic acid | 0.21 |
| 63 | 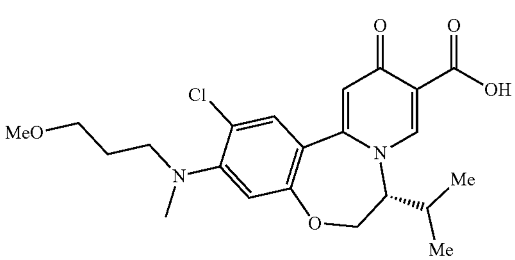 [SMILES: COCCCN(C)c1cc2c(cc1Cl)-c1cc(=O)c(C(=O)O)cn1[C@H](C(C)C)CO2] | (R)-2-chloro-7-isopropyl-3-((3-methoxypropyl)(methyl)amino)-11-oxo-6,7-dihydro-11H-benzo[f]pyrido[1,2-d][1,4]oxazepine-10-carboxylic acid | 0.030 |
| 64 | 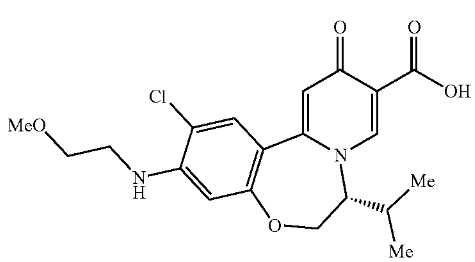 [SMILES: COCCNc1cc2c(cc1Cl)-c1cc(=O)c(C(=O)O)cn1[C@H](C(C)C)CO2] | (R)-2-chloro-7-isopropyl-3-((2-methoxyethyl)amino)-11-oxo-6,7-dihydro-11H-benzo[f]pyrido[1,2-d][1,4]oxazepine-10-carboxylic acid | 0.066 |

TABLE 1-continued

| Ex. No. | Structure | Nomenclature | sAg EC$_{50}$, μM |
|---|---|---|---|
| 65 | 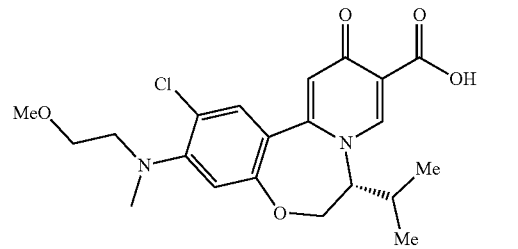 [SMILES: COCCN(C)c1cc2c(cc1Cl)-c1cc(=O)c(C(=O)O)cn1[C@H](C(C)C)CO2] | (R)-2-chloro-7-isopropyl-3-((2-methoxyethyl)(methyl)amino)-11-oxo-6,7-dihydro-11H-benzo[f]pyrido[1,2-d][1,4]oxazepine-10-carboxylic acid | 0.27 |
| 66 | 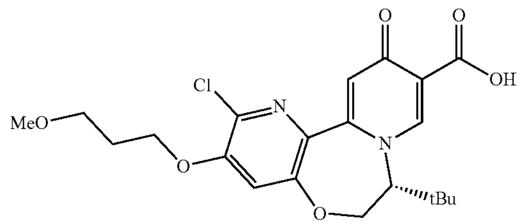 [SMILES: COCCCOc1cc2c(nc1Cl)-c1cc(=O)c(C(=O)O)cn1[C@H](C(C)(C)C)CO2] | (R)-7-(tert-butyl)-2-chloro-3-(3-methoxypropoxy)-11-oxo-6,7-dihydro-11H-dipyrido[1,2-d:2',3'-f][1,4]oxazepine-10-carboxylic acid | 0.002 |
| 67 | 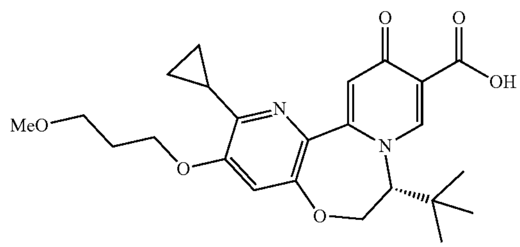 [SMILES: COCCCOc1cc2c(nc1C1CC1)-c1cc(=O)c(C(=O)O)cn1[C@H](C(C)(C)C)CO2] | (R)-7-(tert-butyl)-2-cyclopropyl-3-(3-methoxypropoxy)-11-oxo-6,7-dihydro-11H-dipyrido[1,2-d:2',3'-f][1,4]oxazepine-10-carboxylic acid | 0.0009 |
| 68 | 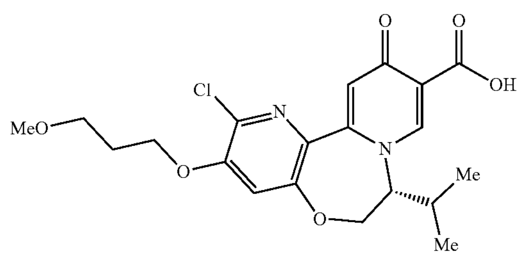 [SMILES: COCCCOc1cc2c(nc1Cl)-c1cc(=O)c(C(=O)O)cn1[C@H](C(C)C)CO2] | (R)-2-chloro-7-isopropyl-3-(3-methoxypropoxy)-11-oxo-6,7-dihydro-11H-dipyrido[1,2-d:2',3'-f][1,4]oxazepine-10-carboxylic acid | 0.017 |
| 104 | 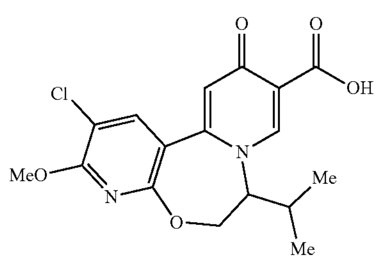 [SMILES: COc1nc2c(cc1Cl)-c1cc(=O)c(C(=O)O)cn1C(C(C)C)CO2] | 2-chloro-7-isopropyl-3-methoxy-11-oxo-6,7-dihydro-11H-dipyrido[1,2-d:3',2'-f][1,4]oxazepine-10-carboxylic acid | 24.2 |
| 134 | 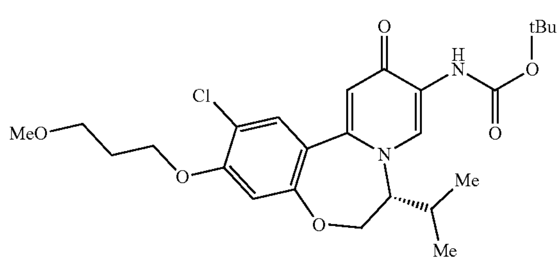 [SMILES: COCCCOc1cc2c(cc1Cl)-c1cc(=O)c(NC(=O)OC(C)(C)C)cn1[C@H](C(C)C)CO2] | tert-butyl (R)-(2-chloro-7-isopropyl-3-(3-methoxypropoxy)-11-oxo-6,7-dihydro-11H-benzo[f]pyrido[1,2-d][1,4]oxazepin-10-yl)carbamate | 45 |

TABLE 1-continued

| Ex. No. | Structure | Nomenclature | sAg EC$_{50}$, μM |
|---|---|---|---|
| 135 | 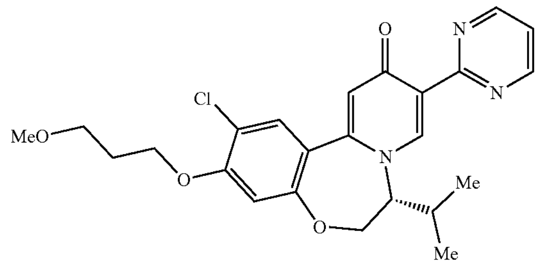 [SMILES: COCCCOc1cc2c(cc1Cl)-c1cc(=O)c(-c3ncccn3)cn1[C@H](C(C)C)CO2] | (R)-2-chloro-7-isopropyl-3-(3-methoxypropoxy)-10-(pyrimidin-2-yl)-6,7-dihydro-11H-benzo[f]pyrido[1,2-d][1,4]oxazepin-11-one | 2 |
| 136 | 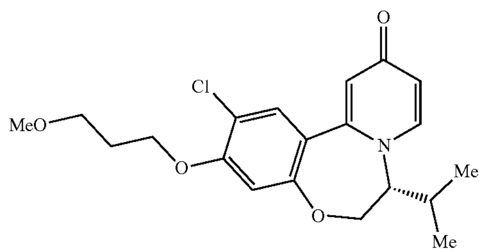 [SMILES: COCCCOc1cc2c(cc1Cl)-c1cc(=O)ccn1[C@H](C(C)C)CO2] | (R)-2-chloro-7-isopropyl-3-(3-methoxypropoxy)-6,7-dihydro-11H-benzo[f]pyrido[1,2-d][1,4]oxazepin-11-one | 0.57 |
| 137 | 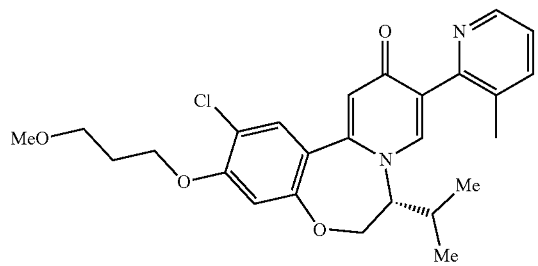 [SMILES: COCCCOc1cc2c(cc1Cl)-c1cc(=O)c(-c3ncccc3C)cn1[C@H](C(C)C)CO2] | (R)-2-chloro-7-isopropyl-3-(3-methoxypropoxy)-10-(3-methylpyridin-2-yl)-6,7-dihydro-11H-benzo[f]pyrido[1,2-d][1,4]oxazepin-11-one | 10 |
| 138 | 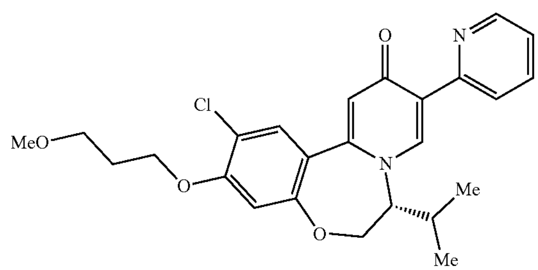 [SMILES: COCCCOc1cc2c(cc1Cl)-c1cc(=O)c(-c3ccccn3)cn1[C@H](C(C)C)CO2] | (R)-2-chloro-7-isopropyl-3-(3-methoxypropoxy)-10-(pyridin-2-yl)-6,7-dihydro-11H-benzo[f]pyrido[1,2-d][1,4]oxazepin-11-one | 12 |
| 139 | 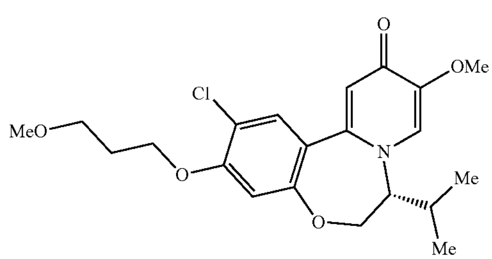 [SMILES: COCCCOc1cc2c(cc1Cl)-c1cc(=O)c(OC)cn1[C@H](C(C)C)CO2] | (R)-2-chloro-7-isopropyl-10-methoxy-3-(3-methoxypropoxy)-6,7-dihydro-11H-benzo[f]pyrido[1,2-d][1,4]oxazepin-11-one | 14 |
| 140 | 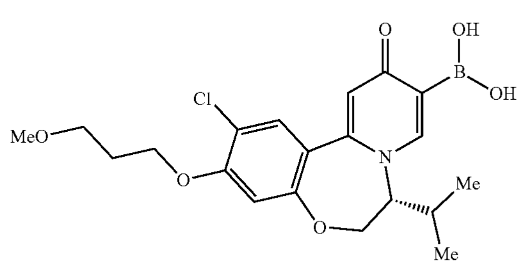 [SMILES: COCCCOc1cc2c(cc1Cl)-c1cc(=O)c(B(O)O)cn1[C@H](C(C)C)CO2] | (R)-(2-chloro-7-isopropyl-3-(3-methoxypropoxy)-11-oxo-6,7-dihydro-11H-benzo[f]pyrido[1,2-d][1,4]oxazepin-10-yl)boronic acid | 2.1 |

TABLE 1-continued

| Ex. No. | Structure | Nomenclature | sAg EC$_{50}$, μM |
|---|---|---|---|
| 141 | 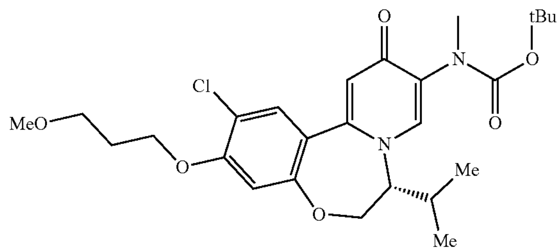 [SMILES: COCCCOc1cc2c(cc1Cl)-c1cc(=O)c(N(C)C(=O)OC(C)(C)C)cn1[C@H](C(C)C)CO2] | tert-butyl (R)-(2-chloro-7-isopropyl-3-(3-methoxypropoxy)-11-oxo-6,7-dihydro-11H-benzo[f]pyrido[1,2-d][1,4]oxazepin-10-yl)(methyl)carbamate | 1.0 |
| 150 | 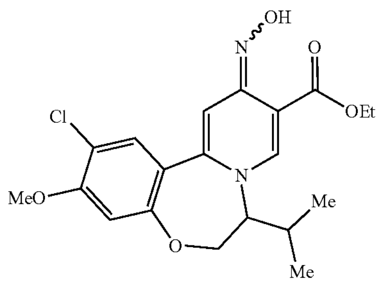 [SMILES: CCOC(=O)c1cn2c(cc1=NO)-c1cc(Cl)c(OC)cc1OCC2C(C)C] | ethyl 2-chloro-11-(hydroxyimino)-7-isopropyl-3-methoxy-6,7-dihydro-11H-benzo[f]pyrido[1,2-d][1,4]oxazepine-10-carboxylate | 24 |
| 151 | 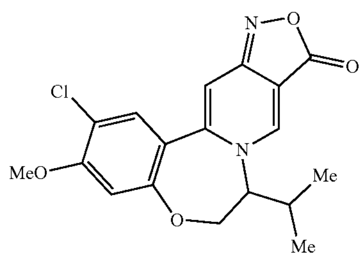 [SMILES: COc1cc2c(cc1Cl)-c1cc3noc(=O)c-3cn1C(C(C)C)CO2] | 2-chloro-7-isopropyl-3-methoxy-6,7-dihydro-10H-benzo[f]isoxazolo[3',4':4,5]pyrido[1,2-d][1,4]oxazepin-10-one | 13 |
| 168 | 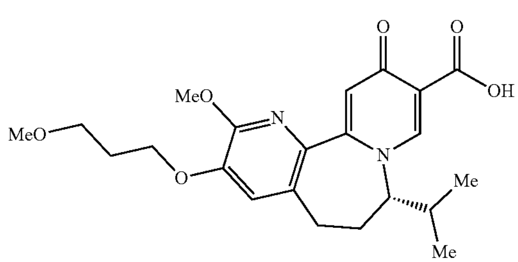 [SMILES: COCCCOc1cc2c(nc1OC)-c1cc(=O)c(C(=O)O)cn1[C@H](C(C)C)CC2] | (S)-7-isopropyl-2-methoxy-3-(3-methoxypropoxy)-11-oxo-5,6,7,11-tetrahydrodipyrido[1,2-a:2',3'-c]azepine-10-carboxylic acid | 0.071 |
| 169 | 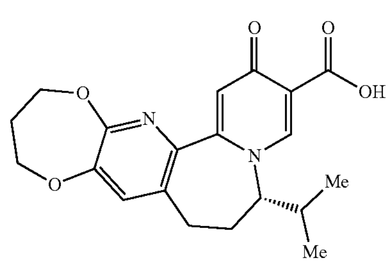 [SMILES: CC(C)[C@@H]1CCc2cc3c(nc2-c2cc(=O)c(C(=O)O)cn21)OCCCO3] | (S)-6-isopropyl-2-oxo-2,6,7,8,12,13-hexahydro-11H-[1,4]dioxepino[2',3':5,6]pyrido[2,3-c]pyrido[1,2-a]azepine-3-carboxylic acid | 2.2 |

TABLE 1-continued

| Ex. No. | Structure | Nomenclature | sAg EC$_{50}$, μM |
|---|---|---|---|
| 170 | 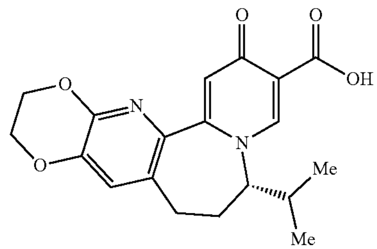 [SMILES: CC(C)[C@@H]1CCc2cc3c(nc2-c2cc(=O)c(C(=O)O)cn21)OCCO3] | (S)-6-isopropyl-2-oxo-2,6,7,8,11,12-hexahydro-[1,4]dioxino[2',3':5,6]pyrido[2,3-c]pyrido[1,2-a]azepine-3-carboxylic acid | 5.0 |

TABLE 2

| Ex. No. | Structure | Nomenclature | sAg EC$_{50}$, μM |
|---|---|---|---|
| 172 | 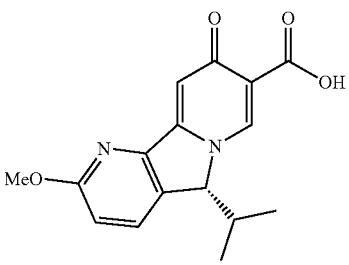 [SMILES: COc1ccc2c(n1)-c1cc(=O)c(C(=O)O)cn1[C@@H]2C(C)C] | (R)-5-isopropyl-2-methoxy-9-oxo-5,9-dihydropyrido[2,3-a]indolizine-8-carboxylic acid | 0.82 |
| 173 | 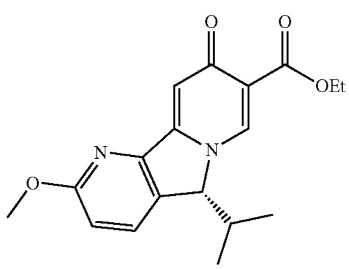 [SMILES: CCOC(=O)c1cn2c(cc1=O)-c1nc(OC)ccc1[C@H]2C(C)C] | ethyl (R)-5-isopropyl-2-methoxy-9-oxo-5,9-dihydropyrido[2,3-a]indolizine-8-carboxylate | 8.6 |

TABLE 3

| Ex. No. | Structure | Nomenclature | sAg EC$_{50}$, μM |
|---|---|---|---|
| 20 | 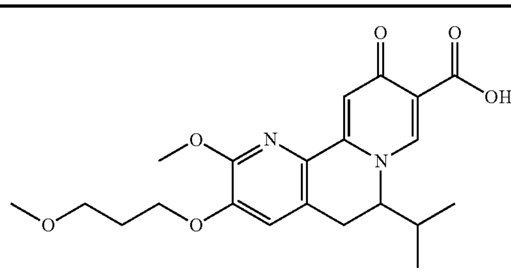 | 6-isopropyl-2-methoxy-3-(3-methoxypropoxy)-10-oxo-5,10-dihydro-6H-pyrido[1,2-h][1,7]naphthyridine-9-carboxylic acid | 0.005 |

TABLE 3-continued

| Ex. No. | Structure | Nomenclature | sAg EC$_{50}$, μM |
|---|---|---|---|
| 21 | 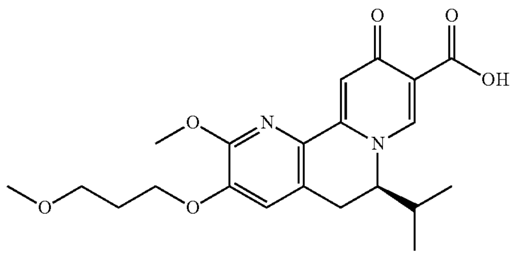 | (R)-6-isopropyl-2-methoxy-3-(3-methoxypropoxy)-10-oxo-5,10-dihydro-6H-pyrido[1,2-h][1,7]naphthyridine-9-carboxylic acid | 0.53 |
| 22 | 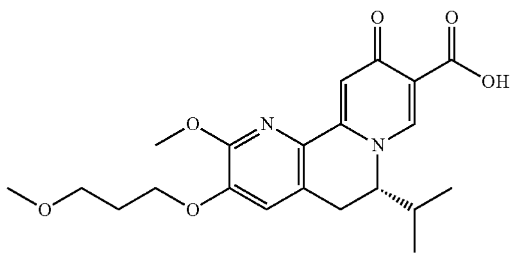 | (S)-6-isopropyl-2-methoxy-3-(3-methoxypropoxy)-10-oxo-5,10-dihydro-6H-pyrido[1,2-h][1,7]naphthyridine-9-carboxylic acid | 0.002 |
| 23 | 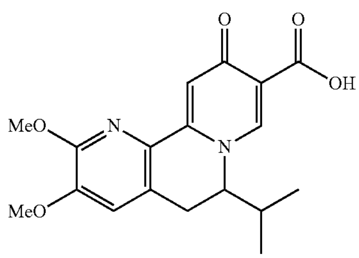 [SMILES: COc1cc2c(nc1OC)-c1cc(=O)c(C(=O)O)cn1C(C(C)C)C2] | 6-isopropyl-2,3-dimethoxy-10-oxo-5,10-dihydro-6H-pyrido[1,2-h][1,7]naphthyridine-9-carboxylic acid | 0.019 |
| 24 | 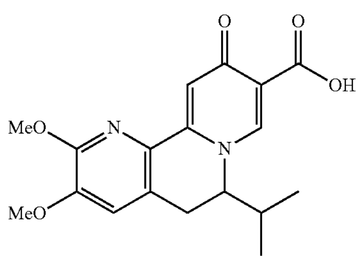 [SMILES: COc1cc2c(nc1OC)-c1cc(=O)c(C(=O)O)cn1C(C(C)C)C2] | 6-isopropyl-2,3-dimethoxy-10-oxo-5,10-dihydro-6H-pyrido[1,2-h][1,7]naphthyridine-9-carboxylic acid (single enantiomer I) | 0.25 |
| 25 | 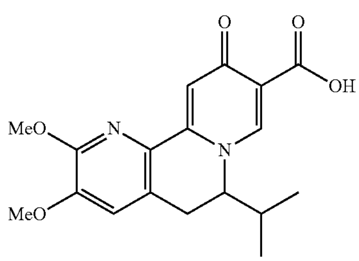 [SMILES: COc1cc2c(nc1OC)-c1cc(=O)c(C(=O)O)cn1C(C(C)C)C2] | 6-isopropyl-2,3-dimethoxy-10-oxo-5,10-dihydro-6H-pyrido[1,2-h][1,7]naphthyridine-9-carboxylic acid (single enantiomer II) | 0.007 |
| 26 | 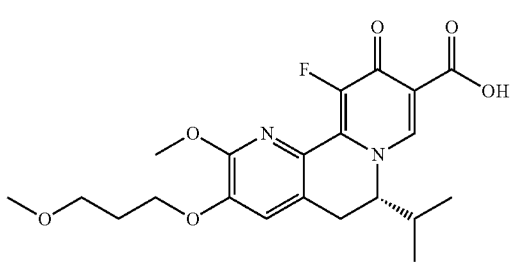 [SMILES: COCCCOc1cc2c(nc1OC)-c1c(F)c(=O)c(C(=O)O)cn1[C@H](C(C)C)C2] | (S)-11-fluoro-6-isopropyl-2-methoxy-3-(3-methoxypropoxy)-10-oxo-5,10-dihydro-6H-pyrido[1,2-h][1,7]naphthyridine-9-carboxylic acidd | 0.002 |

TABLE 3-continued

| Ex. No. | Structure | Nomenclature | sAg EC$_{50}$, μM |
|---|---|---|---|
| 84 | 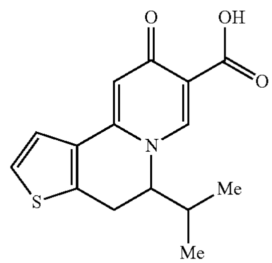 [SMILES: CC(C)C1Cc2sccc2-c2cc(=O)c(C(=O)O)cn21] | 5-isopropyl-9-oxo-4,9-dihydro-5H-thieno[3,2-a]quinolizine-8-carboxylic acid | 3.2 |
| 85 | 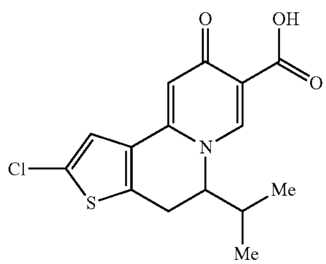 [SMILES: CC(C)C1Cc2sc(Cl)cc2-c2cc(=O)c(C(=O)O)cn21] | 2-chloro-5-isopropyl-9-oxo-4,9-dihydro-5H-thieno[3,2-a]quinolizine-8-carboxylic acid | 16 |
| 86 | 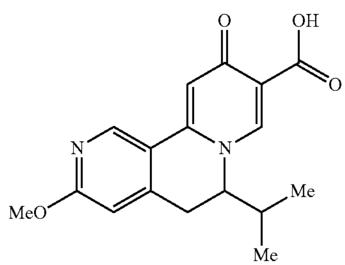 [SMILES: COc1cc2c(cn1)-c1cc(=O)c(C(=O)O)cn1C(C(C)C)C2] | 6-isopropyl-3-methoxy-10-oxo-5,10-dihydro-6H-pyrido[2,1-a][2,7]naphthyridine-9-carboxylic acid | 1.0 |
| 87 | 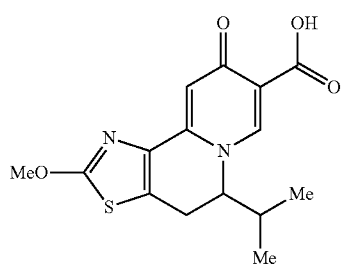 [SMILES: COc1nc2c(s1)CC(C(C)C)n1cc(C(=O)O)c(=O)cc1-2] | 5-isopropyl-2-methoxy-9-oxo-4,9-dihydro-5H-thiazolo[4,5-a]quinolizine-8-carboxylic acid | 3.8 |
| 88 | 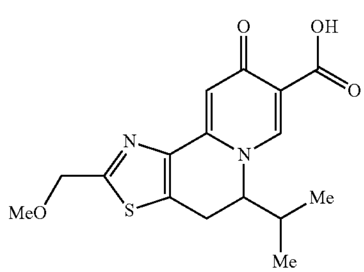 [SMILES: COCc1nc2c(s1)CC(C(C)C)n1cc(C(=O)O)c(=O)cc1-2] | 5-isopropyl-2-(methoxymethyl)-9-oxo-4,9-dihydro-5H-thiazolo[4,5-a]quinolizine-8-carboxylic acid | 3.1 |
| 90 | 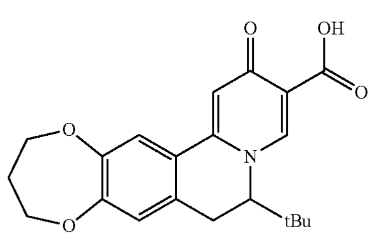 [SMILES: CC(C)(C)C1Cc2cc3c(cc2-c2cc(=O)c(C(=O)O)cn21)OCCCO3] | 6-(tert-butyl)-2-oxo-6,7,11,12-tetrahydro-2H,10H-[1,4]dioxepino[2,3-g]pyrido[2,1-a]isoquinoline-3-carboxylic acid | 0.095 |

TABLE 3-continued

| Ex. No. | Structure | Nomenclature | sAg EC$_{50}$, μM |
|---|---|---|---|
| 91 | 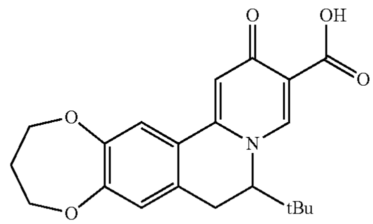 [SMILES: CC(C)(C)C1Cc2cc3c(cc2-c2cc(=O)c(C(=O)O)cn21)OCCCO3] | 6-(tert-butyl)-2-oxo-6,7,11,12-tetrahydro-2H,10H-[1,4]dioxepino[2,3-g]pyrido[2,1-a]isoquinoline-3-carboxylic acid (single enantiomer I) | 0.94 |
| 92 | 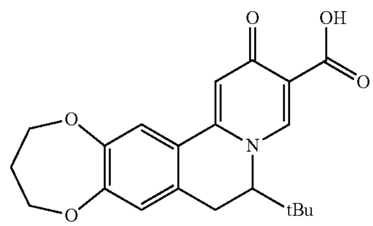 [SMILES: CC(C)(C)C1Cc2cc3c(cc2-c2cc(=O)c(C(=O)O)cn21)OCCCO3] | 6-(tert-butyl)-2-oxo-6,7,11,12-tetrahydro-2H,10H-[1,4]dioxepino[2,3-g]pyrido[2,1-a]isoquinoline-3-carboxylic acid (single enantiomer II) | 0.011 |
| 93 | 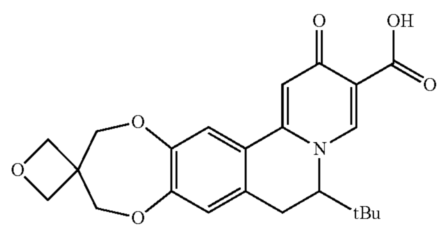 [SMILES: CC(C)(C)C1Cc2cc3c(cc2-c2cc(=O)c(C(=O)O)cn21)OCC1(COC1)CO3] | 6'-(tert-butyl)-2'-oxo-6',7'-dihydro-2'H,10'H,12'H-spiro[oxetane-3,H'-[1,4]dioxepino[2,3-g]pyrido[2,1-a]isoquinoline]-3'-carboxylic acid | 0.42 |
| 94 | 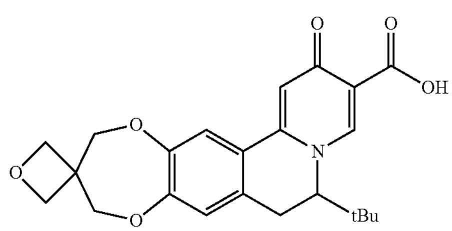 [SMILES: CC(C)(C)C1Cc2cc3c(cc2-c2cc(=O)c(C(=O)O)cn21)OCC1(COC1)CO3] | 6'-(tert-butyl)-2'-oxo-6',7'-dihydro-2'H,10'H,12'H-spiro[oxetane-3,11'-[1,4]dioxepino[2,3-g]pyrido[2,1-a]isoquinoline]-3'-carboxylic acid (single enantiomer I) | 2.2 |
| 95 | 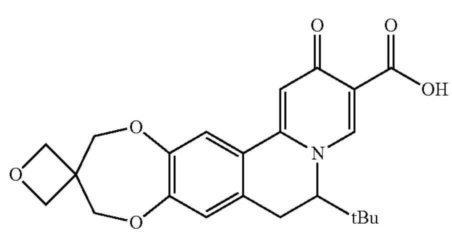 [SMILES: CC(C)(C)C1Cc2cc3c(cc2-c2cc(=O)c(C(=O)O)cn21)OCC1(COC1)CO3] | 6'-(tert-butyl)-2'-oxo-6',7'-dihydro-2'H,10'H,12'H-spiro[oxetane-3,11'-[1,4]dioxepino[2,3-g]pyrido[2,1-a]isoquinoline]-3'-carboxylic acid (single enantiomer II) | 0.08 |
| 96 | 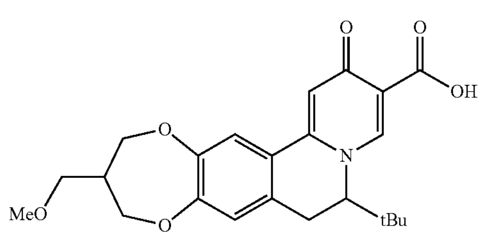 [SMILES: COCC1COc2cc3c(cc2OC1)-c1cc(=O)c(C(=O)O)cn1C(C(C)(C)C)C3] | 6-(tert-butyl)-11-(methoxymethyl)-2-oxo-6,7,11,12-tetrahydro-2H,10H-[1,4]dioxepino[2,3-g]pyrido[2,1-a]isoquinoline-3-carboxylicacid | 0.14 |

TABLE 3-continued

| Ex. No. | Structure | Nomenclature | sAg EC$_{50}$, μM |
|---|---|---|---|
| 97 | 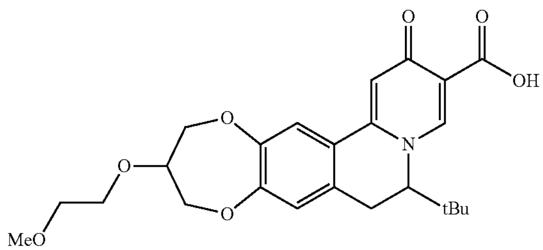 [SMILES: COCCOC1COc2cc3c(cc2OC1)-c1cc(=O)c(C(=O)O)cn1C(C(C)(C)C)C3] | 6-(tert-butyl)-11-(2-methoxyethoxy)-2-oxo-6,7,11,12-tetrahydro-2H,10H-[1,4]dioxepino[2,3-g]pyrido[2,1-a]isoquinoline-3-carboxylic acid | 1.4 |
| 98 | 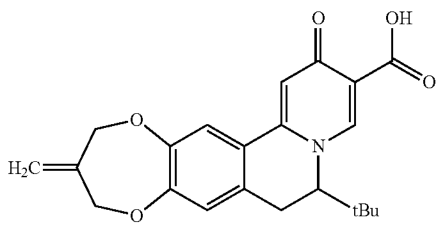 [SMILES: C=C1COc2cc3c(cc2OC1)-c1cc(=O)c(C(=O)O)cn1C(C(C)(C)C)C3] | 6-(tert-butyl)-11-methylene-2-oxo-6,7,11,12-tetrahydro-2H,10H-[1,4]dioxepino[2,3-g]pyrido[2,1-a]isoquinoline-3-carboxylic acid | 0.1 |
| 99 | 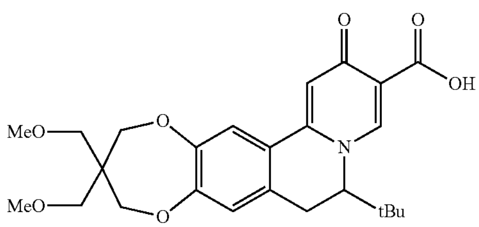 [SMILES: COCC1(COC)COc2cc3c(cc2OC1)-c1cc(=O)c(C(=O)O)cn1C(C(C)(C)C)C3] | 6-(tert-butyl)-11,11-bis(methoxymethyl)-2-oxo-6,7,11,12-tetrahydro-2H,10H-[1,4]dioxepino[2,3-g]pyrido[2,1-a]isoquinoline-3-carboxylic acid | 0.49 |
| 100 | 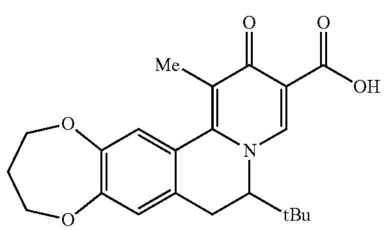 [SMILES: Cc1c2n(cc(C(=O)O)c1=O)C(C(C)(C)C)Cc1cc3c(cc1-2)OCCCO3] | 6-(tert-butyl)-1-methyl-2-oxo-6,7,11,12-tetrahydro-2H,10H-[1,4]dioxepino[2,3-g]pyrido[2,1-a]isoquinoline-3-carboxylic acid | 10 |
| 101 | 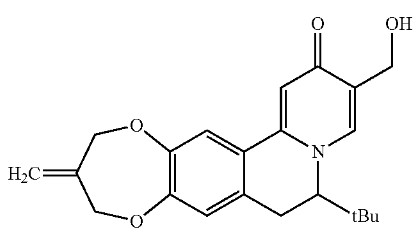 [SMILES: C=C1COc2cc3c(cc2OC1)-c1cc(=O)c(CO)cn1C(C(C)(C)C)C3] | 6-(tert-butyl)-3-(hydroxymethyl)-11-methylene-6,7,11,12-tetrahydro-2H,10H-[1,4]dioxepino[2,3-g]pyrido[2,1-a]isoquinolin-2-one | 5.8 |
| 102 | 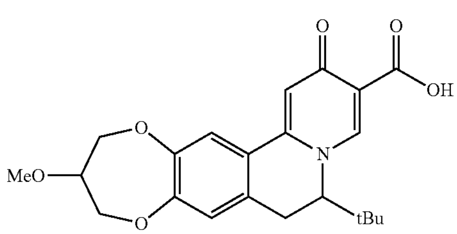 [SMILES: COC1COc2cc3c(cc2OC1)-c1cc(=O)c(C(=O)O)cn1C(C(C)(C)C)C3] | 6-(tert-butyl)-11-methoxy-2-oxo-6,7,11,12-tetrahydro-2H,10H-[1,4]dioxepino[2,3-g]pyrido[2,1-a]isoquinoline-3-carboxylic acid | 0.18 |

TABLE 3-continued

| Ex. No. | Structure | Nomenclature | sAg EC$_{50}$, μM |
|---|---|---|---|
| 103 | 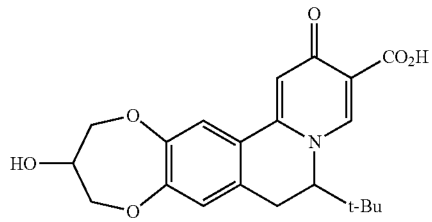 [SMILES: CC(C)(C)C1Cc2cc3c(cc2-c2cc(=O)c(C(=O)O)cn21)OCC(O)CO3] | 6-(tert-butyl)-11-hydroxy-2-oxo-6,7,11,12-tetrahydro-2H,10H-[1,4]dioxepino[2,3-g]pyrido[2,1-a]isoquinoline-3-carboxylic acid | 0.050 |
| 105 | 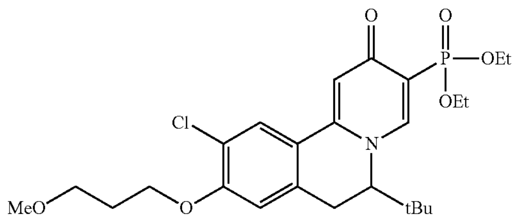 [SMILES: CCOP(=O)(OCC)c1cn2c(cc1=O)-c1cc(Cl)c(OCCCOC)cc1CC2C(C)(C)C] | diethyl (6-(tert-butyl)-10-chloro-9-(3-methoxypropoxy)-2-oxo-6,7-dihydro-2H-pyrido[2,1-a]isoquinolin-3-yl)phosphonate | 6.1 |
| 106 | 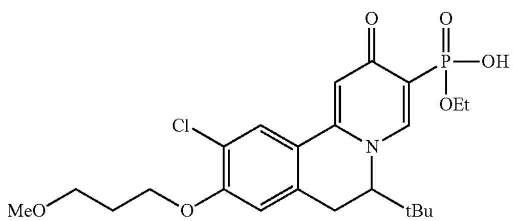 | ethyl hydrogen (6-(tert-butyl)-10-chloro-9-(3-methoxypropoxy)-2-oxo-6,7-dihydro-2H-pyrido[2,1-a]isoquinolin-3-yl)phosphonate | 7.2 |
| 107 | 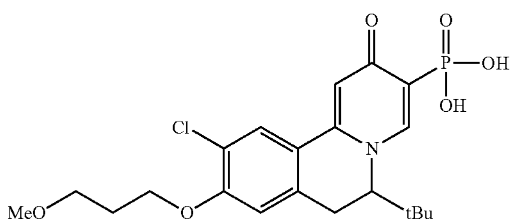 [SMILES: COCCCOc1cc2c(cc1Cl)-c1cc(=O)c(P(=O)(O)O)cn1C(C(C)(C)C)C2] | (6-(tert-butyl)-10-chloro-9-(3-methoxypropoxy)-2-oxo-6,7-dihydro-2H-pyrido[2,1-a]isoquinolin-3-yl)phosphonic acid | 2.5 |
| 108 | 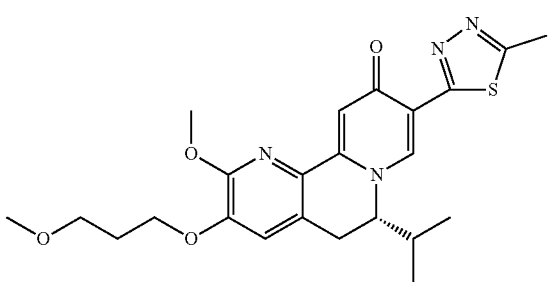 | (S)-6-isopropyl-2-methoxy-3-(3-methoxypropoxy)-9-(5-methyl-1,3,4-thiadiazol-2-yl)-5,6-dihydro-10H-pyrido[1,2-h][1,7]naphthyridin-10-one | 0.045 |
| 109 | 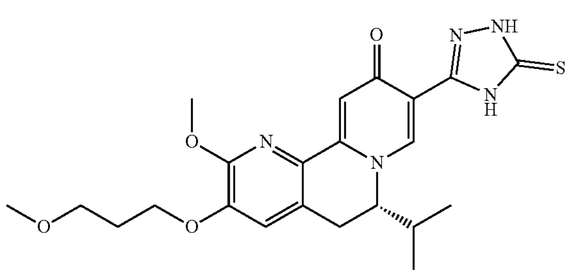 [SMILES: COCCCOc1cc2c(nc1OC)-c1cc(=O)c(-c3n[nH]c(=S)[nH]3)cn1[C@H](C(C)C)C2] | (S)-6-isopropyl-2-methoxy-3-(3-methoxypropoxy)-9-(5-thioxo-4,5-dihydro-1H-1,2,4-triazol-3-yl)-5,6-dihydro-10H-pyrido[1,2-h][1,7]naphthyridin-10-one | 0.029 |

TABLE 3-continued

| Ex. No. | Structure | Nomenclature | sAg EC$_{50}$, μM |
|---|---|---|---|
| 110 | 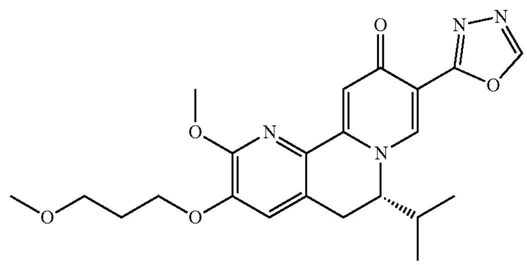 [SMILES: COCCCOc1cc2c(nc1OC)-c1cc(=O)c(-c3nnco3)cn1[C@H](C(C)C)C2] | (S)-6-isopropyl-2-methoxy-3-(3-methoxypropoxy)-9-(1,3,4-oxadiazol-2-yl)-5,6-dihydro-10H-pyrido[1,2-h][1,7]naphthyridin-10-one | 0.057 |
| 111 | 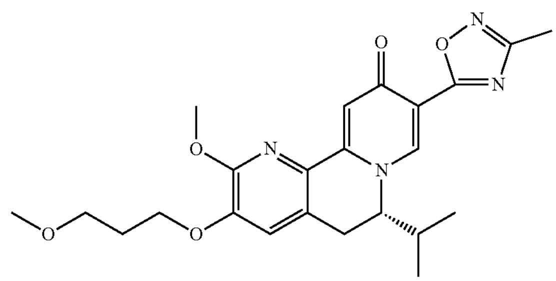 | (S)-6-isopropyl-2-methoxy-3-(3-methoxypropoxy)-9-(3-methyl-1,2,4-oxadiazol-5-yl)-5,6-dihydro-10H-pyrido[1,2-h][1,7]naphthyridin-10-one | 0.29 |
| 112 | 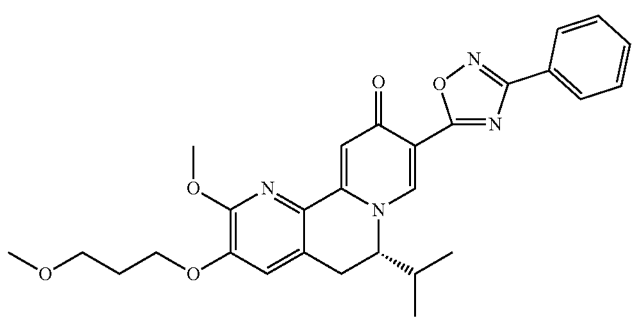 [SMILES: COCCCOc1cc2c(nc1OC)-c1cc(=O)c(-c3nc(-c4ccccc4)no3)cn1[C@H](C(C)C)C2] | (S)-6-isopropyl-2-methoxy-3-(3-methoxypropoxy)-9-(3-phenyl-1,2,4-oxadiazol-5-yl)-5,6-dihydro-10H-pyrido[1,2-h][1,7]naphthyridin-10-one | 0.87 |
| 113 | 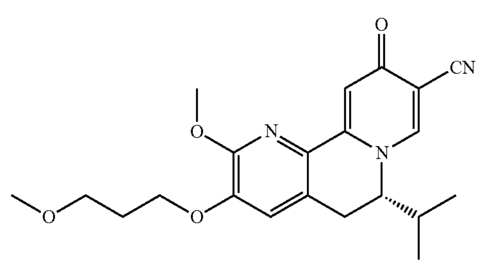 [SMILES: COCCCOc1cc2c(nc1OC)-c1cc(=O)c(C#N)cn1[C@H](C(C)C)C2] | (S)-6-isopropyl-2-methoxy-3-(3-methoxypropoxy)-10-oxo-5,10-dihydro-6H-pyrido[1,2-h][1,7]naphthyridine-9-carbonitrile | 1.0 |
| 114 | 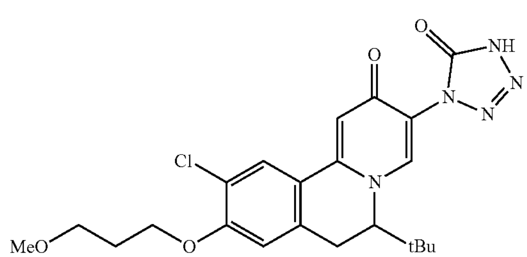 [SMILES: COCCCOc1cc2c(cc1Cl)-c1cc(=O)c(-n3nn[nH]c3=O)cn1C(C(C)(C)C)C2] | 6-(tert-butyl)-10-chloro-9-(3-methoxypropoxy)-3-(5-oxo-4,5-dihydro-1H-tetrazol-1-yl)-6,7-dihydro-2H-pyrido[2,1-a]isoquinolin-2-one | 3.0 |

TABLE 3-continued

| Ex. No. | Structure | Nomenclature | sAg EC$_{50}$, μM |
|---|---|---|---|
| 115 | 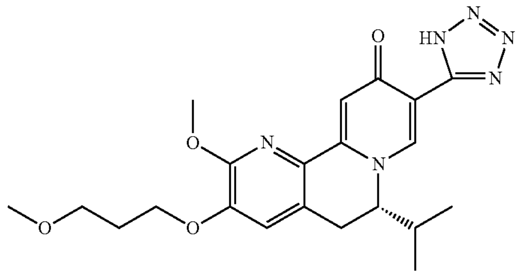 [SMILES: COCCCOc1cc2c(nc1OC)-c1cc(=O)c(-c3nnn[nH]3)cn1[C@H](C(C)C)C2] | (S)-6-isopropyl-2-methoxy-3-(3-methoxypropoxy)-9-(1H-tetrazol-5-yl)-5,6-dihydro-10H-pyrido[1,2-h][1,7]naphthyridin-10-one | 0.09 |
| 116 | 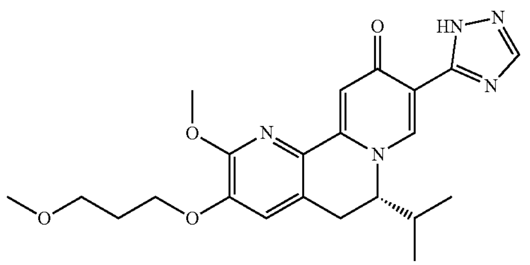 [SMILES: COCCCOc1cc2c(nc1OC)-c1cc(=O)c(-c3ncn[nH]3)cn1[C@H](C(C)C)C2] | (S)-6-isopropyl-2-methoxy-3-(3-methoxypropoxy)-9-(1H-1,2,4-triazol-5-yl)-5,6-dihydro-10H-pyrido[1,2-h][1,7]naphthyridin-10-one | 0.009 |
| 117 | 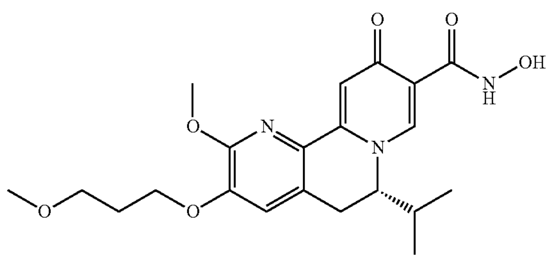 [SMILES: COCCCOc1cc2c(nc1OC)-c1cc(=O)c(C(=O)NO)cn1[C@H](C(C)C)C2] | (S)-N-hydroxy-6-isopropyl-2-methoxy-3-(3-methoxypropoxy)-10-oxo-5,10-dihydro-6H-pyrido[1,2-h][1,7]naphthyridine-9-carboxamide | 0.054 |
| 118 | 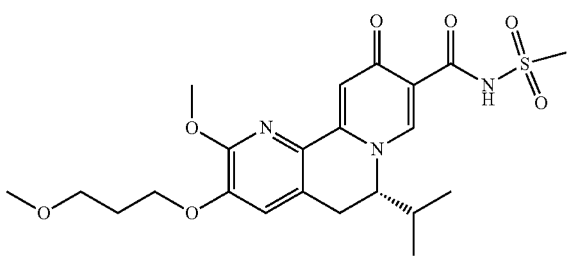 | (S)-6-isopropyl-2-methoxy-3-(3-methoxypropoxy)-N-(methylsulfonyl)-10-oxo-5,10-dihydro-6H-pyrido[1,2-h][1,7]naphthyridine-9-carboxamide | 0.051 |
| 119 | 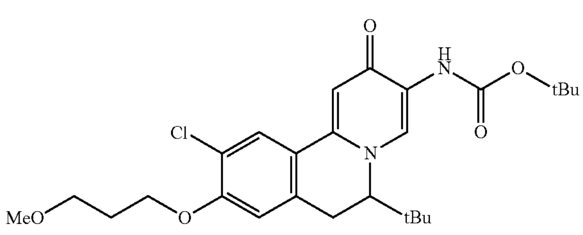 [SMILES: COCCCOc1cc2c(cc1Cl)-c1cc(=O)c(NC(=O)OC(C)(C)C)cn1C(C(C)(C)C)C2] | tert-butyl (6-(tert-butyl)-10-chloro-9-(3-methoxypropoxy)-2-oxo-6,7-dihydro-2H-pyrido[2,1-a]isoquinolin-3-yl)carbamate | 0.14 |
| 120 | 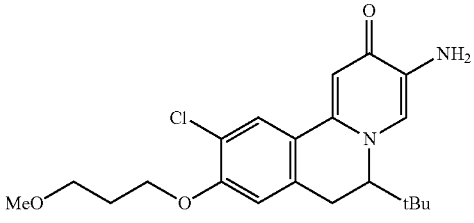 [SMILES: COCCCOc1cc2c(cc1Cl)-c1cc(=O)c(N)cn1C(C(C)(C)C)C2] | 3-amino-6-(tert-butyl)-10-chloro-9-(3-methoxypropoxy)-6,7-dihydro-2H-pyrido[2,1-a]isoquinolin-2-one hydrochloride | 3.9 |

TABLE 3-continued

| Ex. No. | Structure | Nomenclature | sAg EC$_{50}$, μM |
|---|---|---|---|
| 121 | 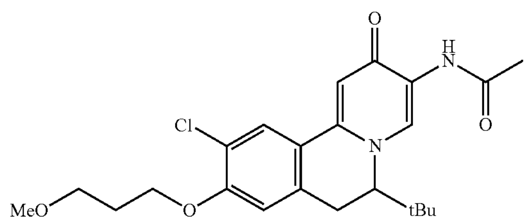 [SMILES: COCCCOc1cc2c(cc1Cl)-c1cc(=O)c(NC(C)=O)cn1C(C(C)(C)C)C2] | N-(6-(tert-butyl)-10-chloro-9-(3-methoxypropoxy)-2-oxo-6,7-dihydro-2H-pyrido[2,1-a]isoquinolin-3-yl)acetamide | 8.6 |
| 122 | 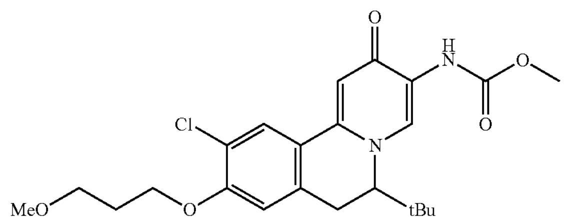 [SMILES: COCCCOc1cc2c(cc1Cl)-c1cc(=O)c(NC(=O)OC)cn1C(C(C)(C)C)C2] | methyl (6-(tert-butyl)-10-chloro-9-(3-methoxypropoxy)-2-oxo-6,7-dihydro-2H-pyrido[2,1-a]isoquinolin-3-yl)carbamate | 17 |
| 123 | 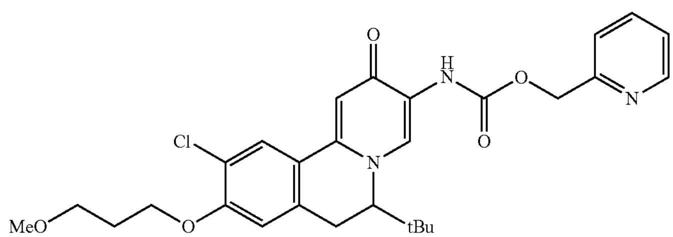 [SMILES: COCCCOc1cc2c(cc1Cl)-c1cc(=O)c(NC(=O)OCc3ccccn3)cn1C(C(C)(C)C)C2] | pyridin-2-ylmethyl(6-(tert-butyl)-10-chloro-9-(3-methoxypropoxy)-2-oxo-6,7-dihydro-2H-pyrido[2,1-a]isoquinolin-3-yl)carbamate | 2.4 |
| 124 | 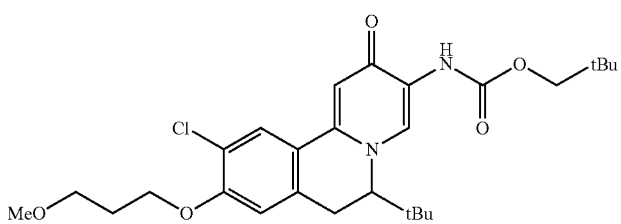 [SMILES: COCCCOc1cc2c(cc1Cl)-c1cc(=O)c(NC(=O)OCC(C)(C)C)cn1C(C(C)(C)C)C2] | neopentyl (6-(tert-butyl)-10-chloro-9-(3-methoxypropoxy)-2-oxo-6,7-dihydro-2H-pyrido[2,1-a]isoquinolin-3-yl)carbamate | 16 |
| 125 | 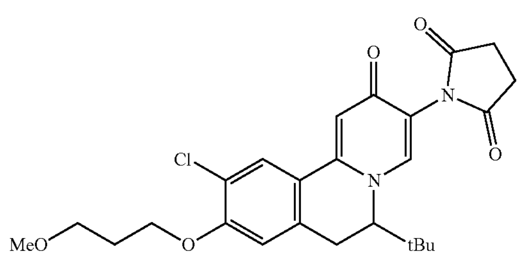 [SMILES: COCCCOc1cc2c(cc1Cl)-c1cc(=O)c(N3C(=O)CCC3=O)cn1C(C(C)(C)C)C2] | 1-(6-(tert-butyl)-10-chloro-9-(3-methoxypropoxy)-2-oxo-6,7-dihydro-2H-pyrido[2,1-a]isoquinolin-3-yl)pyrrolidine-2,5-dione | 12 |
| 126 | 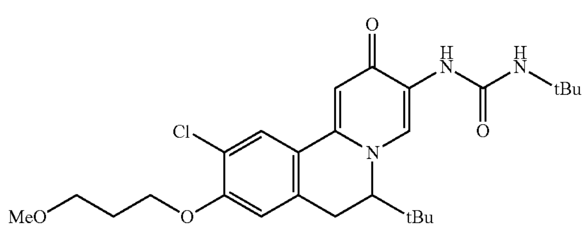 [SMILES: COCCCOc1cc2c(cc1Cl)-c1cc(=O)c(NC(=O)NC(C)(C)C)cn1C(C(C)(C)C)C2] | 1-(tert-butyl)-3-(6-(tert-butyl)-10-chloro-9-(3-methoxypropoxy)-2-oxo-6,7-dihydro-2H-pyrido[2,1-a]isoquinolin-3-yl)urea | 6.1 |

TABLE 3-continued

| Ex. No. | Structure | Nomenclature | sAg EC$_{50}$, μM |
|---|---|---|---|
| 127 | 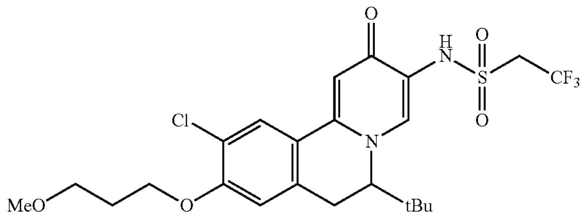 [SMILES: COCCCOc1cc2c(cc1Cl)-c1cc(=O)c(NS(=O)(=O)CC(F)(F)F)cn1C(C(C)(C)C)C2] | N-(6-(tert-butyl)-10-chloro-9-(3-methoxypropoxy)-2-oxo-6,7-dihydro-2H-pyrido[2,1-a]isoquinolin-3-yl)-2,2,2-trifluoroethane-1-sulfonamide | 15 |
| 128 | 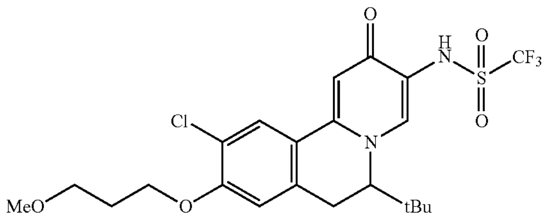 [SMILES: COCCCOc1cc2c(cc1Cl)-c1cc(=O)c(NS(=O)(=O)C(F)(F)F)cn1C(C(C)(C)C)C2] | N-(6-(tert-butyl)-10-chloro-9-(3-methoxypropoxy)-2-oxo-6,7-dihydro-2H-pyrido[2,1-a]isoquinolin-3-yl)-1,1,1-trifluoromethanesulfonamide | 4.7 |
| 129 | 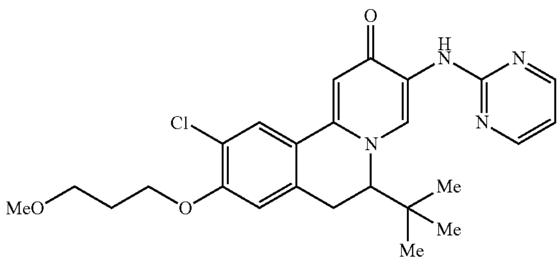 [SMILES: COCCCOc1cc2c(cc1Cl)-c1cc(=O)c(Nc3ncccn3)cn1C(C(C)(C)C)C2] | 6-(tert-butyl)-10-chloro-9-(3-methoxypropoxy)-3-(pyrimidin-2-ylamino)-6,7-dihydro-2H-pyrido[2,1-a]isoquinolin-2-one | 5.9 |
| 130 | 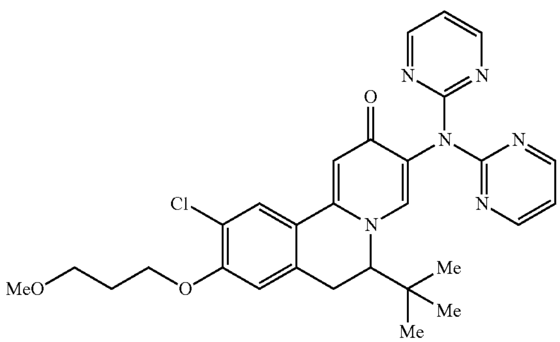 [SMILES: COCCCOc1cc2c(cc1Cl)-c1cc(=O)c(N(c3ncccn3)c3ncccn3)cn1C(C(C)(C)C)C2] | 6-(tert-butyl)-10-chloro-3-(di(pyrimidin-2-yl)amino)-9-(3-methoxypropoxy)-6,7-dihydro-2H-pyrido[2,1-a]isoquinolin-2-one | 0.91 |
| 131 | 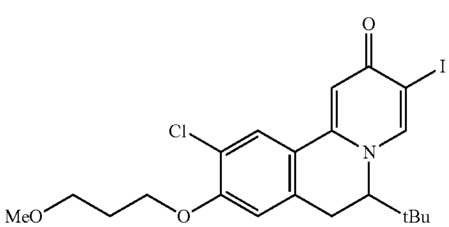 [SMILES: COCCCOc1cc2c(cc1Cl)-c1cc(=O)c(I)cn1C(C(C)(C)C)C2] | 6-(tert-butyl)-10-chloro-3-iodo-9-(3-methoxypropoxy)-6,7-dihydro-2H-pyrido[2,1-a]isoquinolin-2-one | 2.4 |
| 132 | 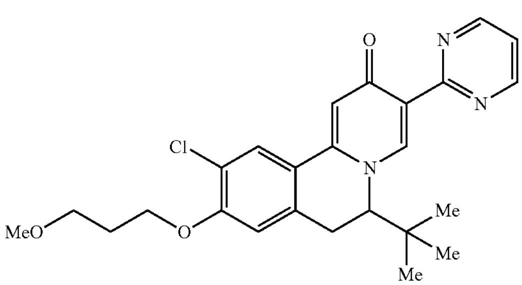 [SMILES: COCCCOc1cc2c(cc1Cl)-c1cc(=O)c(-c3ncccn3)cn1C(C(C)(C)C)C2] | 6-(tert-butyl)-10-chloro-9-(3-methoxypropoxy)-3-(pyrimidin-2-yl)-6,7-dihydro-2H-pyrido[2,1-a]isoquinolin-2-one | 0.078 |

TABLE 3-continued

| Ex. No. | Structure | Nomenclature | sAg EC$_{50}$, μM |
|---|---|---|---|
| 133 | 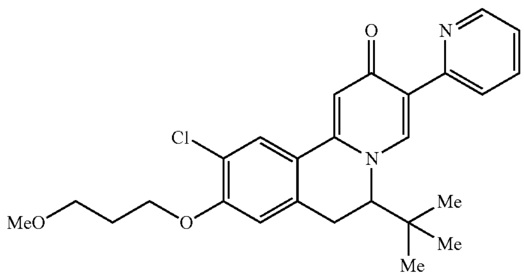 [SMILES: COCCCOc1cc2c(cc1Cl)-c1cc(=O)c(-c3ccccn3)cn1C(C(C)(C)C)C2] | 6-(tert-butyl)-10-chloro-9-(3-methoxypropoxy)-3-(pyridin-2-yl)-6,7-dihydro-2H-pyrido[2,1-a]isoquinolin-2-one | 4.0 |
| 142 | 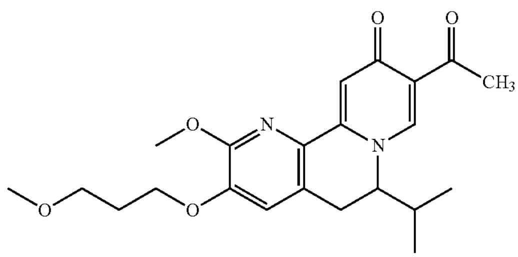 [SMILES: COCCCOc1cc2c(nc1OC)-c1cc(=O)c(C(C)=O)cn1C(C(C)C)C2] | 9-acetyl-6-isopropyl-2-methoxy-3-(3-methoxypropoxy)-5,6-dihydro-10H-pyrido[1,2-h][1,7]naphthyridin-10-one | 0.62 |
| 143 | 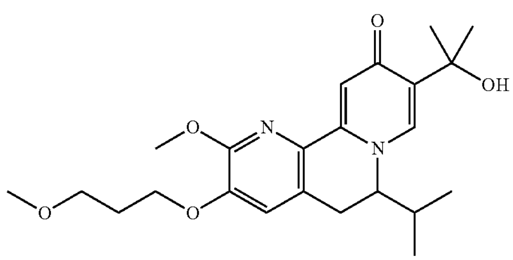 [SMILES: COCCCOc1cc2c(nc1OC)-c1cc(=O)c(C(C)(C)O)cn1C(C(C)C)C2] | 9-(2-hydroxypropan-2-yl)-6-isopropyl-2-methoxy-3-(3-methoxypropoxy)-5,6-dihydro-10H-pyrido[1,2-h][1,7]naphthyridin-10-one | 0.91 |
| 144 | 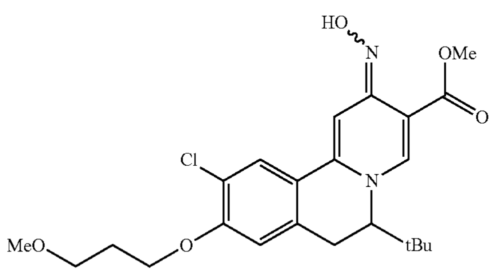 [SMILES: COCCCOc1cc2c(cc1Cl)-c1cc(=NO)c(C(=O)OC)cn1C(C(C)(C)C)C2] | methyl 6-(tert-butyl)-10-chloro-2-(hydroxyimino)-9-(3-methoxypropoxy)-6,7-dihydro-2H-pyrido[2,1-a]isoquinoline-3-carboxylate | 0.17 |
| 145 | 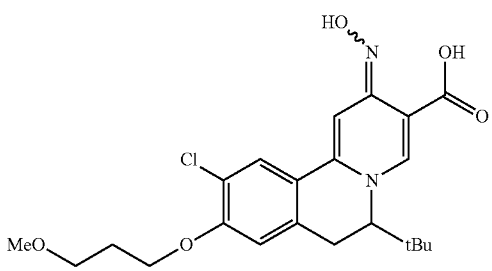 [SMILES: COCCCOc1cc2c(cc1Cl)-c1cc(=NO)c(C(=O)O)cn1C(C(C)(C)C)C2] | 6-(tert-butyl)-10-chloro-2-(hydroxyimino)-9-(3-methoxypropoxy)-6,7-dihydro-2H-pyrido[2,1-a]isoquinoline-3-carboxylic acid | 0.15 |
| 146 | 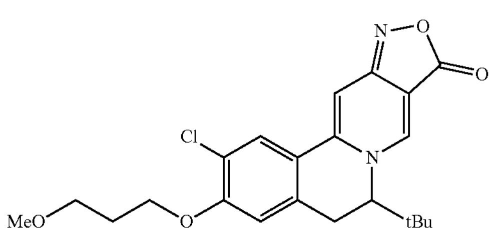 [SMILES: COCCCOc1cc2c(cc1Cl)-c1cc3noc(=O)c-3cn1C(C(C)(C)C)C2] | 6-(tert-butyl)-2-chloro-3-(3-methoxypropoxy)-5,6-dihydro-9H-isoxazolo[3',4':4,5]pyrido[2,1-a]isoquinolin-9-one | 0.031 |

TABLE 3-continued

| Ex. No. | Structure | Nomenclature | sAg EC$_{50}$, μM |
|---|---|---|---|
| 147 | 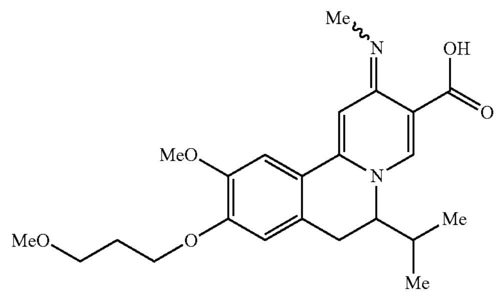 | 6-isopropyl-10-methoxy-9-(3-methoxypropoxy)-2-(methylimino)-6,7-dihydro-2H-pyrido[2,1-a]isoquinoline-3-carboxylic acid | 0.65 |
| 148 | 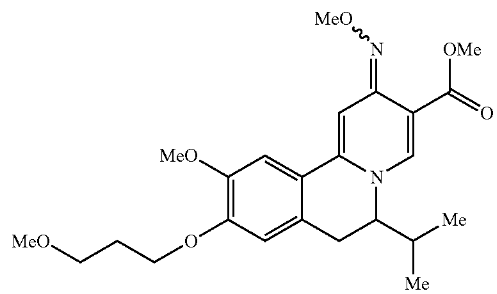 [SMILES: COCCCOc1cc2c(cc1OC)-c1cc(=NOC)c(C(=O)OC)cn1C(C(C)C)C2] | methyl 6-isopropyl-10-methoxy-2-(methoxyimino)-9-(3-methoxypropoxy)-6,7-dihydro-2H-pyrido[2,1-a]isoquinoline-3-carboxylate | 13 |
| 149 | 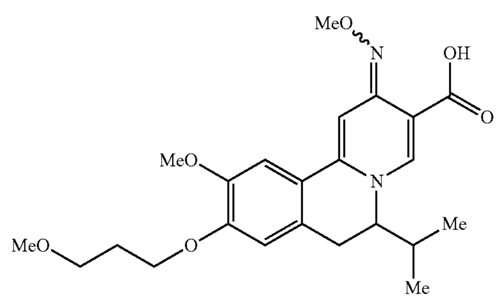 [SMILES: COCCCOc1cc2c(cc1OC)-c1cc(=NOC)c(C(=O)O)cn1C(C(C)C)C2] | 6-isopropyl-10-methoxy-2-(methoxyimino)-9-(3-methoxypropoxy)-6,7-dihydro-2H-pyrido[2,1-a]isoquinoline-3-carboxylic acid | 7.4 |
| 152 | 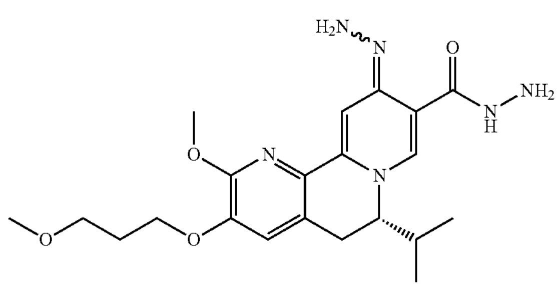 [SMILES: COCCCOc1cc2c(nc1OC)-c1cc(=NN)c(C(=O)NN)cn1[C@H](C(C)C)C2] | (S)-10-hydrazineylidene-6-isopropyl-2-methoxy-3-(3-methoxypropoxy)-5,10-dihydro-6H-pyrido[1,2-h][1,7]naphthyridine-9-carbohydrazide | 0.030 |
| 153 | 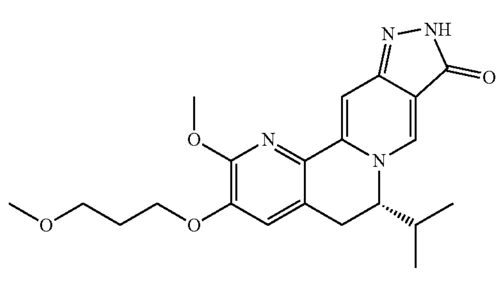 [SMILES: COCCCOc1cc2c(nc1OC)-c1cc3n[nH]c(=O)c-3cn1[C@H](C(C)C)C2] | (S)-6-isopropyl-2-methoxy-3-(3-methoxypropoxy)-5,10-dihydropyrazolo[3',4':4,5]pyrido[1,2-h][1,7]naphthyridin-9(6H)-one | 0.23 |

TABLE 3-continued

| Ex. No. | Structure | Nomenclature | sAg EC$_{50}$, µM |
|---|---|---|---|
| 154 | 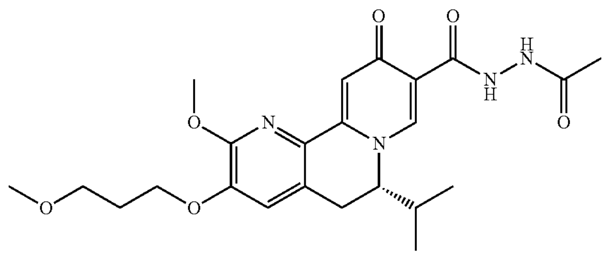 [SMILES: COCCCOc1cc2c(nc1OC)-c1cc(=O)c(C(=O)NNC(C)=O)cn1[C@H](C(C)C)C2] | (S)-N'-acetyl-6-isopropyl-2-methoxy-3-(3-methoxypropoxy)-10-oxo-5,10-dihydro-6H-pyrido[1,2-h][1,7]naphthyridin-9-carbohydrazide | 0.029 |
| 155 | 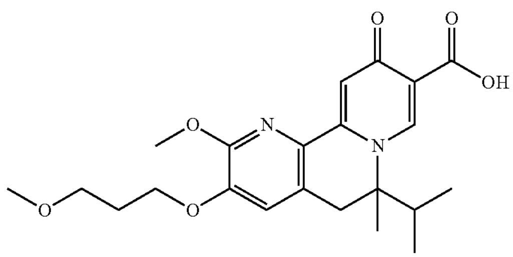 [SMILES: COCCCOc1cc2c(nc1OC)-c1cc(=O)c(C(=O)O)cn1C(C)(C(C)C)C2] | 6-isopropyl-2-methoxy-3-(3-methoxypropoxy)-6-methyl-10-oxo-5,10-dihydro-6H-pyrido[1,2-h][1,7]naphthyridine-9-carboxylic acid | 0.002 |
| 156 | 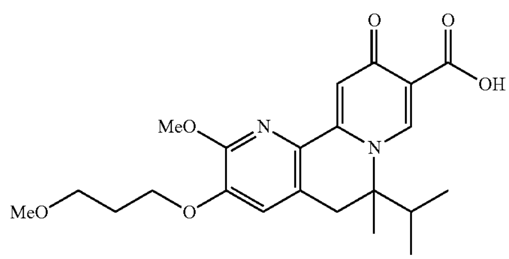 [SMILES: COCCCOc1cc2c(nc1OC)-c1cc(=O)c(C(=O)O)cn1C(C)(C(C)C)C2] | 6-isopropyl-2-methoxy-3-(3-methoxypropoxy)-6-methyl-10-oxo-5,10-dihydro-6H-pyrido[1,2-h][1,7]naphthyridine-9-carboxylic acid (single enantiomer I) | 0.001 |
| 157 | 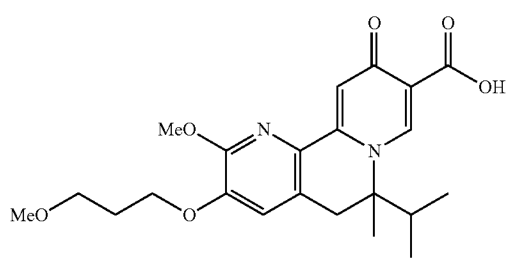 [SMILES: COCCCOc1cc2c(nc1OC)-c1cc(=O)c(C(=O)O)cn1C(C)(C(C)C)C2] | 6-isopropyl-2-methoxy-3-(3-methoxypropoxy)-6-methyl-10-oxo-5,10-dihydro-6H-pyrido[1,2-h][1,7]naphthyridine-9-carboxylic acid (single enantiomer II) | 0.11 |
| 158 | 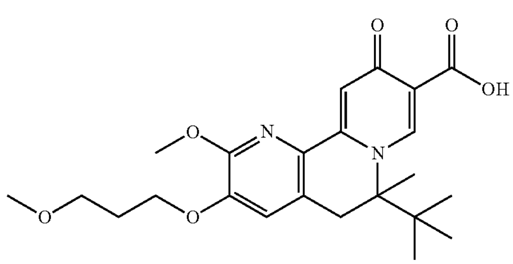 [SMILES: COCCCOc1cc2c(nc1OC)-c1cc(=O)c(C(=O)O)cn1C(C)(C(C)(C)C)C2] | 6-(tert-butyl)-2-methoxy-3-(3-methoxypropoxy)-6-methyl-10-oxo-5,10-dihydro-6H-pyrido[1,2-h][1,7]naphthyridine-9-carboxylic acid | 0.001 |
| 159 | 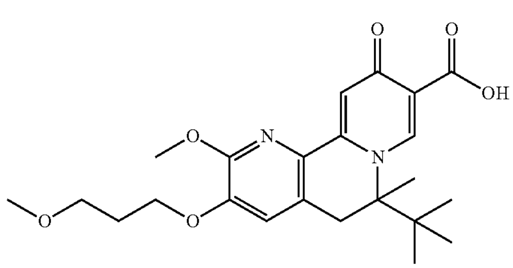 [SMILES: COCCCOc1cc2c(nc1OC)-c1cc(=O)c(C(=O)O)cn1C(C)(C(C)(C)C)C2] | 6-(tert-butyl)-2-methoxy-3-(3-methoxypropoxy)-6-methyl-10-oxo-5,10-dihydro-6H-pyrido[1,2-h][1,7]naphthyridine-9-carboxylic acid (single enantiomer I) | 0.0009 |

TABLE 3-continued

| Ex. No. | Structure | Nomenclature | sAg EC$_{50}$, μM |
|---|---|---|---|
| 160 | 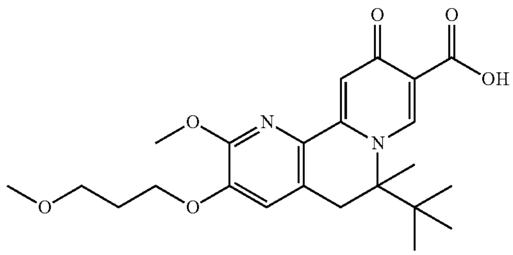 [SMILES: COCCCOc1cc2c(nc1OC)-c1cc(=O)c(C(=O)O)cn1C(C)(C(C)(C)C)C2] | 6-(tert-butyl)-2-methoxy-3-(3-methoxypropoxy)-6-methyl-10-oxo-5,10-dihydro-6H-pyrido[1,2-h][1,7]naphthyridine-9-carboxylic acid (single enantiomer II) | 0.038 |
| 162 | 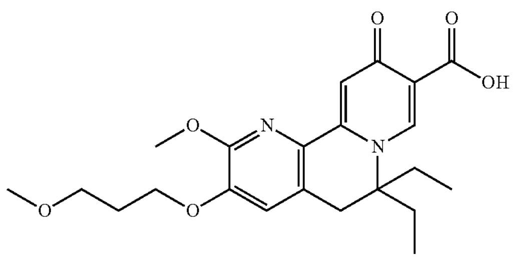 [SMILES: CCC1(CC)Cc2cc(OCCCOC)c(OC)nc2-c2cc(=O)c(C(=O)O)cn21] | 6,6-diethyl-2-methoxy-3-(3-methoxypropoxy)-10-oxo-5,10-dihydro-6H-pyrido[1,2-h][1,7]naphthyridine-9-carboxylic acid | 0.014 |
| 165 | 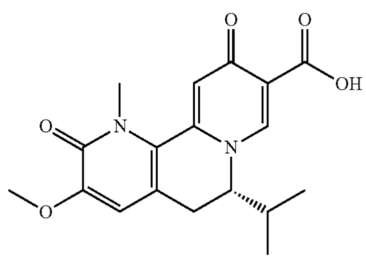 [SMILES: COc1cc2c(n(C)c1=O)-c1cc(=O)c(C(=O)O)cn1[C@H](C(C)C)C2] | (S)-6-isopropyl-3-methoxy-1-methyl-2,10-dioxo-2,5,6,10-tetrahydro-1H-pyrido[1,2-h][1,7]naphthyridine-9-carboxylic acid | 4.3 |
| 164 | 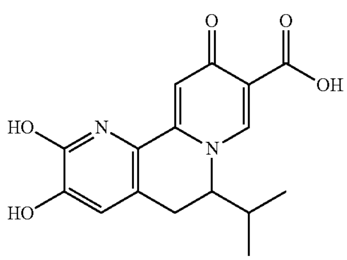 [SMILES: CC(C)C1Cc2cc(O)c(O)nc2-c2cc(=O)c(C(=O)O)cn21] | 2,3-dihydroxy-6-isopropyl-10-oxo-5,10-dihydro-6H-pyrido[1,2-h][1,7]naphthyridine-9-carboxylic acid | 10 |
| 166 | 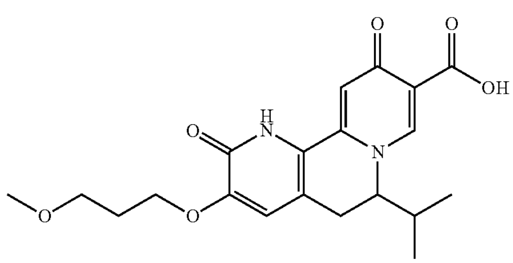 [SMILES: COCCCOc1cc2c([nH]c1=O)-c1cc(=O)c(C(=O)O)cn1C(C(C)C)C2] | 6-isopropyl-3-(3-methoxypropoxy)-2,10-dioxo-2,5,6,10-tetrahydro-1H-pyrido[1,2-h][1,7]naphthyridine-9-carboxylic acid (single enantiomer I) | 0.45 |
| 167 | 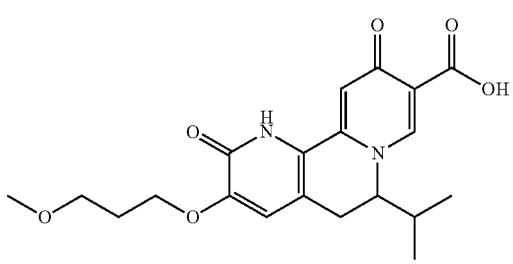 [SMILES: COCCCOc1cc2c([nH]c1=O)-c1cc(=O)c(C(=O)O)cn1C(C(C)C)C2] | 6-isopropyl-3-(3-methoxypropoxy)-2,10-dioxo-2,5,6,10-tetrahydro-1H-pyrido[1,2-h][1,7]naphthyridine-9-carboxylic acid (single enantiomer II) | 1 |

TABLE 3-continued

| Ex. No. | Structure | Nomenclature | sAg EC$_{50}$, µM |
|---|---|---|---|
| 161 | 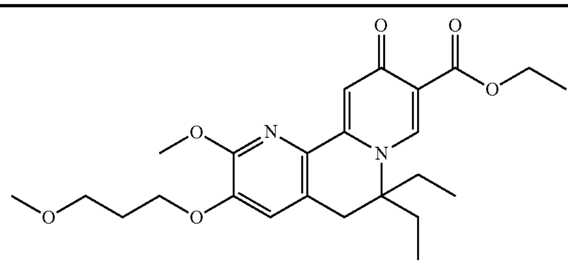 | ethyl 6,6-diethyl-2-methoxy-3-(3-methoxypropoxy)-10-oxo-5,10-dihydro-6H-pyrido[1,2-h][1,7]naphthyridine-9-carboxylate | 0.1 |
| 163 | 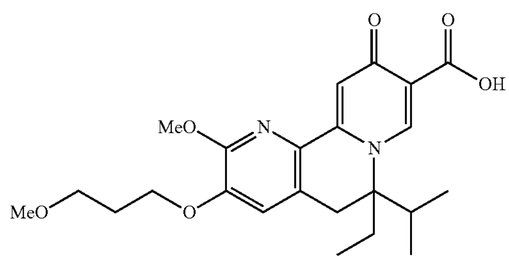 [SMILES: CCC1(C(C)C)Cc2cc(OCCCOC)c(OC)nc2-c2cc(=O)c(C(=O)O)cn21] | 6-ethyl-6-isopropyl-2-methoxy-3-(3-methoxypropoxy)-10-oxo-5,10-dihydro-6H-pyrido[1,2-h][1,7]naphthyridine-9-carboxylic acid | 0.13 |
| 171 | 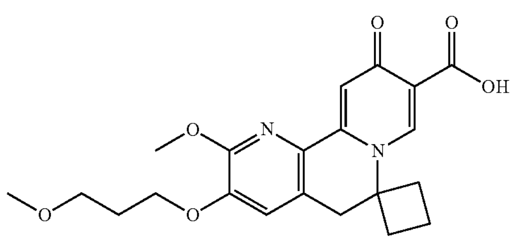 [SMILES: COCCCOc1cc2c(nc1OC)-c1cc(=O)c(C(=O)O)cn1C1(CCC1)C2] | 2'-methoxy-3'-(3-methoxypropoxy)-10'-oxo-5',10'-dihydrospiro[cyclobutane-1,6'-pyrido[1,2-h][1,7]naphthyridine]-9'-carboxylic acid | 0.018 |

HBV Production Assay

HepG2.2.15 cells were maintained and seeded as described above. After administration of test compounds for 6 days, supernatant was collected and clarified by low speed centrifugation. HBV DNA was released from virion in the supernatant by incubating in lysis buffer (Roche, Catalog #07248431001). HBV DNA levels were quantified by qPCR/TaqMan assay. The nucleoside analog Entecavir (ETV) was used as a control to determine inhibition of HBV virion production in the supernatant. Table 4 illustrates EC$_{50}$ values obtained by the HBV production assay for selected compounds.

TABLE 4

Activity in HBV production assay

| Compound | EC$_{50}$, µM |
|---|---|
| 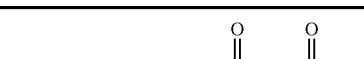 (2) | 0.077 |

TABLE 4-continued

| Activity in HBV production assay | |
|---|---|
| Compound | EC$_{50}$, μM |
| (92) single enantiomer II | 0.007 |
| (3) | 0.030 |
| (27) | 0.009 |
| (22) | 0.0004 |
| (36) | 0.007 |

TABLE 4-continued

Activity in HBV production assay

| Compound | EC$_{50}$, µM |
|---|---|
| 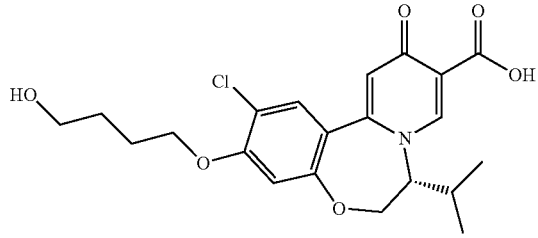<br>(39) | 0.02 |
| 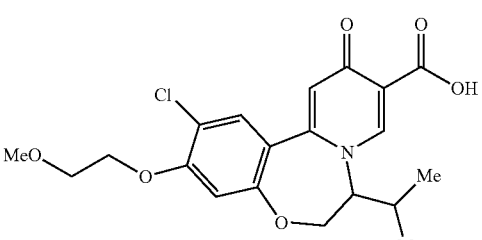<br>(29) | 0.046 |
| 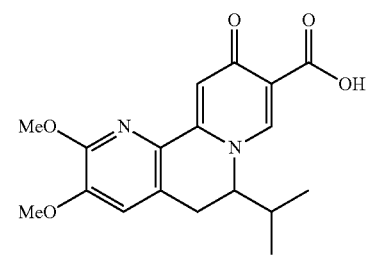<br>single enantiomer II<br>(25) | 0.002 |

Example 175: In Vitro Combination Studies

In Vitro HBV Infection Studies in HepG2.2.15 Cells were Performed Using Compounds A and B of the present invention, in combination with certain lipid nanoparticles (LNP-1 and LNP-2), which encapsulate distinct siRNA mixtures (siRNA Mix 1 and siRNA Mix 2, respectively).

Compound A (22)

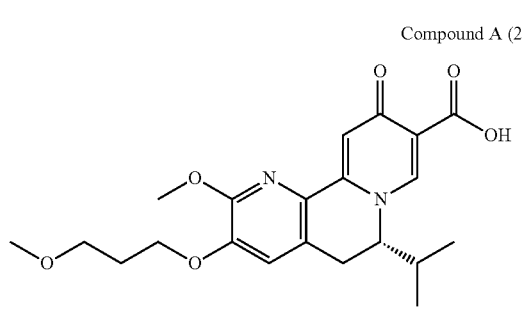

Compound B (27)

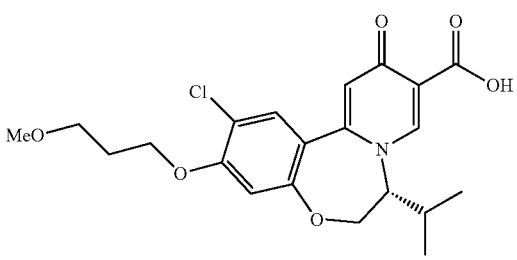

Lipid Nanoparticle Formulations:

LNP-1 and LNP-2 are lipid nanoparticle formulations of a mixture of three siRNAs targeting the HBV genome. The following lipid nanoparticle (LNP) product was used to deliver the HBV siRNAs in the experiments reported herein. The values shown in the table are mole percentages. Distearoylphosphatidylcholine is abbreviated as DSPC.

TABLE 5

| PEG-C-DMA | Cationic lipid | Cholesterol | DSPC |
|---|---|---|---|
| 1.6 | 54.6 | 32.8 | 10.9 |

The cationic lipid has the following structure:

SiRNA
The sequences of three siRNAs comprised in LNP-1 are:

TABLE 6

| Sense Sequence (5'-3') | Antisense Sequence (5'-3') |
|---|---|
| CCGUguGCACUuCGCuuCAUU (SEQ ID NO: 1) | UGAAGCGAAGUgCACACgGUU (SEQ ID NO: 2) |
| CuggCUCAGUUUACuAgUGUU (SEQ ID NO: 3) | CACUAgUAAACUgAgCCAGUU (SEQ ID NO: 4) |
| GCCgAuCCAUACugCGgAAUU (SEQ ID NO: 5) | UUCCGCAgUAUGgAUCGgCUU (SEQ ID NO: 6) | lower case = 2'-O-methyl modification
Underline = unlocked nucleobase analogue (UNA) moiety The sequences of three siRNAs comprised in LNP-2 are:

TABLE 7

| Sense Sequence (5'-3') | Antisense Sequence (5'-3') |
|---|---|
| rCrCmGrUmGmUrGrCrArCr UmUrCmGrCmUmUrCrArUrU (SEQ ID NO: 7) | rUrGrArAmGrCmGrArArGm UmGrCrAmCrAmCmGrGrUrU (SEQ ID NO: 8) |
| rCmUmGmGrCmUrCrArGmUr UmUrAmCmUrAmGmUmGrUrU (SEQ ID NO: 9) | rCrArCrUrAmGmUrArArAm CrUmGrAmGrCmCrArGrUrU (SEQ ID NO: 10) |
| rAmCrCmUrCmUrGmCrCmUr AmArUmCrArUrCrUrCrUrU (SEQ ID NO: 11) | rGrArGrArUrGmArUmUrAr GrGmCrAmGrAmGrGrUrUrU (SEQ ID NO: 12) | rN = RNA of base N
mN = 2'O-methyl modification of base N

In Vitro Combination Experimental Protocol:

In vitro combination studies were conducted using the method of Prichard & Shipman, 1990, Antiviral Res. 14(4-5):181-205, and Prichard, et al., MacSynergy II). The HepG2.2.15 cell culture system is a cell line derived from human hepatoblastoma HepG2 cells, that have been stably transfected with the adw2-subtype HBV genome (Sells, et al., 1987, Proc. Natl. Acad. Sci. U.S.A 84:1005-1009). HepG2.2.15 cells secrete Dane-like viral particles, produce HBV DNA, and produce the viral proteins, HBeAg and HBsAg.

Non-limiting examples of HBV RNA destabilizers are Compound A and Compound B. The $EC_{50}$ values of these agents are shown in Table 12. Although inhibition of HBV DNA, RNA and proteins can be determined in the presence of the compounds of the invention and LNPs (both referred to herein as "agents"), the assay that can quantitatively measure the level of HBsAg was used in this study. To test the agent combinations, HepG2.2.15 (30,000 cells/well) were plated in 96 well tissue-culture treated microtiter plates in DMEM+L-Glutamine medium supplemented with 1% penicillin-streptomycin, 20 μg/mL geneticin (G418), 10% fetal bovine serum, and incubated in a humidified incubator at 37° C. and 5% $CO_2$ overnight. The next day, the cells were replenished with fresh medium followed by the addition of compound of the invention (dissolved in 100% DMSO), and LNP (dissolved in 100% RPMI medium). The agents were added to cells in a checkerboard fashion. The microtiter cell plates were incubated for a total duration of 6 days in a humidified incubator at 37° C. and 5% $CO_2$. On the $3^{rd}$ day of incubation, the cells were replenished with fresh medium and agents. The serial dilutions spanned concentration ranges respective to the $EC_{50}$ value of each agent, with the final DMSO concentration of the assay being 0.5%. In addition to combination testing of the agents in a checkerboard fashion, the compound and LNP were also tested alone.

Untreated positive control samples (0.5% DMSO in media) were included on each plate in multiple wells. Following a 6 day-incubation, media was removed from treated cells for use in an HBsAg chemiluminescence immunoassay (CLIA) (Autobio Diagnostics, Cat No. CL0310-2). An HBsAg standard curve was generated to verify that the levels of HBsAg quantification were within the detection limits of the assay. The remaining inhibitor-treated cells were assessed for cytotoxicity by determination of the intracellular adenosine triphosphate (ATP) using a Cell-Titer Glo reagent (Promega) as per manufacturers instructions and by microscopic analysis of the cells throughout the duration of inhibitor treatment. Cell viability was calculated as a percentage of the untreated positive control wells.

The plates were read using an EnVision multimode plate reader (PerkinElmer Model 2104). The relative luminescence units (RLU) data generated from each well was used to calculate HBsAg levels as % t inhibition of the untreated positive control wells and analyzed using the Prichard-Shipman combination model using the MacSynergyII program (Prichard & Shipman, 1990, Antiviral Res. 14(4-5): 181-205, and Prichard, et al., MacSynergy II) to determine whether the combinations were synergistic, additive or antagonistic using the interpretive guidelines established by Prichard & Shipman as follows: synergy volumes <25 $μM^2$% (log volume <2) at 95% CI=probably insignificant; 25-50 (log volume >2 and <5)=minor but significant 50-100 (log volume >5 and <9)=moderate, may be important in vivo; Over 100 (log volume >9)=strong synergy, probably important in vivo; volumes approaching 1000 (log volume >90)=unusually high, check data. The RLU data from the single agent treated cells were analyzed using XL-Fit module in Microsoft Excel to determine $EC_{50}$ values using a 4-parameter curve fitting algorithm.

Sub-Example 175.1: In Vitro Combination of Compound A and LNP-1

Compound A (concentration range of 0.1 LM to 0.000015 μM in a half-log, 3.16-fold dilution series and 9-point titration) was tested in combination with LNP-1 (concentration range of 2.5 nM to 0.025 nM in a half-log, 3.16-fold dilution series and 5-point titration). The combination results were completed in duplicate with each assay consisting of 4 technical repeats. The measurements of synergy and antagonism volumes according to Prichard & Shipman, and interpretation, are shown in Table 12. The antiviral activity of this combination is shown in Table 8A; synergy and antagonism volumes are shown in Table 8B. The additive inhibition activity of this combination is shown in Table 8D. In this assay system, the combination results in additive inhibition of HBsAg secretion. No significant inhibition of cell viability or proliferation was observed by microscopy or Cell-Titer Glo assay (Table 8C).

TABLE 8A

Antiviral Activity of Compound A and LNP-1 Combination.
Average percent inhibition versus negative control (n = 4 samples per data point)

| LNP-1, µM Avg % Inhibition | 0.0025 | 85.62 | 87.78 | 85.15 | 89.14 | 90.23 | 92.7 | 94.43 | 96.68 | 96.91 | 97.25 |
|---|---|---|---|---|---|---|---|---|---|---|---|
| | 0.00079 | 63.75 | 72.77 | 65.44 | 70.51 | 75.74 | 81.16 | 88.16 | 93.24 | 92.99 | 89.54 |
| | 0.00025 | 38.19 | 48.06 | 49.16 | 49.11 | 51.51 | 64 | 78.69 | 90.35 | 93.69 | 93.07 |
| | 7.9E−05 | 17.82 | 30.39 | 28.84 | 29.97 | 36.54 | 52.99 | 72.55 | 86.96 | 91.46 | 93.07 |
| | 2.5E−05 | 11.11 | 24.54 | 20.58 | 24.96 | 31.68 | 47.94 | 68.95 | 84.22 | 90.56 | 92.62 |
| | 0 | 0 | 17.73 | 8.39 | 16.81 | 23.55 | 47.52 | 66.21 | 84.38 | 90.37 | 92.38 |
| | | 0 | 1.00E−06 | 3.16E−06 | 1.0E−05 | 3.17E−05 | 0.0001 | 0.000316 | 0.001 | 0.00316 | 0.1 |
| Compound | | | | | | Compound A, µM | | | | | |

TABLE 8B

MacSynergy Volume Calculations of Compound A and LNP-1 Combination.
99.99% confidence interval (Bonferroni Adj. 96%)

| LNP-1, µM SYNERGY 0 Log volume 0 Antagonism −3.44 Log volume −0.86 | 0.0025 | 0 | 0 | 0 | 0 | 0 | 0 | 0 | −0.02 | 0 | 0 |
|---|---|---|---|---|---|---|---|---|---|---|---|
| | 0.00079 | 0 | 0 | 0 | 0 | 0 | 0 | 0 | 0 | 0 | −3.42 |
| | 0.00025 | 0 | 0 | 0 | 0 | 0 | 0 | 0 | 0 | 0 | 0 |
| | 7.9E−05 | 0 | 0 | 0 | 0 | 0 | 0 | 0 | 0 | 0 | 0 |
| | 2.5E−05 | 0 | 0 | 0 | 0 | 0 | 0 | 0 | 0 | 0 | 0 |
| | 0 | 0 | 0 | 0 | 0 | 0 | 0 | 0 | 0 | 0 | 0 |
| | | 0 | 1.00E−06 | 3.16E−06 | 1.0E−05 | 3.17E−05 | 0.0001 | 0.000316 | 0.001 | 0.00316 | 0.1 |
| Compound | | | | | | Compound A, µM | | | | | |

TABLE 8C

Cytotoxicity of Compound A and LNP-1 Combination.
Average percent of cell viability vs control

| LNP-1, µM Avg % Cell Viability | 0.0025 | 99 | 99 | 95 | 114 | 106 | 96 | 102 | 106 | 115 | 106 |
|---|---|---|---|---|---|---|---|---|---|---|---|
| | 0.00079 | 98 | 85 | 96 | 89 | 87 | 82 | 91 | 95 | 93 | 111 |
| | 0.00025 | 81 | 83 | 82 | 81 | 77 | 80 | 83 | 89 | 98 | 105 |
| | 7.9E−05 | 101 | 75 | 93 | 80 | 86 | 91 | 94 | 74 | 107 | 106 |
| | 2.5E−05 | 87 | 82 | 85 | 94 | 80 | 87 | 90 | 97 | 101 | 105 |
| | 0 | 100 | 114 | 121 | 121 | 119 | 125 | 123 | 138 | 138 | 133 |
| | | 0 | 1.00E−06 | 3.16E−06 | 1.0E−05 | 3.17E−05 | 0.0001 | 0.000316 | 0.001 | 0.00316 | 0.1 |
| Compound | | | | | | Compound A, µM | | | | | |

TABLE 8D

Antiviral Activity of Compound A and LNP-1 Combination.
Additive percent inhibition versus negative control (n = 4 samples per data point)

| LNP-1, µM Additive % Inhibition | 0.0025 | 85.62 | 88.17 | 86.83 | 88.04 | 89.01 | 92.45 | 95.14 | 97.75 | 98.62 | 98.9 |
|---|---|---|---|---|---|---|---|---|---|---|---|
| | 0.00079 | 63.75 | 70.18 | 66.79 | 69.84 | 72.29 | 80.98 | 87.75 | 94.34 | 96.51 | 97.24 |
| | 0.00025 | 38.19 | 49.15 | 43.38 | 48.58 | 52.75 | 67.56 | 79.11 | 90.35 | 94.05 | 95.29 |
| | 7.9E−05 | 17.82 | 32.39 | 24.71 | 31.63 | 37.17 | 56.87 | 72.23 | 87.16 | 92.09 | 93.74 |
| | 2.5E−05 | 11.11 | 26.87 | 18.57 | 26.05 | 32.04 | 53.35 | 69.96 | 86.12 | 91.44 | 93.23 |
| | 0 | 0 | 17.73 | 8.39 | 16.81 | 23.55 | 47.52 | 66.21 | 84.38 | 90.37 | 92.38 |
| | | 0 | 1.00E−06 | 3.16E−06 | 1.0E−05 | 3.17E−05 | 0.0001 | 0.000316 | 0.001 | 0.00316 | 0.1 |
| Compound | | | | | | Compound A, µM | | | | | |

Sub-Example 175.2: In Vitro Combination of Compound A and LNP-2

Compound A (concentration range of 0.1 µM to 0.000015 µM in a half-log, 3.16-fold dilution series and 9-point titration) was tested in combination with LNP-2 (concentration range of 2.5 nM to 0.025 nM in a half-log, 3.16-fold dilution series and 5-point titration). The combination results were completed in duplicate with each assay consisting of 4 technical repeats. The measurements of synergy and antagonism volumes according to Prichard & Shipman, and interpretation, are shown in Table 12. The antiviral activity of this combination is shown in Table 9A; synergy and antagonism volumes are shown in Table 9B. The additive inhibition activity of this combination is shown in Table 9D. In this assay system, the combination results in additive inhibition of HBsAg secretion. No significant inhibition of cell viability or proliferation was observed by microscopy or Cell-Titer Glo assay (Table 9C).

TABLE 9A

Antiviral Activity of Compound A and LNP-2 Combination.
Average percent inhibition versus negative control (n = 4 samples per data point)

| LNP-2, µM | 0.0025 | 85.18 | 88.13 | 88.8 | 90.59 | 91.38 |
|---|---|---|---|---|---|---|
| Avg % | 0.00079 | 51.79 | 44.43 | 47.27 | 63.84 | 69.47 |
| Inhibition | 0.00025 | 36.85 | 35.03 | 38.78 | 41.19 | 48.29 |
|  | 7.9E−05 | 13.81 | 28.58 | 28.73 | 28.4 | 37.14 |
|  | 2.5E−05 | 5.38 | 18.65 | 21.24 | 22.76 | 34.16 |
|  | 0 | 0 | 16 | 20.62 | 27.46 | 34.41 |
|  |  | 0 | 1.00E−06 | 3.16E−06 | 1.0E−05 | 3.17E−05 |
| Compound |  |  | Compound A, µM |  |  |  |

| LNP-2, µM | 93.76 | 95.84 | 97.35 | 98.02 | 98.19 |
|---|---|---|---|---|---|
| Avg % | 74.68 | 86.09 | 93.19 | 95.34 | 96.27 |
| Inhibition | 60.31 | 80.78 | 90.92 | 94.16 | 95.04 |
|  | 53.07 | 76.86 | 89.25 | 92.86 | 93.73 |
|  | 51.26 | 75.26 | 88.55 | 92.5 | 94.17 |
|  | 48.07 | 74.6 | 87.41 | 92.04 | 93.74 |
|  | 0.0001 | 0.000316 | 0.001 | 0.00316 | 0.1 |
| Compound |  | Compound A, µM |  |  |  |

TABLE 9B

MacSynergy Volume Calculations of Compound A and LNP-2 Combination.
99.99% confidence interval (Bonferroni Adj. 96%)

| LNP-2, µM | 0.0025 | 0 | 0 | 0 | 0 | 0 | 0 | 0 | 0 | 0 | 0 |
|---|---|---|---|---|---|---|---|---|---|---|---|
|  | 0.00079 | 0 | 0 | 0 | 0 | 0 | 0 | 0 | 0 | 0 | 0 |
| SYNERGY 0 | 0.00025 | 0 | 0 | 0 | 0 | 0 | 0 | 0 | 0 | 0 | 0 |
| Log volume 0 | 7.9E−05 | 0 | 0 | 0 | 0 | 0 | 0 | 0 | 0 | 0 | 0 |
| Antagonism 0 | 2.5E−05 | 0 | 0 | 0 | 0 | 0 | 0 | 0 | 0 | 0 | 0 |
| Log volume 0 | 0 | 0 | 0 | 0 | 0 | 0 | 0 | 0 | 0 | 0 | 0 |
|  |  | 0 | 1.00E−06 | 3.16E−06 | 1.0E−05 | 3.17E−05 | 0.0001 | 0.000316 | 0.001 | 0.00316 | 0.1 |
| Compound |  |  |  |  |  | Compound A, µM |  |  |  |  |  |

TABLE 9C

Cytotoxicity of Compound A and LNP-2 Combination.
Average percent of cell viability vs control

| LNP-2, µM | 0.0025 | 93 | 107 | 105 | 102 | 99 | 98 | 102 | 97 | 101 | 126 |
|---|---|---|---|---|---|---|---|---|---|---|---|
|  | 0.00079 | 98 | 110 | 101 | 88 | 93 | 92 | 88 | 100 | 107 | 118 |
| Avg % Cell | 0.00025 | 100 | 95 | 92 | 83 | 85 | 92 | 85 | 98 | 103 | 108 |
| Viability | 7.9E−05 | 111 | 105 | 98 | 81 | 84 | 100 | 90 | 100 | 102 | 118 |
|  | 2.5E−05 | 95 | 96 | 94 | 93 | 87 | 91 | 87 | 94 | 105 | 118 |
|  | 0 | 100 | 107 | 122 | 107 | 104 | 127 | 100 | 126 | 131 | 127 |
|  |  | 0 | 1.00E−06 | 3.16E−06 | 1.0E0−5 | 3.17E−05 | 0.0001 | 0.000316 | 0.001 | 0.00316 | 0.1 |
| Compound |  |  |  |  |  | Compound A, µM |  |  |  |  |  |

TABLE 9D

Antiviral Activity of Compound A and LNP-2 Combination:
Additive percent inhibition versus negative control (n = 4 samples per data point)

| LNP-2, | 0.0025 | 85.18 | 87.55 | 88.24 | 89.25 | 90.28 | 92.3 | 96.24 | 98.13 | 98.82 | 99.07 |
|---|---|---|---|---|---|---|---|---|---|---|---|
| µM | 0.00079 | 51.79 | 59.5 | 61.73 | 65.03 | 68.38 | 74.96 | 87.75 | 93.93 | 96.16 | 96.98 |

TABLE 9D-continued

Antiviral Activity of Compound A and LNP-2 Combination:
Additive percent inhibition versus negative control (n = 4 samples per data point)

| Additive % Inhibition | 0.00025 | 36.85 | 46.95 | 49.87 | 54.19 | 58.58 | 67.21 | 83.96 | 92.05 | 94.97 | 96.05 |
|---|---|---|---|---|---|---|---|---|---|---|---|
| | 7.9E−05 | 13.81 | 27.6 | 31.58 | 37.48 | 43.47 | 55.24 | 78.11 | 89.15 | 93.14 | 94.6 |
| | 2.5E−05 | 5.38 | 20.52 | 24.89 | 31.36 | 37.94 | 50.86 | 75.97 | 88.09 | 92.47 | 94.08 |
| | 0 | 0 | 16 | 20.62 | 27.46 | 34.41 | 48.07 | 74.6 | 87.41 | 92.04 | 93.74 |
| | | 0 | 1.00E−06 | 3.16E−06 | 1.0E−05 | 3.17E−05 | 0.0001 | 0.000316 | 0.001 | 0.00316 | 0.1 |
| Compound | | | | | | Compound A, μM | | | | | |

Sub-Example 175.3: In Vitro Combination of Compound B and LNP-1

Compound B (concentration range of 2 μM to 0.0002 μM in a half-log, 3.16-fold dilution series and 9-point titration) was tested in combination with LNP-1 (concentration range of 2.5 nM to 0.025 nM in a half-log, 3.16-fold dilution series and 5-point titration). The combination results were completed in duplicate with each assay consisting of 4 technical repeats. The measurements of synergy and antagonism volumes according to Prichard & Shipman, and interpretation, are shown in Table 12. The antiviral activity of this combination is shown in Table 10A; synergy and antagonism volumes are shown in Table 10B. The additive inhibition activity of this combination is shown in Table 10D. In this assay system, the combination results in additive inhibition of HBsAg secretion. No significant inhibition of cell viability or proliferation was observed by microscopy or CellTiter Glo assay (Table 10C).

TABLE 10A

Antiviral Activity of Compound B and LNP-1 Combination.
Average percent inhibition versus negative control (n = 4 samples per data point)

| LNP-1, μM Avg % Inhibition | 0.0025 | 88.03 | 91.04 | 92.01 | 91.94 | 92.72 | 94.9 | 96.62 | 97.68 | 98.37 | 97.16 |
|---|---|---|---|---|---|---|---|---|---|---|---|
| | 0.00079 | 66.51 | 67.82 | 75.32 | 69.03 | 76.27 | 80.18 | 88.62 | 93.77 | 95.04 | 95.92 |
| | 0.00025 | 34.75 | 45.37 | 41.55 | 45 | 53.68 | 68.34 | 82.07 | 90.67 | 93.78 | 94.56 |
| | 7.9E−05 | 23.09 | 26.96 | 29.45 | 34 | 40.75 | 60.31 | 80.8 | 89.24 | 93.06 | 93.54 |
| | 2.5E−05 | 8.85 | 21.28 | 24.16 | 30.18 | 36.46 | 57.93 | 78.97 | 89.18 | 92.6 | 93.61 |
| | 0 | 0 | 19.99 | 22.24 | 28.73 | 39.16 | 61.93 | 80.51 | 89.95 | 92.6 | 93.51 |
| | | 0 | 0.0002 | 0.0006 | 0.002 | 0.006 | 0.02 | 0.06 | 0.20 | 0.63 | 2 |
| Compound | | | | | | Compound B, μM | | | | | |

TABLE 10B

MacSynergy Volume Calculations of Compound B and LNP-1 Combination.
99.99% confidence interval (Bonferroni Adj. 96%)

| LNP-1, μM SYNERGY 0 Log volume 0 Antagonism −9.98 Log volume −2.49 | 0.0025 | 0 | 0 | 0 | 0 | 0 | 0 | 0 | −0.56 | 0 | 0 |
|---|---|---|---|---|---|---|---|---|---|---|---|
| | 0.00079 | 0 | 0 | 0 | 0 | 0 | 0 | −1.33 | −1.44 | −1.26 | −0.23 |
| | 0.00025 | 0 | 0 | 0 | 0 | 0 | 0 | 0 | 0 | 0 | 0 |
| | 7.9E−05 | 0 | −2.84 | 0 | 0 | 0 | 0 | −1.58 | −0.73 | 0 | 0 |
| | 2.5E−05 | 0 | 0 | 0 | 0 | 0 | 0 | 0 | 0 | 0 | 0 |
| | 0 | 0 | 0 | 0 | 0 | 0 | 0 | 0 | 0 | 0 | 0 |
| | | 0 | 0.0002 | 0.0006 | 0.002 | 0.006 | 0.02 | 0.06 | 0.20 | 0.63 | 2 |
| Compound | | | | | | Compound B, μM | | | | | |

TABLE 10C

Cytotoxicity of Compound B and LNP-1 Combination.
Average percent of cell viability vs control

| LNP-1, μM Avg % Cell Viability | 0.0025 | 91 | 89 | 88 | 88 | 93 | 86 | 89 | 87 | 87 | 90 |
|---|---|---|---|---|---|---|---|---|---|---|---|
| | 0.00079 | 92 | 87 | 87 | 90 | 89 | 90 | 90 | 89 | 92 | 91 |
| | 0.00025 | 92 | 90 | 89 | 87 | 87 | 80 | 87 | 91 | 87 | 95 |
| | 7.9E−05 | 93 | 85 | 83 | 82 | 91 | 91 | 88 | 93 | 83 | 84 |
| | 2.5E−05 | 95 | 90 | 82 | 87 | 93 | 84 | 85 | 84 | 84 | 88 |
| | 0 | 102 | 103 | 98 | 85 | 98 | 101 | 92 | 104 | 88 | 97 |
| | | 0 | 0.0002 | 0.0006 | 0.002 | 0.006 | 0.02 | 0.06 | 0.20 | 0.63 | 2 |
| Compound | | | | | | Compound B, μM | | | | | |

TABLE 10D

Antiviral Activity of Compound B and LNP-1 Combination.
Additive percent inhibition versus negative control (n = 4 samples per data point)

| LNP-1, µM Additive % Inhibition | | | | | | | | | | |
|---|---|---|---|---|---|---|---|---|---|---|
| | 0.0025 | 88.03 | 90.42 | 90.69 | 91.47 | 92.72 | 95.44 | 97.67 | 98.8 | 99.11 | 99.22 |
| | 0.00079 | 66.51 | 73.2 | 73.96 | 76.13 | 79.62 | 87.25 | 93.47 | 96.63 | 97.52 | 97.83 |
| | 0.00025 | 34.75 | 47.79 | 49.26 | 53.5 | 60.3 | 75.16 | 87.28 | 93.44 | 95.17 | 95.77 |
| | 7.9E−05 | 23.09 | 38.46 | 40.19 | 45.19 | 53.21 | 70.72 | 85.01 | 92.27 | 94.31 | 95.01 |
| | 2.5E−05 | 8.85 | 27.07 | 29.12 | 35.04 | 44.54 | 65.3 | 82.23 | 90.84 | 93.25 | 94.08 |
| | 0 | 0 | 19.99 | 22.24 | 28.73 | 39.16 | 61.93 | 80.51 | 89.95 | 92.6 | 93.51 |
| | | 0 | 0.0002 | 0.0006 | 0.002 | 0.006 | 0.02 | 0.06 | 0.20 | 0.63 | 2 |
| Compound | | | | | Compound B, µM | | | | | | |

Sub-Example 175.4: In Vitro Combination of Compound B and LNP-2

Compound B (concentration range of 2 µM to 0.0002 µM in a half-log, 3.16-fold dilution series and 9-point titration) was tested in combination with LNP-2 (concentration range of 2.5 nM to 0.025 nM in a half-log, 3.16-fold dilution series and 5-point titration). The combination results were completed in duplicate with each assay consisting of 4 technical repeats. The measurements of synergy and antagonism volumes according to Prichard & Shipman, and interpretation, are shown in Table 12. The antiviral activity of this combination is shown in Table 11A; synergy and antagonism volumes are shown in Table 11B. The additive inhibition activity of this combination is shown in Table 11D. In this assay system, the combination results in additive inhibition of HBsAg secretion. No significant inhibition of cell viability or proliferation was observed by microscopy or Cell-Titer Glo assay (Table 11C).

TABLE 11A

Antiviral Activity of Compound B and LNP-2 Combination.
Average percent inhibition versus negative control (n = 4 samples per data point)

| LNP-2, µM Avg % Inhibition | | | | | | | | | | |
|---|---|---|---|---|---|---|---|---|---|---|
| | 0.0025 | 88.03 | 91.04 | 92.01 | 91.94 | 92.72 | 94.9 | 96.62 | 97.68 | 98.37 | 97.16 |
| | 0.00079 | 66.51 | 67.82 | 75.32 | 69.03 | 76.27 | 80.18 | 88.62 | 93.77 | 95.04 | 95.92 |
| | 0.00025 | 34.75 | 45.37 | 41.55 | 45 | 53.68 | 68.34 | 82.07 | 90.67 | 93.78 | 94.56 |
| | 7.9E−05 | 23.09 | 26.96 | 29.45 | 34 | 40.75 | 60.31 | 80.8 | 89.24 | 93.06 | 93.54 |
| | 2.5E−05 | 8.85 | 21.28 | 24.16 | 30.18 | 36.46 | 57.93 | 78.97 | 89.18 | 92.6 | 93.61 |
| | 0 | 0 | 19.99 | 22.24 | 28.73 | 39.16 | 61.93 | 80.51 | 89.95 | 92.6 | 93.51 |
| | | 0 | 0.0002 | 0.0006 | 0.002 | 0.006 | 0.02 | 0.06 | 0.20 | 0.63 | 2 |
| Compound | | | | | Compound B, µM | | | | | | |

TABLE 11B

MacSynergy Volume Calculations of Compound B and LNP-2 Combination.
99.99% confidence interval (Bonferroni Adj. 96%)

| LNP-2, µM SYNERGY 0 Log volume 0 Antagonism −16.95 Log volume −4.23 | | | | | | | | | | |
|---|---|---|---|---|---|---|---|---|---|---|
| | 0.0025 | 0 | 0 | 0 | 0 | 0 | 0 | −0.08 | −0.22 | −1.24 | −0.77 |
| | 0.00079 | 0 | 0 | 0 | 0 | 0 | 0 | −2.94 | −0.01 | 0 | 0 |
| | 0.00025 | 0 | 0 | 0 | 0 | 0 | 0 | 0 | 0 | 0 | 0 |
| | 7.9E−05 | 0 | −3.38 | −0.18 | −1.4 | −2.49 | −4.25 | 0 | 0 | 0 | 0 |
| | 2.5E−05 | 0 | 0 | 0 | 0 | 0 | 0 | 0 | 0 | 0 | 0 |
| | 0 | 0 | 0 | 0 | 0 | 0 | 0 | 0 | 0 | 0 | 0 |
| | | 0 | 0.0002 | 0.0006 | 0.002 | 0.006 | 0.02 | 0.06 | 0.20 | 0.63 | 2 |
| Compound | | | | | Compound B, µM | | | | | | |

TABLE 11C

Cytotoxicity of Compound B and LNP-2 Combination.
Average percent of cell viability vs control

| LNP-2, µM Avg % Cell Viability | | | | | | | | | | |
|---|---|---|---|---|---|---|---|---|---|---|
| | 0.0025 | 127 | 115 | 114 | 105 | 117 | 103 | 104 | 102 | 99 | 108 |
| | 0.00079 | 118 | 105 | 107 | 96 | 102 | 102 | 103 | 101 | 113 | 99 |
| | 0.00025 | 103 | 100 | 101 | 94 | 107 | 111 | 110 | 107 | 113 | 118 |
| | 7.9E−05 | 103 | 90 | 103 | 97 | 104 | 107 | 108 | 109 | 111 | 116 |
| | 2.5E−05 | 100 | 102 | 107 | 97 | 90 | 98 | 112 | 106 | 104 | 104 |
| | 0 | 100 | 113 | 112 | 111 | 108 | 116 | 120 | 117 | 104 | 105 |
| | | 0 | 0.0002 | 0.0006 | 0.002 | 0.006 | 0.02 | 0.06 | 0.20 | 0.63 | 2 |
| Compound | | | | | Compound B, µM | | | | | | |

TABLE 11D

Antiviral Activity of Compound B and LNP-2 Combination.
Additive percent inhibition versus negative control (n = 4 samples per data point)

| LNP-2, μM Additive % Inhibition | 0.0025 | 86.19 | 88.42 | 88.73 | 89.11 | 90.56 | 93.36 | 96.54 | 98.19 | 98.78 | 98.97 |
|---|---|---|---|---|---|---|---|---|---|---|---|
| | 0.00079 | 62.27 | 68.36 | 69.21 | 70.25 | 74.22 | 81.86 | 90.54 | 95.04 | 96.68 | 97.18 |
| | 0.00025 | 29.45 | 40.84 | 42.42 | 44.38 | 51.79 | 66.09 | 82.31 | 90.73 | 93.79 | 94.72 |
| | 7.9E−05 | 18.98 | 32.06 | 33.88 | 36.12 | 44.63 | 61.05 | 79.68 | 89.35 | 92.87 | 93.94 |
| | 2.5E−05 | 5.31 | 20.6 | 22.72 | 25.35 | 35.29 | 54.48 | 76.25 | 87.56 | 91.67 | 92.92 |
| | 0 | 0 | 16.15 | 18.39 | 21.16 | 31.66 | 51.93 | 74.92 | 86.86 | 91.2 | 92.52 |
| Compound | | 0 | 0.0002 | 0.0006 | 0.002 | 0.006 | 0.02 | 0.06 | 0.20 | 0.63 | 2 |
| | | | | | Compound B, μM | | | | | | |

TABLE 12

Summary of results of in vitro combination studies in HepG2.2.15 cell culture system with HBsAg quantitation by CLIA

| Example Number | 1st Inhibitor | 2nd Inhibitor | 1st Inhibitor $EC_{50}$ (μM) | 2nd Inhibitor $EC_{50}$ (μg/mL) | Synergy Volume (μM² %) | Synergy Log Volume | Antagonism Volume (μM² %)* | Antagonism Log Volume | Interpretation |
|---|---|---|---|---|---|---|---|---|---|
| 175.1 | Compound A | LNP-1 | 0.001 | 0.00039 | 0 | 0 | −3.44 | −0.86 | Additive |
| 175.2 | Compound A | LNP-2 | 0.001 | 0.00054 | 0 | 0 | 0 | 0 | Additive |
| 175.3 | Compound B | LNP-1 | 0.008 | 0.00039 | 0 | 0 | −9.98 | −2.49 | Additive |
| 175.4 | Compound B | LNP-2 | 0.014 | 0.00048 | 0 | 0 | −16.95 | −4.23 | Additive |

*at 99.9% confidence interval

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (Ia), or a salt, solvate, stereoisomer, geometric isomer, tautomer, or any mixtures thereof:

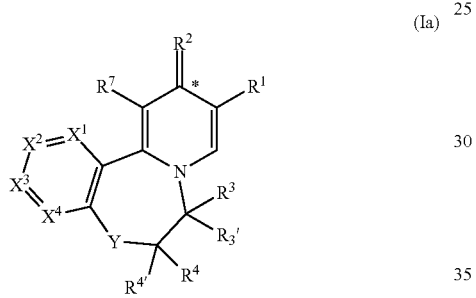

(Ia)

wherein:
Y is selected from the group consisting of $CHR^5$ and O;
each occurrence of $R^5$ is independently selected from the group consisting of H, optionally substituted $C_1$-$C_6$ alkyl, and optionally substituted $C_3$-$C_8$ cycloalkyl;
$R^1$ is —C(=O)$OR^8$;
$R^2$ is =O;
$R^3$, $R^{3'}$, $R^4$, and $R^{4'}$ are each independently selected from the group consisting of H, alkyl-substituted oxetanyl, optionally substituted $C_1$-$C_6$ alkyl, and optionally substituted $C_3$-$C_8$ cycloalkyl;
or one pair selected from the group consisting of $R^3/R^{3'}$, $R^4/R^{4'}$, and $R^3/R^4$ combine to form a divalent group selected from the group consisting of $C_1$-$C_6$ alkanediyl, $(CH_2)_nO(CH_2)_n$—, —$(CH_2)_nNR^9$ $(CH_2)_n$—, —$(CH_2)_nS(CH_2)_n$—, —$(CH_2)_nS(=O)$ $(CH_2)_n$—, and —$(CH_2)_nS(=O)_2(CH_2)_n$—, wherein each occurrence of n is independently selected from the group consisting of 1 and 2 and each divalent group is optionally substituted with at least one $C_1$-$C_6$ alkyl or halogen;
$X^1$ is N;
$X^2$ is $CR^{6II}$;
$X^3$ is $CR^{6III}$;
$X^4$ is $CR^{6IV}$;
$R^{6II}$, $R^{6III}$, and $R^{6IV}$ are independently selected from the group consisting of H, halogen, —CN, pyrrolidinyl, optionally substituted $C_1$-$C_6$ alkyl, optionally substituted $C_1$-$C_6$ alkenyl, optionally substituted $C_3$-$C_8$ cycloalkyl, optionally substituted heterocyclyl, —OR, $C_1$-$C_6$ haloalkoxy, —N(R)(R), —$NO_2$, —S(=O)$_2$N(R) (R), acyl, and $C_1$-$C_6$ alkoxycarbonyl, wherein each occurrence of R is independently selected from the group consisting of H, $C_1$-$C_6$ alkyl, R'-substituted $C_1$-$C_6$ alkyl, $C_1$-$C_6$ hydroxyalkyl, optionally substituted ($C_1$-$C_6$ alkoxy)-$C_1$-$C_6$ alkyl, and optionally substituted $C_3$-$C_8$ cycloalkyl, wherein each occurrence of R' is independently selected from the group consisting of —$NH_2$, —NH ($C_1$-$C_6$ alkyl), —N($C_1$-$C_6$ alkyl)($C_1$-$C_6$ alkyl), —NHC(=O)O$^t$Bu, —N($C_1$-$C_6$ alkyl)C(=O)O$^t$Bu, and a 5- or 6-membered heterocyclic group, which is optionally N-linked;

or $R^{6II}$ and $R^{6III}$ combine to form a divalent group selected from the group consisting of —O(CHF) O—, —O($CF_2$)O—, —O($CR^9R^9$)O—, —O($CH_2$) ($CH_2$)O—, and —O($CH_2$)($CR^{11}R^{11}$)($CH_2$)O—;

$R^7$ is selected from the group consisting of H, OH, halogen, $C_1$-$C_6$ alkoxy, and optionally substituted $C_1$-$C_6$ alkyl;

$R^8$ is selected from the group consisting of H, optionally substituted $C_1$-$C_6$ alkyl, and optionally substituted $C_3$-$C_8$ cycloalkyl;

each occurrence of $R^9$ is independently selected from the group consisting of H and $C_1$-$C_6$ alkyl; and each occurrence of $R^{11}$ is independently selected from the group consisting of H, OH, $C_1$-$C_6$ alkyl, $C_1$-$C_6$ alkoxy, alkoxy-$C_1$-$C_6$ alkyl, and alkoxy-$C_1$-$C_6$ alkoxy, wherein two $R^{11}$ groups bound to the same carbon atom are not simultaneously OH; or two $R^{11}$ groups combine with the carbon atom to which they are bound to form a moiety selected from the group consisting of C=O, C=$CH_2$ and oxetane-3,3-diyl.

2. The compound of claim 1, wherein each occurrence of alkyl or cycloalkyl is independently optionally substituted with at least one substituent selected from the group consisting of $C_1$-$C_6$ alkyl, halogen, —OR", phenyl, and —N(R")(R"), wherein each occurrence of R" is independently H, $C_1$-$C_6$ alkyl, or $C_3$-$C_8$ cycloalkyl.

3. The compound of claim 1, wherein the compound of formula (Ia) is

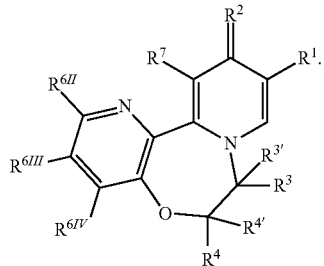

(In)

4. The compound of claim 1, wherein the compound of formula (Ia) is

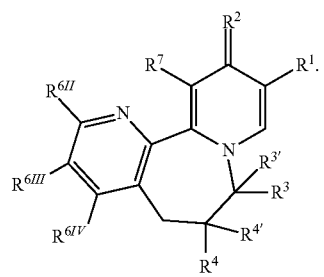

(Iv)

5. The compound of claim 1, wherein R is selected from the group consisting of —C(=O)OH, —C(=O)OMe, —C(=O)OEt, —C(=O)O-nPr, —C(=O)O-iPr, —C(=O)O-cyclopentyl, and —C(=O)O-cyclohexyl.

6. The compound of claim 1, wherein at least one applies:
(a) $R^3$ and $R^{3'}$, and $R^4$ and $R^{4'}$, are each independently selected from the group consisting of H, methyl, ethyl, n-propyl, isopropyl, n-butyl, isobutyl, sec-butyl, t-butyl, hydroxymethyl, 2-hydroxy-ethyl, 2-methoxy-ethyl, methoxymethyl, and 2-methyl-1-methoxy-prop-2-yl;
(b) $R^3$ is H, $R^{3'}$ is isopropyl;
(c) $R^3$ is H, $R^{3'}$ is tert-butyl;
(d) $R^3$ is methyl, $R^{3'}$ is isopropyl;
(e) $R^3$ is methyl, $R^{3'}$ is tert-butyl;
(f) $R^3$ is methyl, $R^{3'}$ is methyl;
(g) $R^3$ is methyl, $R^{3'}$ is ethyl;
(h) $R^3$ is ethyl, $R^{3'}$ is ethyl;
(i) $R^3$ and $R^{3'}$ are not H;
(j) $R^4$ and $R^{4'}$ are H;
(k) $R^3/R^{3'}$ combine to form a divalent group selected from the group consisting of $C_1$-$C_6$ alkanediyl, —$(CH_2)_nO(CH_2)_n$—, —$(CH_2)_nNR^9(CH_2)_n$—, —$(CH_2)_nS(CH_2)_n$—, —$(CH_2)_nS(=O)(CH_2)_n$—, and —$(CH_2)_nS(=O)_2(CH_2)_n$—, wherein each occurrence of n is independently selected from the group consisting of 1 and 2 and wherein each divalent group is optionally substituted with at least one $C_1$-$C_6$ alkyl or halogen.

7. The compound of claim 1, wherein $R^{6II}$, $R^{6III}$ and $R^{6IV}$ are independently selected from the group consisting of H, F, Cl, Br, I, CN, amino, methylamino, dimethylamino, methoxyethylamino, pyrrolidinyl, methoxy, ethoxy, n-propoxy, isopropoxyl, n-butoxy, sec-butoxy, isobutoxy, t-butoxy, 2-methoxy-ethoxy, 2-hydroxy-ethoxy, 3-methoxy-prop-1-yl, 3-hydroxy-prop-1-yl, 3-methoxy-prop-1-oxy, 3-hydroxy-prop-1-oxy, 4-methoxy-but-1-yl, 4-hydroxy-but-1-yl, 4-methoxy-but-1-oxy, 4-hydroxy-but-1-oxy, 2-hydroxy-ethoxy, 3-hydroxy-prop-1-yl, 4-hydroxy-but-1-yl, 3-hydroxy-2,2-dimethyl-prop-1-oxy, cyclopropylmethoxy, 2,2,2-trifluoroethoxy, 2-(2-haloethoxy)-ethoxy, 2-(N-morpholino)-ethyl, 2-(N-morpholino)-ethoxy, 3-(N-morpholino)-prop-1-yl, 3-(N-morpholino)-prop-1-oxy, 4-(N-morpholino)-but-1-yl, 4-(N-morpholino)-but-1-oxy, 2-amino-ethyl, 2-(NHC(=O)O$^t$Bu)-ethyl, 2-amino-ethoxy, 2-(NHC(=O)O$^t$Bu)-ethoxy, 3-amino-prop-1-yl, 3-(NHC(=O)O$^t$Bu)-prop-1-yl, 3-amino-prop-1-oxy, 3-(NHC(=O)O$^t$Bu)-prop-1-oxy, 4-amino-but-1-yl, 4-(NHC(=O)O$^t$Bu)-but-1-yl, 4-amino-but-1-oxy, and 4-(NHC(=O)O$^t$Bu)-but-1-oxy.

8. The compound of claim 1, wherein at least one applies:
(a) $X^4$ is CH;
(b) $X^2$ is $CR^{6II}$, $R^{6II}$ is not H, $X^3$ is $CR^{6III}$, and $R^{6III}$ is not H;
(c) $X^1$ is N, $X^2$ is $CR^{6II}$, $X^3$ is $CR^{6III}$, and $X^4$ is CH, and one of the following applies: $R^{6II}$ is methoxy, $R^{6III}$ is 3-methoxy-propoxy; $R^{6II}$ is chloro, $R^{6III}$ is 3-methoxy-propoxy; $R^{6II}$ is cyclopropyl, $R^{6III}$ is 3-methoxy-propoxy; $R^{6II}$ is methoxy, $R^{6III}$ is methoxy; $R^{6II}$ is chloro, $R^{6III}$ is methoxy; and $R^{6II}$ is cyclopropyl, $R^{6III}$ is methoxy;
(d) $X^2$ is $CR^{6II}$, $X^3$ is $CR^{6III}$, and $R^{6II}$ and $R^{6III}$ combine to form a divalent group selected from the group consisting of —O(CF)O—, —O(CF$_2$)O—, —O(CR$^9$R$^9$)O—, —O(CH$_2$)(CH$_2$)O—, and —O(CH$_2$)(CR$^{11}$R$^{11}$)(CH$_2$)O.

9. The compound of claim 1, wherein $R^7$ is selected from the group consisting of H, methyl, ethyl, and F.

10. A compound selected from the group consisting of:

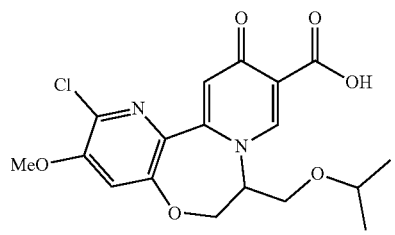 [SMILES: COc1cc2c(nc1Cl)-c1cc(=O)c(C(=O)O)cn1C(COC(C)C)CO2]

2-chloro-7-(isopropoxymethyl)-3-methoxy-11-oxo-6,7-dihydro-11H-dipyrido[1,2-d:2',3'-f][1,4]oxazepine-10-carboxylic acid;

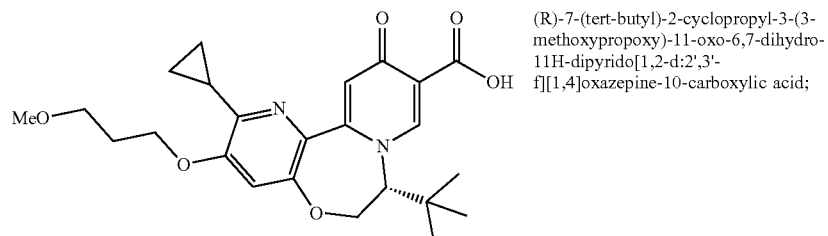 (R)-7-(tert-butyl)-2-chloro-3-(3-methoxypropoxy)-11-oxo-6,7-dihydro-11H-dipyrido[1,2-d:2',3'-f][1,4]oxazepine-10-carboxylic acid;

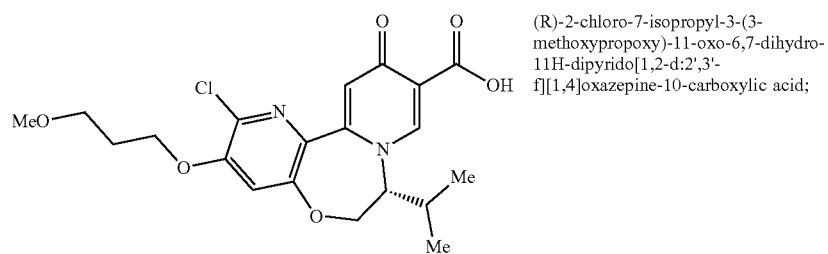 (R)-7-(tert-butyl)-2-cyclopropyl-3-(3-methoxypropoxy)-11-oxo-6,7-dihydro-11H-dipyrido[1,2-d:2',3'-f][1,4]oxazepine-10-carboxylic acid;

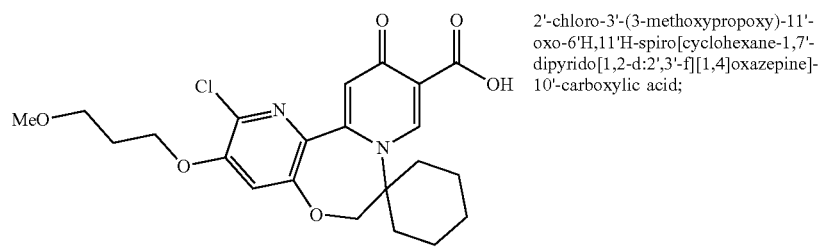 (R)-2-chloro-7-isopropyl-3-(3-methoxypropoxy)-11-oxo-6,7-dihydro-11H-dipyrido[1,2-d:2',3'-f][1,4]oxazepine-10-carboxylic acid;

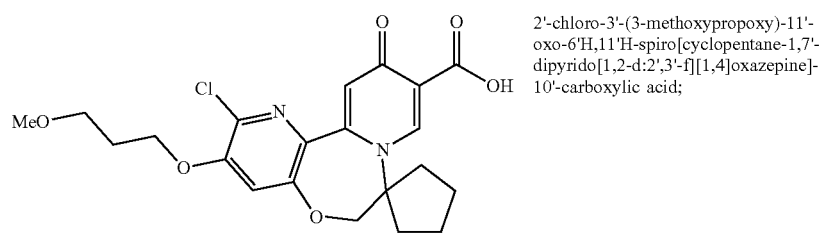 2'-chloro-3'-(3-methoxypropoxy)-11'-oxo-6'H,11'H-spiro[cyclohexane-1,7'-dipyrido[1,2-d:2',3'-f][1,4]oxazepine]-10'-carboxylic acid;

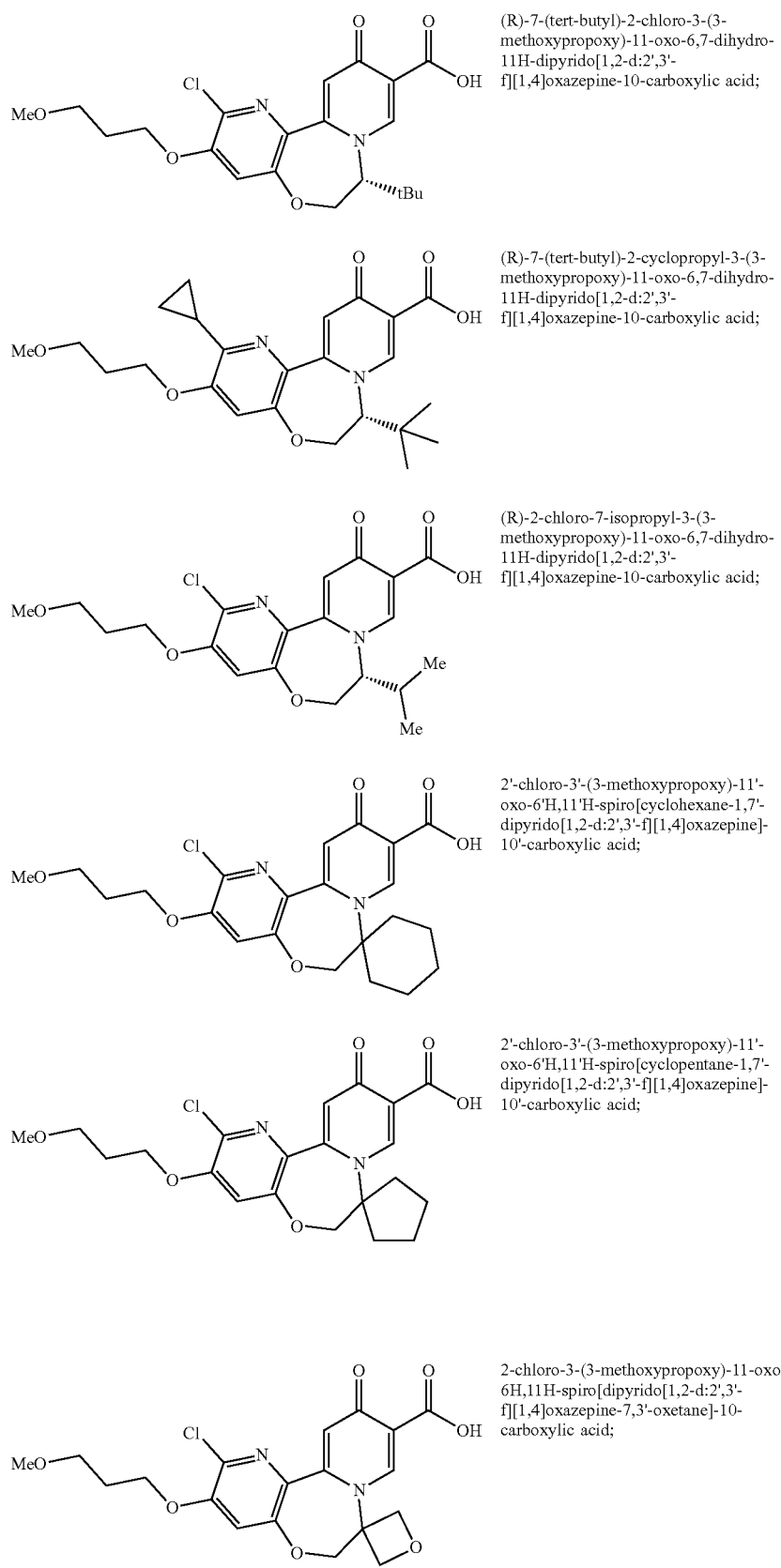 2'-chloro-3'-(3-methoxypropoxy)-11'-oxo-6'H,11'H-spiro[cyclopentane-1,7'-dipyrido[1,2-d:2',3'-f][1,4]oxazepine]-10'-carboxylic acid;

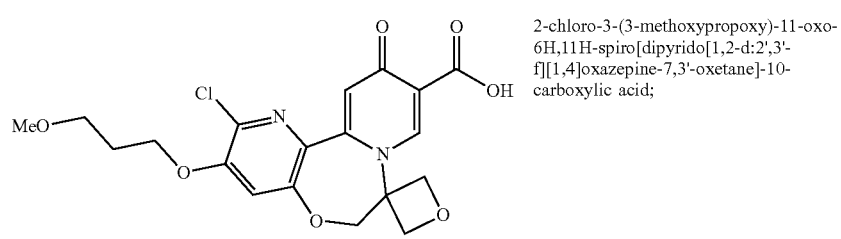 2-chloro-3-(3-methoxypropoxy)-11-oxo-6H,11H-spiro[dipyrido[1,2-d:2',3'-f][1,4]oxazepine-7,3'-oxetane]-10-carboxylic acid;

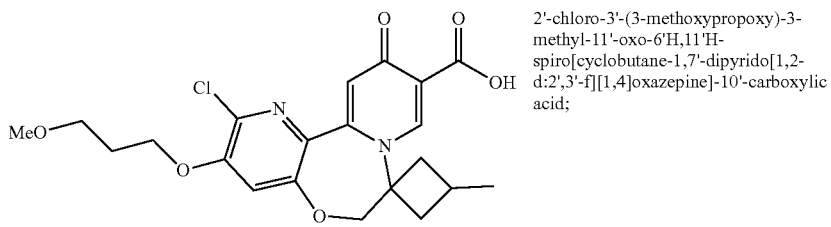

2'-chloro-3'-(3-methoxypropoxy)-3,3-dimethyl-11'-oxo-6'H,11'H-spiro[cyclobutane-1,7'-dipyrido[1,2-d:2',3'-f][1,4]oxazepine]-10'-carboxylic acid;

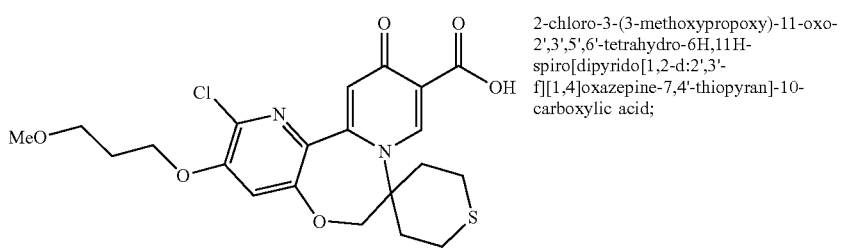

2'-chloro-3'-(3-methoxypropoxy)-3-methyl-11'-oxo-6'H,11'H-spiro[cyclobutane-1,7'-dipyrido[1,2-d:2',3'-f][1,4]oxazepine]-10'-carboxylic acid;

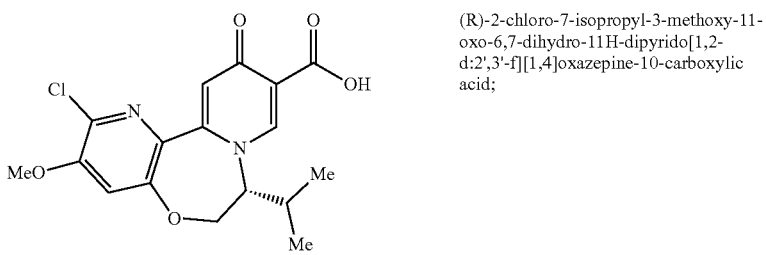

2-chloro-3-(3-methoxypropoxy)-11-oxo-2',3',5',6'-tetrahydro-6H,11H-spiro[dipyrido[1,2-d:2',3'-f][1,4]oxazepine-7,4'-thiopyran]-10-carboxylic acid;

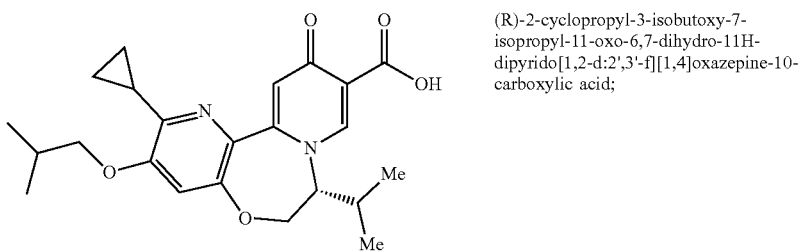

(R)-2-chloro-7-isopropyl-3-methoxy-11-oxo-6,7-dihydro-11H-dipyrido[1,2-d:2',3'-f][1,4]oxazepine-10-carboxylic acid;

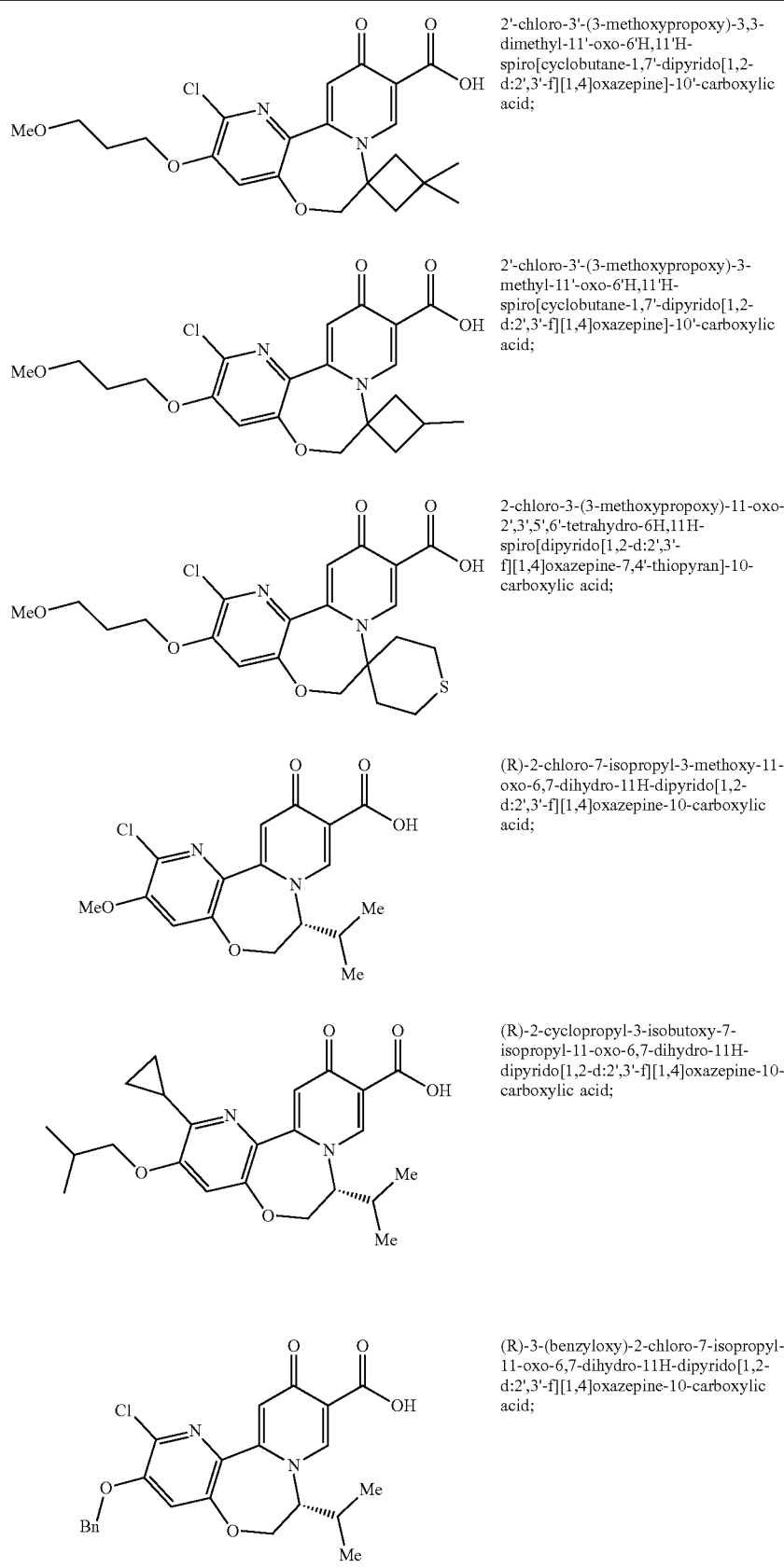

(R)-2-cyclopropyl-3-isobutoxy-7-isopropyl-11-oxo-6,7-dihydro-11H-dipyrido[1,2-d:2',3'-f][1,4]oxazepine-10-carboxylic acid;

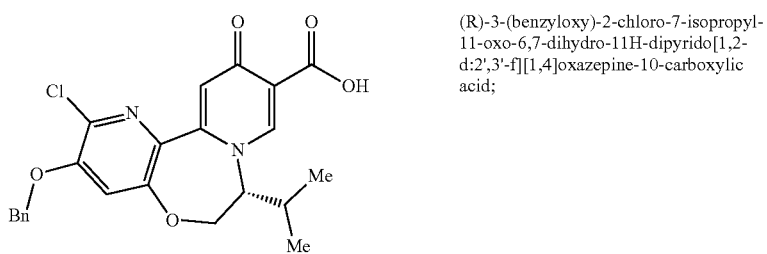

(R)-3-(benzyloxy)-2-chloro-7-isopropyl-11-oxo-6,7-dihydro-11H-dipyrido[1,2-d:2',3'-f][1,4]oxazepine-10-carboxylic acid;

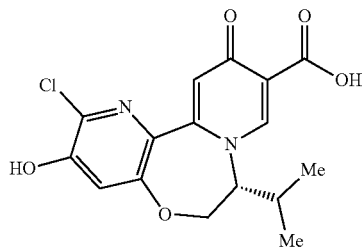

(R)-2-chloro-3-hydoxy-7-isopropyl-11-oxo-6,7-dihydro-11H-dipyrido[1,2-d:2',3'-f][1,4]oxazepine-10-carboxylic acid;

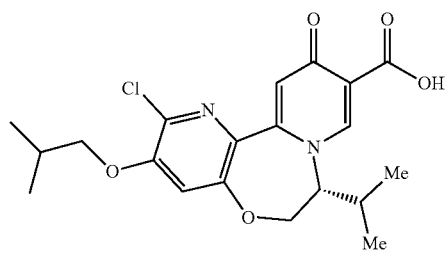 [SMILES: CC(C)COc1cc2c(nc1Cl)-c1cc(=O)c(C(=O)O)cn1[C@H](C(C)C)CO2]

(R)-2-chloro-3-isobutoxy-7-isopropyl-11-oxo-6,7-dihydro-11H-dipyrido[1,2-d:2',3'-f][1,4]oxazepine-10-carboxylic acid;

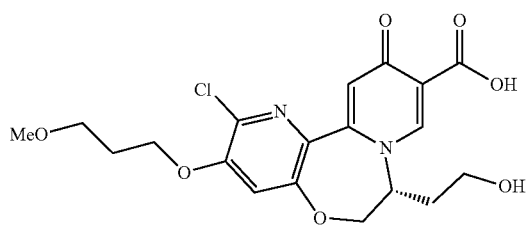 [SMILES: COCCCOc1cc2c(nc1Cl)-c1cc(=O)c(C(=O)O)cn1[C@H](CCO)CO2]

(R)-2-chloro-7-(2-hydroxyethyl)-3-(3-methoxypropoxy)-11-oxo-6,7-dihydro-11H-dipyrido[1,2-d:2',3'-f][1,4]oxazepine-10-carboxylic acid;

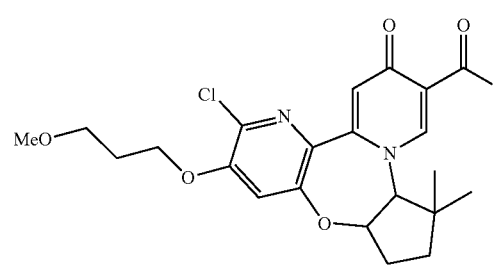

6-chloro-7-(3-methoxypropoxy)-12,12-dimethyl-3-oxo-9a,11,12,12a-tetrahydro-3H,10H-cyclopenta[b]dipyrido[1,2-d:2',3'-f][1,4]oxazepine-2-carboxylic acid;

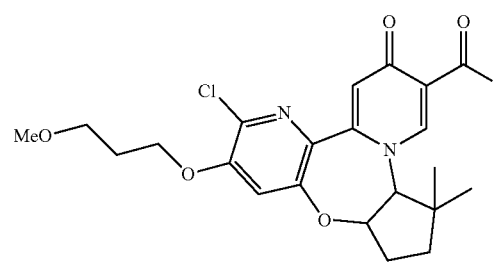

6-chloro-7-(3-methoxypropoxy)-12,12-dimethyl-3-oxo-9a,11,12,12a-tetrahydro-3H,10H-cyclopenta[b]dipyrido[1,2-d:2',3'-f][1,4]oxazepine-2-carboxylic acid (single enantiomer I);

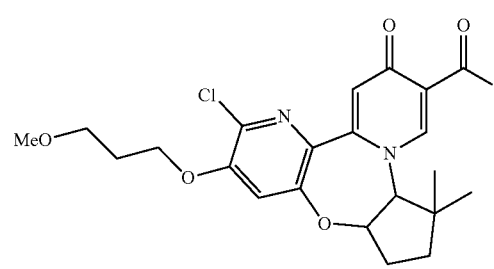

6-chloro-7-(3-methoxypropoxy)-12,12-dimethyl-3-oxo-9a,11,12,12a-tetrahydro-3H,10H-cyclopenta[b]dipyrido[1,2-d:2',3'-f][1,4]oxazepine-2-carboxylic acid (single enantiomer II);

-continued

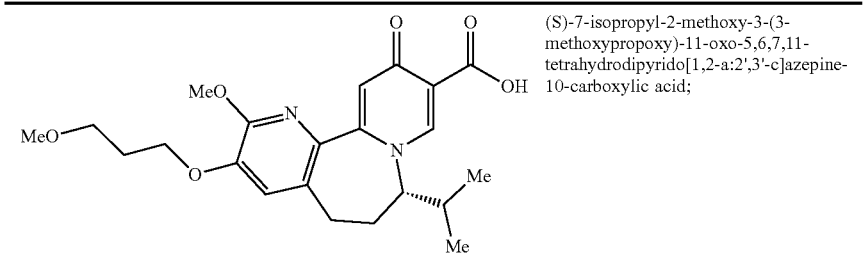

(S)-7-isopropyl-2-methoxy-3-(3-methoxypropoxy)-11-oxo-5,6,7,11-tetrahydrodipyrido[1,2-a:2',3'-c]azepine-10-carboxylic acid;

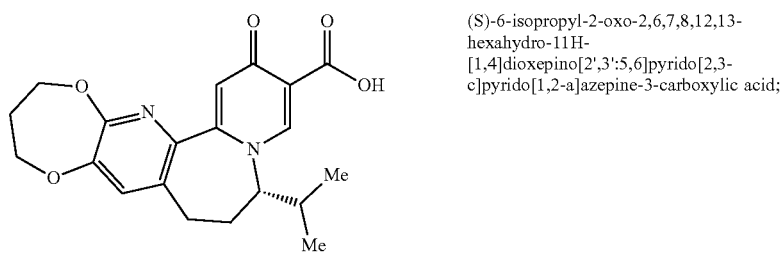

(S)-6-isopropyl-2-oxo-2,6,7,8,12,13-hexahydro-11H-[1,4]dioxepino[2',3':5,6]pyrido[2,3-c]pyrido[1,2-a]azepine-3-carboxylic acid;

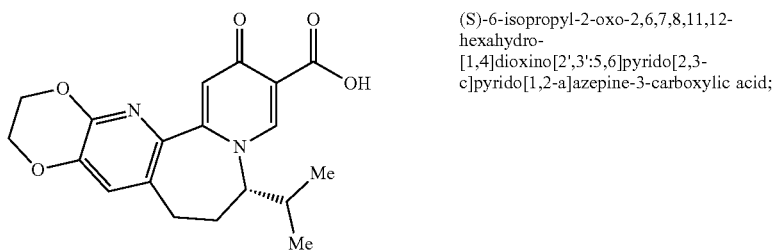

(S)-6-isopropyl-2-oxo-2,6,7,8,11,12-hexahydro-[1,4]dioxino[2',3':5,6]pyrido[2,3-c]pyrido[1,2-a]azepine-3-carboxylic acid;

or a salt, solvate, stereoisomer, tautomer, geometric isomer, or any mixtures thereof.

11. A pharmaceutical composition comprising at least one compound of claim 1 and a pharmaceutically acceptable carrier.

12. The pharmaceutical composition of claim 11, further comprising at least one additional agent useful for treating hepatitis virus infection.

13. The pharmaceutical composition of claim 12, wherein the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; and immunostimulator.

14. A method of treating or ameliorating hepatitis B virus (HBV) infection in a subject, the method comprising administering to the subject in need thereof a therapeutically effective amount of at least one compound of formula (Ia), or a salt, solvate, stereoisomer, geometric isomer, tautomer, or any mixtures thereof:

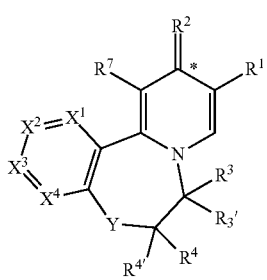

(Ia)

wherein:
Y is selected from the group consisting of $CHR^5$ and O;
each occurrence of $R^5$ is independently selected from the group consisting of H, optionally subtituted $C_1$-$C_6$ alkyl, and optionally substituted $C_3$-$C_8$ cycloalkyl;

$R^1$ is -C(=O)OR$^8$;
$R^2$ is =O;
$R^3$, $R^{3'}$, $R^4$, and $R^{4'}$ are each independently selected from the group consisting of H, alkyl-substituted oxetanyl, optionally substituted $C_1$-$C_6$ alkyl, and optionally substituted $C_3$-$C_8$ cycloalkyl;
or one pair selected from the group consisting of $R^3/R^{3'}$, $R^4/R^{4'}$, and $R^3/R^4$ combine to form a divalent group selected from the group consisting $C_1$-$C_6$alkanediyl, $(CH_2)_nO(CH_2)_n$-,-$(CH_2)_nNR^9$ $(CH_2)_n$-, -$(CH_2)_nS(CH_2)_n$-, -$(CH_2)_nS(=O)$ $(CH_2)_n$-, and -$(CH_2)_nS(=O)_2(CH_2)_n$-, wherein each occurrence of n is independently selected from the group consisting of 1 and 2 and each divalent group is optionally substituted with at least one $C_1$-$C_6$ alkyl or halogen;
$X^1$ is N;
$X^2$ is CR$^{6II}$;
$X^3$ is CR$^{6III}$;
$X^4$ is CR$^{6IV}$;
$R^{6II}$, $R^{6III}$, and $R^{6IV}$ are independently selected from the group consisting of H, halogen, -CN, pyrrolidinyl, optionally substituted $C_1$-$C_6$ alkyl, optionally substituted $C_1$-$C_6$ alkenyl, optionally substituted $C_3$-$C_8$ cycloalkyl, optionally substituted heterocyclyl, -OR, $C_1$-$C_6$ haloalkoxy, -N(R)(R), -NO$_2$, -S(=O)$_2$N(R)(R), acyl, and $C_1$-$C_6$ alkoxycarbonyl,
wherein each occurrence of R is independently selected from the group consisting of H, $C_1$-$C_6$ alkyl, R'-substituted $C_1$-$C_6$ alkyl, $C_1$-$C_6$ hydroxy-alkyl, optionally substituted ($C_1$-$C_6$ alkoxy)-$C_1$-$C_6$ alkyl, and optionally substituted $C_3$-$C_8$ cycloalkyl,
wherein each occurrence of R' is independently selected from the group consisting of -NH$_2$, -NH($C_1$-$C_6$ alkyl), -N($C_1$-$C_6$ alkyl)($C_1$-$C_6$ alkyl), -NHC(=O)O$^t$Bu, -N($C_1$-$C_6$ alkyl)C(=O)O$^t$Bu, and a 5- or 6-membered heterocyclic group, which is optionally N-linked;
or $R^{6II}$ and $R^{6III}$ combine to form a divalent group selected from the group consisting of -O(CHF)O-, -O(CF$_2$)O-, -O(CR$^9$R$^9$)O-, -O(CH$_2$)(CH$_2$)O-, and -O(CH$_2$)(CR$^{11}$R$^{11}$)(CH$_2$)O-;
$R^7$ is selected from the group consisting of H, OH, halogen, $C_1$-$C_6$ alkoxy, and optionally substituted $C_1$-$C_6$ alkyl;
$R^8$ is selected from the group consisting of H, optionally substituted $C_1$-$C_6$ alkyl, and optionally substituted $C_3$-$C_8$ cycloalkyl;
each occurrence of $R^9$ is independently selected from the group consisting of H and $C_1$-$C_6$ alkyl; and
each occurrence of is independently selected from the group consisting of H, OH, $C_1$-$C_6$ alkyl, $C_1$-$C_6$ alkoxy, alkoxy-$C_1$-$C_6$ alkyl, and alkoxy-$C_1$-$C_6$ alkoxy, wherein two $R^{11}$ groups bound to the same carbon atom are not simultaneously OH; or two groups combine with the carbon atom to which they are bound to form a moiety selected from the group consisting of C=O, C=CH2 and oxetane-3,3-diyl.

15. The method of claim 14, wherein the at least one compound is administered to the subject in a pharmaceutically acceptable composition.

16. The method of claim 14, wherein the subject is further administered at least one additional agent useful for treating the hepatitis B virus infection.

17. The method of claim 16, wherein the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; and immunostimulator.

18. The method of claim 16, wherein the subject is co-administered the at least one compound and the at least one additional agent.

19. The method of claim 16, wherein the at least one compound and the at least one additional agent are coformulated.

20. The method of claim 14, wherein the subject is a mammal.

21. A method of reducing or minimizing levels of at least one selected from the group consisting of hepatitis B virus surface antigen (HBsAg), hepatitis B e-antigen (HBeAg), hepatitis B core protein, and pregenomic (pg) RNA, in a HBV-infected subject, the method comprising administering to the subject in need thereof a therapeutically effective amount of at least one compound of formula (Ia), or salt, solvate, stereoisomer, geometric isomer, tautomer, or any mixtures thereof:

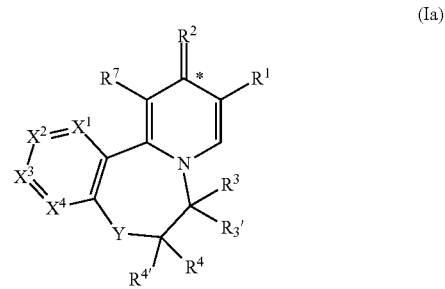

(Ia)

wherein:
Y is selected from the group consisting of CHR$^5$ and O;
each occurrence of le is independently selected from the group consisting of H, optionally substituted Ci-C6 alkyl, and optionally substituted $C_3$-$C_8$ cycloalkyl;
$R^1$ is -C(=O)OR$^8$;
$R^2$ is =O;
$R^3$, $R^{3'}$, $R^4$, and $R^{4'}$ are each independently selected from the group consisting of H, alkyl-substituted oxetanyl, optionally substituted $C_1$-$C_6$ alkyl, and optionally substituted $C_3$-$C_8$ cycloalkyl;
or one pair selected from the group consisting of $R^3/R^{3'}$, $R^4/R^{4'}$, and $R^3/R^4$ combine to form a divalent group selected from the group consisting of $C_1$-$C_6$ alkanediyl, $(CH_2)_nO(CH_2)_n$-, -$(CH_2)_n$ NR$^9$(CH$_2$)$_n$-, -$(CH_2)_nS(CH_2)_n$-, -$(CH_2)_nS(=O)$ $(CH_2)_n$-, and -$(CH_2)_nS(=O)_2(CH_2)_n$-, wherein each occurrence of n is independently selected from the group consisting of 1 and 2 and each divalent group is optionally substituted with at least one $C_1$-$C_6$ alkyl or halogen;
$X^1$ is N;
$X^2$ is CR$^{6II}$;
$X^3$ is CR$^{6III}$;
$X^4$ is CR$^{6IV}$;
$R^{6II}$ $R^{6III}$, and $R^{6IV}$ are independently selected from the group consisting of H, halogen, -CN, pyrrolidinyl, optionally substituted $C_3$-$C_6$ alkyl, optionally substituted $C_1$-$C_6$ alkenyl, optionally substituted $C_3$-$C_8$ cycloalkyl, optionally substituted heterocyclyl, -OR, $C_1$-$C_6$ haloalkoxy, -N(R)(R), -NO$_2$, -S(=O)$_2$N(R)(R), acyl, and $C_1$-$C_6$ alkoxycarbonyl, wherein each occurrence of R is independently selected from the group consisting of H, $C_1$-$C_6$ alkyl, R'-substituted $C_1$-$C_6$ alkyl, $C_1$-$C_6$ hydroxyalkyl, optionally substituted ($C_1$-$C_6$ alkoxy)-$C_1$-$C_6$ alkyl, and optionally substituted $C_3$-$C_8$ cycloalkyl, wherein each occurrence of R' is independently selected from the group consisting of -NH$_2$, -NH($C_1$-$C_6$ alkyl), -N($C_1$-$C_6$ alkyl)($C_1$-$C_6$ alkyl), -NHC(=O)O$^t$Bu, -N($C_1$-$C_6$ alkyl)C(=O)O$^t$Bu, and a 5- or 6-membered heterocyclic group, which is optionally N-linked;

or $R^{6II}$ and $R^{6III}$ combine to form a divalent group selected from the group consisting of -O(CHF)O-, -O(CF$_2$)O-, -O(CR$^9$R$^9$)O-, -O(CH$_2$)(CH$_2$)O-, and -O(CH$_2$)(CR$^H$R$^H$)(CH$_2$)O-;

$R^7$ is selected from the group consisting of H, OH, halogen, $C_1$-$C_6$ alkoxy, and optionally substituted $C_1$-$C_6$ alkyl;

$R^8$ is selected from the group consisting of H, optionally substituted $C_1$-$C_6$ alkyl, and optionally substituted $C_3$-$C_8$ cycloalkyl;

each occurrence of $R^9$ is independently selected from the group consisting of H and $C_1$-$C_6$ alkyl; and each occurrence of is independently selected from the group consisting of H, OH, $C_1$-$C_6$ alkyl, $C_1$-$C_6$ alkoxy, alkoxy-$C_1$-$C_6$ alkyl, and alkoxy-$C_1$-$C_6$ alkoxy, wherein two $R^{11}$ groups bound to the same carbon atom are not simultaneously OH; or two $R^{11}$ groups combine with the carbon atom to which they are bound to form a moiety selected from the group consisting of C=O, C=CH$_2$ and oxetane-3,3-diyl.

22. The method of claim 21, wherein the at least one compound is administered to the subject in a pharmaceutically acceptable composition.

23. The method of claim 21, wherein the subject is further administered at least one additional agent useful for treating the viral infection.

24. The method of claim 23, wherein the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; and immunostimulator.

25. The method of claim 23, wherein the subject is co-administered the at least one compound and the at least one additional agent.

26. The method of claim 23, wherein the at least one compound and the at least one additional agent are coformulated.

27. The method of claim 21, wherein the subject is a mammal.

* * * * *